US008791083B2

(12) United States Patent
Monia et al.

(10) Patent No.: US 8,791,083 B2
(45) Date of Patent: Jul. 29, 2014

(54) CHIMERIC OLIGOMERIC COMPOUNDS COMPRISING ALTERNATING REGIONS OF NORTHERN AND SOUTHERN CONFORMATIONAL GEOMETRY

(75) Inventors: Brett P. Monia, Encinitas, CA (US); Madeline M. Butler, Rancho Santa Fe, CA (US); Robert McKay, Oceanside, CA (US); Brenda F. Baker, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 628 days.

(21) Appl. No.: 12/388,856

(22) Filed: Feb. 19, 2009

(65) Prior Publication Data

US 2009/0258931 A1 Oct. 15, 2009

Related U.S. Application Data

(63) Continuation of application No. 10/936,273, filed on Sep. 8, 2004, now abandoned.

(60) Provisional application No. 60/501,719, filed on Sep. 9, 2003, provisional application No. 60/568,489, filed on May 6, 2004.

(51) Int. Cl.
*C12N 15/11* (2006.01)

(52) U.S. Cl.
USPC .......................................................... 514/44 A

(58) Field of Classification Search
USPC .......................................................... 514/44 A
See application file for complete search history.

(56) References Cited

U.S. PATENT DOCUMENTS

| | | | |
|---|---|---|---|
| 4,904,582 | A | 2/1990 | Tullis |
| 5,898,031 | A | 4/1999 | Crooke |
| 6,033,910 | A | 3/2000 | Monia et al. |
| 6,261,840 | B1 | 7/2001 | Cowsert et al. |
| 2003/0143732 | A1 | 7/2003 | Fosnaugh et al. |
| 2004/0180351 | A1 | 9/2004 | Giese et al. |

FOREIGN PATENT DOCUMENTS

| | | |
|---|---|---|
| WO | WO 00/66609 | 11/2000 |
| WO | WO 01/16306 | 3/2001 |

OTHER PUBLICATIONS

Wahlestadt et al. (PNAS, 2000; 97(10), pp. 5633-5638).*

Abe et al., "Conformational Energies and the Random-Coil Dimensions and Dipole Moments of the Polyoxides CH3O[(CH2)yO]xCH3" J. Am. Chem. Soc. (1976) 98:6468-6476.

Arnott et al., "Optimized Parameters for A-DNA and B-DNA" Biochem. Biophys. Res. Comm. (1972) 47:1504.

Berger et al., "Crystal structures of B-DNA with incorporated 2'-deoxy-2'-fluoro-arabino-furanosyl thymines: implications of conformational preorganization for duplex stability" Nucleic Acids Res. (1998) 26(10):2473-2480.

Conte et al., "Conformational properties and thermodynamics of the RNA duplex r(CGCAAAUUUGCG)2: comparison with the DNA analogue d(CGCAAATTTGCG)2" Nucleic Acids Res. (1997) 25(13):2627-2634.

Cornell et al., "Second Generation Force Field for the Simulation of Proteins, Nucleic Acids, and Organic Molecules" J. Am. Chem. Soc. (1995) 117(19):5179-5197.

Egli et al., "RNA Hydration: A Detailed Look" Biochemistry (1996) 35(26):8489-8494.

Fedoroff et al., "Structure of a DNA:RNA Hybrid Duplex: Why RNase H Does Not Cleave Pure RNA" J. Mol. Biol. (1993) 233:509-523.

Fraser et al., "Synthesis and Conformational Properties of 2'-Deoxy-2'-Methylthio-Pyrimidine and -Purine Nucleosides: Potential Antisense Applications" J. Heterocycl. Chem. (1993) 30:1277-1287.

Freier et al., "The ups and downs of nucleic acid duplex stability: structure-stability studies on chemically-modified DNA:RNA duplexes" Nucl. Acids Res. (1997) 25:4429-4443.

Gallo et al., "2'-C-Methyluridine phosphoramidite: a new building block for the preparation of RNA analogues carrying the 2'-hydroxyl group" Tetrahedron (2001) 57(27):5707-5713.

Gonzalez et al., "Structure and Dynamics of a DNA.cntdot.RNA Hybrid Duplex with a Chiral Phosphorothioate Moiety: NMR and Molecular Dynamics and Conventional and Time-Averaged Restraints" Biochemistry (1995) 34(15):4969-4982.

Guillerm et al., "Synthesis of 4'-fluoroadenosine as an inhibitor of S-adenosyl-L-homocysteine hydrolase" Bioorganic and Medicinal Chemistry Letters (1995) 5(14):1455-1460.

Harry-O'Kura et al., "A Short, Flexible Route toward 2'-C-Branched Ribonucleosides" J. Org. Chem. (1997) 62(6):1754-1759.

Horton et al., "The Structure of an RNA/DNA Hybrid: A Substrate of the Ribonuclease Activity of HIV-1 Reverse Transcriptase" J. Mol. Biol. (1996) 264:521-533.

Jacobson et al., "Methanocarba analogues of purine nucleosides as potent and selective adenosine receptor agonists" J. Med. Chem. (2000) 43(11):2196-2203.

Kawasaki et al., "Uniformly modified 2'-deoxy-2'-fluoro phosphorothioate oligonucleotides as nuclease-resistant antisense compounds with high affinity and specificity for RNA targets" J. Med. Chem. (1993) 36(7):831-841.

(Continued)

*Primary Examiner* — Jon E. Angell

(74) *Attorney, Agent, or Firm* — Isis Pharmaceuticals, Inc. Patent Dept.

(57) ABSTRACT

The present invention relates to novel chimeric oligomeric compounds having a plurality of alternating regions having either RNA like having northern or 3'-endo conformational geometry (3'-endo regions) or DNA like having southern or C2'-endo/O4'-endo conformational geometry. The oligomeric compounds of the present invention have shown reduction in mRNA levels in multiple in vitro and in vivo assay systems and are useful, for example, for investigative and therapeutic purposes.

21 Claims, 7 Drawing Sheets

(56) References Cited

OTHER PUBLICATIONS

Lane et al., "NMR assignments and solution conformation of the DNA.RNA hybrid duplex d(GTGAACTT).r(AAGUUCAC)" Eur. J. Biochem. (1993) 215(2):297-306.
Lee et al., "Ring-Constrained (N)-methanocarba nucleosides as adenosine receptor agonists: independent 5'- uronamide and 2'-deoxy modifications" Bioorg. Med. Chem. Lett. (2001) 11(10):1333-1337.
Lesnik et al., "Relative Thermodynamic Stability of DNA, RNA, and DNA:RNA Hybrid Duplexes: Relationship with Base Composition and Structure" Biochemistry (1995) 34(34):10807-10815.
Leydier et al., "4'-Thio-RNA: Synthesis of Mixed Base 4'-Thio-Oligoribonucleotides, Nuclease Resistance, and Base Paiirng Properties with Complementary Single and Double Strand" Antisense Research and Development (1995) 5:167-174.
Morita et al., "2'-O,4'-C-ethylene-bridged nucleic acids (ENA): highly nuclease-resistant and thermodynamically stable oligonucleotides for antisense drug" Bioorg. Med. Chem. Lett. (2002) 12(1):73-76.
Owen et al., "4'-substituted nucleosides. 3. Synthesis of some 4'0fluorouridine derivatives" J. Org. Chem. (1976) 41(18):3010-3017.
Poopeiko et al., "Xylo-Configured oligonucleotides (XNA, xylo nucleic acid): synthesis of conformationally restricted derivatives and hybridization towards DNA and RNA complements" Bioorganic & Medicinal Chemistry Letters (2003) 13:2285-2290.
Searle et al., "On the stability of nucleic acid structures in solution: enthalpy-entropy compensations, internal rotations and reversibility" Nucleic Acids Res. (1993) 21:2051-2056.
Singh et al., "LNA (locked nucleic acids): synthesis and high-affinity nucleic acid recognition" Chem. Commun. (1998) 4:455-456.
Tang et al., "2'-C-Branched Ribonucleosides: Synthesis of the Phosphoramidite Derivatives of 2'-C-beta-Methylcytidine and their Incorporation into Oligonucleotides" J. Org. Chem. (1999) 64(3):747-754.
Wolfe, "Gauche effect. Stereochemical consequences of adjacent electron pairs and polar bonds" Acc. Chem. Res. (1972) 5(3):102-111.
Wu et al., "Properties of cloned and expressed human RNase Hi." Journal of Biological Chemistry (1999) 274:28270-28278.
Supplemental European Search Report for application No. EP 04788713.8 dated Jan. 28, 2009.
International Search Report for application No. PCT/US04/29821 dated Sep. 20, 2007.

* cited by examiner

Scheme I: *Synthesis of* 1 *(R=$CH_3$) from aranucleoside*

3 4 5 6 7 8 9 10

Scheme I (continued):

10 11 12 13 14 15 16 17

Scheme I (continued):

17 18

19 1

Scheme II: *Synthesis of* 1 *($R = CH_3$) from protected 4-C-hydroxymethylribose*

20, 21, 22, 23, 24, 25, 26, 27, 1

Scheme III

28

29

30

31

32

33

Scheme IV

Scheme V

CHIMERIC OLIGOMERIC COMPOUNDS COMPRISING ALTERNATING REGIONS OF NORTHERN AND SOUTHERN CONFORMATIONAL GEOMETRY

CROSS-REFERENCE TO RELATED APPLICATIONS

This application is a continuation of U.S. application Ser. No. 10/936,273, filed Sep. 8, 2004 now abandoned, which claims priority to U.S. provisional application Ser. No. 60/501,719 filed Sep. 9, 2003 and to U.S. provisional application Ser. No. 60/568,489 filed May 6, 2004, each which is incorporated herein by reference in its entirety.

FIELD OF THE INVENTION

The present invention relates to novel chimeric oligomeric compounds having regions of nucleosides that are RNA like having northern or 3'-endo conformational geometry (3'-endo regions) and regions of nucleosides that are DNA like having southern or C2'-endo/O4'-endo conformational geometry. In certain embodiments the nucleosides that comprise the DNA like regions are 2'-deoxyribonucleosides. Chimeric oligomeric compounds include those having 3'-endo regions positioned at the 3' and 5'-termini with at least two internal C2'-endo/O4'-endo regions that are separated by at least one 3'-endo region. In other embodiments there are at least 5 separate regions that alternate between C2'-endo/O4'-endo and 3'-endo regions. The oligomeric compounds of the present invention are useful in the regulation of gene expression. The oligomeric compounds of the present invention have shown reduction in mRNA levels in multiple in vitro and in vivo assay systems. The chimeric oligomeric compounds of the present invention are useful, for example, for investigative and therapeutic purposes.

BACKGROUND OF THE INVENTION

Nearly all disease states in multicellular organisms involve the action of proteins. Classic therapeutic approaches have focused on the interaction of proteins with other molecules in efforts to moderate the proteins' disease-causing or disease-potentiating activities. In newer therapeutic approaches, modulation of the production of proteins has been sought. A general object of some current therapeutic approaches is to interfere with or otherwise modulate gene expression.

One method for inhibiting the expression of specific genes involves the use of oligonucleotides, particularly oligonucleotides that are complementary to a specific target messenger RNA (mRNA) sequence. Due to promising research results in recent years, oligonucleotides and oligonucleotide analogs are now accepted as therapeutic agents holding great promise for therapeutic and diagnostic methods.

Oligonucleotides and their analogs can be designed to have particular properties. A number of chemical modifications have been introduced into oligomeric compounds to increase their usefulness as therapeutic agents. Such modifications include those designed to increase binding affinity to a target strand, to increase cell penetration, to stabilize against nucleases and other enzymes that degrade or interfere with the structure or activity of the oligonucleotide, to provide a mode of disruption (terminating event) once the oligonucleotide is bound to a target, and to improve the pharmacokinetic properties of the oligonucleotide.

Despite these advances, a need exists in the art for the development of means to improve the binding affinity and nuclease resistance properties of oligomeric compounds. The present invention meets these needs as well as other needs.

SUMMARY OF THE INVENTION

The present invention provides chimeric oligomeric compounds comprising from about 5 to about 80 linked nucleosides wherein the chimeric oligomeric compounds are divided into at least 5 separate regions and each of these regions is a continuous sequence of from 1 to about 5 nucleosides each having a 3'-endo sugar conformational geometry or a continuous sequence of from 1 to about 5 2'-deoxyribonucleosides and wherein each of these regions comprising from 1 to about 5 2'-deoxyribonucleosides is internally located between two of said regions comprising 1 to about 5 nucleosides each having a 3'-endo sugar conformational geometry or at one of the 3' or 5' termini.

DETAILED DESCRIPTION OF THE INVENTION

Figure 1:
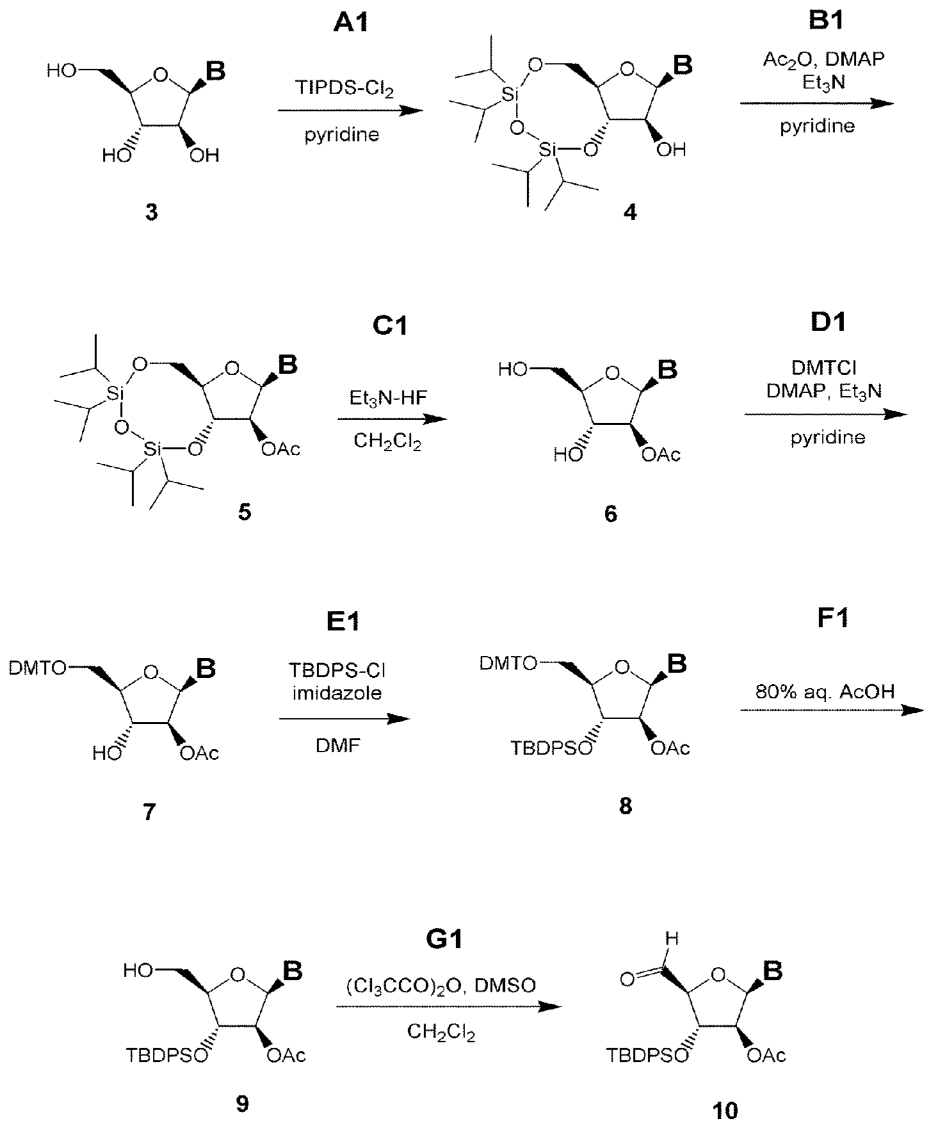
FIG. 1 shows scheme I depicting iterative synthesis of compound 10.

The present invention provides novel chimeric oligomeric compounds comprising regions that alternate between 3'-endo sugar conformational geometry (3'-endo regions) and 2'-endo/O4'-endo sugar conformational geometry (2'-endo regions). Each of the alternating regions comprise from 1 to about 5 nucleosides. The chimeric oligomeric compounds can start (5'-end) or end (3'-end) with either of the 2 regions and can have from about 5 to about 20 separate regions. One or more of the nucleosides of the chimeric oligomeric compound can further comprise a conjugate group. In one aspect of the present invention chimeric oligomeric compounds have the formula: $T_1$-(3'-endo region)-[(2'-endo region)-(3'-endo region)]$_n$-$T_2$ wherein n is at least two and each $T_1$ and $T_2$ is independently an optional conjugate group.

Each of the regions can range from 1 to about 5 nucleosides in length allowing for a plurality of motifs for oligonucleotides having the same length. Such as for example a chimeric oligomeric compound of the present invention having a length of 20 base pairs (bp) would include such motifs as 3-3-2-4-2-3-3, 3-4-1-4-1-4-3 and 4-3-1-4-1-3-4 where each motif has the same number and orientation of regions (bold and italicized numbers are 3'-endo regions, unbold and not underlined numbers are 2'-endo regions and the number corresponding to each region representing the number of base pairs for that particular region).

A plurality of motifs for the chimeric oligomeric compounds of the present invention has been prepared and has shown activity in a plurality of assays against various targets. In addition to in vitro assays some positive data have also been obtained through in vivo assays. A list of motifs is shown below. This list is meant to be representative and not limiting.

| Motifs | | |
|---|---|---|
| # bp's | Regions | Motif |
| 20 mer | 5 | **1**-8-**2**-8-**1** |
| 20 mer | 5 | **2**-6-**4**-6-**2** |
| 20 mer | 5 | **2**-7-**2**-7-**2** |
| 20 mer | 5 | **3**-5-**4**-5-**3** |
| 20 mer | 5 | **3**-6-**1**-7-**3** |
| 20 mer | 5 | **3**-7-**1**-6-**3** |
| 20 mer | 7 | **3**-3-**2**-4-**2**-3-**3** |
| 20 mer | 7 | **3**-4-**1**-4-**1**-4-**3** |
| 20 mer | 7 | **4**-3-**1**-4-**1**-3-**4** |
| 18 mer | 9 | **2**-2-**1**-3-**1**-2-1-3-**3** |
| 20 mer | 9 | **3**-2-**1**-3-**1**-3-1-3-**3** |
| 20 mer | 9 | **3**-2-**1**-3-**1**-2-1-3-**4** |
| 18 mer | 9 | **3**-3-**1**-2-**1**-3-1-2-**2** |
| 20 mer | 9 | **3**-3-**1**-2-**1**-3-1-3-**3** |
| 20 mer | 9 | **3**-3-**1**-2-**1**-2-**1**-3-**4** |
| 20 mer | 9 | **3**-3-**1**-3-**1**-2-**1**-2-**4** |
| 20 mer | 9 | **3**-3-**1**-3-**1**-2-**1**-3-**3** |
| 20 mer | 9 | **5**-2-**1**-2-**1**-2-**1**-1-**5** |
| 20 mer | 11 | **3**-2-**2**-1-**2**-1-**2**-1-**1**-2-**3** |
| 20 mer | 11 | **3**-1-**3**-1-**2**-1-**2**-1-**2**-1-**3** |
| 20 mer | 11 | **3**-1-**2**-1-**2**-1-**2**-1-**2**-1-**4** |
| 20 mer | 11 | **3**-2-**1**-2-**1**-2-**1**-2-**1**-2-**3** |
| 20 mer | 11 | **3**-2-**1**-2-**1**-3-**1**-2-**1**-1-**3** |
| 20 mer | 15 | **2**-1-**1**-2-**1**-1-**1**-1-**1**-1-**1**-1-**1**-3-**2** |
| 20 mer | 15 | **3**-1-**1**-1-**1**-1-**1**-1-**1**-1-**1**-1-**1**-1-**4** |
| 20 mer | 19 | **1**-1-**1**-1-**1**-1-**1**-1-**1**-1-**1**-1-**1**-1-**1**-1-**1**-1-**2** |

# = number of 3'-endo nucleosides in the region (bolded)
# = number of 2'-deoxy ribonucleotides in the region

Compounds of the Invention

The present invention provides chimeric oligomeric compounds that have at least 5 regions that alternate between 3'-endo and 2'-endo in conformational geometry. The nucleoside or nucleosides of a particular region can be modified in a variety of ways to give the region either a 3'-endo or a 2'-endo conformational geometry. The conformational geometry of a selected nucleoside can be modulated in one aspect by modifying the sugar the base or both the sugar and the base. Modifications include attachment of substituent groups or conjugate groups or by directly modifying the base or the sugar.

The sugar conformational geometry (puckering) plays a central role in determining the duplex conformational geometry between an oligonucleotide and its nucleic acid target. By controlling the sugar puckering independently at each position of an oligonucleotide the duplex geometry can be modulated to help maximize desired properties of the resulting chimeric oligomeric compound. Modulation of sugar geometry has been shown to enhance properties such as for example increased lipohpilicity, binding affinity to target nucleic acid (e.g. mRNA), chemical stability and nuclease resistance.

The present invention discloses novel chimeric oligomeric compounds comprised of a plurality of alternating 3'-endo and 2'-endo (including 2'-deoxy) regions wherein each of the regions are independently from about 1 to about 5 nucleosides in length. The chimeric oligomeric compounds can start and end with either 3'-endo or 2'-endo regions and have from about 5 to about 19 regions in total. The nucleosides of each region can be selected to be uniform such as for example uniform 2'-O-MOE nucleosides for one or more of the 3'-endo regions and 2'-deoxynucleosides for the 2'-endo regions. Alternatively the nucleosides can be mixed such that any nucleoside having 3'-endo conformational geometry can be used in any position of any 3'-endo region and any nucleoside having 2'-endo conformational geometry can be used in any position of any 2'-endo region. In some embodiments a 5'-conjugate group is used as a 5'-cap as a method of increasing the 5'-exonuclease resistance but conjugate groups can be used at any position within the chimeric oligomeric compounds of the invention.

3'-Endo Regions

The present invention provides chimeric oligomeric compounds having alternating regions wherein one of the alternating regions has 3'-endo conformational geometry. These 3'-endo regions include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides regions of nucleosides modified in such a way as to favor a C3'-endo type conformation.

Scheme 1

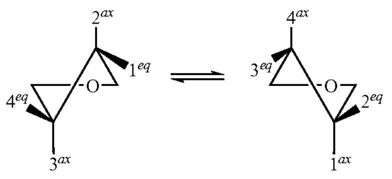

C2'-endo/Southern C3'-endo/Nouthern

Nucleoside conformation is influenced by various factors including substitution at the 2',3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.)

Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, 3'-endo regions can include one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.)

Examples of modified nucleosides amenable to the present invention are shown below in Table 1. These examples are meant to be representative and not exhaustive.

TABLE 1

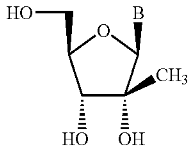

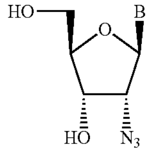

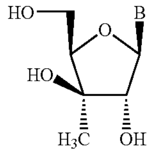

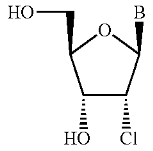

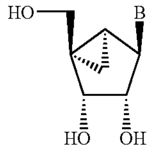

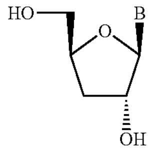

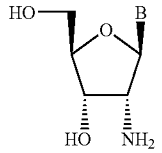

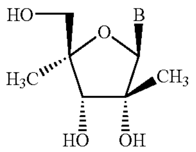

TABLE 1-continued

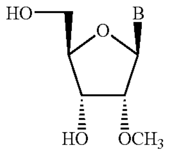

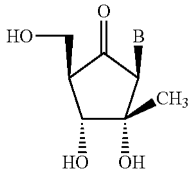

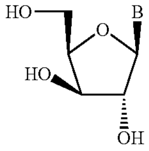

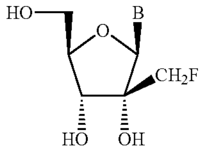

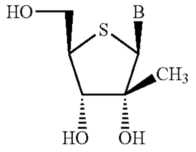

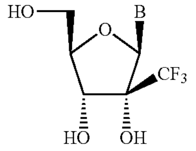

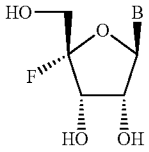

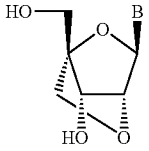

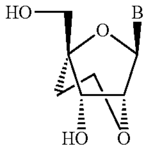

TABLE 1-continued

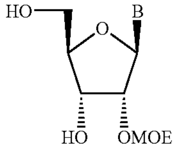

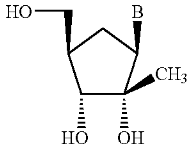

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below). Nucleosides known to be inhibitors/substrates for RNA dependent RNA polymerases (for example HCV NS5B).

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, Biochem. Biophys. Res. Comm., 1970, 47, 1504.) In general, RNA:RNA duplexes are more stable and have higher melting temperatures ($T_m$s) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., Nucleic Acids Research, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as, but not limited to, antisense and RNA interference as these mechanisms require the binding of an oligonucleotide strand to an RNA target strand. In the case of antisense, effective inhibition of the mRNA requires that the antisense DNA have a minimum binding affinity with the mRNA. Otherwise, the desired interaction between the oligonucleotide strand and target mRNA strand will occur infrequently, resulting in decreased efficacy.

One routinely used method of modifying the sugar puckering is the substitution on the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoroadenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-$OCH_2CH_2OCH_3$) side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926). Relative to DNA, the oligonucleotides having the 2'-MOE modification displayed improved RNA affinity and higher nuclease resistance. Chimeric oligomeric compounds having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

To better understand the higher RNA affinity of 2'-O-methoxyethyl substituted RNA and to examine the conformational properties of the 2'-O-methoxyethyl substituent, two dodecamer oligonucleotides were synthesized having SEQ ID NO: 1 (CGC GAA UUC GCG) and SEQ ID NO: 2 (GCG CUU AAG CGC). These self-complementary strands have every 2'-position modified with a 2'-O-methoxyethyl. The duplex was crystallized at a resolution of 1.7 Å and the crystal structure was determined. The conditions used for the crystallization were 2 mM oligonucleotide, 50 mM Na Hepes pH 6.2-7.5, 10.50 mM $MgCl_2$, 15% PEG 400. The crystal data showed: space group C2, cell constants a=41.2 Å, b=34.4 Å, c=46.6 Å, =92.4°. The resolution was 1.7 Å at −170° C. The current R=factor was 20% ($R_{free}$ 26%).

This crystal structure is believed to be the first crystal structure of a fully modified RNA oligonucleotide analogue. The duplex adopts an overall A-form conformation and all modified sugars display C3'-endo pucker. In most of the 2'-O-substituents, the torsion angle around the A'-B' bond, as depicted in Structure II below, of the ethylene glycol linker has a gauche conformation. For 2'-O-MOE, A' and B' of Structure II below are methylene moieties of the ethyl portion of the MOE and R' is the methoxy portion.

II

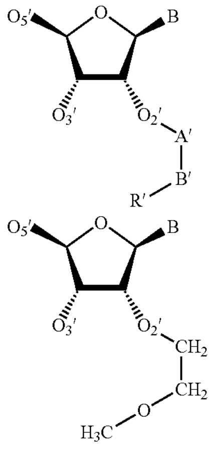

MOE nucleoside

In the crystal, the 2'-O-MOE RNA duplex adopts a general orientation such that the crystallographic 2-fold rotation axis does not coincide with the molecular 2-fold rotation axis. The duplex adopts the expected A-type geometry and all of the 24 2'-O-MOE substituents were visible in the electron density maps at full resolution. The electron density maps as well as the temperature factors of substituent atoms indicate flexibility of the 2'-O-MOE substituent in some cases.

Most of the 2'-O-MOE substituents display a gauche conformation around the C—C bond of the ethyl linker. However, in two cases, a trans conformation around the C—C bond is observed. The lattice interactions in the crystal include packing of duplexes against each other via their minor grooves. Therefore, for some residues, the conformation of the 2'-O-substituent is affected by contacts to an adjacent duplex. In general, variations in the conformation of the substituents (e.g. $g^+$ or $g^-$ around the C—C bonds) create a range of interactions between substituents, both inter-strand, across the minor groove, and intra-strand. At one location, atoms of substituents from two residues are in van der Waals contact across the minor groove. Similarly, a close contact occurs between atoms of substituents from two adjacent intra-strand residues.

Previously determined crystal structures of A-DNA duplexes were for those that incorporated isolated 2'-O-methyl T residues. In the crystal structure noted above for the 2'-O-MOE substituents, a conserved hydration pattern has been observed for the 2'-O-MOE residues. A single water molecule is seen located between O2', O3' and the methoxy oxygen atom of the substituent, forming contacts to all three of between 2.9 and 3.4 Å. In addition, oxygen atoms of substituents are involved in several other hydrogen bonding contacts. For example, the methoxy oxygen atom of a particular 2'-O-substituent forms a hydrogen bond to N3 of an adenosine from the opposite strand via a bridging water molecule.

In several cases a water molecule is trapped between the oxygen atoms O2', O3' and OC' of modified nucleosides. 2'-O-MOE substituents with trans conformation around the C—C bond of the ethylene glycol linker are associated with close contacts between OC' and N2 of a guanosine from the opposite strand, and, water-mediated, between OC' and N3(G). When combined with the available thermodynamic data for duplexes containing 2'-O-MOE modified strands, this crystal structure allows for further detailed structure-stability analysis of other modifications.

In extending the crystallographic structure studies, molecular modeling experiments were performed to study further enhanced binding affinity of oligonucleotides having 2'-O-modifications of the invention. The computer simulations were conducted on compounds of SEQ ID NO: 1, above, having 2'-O-modifications of the invention located at each of the nucleoside of the oligonucleotide. The simulations were performed with the oligonucleotide in aqueous solution using the AMBER force field method (Cornell et al., *J. Am. Chem. Soc.,* 1995, 117, 5179-5197)(modeling software package from UCSF, San Francisco, Calif.). The calculations were performed on an Indigo2 SGI machine (Silicon Graphics, Mountain View, Calif.).

Further 2'-O-modifications that will have a 3'-endo sugar influence include those having a ring structure that incorporates a two atom portion corresponding to the A' and B' atoms of Structure II. The ring structure is attached at the 2' position of a sugar moiety of one or more nucleosides that are incorporated into an oligonucleotide. The 2'-oxygen of the nucleoside links to a carbon atom corresponding to the A' atom of Structure II. These ring structures can be aliphatic, unsaturated aliphatic, aromatic or heterocyclic. A further atom of the ring (corresponding to the B' atom of Structure II), bears a further oxygen atom, or a sulfur or nitrogen atom. This oxygen, sulfur or nitrogen atom is bonded to one or more hydrogen atoms, alkyl moieties, or haloalkyl moieties, or is part of a further chemical moiety such as a ureido, carbamate, amide or amidine moiety. The remainder of the ring structure restricts rotation about the bond joining these two ring atoms.

This assists in positioning the "further oxygen, sulfur or nitrogen atom" (part of the R position as described above) such that the further atom can be located in close proximity to the 3'-oxygen atom (O3') of the nucleoside.

Another 2'-sugar substituent group that gives a 3'-endo sugar conformational geometry is the 2'-OMe group. 2'-Substitution of guanosine, cytidine, and uridine dinucleoside phosphates with the 2'-OMe group showed enhanced stacking effects with respect to the corresponding native (2'-OH) species leading to the conclusion that the sugar is adopting a C3'-endo conformation. In this case, it is believed that the hydrophobic attractive forces of the methyl group tend to overcome the destabilizing effects of its steric bulk.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Freier and Altmann, Nucleic Acids Research, (1997) 25:4429-4443, have previously published a study on the influence of structural modifications of oligonucleotides on the stability of their duplexes with target RNA. In this study, the authors reviewed a series of oligonucleotides containing more than 200 different modifications that had been synthesized and assessed for their hybridization affinity and $T_m$. Sugar modifications studied included substitutions on the 2'-position of the sugar, 3'-substitution, replacement of the 4'-oxygen, the use of bicyclic sugars, and four member ring replacements. Several nucleobase modifications were also studied including substitutions at the 5, or 6 position of thymine, modifications of pyrimidine heterocycle and modifications of the purine heterocycle. Modified internucleoside linkages were also studied including neutral, phosphorus and non-phosphorus containing internucleoside linkages.

Increasing the percentage of C3'-endo sugars in a modified oligonucleotide targeted to an RNA target strand should preorganize this strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This preorganizes an oligonucleotide that incorporates such modifications to have an A-form conformational geometry. This A-form conformation results in increased binding affinity of the oligonucleotide to a target RNA strand.

Molecular modeling experiments were performed to study further enhanced binding affinity of oligonucleotides having 2'-O-modifications. Computer simulations were conducted on compounds having SEQ ID NO: 1, r(CGC GAA UUC GCG), having 2'-O-modifications of the invention located at each of the nucleoside of the oligonucleotide. The simulations were performed with the oligonucleotide in aqueous solution using the AMBER force field method (Cornell et al., *J. Am. Chem. Soc.,* 1995, 117, 5179-5197)(modeling software package from UCSF, San Francisco, Calif.). The calculations were performed on an Indigo2 SGI machine (Silicon Graphics, Mountain View, Calif.).

In addition, for 2'-substituents containing an ethylene glycol motif, a gauche interaction between the oxygen atoms around the O—C—C—O torsion of the side chain may have a stabilizing effect on the duplex (Freier and Altmann, *Nucleic Acids Research,* 1997, 25, 4429-4443). Such gauche interactions have been observed experimentally for a number of years (Wolfe et al., *Acc. Chem. Res.,* 1972, 5, 102; Abe et al., *J. Am. Chem. Soc.,* 1976, 98, 468). This gauche effect may result in a configuration of the side chain that is favorable for duplex formation. The exact nature of this stabilizing configuration has not yet been explained. While not wishing to be bound by theory, it may be that holding the O—C—C—O torsion in a single gauche configuration, rather than a more random distribution seen in an alkyl side chain, provides an entropic advantage for duplex formation.

Representative 2'-substituent groups amenable to the present invention that give A-form conformational properties (3'-endo) to the resultant duplexes include 2'-O-alkyl, 2'-O-substituted alkyl and 2'-fluoro substituent groups. Substituent groups can be various alkyl and aryl ethers and thioethers, amines and monoalkyl and dialkyl substituted amines. It is further intended that multiple modifications can be made to one or more nucleosides and or internucleoside linkages within an oligonucleotide of the invention to enhance activity of the oligonucleotide. Tables 2 through 8 list nucleoside and internucleotide linkage modifications/replacements that have been shown to give a positive $\Delta T_m$ per modification when the modification/replacement was made to a DNA strand that was hybridized to an RNA complement.

TABLE 2

Modified DNA strand having 2'-substituent groups that gave an overall increase in $T_m$ against an RNA complement:

| | Positive $\Delta T_m$/mod |
|---|---|
| 2'-substituents | 2'-OH |
| | 2'-O—$C_1$—$C_4$ alkyl |
| | 2'-O—$(CH_2)_2CH_3$ |
| | 2'-O—$CH_2CH{=}CH_2$ |
| | 2'-F |
| | 2'-O—$(CH_2)_2$—O—$CH_3$ |
| | 2'-[O—$(CH_2)_2]_2$—O—$CH_3$ |
| | 2'-[O—$(CH_2)_2]_3$—O—$CH_3$ |
| | 2'-[O—$(CH_2)_2]_4$—O—$CH_3$ |
| | 2'-[O—$(CH_2)_2]_3$—O—$(CH_2)_8CH_3$ |
| | 2'-O—$(CH_2)_2CF_3$ |
| | 2'-O—$(CH_2)_2OH$ |
| | 2'-O—$(CH_2)_2F$ |
| | 2'-O—$CH_2CH(CH_3)F$ |
| | 2'-O—$CH_2CH(CH_2OH)OH$ |
| | 2'-O—$CH_2CH(CH_2OCH_3)OCH_3$ |
| | 2'-O—$CH_2CH(CH_3)OCH_3$ |
| | 2'-O—$CH_2$—$C_{14}H_7O_2$(—$C_{14}H_7O_2$ = Anthraquinone) |
| | 2'-O—$(CH_2)_3$—$NH_2$* |
| | 2'-O—$(CH_2)_4$—$NH_2$* |

*These modifications can increase the $T_m$ of oligonucleotides but can also decrease the $T_m$ depending on positioning and number (motif dependant).

TABLE 3

Modified DNA strand having modified sugar ring (see structure) that give an overall increase in $T_m$ against an RNA complement:

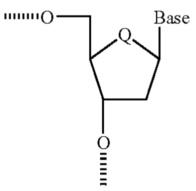

| | Positive $\Delta T_m$/mod |
|---|---|
| Q | —S—<br>—$CH_2$— |

Note: In general ring oxygen substitution with sulfur or methylene had only a minor effect on $T_m$ for the specific motiffs studied. Substitution at the 2'-position with groups shown to stabilize the duplex were destabilizing when $CH_2$ replaced the ring O. This is thought to be due to the necessary gauche interaction between the ring O with particular 2'-substituents (for example —O—$CH_3$ and —(O—$CH_2CH_2$)$_3$—O—$CH_3$.

TABLE 4

Modified DNA strand having modified sugar ring that give an overall increase in $T_m$ against an RNA complement:

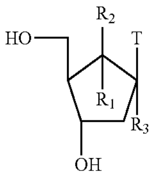

| | Positive $\Delta T_m$/mod |
|---|---|
| —C(H)$R_1$ effects<br>($R_2$, $R_3$ both = H) | OH<br>$CH_3$*<br>$CH_2OH$*<br>$OCH_3$* |

*These modifications can increase the $T_m$ of oligonucleotides but can also decrease the $T_m$ depending on positioning and number (motif dependant).

TABLE 5

Modified DNA strand having bicyclic substitute sugar modifications that give an overall increase in $T_m$ against an RNA complement:

| Formula | Positive $\Delta T_m$/mod |
|---|---|
| I | + |
| II | + |

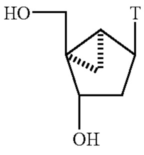

I

TABLE 5-continued

Modified DNA strand having bicyclic substitute sugar modifications that give an overall increase in $T_m$ against an RNA complement:

| Formula | Positive $\Delta T_m$/mod |
|---|---|
| 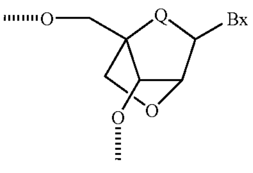<br>II | |

TABLE 6

Modified DNA strand having modified heterocyclic base moieties that give an overall increase in $T_m$ against an RNA complement:

| Modification/Formula | Positive $\Delta T_m$/mod |
|---|---|
| Heterocyclic base modifications | 2-thioT<br>2'-O-methylpseudoU<br>7-halo-7-deaza purines<br>7-propyne-7-deaza purines<br>2-aminoA(2,6-diaminopurine) |
| 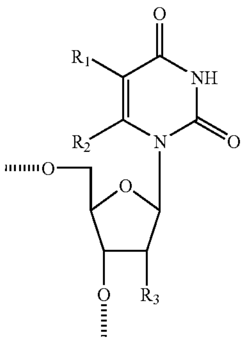<br>($R_2$, $R_3$ = H), $R_1$ = | Br<br>C≡C—$CH_3$<br>$(CH_2)_3NH_2$<br>$CH_3$ |
| Motiffs-disubstitution | |
| $R_1$ = C≡C—$CH_3$,<br>$R_2$ = H, $R_3$ = | F |
| $R_1$ = C≡C—$CH_3$,<br>$R_2$ = H, | $R_3$ = O—$(CH_2)_2$—O—$CH_3$ |
| $R_1$ =O—$CH_3$, $R_2$ = H, | $R_3$ = O—$(CH_2)_2$—O—$CH_3$* |

*This modification can increase the $T_m$ of oligonucleotides but can also decrease the $T_m$ depending on positioning and number (motif dependant).

Substitution at $R_1$ can be stabilizing, substitution at $R_2$ is generally greatly destabilizing (unable to form anti conformation), motiffs with stabilizing 5 and 2'-substituent groups are generally additive e.g. increase stability.

Substitution of the O4 and O2 positions of 2'-O-methyl uridine was greatly duplex destabilizing as these modifications remove hydrogen binding sites that would be an expected result. 6-Aza T also showed extreme destabilization as this substitution reduces the $pK_a$ and shifts the nucleoside toward the enol tautomer resulting in reduced hydrogen bonding.

TABLE 7

| DNA strand having at least one modified phosphorus containing internucleoside linkage and the effect on the $T_m$ against an RNA complement: | |
|---|---|
| $\Delta T_m$/mod+ | $\Delta T_m$/mod− |
| | phosphorothioate[1]<br>phosphoramidate[1]<br>methyl phosphonates[1]<br>([1] one of the non-bridging oxygen atoms replaced with S, N(H)R or —$CH_3$) |
| phosphoramidate<br>(the 3'-bridging atom replaced with an N(H)R group, stabilization effect enhanced when also have 2'-F) | |

TABLE 8

| DNA strand having at least one non-phosphorus containing internucleoside linkage and the effect on the $T_m$ against an RNA complement: Positive $\Delta T_m$/mod |
|---|
| —$CH_2C(=O)NHCH_2$—* |
| —$CH_2C(=O)N(CH_3)CH_2$—* |
| —$CH_2C(=O)N(CH_2CH_2CH_3)CH_2$—* |
| —$CH_2C(=O)N(H)CH_2$— (motif with 5'-propyne on T's) |
| —$CH_2N(H)C(=O)CH_2$—* |
| —$CH_2N(CH_3)OCH_2$—* |
| —$CH_2N(CH_3)N(CH_3)CH_2$—* |

*This modification can increase the $T_m$ of oligonucleotides but can also decrease the $T_m$ depending on positioning and number (motif dependant).

Notes: In general carbon chain internucleotide linkages were destabilizing to duplex formation. This destabilization was not as severe when double and triple bonds were utilized. The use of glycol and flexible ether linkages were also destabilizing.

Suitable ring structures of the invention for inclusion as a 2'-O modification include cyclohexyl, cyclopentyl and phenyl rings as well as heterocyclic rings having spatial footprints similar to cyclohexyl, cyclopentyl and phenyl rings. Particularly suitable 2'-O-substituent groups of the invention are listed below including an abbreviation for each:

2'-O-(trans 2-methoxy cyclohexyl)-2'-O-(TMCHL)

2'-O-(trans 2-methoxy cyclopentyl)-2'-O-(TMCPL)

2'-O-(trans 2-ureido cyclohexyl)-2'-O-(TUCHL)

2'-O-(trans 2-methoxyphenyl)-2'-O-(2 MP)

Structural details for duplexes incorporating such 2-O-substituents were analyzed using the described AMBER force field program on the Indigo2 SGI machine. The simulated structure maintained a stable A-form geometry throughout the duration of the simulation. The presence of the 2' substitutions locked the sugars in the C3'-endo conformation.

The simulation for the TMCHL modification revealed that the 2'-O-(TMCHL) side chains have a direct interaction with water molecules solvating the duplex. The oxygen atoms in the 2'-O-(TMCHL) side chain are capable of forming a water-mediated interaction with the 3' oxygen of the phosphate backbone. The presence of the two oxygen atoms in the 2'-O-(TMCHL) side chain gives rise to favorable gauche interactions. The barrier for rotation around the O—C—C—O torsion is made even larger by this novel modification. The preferential preorganization in an A-type geometry increases the binding affinity of the 2'-O-(TMCHL) to the target RNA. The locked side chain conformation in the 2'-O-(TMCHL) group created a more favorable pocket for binding water molecules. The presence of these water molecules played a key role in holding the side chains in the preferable gauche conformation. While not wishing to be bound by theory, the bulk of the substituent, the diequatorial orientation of the substituents in the cyclohexane ring, the water of hydration and the potential for trapping of metal ions in the conformation generated will additionally contribute to improved binding affinity and nuclease resistance of oligonucleotides incorporating nucleosides having this 2'-O-modification.

As described for the TMCHL modification above, identical computer simulations of the 2'-O-(TMCPL), the 2'-O-(2MP) and 2'-O-(TUCHL) modified oligonucleotides in aqueous solution also illustrate that stable A-form geometry will be maintained throughout the duration of the simulation. The presence of the 2' substitution will lock the sugars in the C3'-endo conformation and the side chains will have direct interaction with water molecules solvating the duplex. The oxygen atoms in the respective side chains are capable of forming a water-mediated interaction with the 3' oxygen of the phosphate backbone. The presence of the two oxygen atoms in the respective side chains give rise to the favorable gauche interactions. The barrier for rotation around the respective O—C—C—O torsions will be made even larger by respective modification. The preferential preorganization in A-type geometry will increase the binding affinity of the respective 2'-O-modified oligonucleotides to the target RNA. The locked side chain conformation in the respective modifications will create a more favorable pocket for binding water molecules. The presence of these water molecules plays a key role in holding the side chains in the preferable gauche conformation. The bulk of the substituent, the diequatorial orientation of the substituents in their respective rings, the water of hydration and the potential trapping of metal ions in the conformation generated will all contribute to improved binding affinity and nuclease resistance of oligonucleotides incorporating nucleosides having these respective 2'-O-modification.

Ribose conformations in C2'-modified nucleosides containing S-methyl groups were examined. To understand the influence of 2'-O-methyl and 2'-S-methyl groups on the conformation of nucleosides, we evaluated the relative energies of the 2'-O- and 2'-S-methylguanosine, along with normal deoxyguanosine and riboguanosine, starting from both C2'-endo and C3'-endo conformations using ab initio quantum mechanical calculations. All the structures were fully optimized at HF/6-31G* level and single point energies with electron-correlation were obtained at the MP2/6-31G*//HF/6-31G* level. As shown in Table 9, the C2'-endo conformation of deoxyguanosine is estimated to be 0.6 kcal/mol more stable than the C3'-endo conformation in the gas-phase. The conformational preference of the C2'-endo over the C3'-endo conformation appears to be less dependent upon electron correlation as revealed by the MP2/6-31G*//HF/6-31G* values which also predict the same difference in energy. The opposite trend is noted for riboguanosine. At the HF/6-31G* and MP2/6-31G*//HF/6-31G* levels, the C3'-endo form of riboguanosine is shown to be about 0.65 and 1.41 kcal/mol more stable than the C2'endo form, respectively.

TABLE 9

| Relative energies* of the C3'-endo and C2'-endo conformations of representative nucleosides | | | | |
|---|---|---|---|---|
| | HF/6-31G | MP2/6-31-G | Continuum Model | Amber |
| dG | 0.60 | 0.56 | 0.88 | 0.65 |
| rG | −0.65 | −1.41 | −0.28 | −2.09 |
| 2'-O-MeG | −0.89 | −1.79 | −0.36 | −0.86 |
| 2'-S-MeG | 2.55 | 1.41 | 3.16 | 2.43 |

*energies are in kcal/mol relative to the C2'-endo conformation

Table 9 also includes the relative energies of 2'-O-methylguanosine and 2'-S-methylguanosine in C2'-endo and C3'-endo conformation. This data indicates the electronic nature of C2'-substitution has a significant impact on the relative stability of these conformations. Substitution of the 2'-O-methyl group increases the preference for the C3'-endo conformation (when compared to riboguanosine) by about 0.4 kcal/mol at both the HF/6-31G* and MP2/6-31G*//HF/6-31G* levels. In contrast, the 2'-S-methyl group reverses the trend. The C2'-endo conformation is favored by about 2.6 kcal/mol at the HF/6-31G* level, while the same difference is reduced to 1.41 kcal/mol at the MP2/6-31G*//HF/6-31G* level. For comparison, and also to evaluate the accuracy of the molecular mechanical force-field parameters used for the 2'-O-methyl and 2'-S-methyl substituted nucleosides, we have calculated the gas phase energies of the nucleosides. The results reported in Table 9 indicate that the calculated relative energies of these nucleosides compare qualitatively well with the ab initio calculations.

Additional calculations were also performed to gauge the effect of solvation on the relative stability of nucleoside conformations. The estimated solvation effect using HF/6-31G* geometries confirms that the relative energetic preference of the four nucleosides in the gas-phase is maintained in the aqueous phase as well (Table 9). Solvation effects were also examined using molecular dynamics simulations of the nucleosides in explicit water. From these trajectories, one can observe the predominance of C2'-endo conformation for deoxyriboguanosine and 2'-S-methylriboguanosine while riboguanosine and 2'-O-methylriboguanosine prefer the C3'-endo conformation. These results are in much accord with the available NMR results on 2'-S-methylribonucleosides. NMR studies of sugar puckering equilibrium using vicinal spin-coupling constants have indicated that the conformation of the sugar ring in 2'-S-methylpyrimidine nucleosides show an average of >75% S-character, whereas the corresponding purine analogs exhibit an average of >90% S-pucker (Fraser, A., Wheeler, P., Cook, P. D. and Sanghvi, Y. S., *J. Heterocycl. Chem.,* 1993, 30, 1277-1287). It was observed that the 2'-S-methyl substitution in deoxynucleoside confers more conformational rigidity to the sugar conformation when compared with deoxyribonucleosides.

Structural features of DNA:RNA, OMe-DNA:RNA and SMe-DNA:RNA hybrids were also observed. The average RMS deviation of the DNA:RNA structure from the starting hybrid coordinates indicate the structure is stabilized over the length of the simulation with an approximate average RMS deviation of 1.0 Å. This deviation is due, in part, to inherent differences in averaged structures (i.e. the starting conformation) and structures at thermal equilibrium. The changes in sugar pucker conformation for three of the central base pairs of this hybrid are in good agreement with the observations made in previous NMR studies. The sugars in the RNA strand maintain very stable geometries in the C3'-endo conformation with ring pucker values near 0°. In contrast, the sugars of the DNA strand show significant variability.

The average RMS deviation of the OMe-DNA:RNA is approximately 1.2 Å from the starting A-form conformation; while the SMe-DNA:RNA shows a slightly higher deviation (approximately 1.8 Å) from the starting hybrid conformation. The SMe-DNA strand also shows a greater variance in RMS deviation, suggesting the S-methyl group may induce some structural fluctuations. The sugar puckers of the RNA complements maintain C3'-endo puckering throughout the simulation. As expected from the nucleoside calculations, however, significant differences are noted in the puckering of the OMe-DNA and SMe-DNA strands, with the former adopting C3'-endo, and the latter, C1'-exo/C2'-endo conformations.

An analysis of the helicoidal parameters for all three hybrid structures has also been performed to further characterize the duplex conformation. Three of the more important axis-base-pair parameters that distinguish the different forms of the duplexes, X-displacement, propeller twist, and inclination, are reported in Table 10. Usually, an X-displacement near zero represents a B-form duplex; while a negative displacement, which is a direct measure of deviation of the helix from the helical axis, makes the structure appear more A-like in conformation. In A-form duplexes, these values typically vary from −4 Å to −5 Å. In comparing these values for all three hybrids, the SMe_DNA:RNA hybrid shows the most deviation from the A-form value, the OMe_DNA:RNA shows the least, and the DNA:RNA is intermediate. A similar trend is also evident when comparing the inclination and propeller twist values with ideal A-form parameters. These results are further supported by an analysis of the backbone and glycosidic torsion angles of the hybrid structures. Glycosidic angles (X) of A-form geometries, for example, are typically near −159° while B form values are near −102°. These angles are found to be −162°, −133°, and −108° for the OMe-DNA, DNA, and SMe-DNA strands, respectively. All RNA complements adopt an X angle close to −160°. In addition, "crankshaft" transitions were also noted in the backbone torsions of the central UpU steps of the RNA strand in the SMe-DNA:RNA and DNA;RNA hybrids. Such transitions suggest some local conformational changes may occur to relieve a less favorable global conformation. Taken overall, the results indicate the amount of A-character decreases as OMe-DNA:RNA>DNA:RNA>SMe-DNA:RNA, with the latter two adopting more intermediate conformations when compared to A- and B-form geometries.

TABLE 10

Average helical parameters derived from the last 500 ps of simulation time (canonical A-and B-form values are given for comparison)

| Helicoidal Parameter | B-DNA (x-ray) | B-DNA (fibre) | A-DNA (fibre) | DNA:RNA | OMe_DNA:RNA | SMe_DNA:RNA |
|---|---|---|---|---|---|---|
| X-disp | 1.2 | 0.0 | −5.3 | −4.5 | −5.4 | −3.5 |
| Inclination | −2.3 | 1.5 | 20.7 | 11.6 | 15.1 | 0.7 |
| Propeller | −16.4 | −13.3 | −7.5 | −12.7 | −15.8 | −10.3 |

Stability of C2'-modified DNA:RNA hybrids was determined. Although the overall stability of the DNA:RNA hybrids depends on several factors including sequence-dependencies and the purine content in the DNA or RNA strands DNA:RNA hybrids are usually less stable than RNA:RNA duplexes and, in some cases, even less stable than DNA:DNA duplexes. Available experimental data attributes the relatively lowered stability of DNA:RNA hybrids largely to its intermediate conformational nature between DNA:DNA (B-family) and RNA:RNA (A-family) duplexes. The overall thermodynamic stability of nucleic acid duplexes may originate from several factors including the conformation of backbone, base-pairing and stacking interactions. While it is difficult to ascertain the individual thermodynamic contributions to the overall stabilization of the duplex, it is reasonable to argue that the major factors that promote increased stability of hybrid duplexes are better stacking interactions (electrostatic π-π interactions) and more favorable groove dimensions for hydration. The C2'-S-methyl substitution has been shown to destabilize the hybrid duplex. The notable differences in the rise values among the three hybrids may offer some explanation. While the 2'-S-methyl group has a strong influence on decreasing the base-stacking through high rise values (~3.2 Å), the 2'-O-methyl group makes the overall structure more compact with a rise value that is equal to that of A-form duplexes (~2.6 Å). Despite its overall A-like structural features, the SMe_DNA:RNA hybrid structure possesses an average rise value of 3.2 Å which is quite close to that of B-family duplexes. In fact, some local base-steps (CG steps) may be observed to have unusually high rise values (as high as 4.5 Å). Thus, the greater destabilization of 2'-S-methyl substituted DNA:RNA hybrids may be partly attributed to poor stacking interactions.

It has been postulated that RNase H binds to the minor groove of RNA:DNA hybrid complexes, requiring an intermediate minor groove width between ideal A- and B-form geometries to optimize interactions between the sugar phosphate backbone atoms and RNase H. A close inspection of the averaged structures for the hybrid duplexes using computer simulations reveals significant variation in the minor groove width dimensions as shown in Table 11. Whereas the O-methyl substitution leads to a slight expansion of the minor groove width when compared to the standard DNA:RNA complex, the S-methyl substitution leads to a general contraction (approximately 0.9 Å). These changes are most likely due to the preferred sugar puckering noted for the antisense strands which induce either A- or B-like single strand conformations. In addition to minor groove variations, the results also point to potential differences in the steric makeup of the minor groove. The O-methyl group points into the minor groove while the S-methyl is directed away towards the major groove. Essentially, the S-methyl group has flipped through the bases into the major groove as a consequence of C2'-endo puckering.

TABLE 11

Minor groove widths averaged over the last 500 ps of simulation time

| Phosphate Distance | DNA:RNA | OMe_DNA:RNA | SMe_DNA:RNA | DNA:RNA (B-form) | RNA:RNA (A-form) |
|---|---|---|---|---|---|
| P5-P20 | 15.27 | 16.82 | 13.73 | 14.19 | 17.32 |
| P6-P19 | 15.52 | 16.79 | 15.73 | 12.66 | 17.12 |
| P7-P18 | 15.19 | 16.40 | 14.08 | 11.10 | 16.60 |
| P8-P17 | 15.07 | 16.12 | 14.00 | 10.98 | 16.14 |
| P9-P16 | 15.29 | 16.25 | 14.98 | 11.65 | 16.93 |
| P10-P15 | 15.37 | 16.57 | 13.92 | 14.05 | 17.69 |

In addition to the modifications described above, the nucleotides of the chimeric oligomeric compounds of the invention can have a variety of other modification so long as these other modifications do not significantly detract from the properties described above. Thus, for nucleotides that are incorporated into oligonucleotides of the invention, these nucleotides can have sugar portions that correspond to naturally-occurring sugars or modified sugars. Representative modified sugars include carbocyclic or acyclic sugars, sugars having substituent groups at their 2' position, sugars having substituent groups at their 3' position, and sugars having substituents in place of one or more hydrogen atoms of the sugar. Other altered base moieties and altered sugar moieties are disclosed in U.S. Pat. No. 3,687,808 and PCT application PCT/US89/02323.

2'-Endo Regions

A number of different nucleosides can be used independently or exclusively to create one or more of the C2'-endo regions to prepare chimeric oligomeric compounds of the present invention. For the purpose of the present invention the terms 2'-endo and C2'-endo are meant to include O4'-endo and 2'-deoxy nucleosides. 2'-Deoxy nucleic acids prefer both C2'-endo sugar pucker and O4'-endo sugar, i.e., also known as Southern pucker, which is thought to impart a less stable B-form geometry (Sanger, W. (1984) Principles of Nucleic Acid Structure, Springer-Verlag, New York, N.Y. and Berger, et. al., Nucleic Acids Research, 1998, 26, 2473-2480). The 2'-deoxyribonucleoside is one suitable nucleoside for the 2'-endo regions but all manner of nucleosides known in the art that have a preference for 2'-endo sugar conformational geometry are amenable to the present invention. Such nucleosides include without limitation 2'-modified ribonucleosides such as for example: 2'-$SCH_3$, 2'-$NH_2$, 2'-NH($C_1$-$C_2$ alkyl), 2'-N($C_1$-$C_2$ alkyl)$_2$, 2'-$CF_3$, 2'=$CH_2$, 2'=CHF, 2'=$CF_2$, 2'-$CH_3$, 2'-$C_2H_5$, 2'-CH=$CH_2$ or 2'-C≡CH. Also amenable to the present invention are modified 2'-arabinonucleosides including without limitation: 2'-CN, 2'-F, 2'-Cl, 2'-Br, 2'-$N_3$ (azido), 2'-OH, 2'-O—$CH_3$ or 2'-dehydro-2'-$CH_3$.

Suitable sugar modifications for the 2'-endo regions of the present invention include without limitation 2'-deoxy-2'-S-methyl, 2'-deoxy-2'-methyl, 2'-deoxy-2'-amino, 2'-deoxy-2'-mono or dialkyl substituted amino, 2'-deoxy-2'-fluoromethyl, 2'-deoxy-2'-difluoromethyl, 2'-deoxy-2'-trifluoromethyl, 2'-deoxy-2'-methylene, 2'-deoxy-2'-fluoromethylene, 2'-deoxy-2'-difluoromethylene, 2'-deoxy-2'-ethyl, 2'-deoxy-2'-ethylene and 2'-deoxy-2'-acetylene. These nucleotides can alternately be described as 2'-$SCH_3$ ribonucleotide, 2'-$CH_3$ ribonucleotide, 2'-$NH_2$ ribonucleotide 2'-NH($C_1$-$C_2$ alkyl) ribonucleotide, 2'-N($C_1$-$C_2$ alkyl)$_2$ ribonucleotide, 2'-$CH_2F$ ribonucleotide, 2'-$CHF_2$ ribonucleotide, 2'-$CF_3$ ribonucleotide, 2'=$CH_2$ ribonucleotide, 2'=CHF ribonucleotide, 2'=$CF_2$ ribonucleotide, 2'-$C_2H_5$ ribonucleotide, 2'-CH=$CH_2$ ribonucleotide, 2'-C̃CH ribonucleotide. A further useful sugar modification is one having a ring located on the ribose ring in a cage-like structure including 3',O,4'-C-methyleneribonucleotides. Such cage-like structures will physically fix the ribose ring in the desired conformation.

Additionally, suitable sugar modifications for the 2'-endo regions of the present invention include without limitation are arabino nucleotides having 2'-deoxy-2'-cyano, 2'-deoxy-2'-fluoro, 2'-deoxy-2'-chloro, 2'-deoxy-2'-bromo, 2'-deoxy-2'-azido, 2'-methoxy and the unmodified arabino nucleotide (that includes a 2'-OH projecting upwards towards the base of the nucleotide). These arabino nucleotides can alternately be described as 2'-CN arabino nucleotide, 2'-F arabino nucleotide, 2'-Cl arabino nucleotide, 2'-Br arabino nucleotide, 2'-$N_3$ arabino nucleotide, 2'-O—$CH_3$ arabino nucleotide and arabino nucleotide.

Such nucleotides are linked together via phosphorothioate, phosphorodithioate, boranophosphate or phosphodiester linkages. Particularly suitable is the phosphorothioate linkage.

Internucleoside Linkages

Specific examples of chimeric oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Modified internucleoside linkages containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In other embodiments of the invention, chimeric oligomeric compounds include one or more phosphorothioate and/or heteroatom internucleoside linkages, in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester internucleotide linkage is represented as —O—P(=O)(OH)—O—$CH_2$—]. The MMI type internucleoside linkages are disclosed in the above referenced U.S. Pat. No. 5,489,677. Amide internucleoside linkages are disclosed in the above referenced U.S. Pat. No. 5,602,240.

Modified internucleoside linkages that do not include a phosphorus atom therein include those formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Conjugate Groups

An additional substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.

The chimeric oligomeric compounds of the invention may also be conjugated to active drug substances, for example, aspirin, warfarin, phenylbutazone, ibuprofen, naproxen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, which is incorporated by reference herein.

Particularly suitable 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602.

Oligomeric Compounds

In the context of the present invention, the term "oligomeric compound" refers to a polymeric structure capable of hybridizing a region of a nucleic acid molecule. This term includes oligonucleotides, oligonucleosides, oligonucleotide analogs, oligonucleotide mimetics and combinations of these. Oligomeric compounds routinely prepared linearly but can be joined or otherwise prepared to be circular and may also include branching. Oligomeric compounds can hybridized to form double stranded compounds which can be blunt ended or may include overhangs. In general an oligomeric compound comprises a backbone of linked momeric subunits where each linked momeric subunit is directly or indirectly attached to a heterocyclic base moiety. The linkages joining the monomeric subunits, the sugar moieties or surrogates and the heterocyclic base moieties can be independently modified giving rise to a plurality of motifs for the resulting oligomeric compounds including hemimers, gapmers and chimeras.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally suitable. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions which function in a similar manner to oligonulceotides. Such non-naturally occurring oligonucleotides are often desired, the naturally occurring forms because of desirable properties such as, for example, enhanced cellular uptake, enhanced affinity for nucleic acid target and increased stability in the presence of nucleases.

In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfon, acetyl, formacetyl, thioformacetyl, methylene formacetyl, thioformacetyl, alkenyl, sulfamate; methyleneimino, methylenehydrazino, sulfonate, sulfonamide, amide and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,561; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Further included in the present invention are oligomeric compounds such as antisense oligomeric compounds, antisense oligonucleotides, alternate splicers and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops or mismatches. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense oligomeric compounds which are "DNA-like" or have "DNA-like" regions elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of antisense acting chimeric oligomeric compound is a single-stranded chimeric oligonucleotide, in many species the introduction of double-stranded structures, such as double-stranded RNA (dsRNA) molecules, has been shown to induce potent and specific antisense-mediated reduction of the function of a gene or its associated gene products. This phenomenon, which has been designated RNA interference (RNAi), occurs in both plants and animals and is believed to have an evolutionary connection to viral defense and transposon silencing. The term RNAi has been generalized to mean antisense-mediated gene silencing involving the introduction of dsRNA leading to the sequence-specific reduction of endogenous targeted mRNA levels (Fire et al., *Nature,* 1998, 391, 806-811). It has been shown that it is, in fact, the single-stranded RNA oligomers of antisense polarity of the dsRNAs which are the potent inducers of RNAi (Tijsterman et al., *Science,* 2002, 295, 694-697). The primary interference effects of dsRNAs are posttranscriptional (Montgomery et al., *Proc. Natl. Acad. Sci. USA,* 1998, 95, 15502-15507).

In addition to the modifications described above, the nucleosides of the oligomeric compounds of the invention can have a variety of other modifications. These modifications either alone or in combination with other nucleosides may enhance one or more of the desired properties described above. Thus, for nucleotides that are incorporated into oligonucleotides of the invention, these nucleotides can have sugar portions that correspond to naturally-occurring sugars or modified sugars. Representative modified sugars include carbocyclic or acyclic sugars, sugars having substituent groups at one or more of their 2', 3' or 4' positions and sugars having substituents in place of one or more hydrogen atoms of the sugar. Additional nucleosides amenable to the present invention having altered base moieties and or altered sugar moieties are disclosed in U.S. Pat. No. 3,687,808 and PCT application PCT/US89/02323.

The oligomeric compounds in accordance with this invention comprise from about 5 to about 80 nucleobases (i.e. from about 5 to about 80 linked nucleosides). One of ordinary skill in the art will appreciate that the invention embodies oligomeric compounds of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length, or any sub-range therewithin.

In a further embodiment, the oligomeric compounds of the invention are 5 to 50 nucleobases in length. One of ordinary skill in the art will appreciate that the invention embodies oligomeric compounds of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleobases in length, or any sub-range therewithin.

In another embodiment, the oligomeric compounds of the invention are 12 to 50 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29 or 30 nucleobases in length, or any sub-range therewithin.

In another embodiment, the oligomeric compounds of the invention are 12 to 30 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length, or any sub-range therewithin.

In a further embodiment, the oligomeric compounds of the invention are 13 to 40 nucleobases in length. One having ordinary skill in the art will appreciate that this embodies oligomeric compounds of 13, 14, 15, 16, 17, 18, 19, 20, 21, 22, 23, 24, 25, 26, 27, 28, 29, 30, 31, 32, 33, 34, 35, 36, 37, 38, 39 or 40 nucleobases in length, or any sub-range therewithin.

In another embodiment, the oligomeric compounds of the invention are 15 to 30 nucleobases in length. One having ordinary skill in the art will appreciate that this embodies oligomeric compounds of 15, 16, 17, 18, 19, 20, 21, 22, 23, 24, 25, 26, 27, 28, 29, or 30 nucleobases in length, or any sub-range therewithin.

In another embodiment, the oligomeric compounds of the invention are 15 to 25 nucleobases in length. One having ordinary skill in the art will appreciate that this embodies oligomeric compounds of 15, 16, 17, 18, 19, 20, 21, 22, 23, 24 or 25 nucleobases in length, or any sub-range therewithin.

In a further embodiment, the oligomeric compounds of the invention are 21 to 25 nucleobases in length. One having ordinary skill in the art will appreciate that this embodies oligomeric compounds of 21, 22, 23, 24 or 25 nucleobases in length, or any sub-range therewithin.

Particularly suitable oligomeric compounds are oligonucleotides comprising from about 12 to about 50 nucleobases, from about 13 to 40 nucleobases, or from about 15 to about 30 nucleobases.

Oligomer Synthesis

Oligomerization of modified and unmodified nucleosides is performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. In addition specific protocols for the synthesis of oligomeric compounds of the invention are illustrated in the examples below.

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The present invention is also useful for the preparation of oligomeric compounds incorporating at least one 2'-O-protected nucleoside. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound. All 2'-O-protecting groups amenable to the synthesis of oligomeric compounds are included in the present invention. In general a protected nucleoside is attached to a solid support by for example a succinate linker. Then the oligonucleotide is elongated by repeated cycles of deprotecting the 5'-terminal hydroxyl group, coupling of a further nucleoside unit, capping and oxidation (alternatively sulfurization). In a more frequently used method of synthesis the completed oligonucleotide is cleaved from the solid support with the removal of phosphate protecting groups and exocyclic amino protecting groups by treatment with an ammonia solution. Then a further deprotection step is normally required for the more specialized protecting groups used for the protection of 2'-hydroxyl groups which will give the fully deprotected oligonucleotide.

A large number of 2'-O-protecting groups have been used for the synthesis of oligoribonucleotides but over the years more effective groups have been discovered. The key to an effective 2'-O-protecting group is that it is capable of selectively being introduced at the 2'-O-position and that it can be removed easily after synthesis without the formation of unwanted side products. The protecting group also needs to be inert to the normal deprotecting, coupling, and capping steps required for oligoribonucleotide synthesis. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese has identified a number of piperidine derivatives (like Fpmp) that are useful in the synthesis of oligoribonucleotides including 1-[(chloro-4-methyl)phenyl]-4'-methoxypiperidin-4-yl (Reese et al., Tetrahedron Lett., 1986, (27), 2291). Another approach was to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group initially used for the synthesis of oligoribonucleotides was the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal such as for example the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, S., Chimia, 2001, (55), 320-324.) The group examined fluoride labile and photolabile protecting groups that are removed using moderate conditions. One photolabile group that was examined was the [2-(nitrobenzyl)oxy]methyl (nbm) protecting group (Schwartz et al., Bioorg. Med. Chem. Lett., 1992, (2), 1019.) Other groups examined included a number structurally related formaldehyde acetal-derived, 2'-O-protecting groups. Also prepared were a number of related protecting groups for preparing 2'-O-alkylated nucleoside phosphoramidites including 2'-O-[(triisopropylsilyl)oxy]methyl (2'-O—$CH_2$—O—$Si(iPr)_3$, TOM). One 2'-O-protecting group that was prepared to be used orthogonally to the TOM group was 2'-O—[(R)-1-(2-nitrophenyl)ethyloxy)methyl] ((R)-mnbm).

Another strategy using a fluoride labile 5'-O-protecting group (non-acid labile) and an acid labile 2'-O-protecting group has been reported (Scaringe, Stephen A., Methods, 2001, (23) 206-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

Although a lot of research has focused on the synthesis of oligoribonucleotides the main RNA synthesis strategies that are presently being used commercially include 5'-O-DMT-2'-O-t-butyldimethylsilyl (TBDMS), 5'-O-DMT-2'-O-[1 (2-fluorophenyl)-4-methoxypiperidin-4-yl] (FPMP), 2'-O-[(triisopropylsilyl)oxy]methyl (2'-O—$CH_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present invention.

The primary groups being used for commercial RNA synthesis are:

TBDMS=5'-O-DMT-2'-O-t-butyldimethylsilyl;

TOM=2'-O-[(triisopropylsilyl)oxy]methyl;

DOD/ACE=(5'-O-bis(trimethylsiloxy)cyclododecyloxysilyl ether-2'-O-bis(2-acetoxyethoxy)methyl FPMP=5'-O-DMT-2'-O-[1 (2-fluorophenyl)-4-methoxypiperidin-4-yl].

All of the aforementioned RNA synthesis strategies are amenable to the present invention. Strategies that would be a hybrid of the above e.g. using a 5'-protecting group from one strategy with a 2'-O-protecting from another strategy is also amenable to the present invention.

The preparation of ribonucleotides and oligomeric compounds having at least one ribonucleoside incorporated and all the possible configurations falling in between these two extremes are encompassed by the present invention. The corresponding oligomeric compounds can be hybridized to further oligomeric compounds including oligoribonucleotides having regions of complementarity to form double-stranded (duplexed) oligomeric compounds, which are commonly referred to as dsRNAs in the art. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697). The effects of nucleoside modifications on RNAi activity are evaluated according to existing literature (Elbashir et al., Nature (2001), 411, 494-498; Nishikura et al., Cell (2001), 107, 415-416; and Bass et al., Cell (2000), 101, 235-238.)

The methods of preparing oligomeric compounds of the present invention can also be applied in the areas of drug discovery and target validation.

Oligomer Mimetics (Oligonucleotide Mimics)

Another group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. Further teaching of PNA oligomeric compounds can be found in Nielsen et al., Science, 1991, 254, 1497-1500.

PNA has been modified in the art to incorporate numerous modifications since the basic PNA structure was first prepared. The basic structure is shown below:

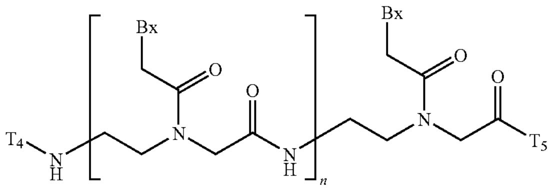

wherein

Bx is a heterocyclic base moiety;

$T_4$ is hydrogen, an amino protecting group, —C(O)$R_5$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(═O)—$(CH_2)_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(═O)—$CH_3$, benzyl, benzoyl, or —$(CH_2)_n$—N(H)$Z_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, Biochemistry, 2002, 41(14), 4503-4510). Morpholino-based oligomeric compounds are disclosed in U.S. Pat. No. 5,034,506, issued Jul. 23, 1991. The morpholino class of oligomeric compounds has been prepared having a variety of different linking groups joining the monomeric subunits.

Morpholino nucleic acids have been prepared having a variety of different linking groups ($L_2$) joining the monomeric subunits. The basic formula is shown below:

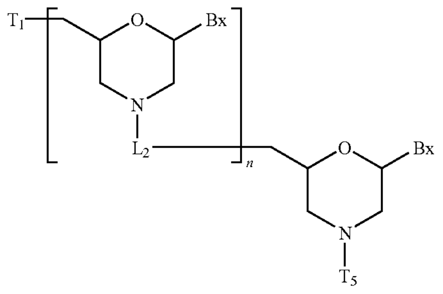

wherein $T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

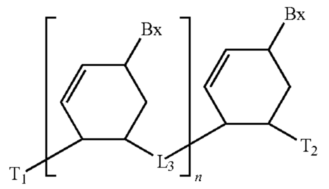

wherein each Bx is a heterocyclic base moiety;

$T_1$ is hydroxyl or a protected hydroxyl; and

T2 is hydroxyl or a protected hydroxyl.

Another class of oligonucleotide mimetic (anhydrohexitol nucleic acid) can be prepared from one or more anhydrohexitol nucleosides (see, Wouters and Herdewijn, Bioorg. Med. Chem. Lett., 1999, 9, 1563-1566) and would have the general formula:

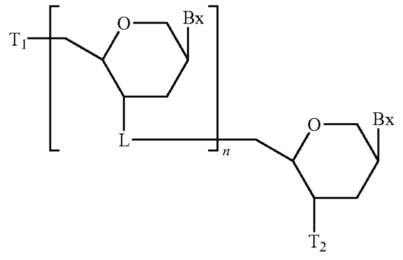

Another group of modifications includes nucleosides having sugar moieties that are bicyclic thereby locking the sugar conformational geometry. The most studied of these nucleosides having a bicyclic sugar moiety is locked nucleic acid or LNA. As can be seen in the structure below the 2'—O— has been linked via a methylene group to the 4' carbon. This bridge attaches under the 3' bonds forcing the sugar ring into a locked 3'-endo conformation geometry. The linkage can be a methylene ($—CH_2—)_n$ group bridging the 2' oxygen atom and the 4' carbon atom wherein n is 1 for LNA. LNA and LNA analogs display very high duplex thermal stabilities with complementary DNA and RNA ($T_m$=+3 to +10 C), stability towards 3'-exonucleolytic degradation and good solubility properties.

An LNA analog that also has been looked at is ENA wherein an additional methylene group has been added to the bridge between the 2' and the 2' carbons ($4'-CH_2—CH_2—O-2'$, Kaneko et al., United States Patent Application Publication No.: US 2002/0147332, Singh et al., Chem. Commun., 1998, 4, 455-456, also see Japanese Patent Application HEI-11-33863, Feb. 12, 1999).

In another publication a large genus of nucleosides having bicyclic sugar moieties is disclosed. The bridging group is variable as are the points of attachment (United States Patent Application Publication No.: U.S. 2002/0068708).

The basic structure of LNA showing the bicyclic ring system is shown below:

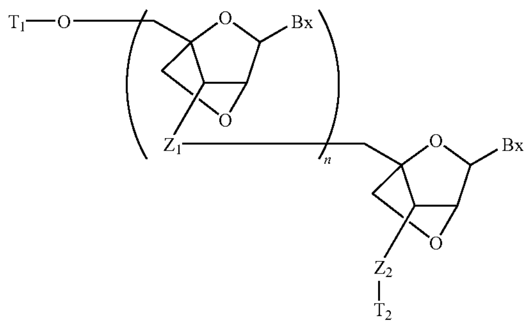

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points ($T_m$=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methylcytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

One group has added an additional methylene group to the LNA 2',4'-bridging group (e.g. 4'-$CH_2$—$CH_2$—O-2' (ENA), Kaneko et al., United States Patent Application Publication No.: US 2002/0147332, also see Japanese Patent Application HEI-11-33863, Feb. 12, 1999).

Further oligonucleotide mimetics have been prepared to include bicyclic and tricyclic nucleoside analogs having the formulas (amidite monomers shown):

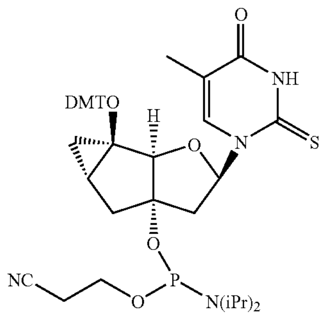

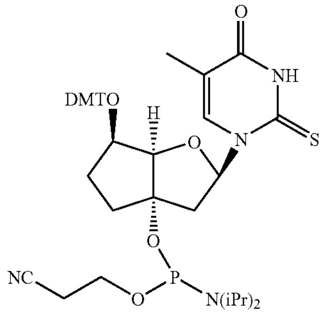

(see Steffens et al., Helv. Chim. Acta, 1997, 80, 2426-2439; Steffens et al., J. Am. Chem. Soc., 1999, 121, 3249-3255; and Renneberg et al., J. Am. Chem. Soc., 2002, 124, 5993-6002). These modified nucleoside analogs have been oligomerized using the phosphoramidite approach and the resulting oligomeric compounds containing tricyclic nucleoside analogs have shown increased thermal stabilities ($T_m$'s) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

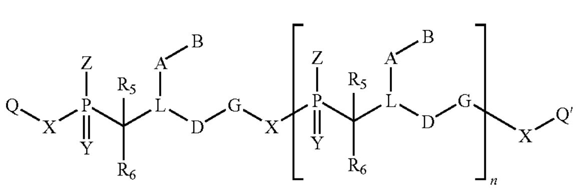

Another oligonucleotide mimetic has been reported wherein the furanosyl ring has been replaced by a cyclobutyl moiety.

Modified Sugars

Oligomeric compounds of the invention may also contain one or more substituted sugar moieties. Oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{12}$ alkyl or $C_2$ to $C_{12}$ alkenyl and alkynyl. Particularly suitable are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other oligonucleotides comprise a sugar substituent group selected from: $C_1$ to $C_{12}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. Another modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other sugar substituent groups include methoxy (—O—$CH_3$), aminopropoxy (—$OCH_2CH_2CH_2NH_2$), allyl (—$CH_2$—CH═$CH_2$), —O-allyl (—O—$CH_2$—CH═$CH_2$) and fluoro (F). 2'-Sugar substituent groups may be in the arabino (up) position or ribo (down) position. One 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Further representative sugar substituent groups include groups of formula $I_a$ or $II_a$:

Ia

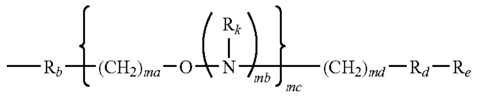

IIa

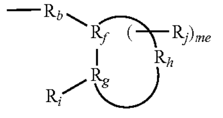

wherein:

$R_b$ is O, S or NH;

$R_d$ is a single bond, O, S or C(═O);

$R_e$ is $C_1$-$C_{12}$ alkyl, $N(R_k)(R_m)$, $N(R_k)(R_n)$, N═$C(R_p)(R_q)$, N═$C(R_p)(R_r)$ or has formula $III_a$;

IIIa

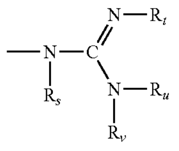

$R_p$ and $R_q$ are each independently hydrogen or $C_1$-$C_{12}$ alkyl;

$R_r$ is —$R_x$—$R_y$;

each $R_s$, $R_t$, $R_u$ and $R_v$ is, independently, hydrogen, C(O)$R_w$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$-$C_{12}$alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_k$ is hydrogen, a nitrogen protecting group or —$R_x$—$R_y$;

$R_p$ is hydrogen, a nitrogen protecting group or —$R_x$—$R_y$;

$R_x$ is a bond or a linking moiety;

$R_y$ is a chemical functional group, a conjugate group or a solid support medium;

each $R_m$ and $R_n$ is, independently, H, a nitrogen protecting group, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_i$ is $OR_z$, $SR_z$, or $N(R_z)_2$;

each $R_z$ is, independently, H, $C_1$-$C_8$ alkyl, $C_1$-$C_8$ haloalkyl, $C(=NH)N(H)R_u$ or $OC(=O)N(H)R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN;

$m_a$ is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

Representative substituents groups of Formula Ia are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula IIa are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Sugar substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$ where n and m are from 1 to about 10.

Representative guanidino substituent groups that are shown in formula IIIa disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxyethyl-Oligomeric compounds", filed Aug. 6, 1999, hereby incorporated by reference in its entirety.

Modified Nucleobases/Naturally Occurring Nucleobases

Chimeric oligomeric compounds of the invention may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently suitable base substitutions, even more particularly when combined with 2'-O-methoxyethyl sugar modifications.

In one aspect of the present invention chimeric oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

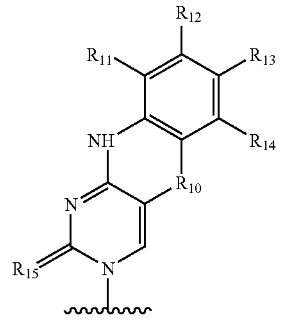

Representative cytosine analogs that make 3 hydrogen bonds with a guanosine in a second strand include 1,3-diazaphenoxazine-2-one ($R_{10}$=O, $R_{11}$-$R_{14}$=H) (Kurchavov, et al., Nucleosides and Nucleotides, 1997, 16, 1837-1846), 1,3-diazaphenothiazine-2-one ($R_{10}$=S, $R_{11}$-$R_{14}$=H), (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one ($R_{10}$=O, $R_{11}$-$R_{14}$=F) (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric oligomeric compounds" filed May 24, 2002, Ser. No. 10/013,295, both of which are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183 and U.S. Pat. No. 6,007,992, each of which is incorporated herein in its entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20 mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518). Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001, each of which is herein incorporated by reference.

Activated Phosphorus Groups

The compositions of the present invention illustrate the use of activated phosphorus compositions (e.g. compounds having activated phosphorus-containing substituent groups) in coupling reactions. As used herein, the term activated phosphorus composition includes monomers and oligomers that have an activated phosphorus-containing substituent group that is reactive with a hydroxyl group of another monomeric or oligomeric compound to form a phosphorus-containing internucleotide linkage. Such activated phosphorus groups contain activated phosphorus atoms in $P^{III}$ valence state and are known in the art and include, but are not limited to, phosphoramidite, H-phosphonate, phosphate triesters and chiral auxiliaries. One synthetic solid phase synthesis utilizes phosphoramidites as activated phosphates. The phosphoramidites utilize $P^{III}$ chemistry. The intermediate phosphite compounds are subsequently oxidized to the $P^{V}$ state using known methods to yield, in one embodiment, phosphodiester or phosphorothioate internucleotide linkages. Additional activated phosphates and phosphites are disclosed in Tetrahedron Report Number 309 (Beaucage and Iyer, Tetrahedron, 1992, 48, 2223-2311).

Activated phosphorus groups are useful in the preparation of a wide range of oligomeric compounds including but not limited to oligonucleosides and oligonucleotides as well as oligonucleotides that have been modified or conjugated with other groups at the base or sugar or both. Also included are oligonucleotide mimetics including but not limited to peptide nucleic acids (PNA), morpholino nucleic acids, cyclohexenyl nucleic acids (CeNA), anhydrohexitol nucleic acids, locked nucleic acids (LNA and ENA), bicyclic and tricyclic nucleic acids, phosphonomonoester nucleic acids and cyclobutyl nucleic acids. A representative example of one type of oligomer synthesis that utilizes the coupling of an activated phosphorus group with a reactive hydroxyl group is the widely used phosphoramidite approach. A phosphoramidite synthon is reacted under appropriate conditions with a reactive hydroxyl group to form a phosphite linkage that is further oxidized to a phosphodiester or phosphorothioate linkage. This approach commonly utilizes nucleoside phosphoramidites of the formula:

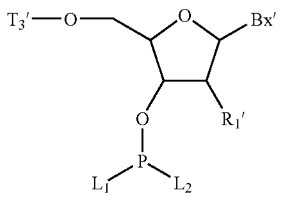

wherein each Bx' is an optionally protected heterocyclic base moiety;

each $R_{1'}$ is, independently, H or an optionally protected sugar substituent group;

$T_{3'}$ is H, a hydroxyl protecting group, a nucleoside, a nucleotide, an oligonucleoside or an oligonucleotide;

$L_1$ is $N(R_1)R_2$;

each $R_2$ and $R_3$ is, independently, $C_1$-$C_{12}$ straight or branched chain alkyl;

or $R_2$ and $R_3$ are joined together to form a 4- to 7-membered heterocyclic ring system including the nitrogen atom to which $R_2$ and $R_3$ are attached, wherein said ring system optionally includes at least one additional heteroatom selected from O, N and S;

$L_2$ is Pg-O—, Pg-S—, $C_1$-$C_{12}$ straight or branched chain alkyl, $CH_3(CH_2)_{0-10}$—O— or —$NR_5R_6$;

Pg is a protecting/blocking group; and each $R_5$ and $R_6$ is, independently, hydrogen, $C_1$-$C_{12}$ straight or branched chain alkyl, cycloalkyl or aryl;

or optionally, $R_5$ and $R_6$, together with the nitrogen atom to which they are attached form a cyclic moiety that may include an additional heteroatom selected from O, S and N; or $L_1$ and $L_2$ together with the phosphorus atom to which $L_1$ and $L_2$ are attached form a chiral auxiliary.

Groups that are attached to the phosphorus atom of internucleotide linkages before and after oxidation ($L_1$ and $L_2$) can include nitrogen containing cyclic moieties such as morpholine. Such oxidized internucleoside linkages include a phosphoromorpholidothioate linkage (Wilk et al., Nucleosides and nucleotides, 1991, 10, 319-322). Further cyclic moieties amenable to the present invention include mono-, bi- or tricyclic ring moieties which may be substituted with groups such as oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, ODMT, alkylsulfonyl, nitro, sulfide, sulfone, sulfonamide, thiol and thioalkoxy. A bicyclic ring structure that includes nitrogen is phthalimido.

Unless otherwise defined herein, alkyl means $C_1$-$C_{12}$, $C_1$-$C_8$, or $C_1$-$C_6$, straight or (where possible) branched chain aliphatic hydrocarbyl.

Unless otherwise defined herein, heteroalkyl means $C_1$-$C_{12}$, $C_1$-$C_8$, or $C_1$-$C_6$, straight or (where possible) branched chain aliphatic hydrocarbyl containing at least one or about 1 to about 3, hetero atoms in the chain, including the terminal portion of the chain. Suitable heteroatoms include N, O and S.

Unless otherwise defined herein, cycloalkyl means $C_3$-$C_{12}$, $C_3$-$C_8$, or $C_3$-$C_6$, aliphatic hydrocarbyl ring.

Unless otherwise defined herein, alkenyl means $C_2$-$C_{12}$, $C_2$-$C_8$, or $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, $C_2$-$C_8$, or $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. The number of carbon atoms can vary from 1 to about 12, or from 1 to about 6, and the total number of ring members can vary from three to about 15, or from about 3 to about 8. Ring heteroatoms can be N, O and S. Heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Ayl rings can have about 6 to about 20 ring carbons. Aryl rings can include phenyl, napthyl, anthracenyl, and phenanthrenyl.

Unless otherwise defined herein, hetaryl means a ring moiety containing at least one fully unsaturated ring, the ring consisting of carbon and non-carbon atoms. The ring system can contain about 1 to about 4 rings. The number of carbon atoms can vary from 1 to about 12, or from 1 to about 6, and the total number of ring members can vary from three to about 15, or from about 3 to about 8. Ring heteroatoms are N, O and S. Hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Halo (halogen) substituents can be Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate.

Phosphate protecting groups include those described in U.S. Pat. Nos. 5,760,209, 5,614,621, 6,051,699, 6,020,475, 6,326,478, 6,169,177, 6,121,437, 6,465,628 each of which is expressly incorporated herein by reference in its entirety.

Hybridization

In the context of this invention, "hybridization" means the pairing of complementary strands of oligomeric compounds. In the present invention, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a reduction in activity, and there is a sufficient degree of complementarity to avoid off-target effects (non-specific binding of the antisense oligomeric compound to non-target nucleic acid sequences under conditions in which specific binding is desired, i.e., under physiological conditions in the case of in vivo assays or therapeutic treatment, or under conditions in which assays are performed in the case of in vitro assays).

In the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing of two nucleobases regardless of where the two are located. For example, if a nucleobase at a certain position of an oligomeric compound is capable of hydrogen bonding (pairing) with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, “specifically hybridizable” and “complementary” are terms which are used to indicate a sufficient degree of precise pairing or complementarity over a sufficient number of nucleobases such that stable and specific binding occurs between the oligonucleotide and a target nucleic acid.

It is understood in the art that the sequence of a chimeric oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It may be desirable that the chimeric oligomeric compounds of the present invention comprise at least 70%, at least 80%, at least 90%, at least 95%, or at least 99% sequence complementarity to a target region within the target nucleic acid to which they are targeted. For example, a chimeric oligomeric compound in which 18 of 20 nucleobases are complementary (the remaining 2 being mismatches) to a target region, which specifically hybridizes, would represent 90 percent complementarity. In this example, the remaining noncomplementary nucleobases may be clustered or interspersed with complementary nucleobases and need not be contiguous to each other or to complementary nucleobases. As such, a chimeric oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of a chimeric oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Targets of the Invention

The chimeric oligomeric compounds of the present invention are targeted to nucleic acid targets in a sequence dependent manner. One nucleic acid target is messenger RNA. More specifically, chimeric oligomeric compounds of the invention will modulate gene expression by hybridizing to a nucleic acid target resulting in alteration of or reduction in normal function of the target nucleic acid. As used herein, the term “target nucleic acid” or “nucleic acid target” is used for convenience to encompass any nucleic acid capable of being targeted including without limitation DNA, RNA (including pre-mRNA and mRNA or portions thereof) transcribed from such DNA, and also cDNA derived from such RNA. In one embodiment of the invention the target nucleic acid is a messenger RNA. The inhibition of the target is typically based upon hydrogen bonding-based hybridization of the chimeric oligomeric compound strands or segments such that at least one strand or segment is cleaved, degraded, or otherwise rendered inoperable. In this regard, it is presently suitable to target specific nucleic acid molecules and their functions for such inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. In the context of the present invention, “modulation” and “modulation of expression” mean either an increase (stimulation) or a decrease (inhibition) in the amount or levels of a nucleic acid molecule encoding the gene, e.g., DNA or RNA. Inhibition is often the desired form of modulation of expression and mRNA is often a suitable target nucleic acid.

In one aspect, the present invention is directed to chimeric oligomeric compounds that are prepared having enhanced activity against nucleic acid targets. As used herein the phrase “enhanced activity” can indicate upregulation or downregulation of a system. A target and a mechanism for its modulation is determined. An oligonucleotide is selected having an effective length and sequence that is complementary to a portion of the target sequence. The selected sequence is divided into regions and the nucleosides of each region are modified to enhance the desired properties of the respective region. Consideration is also given to the 5' and 3'-termini as there are often advantageous modifications that can be made to one or more of the terminal nucleosides. Further modifications are also considered such as internucleoside linkages, conjugate groups, substitute sugars or bases, substitution of one or more nucleosides with nucleoside mimetics and any other modification that can enhance the selected sequence for its intended target.

“Targeting” a chimeric oligomeric compound of the invention to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent.

The targeting process usually also includes determination of at least one target region, target segment, or target site within the target nucleic acid for the antisense interaction to occur (hybridization of the chimeric oligomeric compound to its complementary sense target) such that the desired effect, e.g., modulation of expression, will result. Within the context of the present invention, the term “target region” is defined as a portion of the target nucleic acid having at least one identifiable structure, function, or characteristic. Within regions of target nucleic acids are segments. “Target segments” are defined as smaller or sub-portions of regions within a target nucleic acid. “Target sites,” as used in the present invention, are defined as positions within a target nucleic acid. Since, as is known in the art, the translation initiation codon is typically 5'-AUG (in transcribed mRNA molecules; 5'-ATG in the corresponding DNA molecule), the translation initiation codon is also referred to as the “AUG codon,” the “start codon” or the “AUG start codon”. A minority of genes has a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a nucleic acid target, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the chimeric oligomeric compounds of the present invention.

The open reading frame (ORF) or "coding region," which is known in the art to refer to the region between the translation initiation codon and the translation termination codon, is also a region which may be targeted effectively. Within the context of the present invention, one region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also suitable to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the sites where exons are joined. Targeting exon-exon junctions can be useful in situations where the overproduction of a normal splice product is implicated in disease, or where the overproduction of an aberrant splice product is implicated in disease. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also suitable target sites. mRNA transcripts produced via the process of splicing of two (or more) mRNAs from different gene sources known as "fusion transcripts" are also suitable target sites. It is also known that introns can be effectively targeted using chimeric oligomeric compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequences.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also suitable target nucleic acids.

The locations on the target nucleic acid to which the chimeric oligomeric compounds hybridize are hereinbelow referred to as "suitable target segments." As used herein the term "suitable target segment" is defined as at least a 5-nucleobase portion of a target region to which an active chimeric oligomeric compound of the present invention is targeted. While not wishing to be bound by theory, it is presently believed that these target segments represent portions of the target nucleic acid which are accessible for hybridization.

Exemplary chimeric oligomeric compounds include at least the 5 consecutive nucleobases from the 5'-terminus of a targeted nucleic acid e.g. a cellular gene or mRNA transcribed from the gene (the remaining nucleobases being a consecutive stretch of the same oligonucleotide beginning immediately upstream of the 5'-terminus of the chimeric oligomeric compound which is specifically hybridizable to the target nucleic acid and continuing until the oligonucleotide contains from about 5 to about 80 nucleobases). Similarly, chimeric oligomeric compounds comprise at least the 5 consecutive nucleobases from the 3'-terminus of one of the illustrative chimeric oligomeric compounds (the remaining nucleobases being a consecutive stretch of the same oligonucleotide beginning immediately downstream of the 3'-terminus of the chimeric oligomeric compound which is specifically hybridizable to the target nucleic acid and continuing until the chimeric oligomeric compound contains from about 5 to about 80 nucleobases). One having skill in the art armed with the chimeric oligomeric compounds illustrated herein will be able, without undue experimentation, to identify further chimeric oligomeric compounds.

Once one or more target regions, target segments or target sites have been identified, chimeric oligomeric compounds of the invention are chosen which are sufficiently complementary to the target, i.e., hybridize sufficiently well and with sufficient specificity, to give the desired effect.

The oligomeric antisense compounds can also be targeted to regions of a target nucleobase sequence, such as those disclosed herein. All regions of a nucleobase sequence to which an oligomeric antisense compound can be targeted, wherein the regions are greater than or equal to 5 and less than or equal to 80 nucleobases, are described as follows:

Let R(n, n+m−1) be a region from a target nucleobase sequence, where "n" is the 5'-most nucleobase position of the region, where "n+m−1" is the 3'-most nucleobase position of the region and where "m" is the length of the region. A set "S(m)", of regions of length "m" is defined as the regions where n ranges from 1 to L−m+1, where L is the length of the target nucleobase sequence and L>m. A set, "A", of all regions can be constructed as a union of the sets of regions for each length from where m is greater than or equal to 5 and is less than or equal to 80.

This set of regions can be represented using the following mathematical notation:

$$A = \bigcup_m S(m) \text{ where } m \in N \mid 5 \leq m \leq 80$$

and $$S(m) = \{R_{n,n+m-1} \mid n \in \{1, 2, 3, \ldots, L-m+1\}\}$$

where the mathematical operator | indicates "such that", where the mathematical operator ∈ indicates "a member of a set" (e.g. y ∈ Z indicates that element y is a member of set Z), where x is a variable, where N indicates all natural numbers, defined as positive integers, and where the mathematical operator ∪ indicates "the union of sets".

For example, the set of regions for m equal to 5, 20 and 80 can be constructed in the following manner. The set of regions, each 5 nucleobases in length, S(m=5), in a target nucleobase sequence 100 nucleobases in length (L=100), beginning at position 1 (n=1) of the target nucleobase sequence, can be created using the following expression:

$$S(5)=\{R_{1,5}|n\in\{1,2,3, \ldots ,96\}\}$$

and describes the set of regions comprising nucleobases 1-5, 2-6, 3-7, 4-8, 5-9, 6-10, 7-11, 8-12, 9-13, 10-14, 11-15, 12-16, 13-17, 14-18, 15-19, 16-20, 17-21, 18-22, 19-23, 20-24, 21-25, 22-26, 23-27, 24-28, 25-29, 26-30, 27-31, 28-32, 29-33, 30-34, 31-35, 32-36, 33-37, 34-38, 35-39, 36-40, 37-41, 38-42, 39-43, 40-44, 41-45, 42-46, 43-47, 44-48, 45-49, 46-50, 47-51, 48-52, 49-53, 50-54, 51-55, 52-56, 53-57, 54-58, 55-59, 56-60, 57-61, 58-62, 59-63, 60-64, 61-65, 62-66, 63-67, 64-68, 65-69, 66-70, 67-71, 68-72, 69-73, 70-74, 71-75, 72-76, 73-77, 74-78, 75-79, 76-80, 77-81, 78-82, 79-83, 80-84, 81-85, 82-86, 83-87, 84-88, 85-89, 86-90, 87-91, 88-92, 89-93, 90-94, 91-95, 92-96, 93-97, 94-98, 95-99, 96-100.

An additional set for regions 20 nucleobases in length, in a target sequence 100 nucleobases in length, beginning at position 1 of the target nucleobase sequence, can be described using the following expression:

$$S(20)=\{R_{1,20}|n\in\{1,2,3, \ldots ,81\}\}$$

and describes the set of regions comprising nucleobases 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100.

An additional set for regions 80 nucleobases in length, in a target sequence 100 nucleobases in length, beginning at position 1 of the target nucleobase sequence, can be described using the following expression:

$$S(80)=\{R_{1,80}|n\in\{1,2,3, \ldots ,21\}\}$$

and describes the set of regions comprising nucleobases 1-80, 2-81, 3-82, 4-83, 5-84, 6-85, 7-86, 8-87, 9-88, 10-89, 11-90, 12-91, 13-92, 14-93, 15-94, 16-95, 17-96, 18-97, 19-98, 20-99, 21-100.

Thus, in this example, A would include regions 1-5, 2-6, 3-7 . . . 93-100, 1-20, 2-21, 3-22 . . . 81-100, 1-80, 2-81, 3-82 . . . 21-100.

The union of these aforementioned example sets and other sets for lengths from 10 to 19 and 21 to 79 can be described using the mathematical expression $$A = \bigcup_m S(m)$$

where ∪ represents the union of the sets obtained by combining all members of all sets.

The mathematical expressions described herein defines all possible target regions in a target nucleobase sequence of any length L, where the region is of length m, and where m is greater than or equal to 5 and less than or equal to 80 nucleobases and, and where m is less than L, and where n is less than L−m+1.

In accordance with one embodiment of the present invention, a series of nucleic acid duplexes comprising the chimeric oligomeric compounds of the present invention and their complements can be designed for a specific target or targets. These nucleic acid duplexes are commonly referred to in the art as double-strand RNAs (dsRNAs) or small interfering RNAs (siRNAs). As described herein, such duplexes have been shown in the art to modulate target expression and regulate translation as well as RNA processing via an antisense mechanism. Within a duplex, the ends of the strands may be modified by the addition of one or more natural or modified nucleobases to form an overhang. The sense strand of the duplex is then designed and synthesized as the complement of the antisense strand and may also contain modifications or additions to either terminus. For example, in one embodiment, both strands of the duplex would be complementary over the central nucleobases, each having overhangs at one or both termini. The antisense and sense strands of the duplex comprise from about 17 to 25 nucleotides, or from about 19 to 23 nucleotides. Alternatively, the antisense and sense strands comprise 20, 21 or 22 nucleotides.

For example, a duplex comprising a chimeric oligomeric compound having the sequence CGAGAGGCGGACGG- GACCG (SEQ ID NO: 3) and having a two-nucleobase overhang of deoxythymidine(dT) would have the following structure:

```
cgagaggcggacgggaccgTT  Antisense Strand (SEQ ID NO: 4)
  |||||||||||||||||||
TTgctctccgcctgccctggc  Complement Strand (SEQ ID NO: 5)
```

Overhangs can range from 1 to 6 nucleobases and these nucleobases may or may not be complementary to the target nucleic acid. One of skill in the art will understand that the overhang may be 1, 2, 3, 4, 5 or 6 nucleobases in length. In another embodiment, the duplexes may have an overhang on only on terminus.

In another embodiment, a duplex comprising an antisense strand having the same sequence CGAGAGGCGGACGGGACCG (SEQ ID NO: 3) may be prepared with blunt ends (no single stranded overhang) as shown:

```
cgagaggcggacgggaccg  Antisense Strand (SEQ ID NO: 4)
|||||||||||||||||||
gctctccgcctgccctggc  Complement Strand (SEQ ID NO: 5)
```

The RNA duplex can be unimolecular or bimolecular; i.e., the two strands can be part of a single molecule or may be separate molecules. These sequences are shown to contain thymine (T), but one of skill in the art will appreciate that thymine (T) can generally be replaced with uracil (U) in RNA sequences.

Screening and Target Validation

In a further embodiment, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present invention.

The suitable target segments of the present invention may also be combined with their respective complementary chimeric oligomeric compounds of the present invention to form stabilized double-stranded (duplexed) oligonucleotides. Such double-stranded oligonucleotide moieties have been shown in the art to modulate target expression and regulate translation as well as RNA processing via an antisense mechanism.

The oligomeric compounds of the present invention can also be applied in the areas of drug discovery and target validation. The present invention comprehends the use of the oligomeric compounds and suitable targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

Kits, Research Reagents, Diagnostics, and Therapeutics

The oligomeric compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the oligomeric compounds of the present invention, either alone or in combination with other oligomeric compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more chimeric oligomeric compounds are compared to control cells or tissues not treated with chimeric oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

The oligomeric compounds of the invention are useful for research and diagnostics, because these oligomeric compounds hybridize to nucleic acids encoding proteins. The primers and probes disclosed herein are useful in methods requiring the specific detection of nucleic acid molecules encoding proteins and in the amplification of the nucleic acid molecules for detection or for use in further studies. Hybridization of the primers and probes with a nucleic acid can be detected by means known in the art. Such means may include conjugation of an enzyme to the primer or probe, radiolabelling of the primer or probe or any other suitable detection means. Kits using such detection means for detecting the level of selected proteins in a sample may also be prepared.

The specificity and sensitivity of antisense is also harnessed by those of skill in the art for therapeutic uses. Antisense oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense oligomeric compounds can be useful therapeutic modalities that can be configured to be useful in treatment regimes for the treatment of cells, tissues and animals, especially humans.

For therapeutics, an animal, such as a human, suspected of having a disease or disorder which can be treated by modulating the expression of a selected protein is treated by administering chimeric oligomeric compounds in accordance with this invention. For example, in one non-limiting embodiment, the methods comprise the step of administering to the animal in need of treatment, a therapeutically effective amount of a protein inhibitor. The protein inhibitors of the present invention effectively inhibit the activity of the protein or inhibit the expression of the protein. In one embodiment, the activity or expression of a protein in an animal is inhibited by about 10% or more, by about 20% or more, by about 30% or more, by about 40% or more, by about 50% or more, by about 60% or more, by about 70% or more, by about 80% or more, by about 90% or more, by about 95% or more, or by about 99% or more. For example, the reduction of the expression of a protein may be measured in serum, adipose tissue, liver or any other body fluid, tissue or organ of the animal. The cells contained within the fluids, tissues or organs being analyzed can contain a nucleic acid molecule encoding a protein and/or the protein itself.

The oligomeric compounds of the invention can be utilized in pharmaceutical compositions by adding an effective amount of an oligomeric compound to a suitable pharmaceutically acceptable diluent or carrier. Use of the oligomeric compounds and methods of the invention may also be useful prophylactically.

Formulations

The oligomeric compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The chimeric oligomeric compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the oligomeric compounds of the invention, pharmaceutically acceptable salts of such prodrugs, and other bioequivalents. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligomeric compounds of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Pharmaceutical Compositions and Routes of Administration

The present invention also includes pharmaceutical compositions and formulations which include the oligomeric compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Topical formulations include those in which the oligonucleotides of the invention are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

In some embodiments, an oligonucleotide may be administered to a subject via an oral route of administration. The subjects of the present invention comprise animals. An animal subject may be a mammal, such as a mouse, a rat, a dog, a guinea pig, a monkey, a human, a non-human primate, a cat or a pig. Non-human primates include monkeys and chimpanzees. A suitable animal subject may be an experimental animal, such as a mouse, a rat, a dog, a non-human primate, a cat or a pig.

In some embodiments, the subject may be a human. In certain embodiments, the subject may be a human patient as discussed in more detail herein. In certain embodiments, it may be necessary to modulate the expression of one or more genes of the human patient. In some particular embodiments, it may be necessary to inhibit expression of one or more genes of the human patient. In particular embodiments, it may be necessary to modulate, i.e. inhibit or enhance, the expression of one or more genes in order to obtain therapeutic outcomes discussed herein.

In some embodiments, non-parenteral (e.g. oral) oligonucleotide formulations according to the present invention result in enhanced bioavailability of the oligonucleotide. In this context, the term “bioavailability” refers to a measurement of that portion of an administered drug which reaches the circulatory system (e.g. blood, especially blood plasma) when a particular mode of administration is used to deliver the drug. Enhanced bioavailability refers to a particular mode of administration’s ability to deliver oligonucleotide to the peripheral blood plasma of a subject relative to another mode of administration. For example, when a non-parenteral mode of administration (e.g. an oral mode) is used to introduce the drug into a subject, the bioavailability for that mode of administration may be compared to a different mode of administration, e.g. an IV mode of administration. In some embodiments, the area under a compound’s blood plasma concentration curve ($AUC_0$) after non-parenteral administration may be divided by the area under the drug’s plasma concentration curve after intravenous (i.v.) administration ($AUC_{iv}$) to provide a dimensionless quotient (relative bioavailability, RB) that represents fraction of compound absorbed via the non-parenteral route as compared to the IV route. A composition’s bioavailability is said to be enhanced in comparison to another composition’s bioavailability when the first composition’s relative bioavailability ($RB_1$) is greater than the second composition’s relative bioavailability ($RB_2$).

In general, bioavailability correlates with therapeutic efficacy when a compound’s therapeutic efficacy is related to the blood concentration achieved, even if the drug’s ultimate site of action is intracellular (van Berge-Henegouwen et al., *Gastroenterol.,* 1977, 73, 300). Bioavailability studies have been used to determine the degree of intestinal absorption of a drug by measuring the change in peripheral blood levels of the drug after an oral dose (DiSanto, Chapter 76 *In: Remington’s Pharmaceutical Sciences,* 18th Ed., Gennaro, ed., Mack Publishing Co., Easton, Pa., 1990, pages 1451-1458).

In general, an oral composition (comprising an oligonucleotide) bioavailability is said to be “enhanced” when its relative bioavailability is greater than the bioavailability of a composition substantially consisting of pure oligonucleotide, i.e. oligonucleotide in the absence of a penetration enhancer.

Organ bioavailability refers to the concentration of compound in an organ. Organ bioavailability may be measured in test subjects by a number of means, such as by whole-body radiography. Organ bioavailability may be modified, e.g. enhanced, by one or more modifications to the oligonucleotide, by use of one or more carrier compounds or excipients, etc. as discussed in more detail herein. In general, an increase in bioavailability will result in an increase in organ bioavailability.

Oral oligonucleotide compositions according to the present invention may comprise one or more "mucosal penetration enhancers," also known as "absorption enhancers" or simply as "penetration enhancers." Accordingly, some embodiments of the invention comprise at least one oligonucleotide in combination with at least one penetration enhancer. In general, a penetration enhancer is a substance that facilitates the transport of a drug across mucous membrane(s) associated with the desired mode of administration, e.g. intestinal epithelial membranes. Accordingly it is desirable to select one or more penetration enhancers that facilitate the uptake of an oligonucleotide, without interfering with the activity of the oligonucleotide, and in such a manner the oligonucleotide can be introduced into the body of an animal without unacceptable degrees of side-effects such as toxicity, irritation or allergic response.

Embodiments of the present invention provide compositions comprising one or more pharmaceutically acceptable penetration enhancers, and methods of using such compositions, which result in the improved bioavailability of oligonucleotides administered via non-parenteral modes of administration. Heretofore, certain penetration enhancers have been used to improve the bioavailability of certain drugs. See Muranishi, *Crit. Rev. Ther. Drug Carrier Systems,* 1990, 7, 1 and Lee et al., *Crit. Rev. Ther. Drug Carrier Systems,* 1991, 8, 91. It has been found that the uptake and delivery of oligonucleotides can be greatly improved even when administered by non-parenteral means through the use of a number of different classes of penetration enhancers.

In some embodiments, compositions for non-parenteral administration include one or more modifications to naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property. Modifications may be made to the base, the linker, or the sugar, in general, as discussed in more detail herein with regards to oligonucleotide chemistry. In some embodiments of the invention, compositions for administration to a subject, and in particular oral compositions for administration to an animal (human or non-human) subject, will comprise modified oligonucleotides having one or more modifications for enhancing affinity, stability, tissue distribution, or other biological property.

Suitable modified linkers include phosphorothioate linkers. In some embodiments according to the invention, the oligonucleotide has at least one phosphorothioate linker. Phosphorothioate linkers provide nuclease stability as well as plasma protein binding characteristics to the oligonucleotide. Nuclease stability is useful for increasing the in vivo lifetime of oligonucleotides, while plasma protein binding decreases the rate of first pass clearance of oligonucleotide via renal excretion. In some embodiments according to the present invention, the oligonucleotide has at least two phosphorothioate linkers. In some embodiments, wherein the oligonucleotide has exactly n nucleosides, the oligonucleotide has from one to n-1 phosphorothioate linkages. In some embodiments, wherein the oligonucleotide has exactly n nucleosides, the oligonucleotide has n−1 phosphorothioate linkages. In other embodiments wherein the oligonucleotide has exactly n nucleoside, and n is even, the oligonucleotide has from 1 to n/2 phosphorothioate linkages, or, when n is odd, from 1 to (n−1)/2 phosphorothioate linkages. In some embodiments, the oligonucleotide has alternating phosphodiester (PO) and phosphorothioate (PS) linkages. In other embodiments, the oligonucleotide has at least one stretch of two or more consecutive PO linkages and at least one stretch of two or more PS linkages. In other embodiments, the oligonucleotide has at least two stretches of PO linkages interrupted by at least on PS linkage.

In some embodiments, at least one of the nucleosides is modified on the ribosyl sugar unit by a modification that imparts nuclease stability, binding affinity or some other beneficial biological property to the sugar. In some cases, the sugar modification includes a 2'-modification, e.g. the 2'-OH of the ribosyl sugar is replaced or substituted. Suitable replacements for 2'-OH include 2'-F and 2'-arabino-F. Suitable substitutions for OH include 2'-O-alkyl, e.g. 2-O-methyl, and 2'-O-substituted alkyl, e.g. 2'-O-methoxyethyl, 2'-$NH_2$, 2'-O-aminopropyl, etc. In some embodiments, the oligonucleotide contains at least one 2'-modification. In some embodiments, the oligonucleotide contains at least two 2'-modifications. In some embodiments, the oligonucleotide has at least one 2'-modification at each of the termini (i.e. the 3'- and 5'-terminal nucleosides each have the same or different 2'-modifications). In some embodiments, the oligonucleotide has at least two sequential 2'-modifications at each end of the oligonucleotide. In some embodiments, oligonucleotides further comprise at least one deoxynucleoside. In particular embodiments, oligonucleotides comprise a stretch of deoxynucleosides such that the stretch is capable of activating RNase (e.g. RNase H) cleavage of an RNA to which the oligonucleotide is capable of hybridizing. In some embodiments, a stretch of deoxynucleosides capable of activating RNase-mediated cleavage of RNA comprises about 6 to about 16, e.g. about 8 to about 16 consecutive deoxynucleosides. In further embodiments, oligonucleotides are capable of eliciting cleavage by dsRNAse enzymes which act on RNA:RNA hybrids.

Oligonucleotide compositions of the present invention may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the oligonucleotides or mimetics thereof so administered.

Delivery of a drug via the oral mucosa, as in the case of buccal and sublingual administration, has several desirable features, including, in many instances, a more rapid rise in plasma concentration of the drug (Harvey, Chapter 35 *In: Remington's Pharmaceutical Sciences,* 18th Ed., Gennaro, ed., Mack Publishing Co., Easton, Pa., 1990, page 711).

Endoscopy may be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., *Gan To Kagaku Ryoho,* 1992, 19(10 Suppl.), 1591). Pharmaceutical compositions, including liposomal formulations, can be delivered directly into portions of the alimentary canal, such as, e.g., the duodenum (Somogyi et al., *Pharm. Res.,* 1995, 12, 149) or the gastric submucosa (Akamo et al., *Japanese J. Cancer Res.,* 1994, 85, 652) via endoscopic means. Gastric lavage devices (Inoue et al., *Artif Organs,* 1997, 21, 28) and percutaneous endoscopic feeding devices (Pennington et al., *Ailment Pharmacol. Ther.,* 1995, 9, 471) can also be used for direct alimentary delivery of pharmaceutical compositions.

In some embodiments, oligonucleotide formulations may be administered through the anus into the rectum or lower intestine. Rectal suppositories, retention enemas or rectal catheters can be used for this purpose and may be desired when patient compliance might otherwise be difficult to achieve (e.g., in pediatric and geriatric applications, or when the patient is vomiting or unconscious). Rectal administration can result in more prompt and higher blood levels than the oral route. (Harvey, Chapter 35 *In: Remington's Pharmaceutical Sciences,* 18th Ed., Gennaro, ed., Mack Publishing Co., Easton, Pa., 1990, page 711). Because about 50% of the drug that is absorbed from the rectum will likely bypass the liver, administration by this route significantly reduces the potential for first-pass metabolism (Benet et al., Chapter 1 *In: Goodman & Gilman's The Pharmacological Basis of Therapeutics,* 9th Ed., Hardman et al., eds., McGraw-Hill, New York, N.Y., 1996).

Some embodiments employ various penetration enhancers in order to effect transport of oligonucleotides and other nucleic acids across mucosal and epithelial membranes. Penetration enhancers may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Accordingly, some embodiments comprise oral oligonucleotide compositions comprising at least one member of the group consisting of surfactants, fatty acids, bile salts, chelating agents, and non-chelating surfactants. Further embodiments comprise oral oligonucleotide compositions comprising at least one fatty acid, e.g. capric or lauric acid, or combinations or salts thereof. Other embodiments comprise methods of enhancing the oral bioavailability of an oligonucleotide, the method comprising co-administering the oligonucleotide and at least one penetration enhancer.

Other excipients that may be added to oral oligonucleotide compositions include surfactants (or "surface-active agents"). These are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., *Critical Reviews in Therapeutic Drug Carrier Systems,* 1991, page 92); and perfluorochemical emulsions, such as FC-43 (Takahashi et al., *J. Pharm. Pharmacol.,* 1988, 40, 252).

Fatty acids and their derivatives which act as penetration enhancers and may be used in compositions of the present invention include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., *Critical Reviews in Therapeutic Drug Carrier Systems,* 1991, page 92; Muranishi, *Critical Reviews in Therapeutic Drug Carrier Systems,* 1990, 7, 1; El-Hariri et al., *J. Pharm. Pharmacol.,* 1992, 44, 651).

In some embodiments, oligonucleotide compositions for oral delivery comprise at least two discrete phases, which phases may comprise particles, capsules, gel-capsules, microspheres, etc. Each phase may contain one or more oligonucleotides, penetration enhancers, surfactants, bioadhesives, effervescent agents, or other adjuvant, excipient or diluent. In some embodiments, one phase comprises at least one oligonucleotide and at lease one penetration enhancer. In some embodiments, a first phase comprises at least one oligonucleotide and at least one penetration enhancer, while a second phase comprises at least one penetration enhancer. In some embodiments, a first phase comprises at least one oligonucleotide and at least one penetration enhancer, while a second phase comprises at least one penetration enhancer and substantially no oligonucleotide. In some embodiments, at least one phase is compounded with at least one degradation retardant, such as a coating or a matrix, which delays release of the contents of that phase. In some embodiments, at least one phase In some embodiments, a first phase comprises at least one oligonucleotide, at least one penetration enhancer, while a second phase comprises at least one penetration enhancer and a release-retardant. In particular embodiments, an oral oligonucleotide composition comprises a first phase comprising particles containing an oligonucleotide and a penetration enhancer, and a second phase comprising particles coated with a release-retarding agent and containing penetration enhancer.

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 *In: Goodman & Gilman's The Pharmacological Basis of Therapeutics,* 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 *In: Remington's Pharmaceutical Sciences,* 18th Ed., Gennaro, ed., Mack Publishing Co., Easton, Pa., 1990, pages 782-783; Muranishi, *Critical Reviews in Therapeutic Drug Carrier Systems,* 1990, 7, 1; Yamamoto et al., *J. Pharm. Exp. Ther.,* 1992, 263, 25; Yamashita et al., *J. Pharm. Sci.,* 1990, 79, 579).

In some embodiments, penetration enhancers of the present invention are mixtures of penetration enhancing compounds. One such penetration mixture is UDCA (and/or CDCA) with capric and/or lauric acids or salts thereof e.g. sodium. Such mixtures are useful for enhancing the delivery of biologically active substances across mucosal membranes, in particular intestinal mucosa. Other penetration enhancer mixtures comprise about 5-95% of bile acid or salt(s) UDCA and/or CDCA with 5-95% capric and/or lauric acid. Particular penetration enhancers are mixtures of the sodium salts of UDCA, capric acid and lauric acid in a ratio of about 1:2:2 respectively. Another such penetration enhancer is a mixture of capric and lauric acid (or salts thereof) in a 0.01:1 to 1:0.01 ratio (mole basis). In particular embodiments capric acid and lauric acid are present in molar ratios of e.g. about 0.1:1 to about 1:0.1, in particular about 0.5:1 to about 1:0.5.

Other excipients include chelating agents, i.e. compounds that remove metallic ions from solution by forming complexes therewith, with the result that absorption of oligonucleotides through the alimentary and other mucosa is enhanced. With regards to their use as penetration enhancers in compositions containing DNA-like oligonucleotides in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1; Buur et al., *J. Control Rel.,* 1990, 14, 43).

As used herein, non-chelating non-surfactant penetration enhancers may be defined as compounds that demonstrate insignificant activity as chelating agents or as surfactants but that nonetheless enhance absorption of oligonucleotides through the alimentary and other mucosal membranes (Muranishi, *Critical Reviews in Therapeutic Drug Carrier Systems,* 1990, 7, 1). This class of penetration enhancers includes, but is not limited to, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621).

Agents that enhance uptake of oligonucleotides at the cellular level may also be added to the pharmaceutical, therapeutic and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), can be used.

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a an oligonucleotide and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.).

Oral oligonucleotide compositions may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301).

Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and antioxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, *in: Controlled Release of Drugs: Polymers and Aggregate Systems*, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research,* 1994, 11, 1385-1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research,* 1994, 11, 1385; Ho et al., *J. Pharm. Sci.,* 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

Liposomes

There are many organized surfactant structures besides microemulsions that have been studied and used in the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes and are useful for the delivery of DNA, RNA or any nucleic acid-based construct. Cationic liposomes are positively charged liposomes which interact with negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release,* 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting,* 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., *Antiviral Research,* 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.,* 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.,* 1980, 53, 2778) described liposomes comprising a nonionic detergent, $2C_{12}15G$, that contains a PEG moiety. Illum et al. (*FEBS Lett.,* 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.,* 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta,* 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Pulsatile Delivery

The compounds of the present invention may also be administered by pulsatile delivery. "Pulsatile delivery" refers to a pharmaceutical formulation that delivers a first pulse of drug (e.g. an antisense compound) combined with a penetration enhancer and a second pulse of penetration enhancer to promote absorption of drug which is not absorbed upon release with the first pulse of penetration enhancer.

One embodiment of the present invention is a delayed release oral formulation for enhanced intestinal drug absorption, comprising:

(a) a first population of carrier particles comprising said drug and a penetration enhancer, wherein said drug and said penetration enhancer are released at a first location in the intestine; and (b) a second population of carrier particles comprising a penetration enhancer and a delayed release coating or matrix, wherein the penetration enhancer is released at a second location in the intestine downstream from the first location, whereby absorption of the drug is enhanced when the drug reaches the second location.

Alternatively, the penetration enhancer in (a) and (b) is different.

This enhancement is obtained by encapsulating at least two populations of carrier particles. The first population of carrier particles comprises a biologically active substance and a penetration enhancer, and the second (and optionally additional) population of carrier particles comprises a penetration enhancer and a delayed release coating or matrix.

A "first pass effect" that applies to orally administered drugs is degradation due to the action of gastric acid and various digestive enzymes. One means of ameliorating first pass clearance effects is to increase the dose of administered drug, thereby compensating for proportion of drug lost to first pass clearance. Although this may be readily achieved with i.v. administration by, for example, simply providing more of the drug to an animal, other factors influence the bioavailability of drugs administered via non-parenteral means. For example, a drug may be enzymatically or chemically degraded in the alimentary canal or blood stream and/or may be impermeable or semipermeable to various mucosal membranes.

It is also contemplated that these pharmaceutical compositions are capable of enhancing absorption of biologically active substances when administered via the rectal, vaginal, nasal or pulmonary routes. It is also contemplated that release of the biologically active substance can be achieved in any part of the gastrointestinal tract.

Liquid pharmaceutical compositions of oligonucleotide can be prepared by combining the oligonucleotide with a suitable vehicle, for example sterile pyrogen free water, or saline solution. Other therapeutic compounds may optionally be included.

The present invention also contemplates the use of solid particulate compositions. Such compositions comprise particles of oligonucleotide that are of respirable size. Such particles can be prepared by, for example, grinding dry oligonucleotide by conventional means, fore example with a mortar and pestle, and then passing the resulting powder composition through a 400 mesh screen to segregate large particles and agglomerates. A solid particulate composition comprised of an active oligonucleotide can optionally contain a dispersant which serves to facilitate the formation of an aerosol, for example lactose.

In accordance with the present invention, oligonucleotide compositions can be aerosolized. Aerosolization of liquid particles can be produced by any suitable means, such as with a nebulizer. See, for example, U.S. Pat. No. 4,501,729. Nebulizers are commercially available devices which transform solutions or suspensions into a therapeutic aerosol mist either by means of acceleration of a compressed gas, typically air or oxygen, through a narrow venturi orifice or by means of ultrasonic agitation. Suitable nebulizers include those sold by Blairex® under the name PARI LC PLUS, PARI DURA-NEB 2000, PARI-BABY Size, PARI PRONEB Compressor with LC PLUS, PARI WALKHALER Compressor/Nebulizer System, PARI LC PLUS Reusable Nebulizer, and PARI LC Jet+®Nebulizer.

Formulations for use in nebulizers may consist of an oligonucleotide in a liquid, such as sterile, pyragen free water, or saline solution, wherein the oligonucleotide comprises up to about 40% w/w of the formulation. The oligonucleotide can comprise less than 20% w/w. If desired, further additives such as preservatives (for example, methyl hydroxybenzoate) antioxidants, and flavoring agents can be added to the composition.

Solid particles comprising an oligonucleotide can also be aerosolized using any solid particulate medicament aerosol generator known in the art. Such aerosol generators produce respirable particles, as described above, and further produce reproducible metered dose per unit volume of aerosol. Suitable solid particulate aerosol generators include insufflators and metered dose inhalers. Metered dose inhalers are used in the art and are useful in the present invention.

Liquid or solid aerosols are produced at a rate of from about 10 to 150 liters per minute, from about 30 to 150 liters per minute, or from about 60 to 150 liters per minute.

Enhanced bioavailability of biologically active substances is also achieved via the oral administration of the compositions and methods of the present invention.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy,* 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Two or more antisense compounds may be used together or sequentially.

Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, from 0.1 μg to 10 g per kg of body weight, from 1.0 μg to 1 g per kg of body weight, from 10.0 μg to 100 mg per kg of body weight, from 100 μg to 10 mg per kg of body weight, or from 1 mg to 5 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

The effects of treatments with therapeutic compositions can be assessed following collection of tissues or fluids from a patient or subject receiving said treatments. It is known in the art that a biopsy sample can be procured from certain tissues without resulting in detrimental effects to a patient or subject. In certain embodiments, a tissue and its constituent cells comprise, but are not limited to, blood (e.g., hematopoietic cells, such as human hematopoietic progenitor cells, human hematopoietic stem cells, CD34+ cells CD4+ cells), lymphocytes and other blood lineage cells, bone marrow, breast, cervix, colon, esophagus, lymph node, muscle, peripheral blood, oral mucosa and skin. In other embodiments, a fluid and its constituent cells comprise, but are not limited to, blood, urine, semen, synovial fluid, lymphatic fluid and cerebro-spinal fluid. Tissues or fluids procured from patients can be evaluated for expression levels of the target mRNA or protein. Additionally, the mRNA or protein expression levels of other genes known or suspected to be associated with the specific disease state, condition or phenotype can be assessed. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the disease or condition in the aforementioned tissues and fluids, collected from a patient or subject receiving treatment, by routine clinical methods known in the art. These biomarkers include but are not limited to: glucose, cholesterol, lipoproteins, triglycerides, free fatty acids and other markers of glucose and lipid metabolism; lipoprotein(a) particle and apolipoprotein B-100; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

The present invention also provides methods of reducing target RNA levels in an animal comprising contacting the animal with a gap-disabled compound comprising a gap-disabled motif listed in Table 13 or Table 26 and wherein the gap-disabled compound comprises a nucleobase sequence substantially complementary to a portion of the target RNA. These methods may also comprise identifying an animal in need of reducing target RNA levels.

The present invention also provides methods of lowering cholesterol or triglycerides in an animal comprising contacting the animal with a gap-disabled compound comprising the gap-disabled motif 3-2-1-2-1-2-1-2-1-2-3. These methods may also comprise identifying an animal in need of lowering cholesterol or triglycerides.

The present invention also provides methods of lowering plasma leptin, glucose, or plasma insulin in an animal comprising contacting the animal with a gap-disabled compound having the gap-disabled motif 3-2-1-2-1-2-1-2-1-2-3. These methods may also comprise identifying an animal in need of lowering plasma leptin, glucose, or plasma insulin.

The present invention also provides methods of lowering body weight, fat depot weight or food intake in an animal comprising contacting the animal with a gap-disabled compound comprising the gap-disabled motif 3-2-1-2-1-2-1-2-1-2-3. These methods may also comprise identifying an animal in need of lowering body weight, fat depot weight or food intake.

The present invention also provides methods of reducing serum cholesterol, triglycerides or body weight in an obese animal comprising contacting the animal with a gap-disabled compound comprising the gap-disabled motif of 3-2-1-2-1-2-1-2-1-2-3. These methods may also comprise identifying an obese animal in need of reducing serum cholesterol, triglycerides or body weight.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Examples 1-17

Figure 2:
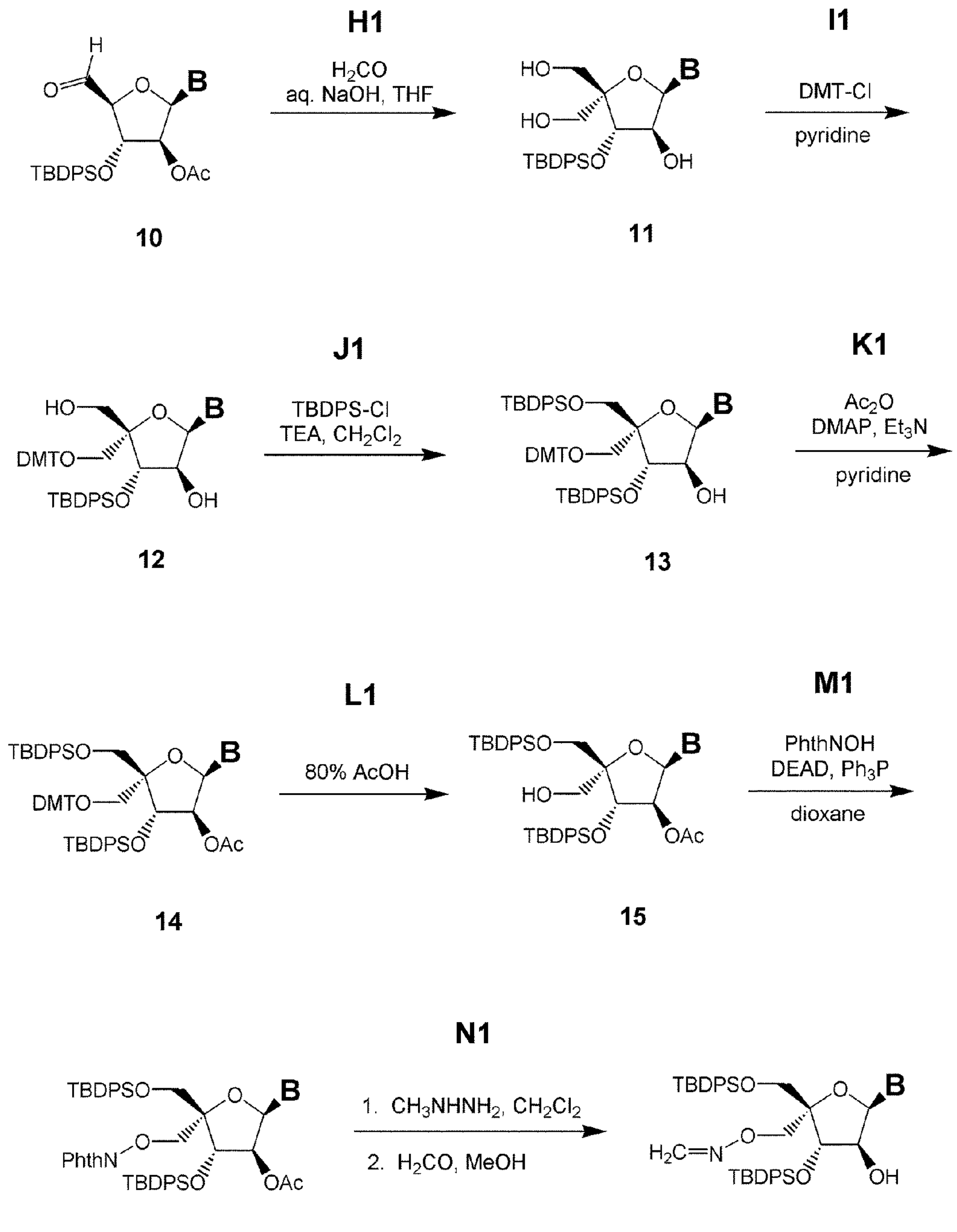
FIG. 2 shows scheme I (continued) depicting iterative synthesis of compound 17.
Figure 3:
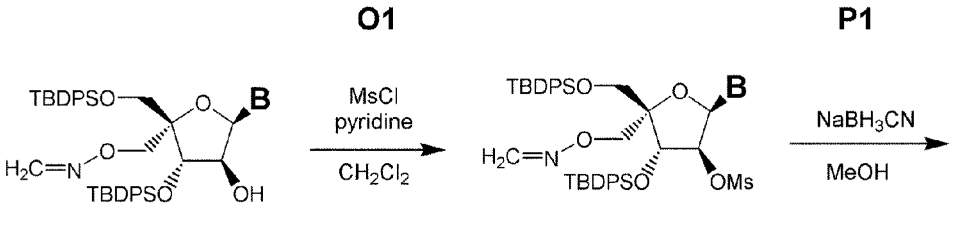
FIG. 3 shows scheme I (continued) depicting iterative synthesis of compound 1.
Figure 3:
Figure 4:
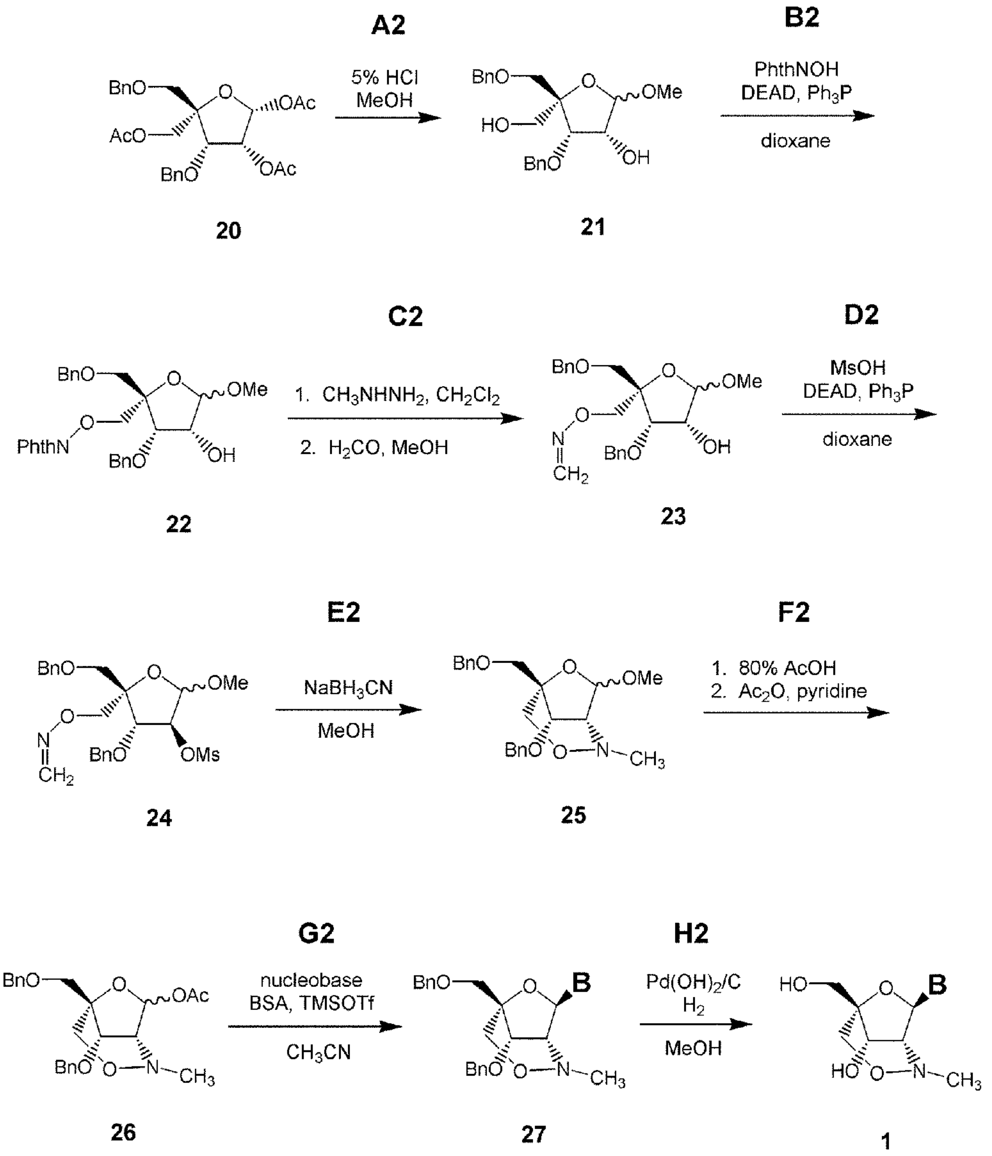
FIG. 4 shows scheme II depicting an alternate iterative synthesis of compound 1 starting with compound 20.
Figure 5:
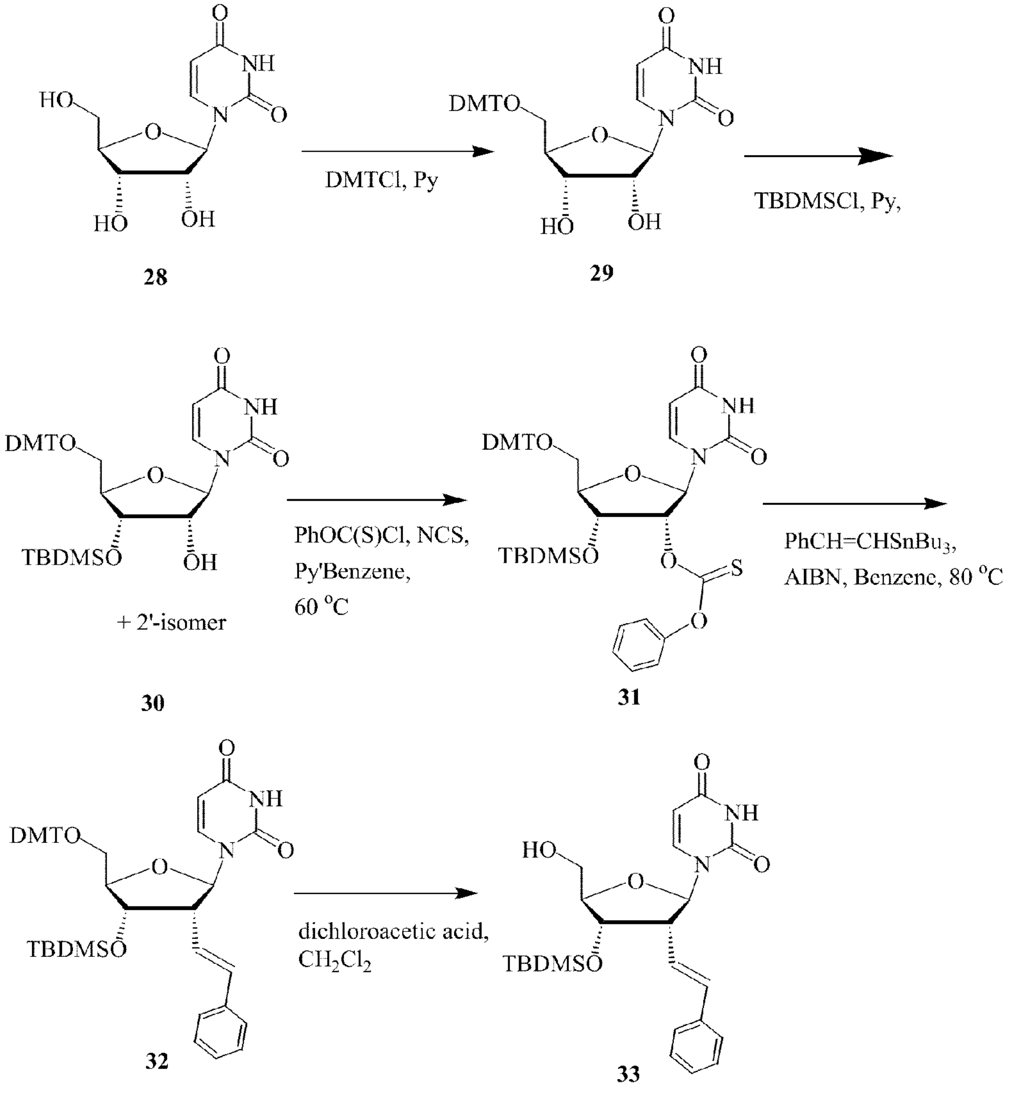
FIG. 5 shows scheme III depicting iterative synthesis of compound 33.
Figure 6:
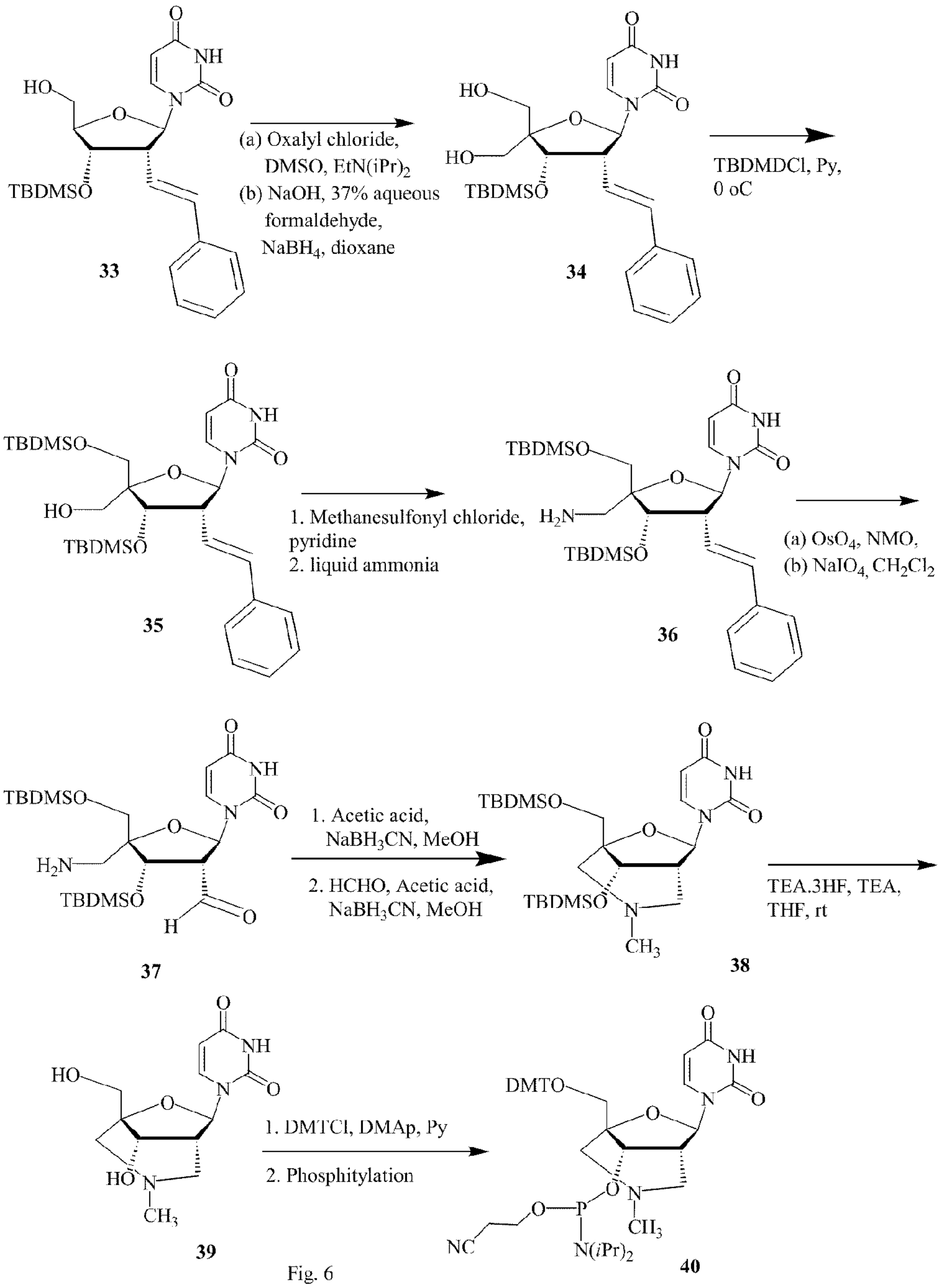
FIG. 6 shows scheme IV depicting iterative synthesis of compound 40.
Figure 7:
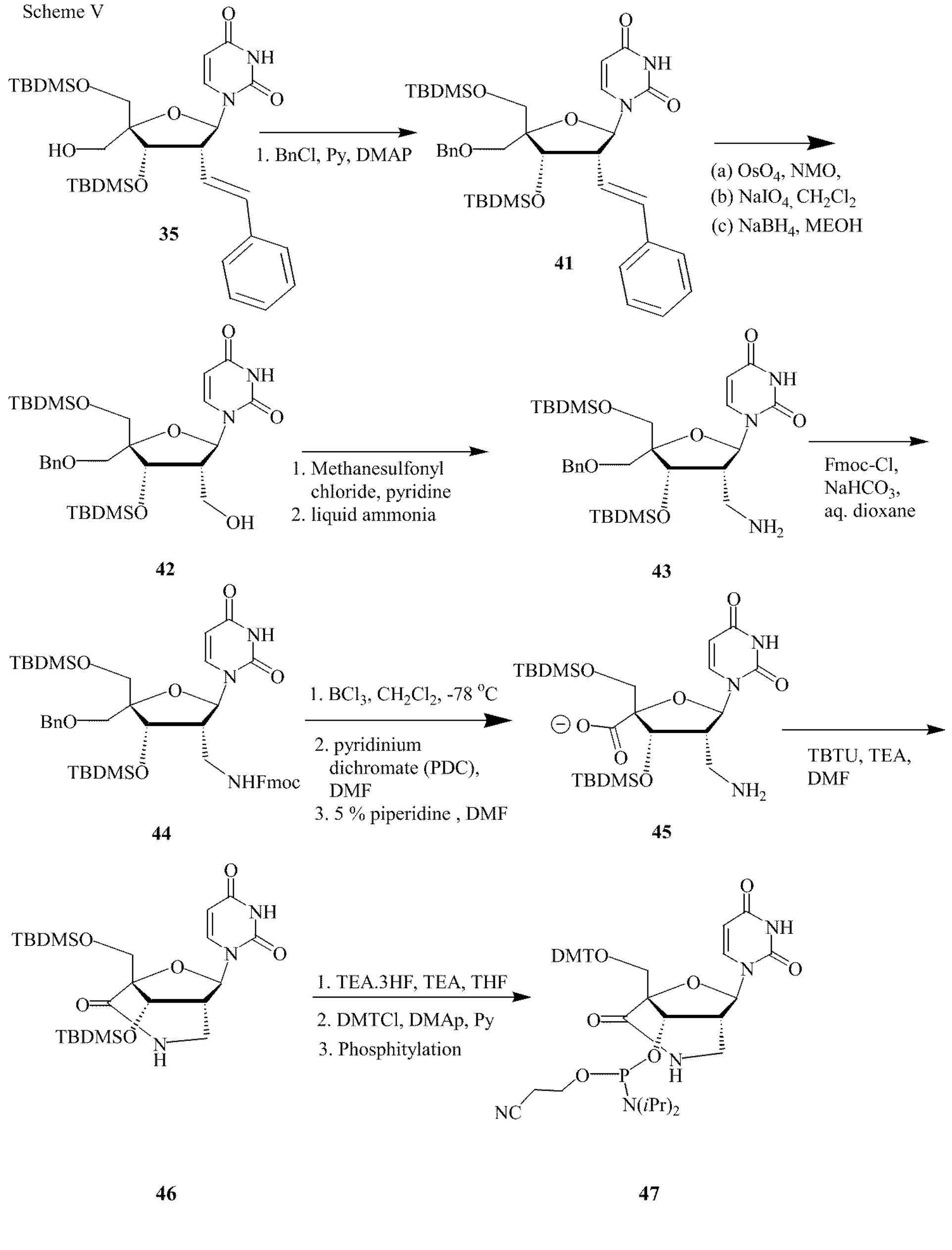
FIG. 7 shows scheme V depicting iterative synthesis of compound 47.

Scheme I, FIGS. 1-3

Preparation of 1-(8-hydroxy-5-hydroxymethyl-2-methyl-3,6-dioxa-2-aza-bicyclo[3.2.1]oct-7-yl)-1H-pyrimidine-2,4-dione (1)

1

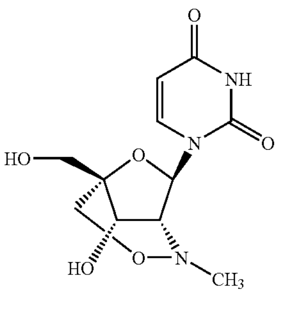

Example 1

1-(3-hydroxy-5,5,7,7-tetraisopropyl-tetrahydro-1,4,6,8-tetraoxa-5,7-disila-cyclopentacycloocten-2-yl)-1H-pyrimidine-2,4-dione (4)

The 3',5'-protected nucleoside is prepared as illustrated in Karpeisky, A., et. al., Tetrahedron Lett. 1998, 39, 1131-1134. To a solution of arabinouridine (3, 1.0 eq., 0° C.) in anhydrous pyridine is added 1,3-dichloro-1,1,3,3-tetraisopropyldisiloxane (1.1 eq.). The resulting solution is warmed to room temperature and stirred for two hours. The reaction mixture is subsequently quenched with methanol, concentrated to an oil, dissolved in dichloromethane, washed with aqueous $NaHCO_3$ and saturated brine, dried over anhydrous $Na_2SO_4$, filtered, and evaporated. Purification by silica gel chromatography will yield Compound 4.

For the preparation of the corresponding cytidine and adenosine analogs, $N^4$-benzoyl arabinocytidine and $N^6$-benzoyl arabinoadenosine are used, respectively, both of which are prepared from the unprotected arabinonucleoside using the transient protection strategy as illustrated in Ti, et al., *J. Am. Chem. Soc.* 1982, 104, 1316-1319. Alternatively, the cytidine analog can also be prepared by conversion of the uridine analog as illustrated in Lin, et al., *J. Med. Chem.* 1983, 26, 1691.

Example 2

Acetic Acid 2-(2,4-dioxo-3,4-dihydro-2H-pyrimidin-1-yl)-5,5,7,7-tetraisopropyl-tetrahydro-1,4,6,8-tetraoxa-5,7-disila-cyclopentacycloocten-3-yl Ester (5)

Compound 4 is O-Acetylated using well known literature procedures (Protective Groups in Organic Synthesis, 3rd edition, 1999, pp. 150-160 and references cited therein and in Greene, T. W. and Wuts, P. G. M., eds, Wiley-Interscience, New York.) Acetic anhydride (2 to 2.5 eq.) and triethylamine (4 eq.) is added to a solution of 4 (1 eq.) and N,N-dimethylaminopyridine (0.1 eq.) in anhydrous pyridine. After stirring at room temperature for 1 hour the mixture is treated with methanol to quench excess acetic anhydride and evaporated. The residue is redissolved in ethyl acetate, washed extensively with aqueous $NaHCO_3$, dried over anhydrous $Na_2SO_4$, filtered, and evaporated. The compound is used without further purification.

Example 3

Acetic Acid 2-(2,4-dioxo-3,4-dihydro-2H-pyrimidin-1-yl)-4-hydroxy-5-hydroxymethyl-tetrahydro-furan-3-yl Ester (6)

The Tips protecting group is removed from Compound 5 as illustrated in the literature (Protective Groups in Organic Synthesis, 3rd edition, 1999, pp. 239 and references therein, Greene, T. W. and Wuts, P. G. M., eds, Wiley-Interscience, New York). To a solution of 5 (1 eq.) in anhydrous dichloromethane is added triethylamine (2 eq.) and triethylamine trihydrofluoride (2 eq.). The reaction mixture is monitored by thin layer chromatography until complete at which point the reaction mixture is diluted with additional dichloromethane, washed with aqueous $NaHCO_3$, dried over anhydrous $Na_2SO_4$, and evaporated. The resulting Compound 6 is optionally purified by silica gel chromatography.

Example 4

Acetic Acid 5-[bis-(4-methoxy-phenyl)-phenyl-methoxymethyl]-2-(2,4-dioxo-3,4-dihydro-2H-pyrimidin-1-yl)-4-hydroxy-tetrahydro-furan-3-yl Ester (7)

Dimethoxytritylation of Compound 6 is performed using known literature procedures. Formation of the primary 4,4'-dimethoxytrityl ether should be achieved using standard conditions (Nucleic Acids in Chemistry and Biology, 1992, pp. 108-110, Blackburn, Michael G., and Gait, Michael J., eds, IRL Press, New York.) Generally, a solution of 6 (1 eq.) and N,N-dimethylaminopyridine (0.1 eq.) in anhydrous pyridine is treated with 4,4'-dimethoxytrityl chloride (DMTCl, 1.2 eq.) and triethylamine (4 eq.). After several hours at room temperature, excess 4,4'-dimethoxytrityl chloride is quenched with the addition of methanol and the mixture is evaporated. The mixture is dissolved in dichloromethane and washed extensively with aqueous $NaHCO_3$ and dried over anhydrous $Na_2SO_4$. Purification by silica gel chromatography will yield Compound 7.

Example 5

Acetic Acid 5-[bis-(4-methoxy-phenyl)-phenyl-methoxymethyl]-4-(tert-butyl-diphenyl-silanyloxy)-2-(2,4-dioxo-3,4-dihydro-2H-pyrimidin-1-yl)-tetrahydro-furan-3-yl Ester (8)

The preparation of tert-butyldiphenylsilyl ethers is a common, routine procedure (Protective Groups in Organic Synthesis, 3rd edition, 1999, pp. 141-144 and references therein, Greene, T. W. and Wuts, P. G. M., eds, Wiley-Interscience, New York). In general, a solution of one eq. of 7 and imidazole (3.5 eq.) in anhydrous N,N-dimethylformamide (DMF) is treated with tert-butyldiphenylsilyl chloride (1.2 eq.). After stirring at room temperature for several hours, the reaction mixture is poured into ethyl acetate and washed extensively with water and saturated brine solution. The resulting organic solution is dried over anhydrous sodium sulfate, filtered, evaporated, and purified by silica gel chromatography to give Compound 8.

Example 6

Acetic Acid 4-(tert-butyl-diphenyl-silanyloxy)-2-(2,4-dioxo-3,4-dihydro-2H-pyrimidin-1-yl)-5-hydroxymethyl-tetrahydro-furan-3-yl Ester (9)

The 5'-O-DMT group is removed as per known literature procedures 4,4'-dimethoxytrityl ethers are commonly removed under acidic conditions (Oligonucleotides and analogues, A Practical Approach, Eckstein, F., ed, IRL Press, New York.) Generally, Compound 8 (1 eq.) is dissolved in 80% aqueous acetic acid. After several hours, the mixture is evaporated, dissolved in ethyl acetate and washed with a sodium bicarbonate solution. Purification by silica gel chromatography will give compound 9.

Example 7

Acetic Acid 4-(tert-butyl-diphenyl-silanyloxy)-2-(2,4-dioxo-3,4-dihydro-2H-pyrimidin-1-yl)-5-formyl-tetrahydro-furan-3-yl Ester (10)

To a mixture of trichloroacetic anhydride (1.5 eq.) and dimethylsulfoxide (2.0 eq.) in dichloromethane at −78° C. is added a solution of Compound 9 in dichloromethane. After 30 minutes, triethylamine (4.5 eq.) is added. Subsequently, the mixture is poured into ethyl acetate, washed with water and brine, dried over anhydrous sodium sulfate, and evaporated to dryness. The resulting material is carried into the next step without further purification. This procedure has been used to prepare the related 4'-C-α-formyl nucleosides (Nomura, M., et. al., *J. Med. Chem.* 1999, 42, 2901-2908).

Example 8

1-[4-(tert-butyl-diphenyl-silanyloxy)-3-hydroxy-5,5-bis-hydroxymethyl-tetrahydro-furan-2-yl]-1H-pyrimidine-2,4-dione (11)

Hydroxymethylation of the 5'-aldehyde is performed as per the method of Cannizzaro which is well documented in the literature (Jones, G. H., et. al., J. Org. Chem. 1979, 44, 1309-1317). These conditions are expected to additionally remove the 2'-O-acetyl group. Generally, Briefly, formaldehyde (2.0 eq., 37% aq.) and NaOH (1.2 eq., 2 M) is added to a solution of Compound 10 in 1,4-dioxane. After stirring at room temperature for several hours, this mixture is neutralized with acetic acid, evaporated to dryness, suspended in methanol, and evaporated onto silica gel. The resulting mixture is added to the top of a silica gel column and eluted using an appropriate solvent system to give Compound 11.

Example 9

1-[5-[bis-(4-methoxy-phenyl)-phenyl-methoxymethyl]-4-(tert-butyl-diphenyl-silanyloxy)-3-hydroxy-5-hydroxymethyl-tetrahydro-furan-2-yl]-1H-pyrimidine-2,4-dione (12)

Preferential protection with DMT at the α-hydroxymethyl position is performed following a published literature procedure (Nomura, M., et. al., J. Med. Chem. 1999, 42, 2901-2908). Generally, a solution of Compound 11 (1 eq.) in anhydrous pyridine is treated with DMTCl (1.3 eq.), then stirred at room temperature for several hours. Subsequently, the mixture is poured into ethyl acetate, washed with water, dried over anhydrous $Na_2SO_4$, filtered, and evaporated. Purification by silica gel chromatography will yield Compound 12.

Example 10

1-[5-[bis-(4-methoxy-phenyl)-phenyl-methoxymethyl]-4-(tert-butyl-diphenyl-silanyloxy)-5-(tert-butyl-diphenyl-silanyloxymethyl)-3-hydroxy-tetrahydro-furan-2-yl]-1H-pyrimidine-2,4-dione (13)

The 5'-hydroxyl position is selectively protected with tert-butyldiphenylsilyl following published literature procedures (Protective Groups in Organic Synthesis, $3^{rd}$ edition, 1999, pp. 141-144 and references therein, Greene, T. W. and Wuts, P. G. M., eds, Wiley-Interscience, New York). Generally, a solution of Compound 12 (1 eq.) and N,N-dimethylaminopyridine (0.2 eq.) in anhydrous dichloromethane is treated with tert-butyldiphenylsilyl chloride (1.2 eq.) and triethylamine (4 eq.). After several hours at room temperature, the reaction is quenched with methanol, poured into ethyl acetate, washed with saturated $NaHCO_3$, saturated brine, dried over anhydrous $Na_2SO_4$, filtered, and evaporated. Purification by silica gel chromatography will yield Compound 13.

Example 11

Acetic Acid 5-[bis-(4-methoxy-phenyl)-phenyl-methoxymethyl]-4-(tert-butyl-diphenyl-silanyloxy)-5-(tert-butyl-diphenyl-silanyloxymethyl)-2-(2,4-dioxo-3,4-dihydro-2H-pyrimidin-1-yl)-tetrahydro-furan-3-yl Ester (14)

Compound 14 is prepared as per the procedure illustrated in Example 2 above.

Example 12

Acetic Acid 4-(tert-butyl-diphenyl-silanyloxy)-5-(tert-butyl-diphenyl-silanyloxymethyl)-2-(2,4-dioxo-3,4-dihydro-2H-pyrimidin-1-yl)-5-hydroxymethyl-tetrahydro-furan-3-yl Ester (15)

Compound 15 is prepared as per the procedure illustrated in Example 9 above.

Example 13

Acetic Acid 4-(tert-butyl-diphenyl-silanyloxy)-5-(tert-butyl-diphenyl-silanyloxymethyl)-5-(1,3-dioxo-1,3-dihydro-isoindol-2-yloxymethyl)-2-(2,4-dioxo-3,4-dihydro-2H-pyrimidin-1-yl)-tetrahydro-furan-3-yl Ester (16)

The use of the Mitsunobu procedure to generate the 5'-O-phthalimido nucleosides starting with the 5'-unprotected nucleosides has been reported previously (Perbost, M., et. al., *J. Org. Chem.* 1995, 60, 5150-5156). Generally, a mixture of Compound 15 (1 eq.), triphenylphosphine (1.15 eq.), and N-hydroxyphthalimide (PhthNOH, 1.15 eq.) in anhydrous 1,4-dioxane is treated with diethyl azodicarboxylate (DEAD, 1.15 eq.). The reaction is stirred at room temperature for several hours until complete by thin layer chromatography. The resulting mixture is evaporated, suspended in ethyl acetate, washed with both saturated $NaHCO_3$ and saturated brine, dried over anhydrous $Na_2SO_4$, filtered and evaporated. Purification by silica gel chromatography will yield Compound 16.

Example 14

1-[4-(tert-butyl-diphenyl-silanyloxy)-5-(tert-butyl-diphenyl-silanyloxymethyl)-3-hydroxy-5-methylene-aminooxymethyl-tetrahydro-furan-2-yl]-1H-pyrimidine-2,4-dione (17)

This transformation is performed smoothly in high yield using published procedures (Bhat, B., et. al., *J. Org. Chem.* 1996, 61, 8186-8199). Generally, a portion of Compound 16 is dissolved in dichloromethane and cooled to −10° C. To this solution is added methylhydrazine (2.5 eq.). After 1-2 hours of stirring at 0° C., the mixture is diluted with dichloromethane, washed with water and brine, dried with anhydrous $Na_2SO_4$, filtered, and evaporated. The resulting residue is immediately redissolved in a 1:1 mixture of ethyl acetate: methanol, and treated with 20% (w/w) aqueous formaldehyde (1.1 eq.). After an hour at room temperature, the mixture is concentrated then purified by silica gel chromatography to give Compound 17.

Example 15

Methanesulfonic Acid 4-(tert-butyl-diphenyl-silanyloxy)-5-(tert-butyl-diphenyl-silanyloxymethyl)-2-(2,4-dioxo-3,4-dihydro-2H-pyrimidin-1-yl)-5-methyleneaminooxymethyl-tetrahydro-furan-3-yl Ester (18)

The mesylation of hydroxyl groups proceeds readily under these conditions (Protective Groups in Organic Synthesis, $3^{rd}$ edition, 1999, pp. 150-160 and references cited therein). Briefly, to a solution of Compound 17 in a 1:1 mixture of anhydrous dichloromethane and anhydrous pyridine is added methanesulfonyl chloride (1.2 eq.). After stirring at room temperature for several hours, this mixture is quenched with methanol, concentrated, diluted with dichloromethane, washed with aqueous $NaHCO_3$ and brine, dried over anhydrous $Na_2SO_4$, filtered and evaporated. Purification by silica gel chromatography will yield Compound 18.

Example 16

1-[8-(tert-butyl-diphenyl-silanyloxy)-5-(tert-butyl-diphenyl-silanyloxymethyl)-2-methyl-3,6-dioxa-2-aza-bicyclo[3.2.1]oct-7-yl]-1H-pyrimidine-2,4-dione (19)

The reduction of the formaldoxime moiety is performed as per known literature procedures. Generally, a solution of Compound 18 in methanol is treated with sodium cyanoborohydride (1.5 eq.). This treatment will result in quantitative reduction of the formaldoxime moiety to yield the 4'-C-(aminooxymethyl) arabinonucleoside. The proximity of the methylated electron-rich amine to the activated 2'-O-mesylate will result in the spontaneous ring closing of this intermediate to yield bicyclic Compound 19. The reaction is monitored by thin layer chromatography until completion. The mixture is then poured into ethyl acetate, washed extensively with aqueous $NaHCO_3$ and brine, dried over anhydrous $Na_2SO_4$, filtered and evaporated. Purification by silica gel chromatography will yield Compound 19.

Example 17

1-(8-hydroxy-5-hydroxymethyl-2-methyl-3,6-dioxa-2-aza-bicyclo[3.2.1]oct-7-yl)-1H-pyrimidine-2,4-dione (1)

The tert-butyldiphenylsilyl ether protecting groups are readily cleaved by treatment with tetrabutylammonium fluoride (Protective Groups in Organic Synthesis, $3^{rd}$ edition, 1999, pp. 141-144 and references therein, Greene, T. W. and Wuts, P. G. M., eds, Wiley-Interscience, New York). Briefly, a solution of Compound 19 in a minimal amount of tetrahydrofuran (THF) is treated with a 1 M solution of tetrabutylammonium fluoride (TBAF, 5-10 eq.) in THF. After several hours at room temperature, this mixture is evaporated onto silica gel and subjected to silica gel chromatography to give Compound 1.

Alternate Synthetic Route to Compound 1, Synthesis of Guanosine Analog

Examples 18-25 Scheme II, FIGS. 4-7

Example 18

4-benzyloxy-5-benzyloxymethyl-5-hydroxymethyl-2-methoxy-tetrahydro-furan-3-ol (21)

The preparation of the protected 4'-C-hydroxymethylribofuranose, Compound 20, follows published literature procedures (Koshkin, A. A., et. al., *Tetrahedron* 1998, 54, 3607-3630). Compound 20 (1 eq.) is dissolved in anhydrous methanol and hydrogen chloride in an anhydrous solvent (either methanol or 1,4-dioxane) is added to give a final concentration of 5% (w/v). After stirring at room temperature for several hours, the mixture is concentrated to an oil, dried under vacuum, and used in the next step without further purification.

Example 19

2-(3-benzyloxy-2-benzyloxymethyl-4-hydroxy-5-methoxy-tetrahydro-furan-2-ylmethoxy)-isoindole-1,3-dione (22)

The O-phthalimido compound is prepared following the reference cited and the procedures illustrated in Example 13 above. The reaction can be adjusted to preferentially react at the primary hydroxyl e.g. the 4'-C-hydroxymethyl group (Bhat, B., et. al., *J. Org. Chem.* 1996, 61, 8186-8199). Generally, a solution of 21 (1 eq.), N-hydroxyphthalimide (1.1 eq.), and triphenylphosphine (1.1 eq.) in anhydrous tetrahydrofuran is treated with diethyl azodicarboxylate (1.1 eq.). After several hours at room temperature, the mixture is concentrated and subjected to silica gel chromatography to give Compound 22.

Example 20

Formaldehyde O-(3-benzyloxy-2-benzyloxymethyl-4-hydroxy-5-methoxy-tetrahydro-furan-2-ylmethyl)-oxime (23)

Compound 23 is prepared as per the procedure illustrated in Example 14 above.

Example 21

Methanesulfonic Acid 4-benzyloxy-5-benzyloxymethyl-2-methoxy-5-methylene-aminooxymethyl-tetrahydro-furan-3-yl Ester (24)

Mesylation is achieved with inversion of configuration using Mitsunobu conditions (Anderson, N. G., et. al., *J. Org. Chem.* 1996, 60, 7955). Generally, a mixture of Compound 23 (1 eq.), triphenylphosphine (1.2 eq.) and methanesulfonic acid (1.2 eq.) in anhydrous 1,4-dioxane is treated with diethyl azodicarboxylate (1.2 eq.). After stirring at room temperature for several hours, the resulting mixture is concentrated and subjected to silica gel chromatography to give Compound 24.

Example 22

8-benzyloxy-5-benzyloxymethyl-7-methoxy-2-methyl-3,6-dioxa-2-aza-bicyclo[3.2.1]octane (25)

Compound 25 is prepared as per the procedure illustrated in Example 16 above.

Example 23

Acetic Acid 8-benzyloxy-5-benzyloxymethyl-2-methyl-3,6-dioxa-2-aza-bicyclo[3.2.1]oct-7-yl Ester (26)

Compound 25 is dissolved in 80% (v/v) aqueous acetic acid. After 1-2 hours at room temperature, the solution is concentrated, then dissolved in dichloromethane and washed with saturated aqueous $NaHCO_3$ and brine. The organic portion is subsequently dried over anhydrous $Na_2SO_4$, filtered, and concentrated. The resulting mixture is coevaporated from anhydrous pyridine, then dissolved in anhydrous pyridine and treated with acetic anhydride (2 eq.). The solution is stirred overnight, quenched with methanol, dissolved in ethyl acetate and washed extensively with saturated $NaHCO_3$. The organic portion is then dried ($Na_2SO_4$), filtered and evaporated without further purification.

Example 24

1-(8-benzyloxy-5-benzyloxymethyl-2-methyl-3,6-dioxa-2-aza-bicyclo[3.2.1]oct-7-yl)-1H-pyrimidine-2,4-dione (27)

Compound 26 is converted to one of several N-glycosides (nucleosides) using published chemistry procedures including either Vorbrüggen chemistry or one of several other methods (Chemistry of Nucleosides and Nucleotides, Volume 1, 1988, edited by Leroy B. Townsend, Plenum Press, New York). To prepare the uradinyl analog, a mixture of Compound 26 (1 eq.) and uracil (1.3 eq.) is suspended in anhydrous acetonitrile. To the suspension is added N,O-bis-(trimethylsilyl)-acetamide (BSA, 4 eq.). The suspension is heated to 70° C. for 1 hour, then cooled to 0° C. and treated with trimethylsilyl-trifluoromethanesulfonate (TMSOTf, 1.6 eq.). The resulting solution is heated at 55° C. until the reaction appears complete by TLC. The reaction mixture is poured into ethyl acetate and washed extensively with saturated $NaHCO_3$, dried over anhydrous $Na_2SO_4$, filtered, evaporated, and purified by silica gel chromatography to give Compound 24.

In order to use the above preparation with nucleobases with reactive functional groups the reactive functional groups are protected prior to use. For example such protected nucleobases include naturally occurring nucleobases such as $N^4$-benzoyl cytosine, $N^6$-benzoyl adenine and $N^2$-isobutyryl guanine.

Example 25

1-(8-hydroxy-5-hydroxymethyl-2-methyl-3,6-dioxa-2-aza-bicyclo[3.2.1]oct-7-yl)-1H-pyrimidine-2,4-dione (1)

To give the desired product, Compound 1 the benzyl ethers protecting groups are removed following published literature procedures (Koshkin, A. A., et. al., *Tetrahedron* 1998, 54, 3607-3630). Generally, the bis-O-benzylated bicyclic Compound 27 is dissolved in methanol. To this solution is added 20% $Pd(OH)_2/C$, and the resulting suspension is maintained under an atmosphere of $H_2$ at 1-2 atm pressure. This mixture is stirred at room temperature for several hours until complete by TLC, at which point the $Pd(OH)_2/C$ is removed by filtration, and the filtrate is concentrated and purified by silica gel chromatography, if necessary, to give Compound 1.

Example 26

2'-O-tert-butyldimethylsilyl-3'-C-styryluridine (33)

Compound 28 is treated with DMTCl, in pyridine in presence of DMAP to get 5'-DMT derivative, Compound 29. Compound 29 is treated with TBDMSCl in pyridine to which yields both the 2' and the 3'-silyl derivative. The 3'-TBDMS derivative is isolated by silica gel flash column chromatography and further heated with phenyl chlorothionoformate and N-chlorosuccinimide in a solution of pyridine in benzene 60° C. to give Compound 31. Compound 31 is treated with β-tributylstannylstyrene and AIBN in benzene give Compound 32. Compound 32 is detritylated with dichloroacetic acid in dichloromethane give compound 33.

Example 27

1-[(1R,3R,8S)-8-[(2-cyanoethyl)bis(1-methylethyl) phosphoramidite)-3-[(4,4'-dimethoxytrityloxy)methyl]-5-methyl-2-oxo-5-azabicyclo[2.3.1]octane-5-methyl-2,4-(1H,3H)-pyrimidinedione (40)

Compound 33 is treated with oxalyl chloride in DMSO in the presence of ethyl diisopropylamine to give the 5'-aldehyde which is then subjected to a tandem aldol condensation and Cannizzaro reaction using aqueous formaldehyde and 1 M NaOH in 1,4-dioxane to yield the diol, Compound 34. Selective silylation with TBDMSCl in pyridine and isolation of the required isomer will give Compound 35. Compound 35 is treated with methanesulfonyl chloride in pyridine to give the methane sulfonyl derivative which is treated with methanolic ammonia to give compound 36. The double bond of Compound 36 is oxidatively cleaved by oxymylation go give the diol and then by cleavage of the diol with sodium periodate to give the aldehyde, Compound 37. The amino and aldehyde groups in Compound 37 are cross coupled under reductive condition followed by methylation of the amino group with formaldehyde in the presence of sodium borohydride will give the Compound 38. Treatment of Compound 38 with triethylamine trihydrofluoride and triethylamine in THF will give Compound 39. The primary alcohol of Compound 39 is selectively titylated with DMTCl in pyridine followed by phosphytilation at 8-position to give Compound 40.

Example 28

1-[(1R,3R,8S)-8-[(2-cyanoethyl)bis(1-methylethyl) phosphoramidite)-3-[(4,4'-dimethoxytrityloxy)methyl]-5-methyl-2-oxo-5-azabicyclo[3.2.1]octan-4-one-5-methyl-2,4-(1H,3H)-pyrimidinedione (47)

Compound 35 is benzylated with benzyl bromide in DMF and sodium hydride to give Compound 41. Oxidative cleavage of Compound 41 will give an aldehyde at the 2'-position which is reduced to the corresponding alcohol using sodium borohydride in methanol to give Compound 42. Compound 42 is converted into the 3'-C-aminomethyl derivative, Compound 43 by in situ generation of the methane sulfonyl derivative and treatment with ammonia. The amino group in Compound 43 is protected with an Fmoc protecting group using Fmoc-Cl and sodium bicarbonate in aqueous dioxane to give Compound 44. Deprotection of the benzyl group is achieved with $BCl_3$ in dichloromethane at −78° C. followed by oxidation of the alcohol with pyridinium dichromate in DMF give the corresponding carboxylic acid. The deprotection of the Fmoc group releases the amino group at the 2'-position to give Compound 45. Compound 45 is treated with TBTU (2-(1H-benzotriazole-1-yl)-1,1,3,3-tetramethyluroniumtetrafluoroborate) and triethylamine in DMF to yield Compound 46. Compound 46 is desilylated with triethylamine trihydrofluoride in triethylamine in THF followed by tritylation at 3 position to give the 3-trityloxymethyl derivative followed by phosphytilation at 8-position to give Compound 47. The DMT phosphoramidite bicyclic nucleoside, Compound 47 is purified by silica gel flash column chromatography.

Example 29

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl)nucleoside amidites and 2'-O-(dimethylaminooxyethyl)nucleoside amidites, 2'-(Dimethylaminooxyethoxy)nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy(2'-DMAEOE)nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 30

Oligonucleotide and Oligonucleoside Synthesis

The chimeric oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P═O) oligonucleotides are synthesized on an automated DNA synthesizer (Applied Biosystems model 394) using standard phosphoramidite chemistry with oxidation by iodine.

Phosphorothioates (P═S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P═O or P═S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 31

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., J. Am. Chem. Soc., 1998, 120, 11820-11821; Matteucci, M. D. and Caruthers, M. H. J. Am. Chem. Soc., 1981, 103, 3185-3191; Beaucage, S. L. and Caruthers, M. H. Tetrahedron Lett., 1981, 22, 1859-1862; Dahl, B. J., et al., Acta Chem. Scand., 1990, 44, 639-641; Reddy, M. P., et al., Tetrahedron Lett., 1994, 25, 4311-4314; Wincott, F. et al., Nucleic Acids Res., 1995, 23, 2677-2684; Griffin, B. E., et al., Tetrahedron, 1967, 23, 2301-2313; Griffin, B. E., et al., Tetrahedron, 1967, 23, 2315-2331).

RNA oligomeric compounds (RNA oligonucleotides) for use in the present invention can be synthesized by the methods herein or purchased from Dharmacon Research, Inc (Lafayette, Colo.). Once synthesized, complementary RNA oligomeric compounds can then be annealed by methods known in the art to form double stranded (duplexed) oligomeric compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed oligomeric compounds can be used in kits, assays, screens, or other methods to investigate the role of a target nucleic acid.

Example 32

Synthesis of Chimeric Oligomeric Compounds

Chimeric oligomeric compounds, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligomeric compounds having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligonucleotide is then recovered by an appropriate method (precipitation, column chromatography, volume reduced in vacuo and analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligomeric compound, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric oligomeric compounds

[2'-O-(2-methoxyethyl phosphodiester]-[2'-deoxy phosphorothioate]-[2'-O-(methoxyethyl) phosphodiester] chimeric oligomeric compounds are prepared as per the above procedure for the 2'-O-methyl chimeric oligomeric compound with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

The above methods are also applicable to the synthesis of chimeric oligomeric compounds having multiple alternating regions such as olignucleotides having the formula: $T_1$-(3'-endo region)-[(2'-deoxy region)-(3'-endo region)]$_n$-$T_2$. The use of 2'-MOE or other nucleoside amidites will enable the preparation of a myriad of different oligonucleotides.

Other chimeric oligomeric compounds, chimeric oligonucleosides and mixed chimeric oligomeric compounds/oligonucleosides are synthesized according to U.S. Pat. No. 5,623,065, herein incorporated by reference.

Example 33

Screening of Duplexed Oligomeric Compounds of the Invention

In accordance with the present invention, nucleic acid duplexes comprising the oligonucleotides of the invention and their complements are tested for their ability to modulate the expression of the nucleic acid molecule to which they are targeted. The desired RNA strand(s) of the duplex can be synthesized by methods disclosed herein or purchased from various RNA synthesis companies such as for example Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of the buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA compound is 20 uM. This solution can be stored frozen (−20° C.) and freeze-thawed up to 5 times.

Once prepared, the desired synthetic duplexes are evaluated for their ability to modulate target expression. When cells reach approximately 60-80% confluency, they are treated with synthetic duplexes comprising at least one oligomeric compound of the invention. The duplexes are mixed with LIPOFECTIN™ (Invitrogen Life Technologies, Carlsbad, Calif.) in 1 mL of Opti-MEM™-1 reduced serum medium (Invitrogen Life Technologies, Carlsbad, Calif.) to achieve the desired final concentration of duplex. This transfection mixture was incubated at room temperature for approximately 0.5 hours. The final concentration of duplex ranges from 10 to 200 nM. LIPOFECTIN™ is used at a concentration of 5 or 6 μg/mL LIPOFECTIN™ per 200 nM of duplex. For cells grown in 96-well plates, wells were washed once with 100 μL OPTI-MEM™-1 and then treated with 130 μL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh medium. Cells were harvested 16-24 hours after oligonucleotide treatment, at which time RNA is isolated and target reduction is measured by real-time PCR or Northern blot.

Example 34

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., J. Biol. Chem. 1991, 266, 18162-18171. Results obtained with HPLC-purified material were similar to those obtained with non-HPLC purified material.

Example 35

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 36

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the oligomeric compounds utilizing electrospray-mass spectroscopy. All assay test plates were diluted from the master plate using single and multi-channel robotic pipettors. Plates were judged to be acceptable if at least 85% of the oligomeric compounds on the plate were at least 85% full length.

Example 37

Cell Culture and Oligonucleotide Treatment

The effect of chimeric oligomeric compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or real-time PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal bovine serum (Invitrogen Corporation, Carlsbad, Calif.), 100 units per mL penicillin and 100 micrograms per mL streptomycin (Invitrogen Corporation, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 4000-6000 cells/well for use in oligomeric compound transfection experiments.

A549 Cells:

The human lung carcinoma cell line A549 was obtained from the American Type Culture Collection (Manassas, Va.). A549 cells were routinely cultured in DMEM, high glucose (Invitrogen Life Technologies, Carlsbad, Calif.) supplemented with 10% fetal bovine serum, 100 units per ml penicillin, and 100 micrograms per ml streptomycin (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 5000 cells/well for use in oligomeric compound transfection experiments.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

HeLa Cells:

The human epitheloid carcinoma cell line HeLa was obtained from the American Tissue Type Culture Collection (Manassas, Va.). HeLa cells were routinely cultured in DMEM, high glucose (Invitrogen Corporation, Carlsbad, Calif.) supplemented with 10% fetal bovine serum (Invitrogen Corporation, Carlsbad, Calif.). Cells were routinely passaged by trypsinization and dilution when they reached approximately 90% confluence. Cells were seeded into 24-well plates (Falcon-Primaria #353846, BD Biosciences, Bedford, Mass.) at a density of 50,000 cells/well or in 96-well plates (Falcon-Primaria #353872, BD Biosciences, Bedford, Mass.) at a density of 5,000 cells/well for use in oligomeric compound transfection experiments. For Northern blotting or other analyses, cells were harvested when they reached approximately 90% confluence.

NIH3T3 Cells:

The mouse embryo-derived NIH3T3 cell line was obtained from American Type Culture Collection (Manassas, Va.). NIH3T3 cells were routinely cultured in DMEM, high glucose (Invitrogen Life Technologies, Carlsbad, Calif.) supplemented with 10% fetal bovine serum, (Invitrogen Life Technologies, Carlsbad, Calif.), 100 μg/ml penicillin and 100 μg/ml streptomycin (Invitrogen Life Technologies, Carlsbad, Calif.). Cells were routinely passaged by trypsinization and dilution when they reached 80% confluencey. Cells were seeded into 96-well plates (Falcon-Primaria #353872, BD Biosciences, Bedford, Mass.) at a density of 3000 cells/well for use in oligomeric compound transfection experiments.

b.END Cells:

The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 3000 cells/well for use in oligomeric compound transfection experiments.

Primary Mouse Hepatocytes:

Primary mouse hepatocytes were prepared from CD-1 mice purchased from Charles River Labs. Primary mouse hepatocytes were routinely cultured in Hepatocyte Attachment Media supplemented with 10% fetal bovine serum, 1% penicillin/streptomycin, 1% antibiotic-antimycotic (Invitrogen Life Technologies, Carlsbad, Calif.) and 10 nM bovine insulin (Sigma-Aldrich, St. Louis, Mo.). Cells were seeded into 96-well plates (Falcon-Primaria #3872) coated with 0.1 mg/ml collagen at a density of approximately 10,000 cells/well for use in oligomeric compound transfection experiments.

Primary Rat Hepatocytes:

Primary rat hepatocytes are prepared from Sprague-Dawley rats purchased from Charles River Labs (Wilmington, Mass.) and are routinely cultured in DMEM, high glucose (Invitrogen Life Technologies, Carlsbad, Calif.) supplemented with 10% fetal bovine serum (Invitrogen Life Technologies, Carlsbad, Calif.), 100 units per mL penicillin, and 100 μg/mL streptomycin (Invitrogen Life Technologies, Carlsbad, Calif.). Cells are seeded into 96-well plates (Falcon-Primaria #353872, BD Biosciences, Bedford, Mass.) at a density of 4000-6000 cells/well for use in oligomeric compound transfection experiments.

MH-S Cells:

The mouse alveolar macrophage cell line was obtained from American Type Culture Collection (Manassas, Va.). MH-S cells were cultured in RPMI Medium 1640 with L-glutamine (Invitrogen Life Technologies, Carlsbad, Calif.), supplemented with 10% fetal bovine serum, 1 mM sodium pyruvate and 10 mM HEPES (all supplements from Invitrogen Life Technologies, Carlsbad, Calif.). Cells were routinely passaged by trypsinization and dilution when they reached 70-80% confluence. Cells were seeded into 96-well plates (Falcon-Primaria #353047, BD Biosciences, Bedford, Mass.) at a density of 6500 cells/well for use in oligomeric compound transfection experiments.

Treatment with Oligomeric Compounds:

When cells reached approximately 65-90% confluency, they were treated with oligomeric compound. Oligomeric compounds were mixed with LIPOFECTIN™ (Invitrogen Life Technologies, Carlsbad, Calif.) in 1 mL of Opti-MEM™-1 reduced serum medium (Invitrogen Life Technologies, Carlsbad, Calif.) to achieve the desired concentration of oligomeric compound. The concentration of oligomeric compound used herein ranges from 5 to 300 nM. This transfection mixture was incubated at room temperature for approximately 0.5 hours. LIPOFECTIN™ is used at a concentration of 2.5 or 3 μg/mL LIPOFECTIN™ per 100 nM oligomeric compound. For cells grown in 96-well plates, wells were washed once with 100 μL OPTI-MEM™ 1 and then treated with 130 μL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh medium. Cells were harvested 16-24 hours after oligonucleotide treatment, at which time RNA was isolated and target expression was measured by real-time PCR.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCT CCTCAGGG, SEQ ID NO: 7) which is targeted to human H-ras, or ISIS 18078 (GTGCGCGCGAGCCCGAAATC, SEQ ID NO: 8) which is targeted to human Jun-N-terminal kinase-2 (JNK2). Both controls are chimeric oligomeric compounds composed of a central "gap" segment comprising 2'-deoxynucleotides, which is flanked on both sides (5' and 3') by "wing" segments comprising 2'-O-methoxyethyl nucleotides (2'-O-methoxyethyls shown in emboldened, underlined type). Internucleoside linkages are phosphorothioate throughout both compounds. All cytosine residues in the wing segments are 5-methylcytosines. For mouse or rat cells the positive control oligonucleotide is ISIS 15770 ( ATGCATTCTGCCCCCAAGGA, SEQ ID NO: 9) is targeted to both mouse and rat C-raf. ISIS 15770 is a chimeric oligomeric compound composed of a central "gap" segment comprising 2'-deoxynucleotides, which is flanked on both sides (5' and 3') by "wing" segments comprising 2'-O-methoxyethyl nucleotides (2'-O-methoxyethyls shown in emboldened, underlined type). Internucleoside linkages are phosphorothioate throughout the compound. The cytosine residue in the 5' wing segment is a 5-methylcytosine. The concentration of positive control oligonucleotide that results in 80% inhibition of c-H-ras (for ISIS 13920), JNK2 (for ISIS 18078) or C-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or C-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 38

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently preferred. RNA analysis can be performed on total cellular RNA or poly(A)+ mRNA. One method of RNA analysis of the present invention is the use of total cellular RNA as described in other examples herein. Methods of RNA isolation are well known in the art. Northern blot analysis is also routine in the art. Quantitative real-time PCR can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 39

Design of Phenotypic Assays for the Use of Target Inhibitors

Once a target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

Example 40

RNA Isolation

Poly(A)+ mRNA Isolation

Poly(A)+ mRNA was isolated according to Miura et al., (Clin. Chem., 1996, 42, 1758-1764). Other methods for poly (A)+ mRNA isolation are routine in the art. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RW1 was added to each well of the RNEASY96™ plate and incubated for 15 minutes and the vacuum was again applied for 1 minute. An additional 500 μL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 41

Real-Time Quantitative PCR Analysis of a Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologics Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

Gene target quantities are obtained by real-time PCR. Prior to the real-time PCR, isolated RNA is subjected to a reverse transcriptase (RT) reaction, for the purpose of generating complementary DNA (cDNA). Reverse transcriptase and PCR reagents were obtained from Invitrogen Corporation (Carlsbad, Calif.). RT, real-time PCR reactions were carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real-time PCR are normalized using either the expression level of GAPDH or cyclophilin A, genes whose expression levels are constant, or by quantifying total RNA. GAPDH expression is quantified by real-time PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Primers and probes used in real-time PCR are designed with the aid of computer software, for example, Primer Express® Software (PE-Applied Biosystems, Foster City, Calif., Operon Technologies Inc., Alameda, Calif.), using publicly available sequence information. It is understood that one of skill in the art will readily be able to design such primers and probes.

Example 42

Northern Blot Analysis of a Target mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human a target, a human target-specific probe is prepared by PCR. To normalize for variations in loading and transfer efficiency membranes are stripped and probed for human glyceraldehyde-3-phosphate dehydrogenase (GAPDH) RNA (Clontech, Palo Alto, Calif.).

Hybridized membranes were visualized and quantitated using a PhosphorImager™ and IMAGEQUANT™ Software V3.3 (Molecular Dynamics, Sunnyvale, Calif.). Data was normalized to GAPDH levels in untreated controls.

Example 43

Western Blot Analysis of a Target Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PhosphorImager™ (Molecular Dynamics, Sunnyvale Calif.).

Example 44

Gene Target Sequences

In accordance with the present invention, a series of oligomeric compounds was designed to hybridize to different regions of target genes or targets. Presented in Table 12 are the target genes, as well as the corresponding sequences, identified by GenBank® accession number, used to design the oligomeric compounds of the invention and other compounds described herein. "Gene symbol" indicates the name used to herein to describe the target nucleic acid molecule, and "Gene Name" indicates an additional name by which the gene target is known.

TABLE 12

Gene target sequences

| Gene Symbol | Gene Name | GenBank ® Accession # | SEQ ID NO |
|---|---|---|---|
| CD86 | CD86 | S70108.1 | 10 |
| DGAT2 | Diacylglycerol Acyltransferase 2 | AK002443.1 | 11 |
| FAS | Fatty Acid Synthase | AF127033.1 | 12 |
| FAS | Fatty Acid Synthase | X62889.1 | 13 |
| FACL2 | Fatty-Acid-Coenzyme A Ligase, Long-Chain 2 | NM_007981.1 | 14 |
| GCGR | Glucagon Receptor | NM_000160.1 | 15 |
| GCGR | Glucagon Receptor | NM_008101.1 | 16 |
| HSL | Hormone-Sensitive Lipase | U08188.1 | 17 |

TABLE 12-continued

| Gene target sequences | | | |
|---|---|---|---|
| Gene Symbol | Gene Name | GenBank ® Accession # | SEQ ID NO |
| HSD11 | Hydroxysteroid 11-Beta Dehydrogenase 1 | X83202.1 | 18 |
| JNK1 | Jun N-Terminal Kinase - 1 | L26318.1 | 19 |
| PP2A-alpha | Protein Phosphatase 2 Catalytic Subunit Alpha | NM_002715.1 | 20 |
| PTEN | Phosphatase And Tensin Homologue | U92436.1 | 21 |
| PTP1B | Protein Tyrosine Phosphatase 1b | M33962.1 | 22 |
| NaDC1 | Solute Carrier Family 13 (Sodium-Dependent Dicarboxylate Transporter), Member 2 | AF201903.1 | 23 |
| SCD1 | Stearoyl-Coenzyme A Desaturase 1 | 1850_038A | 24 |
| Survivin | Survivin | U75285.1 | 25 |
| Survivin | Survivin | AA717921.1 | 26 |
| Survivin | Survivin | AB013819.1 | 27 |
| TRADD | Tumor Necrosis Factor Receptor Associated Death Domain | L41690.1 | 28 |
| C-raf | Raf kinase C | X03484.1 | 29 |
| C-raf | Rafkinase C | assembled from AC026153.10 and AC018500.2 | 30 |
| SRC-2 | steroid receptor coactivator 2 | U39060.1 | 31 |
| SRC-2 | steroid receptor coactivator 2 | complement of nucleotides 10220000 to 10460000 of NW_000149.1 | 32 |
| SRC-2 | steroid receptor coactivator 2 | AK028964.1 | 33 |

Example 45

Chimeric Oligomeric Compounds Having Alternating 3'-Endo and 2'-Endo Regions In one embodiment of the invention, the target sequences presented in Table 12 were used as targets to which oligomeric compounds were designed. These compounds have regions of nucleosides that are “RNA-like”, having northern or 3'-endo conformational geometry (3'-endo regions), and regions of nucleosides that are “DNA-like”, having southern or C2'-endo/O4'-endo conformational geometry. Each of the regions ranges from 1 to 8 nucleosides in length. The motif of each oligomeric compound is illustrated in Table 13, where 3'-endo regions are indicated by bold, underlined type, or by italicized, underlined type in the case of ISIS 199043, and 2'-endo regions are indicated by plain type. The number corresponding to each region represents the number of base pairs for that particular region. The motif further indicates the total number of regions in the compound, for example, a compound having the motif “3-3-1-2-1-2-1-3-4” has a total of 9 regions, with each region ranging from 1 to 4 nucleotides. In the compounds shown in Table 13, the 3'-endo regions shown in bold, underlined type comprise 2'-O-methoxyethyl (2'-MOE) nucleotides; the 3'-endo regions in italicized, underlined type comprise 2'-O-methyl nucleotides; and the 2'-endo regions comprise 2'-deoxynucleotides. Internucleoside linkages are phosphorothioate throughout all compound in Table 13, except where an asterisk “*” is present to indicate a phosphodiester internucleoside linkage. All cytosines are 5-methylcytosines, unless otherwise indicated by a superscript “U” preceding the nucleobase, for example, $^{U}$C, which indicates a natural or unmodified cytosine.

The nucleic acid molecule to which each compound is targeted is indicated by SEQ ID NO. “Target site” indicates the first (5'-most) nucleotide number on the particular target nucleic acid to which the compound binds. Where present, “NA” indicates that “Target SEQ ID NO:” and “Target site” do not apply to a particular oligomeric compound due to its lack of perfect complementarity to any known gene (i.e., it is a mismatched oligomeric compound).

The chimeric oligomeric compounds of the invention, comprising at least 5 regions that alternate between 3'-endo regions and 2'-endo regions, are herein referred to as “gap-disabled” oligomeric compounds. Also described herein are “gapmers”, chimeric oligomeric compounds having 3 regions, where one 2'-endo region comprised of 2'-deoxynucleotides is flanked on both sides (5' and 3' directions) by a 3'-endo region.

TABLE 13

| Oligomeric compounds | | | | | |
|---|---|---|---|---|---|
| ISIS # | TARGET SEQ ID NO | TARGET SITE | SEQUENCE | MOTIF | SEQ ID NO |
| 113715 | 22 | 980 | **GCTCC**TTCCACTGAT**CCTGC** | 5-10-5 | 45 |
| 114905 | 26 | 296 | **GTTGG**TCTCCTTTGC**CTGGA** | 5-10-5 | 49 |
| 116847 | 21 | 2097 | **CTGCT**AGCCTCTGGA**TTTGA** | 5-10-5 | 42 |
| 118929 | 20 | 1492 | **TCTAC**AGTCATGCTG**AGTAA** | 5-10-5 | 53 |
| 121874 | 10 | 289 | **TCAAG**TTTCTCTGTG**CCCAA** | 5-10-5 | 51 |
| 121875 | 10 | 335 | **GTTCC**TGTCAAAGCT**CGTGC** | 5-10-5 | 48 |
| 126965 | 17 | 2263 | **CCAGG**GCTGCCTCA**GACACA** | 5-10-5 | 39 |
| 129605 | NA | NA | **CCTGC**TCCCTCTAAT**GCTGC** | 5-10-5 | 63 |
| 129686 | NA | NA | **CGTTA**TTAACCTCCG**TTGAA** | 5-10-5 | 65 |
| 131906 | NA | NA | **TCAAG**TCCTTCCACA**CCCAA** | 5-10-5 | 70 |
| 141923 | NA | NA | **CCTTC**CCTGAAGGTT**CCTCC** | 5-10-5 | 64 |

TABLE 13-continued

Oligomeric compounds

| ISIS # | TARGET SEQ ID NO | TARGET SITE | SEQUENCE | MOTIF | SEQ ID NO |
|---|---|---|---|---|---|
| 146038 | 18 | 1107 | TTCTCATGATGAGGTGTACC | 5-10-5 | 58 |
| 146039 | 18 | 1119 | TGTTGCAAGAATTTCTCATG | 5-10-5 | 56 |
| 148529 | 12 | 630 | TTCATGAACTGCACAGAGGT | 5-10-5 | 57 |
| 148548 | 12 | 2238 | TTGTTGACATTGTACTCGGC | 5-10-5 | 59 |
| 166659 | 22 | 980 | GCTCCTTCCACTGATCCTGC | 3-3-1-2-1-2-1-3-4 | 45 |
| 180475 | 16 | 1348 | GAGCTTTGCCTTCTTGCCAT | 5-10-5 | 43 |
| 189525 | NA | NA | “C“CTG“CT“C“C“CT“CTAATG“CTG“C | 5-10-5 | 63 |
| 194563 | NA | NA | CCTGCTCCCTCTAATGCTGC | 2-1-1-2-1-1-1-1-1-1-1-1-1-3-2 | 63 |
| 199041 | NA | NA | CCTGCTCCCTCTAATGCTGC | Uniform 2'-MOE | 63 |
| 199042 | NA | NA | CCTGCTCCCTCTAATGCTGC | 5-2-1-2-1-2-1-1-5 | 63 |
| 199043 | NA | NA | CCTGCTCCCTCTAATGCTGC | Uniform 2'-deoxy | 63 |
| 199044 | NA | NA | *CCTGC*TCCCTCTAAT*GCTGC* | *5*-10-*5* | 63 |
| 199046 | NA | NA | C*C*T*G*CTCCCTCTAATG*C*T*G*C | 5-10-5 | 63 |
| 199047 | NA | NA | CCTGATCCCTCTAATGATGC | 5-10-5 | 61 |
| 199048 | NA | NA | CCTGCTCACTCTAATGCTGC | 5-10-5 | 62 |
| 217352 | 11 | 1424 | ATGCACTCAAGAACTCGGTA | 5-10-5 | 35 |
| 217376 | 11 | 2230 | TCCATTTATTAGTCTAGGAA | 5-10-5 | 52 |
| 244504 | 24 | 1329 | GTGTTTCTGAGAACTTGTGG | 5-10-5 | 47 |
| 244541 | 24 | 1435 | ATGTCCAGTTTTCCGCCCTT | 5-10-5 | 36 |
| 249375 | 23 | 846 | GGACCTGTAGCCATAGCCAA | 5-10-5 | 46 |
| 249386 | 23 | 1021 | CTCGTGAACCAGAGCACCAC | 5-10-5 | 41 |
| 256899 | 13 | 12343 | TTGTTGACGTTGTACTCAGC | 5-10-5 | 60 |
| 283586 | 22 | 980 | GCTCCTTCCACTGATCCTGC | Uniform 2'-MOE | 45 |
| 284346 | NA | NA | CTTCTAGCCTCTGGATTGGA | 5-10-5 | 66 |
| 291452 | 14 | 214 | TCAAGGACTGCTGATCTTCG | 5-10-5 | 50 |
| 298682 | NA | NA | GCGATTTCCCGTTTTCACCT | 5-10-5 | 67 |
| 298683 | 16 | 1348 | GAGCTTTGCCTTCTTGCCAT | Uniform 2'-MOE | 43 |
| 298683 | 16 | 1348 | GAGCTTTGCCTTCTTGCCAT | Uniform 2'-MOE | 43 |
| 299228 | 25 | 12665 | TGTGCTATTCTGTGAATT | 2-2-1-3-1-2-1-3-3 | 55 |
| 299229 | 25 | 12665 | TGTGCTATTCTGTGAATT | 3-3-1-2-1-3-1-2-2 | 55 |
| 299230 | 27 | 856 | AACCACACTTACCCATGGGC | 3-2-1-3-1-2-1-3-4 | 34 |
| 299231 | 26 | 296 | GTTGGTCTCCTTTGCCTGGA | 3-2-1-3-1-2-1-3-4 | 49 |
| 299232 | 27 | 303 | TGTCATCGGGTTCCCAGCCT | 3-2-1-3-1-2-1-3-4 | 54 |
| 300861 | 16 | 1348 | GAGCTTTGCCTTCTTGCCAT | 3-2-1-3-1-3-1-3-3 | 43 |
| 303767 | NA | NA | GTTCGTGTTCTCTGGCTCGA | 5-10-5 | 68 |
| 304170 | 13 | 12343 | TTGTTGACGTTGTACTCAGC | 3-2-1-2-1-2-1-2-1-2-3 | 60 |

TABLE 13-continued

Oligomeric compounds

| ISIS # | TARGET SEQ ID NO | TARGET SITE | SEQUENCE | MOTIF | SEQ ID NO |
|---|---|---|---|---|---|
| 304171 | 12 | 2238 | TTGTTGACATTGTACTCGGC | 3-2-1-2-1-2-1-2-1-2-3 | 59 |
| 306058 | 10 | 289 | TCAAGTTTCTCTGTGCCCAA | 3-2-1-2-1-3-1-2-1-1-3 | 51 |
| 307754 | 19 | 341 | ATTTGCATCCATGAGCTCCA | 5-10-5 | 37 |
| 310456 | 15 | 500 | CAGGAGATGTTGGCCGTGGT | 5-10-5 | 38 |
| 310457 | 15 | 532 | GCACTTTGTGGTGCCAAGGC | 5-10-5 | 44 |
| 310514 | 11 | 1424 | ATGCACTCAAGAACTCGGTA | 3-2-1-2-1-2-1-2-1-2-3 | 35 |
| 310515 | 11 | 2230 | TCCATTTATTAGTCTAGGAA | 3-2-1-2-1-2-1-2-1-2-3 | 52 |
| 310516 | 18 | 1107 | TTCTCATGATGAGGTGTACC | 3-2-1-2-1-2-1-2-1-2-3 | 58 |
| 310517 | 18 | 1119 | TGTTGCAAGAATTCTCATG | 3-2-1-2-1-2-1-2-1-2-3 | 56 |
| 312837 | 23 | 846 | GGACCTGTAGCCATAGCCAA | 3-2-1-2-1-2-1-2-1-2-3 | 46 |
| 312844 | 24 | 1329 | GTGTTTCTGAGAACTTGTGG | 3-2-1-2-1-2-1-2-1-2-3 | 47 |
| 319162 | 14 | 214 | TCAAGGACTGCTGATCTTCG | 3-2-1-2-1-2-1-2-1-2-3 | 50 |
| 319237 | NA | NA | TTGTTAACGGTGTTCTCAGC | 5-10-5 | 71 |
| 319238 | NA | NA | TTTGTAACGGTGTTCACTGA | 5-10-5 | 72 |
| 319239 | 12 | 630 | TTCATGAACTGCACAGAGGT | 3-2-1-2-1-2-1-2-1-2-3 | 57 |
| 319240 | NA | NA | TACTTGACCTACAGAGTGGA | 5-10-5 | 69 |
| 330693 | 17 | 2263 | CCAGGGCTGCCTCAGACACA | 2-1-1-2-1-1-1-1-1-1-1-1-1-3-2 | 39 |
| 332520 | 15 | 532 | GCACTTTGTGGTGCCAAGGC | Uniform 2'-MOE | 44 |
| 332521 | 15 | 532 | GCACTTTGTGGTGCCAAGGC | Uniform 2'-deoxy | 44 |
| 332522 | 15 | 532 | GCACTTTGTGGTGCCAAGGC | 3-2-1-2-1-2-1-2-1-2-3 | 44 |
| 332864 | 16 | 1348 | GAGCTTTGCCTTCTTGCCAT | 4-3-1-4-1-3-4 | 43 |
| 332865 | 16 | 1348 | GAGCTTTGCCTTCTTGCCAT | 3-2-1-2-1-2-1-2-1-2-3 | 43 |
| 332866 | 16 | 1348 | GAGCTTTGCCTTCTTGCCAT | 3-5-4-5-3 | 43 |
| 332867 | 16 | 1348 | GAGCTTTGCCTTCTTGCCAT | 3-14-3 | 43 |
| 332868 | 16 | 1348 | GAGCTTTGCCTTCTTGCCAT | 3-3-2-4-2-3-3 | 43 |
| 332869 | 16 | 1348 | GAGCTTTGCCTTCTTGCCAT | 3-1-1-1-1-1-1-1-1-1-1-1-1-1-4 | 43 |
| 333022 | 15 | 500 | CAGGAGATGTTGGCCGTGGT | Uniform 2'-MOE | 38 |
| 333023 | 15 | 500 | CAGGAGATGTTGGCCGTGGT | Uniform 2'-deoxy | 38 |
| 333024 | 15 | 500 | CAGGAGATGTTGGCCGTGGT | 3-2-1-2-1-2-1-2-1-2-3 | 38 |
| 334269 | 21 | 2097 | CTGCTAGCCTCTGGATTTGA | 3-14-3 | 42 |
| 334270 | 21 | 2097 | CTGCTAGCCTCTGGATTTGA | 3-6-1-7-3 | 42 |
| 334271 | 21 | 2097 | CTGCTAGCCTCTGGATTTGA | 3-7-1-6-3 | 42 |
| 334272 | 21 | 2097 | CTGCTAGCCTCTGGATTTGA | 3-4-1-4-1-4-3 | 42 |
| 334273 | 21 | 2097 | CTGCTAGCCTCTGGATTTGA | 3-3-1-2-1-3-1-3-3 | 42 |
| 334274 | 21 | 2097 | CTGCTAGCCTCTGGATTTGA | 3-3-1-3-1-2-1-3-3 | 42 |
| 334275 | 21 | 2097 | CTGCTAGCCTCTGGATTTGA | 3-2-1-2-1-2-1-2-1-2-3 | 42 |

TABLE 13-continued

Oligomeric compounds

| ISIS # | TARGET SEQ ID NO | TARGET SITE | SEQUENCE | MOTIF | SEQ ID NO |
|---|---|---|---|---|---|
| 334276 | 21 | 2097 | C*T*G*C*T*A*G*C*C*T*C*T*G*G*A*T*T*T*G*A | Uniform 2'-deoxy | 42 |
| 335032 | 16 | 1348 | GAGCTTTGCCTTCTTGCCAT | Uniform 2'-deoxy | 43 |
| 335033 | 16 | 1348 | G*A*G*C*T*T*T*G*C*C*T*T*C*T*T*G*C*C*A*T | Uniform 2'-deoxy | 43 |
| 335112 | 16 | 1348 | G*A*G*C*T*T*T*G*C*C*T*T*C*T*T*G*C*C*A*T | 5-10-5 | 43 |
| 335114 | 16 | 1348 | G*A*G*C*T*T*T*G*C*C*T*T*C*T*T*G*C*C*A*T | 3-2-1-3-1-3-1-3-3 | 43 |
| 337205 | 11 | 1424 | ATGCACTCAAGAACTCGGTA | 3-14-3 | 35 |
| 337206 | 11 | 1424 | ATGCACTCAAGAACTCGGTA | 3-6-1-7-3 | 35 |
| 337207 | 11 | 1424 | ATGCACTCAAGAACTCGGTA | 3-7-1-6-3 | 35 |
| 337208 | 11 | 1424 | ATGCACTCAAGAACTCGGTA | 3-4-1-4-1-4-3 | 35 |
| 337209 | 11 | 1424 | ATGCACTCAAGAACTCGGTA | 3-3-1-2-1-3-1-3-3 | 35 |
| 337210 | 11 | 1424 | ATGCACTCAAGAACTCGGTA | 3-3-1-3-1-2-1-3-3 | 35 |
| 337211 | 11 | 1424 | A*T*G*C*A*C*T*C*A*A*G*A*A*C*T*C**G*G*T*A | Uniform 2'-deoxy | 35 |
| 337212 | 11 | 1424 | ATGCACTCAAGAACTCGGTA | 3-2-2-1-2-1-2-1-1-2-3 | 35 |
| 337213 | 11 | 1424 | ATGCACTCAAGAACTCGGTA | 3-1-3-1-2-1-2-1-2-1-3 | 35 |
| 337214 | 11 | 1424 | ATGCACTCAAGAACTCGGTA | 3-1-2-1-2-1-2-1-2-1-4 | 35 |
| 337215 | 11 | 1424 | ATGCACTCAAGAACTCGGTA | 3-1-1-1-1-1-1-1-1-1-1-1-1-1-4 | 35 |
| 337216 | 11 | 1424 | ATGCACTCAAGAACTCGGTA | 1-1-1-1-1-1-1-1-1-1-1-1-1-1-1-1-1-1-2 | 35 |
| 337217 | 21 | 2097 | CTGCTAGCCTCTGGATTTGA | 3-2-2-1-2-1-2-1-1-2-3 | 42 |
| 337218 | 21 | 2097 | CTGCTAGCCTCTGGATTTGA | 3-1-3-1-2-1-2-1-2-1-3 | 42 |
| 337219 | 21 | 2097 | CTGCTAGCCTCTGGATTTGA | 3-1-2-1-2-1-2-1-2-1-4 | 42 |
| 337220 | 21 | 2097 | CTGCTAGCCTCTGGATTTGA | 3-1-1-1-1-1-1-1-1-1-1-1-1-1-4 | 42 |
| 337221 | 21 | 2097 | CTGCTAGCCTCTGGATTTGA | 1-1-1-1-1-1-1-1-1-1-1-1-1-1-1-1-1-1-2 | 42 |
| 337222 | 11 | 1424 | ATGCACTCAAGAACTCGGTA | Uniform 2'-MOE | 35 |
| 338173 | 28 | 802 | CGCTCGTACTCGTAGGCCAG | 5-10-5 | 40 |
| 338174 | 28 | 802 | CGCTCGTACTCGTAGGCCAG | Uniform 2'-MOE | 40 |
| 338175 | 28 | 802 | CGCTCGTACTCGTAGGCCAG | 4-3-1-4-1-3-4 | 40 |
| 338176 | 28 | 802 | CGCTCGTACTCGTAGGCCAG | 3-2-1-2-1-2-1-2-1-2-3 | 40 |
| 338177 | 28 | 802 | CGCTCGTACTCGTAGGCCAG | 3-5-4-5-3 | 40 |
| 338178 | 28 | 802 | CGCTCGTACTCGTAGGCCAG | 3-14-3 | 40 |
| 338179 | 28 | 802 | CGCTCGTACTCGTAGGCCAG | 3-3-2-4-2-3-3 | 40 |
| 338180 | 28 | 802 | CGCTCGTACTCGTAGGCCAG | 3-1-1-1-1-1-1-1-1-1-1-1-1-1-4 | 40 |
| 345888 | 19 | 341 | ATTTGCATCCATGAGCTCCA | 3-2-1-2-1-2-1-2-1-2-3 | 37 |

TABLE 13-continued

| Oligomeric compounds | | | | | |
|---|---|---|---|---|---|
| ISIS # | TARGET SEQ ID NO | TARGET SITE | SEQUENCE | MOTIF | SEQ ID NO |
| 352426 | 16 | 1348 | **GA**GCTTTG**CCTT**CTTGCC**AT** | **2**-6-**4**-6-**2** | 43 |
| 352427 | 16 | 1348 | **GA**GCTTTGC**CT**TCTTGCC**AT** | **2**-7-**2**-7-**2** | 43 |
| 352428 | 16 | 1348 | **G**AGCTTTGC**CT**TCTTGCCA**T** | **1**-8-**2**-8-**1** | 43 |

The target regions to which these sequences are complementary are herein referred to as "target segments" and are therefore suitable for targeting by oligomeric compounds of the present invention. The target segment sequences represent the reverse complement of the chimeric oligomeric compounds.

As these "target segments" have been found by experimentation to be open to, and accessible for, hybridization with the chimeric oligomeric compounds of the present invention, one of skill in the art will recognize or be able to ascertain, using no more than routine experimentation, further embodiments of the invention that encompass other oligomeric compounds that specifically hybridize to these target segments and consequently inhibit the expression of a target.

According to the present invention, chimeric oligomeric compounds include antisense oligomeric compounds, antisense oligonucleotides, siRNAs, alternate splicers and other short oligomeric compounds which hybridize to at least a portion of the target nucleic acid.

Example 46

In Vitro Analysis of Chimeric Oligomeric Compounds Having Alternating 3'-Endo and 2'-Endo Regions In one embodiment, gap-disabled oligomeric compounds were selected from Table 13 and tested for their effects on target expression in cultured cells. Gapmer compounds were also tested in each in vitro assay and served as the positive control for target reduction.

To test the effects of gap-disabled compounds of the invention on mouse survivin expression, NIH 3T3 cells were treated 6.25, 25, 100 and 200 nM of the oligomeric compounds shown in Table 13. ISIS 303767, which contains 6 mismatches to mouse survivin, was used as a negative control in this assay. Cells were transfected using LIPOFECTIN™ and mRNA levels were measured using real-time PCR as described in other examples herein. Results of these studies are shown in Table 14. Data are averages from two or more experiments and are expressed as percent inhibition relative to untreated control. As demonstrated in Table 14, the gap-disabled compounds ISIS 299230 and ISIS 229231 and the gapmer ISIS 114905 inhibited mouse survivin expression in a dose-dependent manner. The gap-disabled compounds ISIS 299229 and ISIS 299232 inhibited mouse survivin expression at the 100 and 200 nM doses.

TABLE 14

Inhibition of mouse survivin expression in NIH 3T3 cells: dose response

| | | % Inhibition Dose of oligonucleotide (nM) | | | |
|---|---|---|---|---|---|
| ISIS # | SEQ ID NO | 6.25 | 25 | 100 | 200 |
| 299228 | 55 | 0 | 0 | 0 | 9 |
| 299229 | 55 | 0 | 0 | 10 | 17 |
| 299230 | 34 | 23 | 28 | 64 | 72 |
| 299231 | 49 | 22 | 44 | 78 | 83 |
| 299232 | 54 | 0 | 0 | 38 | 59 |
| 114905 | 49 | 0 | 51 | 82 | 91 |
| 303767 | 68 | 0 | 0 | 10 | 60 |

Oligomeric compounds targeting mouse SCD1 were also tested. Primary mouse hepatocytes were treated with 15, 44, 133 and 400 nM of the oligomeric compounds shown in Table 15, or the control oligomeric compound ISIS 141923, which does not target mouse SCD1. Cells were transfected using LIPOFECTIN™ and mRNA levels were measured using real-time PCR as described in other examples herein. Results of these studies are shown in Table 15. Data are averages from three experiments and are expressed as percent inhibition relative to untreated control. As demonstrated in Table 15, the gap-disabled compound ISIS 312844 inhibited SCD1 expression in a dose-dependent manner. The gapmer compounds also inhibited SCD1 expression in a dose-dependent manner.

TABLE 15

Inhibition of mouse SCD1 expression in mouse primary hepatocytes: dose response

| | | % Inhibition Dose of oligonucleotide (nM) | | | |
|---|---|---|---|---|---|
| ISIS # | SEQ ID NO | 15 | 44 | 133 | 400 |
| 312844 | 47 | 0 | 15 | 40 | 69 |
| 244504 | 47 | 15 | 32 | 65 | 83 |
| 244541 | 36 | 0 | 1 | 46 | 78 |
| 141923 | 64 | 0 | 0 | 0 | 0 |

To evaluate the effects of oligomeric compounds of the invention on mouse PTEN expression, b.END cells were treated with 12.5, 25, 50 or 100 nM of the oligomeric compounds shown in Table 16. ISIS 141923, which does not target PTEN, was used as a negative control in this assay. Cells were transfected using LIPOFECTIN™ and mRNA levels were measured using real-time PCR as described in other examples herein. Results of these studies are shown in Table 16. Data are averages from two or more experiments and are expressed as percent inhibition relative to untreated control. As demonstrated in Table 16, the gap-disabled compounds ISIS 334269, ISIS 334270, ISIS 334271, ISIS 334272, ISIS 334273, ISIS 334274 and ISIS 334275 inhibited mouse PTEN mRNA expression in a dose-dependent manner, as did the gapmer compound ISIS 116847. ISIS 334269, a gapmer compound with a gap segment 14 nucleotides in length and wing segments 3 nucleotides in length, also inhibited PTEN expression in a dose-dependent manner. The uniform 2'-deoxy compound ISIS 334276 did not exhibit target inhibition greater than 9%.

TABLE 16

Inhibition of mouse PTEN mRNA expression in b.END cells: dose response

| ISIS # | SEQ ID NO | % Inhibition Dose of oligonucleotide (nM) 12.5 | 25 | 50 | 100 |
|---|---|---|---|---|---|
| 334269 | 42 | 9 | 29 | 56 | 71 |
| 334270 | 42 | 31 | 29 | 63 | 75 |
| 334271 | 42 | 18 | 46 | 59 | 66 |
| 334272 | 42 | 0 | 31 | 57 | 64 |
| 334273 | 42 | 19 | 31 | 47 | 60 |
| 334274 | 42 | 9 | 26 | 47 | 50 |
| 334275 | 42 | 10 | 30 | 43 | 63 |
| 334276 | 42 | 3 | 9 | 8 | 0 |
| 116847 | 42 | 12 | 45 | 62 | 75 |
| 141923 | 64 | 0 | 0 | 0 | 0 |

Additional compounds targeted to mouse PTEN were tested in a similar assay in b.END cells. Cells were transfected using LIPOFECTIN™ and mRNA levels were measured using real-time PCR as described in other examples herein. ISIS 337217 inhibited target expression 10% and 15% at doses of 25 and 50 nM, respectively. ISIS 331218 inhibited PTEN expression by 17% at a dose of 100 nM. ISIS 337219, ISIS 337220 and ISIS 337221 did not significantly inhibit PTEN expression in b.END cells in this assay.

Oligomeric compounds targeted to NaDC1 were also tested in an in vitro assay. Primary mouse hepatocytes were treated with 15, 44, 133 or 400 nM of the oligomeric compounds shown in Table 17. ISIS 141923, which does not target mouse NaDC1, was used as a negative control compound in this assay. Cells were transfected using LIPOFECTIN™ and mRNA levels were measured using real-time PCR as described in other examples herein. Results of these studies are shown in Table 17. Data are averages from three experiments and are expressed as percent inhibition relative to untreated control. As demonstrated in Table 17 the gap-disabled compound ISIS 312387 inhibited mouse NaDC1 in a dose-dependent manner, as did the gapmer compounds targeted to NaDC1.

TABLE 17

Inhibition of mouse NaDC1 mRNA expression in mouse primary hepatocytes: dose response

| ISIS NO | SEQ ID NO | % Inhibition Dose of oligonucleotide (nM) 15 | 44 | 133 | 400 |
|---|---|---|---|---|---|
| 312837 | 46 | 16 | 55 | 61 | 79 |
| 249375 | 46 | 29 | 59 | 71 | 90 |
| 249386 | 41 | 0 | 9 | 38 | 76 |
| 141923 | 64 | 0 | 0 | 0 | 0 |

Primary mouse hepatocytes were treated for 4 hours with 15, 44, 133, and 400 nM of the oligomeric compounds shown in Table 18. ISIS 141923, which does not target mouse HSD11, was used as a negative control in this assay. Cells were transfected using LIPOFECTIN™ and mRNA levels were measured using real-time PCR as described in other examples herein. Results of these studies are shown in Table 18. Data are averages from three experiments and are expressed as percent inhibition relative to untreated control. As demonstrated in Table 18, the gap-disabled compound ISIS 310516 inhibited HSD11 expression in a dose-dependent manner, as did the gapmer compound.

TABLE 18

Inhibition of mouse HSD11 mRNA expression in mouse primary hepatocytes: dose response

| ISIS NO | SEQ ID NO | % Inhibition Dose of oligonucleotide (nM) 15 | 44 | 133 | 400 |
|---|---|---|---|---|---|
| 310516 | 58 | 0 | 40 | 69 | 95 |
| 146038 | 58 | 37 | 70 | 94 | 97 |
| 141923 | 64 | 0 | 0 | 0 | 0 |

Gap-disabled compound targeting the mouse glucagon receptor RNA were also tested in an in vitro assay. Primary mouse hepatocytes were treated with 0.5, 1, 5, 10, 25 or 50 nM of the oligomeric compounds shown in Table 19. ISIS 116847, which does not target the mouse glucagon receptor, was used as a negative control in this assay. Cells were transfected using LIPOFECTIN™ and mRNA levels were measured using real-time PCR as described in other examples herein.

Results of these studies are shown in Table 19. Data are averages from three experiments and are expressed as percent inhibition relative to untreated control. "$IC_{50}$" indicates the concentration of oligomeric compound required to inhibit glucagon receptor mRNA expression by 50%. Where present, "ND" indicates "not determined." As demonstrated in Table 19, the gap-disabled compounds ISIS 300861, ISIS 332864, ISIS 332865, ISIS 332866, ISIS 332897 and ISIS 332868 inhibited mouse glucagon receptor expression in a dose-dependent manner, as did the gapmer compound. ISIS 332867, a gap-disabled compound, inhibited mouse glucagon receptor expression. ISIS 332869, a gapmer compound with a gap segment of 14 nucleotides in length and wing segments of 3 nucleotides in length, exhibited dose-dependent inhibition of mouse glucagon receptor mRNA at doses of 5, 10 and 25 nM.

TABLE 19

Inhibition of mouse glucagon receptor mRNA expression in mouse primary hepatocytes: dose response

| ISIS # | SEQ ID NO | % Inhibition Dose of oligonucleotide (nM) 0.5 | 1 | 5 | 10 | 25 | 50 | $IC_{50}$ (nM) |
|---|---|---|---|---|---|---|---|---|
| 300861 | 43 | 1 | 15 | 32 | 20 | 51 | 67 | 24 |
| 332864 | 43 | 10 | 30 | 52 | 45 | 63 | 70 | 14 |
| 332865 | 43 | 6 | 10 | 29 | 36 | 49 | 53 | 33 |
| 332866 | 43 | 27 | 42 | ND | 58 | 70 | 75 | 6 |
| 332867 | 43 | 37 | 48 | 66 | 74 | 74 | 77 | 1 |
| 332868 | 43 | 7 | 34 | 52 | 58 | 68 | ND | 5 |

TABLE 19-continued

| Inhibition of mouse glucagon receptor mRNA expression in mouse primary hepatocytes: dose response | | | | | | | | |
|---|---|---|---|---|---|---|---|---|
| | SEQ ID | % Inhibition Dose of oligonucleotide (nM) | | | | | | $IC_{50}$ |
| ISIS # | NO | 0.5 | 1 | 5 | 10 | 25 | 50 | (nM) |
| 332869 | 43 | 15 | 2 | 5 | 12 | 24 | 25 | >50 |
| 180475 | 43 | 3 | 43 | 58 | 68 | 78 | 80 | 3 |
| 116847 | 42 | 11 | 13 | 0 | 0 | 0 | 0 | >50 |

To evaluate the effects of gap-disabled compounds targeted to mouse DGAT2, primary mouse hepatocytes were treated with 15, 44, 133, and 400 nM of the oligomeric compounds shown in Table 20. ISIS 116847, which does not target the mouse glucagon receptor, was used as a negative control in this assay. Cells were transfected using LIPOFECTIN™ and mRNA levels were measured using real-time PCR as described in other examples herein. Results of these studies are shown in Table 20. Data are averages from three experiments and are expressed as percent inhibition relative to untreated control. As demonstrated in Table 2 the gap-disabled compounds ISIS 310514 and ISIS 310515, like the gapmer compounds, inhibited mouse DGAT2 expression in a dose-dependent manner.

TABLE 20

| Inhibition of mouse DGAT2 expression in mouse primary hepatocytes: dose response | | | | | |
|---|---|---|---|---|---|
| | | % Inhibition Dose of oligonucleotide (nM) | | | |
| ISIS NO | SEQ ID NO | 15 | 44 | 133 | 400 |
| 310514 | 35 | 32 | 64 | 78 | 88 |
| 310515 | 52 | 0 | 39 | 45 | 66 |
| 217352 | 35 | 71 | 87 | 94 | 95 |
| 217376 | 52 | 65 | 75 | 91 | 98 |
| 141923 | 64 | 43 | 44 | 0 | 0 |

An additional assay tested a gap-disabled compound targeted to mouse CD86. MH-S cells were treated with 0.12, 0.37, 1.1, 3.3, 10 and 30 nM of the oligomeric compounds shown in Table 21. ISIS 131906, which contains seven mismatched bases to mouse CD86, served as the negative control compound in this assay. Cells were transfected using LIPOFECTIN™ and mRNA levels were measured using real-time PCR as described in other examples herein. Data are averages from two or more experiments and are expressed as percent inhibition relative to untreated control. Results of these studies are shown in Table 21 and demonstrate that the gap-disabled compound ISIS 306058, inhibited CD86 mRNA expression in a dose-dependent manner at doses of 3.3, 10 and 30 nM.

TABLE 21

| Inhibition of mouse CD86 mRNA expression in MH-S cells: dose response | | | | | | | |
|---|---|---|---|---|---|---|---|
| | SEQ ID | % Inhibition Dose of oligonucleotide (nM) | | | | | |
| ISIS # | NO | 0.12 | 0.37 | 1.1 | 3.3 | 10 | 30 |
| 306058 | 51 | 0 | 6 | 0 | 17 | 32 | 45 |
| 121874 | 51 | 0 | 27 | 42 | 61 | 74 | 70 |
| 121875 | 48 | 0 | 25 | 43 | 62 | 78 | 81 |
| 131906 | 70 | 0 | 1 | 0 | 0 | 0 | 21 |

In a further embodiment, ISIS 306058 was tested for its ability to modulate cell surface expression of CD86 protein. MH-S cells were treated with 0.1, 0.4, 1.2, 3.7, 11.1, 33.3 and 100 nM of the oligomeric compounds shown in Table 22. ISIS 131906, which contains seven mismatched bases to mouse CD86, served as the negative control compound in this assay. Cells were transfected using LIPOFECTIN™ as described in other examples herein. Cell surface expression of CD86 protein was measured by flow cytometry. Cell surface expression of CD80, which shares sequence identify with CD86 at the nucleic acid level, was also measured. Cells were harvested by brief trypsinization, washed with PBS, then resuspended in 100 μL of staining buffer (PBS, 0.2% BSA) containing both 10 μL of FITC-conjugated anti-CD86 antibody (FITC-anti-hCD86; FITC: fluorescien isothiocyanate; BD Biosciences, San Jose, Calif.) and 10 ul of PE-conjugated anti-CD80 antibody (PE: phycoerythrin; PE-anti-hCD80, BD Biosciences, San Jose, Calif.). The cells were stained for 30 minutes at 4° C., washed with PBS, resuspended in 300 μL PBS containing 0.5% paraformaldehyde. Measurements of mean fluorescence activity were made by flow cytometry using the FL-1 and FL-2 channels of a BD Biosciences FACScan (BD Biosciences, San Jose, Calif.). With this method, both CD86 and CD80 protein expression on the surface of the same cell was measured. Data were averaged from two or more experiments and are expressed as percent inhibition relative to untreated control. As shown in Table 22, the gap-disabled compound ISIS 306058 exhibited inhibition of CD86 protein expression in a pattern similar to that observed in cells treated with the gapmer compounds, with dose-dependent inhibition limited to the 5 lower doses. CD80 protein levels were not lowered by the gap-disabled or gapmer compounds targeted to CD86.

TABLE 22

| Inhibition of mouse CD86 protein expression in MH-S cells: dose response | | | | | | | | |
|---|---|---|---|---|---|---|---|---|
| | SEQ ID | % Inhibition Dose of oligonucleotide (nM) | | | | | | |
| ISIS # | NO | 0.1 | 0.4 | 1.2 | 3.7 | 11.1 | 33.3 | 100 |
| 306058 | 51 | 4 | 6 | 12 | 19 | 30 | 31 | 31 |
| 121874 | 51 | 10 | 22 | 43 | 56 | 57 | 57 | 57 |
| 121875 | 48 | 9 | 21 | 34 | 46 | 57 | 55 | 54 |
| 131906 | 70 | 0 | 6 | 9 | 3 | 3 | 15 | 30 |

A gap-disabled compound targeted to mouse ACS1 was tested for its effects on target mRNA expression. Primary mouse hepatocytes were treated with 15, 44, 133 and 400 nM of the oligomeric compounds shown in Table 23. ISIS 141923, which does not target mouse ACS1, was used as a negative control in this assay. Cells were transfected using LIPOFECTIN™ and mRNA levels were measured using real-time PCR as described in other examples herein. Data were averaged from three experiments and are expressed as percent inhibition relative to untreated control. Results of these studies are shown in Table 23 and demonstrate that the gap-disabled compound ISIS 319962 inhibited mouse ACS1 in a dose-dependent manner, as the gapmer compound.

TABLE 23

Inhibition of mouse ACS1 expression in mouse primary hepatocytes: dose response

| ISIS # | SEQ ID NO | % Inhibition Dose of oligonucleotide (nM) 15 | 44 | 133 | 400 |
|---|---|---|---|---|---|
| 319162 | 50 | 9 | 12 | 45 | 77 |
| 291452 | 50 | 20 | 38 | 63 | 90 |
| 141923 | 64 | 32 | 5 | 17 | 29 |

An additional in vitro assay was performed to test a gap-disabled compound targeted to rat HSD11. Primary rat hepatocytes were treated for 4 hours with 15, 44, 133 and 400 nM of the oligomeric compounds shown in Table 24. ISIS 141923, which does not target rat HSD11, was used as a negative control in this assay. Cells were transfected using LIPOFECTIN™ and mRNA levels were measured using real-time PCR as described in other examples herein. Data were averaged from three experiments and are expressed as percent inhibition relative to untreated control. Results of these studies are shown in Table 24 and demonstrate that the gap-disabled compound ISIS 310517 inhibited target mRNA expression in a dose-dependent manner at the 3 higher doses of oligomeric compound.

TABLE 24

Inhibition of rat HSD11 mRNA expression in rat primary hepatocytes: dose response

| ISIS NO | SEQ ID NO | % Inhibition Dose of oligonucleotide (nM) 15 | 44 | 133 | 400 |
|---|---|---|---|---|---|
| 146039 | 56 | 31 | 53 | 76 | 92 |
| 310517 | 56 | 0 | 20 | 54 | 79 |
| 141923 | 64 | 7 | 9 | 0 | 0 |

Gap-disabled compounds targeted to rat FAS were tested for their effects on target mRNA expression. Primary rat hepatocytes were treated with 5, 10, 25, 50, 100, and 200 nM of the oligomeric compounds shown in Table 25. ISIS 319237, ISIS 319238, or ISIS 319240, which contain 3, 8 and 7 mismatches to rat FAS, respectively, were used as negative control compounds in this assay. Cells were transfected using LIPOFECTIN™ and mRNA levels were measured using real-time PCR as described in other examples herein. Results of these studies are shown in Table 25. Data are averages from three experiments and are expressed as percent inhibition relative to untreated control. "$IC_{50}$" indicates the concentration of oligomeric compound required to inhibit FAS mRNA expression by 50%. Where present, "ND" indicates "not determined." The data illustrate that the gap-disabled compound ISIS 304170 inhibited rat FAS mRNA in a dose-dependent manner. With the exception of the 25 nM dose, the treatments with ISIS 319239 inhibited rat FAS expression in a dose-dependent manner. The gapmer compounds also inhibited target expression, whereas the mismatched compounds did not.

TABLE 25

Inhibition of rat FAS mRNA expression in rat primary hepatocytes: dose response

| ISIS # | SEQ ID NO | % Inhibition Dose of oligonucleotide (nm) 5 | 10 | 25 | 50 | 100 | 200 | $IC_{50}$ (nM) |
|---|---|---|---|---|---|---|---|---|
| 304170 | 60 | 1 | 12 | 9 | 13 | 42 | 71 | 104 |
| 319239 | 57 | 4 | 14 | 0 | 38 | 62 | 76 | 67 |
| 148529 | 57 | 0 | 0 | 8 | 28 | 61 | 70 | 75 |
| 256899 | 60 | 17 | 16 | 3 | 25 | 52 | 73 | 97 |
| 319237 | 71 | 0 | 0 | 0 | 0 | 0 | 5 | N.D. |
| 319238 | 72 | 0 | 0 | 0 | 0 | 0 | 0 | N.D. |
| 319240 | 69 | 0 | 0 | 0 | 0 | 0 | 13 | N.D. |

From the data from the in vitro assays presented in Tables 14-25, it is evident that gap-disabled compounds effectively inhibited the expression of the nucleic acid molecules to which they are targeted.

Example 47

Chimeric Oligomeric Gap-Disabled Compounds Having Varying 2' Sugar Modifications The data described herein demonstrate that gap-disabled oligomeric compounds having 2'-MOE nucleotides in the 3'-endo regions are able to inhibit expression of a target gene. In a further embodiment, a series of oligomeric compounds was designed, using various 2' sugar modifications in the 3'-endo region. The oligomeric compounds were designed using SEQ ID NO: 43, which targets the mouse glucagon receptor RNA. The compounds are shown in Table 26. All compounds in Table 26 are chimeric oligomeric compounds comprising regions that alternate between 3'-endo regions and 2'-endo regions. The motif of each oligomeric compound is illustrated in Table 26, where 3'-endo regions are indicated by bold, underlined type and 2'-endo regions are indicated by plain type. The number corresponding to each region represents the number of base pairs for that particular region. The 3'-endo modification of each oligomeric compound is also indicated in Table 26. All internucleoside linkages are phosphorothioate throughout each compound in Table 26. Unmodified cytosines are indicated by a superscript "U" preceding the nucleobase, for example, "$^{U}$C"; all other cytosines are 5-methylcytosines. The 2'-endo regions of ISIS 340662 are comprised of 2'-ribonucleotides. The 2'-endo regions of all other compounds in Table 26 are comprised of 2'-deoxynucleotides. Where indicated by "U" at the 3'-terminal nucleobase position of ISIS 340658, ISIS 340661, ISIS 340663 and ISIS 358699, uracil was used in place of thymidine, making the compounds hybrids of DNA and RNA.

TABLE 26

| Gap-disabled oligomeric compounds targeted to mouse glucagon receptor: varying motifs and 3'-endo nucleosides | | | | |
|---|---|---|---|---|
| ISIS NO | SEQ ID NO | Sequence (5' to 3') | Motif | 3'-endo modification |
| 180475 | 43 | **GAGCT**TTGCCTTCTT**GCCAT** | **5**-10-**5** | 2'-MOE |
| 298683 | 43 | **GAGCTTTGCCTTCTTGCCAT** | **Uniform 2'-MOE** | 2'-MOE |
| 300861 | 43 | **GAG**C**T**TTGC**C**TTC**T**TGC**CAT** | **3**-2-**1**-3-**1**-3-**1**-3-**3** | 2'-MOE |
| 340658 | 43 | **GAG**CT**T**TGC**C**TTC**T**TGC**CAU** | **3**-2-**1**-3-**1**-3-**1**-3-**3** | 2'-O-methyl |
| 340659 | 43 | **GAG**CT**T**TGC**C**TTC**T**TGC**CAT** | **3**-2-**1**-3-**1**-3-**1**-3-**3** | 2'-fluoro |
| 340660 | 43 | **GAG**CT**T**TGC**C**TTC**T**TGC**CAT** | **3**-2-**1**-3-**1**-3-**1**-3-**3** | LNA |
| 340661 | 43 | **GAG**CT**U**TGC$^{U}$**C**TTC**U**TGC$^{U}$**CAU** | **3**-2-**1**-3-**1**-3-**1**-3-**3** | 2'-OH |
| 340662 | 43 | **GAG**$^{U}$CU**T**UG$^{U}$C**C**UU$^{U}$C**T**UG$^{U}$C**CAT** | **3**-2-**1**-3-**1**-3-**1**-3-**3** | 2'-MOE |
| 332866 | 43 | **GAG**CTTTG**CCTT**CTTGC**CAT** | **3**-5-**4**-5-**3** | 2'-MOE |
| 340663 | 43 | **GAG**CTTTG**CCTT**CTTGC**CAU** | **3**-5-**4**-5-**3** | 2'-O-methyl |
| 340673 | 43 | **CAG**CTTTG**CCTT**CTTGC**CAT** | **3**-5-**4**-5-**3** | LNA |
| 358699 | 43 | **GAG**CTTTG**CCTT**CTTGC**CAU** | **3**-5-**4**-5-**3** | 2'-fluoro |

The compounds were tested for their ability to modulate the expression of glucagon receptor mRNA in mouse primary hepatocytes. Cells, cultured as described herein, were treated with 0.1, 0.316, 1, 3.16, 10, 31.6 or 100 nM of oligomeric compounds. Untreated cells served as a control group to which all other data were normalized. Cells were transfected and mRNA was measured as described herein. The data, shown in Table 27, are the average of 3 experiments and are presented as percent of control cell mRNA expression. A number less than or greater than 100% indicates a decrease or increase in mRNA expression, respectively.

TABLE 27

| Oligomeric compounds of varying motifs and 3'-endo regions: effects on mouse glucagon receptor mRNA | | | | | | | | | |
|---|---|---|---|---|---|---|---|---|---|
| | Dose of oligomeric compound (nM) | | | | | | | | |
| | 100 | 31.6 | 10 | 3.16 | 1 | 0.316 | 0.1 | | 3'-endo |
| ISIS # | % Control expression | | | | | | | Motif | modification |
| 180475 | 16 | 58 | 84 | 130 | 140 | 141 | 103 | **5**-10-**5** | 2'-MOE |
| 298683 | 105 | 133 | 149 | 167 | 150 | 133 | 144 | **Uniform 2'-MOE** | 2'-MOE |
| 300861 | 58 | 109 | 116 | 145 | 151 | 162 | 132 | **3**-2-**1**-3-**1**-3-**1**-3-**3** | 2'-MOE |
| 340658 | 78 | 100 | 131 | 141 | 171 | 160 | 119 | **3**-2-**1**-3-**1**-3-**1**-3-**3** | 2'-O-methyl |
| 340659 | 62 | 85 | 118 | 131 | 138 | 154 | 134 | **3**-2-**1**-3-**1**-3-**1**-3-**3** | 2'-fluoro |
| 340660 | 38 | 61 | 97 | 121 | 134 | 146 | 154 | **3**-2-**1**-3-**1**-3-**1**-3-**3** | LNA |
| 340661 | 93 | 129 | 129 | 124 | 165 | 146 | 116 | **3**-2-**1**-3-**1**-3-**1**-3-**3** | 2'-OH |
| 340662 | 99 | 151 | 145 | 149 | 163 | 168 | 128 | **3**-2-**1**-3-**1**-3-**1**-3-**3** | 2'-MOE |
| 332866 | 20 | 64 | 83 | 146 | 133 | 128 | 144 | **3**-5-**4**-5-**3** | 2'-MOE |
| 340663 | 25 | 76 | 112 | 123 | 137 | 138 | 137 | **3**-5-**4**-5-**3** | 2'-O-methyl |
| 340673 | 45 | 59 | 87 | 112 | 128 | 125 | 99 | **3**-5-**4**-5-**3** | LNA |
| 358699 | 42 | 75 | 113 | 118 | 158 | 115 | 147 | **3**-5-**4**-5-**3** | 2'-fluoro |

These data demonstrate that gap-disabled compounds, having a plurality of motifs and 3'-endo modifications, exhibit target reduction activity in this assay. For example, ISIS 300861 (2'-MOE), ISIS 340658 (2'-O-methyl), ISIS 340659 (2'-fluoro), ISIS 340660 (LNA), ISIS 332866 (2'-MOE), ISIS 340663 (2'-O-methyl), ISIS 340673 (LNA) and ISIS 359699 (2'-fluoro) inhibited target expression at the 100 nM dose.

Example 48

Comparison of Gapmers and Gap-Disabled Oligomeric Compounds: Influence on Apoptosis Induction and Cell Viability Programmed cell death, or apoptosis, is an important aspect of various biological processes, including normal cell turnover, as well as immune system and embryonic development. Apoptosis involves the activation of caspases, a family of intracellular proteases through which a cascade of events leads to the cleavage of a select set of proteins. The caspase family can be divided into two groups: the initiator caspases, such as caspase-8 and -9, and the executioner caspases, such as caspase-3, -6 and -7, which are activated by the initiator caspases. The caspase family contains at least 14 members, with differing substrate preferences (Thornberry and Lazebnik, *Science,* 1998, 281, 1312-1316). Measuring caspase-3 activity is one manner in which caspase activity is evaluated. Changes in nucleic acid content also serve as an indicator of cell viability, as well as cytotoxic events or pathological abnormalities that affect cell proliferation.

The ability of gap-disabled and gapmer oligomeric compounds to affect apoptosis and viability in cultured cells was assayed using gap-disabled compounds and their corresponding gapmer compounds. The nucleic acid molecules to which these compounds are targeted, as well as the sequence and motif of each compound, are shown in Table 13. The gap-disabled compounds were: ISIS 330693, ISIS 194563, ISIS 300861 and ISIS 304170. The gapmer compounds were: ISIS 126965, ISIS 129605, ISIS 180475 and ISIS 256899.

These were tested for their effects on caspase-3 activity and cell viability in the human lung carcinoma cell line A549 (American Type Culture Collection; Manassas, Va.). A549 cells were routinely cultured in DMEM basal media (Invitrogen Corporation, Carlsbad, Calif.) supplemented with 10% fetal bovine serum (Invitrogen Corporation, Carlsbad, Calif.) and 1× antibiotic-antimycotic mix (Invitrogen Corporation, Carlsbad, Calif.). Cells were routinely passaged by trypsinization and dilution when they reached approximately 100% confluence. For LIPOFECTIN™-mediated transfection A549 cells were plated on 96-well microtiter plates (Falcon-Primaria #353872, BD Biosciences, Bedford, Mass.) precoated with rat tail collagen (BD Biosciences, Bedford Mass.) at a density of approximately $2*10^5$ cells/ml in Dulbecco's modified Eagle's medium (DMEM) containing 10% fetal bovine serum and antibiotic-antimycotic mix. Cells were cultured overnight at 37° C. in the presence of 5% $CO_2$. The following day the media was aspirated and replaced with prewarmed OPTI-MEM™ (Invitrogen Corporation, Carlsbad, Calif.) containing 300 nM oligonucleotide and 9 μg/mL LIPOFECTIN™ (Invitrogen Corporation, Carlsbad, Calif.). Cells incubated with OPTI-MEM™ alone served as untreated control cells. After four hours the transfection mix was exchanged for fresh culture medium and cells were incubated for an additional 44 hours at 37° C. in the presence of 5% $CO_2$.

Caspase-3 activity was evaluated with a fluorometric HTS Caspase-3 assay (Oncogene Research Products, San Diego, Calif.) that detects cleavage after aspartate residues in the peptide sequence DEVD. The DEVD substrate is labeled with a fluorescent molecule, which exhibits a blue to green shift in fluorescence upon cleavage. Active caspase-3 in the oligonucleotide treated cells is measured by this assay according to the manufacturer's instructions. 48 hours after oligonucleotide treatment, 50 uL of assay buffer was added to each well, followed by addition 20 uL of the caspase-3 fluorescent substrate conjugate. Data were obtained in triplicate. Fluorescence in wells was immediately detected (excitation/emission 400/505 nm) using a fluorescent plate reader (SpectraMAX GeminiXS, Molecular Devices, Sunnyvale, Calif.). The plate was covered and incubated at 37° C. for and additional three hours, after which the fluorescence was again measured (excitation/emission 400/505 nm). The value at time zero was subtracted from the measurement obtained at 3 hours. The measurement obtained from the untreated control cells was designated as 100% activity. The data are presented in Table 28. Values above or below 100% indicate an increase or decrease in caspase-3 activity, respectively.

Cell proliferation and viability were measured using the CyQuant Cell Proliferation Assay Kit (Molecular Probes, Eugene, Oreg.) utilizing the CyQuant GR green fluorescent dye which exhibits strong fluorescence enhancement when bound to cellular nucleic acids. After the 48 hour oligonucleotide treatment, the microplate was gently inverted to remove the medium from the wells, which were each washed once with 200 uL of phosphate-buffered saline. Plates were frozen at −70° C. and then thawed. A volume of 200 uL of the CyQUANT GR dye/cell-lysis buffer was added to each well. The microplate was incubated for 5 minutes at room temperature, protected from light. Data were obtained in triplicate. Fluorescence in wells was immediately detected (excitation/emission 480/520 nm) using a fluorescent plate reader (SpectraMAX GeminiXS, Molecular Devices, Sunnyvale, Calif.). The measurement obtained from the untreated control cells was designated as 100% activity. The data are presented in Table 28. Values above or below 100% indicate an increase or decrease in caspase-3 activity, respectively.

TABLE 28

Apoptosis and cell viability: comparison of gapmer and gap-disabled oligomeric compounds

| ISIS # | Motif | % cell viability | % caspase-3 activity | SEQ ID NO |
|---|---|---|---|---|
| 126965 | **5**-10-**5** | 27 | 2408 | *39* |
| 330693 | **2**-1-**1**-2-**1**-1-**1**-1-**1**-1-**1**-1-**1**-3-**2** | 76 | 119 | *39* |
| 129605 | **5**-10-**5** | 60 | 156 | *63* |
| 194563 | **2**-1-**1**-2-**1**-1-**1**-1-**1**-1-**1**-1-**1**-3-**2** | 51 | 67 | *63* |
| 180475 | **5**-10-**5** | 30 | 436 | *43* |
| 300861 | **3**-2-**1**-3-**1**-3-**1**-3-**3** | 43 | 94 | *43* |
| 256899 | **5**-10-**5** | 68 | 110 | *60* |
| *304170* | ***3**-2-**1**-2-**1**-2-**1**-2-**1**-2-**3*** | *58* | *72* | *60* |

These data demonstrate that when cells were treated with compounds have the nucleobase sequence of SEQ ID NOs: 39 and 43, cell viability was higher and caspase-3 activity was lowered in cells treated with the gap-disabled compounds, as compared to cells treated with the gapmer compounds. Comparison of gap-disabled and gapmer compounds having the nucleobase sequence of SEQ ID NOs: 63 and 60 reveals that both cell viability and caspase-3 activity were lowered in the cells treated with the gap-disabled compounds, as compared to cells treated with the gapmer compounds. These data further illustrate that gap-disabled compounds, like gapmer compounds, are able to modulate cellular pathways.

Example 49

Gap-Disabled vs. Gapmer Oligomeric Compounds: Hepatotoxic Effects

A number of chemical modifications have been introduced into oligomeric compounds to increase their usefulness as therapeutic agents and improve their pharmacokinetic properties. Of particular interest is the elimination of toxicity caused by oligomeric compounds, which can be significant in the liver and kidney due to the relatively high accumulation of oligomeric compounds in these organs. In a further embodiment, the hepatotoxic effects of the gapmer compound ISIS 129605 (SEQ ID NO: 63; no known target) and the gap-disabled compound ISIS 194563 (SEQ ID NO: 63; no known target) were tested in normal mice. Other oligomeric compounds tested included ISIS 118929 (SEQ ID NO: 53), a randomized control ISIS 29848 (NNNNNNNNNNNNNNNNNNNN, where N is A, T, C or G, SEQ ID NO: 75); and ISIS 148548 (SEQ ID NO: 59), all three of which are gapmer oligomeric compounds with 5-methylcytidines and phosphorothioate internucleoside linkages throughout.

Normal mice, maintained on a lean diet, were injected with 50 mg/kg of each oligomeric compound, twice weekly for 2 weeks. Saline-injected animals served as a control group. Each treatment group contained 4 animals. Animals were sacrificed at the end of the treatment period. Liver weights were determined at necropsy, and serum was collected for analysis of liver transaminase levels determined by routine clinical assays.

The serum transaminases ALT and AST are frequently used as indicators of hepatotoxicity. ISIS 129605 caused marked increases in both AST and ALT levels, which were 20 and 17 times, respectively, that observed in saline-treated mice. Conversely, ISIS 194563, which has the same nucleotide sequence as ISIS 129605 but is a gap-disabled compound, caused no increase in ALT and AST levels relative to saline-treated animals. Similarly, treatment ISIS 118929, ISIS 148548 or ISIS 29848 did not result in elevated ALT and AST levels. Increases in liver and spleen weights can also indicate the presence of toxicity. Treatment with ISIS 129605 resulted in an increase in liver weight approximately 1.6 times that of livers from saline-treated animals. Conversely, treatment with ISIS 194563 did not elevate or reduce liver weight. Serum transaminase levels and liver weight data demonstrate that introduction of 2'-MOE nucleotides into the gap segment of ISIS 129605 reduced the toxicity of that compound. Liver weights following treatment with the other gamper compounds were not significantly increased. None of the compounds resulted in significantly elevated spleen weights.

An additional in vivo experiment was performed, using oligomeric compounds described herein: ISIS 129605 (SEQ ID NO: 63), a gapmer having the motif 5-10-5 wherein the wing segments are composed of 2'-MOE nucleotides; ISIS 189525 (SEQ ID NO: 63), a gapmer having the motif 5-10-5, wherein the wings are composed of 2'-MOE nucleotides, and also having unmodified cytosines (rather than 5-methylcytosines); ISIS 199041 (SEQ ID NO: 63), uniformly composed of 2'-MOE nucleotides; ISIS 199042 (SEQ ID NO: 63), a gap-disabled compound having the motif 5-2-1-2-1-2-1-1-5; ISIS 199043 (SEQ ID NO: 63), uniformly composed of 2'-deoxynucleotides; ISIS 199044 (SEQ ID NO: 63), a 5-10-5 gapmer wherein the wing segments are composed of 2'-O-methyl nucleotides and the gap is composed of 2'-deoxynucleotides; and ISIS 199046 (SEQ ID NO: 63), a 5-10-5 gapmer wherein the wing segments are composed of 2'-MOE nucleotides, and wherein the internucleoside linkages in the wings are phosphodiester and the internucleoside linkages in the gap are phosphorothioate. Also tested were ISIS 199047 (SEQ ID NO: 61) and ISIS 199048 (SEQ ID NO: 62), both gapmer compounds with the motif 5-10-5, having wing segments composed of 2'-MOE nucleotides. Unless otherwise noted, internucleoside linkages are phosphorothioate and cytosines are 5-methylcytosines. For each motif presented, emboldened, underlined type indicates 2'-MOE nucleotides and plain type indicated 2'-deoxynucleotides. SEQ ID NOs: 63, 61 and 62 are not perfectly complementary to any known target.

Lean mice were treated with 50 mg/kg oligomeric compound, twice weekly for 3 weeks. The serum transaminases ALT and AST, indicators of toxicity, were measured by routine clinical analysis at the end of the study. ISIS 129605 treatment resulted in AST and ALT levels approximately 6 and 5 times those of saline-treated mice, respectively. ISIS 199044 resulted in dramatically elevated AST and ALT, approximately 15 and 9 times those of saline-treated mice, respectively. Treatment with ISIS 199048 also resulted in elevated AST and ALT, approximately 10 and 15 times those of saline-treated mice, respectively. The gap-disabled compound ISIS 199042 did not significantly elevate ALT and AST levels, demonstrating that an additional gap-disabled compound exhibits significantly fewer toxic properties than the gapmer version having the same nucleotide sequence. ISIS 189525, ISIS 199041, ISIS 199043, ISIS 199046 and ISIS 199047 similarly did not cause significantly elevated ALT and AST levels, illustrating that various chemical modifications of SEQ ID NO: 63 exhibit fewer toxic properties relative to ISIS 129605.

Liver weights, increases in which can also indicate toxicity, were also measured at the end of the study. In accordance with the observation that ISIS 199042 did not elevate ALT and AST levels, this compound did not significantly change liver weight. ISIS 199041 and ISIS 199046 did not cause increases in liver weight. However, ISIS 129605 and ISIS 199044, which did exhibit toxic properties as judged by ALT and AST levels, increased liver weight by approximately 1.6 and 1.8 times that of liver weights from saline-treated mice. These data further demonstrate the toxic properties of these compounds. Although ISIS 189525 and ISIS 199043 did not elevate ALT and AST levels, treatment with these compounds resulted in approximately 1.4-fold increases in liver weights relative to livers from saline-treated mice.

These in vivo studies illustrate that chimeric oligomeric compounds having at least 9 alternating 3'-endo and 2'-endo regions ameliorate hepatotoxicity, thereby improving the pharmacokinetic properties of the compounds. Thus, these compounds have applications in the development of therapeutic agents.

Example 50

In Vivo Comparison of Gapmer and Gap-Disabled Oligomeric Compounds Targeted to JNK1: Target Reduction and Toxicity In a further embodiment, gap-disabled and gapmer oligomeric compounds targeted to both human and mouse jun N-terminal kinase-1 (JNK1) were tested for their effects on both toxicity and target reduction in vivo. The gap-disabled compound ISIS 345888 (SEQ ID NO: 37) and the gapmer compound ISIS 307754 (SEQ ID NO: 37) are both shown in Table 13 and were selected for this study.

Male Balb/c mice, 6 to 7 weeks of age, received twice weekly intraperitoneal injections of 12.5, 25 or 50 mg/kg of either ISIS 307754 or ISIS 345888, for a period of three weeks. ISIS 141923 (SEQ ID NO: 64) was used as a negative control oligomeric compound and was injected at 50 mg/kg. Saline-injected animals served as a control group and were injected in the same manner as the oligomeric compounds. Each treatment group contained 4 animals. Body weights were monitored throughout the study (Days 1, 5, 8, 12, 15 and 19). Two days following the final injection, animals were sacrificed (Day 20). Liver and spleen weights, increases in which can indicate toxicity, were determined at time of necropsy. Serum was collected for analysis of the liver transaminase ALT, an indicator of toxicity. ALT levels were determined by routine clinical analysis. Liver tissue was collected for measurement of target mRNA expression by real-time PCR. Liver and kidney tissue were evaluated for concentration of total and full-length oligomeric compound by capillary gel electrophoresis.

ALT levels are shown in Table 29, in international units per liter (IU/L), with the saline control levels included for comparison. Body, liver and spleen weights are also presented in Table 29. Body weights are shown as percentage relative to the weight of each animal at the start of the study. Liver and spleen weights are normalized to saline-treated control weights.

TABLE 29

Indicators of toxicity: gap-disabled vs. gapmer oligomeric compounds targeted to JNK1

| | | ALT | Body Weights % relative to Day 1 | | | | | Liver Weight | Spleen Weight |
|---|---|---|---|---|---|---|---|---|---|
| | Dose, | IU/L | | | Day | Day | Day | % relative to saline | |
| Treatment | mg/kg | Day 20 | Day 5 | Day 8 | 12 | 15 | 19 | Day 20 | Day 20 |
| Saline | none | 46 | 100 | 106 | 104 | 108 | 108 | 100 | 100 |
| 141923 | 50 | 64 | 100 | 104 | 105 | 107 | 109 | 99 | 106 |
| 307754 | 50 | 292 | 101 | 102 | 103 | 102 | 105 | 131 | 147 |
| 307754 | 25 | 218 | 98 | 101 | 101 | 105 | 107 | 118 | 122 |
| 307754 | 12.5 | 40 | 101 | 105 | 106 | 106 | 109 | 109 | 120 |
| 345888 | 50 | 58 | 100 | 104 | 103 | 106 | 106 | 101 | 125 |
| 345888 | 25 | 103 | 102 | 105 | 105 | 107 | 110 | 110 | 124 |
| 345888 | 12.5 | 48 | 98 | 103 | 103 | 107 | 110 | 107 | 119 |

From these data, it is evident that at doses of 25 or 50 mg/kg, treatment with the gap-disabled compound ISIS 345888 resulted in markedly lower ALT levels, relative to treatment with the gapmer compound ISIS 307754. These data further reveal that at the 25 and 50 mg/kg doses, ISIS 307754 caused increases in liver weight, relative to saline-treatment. The 12.5 mg/kg dose of ISIS 307754 did not increase liver weight, relative to saline-treatment. None of the doses of the gap-disabled compound ISIS 345888 resulted in an increase in liver weight, relative to saline-treatment. Thus, ISIS 345888 exhibits fewer toxic properties than ISIS 307754.

Oligomeric compounds isolated from kidney and liver tissue were subjected to capillary gel electrophoresis, to determine the concentrations of total and full-length oligomeric compound. The total concentration of oligomeric compound following treatment with ISIS 307754 (gapmer) was 163 μg/g in kidney and 176 μg/g in liver. Full-length ISIS 307754 represented 94% of the total compound present in kidney and 98% of the total compound present in liver. The total concentration following treatment with ISIS 345888 was 126 μg/g in kidney and 174 μg/g in liver. Full-length ISIS 345888 represented 82% of the total compound present in kidney and 78% of the total compound present in liver. These data demonstrate that full-length ISIS 345888 accumulates in liver and kidney tissue.

Liver RNA was analyzed for JNK1 expression levels by quantitative real-time PCR as described by other examples herein, using the housekeeping gene cyclophilin A to normalize RNA levels among samples. In Table 30, JNK1 mRNA expression levels are shown as normalized to saline-treated control JNK1 levels.

TABLE 30

Target reduction and serum transaminases: gap-disabled vs. gapmer oligomeric compounds targeted to JNK1

| Treatment | Dose, mg/kg | JNK1 mRNA % control |
|---|---|---|
| 141923 | 50 | 93 |
| 307754 | 50 | 15 |
| 307754 | 25 | 16 |
| 307754 | 12.5 | 31 |
| 345888 | 50 | 23 |
| 345888 | 25 | 26 |
| 345888 | 12.5 | 49 |

These results demonstrate a substantial reduction in target expression following treatment with both the gap-disabled and gapmer compounds. Furthermore, the hepatoxicity caused by the gapmer, as judged by liver weights and ALT levels, is ameliorated by the introduction of 2'-MOE nucleotides into the gap segment. The significant reduction of JNK1 mRNA in livers of mice treated with ISIS 345888 also illustrates that the concentration of ISIS 345888 accumulated in the liver is an amount sufficient to elicit substantial target reduction.

Example 51

Antisense Inhibition by Gap-Disabled Oligomeric Compounds Target to Human C-Raf

In a further embodiment, a series of oligomeric compounds was designed to target human C-raf RNA, using publicly available sequences (GenBank accession number X03484.1, incorporated herein as SEQ ID NO: 29; and a sequence assembled from GenBank accession numbers AC026153.10 and AC018500.2, incorporated herein as SEQ ID NO: 30). The compounds are shown in Table 31. "Target site" indicates the first (5'-most) nucleotide number on the particular target sequence to which the compound binds. All compounds in Table 31 are chimeric oligomeric compounds, comprising regions that alternate between 3'-endo regions and 2'-endo regions, also known as gap-disabled compounds. The motif of each compound in Table 31 is 3-2-1-2-1-2-1-2-1-2-3, where the number indicates the number of nucleosides in that region. Regions consisting of 2'-MOE nucleotides are indicated by bold, underlined type and the remaining regions in plain type consist of 2'-deoxynucleotides. All internucleoside linkages are phosphorothioate linkages, and all cytosines are 5-methylcytosines.

The compounds were tested for their effect on human C-raf mRNA levels by quantitative real-time PCR as described in other examples herein. Data are averages from two experiments in which A549 cells were treated with 75 nM of the compounds in Table 31. ISIS 18078 (SEQ ID NO: 8), which does not target Raf kinase C, was used as a negative control oligonucleotide in this assay.

TABLE 31

Antisense inhibition by gap-disabled oligomeric compounds targeted to human C-raf

| Isis # | Region | Target SEQ ID NO | Target Site | Sequence (5' to 3') | % Inhib | Seq ID NO |
|---|---|---|---|---|---|---|
| 336818 | Coding | 29 | 94 | attcttaaacctgagggagc | 26 | 76 |
| 336819 | Coding | 29 | 144 | tgatcgtcttccaagctccc | 46 | 77 |
| 336820 | Coding | 29 | 198 | gagagatgcagctggagcca | 61 | 78 |
| 336821 | Coding | 29 | 249 | tgccatcatctgatgcccgg | 77 | 79 |
| 336822 | Coding | 29 | 268 | ttagaaggatctgtgagttt | 67 | 80 |
| 336823 | Coding | 29 | 327 | gcacattgaccactgttctt | 43 | 81 |
| 336824 | Coding | 29 | 367 | agtgctttcataaggcagtc | 38 | 82 |
| 336825 | Coding | 29 | 392 | ctctggttgcaggcccctca | 59 | 83 |
| 336826 | Coding | 29 | 413 | aagtctgaacactgcacagc | 57 | 84 |
| 336827 | Coding | 29 | 433 | ttacctttgtgttcgtggag | 75 | 85 |
| 336828 | Coding | 29 | 466 | gcagcatcagtattccaatc | 58 | 86 |
| 336829 | Coding | 29 | 543 | tcttccgagcaaagttgtgt | 35 | 87 |
| 336830 | Coding | 29 | 591 | tgagcaggaatttctgacag | 53 | 88 |
| 336831 | Coding | 29 | 701 | tggaaacaataagagttgtc | 40 | 89 |
| 336832 | Coding | 29 | 776 | ggaaacagactctcgcatac | 38 | 90 |
| 336833 | Coding | 29 | 800 | gtgctgagaactaacaggca | 78 | 91 |
| 336834 | Coding | 29 | 909 | tgaccatgtggacattaggt | 70 | 92 |
| 336835 | Coding | 29 | 931 | ctgtccacaggcagcgtggt | 40 | 93 |
| 336837 | Coding | 29 | 954 | gaaggtgaggctgattcgct | 43 | 94 |
| 336838 | Coding | 29 | 982 | cacgaggcctaattttgttt | 91 | 95 |
| 336839 | Coding | 29 | 1110 | atttcccaataatagcttga | 68 | 96 |
| 336840 | Coding | 29 | 1141 | gcaacatctccgtgccattt | 48 | 97 |
| 336841 | Coding | 29 | 1228 | tcctgaaggcctggaattgc | 53 | 98 |
| 336842 | Coding | 29 | 1284 | ccgtgttttgcgcagaacag | 50 | 99 |
| 336843 | Coding | 29 | 1313 | caggttgtcctttgtcatgt | 17 | 100 |
| 336844 | Coding | 29 | 1361 | ggacatgcaggtgtttgtag | 27 | 101 |

TABLE 31-continued

Antisense inhibition by gap-disabled oligomeric compounds targeted to human C-raf

| Isis # | Region | Target SEQ ID NO | Target Site | Sequence (5' to 3') | % Inhib | Seq ID NO |
|---|---|---|---|---|---|---|
| 336845 | Coding | 29 | 1416 | attagctggaacatctgaaa | 19 | 102 |
| 336846 | Coding | 29 | 1447 | atgcaaatagtccattccct | 21 | 103 |
| 336847 | Coding | 29 | 1490 | gaaatatattgttggatttc | 61 | 104 |
| 336848 | Coding | 29 | 1536 | cgtgactttactgttgccaa | 34 | 105 |
| 336849 | Coding | 29 | 1594 | gggccatccagaggacagag | 58 | 106 |
| 336850 | Coding | 29 | 1650 | tgaagatgatctgatctcgg | 31 | 107 |
| 336851 | Coding | 29 | 1788 | atatagcttactaagatctg | 33 | 108 |
| 336852 | Coding | 29 | 1832 | aatggaagacaggatctggg | 34 | 109 |
| 336853 | Coding | 29 | 1928 | cttcggtagagagtgttgga | 52 | 110 |
| 336854 | Coding | 29 | 1955 | tatcctcagtgtgggctgcc | 39 | 111 |
| 336855 | Coding | 29 | 2010 | tgcaaagtcaactagaagac | 49 | 112 |
| 336856 | Coding | 29 | 2068 | ttctgcctctggagaaaggg | 20 | 113 |
| 336857 | Intron | 29 | 2144 | aggtccttagcagagcttct | 33 | 114 |
| 336858 | Intron | 29 | 2177 | aaatggcttccttctcccag | 13 | 115 |
| 336859 | Intron | 29 | 2255 | tacagaaggctgggccttga | 67 | 116 |
| 336860 | Intron | 29 | 2317 | tttttgtactaccatcaaca | 50 | 117 |
| 336861 | Intron | 29 | 2351 | acttcctctaaatactcatg | 24 | 118 |
| 336862 | Intron | 29 | 2399 | tccacatcagggctggactg | 32 | 119 |
| 336863 | Intron | 29 | 2430 | gaagctgatttccaaaatcc | 14 | 120 |
| 336864 | Intron | 29 | 2458 | tcccgcctgtgacatgcatt | 39 | 121 |
| 336865 | Intron | 29 | 2484 | accactctctgaagaaagtc | 25 | 122 |
| 336866 | Intron | 29 | 2502 | gtgccttatgtgcaaaatgt | 36 | 123 |
| 336867 | Intron | 29 | 2532 | ggcggccagagtctcggcag | 13 | 124 |
| 336868 | Intron | 29 | 2566 | ctaagaaaagttccatagta | 14 | 125 |
| 336869 | Intron | 29 | 2604 | gaagctgtgaaaggaggacg | 9 | 126 |
| 336870 | Intron | 29 | 2630 | gggcagctcctggaagacaa | 31 | 127 |
| 336871 | Intron | 29 | 2746 | tgtatacacatgatgtgact | 25 | 128 |
| 336872 | Intron | 30 | 2834 | aacatagctatttgaagcta | 47 | 129 |
| 336873 | Intron | 30 | 27366 | aagcaataatttcaatttct | 35 | 130 |
| 336874 | Intron | 30 | 27473 | gcccagcttaacgtgtattt | 12 | 131 |
| 336875 | Intron | 30 | 27513 | tcatcaggcccagcttaacg | 52 | 132 |
| 336876 | Intron | 30 | 27520 | ccatccatggaaacattatc | 35 | 133 |
| 336877 | Intron | 30 | 28081 | acagcatctaacatcactgt | 24 | 134 |
| 336878 | Intron | 30 | 28103 | agtcaatctcccgaggatag | 38 | 135 |
| 336879 | Intron | 30 | 28215 | agtgacgctttccaagaaga | 27 | 136 |
| 336880 | Intron | 30 | 28503 | atgtaagctaacgatgaata | 10 | 137 |
| 336881 | Exon-Exon Junction | 30 | 28528 | ttccctgggctattctccca | 51 | 138 |

TABLE 31-continued

Antisense inhibition by gap-disabled oligomeric compounds targeted to human C-raf

| Isis # | Region | Target SEQ ID NO | Target Site | Sequence (5' to 3') | % Inhib | Seq ID NO |
|---|---|---|---|---|---|---|
| 336882 | Exon-Exon Junction | 30 | 28577 | aattgagaattacactcacc | 55 | 139 |
| 336883 | Exon-Exon Junction | 30 | 28613 | aacgcctcctaaattgagaa | 27 | 140 |
| 336884 | Exon-Exon Junction | 30 | 28624 | tggattggcttagggaccca | 25 | 141 |
| 336885 | Exon-Exon Junction | 30 | 28700 | actattttgcccttatgaag | 81 | 142 |
| 336886 | Exon-Exon Junction | 30 | 28886 | tcttaaaatctactctgaaa | 29 | 143 |
| 336887 | Exon-Exon Junction | 30 | 29191 | cttaactgtcttaaaatcta | 47 | 144 |
| 336888 | Exon-Exon Junction | 30 | 29199 | tgaaaaatgtacttttctat | 51 | 145 |
| 336889 | Exon-Exon Junction | 30 | 29273 | aaagttttctttaaacaatg | 44 | 146 |
| 336890 | Exon-Exon Junction | 30 | 29462 | gcccatgttctcagaataaa | 63 | 147 |
| 336891 | Exon-Exon Junction | 30 | 29641 | aatctaggtctgttgaactc | 6 | 148 |
| 336892 | Exon-Exon Junction | 30 | 29665 | aaggtaatttgctcaaggcc | 46 | 149 |
| 336893 | Exon-Exon Junction | 30 | 29713 | agaaaactgggactctaaga | 60 | 150 |
| 336894 | Exon-Exon Junction | 30 | 29732 | tatttctatctgaaaaataa | 48 | 151 |
| 336895 | Exon-Exon Junction | 30 | 29751 | aacaaacctatgaagtaggt | 59 | 152 |
| 337561 | Exon 1: Intron 1 | 30 | 29773 | tgccacctacctgagggagc | 43 | 153 |
| 337562 | Exon 10: Intron 10 | 30 | 20510 | attcttaaacctggtaagaa | 64 | 154 |
| 337563 | Exon 11: Intron 11 | 30 | 20743 | gttcacataccactgttctt | 48 | 155 |
| 337564 | Exon 12: Intron 12 | 30 | 27195 | gcacattgacctacaaacaa | 57 | 156 |
| 337565 | Exon 13: Intron 13 | 30 | 27308 | gagctcttaccctttgtgtt | 45 | 157 |
| 337566 | Exon 14: Intron 14 | 30 | 30025 | tgcaacttacaaagttgtgt | 67 | 158 |
| 337567 | Exon 15: Intron 15 | 30 | 30334 | tcttccgagcctacaacaag | 43 | 159 |
| 337568 | Exon 2: Intron 2 | 30 | 30492 | aatgccttacaagagttgtc | 48 | 160 |
| 337569 | Exon 3: Intron 3 | 30 | 34981 | gtgctgagaactaggaggag | 63 | 161 |
| 337570 | Exon 4: Intron 4 | 30 | 35135 | gccctattacctcaatcatc | 48 | 162 |
| 337571 | Exon 5: Intron 5 | 30 | 38855 | gaattgcatcctgaaacaga | 69 | 163 |
| 337572 | Exon 7: Intron 7 | 30 | 38883 | ggaaaagtacctgattcgct | 43 | 164 |
| 337573 | Exon 8: Intron 8 | 30 | 38991 | gaaggtgaggcttaatagac | 84 | 165 |
| 337574 | Intron 1: Exon 2 | 30 | 39462 | cacgaggcctctgaaacaag | 60 | 166 |
| 337575 | Intron 10: Exon 11 | 30 | 39580 | ccaagcttaccgtgccattt | 65 | 167 |
| 337576 | Intron 12: Exon 13 | 30 | 47482 | gcaacatctcctgcaaaatt | 40 | 168 |
| 337577 | Intron 13: Exon 14 | 30 | 47567 | ttctactcaccgcagaacag | 28 | 169 |
| 337578 | Intron 15: Exon 16 | 30 | 48476 | tctactcactccattccctg | 38 | 170 |
| 337579 | Intron 16: Exon 17 | 30 | 51633 | atgcaaatagctgtgaaggg | 58 | 171 |
| 337580 | Intron 2: Exon 3 | 30 | 51680 | caaaggatactgttggattt | 76 | 172 |
| 337581 | Intron 4: Exon 5 | 30 | 53471 | agaaatatatctcaatgctt | 58 | 173 |
| 337582 | Intron 6: Exon 7 | 30 | 53590 | agattctcaccatccagagg | 79 | 174 |

TABLE 31-continued

Antisense inhibition by gap-disabled oligomeric compounds targeted to human C-raf

| Isis # | Region | Target SEQ ID NO | Target Site | Sequence (5' to 3') | % Inhib | Seq ID NO |
|---|---|---|---|---|---|---|
| 337583 | Intron 7: Exon 8 | 30 | 54149 | acagacttacctgatctcgg | 44 | 175 |
| 337584 | Intron 8: Exon 9 | 30 | 54289 | tgaagatgatctaagggaaa | 65 | 176 |
| 337585 | Intron 9: Exon 10 | 30 | 54615 | ggaagacaggatctgaaaca | 56 | 177 |

These data reveal that SEQ ID NOs 77, 78, 79, 80, 81, 83, 84, 85, 86, 88, 91, 92, 94, 95, 96, 97, 98, 99, 104, 106, 110, 112, 116, 117, 129, 132, 138, 139, 142, 144, 145, 146, 147, 149, 150, 151, 152, 153, 154, 155, 156, 157, 158, 159, 160, 161, 162, 163, 164, 165, 166, 167, 171, 172, 173, 174, 175, 176 and 177 exhibited at least 43% inhibition of human C-raf mRNA expression in this assay.

Example 52

Antisense Inhibition by Gap-Disabled Oligomeric Compounds Target to Mouse SRC-2

In a further embodiment, a series of oligomeric compounds was designed to target mouse SRC-2 RNA, using publicly available sequences (GenBank accession number U39060.1, incorporated herein as SEQ ID NO: 31; the complement of nucleotides 10220000 to 10460000 of the sequence with GenBank accession number NW_000149.1, incorporated herein as SEQ ID NO: 32; and GenBank accession number AK028964.1, incorporated herein as SEQ ID NO: 33). The compounds are shown in Table 32. "Target site" indicates the first (5'-most) nucleotide number on the particular target sequence to which the compound binds. All compounds in Table 32 are chimeric oligomeric compounds, comprising alternating 3'-endo regions and 2'-endo regions, also known as gap disabled compounds. The motif of each compound in Table 19 is 3-2-1-2-1-2-1-2-1-2-3, where the number indicates the number of nucleosides in that region. Regions consisting of 2'-MOE nucleotides are indicated by bold, underlined type and the remaining regions in plain type consist of 2'-deoxynucleotides. All internucleoside linkages are phosphorothioate linkages, and all cytosines are 5-methylcytosines.

The compounds were tested for their effect on mouse SRC-2 mRNA levels by quantitative real-time PCR as described in other examples herein. Data are averages from two experiments in which b.END cells were treated with 50 nM of the compounds in Table 32. ISIS 337599 (GTGCGCGCGAGCCCGAAATC, SEQ ID NO: 178), which does not target Raf kinase C, is a gap-disabled compound having the same motif as the compounds in Table 32 and was used as a negative control compound in this assay.

TABLE 32

Antisense inhibition by gap-disabled oligomeric compounds targeted to human Raf kinase C

| ISIS # | Region | TARGET SEQ ID NO | TARGET SITE | SEQUENCE (5' to 3') | % INHIB | SEQ ID NO |
|---|---|---|---|---|---|---|
| 337600 | 5' UTR | 31 | 174 | tatcagcaactgtgcctgta | 6 | 179 |
| 337601 | 5' UTR | 31 | 193 | cccactcatcttgaacacat | 21 | 180 |
| 337602 | Coding | 31 | 479 | tctgcacttcatctatgttg | 45 | 181 |
| 337603 | Coding | 31 | 646 | cagctcttcttggttatacc | 37 | 182 |
| 337604 | Coding | 31 | 1170 | tgtctcagaacttcatggtg | 34 | 183 |
| 337605 | Coding | 31 | 1257 | gaacggatgagtttgctctt | 9 | 184 |
| 337606 | Coding | 31 | 1272 | tcattagtagtctgagaacg | 0 | 185 |
| 337607 | Coding | 31 | 1426 | acctgggttcccactgcaca | 49 | 186 |
| 337608 | Coding | 31 | 1462 | gggaaaatttatattgctac | 9 | 187 |
| 337609 | Coding | 31 | 1491 | atgcccatttgttcctttgg | 22 | 188 |
| 337610 | Coding | 31 | 2244 | tgcttctccttgagcgaggt | 31 | 189 |
| 337611 | Coding | 31 | 2509 | aggatctgtcttactgtcca | 53 | 190 |
| 337612 | Coding | 31 | 2519 | tgttactggcaggatctgtc | 20 | 191 |
| 337613 | Coding | 31 | 2625 | tgcaaatcatccaaaatctc | 26 | 192 |

TABLE 32-continued

Antisense inhibition by gap-disabled oligomeric compounds targeted to human Raf kinase C

| ISIS # | Region | TARGET SEQ ID NO | TARGET SITE | SEQUENCE (5' to 3') | % INHIB | SEQ ID NO |
|---|---|---|---|---|---|---|
| 337614 | Coding | 31 | 2700 | atggcttgcttgtcaactga | 53 | 193 |
| 337615 | Coding | 31 | 2705 | tgatgatggcttgcttgtca | 35 | 194 |
| 337616 | Coding | 31 | 2720 | gttgcatgaggtcattgatg | 31 | 195 |
| 337617 | Coding | 31 | 2804 | gtgggttattaaaagtgctc | 7 | 196 |
| 337618 | Coding | 31 | 2809 | tggtcgtgggttattaaaag | 16 | 197 |
| 337619 | Coding | 31 | 2819 | ccagttgccctggtcgtggg | 39 | 198 |
| 337620 | Coding | 31 | 2824 | cctgcccagttgccctggtc | 10 | 199 |
| 337621 | Coding | 31 | 2839 | ctggtttggcaataacctgc | 1 | 200 |
| 337622 | Coding | 31 | 2885 | gtccagcaccagttgggctt | 27 | 201 |
| 337623 | Coding | 31 | 2890 | gaaaggtccagcaccagttg | 33 | 202 |
| 337624 | Coding | 31 | 2900 | tgattggtgggaaaggtcca | 11 | 203 |
| 337625 | Coding | 31 | 2910 | ctactgtttctgattggtgg | 33 | 204 |
| 337626 | Coding | 31 | 2934 | ggctgaggtatcactgagta | 62 | 205 |
| 337627 | Coding | 31 | 2939 | ttcctggctgaggtatcact | 34 | 206 |
| 337628 | Coding | 31 | 2949 | ttacccatcattcctggctg | 36 | 207 |
| 337629 | Coding | 31 | 3182 | gtctttggccaggctggctg | 27 | 208 |
| 337630 | Coding | 31 | 3513 | tggctctggctgaccagttc | 20 | 209 |
| 337631 | Coding | 31 | 3650 | agtttggatcttgcatggga | 28 | 210 |
| 337632 | Coding | 31 | 3789 | ttctgctgtgcttggaggcg | 24 | 211 |
| 337633 | Coding | 31 | 4137 | gtcgtagccccagtaaagcc | 2 | 212 |
| 337634 | 3' UTR | 31 | 4833 | agttgcactacggtgaatgc | 43 | 213 |
| 337635 | Exon 1a: Intron 1c | 32 | 77182 | gcatctttaccacttcagga | 39 | 214 |
| 337636 | Exon 11: Intron 11 | 32 | 200699 | gaaaactcacctggtcactg | 0 | 215 |
| 337637 | 3' UTR | 33 | 2520 | aacaggtcgagctcagtagt | 34 | 216 |

These data demonstrate that SEQ ID NOs 180, 181, 182, 183, 186, 188, 189, 190, 191, 192, 193, 194, 195, 198, 201, 202, 204, 205, 206, 207, 208, 209, 210, 211, 213, 214 and 216 demonstrated at least 20% inhibition of mouse SRC-2 in this assay. These results provide another example of target inhibition by gap-disabled oligomeric compounds.

Example 53

Recombinant Human RNase H Analysis

RNase H is a cellular endonuclease which cleaves the RNA strand of an RNA:DNA duplex. It is known in the art that single-stranded antisense oligomeric compounds which are "DNA-like" or have DNA-like regions elicit RNase H activity. Activation of RNase H, therefore, results in cleavage of the RNA target, thereby allowing oligonucleotide-mediated inhibition of gene expression.

In a further embodiment, the ability of oligomeric compounds to elicit RNase H activity was tested using RNase H activity assays. Where the motif of each compound is indicated, 2'-MOE nucleotides are in bold, underlined type and 2'-deoxynucleotide regions are in plain type. The number in each region represents the number of nucleotides in that region. Oligomeric compounds tested included ISIS 300861 (SEQ ID NO: 43), a gap-disabled compound having the motif 3-2-1-3-1-3-1-3-3 and phosphorothioate (P═S) internucleoside linkages throughout the compound, and ISIS 335114 (SEQ ID NO: 43), also a gap-disabled compound having the motif 3-2-1-3-1-3-1-3-3 and phosphodiester (P═O) internucleoside linkages throughout the compound. Also tested was ISIS 335112 (SEQ ID NO: 43), a chimeric oligonucleotide 20 nucleotides in length, having a 10-nucleotide gap segment flanked on both sides (5' and 3') by 5-nucleotide wing segments, wherein the gap segment consists of 2'-deoxynucleotides and the wing segments consist of 2'-MOE nucleotides. Internucleoside linkages are phosphodiester (P═O) throughout the compound. An additional oligomeric compound tested was ISIS 335033 (SEQ ID NO: 43), uniformly composed of 2'-deoxynucleotides with phosphodiester (P═O) internucleoside linkages throughout the compound. In these compounds, all cytosines are 5-methylcytosines.

RNase H1 activity was evaluated using 40 oligoribonucleotides of mouse glucagon receptor RNA (GTTGGAGGCAATGGCAAGAAGGCAAAGCTCTTCAGGAGGA, incorporated herein as SEQ ID NO: 217) as the target RNA. This target RNA was radiolabelled with $^{32}P$ at the 5'-end as described by Wu et al. (*J. Biol. Chem.,* 2001, 276, 23547-23553). In a volume of 100 μL, 100 nM of radiolabelled RNA and 200 nM of oligomeric compound were incubated in a reaction containing 20 mM Tris HCl, pH 7.5, 20 mM KCl, 1 mM $MgCL_2$, 0.1 mM Tris(2-carboxyethyl)phosphine hydrochloride (TCEP) and 4% RNaseOUT™ (Invitrogen Corporation, Carlsbad, Calif.). Reactions were melted by heating to 95° C. for 5 minutes then allowed to cool slowly to room temperature. Formation of the heteroduplex between the target RNA and an oligomeric compound was confirmed by the shift in mobility between the single-stranded end labeled sense RNA and the annealed duplex on non-denaturing polyacrylamide gels. The resulting heteroduplexes were tested as substrates for digestion by recominant human RNase H1, which was expressed and purified as described by Wu et al. (*J. Biol. Chem.,* 2004, 279, 17181-17189). An aliquot of annealed heteroduplex reaction was removed for use as the t=0 timepoint. 70 ng of purified recombinant RNase H1 in a solution of 50 mM Tris HCl, pH 7.5, 50 mM NaCl, 50% glycerol, 1 mM TCEP and 4% RNaseOUT™ was added to 100 μL of the duplex reaction and was incubated at 37° C. The reaction was terminated at 15, 60 and 240 minute timepoints by the addition of 4M Urea and 20 mM EDTA. The reactions were heated at 90° C. for 2 minutes and the reaction products were resolved on a 12% polyacrylamide gel containing 7 M Urea and visualized and quantitated using a PhosphorImager™ and IMAGEQUANT™ Software (Molecular Dynamics, Sunnyvale, Calif.).

Recombinant human RNase H1 was tested for its ability to cleave four different heteroduplexes formed between the target RNA and each of the oligomeric compounds ISIS 335112, ISIS 335033, ISIS 335114 and ISIS 300861. The percentage of target RNA cleaved was calculated using the following formula: [(fraction of RNA cleaved/total RNA input)×100]−% background. The data from the 15, 60 and 240 minute time points were normalized to the data from the t=0 timepoint. The results are shown in Table 33.

TABLE 33

Recombinant human Rnase-H1 mediated cleavage of heteroduplexes

| Reaction time (minutes) | % target mRNA cleavage | | | |
|---|---|---|---|---|
| | ISIS 335112 Gapmer P═O | ISIS 335033 2'-deoxy P═O | ISIS 335114 Gap-disabled P═O | ISIS 300861 Gap-disabled P═S |
| 15 | 3 | 5 | 1 | 0 |
| 60 | 15 | 30 | 1 | 1 |
| 240 | 38 | 74 | 1 | 1 |

These data demonstrate that whereas ISIS 335112 (gapmer) and ISIS 335033 (uniform 2'-deoxy) oligomeric compounds elicited RNase H1-mediated cleavage, the gap-disabled compounds (ISIS 335114 or ISIS 300861) were unable to utilize recombinant RNase H1 to effect the detectable cleavage of target mRNA in this assay.

Example 54

Immunoprecipitated RNase H Activity

In a further embodiment, the ability of gap-disabled oligomeric compounds to utilize immunoprecipitated RNase H1 and RNase H2 to direct the cleavage of target RNA was tested. Polyclonal antibodies were generated by Biosolutions (Ramona, Calif.) using RNase H1 and RNase H2 proteins purified as described by Wu, et al. (*J. Biol. Chem.,* 2004, 279, 17181-17189). Immunoprecipitations were also performed as described by Wu, et al. (*J. Biol. Chem.,* 2004, 279, 17181-17189). Duplex formation was performed as described herein, using ISIS 300861 (SEQ ID NO: 43, gap-disabled), ISIS 335112 (SEQ ID NO: 43, gapmer) and ISIS 335033 (SEQ ID NO: 43, uniform 2'-deoxy) as the oligomeric compounds and the mouse glucagon receptor (SEQ ID NO: 217) as the target RNA. The cleavage assay was performed as described herein for recombinant RNase H1, using RNase H1 or RNase H2 immunoprecipitated with 10 μg of the respective antibody per 1 mg total cellular protein. Samples of the cleavage assay were collected at t=0 (start of the reaction), 15, 60 and 180 minutes and products were resolved by denaturing polyacrylamide electrophoresis and visualized by using a PhosphorImager™ and IMAGEQUANT™ Software (Molecular Dynamics, Sunnyvale, Calif.). Whereas both ISIS 335033 (uniform 2'deoxy) and ISIS 335112 (gapmer) were able to direct cleavage of the target RNA by both immunoprecipitated RNase H1 and RNase H2, ISIS 300861 (gap-disabled) did not elicit detectable cleavage of the target RNA by immunoprecipitated RNase H1 or RNase H2 in this assay.

Example 55

In Vitro Nuclease Assay

In a further embodiment, the ability of gap-disabled compounds to elicit target cleavage in subcellular fractions was evaluated. HeLa cell nuclear, nuclear membrane and cytosolic fractions were isolated as described previously (Dignam, et al., *Nucleic Acids Research.,* 1983, 11, 1475-1489) and used to test the ability of gap-disabled oligomeric compounds to elicit target reduction. Following isolation of the subcellular fractions, the cleavage assay was performed as described for recombinant RNase H1.

Duplexes between the mouse glucagon receptor RNA and oligomeric compound were prepared as described herein, using as the oligomeric compounds ISIS 335033 (SEQ ID NO: 43, uniform 2'-deoxy), ISIS 335112 (SEQ ID NO: 43, gapmer), ISIS 300861 (SEQ ID NO: 43, gap-disabled) and ISIS 298683 (SEQ ID NO: 43, uniform 2'-MOE). Annealed duplexes (10 μl) were incubated with 3 μg of the HeLa cytosolic extract at 37° C. The assay was also performed with a 4-fold higher concentration of cytosolic extract. Samples were collected at t=0 (reaction start time), 15, 60 and 180 minutes. The reaction was terminated by phenol/chloroform extraction and ethanol precipitated with the addition of 10 μg of tRNA as a carrier. Pellets were resuspended in 10 μl of denaturing loading dye and products were resolved on 12% denaturing acrylamide gels as described herein. Visualization of cleavage patterns by PhosphorImager™ detection revealed that while HeLa cytosolic extracts were capable of supporting target cleavage mediated by ISIS 335112 (gapmer) and ISIS 335033 (uniform 2'-deoxy) in a time-dependent manner, this fraction was unable to support target reduction by ISIS 300861 (gap-disabled). Additionally, ISIS 298683 (uniform 2'-MOE) was unable to direct cleavage in the cytosolic extracts.

The ability of ISIS 300861 (gap-disabled) and ISIS 335112 (gapmer) to mediate target cleavage was also tested in the nuclear fraction isolated from HeLa cells. In this assay, the mouse glucagon receptor target RNA contained a 3' phosphorothioate cap, to improve its resistance to exonuclease activity, which, as is known in the art, is present in nuclear extracts and results in non-specific degradation of the target RNA. Annealed duplexes (10 μl) were incubated with 3 μg of the HeLa nuclear extract at 37° C. The assay was performed both in the presence and absence of beta-mercapoethanol. Samples were collected at t=0 (start of the reaction), 10 and 60 minutes. Resolution of the products on a denaturing polyacrylamide gel, followed by PhosphorImager™ detection, revealed that ISIS 300861 (gap-disabled) and ISIS 355112 (gapmer) elicited target cleavage in HeLa nuclear extracts in a time-dependent manner, both in the presence and absence of beta-mercaptoethanol. A four-fold higher concentration of nuclear extract was also able to support cleavage by both compounds.

The assay was also performed using HeLa nuclear membrane extract as source of RNase activity. Annealed duplexes (10 μl) were incubated with 3 μg of the HeLa nuclear membrane extract at 37° C. Neither ISIS 331112 (gapmer) nor ISIS 335114 (gap-disabled) was able to elicit cleavage of the target RNA in HeLa nuclear membrane extracts.

Together, these data reveal that the enzyme activity responsible for the cleavage of duplexes formed between gap-disabled oligomeric compounds and target RNAs resides in the nuclear fraction of the cell, not in the cytosolic or nuclear membrane fractions.

In the nuclear extracts, comparison of the target RNA cleavage pattern to a molecular weight ladder revealed that cleavage of the target RNA occurred only at nucleobase positions complementary to a 2'deoxynucleotide of the gap-disabled oligomeric compound, i.e. the cleavage sites were positioned within the 2'-deoxynucleotide gaps. Furthermore, within the target site for ISIS 300861, cleavage occurred preferentially at guanines.

Example 56

Influence of Divalent Cations on Rnase Activity in Subcellular Extracts

Multiple RNase H-like activities exist in human cells, and these activities are differentially activated by magnesium and manganese (Wu et al., *J. Biol. Chem.,* 2004, 279, 17181-17189). Thus, it was of interest to determine the influence of these divalent cations on the ability of RNase enzymes to cleave heteroduplexes comprising gap-disabled oligomeric compounds.

ISIS 300861 (SEQ ID NO: 43, gap-disabled) and ISIS 335112 (SEQ ID NO: 43, gapmer) were tested for their ability to direct RNase mediated cleavage in the presence of manganese or mangesium. Duplex formation and subcellular fractionation of HeLa cells were performed as described herein. The cleavage assay was also conducted as described herein, with the addition of 0.05 mM magnesium, 5 mM magnesium, 0.05 mM manganese or 5 mM manganese. The cleavage reaction was terminated at t=0 (start of the reaction), 15, 60 and 120 minutes, and samples from each of these timepoints were resolved on a denaturing polyacrylamide gel. Cleavage products were detected using a PhosphorImager™.

In nuclear extracts, prepared as described herein, both magnesium- and manganese-dependent degradation of ISIS 300861 (gap-disabled) and ISIS 335112 (gapmer) heteroduplexes was observed. The cleavage activity in the presence of 0.05 mM manganese was approximately equal to that observed in the presence of 5 mM mangesium, demonstrating that manganese is more effective than magnesium at enhancing RNase activity in HeLa cell nuclear extracts.

The influence of divalent cations on cleavage activity was similarly tested in cytosolic extracts. The assay was performed as described herein. In the presence of either 5 mM magnesium or 5 mM manganese, ISIS 300861 (gap-disabled) did not elicit cleavage of the target RNA. ISIS 335112 (gapmer) was, however, able to direct cleavage of the target RNA in cytosolic extracts.

The effects of divalent cations on cleavage by immunoprecipitated RNase H1 were also evaluated. Duplex formation between the target RNA and ISIS 300861 (gap-disabled) or ISIS 335112 (gapmer) was conducted as described herein. Immunoprecipitation and the cleavage assay were performed as described herein, with the addition of 0.05 mM mangesium, 5 mM magnesium, 0.05 mM manganese or 5 mM manganese to the cleavage assay. ISIS 335112 (gapmer) resulted in target RNA cleavage in the presence of either divalent cation at all concentrations. In contrast to the results observed in the absence of divalent cation, the addition of 5 mM manganese allowed the gap-disabled compound ISIS 300861 to direct the cleavage of the target RNA by immunoprecipitated RNase H1 in a pattern consistent with that observed for gap-disabled cleavage activity in nuclear extracts. Coupled with the observation that without additional manganese, a gap-disabled compound was unable to utilize immunoprecipitated RNase H1 to effect target RNA cleavage, these data demonstrate that additional manganese is required for immunoprecipitated RNase H1 to cleave heteroduplexes formed between a gap-disabled oligomeric compound and a target RNA.

A similar assay was performed using immunoprecipitated RNase H2, however, neither the gap-disabled nor gapmer oligomeric compound elicited target RNA cleavage by immunoprecipitated RNase H2, regardless of the presence of a divalent cation in the cleavage assay.

Further tested was the effect of divalent cations on the activity of recombinant human RNase H1. The assay was performed as described herein, using ISIS 300861 as the gap-disabled compound and ISIS 335112 as the gapmer compound. Manganese at a concentration of 5 mM was added to the cleavage assay. In contrast to the results described for the activity of recombinant RNase H1 in the absence of additional manganese, in the presence of 5 mM manganese ISIS 300861 was able to direct cleavage of its target RNA by recombinant RNase H1. The cleavage pattern mimicked those observed for nuclear extracts and for immunoprecipitated RNase H1 in the presence of manganese. These data demonstrate that manganese is required for recombinant RNase H1 to cleave heteroduplexes formed between a gap-disabled oligomeric compound and a target RNA.

To extend the observation that the presence of manganese influences the potency of gap-disabled oligomeric compounds, the extent of cleavage and the rate at which it occurs were evaluated as a function of manganese concentration. Duplex formation between ISIS 300861 and the mouse glucagon target RNA was performed as described herein. A cleavage assay was performed as described herein using recombinant human RNase H1, with the addition of manganese at 0.5, 1, 5, 20 or 50 mM. To measure the rate at which cleavage occurs, reactions were terminated at t=0 (start of the reaction), 10, 60 and 180 minutes and the percentage of RNA cleaved was calculated as described herein, using the t=0 timepoint to normalize the data from the 10, 60 and 180 minute timepoints. The data are shown in Table 34.

TABLE 34

Dependence of RNA cleavage by recombinant RNase H1 on manganese concentration

| Time | Concentration of manganese (mM) | | | | |
|---|---|---|---|---|---|
| (minutes) | 0.5 | 1 | 5 | 20 | 50 |
| 10 | 3 | 56 | 68 | 63 | 0 |
| 60 | 6 | 69 | 74 | 69 | 0 |
| 180 | 12 | 75 | 75 | 70 | 12 |

These data demonstrate concentration-dependent cleavage at 0.5 and 1 mM manganese, however, the addition of 5 or 20 nM manganese did not further increase target cleavage. The addition of 50 mM manganese inhibited cleavage of the target RNA.

A comparison of cleavage rates achieved by ISIS 335112 (gapmer) and ISIS 300861 (gap-disabled) was conducted. Duplexes formed with the target RNA and ISIS 335112 were cleaved at rates of 0.7 and 1.3 nM per minute in the presence of 50 and 500 uM manganese, respectively. Duplexes formed with the target RNA and ISIS 300861 were cleaved at 0.1 and 0.3 uM per minute at manganese concentrations of 50 and 500 uM, respectively. These data demonstrate that cleavage elicited by the gapmer oligomeric compound occurs at a higher rate than that elicited by the gap-disabled oligomeric compound.

Example 57 siRNA-Mediated Disruption of RNase H1 Activity: Influence on Gap-Disabled Oligomeric Compound Potency In a further embodiment, the participation of RNase H1 in the cleavage of target RNA mediated by gap-disabled oligomeric compounds was tested following disruption of cellular RNase H1 mRNA by siRNAs. Because siRNAs elicit target reduction through mechanisms not dependent on RNase H1, the use of siRNAs to disrupt the expression of RNase H1 is a method by which the activity of RNase H1 can be reduced, while not interfering with the pathway through which it acts. In this assay, cells receive a first treatment with an siRNA to reduce RNase H1 mRNA, followed by a second treatment with a known or putative RNase H1-dependent compound. The target RNA cleavage following the second treatment is used to assess whether the siRNA affected the enzyme activity stimulated by the addition of the oligomeric compound.

A549 cells were treated with 100 nM of an siRNA directed to RNase H1, comprised of the antisense strand with the sequence CUCAUCCUCUGUGGCAAACUU (SEQ ID NO: 218) annealed to the complementary sense strand (AAGUUUGCCACAGAGGAUGAG, SEQ ID NO: 219). Both strands are oligoribonucleotides with phosphodiester linkages throughout the compounds. As controls, cells were treated with 100 nM of the single-strand sense RNA (SEQ ID NO: 219) or were left untreated. Following 10 hours of treatment, RNase H1 mRNA expression was measured by quantitative real-time PCR and was reduced by 49% in cells treated with the RNase H1 siRNA. Untreated cells and cells treated with the control siRNA showed no reduction in RNase H1 mRNA expression. Cells were split into 96-well format cell culture plates at a density of 6000 cells per well and were cultured for an additional 10 hours. Next, cells were treated with ISIS 336848 (SEQ ID NO: 105) at 5, 10 or 30 nM. ISIS 336848 is a gap-disabled compound targeted to C-raf and having the motif <u>3</u>-2-<u>1</u>-2-<u>1</u>-2-<u>1</u>-2-<u>1</u>-2-<u>3</u>; internucleoside linkages are phosphorothioate throughout the compound and all cytosines are 5-methylcytosines. C-raf mRNA was measured by quantitative real-time PCR as described herein. Untreated cells served as the control to which data were normalized. The data are presented in Table 35 as percentage reduction in C-raf mRNA.

TABLE 35

Gap-disabled mediated reduction of C-raf mRNA in A549 cells with lowered RNase H1 activity

| | Reduction in C-raf mRNA Concentration of gap-disabled compound (nM) | | |
|---|---|---|---|
| | 5 | 10 | 30 |
| Single-strand sense RNA | 40 | 61 | 89 |
| No siRNA | 39 | 55 | 89 |
| RNase H1 siRNA | 32 | 48 | 83 |

These data demonstrate that, in comparison to cells treated with a control sense RNA or cells left untreated, the reduction in expression of RNase H1 mRNA results in a decrease in the ability of the gap-disabled oligomeric compound to result in cleavage of its target mRNA. For example, whereas a dose of 5 nM of ISIS 336848 results in 39% and 40% reductions in target mRNA in cells receiving no siRNA or single-strand sense RNA, respectively, C-raf mRNA is reduced by only 32% in cells in which RNase H1 has been reduced by siRNA treatment.

This assay was also performed in HeLa cells, in which either RNase H1 or RNase H2 was disrupted using siRNAs directed to the mRNA sequence encoding each respective enzyme. The siRNA directed to RNase H1 was comprised of SEQ ID NOs: 218 and 219. The siRNA directed to RNase H2 was comprised of the antisense strand with the sequence GGAGCCUUGCGUCCUGGGCTT (SEQ ID NO: 220), annealed to the complementary sense strand GCCCAGGACGCAAGGCTCCTT (SEQ ID NO: 221). SEQ ID NOs 220 and 221 are oligoribonucleotides 19 nucleobases in length each having a two-nucleobase overhang of deoxythymidine. In cells receiving no first treatment with siRNA, the second treatment with 5, 10 or 30 nM of ISIS 336848 (gap-disabled) resulted in 18, 32 and 75% reductions in C-raf mRNA. In cells in which RNase H2 was disrupted, a second treatment with 5, 10 or 30 nM of ISIS 336848 (gap-disabled) resulted in 23, 38 and 73% reductions in C-raf mRNA. Thus, disruption of RNase H2 did not significantly affect gap-disabled oligomeric compound activity. However, in cells in which RNase H1 was disrupted, a second treatment with 5, 10 or 30 nM of the gap-disabled oligomeric compound resulted in 14, 28 and 58% reductions in C-raf mRNA. These data illustrate that siRNA-mediated reduction of RNase H1 mRNA reduced the potency of the gap-disabled compound. Thus, gap-disabled compounds elicit target RNA cleavage through the activity of RNase H1.

Example 58

Overexpression of RNase H

In a further embodiment, RNase H overexpression in cultured cells was tested for its effects on the potency of gap-disabled oligomeric compounds. RNase H overexpression was accomplished using the RNase H full-length coding regions packaged in adenoviral vectors, which were prepared as previously described (Wu et al., *J. Biol. Chem.,* 2004, 279, 17181-17189). An RNase H1 adenoviral vector was prepared using the full-length RNase H1 coding region. An RNase H2 adenoviral vector was prepared in the same manner, using the RNase H2 full-length coding region. An additional vector was prepared using a truncated human RNase H1 cDNA that encodes a protein lacking the 26 N-terminal amino acids; this construct is named RNase H1(−26). Two native isoforms of human RNase H1 exist in the cell: a full length RNase H1 and the truncated RNase H1. The N-terminal 26 amino acids of human RNase H1 comprise a mitochondrial localization signal, thus the full-length isoform is found predominantly in the cytosol and mitochondria and the truncated protein (lacking the localization signal) is found predominantly in the nucleus. When compared in the in vitro assays described herein, both isoforms behave similarly with respects to enzyme kinetics. A control vector, pLox, contained the shuttle vector used in preparation of the RNase H-containing viruses and lacked the inserted genes.

In this assay, HeLa cells were cultured in DMEM supplemented with 10% fetal bovine serum, 0.005 mg/mL insulin, 0.005 mg/mL transferring, 5 ng/mL selenium, 40 ng/mL dexamethasone (medium and all supplements from Invitrogen Corporation, Carlsbad, Calif.). Cells were plated at a density of approximately 6000 cells per well in 96-well plates and infected with RNase H1, RNase H2, RNase H1(−26) or pLox adenovirus at 200 plaque forming units per cell (pfu/cell). After 12 hours, cells transfected with each virus were collected for RNA isolation and real-time PCR quantitation of RNase H mRNA. The remaining cells were transfected with the gap-disabled compound ISIS 336848 (SEQ ID NO: 105) at concentrations of 15, 30 and 45 nM, using LIPOFECTIN™ as described herein. Cells were harvested 24 hours later, RNA was isolated and C-raf mRNA levels were measured using real-time PCR, as described herein. Real-time PCR measurements of RNase H1, RNase H2, RNase H1(−26) and C-raf were normalized using the housekeeping gene cyclophilin. The results of this assay are shown in Table 36. RNases H mRNA levels are shown as percent relative to RNase H expression in pLox-infected cells. C-raf mRNA levels are presented as percent reduction relative to cells that did not receive oligomeric compound treatment.

TABLE 36

Gap-disabled compound potency in cells overexpressing RNases H

| | Virus | | | |
|---|---|---|---|---|
| | pLox | RNase H1 | RNase H1(−26) | RNase H2 |
| RNase H level | 100% | 2938% | 801% | 1216% |
| Dose of ISIS 336848 | % Reduction in C-raf mRNA | | | |
| 15 nM | 30 | 45 | 37 | 26 |
| 30 nM | 54 | 55 | 56 | 46 |
| 45 nM | 63 | 67 | 74 | 60 |

These data demonstrate that when RNase H1 is present at a level approximately 30 times higher than that in pLox-infected cells, treatment with a 15 nM dose of the gap-disabled compound resulted in a 45% reduction in C-raf mRNA, whereas target mRNA was reduced by only 30% in pLox-infected cells. Overexpression of RNase H1(−26) to levels approximately 8 times higher than that in p-Lox-infected cells also improved the potency of the gap-disabled compound. An excess of RNase H2 did not improve the activity of the gap-disabled compound. When the % reduction in C-raf mRNA is plotted against the base-10 logarithm of the gap-disabled compound concentration, an increase in gap-disabled compound activity is apparent at all oligomeric compound concentrations tested in this assay. Similar observations were made in cells expressing any of the RNases H at levels 5 to 7 times that of the p-Lox-infected cells. These data suggest that overexpression of either isoform improves gap-disabled oligomeric compound activity and that gap-disabled oligomeric compounds are active in both the nucleus and cytosol. These data further illustrate that gap-disabled compounds elicit target RNA cleavage through RNase H1.

Example 59

In Vivo Analysis of Gap-Disabled Compounds Targeted to Mouse Glucagon Receptor In a further embodiment, gap-disabled chimeric oligomeric compounds targeted to mouse glucagon receptor were tested for their effects on target reduction in vivo. The gap-disabled compounds were: ISIS 332866, ISIS 332868, ISIS 352426 and ISIS 352427 (all with the nucleotide sequence of SEQ ID NO: 43). Also tested were ISIS 180475 (SEQ ID NO: 43), a gapmer compound; ISIS 332867, also a gapmer compound; ISIS 335032 (SEQ ID NO: 43), an oligomeric compound uniformly comprised of 2'-deoxynucleotides and ISIS 298683 (SEQ ID NO: 43), an oligomeric compound uniformly comprised of 2'-MOE nucleotides. The motif of each compound is shown in Table 37 as described for other compounds herein. Male Balb/c mice, 6 to 7 weeks of age, received twice weekly intraperitoneal injections of approximately 1, 3 or 10 mg/kg of the compounds shown in Table 37. Saline-injected animals served as a control group and were injected in the same manner as the oligomeric compounds. Each treatment group contained 4 animals.

Liver RNA was analyzed for glucagon receptor expression levels by quantitative real-time PCR as described by other examples herein, using the housekeeping gene cyclophilin A to normalize RNA levels among samples. In Table 37, glucagon receptor mRNA expression levels are shown as percentage of saline-treated control glucagon receptor levels. A value less than or greater than 100 indicates a decrease or increase in mRNA expression, respectively. If present, "ND" indicates "not determined".

TABLE 37

Target reduction following treatment with chimeric oligomeric compounds targeted to mouse glucagon receptor

| | SEQ | | % Control Dose of oligonucleotide | | |
|---|---|---|---|---|---|
| ISIS # | ID NO | Motif | 10 mg/kg | 3 mg/kg | 1 mg/kg |
| 335032 | 43 | Uniform 2'-deoxy | 10 | 85 | 117 |
| 332866 | 43 | <u>3</u>-5-<u>4</u>-5-<u>3</u> | 27 | 53 | 115 |
| 332867 | 43 | <u>3</u>-14-<u>3</u> | 12 | 111 | 112 |
| 332868 | 43 | <u>3</u>-3-<u>2</u>-4-<u>2</u>-3-<u>3</u> | 40 | 77 | 107 |
| 352426 | 43 | <u>2</u>-6-<u>4</u>-6-<u>2</u> | 21 | 66 | 115 |
| 352427 | 43 | <u>2</u>-7-<u>2</u>-7-<u>2</u> | 9 | 48 | 122 |
| 298683 | 43 | **<u>Uniform 2'-MOE</u>** | 84 | ND | ND |
| 180475 | 43 | <u>5</u>-10-<u>5</u> | 15 | 53 | 93 |

These results demonstrate that treatment with 3 mg/kg and 10 mg/kg doses of the gap-disabled compounds ISIS 332866, ISIS 332868, ISIS 352426 and ISIS 352427, in addition to the gapmer compound ISIS 180475 and the uniform 2'-deoxy compound ISIS 335032, inhibited mouse glucagon receptor mRNA expression in a dose-dependent manner in vivo. ISIS 332867 inhibited mouse glucagon receptor mRNA expression at the 10 mg/kg dose.

Example 60

In Vivo Analysis of Chimeric Oligomeric Compounds Targeted to FAS: Levin Rat Model The Levin model is a polygenic model of rats selectively bred to develop diet-induced obesity (DIO) associated with impaired glucose tolerance, dyslipidemia and insulin resistance when fed a high-fat diet. The advantage of this model is that it displays traits more similar to human obesity and glucose intolerance than in animals that are obese/hyperinsulinemic due to genetic defects, for example, a defect in leptin signaling. In a further embodiment, the gap-disabled compound ISIS 304170 (SEQ ID NO: 60), targeted to rat fatty acid synthase (FAS), was tested for its effects on target reduction in the Levin rat model. Male Levin rats were purchases from Charles River Laboratories at approximately 8 weeks of age. Rats were fed a high-fat diet (60% fat) for 8 weeks, after which the animals were divided into three groups and treated with saline, ISIS 304170 or the gapmer ISIS 256899 (SEQ ID NO: 60). ISIS 256899, also targeted to rat FAS, was used as a positive control for target reduction. Treatments were administered subcutaneously at a dose of 25 mg/kg, twice weekly, for 8 weeks. Control groups consisted of animals on the high-fat diet receiving saline treatment and animals on a standard rodent diet receiving saline treatment. Each treatment group included 5 to 6 animals.

At the end of the 8 week treatment period, animals were sacrificed and liver was collected for FAS protein analysis and white adipose tissue (WAT) and brown adipose tissue (BAT) were collected for measurement of FAS mRNA expression. mRNA was measured by real-time PCR as described herein and were normalized to levels in saline treated animals that received a high-fat diet. Protein levels were measured by western blot as described herein, using an antibody recognizing rodent FAS (BD Transduction Laboratories of the BD Pharmingen Unit, San Diego, Calif.) and were normalized to levels in saline treated animals that received a high-fat diet. Data are shown in Table 38 and are expressed as percentage of high-fat diet saline control. If present, "ND" indicates "not determined". Also shown in Table 38 are serum cholesterol (mg/dL), triglyceride (mg/dL) and liver transaminase (ALT and AST, IU/L) levels, which were measured at the end of the study using routine clinical analyzer instruments (e.g. Olympus Clinical Analyzer, Melville, N.Y.).

TABLE 38

FAS, cholesterol and triglycerides in Levin rats treated with chimeric oligomeric compounds

| | Standard | High Fat | High Fat | High Fat |
|---|---|---|---|---|
| Treatment | Saline | Saline | ISIS 304170 | ISIS 256899 |
| % FAS protein, Liver | 110 | 100 | 55 | 39 |
| % FAS mRNA, WAT | ND | 100 | 21 | 17 |
| % FAS mRNA, BAT | ND | 100 | 5 | 6 |
| Serum Cholesterol (mg/dL) | 81 | 81 | 69 | 160 |
| Serum Triglyceride (mg/dL) | 269 | 377 | 104 | 607 |
| ALT (IU/L) | 79 | 73 | 158 | 61 |
| AST (IU/L) | 45 | 30 | 51 | 32 |

These data demonstrate that the gap-disabled compound ISIS 304170 resulted in a marked reduction in rat FAS mRNA expression in both white and brown adipose tissue. Furthermore, rat FAS protein levels were reduced in liver following treatment with ISIS 304170. FAS mRNA and protein levels were similar to those observed following treatment with the gapmer compound. Furthermore, cholesterol and triglycerides in Levin rats receiving a high-fat diet were markedly lowered by treatment with ISIS 304170, whereas ISIS 256899 did not lower cholesterol and triglycerides in Levin rats receiving a high-fat diet. AST and ALT levels were not at levels considered indicative of toxicity.

Plasma glucose concentrations were measured at 0 (beginning of study) and 8 (end of study) weeks of treatment by routine clinical analysis using a YSI2700 Select™ Biochemistry Analyzer (YSI Inc., Yellow Spring, Ohio). Plasma insulin levels were measured at 0 and 8 weeks of treatment using an insulin ELISA kit (ALPCO Diagnostics, Windham, N.H.) according to the manufacturer's instructions. Plasma leptin levels were measured at 0 and 8 weeks using a rat leptin ELISA kit (Crystal Chem. Inc., Downer's Grove, Ill.). Leptin is a hormone that regulates appetite. Plasma insulin, glucose and leptin levels are shown in Table 39.

TABLE 39

Plasma leptin, glucose and insulin in Levin rats treated with chimeric oligomeric compounds

| | | Diet and Treatment | | | |
|---|---|---|---|---|---|
| | Study week | Standard Saline | High Fat Saline | High Fat 304170 | High Fat 256899 |
| Plasma Leptin (ng/mL) | 0 | 11 | 42 | 46 | 46 |
| Plasma Leptin (ng/mL) | 8 | 10 | 57 | 8 | 24 |
| Plasma Glucose (mg/dL) | 0 | 106 | 103 | 100 | 105 |
| Plasma Glucose (mg/dL) | 8 | 95 | 115 | 106 | 98 |
| Plasma Insulin (ng/mL) | 0 | 1.3 | 3.3 | 3.6 | 2.9 |
| Plasma Insulin (ng/mL) | 8 | 1.0 | 1.8 | 0.9 | 0.8 |

These data demonstrate that after 8 weeks, relative to animals receiving a high-fat diet and saline treatment, treatment with ISIS 304170 and ISIS 256899 lowered plasma leptin, glucose and insulin levels. ISIS 304170 lowered plasma leptin and insulin levels to those observed in rats on a standard diet. ISIS 256899 lowered plasma glucose levels to those observed in rats on a standard diet.

After 4 weeks of treatment, an insulin tolerance test was performed. After 7 weeks of treatment, a glucose tolerance test was performed. For the tolerance tests, a baseline tail blood glucose measurement was obtained, after which 1.0 g/kg glucose or 0.5 units/kg insulin was administered orally or intraperitoneally, respectively. Tail blood glucose levels were measured using a Glucometer® instrument (Abbott Laboratories, Bedford, Mass.) at 15, 30, 60, 90, 120, 150 and 180 minutes following the challenge with insulin and 30, 60, 90 and 120 minutes following the glucose challenge. Insulin sensitivity in the animals receiving ISIS 304170 and ISIS 256899 was similar to animals on a standard diet receiving saline treatment and was improved relative to saline-treated animals on a high-fat diet. Glucose tolerance was not improved by treatment with ISIS 304170 or ISIS 256899.

Body weight and food intake were measured weekly throughout the study. At the beginning of the study, animals on the high-fat diet weighed approximately 670 grams. Whereas the saline-treated rats maintained this weight throughout the treatment period, the body weights of rats treated with ISIS 304170 and ISIS 256899 dropped to approximately 500 g, the same body weight as the rats on a standard rodent diet, by the end of the study. Throughout the study, food intake among rats treated with ISIS 304170 and ISIS 256899 was approximately half that among saline treated rats. Thus, concomitant with a reduction in FAS mRNA and protein, body weight and food intake were lowered.

At the end of the study, liver and spleen weights, increases in which can indicate toxicity, were measured. Relative to saline-treated rats on a high-fat diet, liver weights were lower in rats receiving ISIS 304170 and slightly higher in rats receiving ISIS 256899. The converse was true for spleen weights, which were slightly raised in rats receiving ISIS 304170. Fat depot weights were also determined. Treatment with ISIS 304170 and ISIS 256899 prevented increases in brown adipose tissue and intra-abdominal white adipose tissue (both epididymal and perinephric fat) weights, which were all significantly raised in saline-treated rats on a high-fat diet.

Metabolic rate was measured after 4 weeks and 8 weeks of oligomeric compound treatment using indirect calorimetry in a metabolic chamber (Oxymax System, Columbus Instruments, Columbus, Ohio). No significant differences in metabolic rates were observed when oligomeric compound-treated mice were compared to saline-treated mice.

This study in a rat model of diabetes and obesity illustrates that treatment with the gap-disabled compound ISIS 304170 reduces rat FAS protein expression. Concomitant reductions are observed in body weight, fat depot weight, food intake, plasma leptin, plasma insulin, serum cholesterol, serum triglycerides and insulin sensitivity. Thus, this compound has applications in the treatment of diabetes, obesity and related conditions.

Example 61

In Vivo Analysis of Chimeric Oligomeric Compounds Targeted to FAS: Mouse Model of Diabetes and Obesity Leptin is a hormone produced by fat that regulates appetite. Deficiencies in this hormone lead to obesity in animals. ob/ob mice have a mutation in the leptin gene which results in obesity and hyperglycemia. As such, these mice are a useful model for the investigation of obesity and diabetes and treatments designed to treat these conditions. ob/ob mice have higher circulating levels of insulin and are less hyperglycemic than db/db mice, which harbor a mutation in the leptin receptor. In accordance with the present invention, the oligomeric compounds of the invention are tested in the ob/ob model of obesity and diabetes.

Seven-week old male C57B1/6J-Lep ob/ob mice (Jackson Laboratory, Bar Harbor, Me.) were fed a diet with a fat content of approximately 11% and were subcutaneously injected with ISIS 304171 (SEQ ID NO: 59) or ISIS 148548 (SEQ ID NO: 59) at a dose of 25 mg/kg two times per week for 8 weeks. Saline-injected animals served as a control group. Each treatment group contained 8 mice.

After the treatment period, mice were sacrificed and FAS protein levels were measured by western blot in liver and white adipose tissue (WAT), using an antibody that recognizes mouse FAS (BD Transduction Laboratories of the BD Pharmingen Unit, San Diego, Calif.). Relative to FAS protein levels in saline-treated mice, treatment with ISIS 304171 reduced protein expression by 66% in liver and by 62% in white adipose tissue. Treatment with ISIS 148548 resulted in 93% and 81% reductions in fatty acid protein in liver and white adipose tissue, respectively.

To assess the physiological effects resulting from reduction of FAS expression, the mice were further evaluated at the end of the treatment period for serum triglycerides, serum cholesterol, and serum transaminase levels. Triglycerides, cholesterol and transaminases were measured by routine clinical analyzer instruments (e.g. Olympus Clinical Analyzer, Melville, N.Y.). Triglyceride levels were 173, 101 and 118 mg/dL in mice receiving treatment with saline, ISIS 304171 or ISIS 148548, respectively. Cholesterol levels were 312, 221 and 218 mg/dL in mice receiving treatment with saline, ISIS 304171 or ISIS 148548, respectively. These data demonstrate that treatment with either the gap-disabled compound or gapmer compound targeted to FAS reduced both cholesterol and triglyceride levels in ob/ob mice on a high fat diet. Also reduced were the liver transaminases ALT and AST (measured in international units/liter, or IU/L), indicating an improvement in liver function following treatment of ob/ob animals with a gap-disabled or gapmer compound. AST levels were 511, 277 and 334 IU/L in mice receiving treatment with saline, ISIS 304171 or ISIS 148548, respectively. ALT levels were 751, 481 and 344 IU/L in mice receiving treatment with saline, ISIS 304171 or ISIS 148548, respectively.

Body weight was monitored throughout the study. Body weights in all 3 treatment groups increased steadily throughout the first 5 weeks. After 6, 7 and 8 weeks of treatment, the average body weight in ISIS 304171-treated mice was 59 grams. The average body weight in ISIS 148548-treated mice after 6, 7 and 8 weeks of treatment was 58 grams. However, in the saline-treated mice, the average body weight at 6, 7 and 8 weeks was 64 grams. Thus, treatment with the gap-disabled or gapmer compound targeted to FAS resulted in reduced weight gain in ob/ob mice on a high fat diet.

Metabolic rate was measured after 5 weeks of oligomeric compound treatment using indirect calorimetry in a metabolic chamber (Oxymax System, Columbus Instruments, Columbus, Ohio). No significant differences in metabolic rates were observed when oligomeric compound-treated mice were compared to saline-treated mice.

Adipose tissue weight was also measured at the end of the study. No significant differences were observed when the oligomeric compound-treated mice were compared to saline-treated mice.

The effects of target inhibition on glucose metabolism were also evaluated. After 7 weeks of treatment with oligomeric compounds, an oral glucose tolerance test was performed. Mice received an oral dose of approximately 1 g/kg of glucose, and blood glucose levels were measured at 30 minute intervals for up to 2 hours. Glucose levels are measured using a YSI glucose analyzer (YSI Scientific, Yellow Springs, Ohio). No differences in glucose tolerance were observed when oligomeric compound-treated mice were compared to saline-treated mice.

These data demonstrate that the gap-disabled compound ISIS 304171, like the gapmer compound ISIS 148548, reduced FAS expression in the livers of ob/ob mice. Furthermore, reductions were observed in serum cholesterol and triglycerides, body weight and liver transaminases.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of reducing cell surface expression of CD86 in an MH-S cell comprising contacting the cell with a compound having at least 5 separate regions, wherein each of the regions is a continuous sequence from 1 to 5 nucleosides each comprising a 3'-endo sugar conformational geometry or a continuous sequence of 1 to 4 2'-deoxyribonucleosides, and wherein each of the regions comprising from 1 to 4 2'-deoxyribonucleosides is internally located between two of the regions comprising 1 to 5 nucleosides each comprising a 3'-endo sugar conformational geometry or at one of the 3' or 5'-termini, wherein the compound has a nucleobase sequence at least 90% complementary to SEQ ID NO. 10, and thereby reducing cell surface expression of CD86 in said MH-S cell; wherein said nucleosides comprising 3'-endo sugar conformational geometry comprise, independently, a 2'-substituent group selected from 2'-F, 2'-$OCH_3$ and 2'-MOE.

2. The method of claim 1, wherein said compound has the motif 2-1-1-2-1-1-1-1-1-1-1-1-1-3-2, wherein bolded and underlined numbers represent sugar modified nucleosides, independently, comprising a 2'-substituent group selected from 2'-F, 2'-$OCH_3$ and 2'-MOE.

3. The method of claim 1, wherein said compound has the motif 3-2-1-3-1-3-1-3-3, wherein bolded and underlined numbers represent sugar modified nucleosides, independently, comprising a 2'-substituent group selected from 2'-F, 2'-$OCH_3$ and 2'-MOE.

4. The method of claim 1, wherein said compound has the motif 3-2-1-2-1-2-1-2-1-2-3, wherein bolded and underlined numbers represent sugar modified nucleosides, independently, comprising a 2'-substituent group selected from 2'-F, 2'-$OCH_3$ and 2'-MOE.

5. The method of claim 1, wherein said compound has the motif 3-3-1-2-1-2-1-3-4 wherein bolded and underlined numbers represent sugar modified nucleosides, independently, comprising a 2'-substituent group selected from 2'-F, 2'-$OCH_3$ and 2'-MOE.

6. The method of claim 1, wherein said compound has the motif 5-2-1-2-1-2-1-1-5, wherein bolded and underlined numbers represent sugar modified nucleosides, independently, comprising a 2'-substituent group selected from 2'-F, 2'-$OCH_3$ and 2'-MOE.

7. The method of claim 1, wherein said compound has the motif 2-2-1-3-1-2-1-3-3, wherein bolded and underlined numbers represent sugar modified nucleosides, independently, comprising a 2'-substituent group selected from 2'-F, 2'-$OCH_3$ and 2'-MOE.

8. The method of claim 1, wherein said compound has the motif 3-3-1-2-1-3-1-2-2, wherein bolded and underlined numbers represent sugar modified nucleosides, independently, comprising a 2'-substituent group selected from 2'-F, 2'-$OCH_3$ and 2'-MOE.

9. The method of claim 1, wherein said compound has the motif 3-2-1-3-1-2-1-3-4, wherein bolded and underlined numbers represent sugar modified nucleosides, independently, comprising a 2'-substituent group selected from 2'-F, 2'-$OCH_3$ and 2'-MOE.

10. The method of claim 1, wherein said compound has the motif 3-2-1-3-1-3-1-3-3, wherein bolded and underlined numbers represent sugar modified nucleosides, independently, comprising a 2'-substituent group selected from 2'-F, 2'-$OCH_3$ and 2'-MOE.

11. The method of claim 1, wherein said compound has the motif 3-2-1-2-1-3-1-2-1-1-3, wherein bolded and underlined numbers represent sugar modified nucleosides, independently, comprising a 2'-substituent group selected from 2'-F, 2'-$OCH_3$ and 2'-MOE.

12. The method of claim 1, wherein said compound has the motif 4-3-1-4-1-3-4, wherein bolded and underlined numbers represent sugar modified nucleosides, independently, comprising a 2'-substituent group selected from 2'-F, 2'-$OCH_3$ and 2'-MOE.

13. The method of claim 1, wherein said compound has the motif 3-3-2-4-2-3-3, wherein bolded and underlined numbers represent sugar modified nucleosides, independently, comprising a 2'-substituent group selected from 2'-F, 2'-$OCH_3$ and 2'-MOE.

14. The method of claim 1, wherein said compound has the motif 3-1-1-1-1-1-1-1-1-1-1-1-1-1-4, wherein bolded and underlined numbers represent sugar modified nucleosides, independently, comprising a 2'-substituent group selected from 2'-F, 2'-$OCH_3$ and 2'-MOE.

15. The method of claim 1, wherein said compound has the motif 3-4-1-4-1-4-3, wherein bolded and underlined numbers represent sugar modified nucleosides, independently, comprising a 2'-substituent group selected from 2'-F, 2'-$OCH_3$ and 2'-MOE.

16. The method of claim 1, wherein said compound has the motif 3-3-1-2-1-3-1-3-3, wherein bolded and underlined numbers represent sugar modified nucleosides, independently, comprising a 2'-substituent group selected from 2'-F, 2'-$OCH_3$ and 2'-MOE.

17. The method of claim 1, wherein said compound has the motif 3-3-1-3-1-2-1-3-3, wherein bolded and underlined numbers represent sugar modified nucleosides, independently, comprising a 2'-substituent group selected from 2'-F, 2'-$OCH_3$ and 2'-MOE.

18. The method of claim 1, wherein said compound has the motif 3-2-2-1-2-1-2-1-1-2-3, wherein bolded and underlined numbers represent sugar modified nucleosides, independently, comprising a 2'-substituent group selected from 2'-F, 2'-$OCH_3$ and 2'-MOE.

19. The method of claim 1, wherein said compound has the motif 3-1-3-1-2-1-2-1-2-1-3, wherein bolded and underlined numbers represent sugar modified nucleosides, independently, comprising a 2'-substituent group selected from 2'-F, 2'-$OCH_3$ and 2'-MOE.

20. The method of claim 1, wherein said compound has the motif 3-1-2-1-2-1-2-1-2-1-4, wherein bolded and underlined numbers represent sugar modified nucleosides, independently, comprising a 2'-substituent group selected from 2'-F, 2'-$OCH_3$ and 2'-MOE.

21. The method of claim 1, wherein said compound has the motif 1-1-1-1-1-1-1-1-1-1-1-1-1-1-1-1-1-1-1-2, wherein bolded and underlined numbers represent sugar modified nucleosides, independently, comprising a 2'-substituent group selected from 2'-F, 2'-$OCH_3$ and 2'-MOE.

* * * * *

SEQUENCE LISTING

```
<160> NUMBER OF SEQ ID NOS: 221

<210> SEQ ID NO 1
<211> LENGTH: 12
<212> TYPE: RNA
<213> ORGANISM: Artificial Sequence
<220> FEATURE:
<223> OTHER INFORMATION: Oligomeric Compound

<400> SEQUENCE: 1

cgcgaauucg cg                                                    12


<210> SEQ ID NO 2
<211> LENGTH: 12
<212> TYPE: RNA
<213> ORGANISM: Artificial Sequence
<220> FEATURE:
<223> OTHER INFORMATION: Oligomeric Compound

<400> SEQUENCE: 2

gcgcuuaagc gc                                                    12


<210> SEQ ID NO 3
<211> LENGTH: 19
<212> TYPE: DNA
<213> ORGANISM: Artificial Sequence
<220> FEATURE:
<223> OTHER INFORMATION: Oligomeric Compound

<400> SEQUENCE: 3

cgagaggcgg acgggaccg                                             19


<210> SEQ ID NO 4
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 4

cgagaggcgg acgggaccgt t                                          21


<210> SEQ ID NO 5
<211> LENGTH: 21
<212> TYPE: DNA
<213> ORGANISM: Artificial Sequence
<220> FEATURE:
<223> OTHER INFORMATION: Oligomeric Compound

<400> SEQUENCE: 5

ttgctctccg cctgccctgg c                                          21
```

<210> SEQ ID NO 6
<211> LENGTH: 19
<212> TYPE: DNA
<213> ORGANISM: Artificial Sequence
<220> FEATURE:
<223> OTHER INFORMATION: Oligomeric Compound

<400> SEQUENCE: 6
gctctccgcc tgccctggc 19

<210> SEQ ID NO 7
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 7
tccgtcatcg ctcctcaggg 20

<210> SEQ ID NO 8
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 8
gtgcgcgcga gcccgaaatc 20

<210> SEQ ID NO 9
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 9
atgcattctg cccccaagga 20

<210> SEQ ID NO 10
<211> LENGTH: 1115
<212> TYPE: DNA
<213> ORGANISM: M. spretus

<400> SEQUENCE: 10
aagagtggct cctgtaggca gcacggactt gaacaaccag actcctgtag acgtgttcca 60
gaacttacgg aagcacccac gatggacccc agatgcacca tgggcttggc aatccttatc 120
tttgtgacag tcttgctgat ctcagatgct gtttccgtgg agacgcaagc ttatttcaat 180
gggactgcat atctgccgtg cccatttaca aaggctcaaa acataagcct gagtgagctg 240
gtagtatttt ggcaggacca gcaaaagttg gttctgtacg agcactattt gggcacagag 300
aaacttgata gtgtgaatgc caagtacctg ggccgcacga gctttgacag gaacaactgg 360
actctacgac ttcacaatgt tcagatcaag gacatgggct cgtatgattg ttttatacaa 420
aaaaagccac ccacaggatc aattatcctc caacagacat taacagaact gtcagtgatc 480
gccaacttca gtgaacctga aataaaactg gctcagaatg taacaggaaa ttctggcata 540
aatttgacct gcacgtctaa gcaaggtcac ccgaaaccta agaagatgta ttttctgata 600
actaattcaa ctaatgagta tggtgataac atgcagatat cacaagataa tgtcacagaa 660

-continued ctgttcagta tctccaacag cctctctctt tcattcccgg atggtgtgtg gcatatgacc 720
gttgtgtgtg ttctggaaac ggagtcaatg aagatttcct ccaaacctct caatttcact 780
caagagtttc catctcctca aacgtattgg aaggagatta cagcttcagt tactgtggcc 840
ctcctccttg tgatgctgct catcattgta tgtcacaaga agccgaatca gcctagcagg 900
cccagcaaca cagcctctaa gttagagcgg gatagtaacg ctgacagaga gactatcaac 960
ctgaaggaac ttgaacccca aattgcttca gcaaaaccaa atgcagagtg aaggcagtga 1020
gagcctgagg aaagagttaa aaattgcttt gcctgaaata agaagtgcag agtttctcag 1080
aattcaaaaa tgttctcagc tgattggaat tctac 1115

<210> SEQ ID NO 11
<211> LENGTH: 2262
<212> TYPE: DNA
<213> ORGANISM: M. musculus

<400> SEQUENCE: 11
ggtggccgcg cttcgctggc tttctgctca tctagggtgg cagcggctac ctacctcagc 60
tctcgccctg ctgccgccac ggcctgggcg ctgtccctca gctcccggag ctcagcgcga 120
agccctggcc ccggcggccg gggcatgggt caggggcgcg gcgtgaggcg gctttctgca 180
cggccgtgac gtgcattggc ttcagcatga agaccctcat cgccgcctac tccggggtcc 240
tgcggggtga gcgtcgggcg gaagctgccc gcagcgaaaa caagaataaa ggatctgccc 300
tgtcacgcga ggggtctggg cgatggggca ctggctccag catcctctca gccctccaag 360
acatcttctc tgtcacctgg ctcaacagat ctaaggtgga aaaacagctg caggtcatct 420
cagtactaca atgggtccta tccttcctgg tgctaggagt ggcctgcagt gtcatcctca 480
tgtacacctt ctgcacagac tgctggctga tagctgtgct ctacttcacc tggctggcat 540
ttgactggaa cacgcccaag aaaggtggca ggagatcgca gtgggtgcga aactgggccg 600
tgtggcgcta cttccgagac tactttccca tccagctggt gaagacacac aacctgctga 660
ccaccaggaa ctatatcttt ggataccacc cccatggcat catgggcctg ggtgccttct 720
gtaacttcag cacagaggct actgaagtca gcaagaagtt tcctggcata aggccctatt 780
tggctacgtt ggctggtaac ttccggatgc ctgtgcttcg cgagtacctg atgtctggag 840
gcatctgccc tgtcaaccga gacaccatag actacttgct ctccaagaat gggagtggca 900
atgctatcat catcgtggtg ggaggtgcag ctgagtccct gagctccatg cctggcaaga 960
acgcagtcac cctgaagaac cgcaaaggct ttgtgaagct ggccctgcgc catggagctg 1020
atctggttcc cacttattcc tttggagaga atgaggtata caagcaggtg atctttgagg 1080
agggttcctg ggccgatggg gtccagaaga agttccagaa gtatattggt ttcgcccccct 1140 gcatcttcca tggccgaggc ctcttctcct ctgacacctg gggctggtg ccctactcca 1200 agcccatcac caccgtcgtg ggggagccca tcactgtccc caagctggag cacccgaccc 1260
agaaagacat cgacctgtac catgccatgt acatggaggc cctggtgaag ctctttgaca 1320
atcacaagac caaatttggc cttccagaga ctgaggtgct ggaggtgaac tgacccagcc 1380
ctcgcgtgcc agctcctggg agggacgact gcagatcctt ttctaccgag ttcttgagtg 1440
cattttgttc tgtaaatttg gaagcgtcat gggtgtctgt gggttattta aaagaaatta 1500
taatgtgtta aaccattgca atgttagatg tttttttaag aagggaagag tcagtatttt 1560
aagctcactt ctagtgtgtc ctgctcaagg tggaggctga tatttatggg ccttggtggt 1620
ttcttaccca ccccttctag cgttccccag acgacagaca cttggccctg gctagctggg 1680
caagggcagt ccttagtgac tccagggatt cttgagaggc agaggccatg tcccacccgt 1740
ggctgcaggt cgggttcctc gtaccaaggg gaggctgagg gcacagctgg ccccacttgg 1800
ggagggtaga taacatctgg actgcccggc ttgggtctct gctcctcacc ctagccctct 1860
tctccaatct gagcctaccc tggcctcctg tctcctggct agggacacgg ctgtcccaca 1920
ggtgccgtct tgggttatct cgctgctgtt ggctggtttc actctggagg ttggcaccat 1980
ggacacagct cagcgttgct ctggcgcata tcctcctgag ccacacccca agtctggtgt 2040
gaggaagggc ttctcttctc ttcacagagg tgcctggctt cctgtgcagc acactgggtc 2100
caggacagga ggcccccccc ccaaaccaag cctcacgtgt gtgcctttat gaggcgttgg 2160
gagaaagcta ccctcctgtg tattctgttt tctccatgag attgttgtgc catgtcacac 2220
ttttgtatat tcctagacta ataaatggaa acaagaacag cc 2262

<210> SEQ ID NO 12
<211> LENGTH: 8363
<212> TYPE: DNA
<213> ORGANISM: M. musculus

<400> SEQUENCE: 12
tcctcgcttg tcgtctgcct ccagagccca gacagagaag agccatggag gaggtggtga 60
tagccggtat gtcggggaag ttgcccgagt cagagaacct acaggagttc tgggccaacc 120
tcattggtgg tgtggacatg gtcacagatg atgacaggag atggaaggct gggctctatg 180
gattacccaa gcggtctgga aagctgaagg atctctccaa gttcgacgcc tcctttttg 240 gggtccaccc caagcaggca cacacaatgg acccccagct tcggctgctg ttggaagtca 300
gctatgaagc aattgtggat ggaggtatca acccagcctc actccgagga acgaacactg 360
gcgtctgggt gggtgtgagt ggttcagagg catccgaggc ccttagcaga gatcccgaga 420
cgcttctggg ctacagcatg gtgggctgcc agcgtgcaat gatggccaac cggctctctt 480
tcttcttcga cttcaaagga ccaagcattg ccctggacac agcctgctcc tccagcttgc 540
tggcactaca gaatgcctac caggccatcc gtagtgggga atgccccgcg gcccttgtgg 600
gtgggatcaa cctgctcctg aagccgaaca cctctgtgca gttcatgaag ctgggcatgc 660
tcagcccgga cggcacctgc agatcctttg atgattcagg gagtggatat tgtcgctctg 720
aggctgttgt agcagttctg ctgactaaga agtccctggc tcggcgggtc tatgccacga 780
ttctgaatgc cggcaccaat acagatggca gcaaggagca aggtgtaaca ttcccctctg 840
gagaagtcca agaacaactc atctgctctc tgtatcagcc agctggtctg gccccggagt 900
cgcttgagta tattgaagcc catggcacgg gcaccaaggt gggtgacccc caggaactga 960
atggcattac tcggtccctg tgcgccttcc gccaggcccc tctgttaatt ggctccacca 1020
aatccaacat gggacaccct gagcctgcct ctgggcttgc agccctgacc aaggtgctgt 1080
tatccctgga gcatggggtc tgggccccta acctgcactt ccacaacccc aaccctgaga 1140
tcccagcact tcttgatggg cggctgcagg tggtcgatag gcccctgcct gttcgtggtg 1200
gcaacgtggg catcaactca tttggcttcg gaggctccaa tgttcatgtc atcctccagc 1260
ccaacacacg gcaggcccct gcgcccactg cacacgctgc ccttccccat ttgctgcacg 1320
ccagtggacg caccttagag gcagtgcagg acctgctgga acagggccgc cagcacagcc 1380
aggacctggc ctttgtgagc atgctcaatg acattgcggc aacccctaca gcagccatgc 1440
ccttcagggg ttacactgtg ctaggtgttg agggccgtgt ccaagaagtg cagcaagtgt 1500

-continued

```
ccaccaacaa gcgcccactc tggttcatct gctcagggat gggcacgcag tggcgcggga   1560
tggggctgag cctcatgcgc ctggacagct tccgtgagtc tatcctgcgc tccgatgagg   1620
ctgtgaagcc gttgggagtg aaagtgtcag atctgctgtt gagcacagat gagcgcacct   1680
ttgatgacat cgtgcatgcc tttgtgagcc tcactgccat ccagattgcc ctcatcgacc   1740
tactgacttc tgtgggactg aaacctgacg gcatcattgg gcactccttg ggagaggttg   1800
cctgtggcta tgcagatggc tgtctctccc agagagaggc tgtgcttgca gcttactggc   1860
gaggccagtg catcaaagat gcccacctcc cgcctggatc catggcagct gttggtttgt   1920
cctgggagga atgtaaacag cgctgccccg ctggcgtggt gcctgcctgc cacaactctg   1980
aggacaccgt gaccatctct ggacctcagg ctgcagtgaa tgaatttgtg gagcagctaa   2040
agcaagaagg tgtgtttgcc aaggaggtac gaacaggagg cctggctttc cactcctact   2100
tcatggaagg aattgccccc acattgctgc aggctctcaa gaaggtgatc cgggaaccac   2160
ggccgcgctc ggctcgatgg ctcagcacct ctatccctga ggcccagtgg cagagcagcc   2220
tggcccgcac atcttctgcc gagtacaatg tcaacaacct ggtgagccct gtgctcttcc   2280
aggaagcact gtggcacatc cctgagcatg ccgtggtgct ggagattgcg ccccacgcac   2340
tgttgcaggc tgtcctgaag cgaggcgtga agtccagctg caccatcatt cccttgatga   2400
agagggatca taaagataac ttggagttct ttctcaccaa ccttggcaag gtgcacctca   2460
caggcatcaa tgtcaaccct aacgccttgt tcccacctgt ggagttcccg gctccccgag   2520
ggactcctct catctcccct cacatcaagt gggaccacag tcagacttgg gatgtcccgg   2580
ttgctgagga cttcccaaac ggctccagct cctcctctgc tacagtctac agcatcgacg   2640
ccagtcctga gtcgcccgac cactacctgg tagaccactg cattgacggc cgggtcatct   2700
tccctggcac tggctacctg tgcctggtgt ggaagacact ggctcgcagc ctgggcttgt   2760
ccctagaaga gacccctgtg gtatttgaga atgtgtcgtt tcatcaggcc actatactac   2820
ccaagacagg aaccgtggcg ctggaggtga ggctgctaga ggcctcccat gcctttgagg   2880
tgtctgacac tggcaatctg attgtgagcg gaaaagtgta cctgtgggaa gacccgaact   2940
ccaagttatt cgaccaccca gaagtcccaa cacccccctga gtctgcatcg gtctcccgcc   3000
tgacccaggg agaagtatac aaggagctgc ggctgcgtgg ctatgattat ggccctcagt   3060
tccagggcat ctgtgaggcc acccttgaag gtgaacaagg caagctgctc tggaaagata   3120
actgggtgac cttcatggac acaatgctgc aggtatccat tctgggttct agccagcaga   3180
gtctacagct acctacccgt gtgaccgcca tctatatcga ccctgccacc caccgtcaga   3240
aggtgtacag gctgaaggag gacactcaag tggctgatgt gacaacgagc cgctgtctgg   3300
gcataacggt ctctggtggt atccacatct caagactaca gacgacagca acctcacggc   3360
ggcagcaaga acagctggtc cccaccttgg aaaagttcgt tttcacaccg cacatggagg   3420
ctgagtgcct gtctgagagc actgccctgc agaaggagct gcaactgtgc aagggtctgg   3480
cacgggctct gcagaccaag gccacccagc aagggctgaa ggcggcaatg cttgggcaag   3540
aggaccctcc acagcacggg ctgcctcgac tcctggcagc tgcttgccag ttgcagctca   3600
acgggaacct gcagctggag ctgggagaag cgctggctca agagaggctc ctgctgccag   3660
aagaccctct gatcagtggc ctcctcaact cccaggccct caaggcctgc gtagacacag   3720
ccctggagaa cttgtctact ctcaagatga aggtggcaga ggtgctggct ggagaaggcc   3780
acttgtattc ccgaatcccg gcactgctca acacccagcc catgctacaa ctggaataca   3840
cagccaccga ccggcacccc caggccctga aggatgttca gaccaaactg cagcagcatg   3900
```

atgtggcgca gggccagtgg aacccttccg accctgcgcc cagcagcctg ggtgcccttg 3960
accttctggt gtgcaactgt gcattagcca ccctgggga tccagccttg gccctggaca 4020
acatggtagc tgccctcaag gaaggtggtt tcctgctagt gcacacagtg ctcaaaggac 4080
atgcccttgg ggagaccctg gcctgcctac cctctgaggt gcagcctgcg cccagcctcc 4140
taagccagga ggagtgggag agcctgttct cgaggaaggc actacacctg gtgggcctta 4200
aaaggtcctt ctacggtact gcgctgttcc tgtgccggcg agccatccca caggagaaac 4260
ctatcttcct gtctgtggag gataccagct tccagtgggt ggactctctg aagagcactc 4320
tggccacgtc ctcctcccag cctgtgtggc taacggccat ggactgcccc acctcgggtg 4380
tggtgggttt ggtgaattgt ctccgaaaag agccgggtgg acaccggatt cggtgtatcc 4440
tgctgtccaa cctcagcaac acatctcacg cccccaagtt ggaccctggc tctccagagc 4500
tacagcaggt gctaaagcat gacctcgtga tgaacgtgta ccgggacggg gcctggggtg 4560
ccttccgtca cttccagtta gagcaggaca agcccaagga gcagacagcg catgcctttg 4620
taaacgtcct cacccgaggg gacctcgcct ccatccgctg ggtctcctcc cccctgaagc 4680
acacgcagcc ctcgagctca ggagcacagc tctgcactgt ctactacgcc tcactgaact 4740
tccgagacat catgctggcc acgggcaagc tgtcccctga tgccattcca ggtaaatggg 4800
ccagccgaga ctgcatgctc ggcatggagt tctcaggccg ggataggtgt ggccggcgtg 4860
tgatggggct ggttcctgca gaaggcctgg ccacctcagt cctgctatca tctgacttcc 4920
tctgggatgt accctccagc tggaccctgg aggaggcggc ctctgtgccc gtcgtctata 4980
ccactgctta ctactcgtta gtggttcgcg ggcgcatcca gcgtggggag accgtgctca 5040
tccactcagg ttcaggtggt gtgggccaag cggccatttc cattgccctc agtctgggct 5100
gccgcgtctt caccactgtg ggctctgcag agaagcgagc atacctccag gccaggttcc 5160
ctcagcttga tgacaccagc tttgccaact cgagggacac atcatttgag cagcacgtgt 5220
tactgcacac aggtggcaaa ggggtcgacc tggtcctcaa ctcactggca gaagagaagc 5280
tgcaggccag tgtgcggtgc ttggctcagc atggtcgctt cttagagatt ggcaaatttg 5340
atctttctaa caaccaccct ctgggcatgg ctatcttctt gaagaacgtc actttccatg 5400
ggatcctgct ggacgccctt tttgaggagg ccaatgacag ctggcgggag gtggcggcac 5460
tcctgaaggc tggcattcgt gatggagtcg tgaagcccct caagtgcaca gtgtttccca 5520
aggcccaggt ggaagatgcc ttccgctaca tggctcaggg gaaacacatt ggcaaagtcc 5580
ttgtccaggt acgggaggag gagcctgagg ctgtgctgcc aggggctcag cccaccctga 5640
tttctgccat ctccaagacc ttctgcccag cccataagag ttacatcatc actggtggcc 5700
taggtggctt tggcctggag ctggcccggt ggctcgtgct tcgcggagcc cagaggcttg 5760
tgctgacttc ccgatctgga atccgcaccg gctaccaagc caagcacatt cgggagtgga 5820
gacgccaggg catccaagtg ctcgtgtcaa caagcaacgt gagctcactg gagggggccc 5880
gtgctctcat cgccgaagcc acaaagctgg ggcccgttgg gggtgtcttc aacctggcca 5940
tggttttgag ggatgccatg ctggagaacc agaccccaga gctcttccag gatgtcaaca 6000
agcccaaata caatggcacc ctgaaccttg acagggcaac ccgggaagcc tgccctgagc 6060
tggactactt tgtggccttc tcctctgtaa gctgcgggcg tggtaatgct ggccaaacta 6120
actacggctt cgccaactct accatggagc gtatatgtga acagcgcagg cacgatggcc 6180
tcccaggcct tgccgtgcag tggggtgcca ttggtgacgt gggcattgtc ctggaagcga 6240

```
tgggcaccaa tgacacagtc atcggaggta cgctgcctca gcgcatctcc tcctgcatgg   6300
aggtactgga cctcttcctg aatcagcccc acgcagtcct gagcagcttt gtgctggcag   6360
agaagaaagc tgtggcccat ggggacgggg acacccagag ggatctggtg aaagctgtag   6420
cacacatcct aggcatccga gacctcgcag gtattaacct ggacagcacg ctggcagacc   6480
tcggcctgga ctcgctcatg ggtgtggaag ttcgtcagat cctggaacga gaacacgatc   6540
tggtgctgcc catgcgtgag gtgcggcagc tcacgctgcg gaaacttcag gaaatgtcct   6600
ccaagactga ctcggctact gacacgacag cccccaagtc caggagtgac acgtctctga   6660
agcagaacca actgaacctg agcacactgc tggtgaaccc tgagggtcct accctaaccc   6720
agctcaactc ggtgcagagc tctgagcggc ctctgttcct tgtgcacccc attgagggtt   6780
ccaccaccgt gttccacagt ctggctgcca agctcagtgt gcccacctac ggcctgcagt   6840
gcacccaagc tgccccccctg gatagcattc cgaacctggc tgcctactac atagattgca   6900
tcaagcaagt gcagcctgag ggaccctacc gcatagctgg gtactcattt ggagcctgtg   6960
tagccttcga gatgtgctcc cagctgcagg cccagcaggg cccagccccg acccacaaca   7020
acctcttcct gtttgacggc tcacacacct acgtgttggc ctacacccag agctaccggg   7080
caaagatgac cccaggctgt gaagccgagg ccgaggctga ggccttatgc ttcttcataa   7140
agcagtttct tgatgtggaa cacagcaagg tgctggaggc cctgctgcca ctgaagagcc   7200
tggaagatcg ggtggctgcc tccgtggacc ttatcactaa gagtcaccac agcctggacc   7260
gccgagagct gagctttgct gccgtgtcct tctaccacaa gctccgggca gctgatcagt   7320
ataagcccaa ggccaagtac catggcaacg tgacactgct gcgtgccaag acaggcggca   7380
cctatggcga ggacttgggt gctgactaca acctctccca ggtgtgtgac gggaaggtgt   7440
ctgtgcacat cattgagggt gaccaccgca cactgctgga gggcagtggc ctggaatcca   7500
tcatcaacat catccatagc tccctggctg agccacgagt gagtgtacgg gagggctaga   7560
cctgccgacc accatgaagc cacgctccac acctgccacc agagatgctc cgatccccac   7620
cacaccctga gtgcaggaac tggggagggt cctgctggtg ggacccctcc ccccagtggc   7680
ccagcaccac ccgctcccct ggtggctgct acaaacagac catcacgcgt gtgtttccca   7740
gccgcgtagt ggggttccca gagccactga cttggagaca ccctggtctg tgaagagtca   7800
gtggaggcag gagccaaact gagccttttc taccgtgtgg catttgccac gctggtcgtt   7860
tctccattaa attctcatat ttattgcatt gctgggaaag acccccaggg gtgactcatt   7920
ccagaacccc ctaaaatggg agaagccatg tggggaagat ttctgggaaa gtttctagac   7980
tcaatacaca ggctgctggc tggagcccct ttttgtcttg tcctgtccct gctcactgca   8040
gggcaggata tggagagggc tggttcccag ggaacaagga ccccagcaga cactgtagcc   8100
cgtggccctt ggtccccagc atccccggct gccccatgat gcagggccat cctgactctg   8160
cggaccgcac cgggcactga ctgtctgttt tccaagacga aaatgatgct tgggttttga   8220
cttttctgca gctgtcagtg tgaagaagtg tctggactgt gtcattttta caccaacctg   8280
gtaaaaatgc tgctcttgat gctctcctga tcccacaatt aaactgcacg tgagcgaaaa   8340
aaaaaaaaaa aaaaaaaaaa aaa                                           8363
```

<210> SEQ ID NO 13
<211> LENGTH: 23713
<212> TYPE: DNA
<213> ORGANISM: R. norvegicus

<400> SEQUENCE: 13

-continued

```
ggtacctcct tcccccacac agggaggact gtctaaagag aggccaccaa gaagagtgtc     60
ctgttcttcc tttaactaga cctacttagg aacagctcaa gtaagtgtgt ctagctcttg    120
gtgccagtta gaagctactt gtctgacact ggcctgagtc atgaacagct ccactgtgac    180
cactggttag atcaggctag ttccttcctt ggcctttgct cctacctggc tgggccaggt    240
cggcagcaag aggacctagc atggagccct tctatgattc ctgccctcca tgatgccttc    300
tggaagactt agaggagaag agccatgtga tatggttagc tggtgctggg aggaacatgt    360
gtataagagg agggtggtct aggtttggag aaccaggcat agctagcagg tgtcctcagg    420
atcctgagtc agcacagcct tgtcctgcag gagctagggc agaaatgacc ctaatgaggt    480
tgctgcttct aaatgtttca aaaagttcct tcctcagaaa gctgggcatg gtatcacata    540
ctgcgttctc acaagcctga agcaagagga ttgccatgac tccagcctgc attacaaagc    600
aagaccctga tttaaaagaa accaaagaaa aagagaccca cacagtctca ggacagggag    660
gagggcagct cacttctctg gagcctatgc aagcactcag gctccatgcc cacagcacat    720
tagattctgc caggcactct gtggctctac tgactcttac cctacctacc ctgtgcccat    780
gcggcatgtt ccaggtccac gggagtcaca gagataggct cctcagctct ggacagacat    840
gcacataaga cagctgagct aagactggca agcagtgggc tgtgtcccca agacaccaga    900
ctctgctgta agatatagtg catggtgttg tgttgcatgc tcttaatccc tccacttggg    960
aggcagaggc aggtgtgtcc ctaatgtcta ggccaagcag tttacatagt gagttccagg   1020
taaaccagaa ctgcatagta gttcctgtct aaaaaggagg gaaaaaaaag tataaaaatg   1080
caaaagcccc agaagcttcc tgtctgctgg gccaggttgc cagggaggaa ggataggtct   1140
gtctgtgtgc ctgagggagg tgaaatagtt ttagaaaaga tagacattgg ggttggggat   1200
ttagctcagt ggtagagcgc ttgcctagga agcgcaaggc cctgggttcg gtccccagct   1260
ccgaaaaaaa gaaccaaaaa aaaaaaaaaa aaagataaga catttttagt atcaaagatt   1320
caaagtacac aaaagatcaa aagataaaga tgatcatcta caaaagctag tgggacttac   1380
tagtgggcta actagtgggg cttactaact agtggggctt actaactagt ggggcttact   1440
aactagtggg gcttactagc aggcccttac ccatgaagtc tgggttctag cagcagccgc   1500
agcagcggca ataaagtgac cactttgact acggctcaag tggactctgg cagagctgct   1560
ctaggcttta acctgtgcct gtgtgtgtgg tacagcttac cagacagtcc ttggcctgtc   1620
tgtgtcagaa gtgttcacga acactccctg tacacgcaag ccccaagcac aggacaactc   1680
actgaactct cgatgaggtg gcttggcttg aatgggaggt ggggccacct gcccccatgc   1740
ccttaggaaa tggttataac agctcagggt gttttgttca gtgctttctt ttgtttccag   1800
agcccagatt tctgtgcggt agggaagagg caggcccagg atcagttgaa gatatgtgaa   1860
gcctgtgccc acacagacct cctacaccct agtcaggacc caataccgtt gctgccactg   1920
gccagggcta gggcactccg gaggcctgct ggcctgtata ggctcctgca gagaaaagca   1980
gactgagtcc ttacaggctg ctgattatga tatgaccaac tctgggcaca tacccacctc   2040
cgtttcctgt gatcctaacc tacatctttt tctacttctt gcctgtagag tgtcccgcac   2100
ctctgggacc cagctgtttc caaaaggtca gccggagccc tgtccccaca caaagggtca   2160
gccggagccc tgtccccaca caaagggcct ttgctgtcaa agggctaaag atggaagctc   2220
agccaaaagc ctcacacccc agacccagca agtcgcatcc agcaaagcct gcaaactgcc   2280
agccacagcg gcacccaagg atccgcaact acaacctcaa ggactagatc tcagcctcct   2340
```

-continued

```
gcagggcact gcacaggggc ctccaccttg gtccacgggg cctgtgcatg tacaagttgg   2400
gagtgagtac acacataata cacaggtgga ctgtgacaca ggacagactc ccaaatgctg   2460
gcctgcctga tactaaagag aaattaaaac cctcctccat ctgcttggcc tgtgaagttg   2520
tctgtcttgt cctacttggg aaatgaagta tcaacatgca ggctagatcc tgggctggtc   2580
tctgccacct gcctgtgtca ccacccacag ccactgtgca ctgaccctgt cagtgacact   2640
attcttctct agaatctggt gggcagaata gagtggccac ctgcaaagta tgtccccaag   2700
gaacattgtg agagaggtcc tcccaggagc atgagcctgg ccgaggccct atctcagaaa   2760
tatactcatc tgccgactga aacctcatc aagggacctg cctgaccatt cctgcccaca   2820
gtagatctta aagagggtca tggccttagc cttgctgggc ataagacaca cagggctgca   2880
ggggtggaag cagctcccag gtccaggttg ctgtgtgtcc ctgattaatc atgtgactct   2940
tacagcttca ttttgcatct gtgtaaaatc ctgatagtgg ttcccgctgg ctggctcaca   3000
tgtgtgggcc acacaaacat cacaagaaag cccacgctca gtaatgtggt cttgggacgc   3060
tagctgaaac cctcaggcct aggtatcaca caactgcaga tcactcttgc tgtgtctgta   3120
gtaggctgct ctcgaggtgc atacgccaag agacatagga tgatgtcttc acaacagccc   3180
acctaggcac actgtgcttt caagaccagc aagggcaatg gcaggccatc ttgatgtggc   3240
tctcccacat ccacatctgg cagtccactc tctttgctga gatgtagcct gcaacctcta   3300
tgggtaaaaa gatgagcaga gaagtctgct gaccccagca tcctcctctg cacaggccca   3360
tactctgcat tccagcctgc tctccttggt tacaacccct ccactgaaga ccccagtagc   3420
tgcagagggc agagctctgc tgaccaagta tggttagcca gcagcctggc cagcgagaag   3480
gcaaacacag ggcacctgga ggtggggtgg gacagctctg gctggcacat gcacaagcca   3540
tttataaaac tctcctaggc tgaccctgaa acccaaagac acaacaaagt gaagaccctc   3600
caatagagag agtgcaggac ctgggtcctg cactcctcac ctccatagaa tacacattac   3660
aacaagagat gccatcagta ggccatggaa caggccctaa agacacaggg gcactaatag   3720
gagaacttgg gggcaagccg gcatgtgggc agaatacacc tgccagtcct acaggctgcc   3780
cttcagggtc cccacttagc ctccttccac agagagcctg tggacagcca agctggagaa   3840
gctagaagcc agggttgaca agcaaggctc tgaggctctg gcttttgcta tagacatgca   3900
gtcaaggacc actgacacta ctccctcctt agcgcccccc ccccccaaag ccactgccca   3960
taaggttggt cttagtggcc tgggcctgta gtggaagggc agaaggaaag ggatcaactc   4020
tgagcagtct gtgtcttttt ggtcggtgag ttttcatcat ctcccgtccc caaattcgat   4080
aaccctttca aaagaggaat ttaaagggag ggagggtgag ggtcccggaa accagcaact   4140
cagggaggcg cgcagacgct cctttgttcc caccaggcgg gggaggggtg gtatcccgct   4200
cgccagatgg ccgcgcctgg acactgaacg gactcaggag accgcggcac gcgcccgtca   4260
gtgttcccta tcctgcctac tgctctcgtc cctgcccgca tcctggtctc caaggcggcc   4320
acagaaaggg tgggtgtctg agaaagctgg gccacgatga ccggtagtaa ccccgcctga   4380
ggcgccctcc gccagggtca acgaccgcgc ttgcgcgggg gcccgagaag cgctttgccg   4440
cttttgccgg cccatcaccc tattgcctag caacgcccac ccgcgcgcca ccattgggcc   4500
accgagaacg gcctcggtgt ccaattggtc tcgatgtgga gcaggccacg cccctcggct   4560
ctgcgcgcgc tacgatcacg gcgtggaatc gcagcgacac ggacctgttc tgttcccccg   4620
cgtggcccca gtgtcctcag tgcagttccc agtgtgacca agcacgcccg acccacactg   4680
cgcgcgcaca gtgcacacct ggccccggcc gcgggggtgg gggggtgaga gaaaggacag   4740
```

-continued agatgagggc gtcgggatga gccccgcgtg gcccgcggga ggccgggggc ggggacggaa 4800
gcgggcgggg gctgcgcgtt ccttgtgctc cagcgcgcgc ctgtgcaggg tcccggctgg 4860
gggcggcgcg cgcgggcatc accccaccga cggcggcgcg ccgggtcccg gggcgcagcc 4920
ccgacgctca ttggcctggg cggcgcagcc aagctgtcag cccatgtggc gtggccgcgc 4980
ggggatggcc gcggtttaaa tagcgccggc gcggcctaga gggagccaga gagacggcag 5040
cagcgtcccg tccagttcgc ctgccgcgct cctcgcttgt cgtctgcctc cagatcccag 5100
acaggtacgc cgctgcgttc ggggttccgg gatggcaggc cggtgtcggg gtgccgcggc 5160
tccagtggga ggacaggcgg gcgcccatcc tcaacagccc tgcgctcaca aaagcgccgc 5220
cgcgcccctc cgacagccaa ccacccggct gtgcgccgcg gtccggccga gaggggcgcg 5280
ggaggggtgt gcggagagcc agcgcggcgg gccgctgtca cgtgggcgcc gcgccagccg 5340
ggtgcaggag gctgggtgcc tcgtggatgg ggccggggcc tccactctca tccggaggct 5400
ttggcagggc acaggaggcc gcggtggtac ccgggctcca gtttggagag gccagttgtg 5460
ggtctgggag cgcacgaggc cccaggggcc tcagcggaag tcatcagacc atccaggcct 5520
caccggctgg gtggcgcgga agccttctcc ttggactacg gctgcaaggc ctgaactgcc 5580
ctgggcaagt gccttaggga ccagaggatc tatcaaaccc ttcagctggc tcagccaggt 5640
tacaaggtgt tcgaccaaat ggcgagaggc ttctcctgtc ccggatccgc acctagttag 5700
gagtggtact ctaggtcgga tcttgctgaa aggatccgtt ggcaggggat cggtttgcct 5760
cagccctgct aggcctgagc actaagtagt cgggcctgtt ctctctgggt ccttaccatg 5820
cctggcgttc tggctggccc tgcagggcag tcagtctcca ccctcatcat gaaagggaag 5880
cgttggcttc cccgtggctt gaggtgagag tgtcccagac cctgcttctt gaagccccac 5940
ttctgtttgc aagttcctta tgattgggat ggagcaccca gtaggcaact ggagatcata 6000
tggtcccagg taactagcaa ggcatggtag ggtcaggcca ggtcatgtgt ctggaaggga 6060
ttaaaaacct cagaagtagc tatcccgtgc aagggaaccc gagcacccgg gctcatccat 6120
tgattatagc tgggtcctgc tagtttccac cactgggggg ctttctgagc cctttgctct 6180
cagaaagtca gggcctggct gtgaggtgtg ctacctgtgg attcaggtgg ctgtagctgg 6240
gaatgactct atgagggagg cccaccaggc tacctacctt cccccacaga gaagagccat 6300
ggaggaggtg gtgatagccg gtatgtccgg gaaattgccc gagtcagaga acctgcagga 6360
gttctgggcc aacctcattg gcggtgtgga catggtcaca gacgatgaca ggaggtggaa 6420
ggctggtgag tgtcccctcg ggatcaggca gcaggacaga ctgagagtct cacccaagat 6480
gcttctagag acagtgaact ccctgtagag ctgtgaggtt gagaaccggt tagaatgaga 6540
agggacaggt gtcttggttg gttccgcatg caagacaccc aaggtgggcc gtagaagagg 6600
actggccctt tggatctccc atctgtaacc tctgccctga gctggcggat agtgtctaag 6660
atgacgctca cacccagtgg attctaacag tgccatagag cagctagctc tacctgatgg 6720
gcaggtgtga gtcagcactg ggctggcctg gccagcctcg gagtaggcag agggtctccc 6780
agtcaggtcg gggttaccag gggtgatcg ccagcctcac ttcctgctcc tacaggtttt 6840
gctttgggtc acccacatgt ggcggttttg gggctcctca ttagcagtga ggctgggtca 6900
ctctctggga accttcctcc aggagaggtt ggttccctgg cctcagactg tgatgttcca 6960
cagggctcta tgggttgcct aagcggtctg gaaagctgaa ggatctgtcc aagttcgacg 7020
cctccttttt tggggtccac cccaagcagg cacacacaat ggacccgcag ctccggctgc 7080

-continued

```
tgctggaagt cagctatgaa gctattgtgg acggaggtgg gtcattgggg tattattatt   7140
gccctttttta ggacttactg tcatgagggc tggggacgta gtccagtggg agagcacttg   7200
cctagtatgc acaaggacct gggaacatca tcatccccag tccaggaaaa ggaaacacaa   7260
caatgatacc ttcttggctc tgagatgtca agagctcaga gacaggcatg gatggcatgg   7320
gtccctctag ctatgtcccc aaccctgatg tagggccagt ggctcaggag gcgggggccc   7380
tgagcagggc acgggtttca caaccacaca cttagtgtcc caggcgcgcc ctgttacccc   7440
agttacttca ctccccgacg tctggttgtt cttggactga gggcggggct tacagcaggt   7500
agcactgcag gggctcagcc tcagctttgg caacaaccca gtcccactgg ctgtctctca   7560
ctctggatcc tgctgcttgg gtcatggacg tgtccccagg gatagaaggc cccatagtgg   7620
gcagccagtg tgggttagta tggcgggggt gagcttcagg ttggtagatg ctaattaacc   7680
ctgtacttga taaacagctt gatgtataac tgccctgggg tagagtagaa gaccagagga   7740
tgcaggatcc tggtaacctc ggtggtgaaa atgaaggtcc tcaccttggg cctgtctggc   7800
tgcccaggct ctatcaatgg ctgggcacag ctcccagggg gttacccact gtcctctgct   7860
ttcccagctt ggacacttgg tctttgtctt cttgtatctc cttatcacag cctgtcccag   7920
ggcaggctgc ccttggcact agagaactca ttggccagcg gcctctcgag acccaccagt   7980
aacaccagag cccgagggag ttgccctcag acaatgctgt cctctgtctt aactatagcc   8040
tcctatggtt gcagctctga cccagacctt agaggtccac tgtggcccct atggtacccc   8100
tctgacccaa acccatgtgg ttattgctgc cccccggcagg tatcaacccg gcctcactcc   8160
gaggaacaaa cactggtgtc tgggtgggtg tgagtggttc cgaggcgtcg gaggccctga   8220
gcagagatcc tgagactctt ctgggctaca gcatggtggg ctgccagaga gcaatgatgg   8280
ccaaccggct ctctttcttc ttcgacttca aaggtgggtg ggcagcccag ctctgggcac   8340
gacccagctg tatgtgcatt cacctacaca acccttttgg actcagactt ccttattcct   8400
ggggaaggca ctgagtgggg tactcacagc ccgggaggcg gggggtgtgg gacagcatct   8460
gcccaagggt acccacaccc actttatgac cttgtccaca ggacccagca ttgccctgga   8520
cacagcctgc tcctctagcc tactggcact acagaatgcc tatcaggcta tccgcagtgg   8580
ggagtgccct gctgccattg tgggcgggat caacctgctg ctaaagccta acacctctgt   8640
gcagttcatg aagctaggca tgctcagccc cgatggcacc tgcagatcct ttgatgattc   8700
aggtaaggtt ggcctgggta gggatcgtta ggctctactt tgcagggctc cagcctgtac   8760
cctgagtggc atctgggctc ctggtggtgt ggggaaggga ggacgtgtgc atgtatagac   8820
tcatagcaca caccccatca caccagagca cctagctgag gtgttgatct actctaggga   8880
acgggtattg ccgtgctgag gctgtcgtgg cagttctgct gactaagaag tccttggctc   8940
ggcgagtcta tgccactatt ctgaatgccg ggacgaacac agatggctgc aaggagcaag   9000
gtgggcatgg agggaaagag catggggaat ggggacgtgg agcacacaag gcttgacacc   9060
gtactgtacc attacccatc tccgtaggcg tgacattccc ctctggagaa gcccaggaac   9120
aactcatccg ttctctgtat cagccgggcg gtgtggcccc cgagtctctt gaatatattg   9180
aagcccatgg cacgggcacc aaggtgaaag ccctttccag cccatacctg ccactcctct   9240
atcctcacta gagggacctg gctgcagcct taacctactc tgtcccctgc aggtggggga   9300
cccccaggaa ctgaacggca ttactcggtc cctgtgtgct ttccgccaga gccctttgtt   9360
aattggctcc accaaatcca acatgggaca ccctgagcct gcctcggggc ttgcagccct   9420
gaccaaggtg agcaggctgg gggctctgag tcaagaatga tgtggatagg tctgtactgt   9480
```

```
gaccaccact tgacctaccc cggggctcct gcctgctcac caaccagccc tttggctgta   9540
ccgttgctga agtggcaggg agactgggta cactccctgt ggttgctgtg ctgacttaca   9600
tagcttctgg ctgaaggaaa cacttggctg cataaaggac aggtgcagtt ctgaggaagt   9660
atctaggcag ccaggtctag cagaatgccc cattctgaga tgaggagaga ggagcgagcc   9720
agtgtctgat ctggtgtgtt ctttccctgg gtgaccctgc acgtgtaggc accttcagct   9780
tgtttctatg ctgggaggtg tgcggttgtc tggatgacct atctgttggg gcttctgggc   9840
ctggcttcag agtttgtgcg ctcaggccta ctgccccttg acttgggcac catgcaccct   9900
ggaccactgg tggcaaggcc agagaagaca agggtcttgg tgcccagtac catacacagc   9960
tcatgggccc tggggaggta ggtggccacg cttggtgggg acagctgccc agtaaccatg  10020
tgttttgtct acaggtgctg ttatccctag aaaatggggt ttgggccccc aacctgcatt  10080
tccacaaccc caaccctgaa atcccagcac ttcttgatgg gcggctgcag gtggtcgata  10140
ggcccctgcc tgttcgtggt ggcatcgtgg gcatcaactc gtttggcttc ggaggtgcca  10200
atgttcacgt catcctccag cccaacacac agcaggcccc agcacctgcc ccacatgctg  10260
ccctaccgca tttgctgcat gccagtggac ggaccatgga ggcagtgcag ggcctgctgg  10320
aacagggccg ccagcacagt caggacttgg cctttgtgag catgctcaat gacattgcag  10380
caacccctac agcagccatg cccttcagag gttacactgt gttaggtgtt gagggccatg  10440
tccaggaagt gcagcaagtg cctgccagcc agcgcccact ctggttcatc tgctcaggtg  10500
agcctgctcc catgttccca ggctggcccc aaaggaggag gggagtcggt ccctttttctt  10560
gagggtgagg ctggaggttg gccatgctat ggccctgata agctttctgg tacagggatg  10620
ggcacacagt ggcgtggaat ggggctgagc cttatgcgcc tggacagttt ccgtgagtcc  10680
atcctgcgct ctgatgaggc tctgaagccc ttgggagtca aagtgtcaga cctgctgctg  10740
agcactgatg agcacacctt tgatgacatc gtgcattcct ttgtgagcct caccgccatc  10800
caggtatgcc accttcgtgg tactcggacc ccgggacact ccacaccaga gtcacgtagt  10860
cctggccctg actggtatgt aggcagagcc ttaaataggt acacctgagg aggagcaggg  10920
tcttctcaga ggaccctaag agaggcttgg cgtgcttggt gtgctcagct ttactgtgag  10980
ggatggtcag gctagtgatc tagggtctac gtgacatggc ttatatcccc acttcgcaga  11040
ttgccctcat cgacctgctg acgtctatgg ggctgaaacc tgatggcatc attgggcact  11100
ccttgggaga ggttgcctgt ggctatgcag atggctgtct ctcccagaga gaggctgtgc  11160
ttgcagccta ctggagaggc cagtgcatta aggatgccaa ccttccggct ggatccatgg  11220
cagctgttgg taggtatcct ctcaagggcc cccgacctca ttaggcacca ggatcttctt  11280
ggaaggggtt tctgtcctgg gtcctccaaa agaatcagtt gctttgttgt gagacatggg  11340
gttgcaaagg gagaagtcac tctgctcaga ttatctttat aggaggcttc agttctgacc  11400
ccacaggccc gagcaaggta tgaaacacca tacacatcag atgagggttc caggagctga  11460
ggagagccac ttaccaaccc taggtgttca tcgcccagct tctcagctgc ttacccccta  11520
caccacttag gtgtcatttc tgaggtccgg ctcctttcct acactccctc cataatgaca  11580
cctctcttga gatcagaaac agcagggagg gagtaaaggt gccctggaag gtcgactctt  11640
agcatcccaa caccattggc tctaagtagt gctcatggtc caggaggatg ggctgagttc  11700
gggccagctc tgaggccagc ctctctgctt ataggtttgt cctgggaaga atgtaaacaa  11760
cgctgccctc ctggtgtggt gcctgcctgc cacaactctg aggacactgt gaccatctct  11820
```

-continued

```
ggacctcagg taggccctgc aatcatagca ggacttctgt tccctgcaat tttgccctgg  11880
ccctgcctag gaggcaaggc ctcctcagtc tgtgtccacc aagttctgaa gggcccagct  11940
ggtgagctac acttgtcgca ggccctctgg gtggactgtg tccctgacca gggaaagcca  12000
gtccaggccc cctgaccact ggccttgatg cctgcaggct gcagtgaatg aatttgtgga  12060
gcagctaaag caagagggcg tgtttgccaa ggaggtgcga acaggtggcc tggccttcca  12120
ctcctacttc atggaaggaa ttgcccccac gctgctgcag gctctcaaga aggtgagtac  12180
ctggccatgt gcttggaccc cagggcacgg tgacttgacc tcactcgcta accaagcgtc  12240
tgtgtgcagg tgatccggga gccacggcca cgctcagcac gctggctcag cacctctatc  12300
cctgaggccc agtggcagag cagcctggcc cgcacatctt ctgctgagta caacgtcaac  12360
aacctggtga gccctgtgct cttccaggaa gcactgtggc acgtccccga gcacgccgtg  12420
gtgctggaga ttgcacccca tgcactgttg caggtgagca ctggtccgcc tgggatgggg  12480
cacatcagcc tgccagtcac tggcgaaggc gagtggcacg gaaggggtcg gagcctagct  12540
ctcctttgct atgtgtaggc tgtcctgaag cgaggcgtga agcctagctg caccatcatc  12600
cccttgatga agagggacca taaagataac ttggagttct tcctcaccaa cctcggcaag  12660
gtgcacctca cagggtaggt ctcccttctg tctgctgctc gtgtgcaggc ccacaccaac  12720
ccccatgaga ggggttgctg tggcctagct cagtgctggc cctcggtcct catcttggcc  12780
atcttggggt cttagagcaa aactagggcc acagactctc agggacaggt gtgtcactta  12840
acttgtttgt caccagcatc gacatcaacc ctaatgcctt gttcccacct gtggaattcc  12900
cggttccccg agggactcct ctcatctccc ctcacatcaa gtgggaccac agtcagactt  12960
gggatatccc agttgctgaa gacttcccca acggttccag ctcctcctca gctacagtct  13020
acaacattgg tgagccaggc tccgtggtca gtgggttcct cccaggcctg tgggcccgtg  13080
ctgaggcatt gtccttacag acgccagttc cgagtcatct gaccactacc tggtcgacca  13140
ctgcattgac ggccgtgtcc tcttccctgg cactggctac ctgtacctgg tgtggaagac  13200
actggctcga agcctgagct tgtccctaga agagacccct gtggtgtttg agaacgtgac  13260
atttcatcag gccaccatcc tgcccaggac aggtaagagg cccttcagtg ggggctggtg  13320
aggtggttgt gactactccg ctctgacctt ctttttttct ctgcaggaac cgtgcctctg  13380
gaggtgcggc tgctagaggc ctcacatgca tttgaggtgt ctgacagtgg caacctgata  13440
gtgagcggtg agtagtacct ggctgggcct gtgtggctga ggacctcagc tcctagcctg  13500
ccccatgctc agaccctcct gttgccctgc ctcctacagg gaaagtgtac cagtgggaag  13560
accctgactc caagttattc gaccacccag aagtcccgat ccccgccgag tccgagtctg  13620
tctcccgctt gacgcaggga gaagtataca aggagctgcg gctacgtggc tatgactatg  13680
gccctcattt ccagggcgtc tatgaggcca ccctcgaagg tgggcaggag caatccccga  13740
gtcagtgagc atgatgacca ggagccattg tcactcctgg gccatgtctt gctgggggtc  13800
agggaagacg gaggaagggt agtagaggcc ctggagcagg tgaggcctcg tgtgctgagc  13860
agccccccta ctgcaggtga gcaaggcaag ctgctctgga aagacaactg ggtgaccttc  13920
atggacacaa tgctgcagat atccatcctg ggcttcagca agcagagtct gcagctaccc  13980
acccgtgtga ctgccatcta tattgaccct gcaacccacc tgcagaaggt gtacatgctg  14040
gagggagaca ctcaaggtag ctctggccct cgctctgtcc acttgtcctg gactgagcat  14100
tgcctacact gaccagtgtg tctcatagtg gctgacgtga ccacgagccg ctgtctgggc  14160
gtgaccgtct ctggtggtgt ctacatttcg agactacaga caacagcaac ctcacggcgg  14220
```

-continued

```
cagcaggaac agctggtccc caccctggag aagtttgtct tcacacccca tgtggagcct  14280
gagtgcctgt ctgagagtgc tatcctgcag aaagagctgc agctgtgcaa gggttgagga  14340
tccaaacctt ccctcttctt cctcagtctt tgcctttgaa actcctgagg caaggcctgg  14400
atggcgggga gctcagggtt ggtgagagca cagcctacct tccatgggta gcacggcact  14460
gctgcatcct tcctattgag tttccgctct tcccattgct gtgggcttgt cctgtggaca  14520
cgctagaagc aggccctggc agtaggctgg aggccgtaga gagagaacgt aggcctttct  14580
ttgtccctcc caggtctggc aaaggctctg cagaccaagg ccacccagca agggctgaag  14640
atgacagtgc ctgggctaga ggaccttccc cagcatggac tgcctcgact cttggctgct  14700
gcctgccagc tgcagctcaa cgggaacctg caactggagt taggtgaggt actggctcga  14760
gagaggctcc tgctgccaga agaccctctg atcagtggcc tccttaactc ccaggccctc  14820
aaggcctgca tagacacagc cctggagaac ttgtctactc tcaagatgaa ggtggtggag  14880
gtgagtgctg ggaaggtaga caggccatgt gcgtggatcc agggcaatct cagacccgag  14940
cccaaggcag gcagccatga tgtagcagct ttctatggcc tttgtgcttt ggtttgttcc  15000
accctaaaag attgtgggga acttttcact gctaccagtc caggggatga gatatcagaa  15060
ggaaggcttc tgggaaagaa tcctgggatg ctctgagctc tagcctggga tgtcgcagac  15120
agtctccaca ggagagtaga ggagaacact ggaagagcct cccggccagc attgccacaa  15180
aactgagcat gagcagcacg gagaggctca cccaggcccc agggttttct gcctcctaga  15240
aacaacagat ctaagatgct ctcccacacc aggtgctggc tggagaaggc cacttgtatt  15300
cccacatctc agcactgctc aacacccagc ctatgctgca actggagtat acagccaccg  15360
accggcaccc ccaggccctg aaggatgttc agaccaagct gcagcagcat gatgtagcac  15420
agggccagtg ggacccttct ggtcctgctc ctaccaacct gggtgctctt gaccttgtgg  15480
tgtgcaactg tgcgttagcc accctggggg atccagccct ggccctggac aacatggtag  15540
ctgccctcaa ggatggtggt ttcctgctaa tgcacacagt gctcaaagga catgcccttg  15600
gggagaccct ggcctgcctc ccttctgagg tgcagcctgg gcccagcttc ttaagccagg  15660
tactgctcct gggcatgcag ggcaggtaag ggctgggtat ggttccgcca gttcagtact  15720
tacaagactt catacacata ggaagagtgg gagagcctgt tctcaaggaa ggcactgcac  15780
ctggtgggcc ttaaaaagtc attctacggt actgcgctgt tcctgtgccg ccgtctcagc  15840
ccacaggaca agcccatctt cctgcctgtg gaggatacta gtttccagtg ggtggactct  15900
ctgaaggtca ggctctgggg ctgggtacct tggcttcccc tgacgtatga tcaccctaga  15960
ggctgaccct actttatcct gcagagcatt ctggccacat cctcctccca gcctgtgtgg  16020
ctaacagcca tgaactgccc cacctcaggt gtggtaggct tggtgaactg tctccgaaaa  16080
gagccgggtg gacaccggat tcggtaggaa aggccctgag aggtgcctac ccttcctccc  16140
tcacccccctc cattcttggt atccttaccc actttgcccc cacaggtgta tcctgctgtc  16200
caacctcagc agcacatctc acgtccccaa gctggaccct ggctcttcag agctacagaa  16260
ggtgctagag agtgatctgg tgatgaacgt gtacagggac ggtgcctggg gtgccttccg  16320
tcacttccag ttagagcagg gtaagcctgt ccatgcccta tatacttaat aggcttgtga  16380
ggtggcaggg gaacaaggag ctggccaggt aggcccctgt ggcatccttg ctttctttcc  16440
cctcagacaa gcccgaggag cagacagcac atgcctttgt aaacgtcctt acccgagggg  16500
accttgcctc catccgctgg gtctcttctc ccctgaaaca catgcagccg ccctcgagct  16560
```

-continued caggagcaca gctctgcact gtctactatg cctcactgaa cttccgagat atcatgctgg 16620
ccacgggcaa gctgtcccct gatgccattc caggtgccaa ccaggatggg ggcttatgat 16680
tgggttgctg ggagtagaga aggtgcctgt actgtagcag cccagtgagg aggagtcctg 16740
cccggctcct ggggaagaga gggttcccag caccagaggc tgcacttgca tcctgctccc 16800
ctgacaacct gtcctagggt ctgggctaac aggagcctcc ctctgtctac acacaggtaa 16860
atgggccagc cgggactgca tgcttggcat ggagttctca ggccgtgata agtgcggccg 16920
gcgtgtgatg gggctggtac ccgcagaagg cctggccacc tcagtcctgt tatcacccga 16980
cttcctctgg gatgtaccct ctagctggtg agtggctggc tgcagttggg ggttatgtga 17040
tcttagttgg tggccaggct gaattgatcc tgtgctccgt tccctcagga ccctggagga 17100
ggcggcttct gtgcctgttg tctacaccac cgcctactac tccttagtag tgcgtggtcg 17160
tattcagcac ggggaaactg tgctcattca ctcgggctcc ggtggtgtgg gccaagcggc 17220
catttccatt gcccttagcc tggctgccg agtcttcacc actgtgggta aggccctcac 17280
cccctcccga tcccaatcaa ggagcttctt gaaccctgtg ggccaaactt actggggtct 17340
cccttgactg acaggctccg ctgagaagcg agcttacctc caggccagat tccctcagct 17400
ggatgacacc agctttgcta actctcgaga cacatcgttt gagcagcatg tgttactgca 17460
cacaggtggc aaaggtaaat accccctggg ccattgcctg agagtgagtg ggtcacatag 17520
tcagtccagc gctgaggact gaggtacagg tgagcccagt atgaccgact gacatgtttg 17580
ccaccgtagg ggtggacctg gtcctcaact ccctggcaga agagaagctg caggccagtg 17640
tgcggtgctt ggctcagcat ggccgcttcc tagagatcgg caaatttgat ctttctaaca 17700
accaccctct gggtatgact cgtagtcagg agcaggggtg ggcgctggtg ttggggccag 17760
gggcatccca cagtgaacag gattctcgaa tacaggcatg gccatcttct tgaagaacgt 17820
cactttccat gggatcctgc tggatgcact ttttgagggg gccaacgaca gctggcggga 17880
ggtggcagag ctgctgaagg ccggcatccg tgatggggtt gtgaagcctc tcaagtgtac 17940
agtgtttccc aaggcccagg tggaggacgc cttccgatac atggctcaag gaaaacatat 18000
tggcaaagtc cttgtccagg tgaagtgagg ccctcgggca ccaagcctgg tttcgccttt 18060
tgtagtgcat ttttttcta attatattta cttacttttg atggttgtga gtggcatgtg 18120
tgggtaccag aggacaactt gcaggagttg gttctcctcc atgggtcatc aggttttttt 18180
ttattttttt ggttcttttt tttcggagct ggggaccgaa cccagggcct tgcgcttctt 18240
aggtaagcgc tctaccactg agctaaatcc ccagcccggg tcatcaggtt tgatagaagc 18300
actgttaact acccagctgt ctcgctggtc ctgggacagc ttctgaacca ctgctacttg 18360
tatgcaggta cgggaggagg agcccgaggc tatgctgcca ggggctcagc ccaccctgat 18420
ttccgccatc tccaagacct tctgcccaga gcataagagt tacatcatca ctggtggcct 18480
aggtggcttt ggcctggaac tggcccggtg gcttgtgctt cgtggggccc aaaggcttgt 18540
actaacttcc cgatctggaa tccgcacagg taggcaagta gaagcagttg gtagtgtagg 18600
cttcccttca gtggaaagtg tcctgggagg gctgtaggcc actgctttcc tctggtgcag 18660
ccccatttcc ctgtgtccca taggctacca agccaagcac gttcgggagt ggaggcgcca 18720
gggcatccat gtgctagtgt cgacaagcaa tgtcagttca ctggaggggg cccgtgctct 18780
catcgctgaa gccacaaagc ttgggcccgt tggaggtgtc ttcaacctgg ccatggtgag 18840
aaaagcatgc agggctctgc gtacctccag agcctgagac ccaggctgct gctaagtggg 18900
gttagaacct cagagctgca gcagacacta aaaccccttc ttctaggttt taagggatgc 18960

-continued

```
catgctggag aaccagactc cagaactctt ccaggatgtc aacaagccca agtacaatgg  19020
caccctgaac cttgacaggt aggcagttgg tccctctgct gagtttcatg tatgcttgca  19080
atgtatactg gtccctgctg gacttgaggg tctggggaag tgaaactgtg ccacccgtgg  19140
ccttctgggc ctgccctggg gaggtacgga catgaaagtt atcagactga catgagtacc  19200
cacagggcga cccgggaagc ctgtcctgag ctggactact ttgtggcctt ctcctctgta  19260
agctgcgggc gtggtaatgc tggccaatcc aactatggct tcgccaactc taccatggag  19320
cgtatttgcg aacagcgccg gcacgatggc ctcccaggtg ggcctctttg tctagcccac  19380
ccctgcttgt ggtctcactc cccaaagcac ctcaccggct gcctcccttg ctctcaggtc  19440
ttgccgtgca atggggtgcc attggtgacg tgggcattat cttggaagcg atgggtacca  19500
atgacacagt cgttggcggc acactgccac agcgcatctc ctcctgcatg gaggtgctgg  19560
acctcttcct gaatcagccc cacgcagtcc tgagcagttt tgtgctggct gagaagaaag  19620
ctgtggccca tggtgatggt gaagcccaga gggatctggt gaaagcagtg gcacacatcc  19680
taggtaagcc agcttccggg accttcccgg cttaggtgac ttggagcctt agttttccca  19740
tctgtagaag cagacgacag agttctgtgg tctgaatgct ggccaggcca ggtgattggc  19800
agtgatgctg gagagccaca gtatgtacct ggttcccacg tccccttctc agtaatgacc  19860
agttacccat cccctttgtt aggcatccgc gacctcgcag ggattaacct ggacagctcg  19920
ctggcagacc tcggcctgga ctcgctcatg ggtgtggaag tgcgccagat cctggaacgt  19980
gaacatgatc tggtgctacc cattcgtgaa gtacggcaac tcacactgcg gaagcttcag  20040
gaaatgtcct ccaaggctgg ctcagacact ggtgcgtacc aggcagcagg ctgtgagaga  20100
cacaagtgca tcctagtatt gtaggcagca gcgctgccct tttgcaaaga acacatgggc  20160
ctgtgcttaa tctgtgtgtg tatgacctca caaggggatg tgtaccagag cccatgtgcc  20220
aaggctaccc tacaccctct gtctttacag agttggcagc cccaagtcc aagaatgata  20280
catccctgaa gcaggcccag ctgaatctga gtatcctgct ggtgaaccct gagggcccta  20340
ccttaacacg actcaactca gtgcagagct ctgagcggcc tctgttcctg gtgcacccca  20400
ttgaaggttc catcactgtg ttccacagcc tggctgccaa gctcagtgtg cccacctacg  20460
gtctgcagtg cacccaaggt actgtgcaca tggcgaagca gtacatgctg ccttgggcct  20520
ccgttcctca ctgactgctg gctgagtcct ctgtttgtcc ttacagcggc ccccctggac  20580
agcattccaa acctggctgc ctactacatt gattgcatca agcaggtgca gcctgagggg  20640
ccctaccgag tggctgggta ttcttttgga gcttgtgtag ccttcgagat gtgctcccag  20700
ctgcaggccc agcagggccc agcccccgcc cacaacaacc tcttcttgtt tgatggctca  20760
cacacctacg tattggcgta cacccaggtg agagccgggc caactggtcc taagcattgc  20820
cgcctatgtc ttggctctga acacacttct gggagggtcc tggttacttt agcccttgca  20880
gcatcaatct ctccttccct gacagagcta ccgggcaaag ctgaccccag gctgtgaggc  20940
tgaggctgaa gctgaagcca tatgcttctt cattaagcag tttgttgatg cagagcatag  21000
caaggtgggc ctggacacac cctagagagg gcaggaaagg caaggctggg agggttgggg  21060
tctctgtgcc tttaaaatgg agcagggaaa tccaagcgct tcttcagaaa cccgtctgcc  21120
cagagaaggc agggcagacc gtgtagcccc ccatcccacc ccacatgctc agagctgttg  21180
cttttaggtg ctagaggccc tgctaccact gaagagcctg gaggaccggg ttgctgctgc  21240
tgtggacctc atcactagaa gccaccagag cctggaccgc cgtgacctga gctttgctgc  21300
```

-continued

```
cgtgtccttc tactacaagc ttcgagccgc cgaccagtat aaacccaagg ccaagtacca  21360
cggcaatgtg atcctgctgc gggccaagac aggtggcacc tacggcgagg acttgggtgc  21420
cgattacaac ctgtcccagg taagcgagtg agtggggcag acgaggcggt gtgggacgga  21480
cgcctgctgg tggtcacaga atgacacctg aatgtttaca ggtgtgtgat gggaaggtgt  21540
ctgtgcacat cattgagggt gaccaccgta cgctgctgga gggcaggggc ctggagtcta  21600
tcatcaacat catccacagc tccctggctg agcctcgagt gagtgtacgg gagggctaga  21660
cctgcctacc atgaagccac gacccacacc ggccaccaga gatgctccga tccccaccac  21720
accctgagtg cagggactgg ggagggtcct gctggtggga ccccctcacc ccagtggccc  21780
agcaccaccc cctcccctgg tggctgctac aaacaggacc atcacatgtg tcccagccac  21840
ttagtggggt tcccagagcc actgacttgg aggcaccctg gtctgtgaag agtcagtgga  21900
ggccagcaag agccaaactg agccttttct gccaagtgac atttgtcaca ctggttgttt  21960
ctccattaaa ttctcatatt tattgcattg ctgggaaaga ccgcccaccc cagggttaac  22020
tcattccaga accccctaaag tgggaaaagc catgtgggga aggctgctgg ctggagcccc  22080
tttttgtctt agccctgtac ccgctcactg cagggcaggg tatggagagg gctggttcgc  22140
ggggaacgag gaccccagca gacactgtag cccatggccc ttggtcccca gcactcccgg  22200
ctgcacccat gatgcagggc ctaccagact ctgcggaccg caccgggcac tcactgtatt  22260
tgttttccaa gattcaaatt gctgcttggg ttttgaattt actgcagctg tcagtgtaaa  22320
gaaacatgtc tgaactgtgt ccttttttaca ccaacctggt aaaaatgctc ttgatgctgt  22380
cccgttgcca caattaaact gcacgtgagc tctggcttcc gttcagtctc tttccagtcc  22440
cagacctgag tccccagagc ctccacagct cttacagtga gaatcaaatt ggcccactcc  22500
ttggaaggcg tggcattctg tcagagtaaa aggaaagtag agtgtgctga ttcacgttca  22560
gcgtgtgggg ctggctagag accttggcac tgtagtgaac agaatgtgtc cacctttaag  22620
tcaccctgaa ggcatcacca tagctacagc ctcacccagg ggtagagaat agtactgtct  22680
acttgttgac tacctggcag ttggtgccag ccccctataga ggaaaacagc agtgtgtggc  22740
cactgtgaga agcatatccc tggaaacagg tgaccagagc agagggctaa cgcctacctg  22800
agtcacacaa aactgaccag gcttgagtgt ccagaagagt ctatcagaag gccacagcat  22860
tcagtcctat ccacagagag cagcagacta agttgtctcc ttgccagctt agaaaactgc  22920
agtgctgggg tacaggtagg gtgttcagga ggtccgggcc ccagtgatta gtctaagact  22980
gaagcatctg gttggctgtg gtcccaccta gaaaattctt aaagctcttg tcatgtactt  23040
cctgggaagg acctaccctg tctcaataat gtctctagct cgttggagtc tactgactca  23100
aacatttata aagtgtccta gaaaggcctg actcccctac aaggctgtgt gatccttcaa  23160
actcacatat gtgagccaat aaaaccttga gactctagtc ttatggccac cttgctcctt  23220
cctgctcttc gtgctcatgt aacaagactt ccactgcgtc tgatgagatt gctctgggta  23280
gagtcggagt ttgatcactg gaacccacgt aaaggttgtc atctgacttc cacacgtgtt  23340
gagtggagca atactaaaat gaaaatttaa aagagcagtt gctgttcatg gggatcttaa  23400
aatacaggta gaggaccaaa tttagcatct ggcttgttgg tacgacactg agttcttaca  23460
tcagtcagga ataggagtgc tcctaggaac ttcagcaata aaaatgacta agagggtaga  23520
gaagcgactc tacagttaaa ggacccagat taggttccca gcaaccatag caactccagc  23580
cccaagggac ctgacaccct gtgcaggaac cactgagagt actcagacat gcatgcaagc  23640
aaaatgttca cacacataaa actaattaaa cttttaaaca aaagctcaaa gagcttaaag  23700
```

gtcaaagttt ctg 23713

<210> SEQ ID NO 14
<211> LENGTH: 2848
<212> TYPE: DNA
<213> ORGANISM: M. musculus

<400> SEQUENCE: 14
ggtggattgc agtgacagcc gcctgtggag cagcccgggc agcggaggag aattctgcat 60
agagaaccac caacccagaa ccatggaagt ccatgaattg ttccggtatt ttcgaatgcc 120
agagctgatt gacattcggc agtacgtgcg cacccttcca accaacaccc tcatggggtt 180
tggggctttt gcagcgctca ccaccttctg gtatgccacc aggcctaagg ccctgaagcc 240
accatgtgac ctctccatgc agtcagtgga aatagcgggt accactgatg gtattcgaag 300
atcagcagtc cttgaagatg acaagctctt ggtgtactac tacgacgatg tcagaaccat 360
gtacgatggc ttccagaggg ggattcaggt gtcaaataat ggtccttgtt taggttctcg 420
gaagccaaac cagccctatg agtggatttc ctacaaagag gtggcagaac tggctgagtg 480
cataggctcc gggctgatcc agaaggggtt caagccttgc tccgagcagt tcatcggcct 540
cttctctcaa aacagacccg agtgggtgat cgtcgagcaa ggatgcttct cttactcaat 600
ggtggtcgtc ccgctctatg acacccttgg agctgacgcc atcacctaca tagtgaacaa 660
agctgaactc tctgtgattt ttgctgacaa gccagaaaaa gccaaactct tattagaagg 720
tgtagaaaac aagttaacac catgccttaa aatcatagtc atcatggact cctacggcag 780
tgatctggtg gaacgaggca agaagtgtgg ggtggaaatc atcagcctca aagctctgga 840
ggaccttgga agagtgaaca gagtgaagcc caagcctcca gaacccgaag atcttgcgat 900
aatttgtttc acaagtggaa ctacaggcaa ccccaaagga gcaatgatca ctcaccaaaa 960
cattataaac gactgctcag gttttataaa agcaacagag agtgcattca tcgcttccac 1020
agatgatgtg ctgatatctt tcttgcctct cgcccatatg tttgagaccg ttgtagagtg 1080
tgtaatgctg tgtcatggag ctaagatagg atttttccaa ggagatatca ggctgcttat 1140
ggacgacctc aaggtgcttc agcccaccat cttccctgtg gttcccaggc tgctgaaccg 1200
gatgttcgac agaatttttg gacaagcaaa cacttccttg aagcgatggc tgttggactt 1260
tgcctccaaa aggaaagagg cggagcttcg cagtggcatc gtcagaaaca acagcctgtg 1320
ggataaactc atcttccaca agatacagtc gagcctgggt gggaaagtcc ggctgatgat 1380
cacaggagca gccccggtgt ctgccacagt gctgacgttt ctgaggacag cgctcggctg 1440
ccagttctat gaaggctacg gacagaccga gtgcactgct ggttgctgcc tgagcttgcc 1500
cggagactgg acggcaggcc atgttggagc ccccatgcct tgcaattatg taaagcttgt 1560
ggatgtggaa gaaatgaatt acctggcatc caagggcgag ggtgaggtgt gtgtgaaagg 1620
ggcaaatgtg ttcaaaggct acttgaaaga cccagcaaga acagctgaag ccctggataa 1680
agatggctgg ttacacacgg gggacattgg aaaatggctg ccaaatggca ccttgaagat 1740
tatcgacagg aaaaagcaca tatttaaact agcccaagga gagtacatag caccagaaaa 1800
gattgaaaat atctacctgc ggagtgaagc cgtggcccag gtgtttgtcc acggagaaag 1860
cttgcaggcc tttctcatag cagttgtggt acccgacgtt gagagcctac cgtcctgggc 1920
acagaagaga ggcttacaag ggtccttcga agaactgtgc aggaacaagg atatcaataa 1980
agctatcctg gacgacttgt tgaaacttgg gaaggaagcc ggtctgaagc catttgaaca 2040
ggtcaaaggc attgctgtgc acccggaatt attttctatt gacaacggcc ttctgactcc 2100
aacactgaag gcgaagaggc cagagctacg gaactatttc aggtcgcaga tagatgaact 2160
gtacgccacc atcaagatct aacgtgagga aggatactta gaagaaatgg cgcatctcca 2220
caatcctcct cgtaccaatg gccttcgagt tggtaacttt gcctgcagcg agtgtgggaa 2280
aggaaatgcc ctgccgccgg acttgtccac ggggtcttac catagggata gtcgagggca 2340
cggaacactg ccttacttac agtcacctgt gttgcagccc atgatcccgg ggacacacaa 2400
tttccaaaac gagccttaaa cattgtaaag gggaacccat aaaagtgcta agttatttaa 2460
gacttcttca accaataagg tggatgctac aagttctgtc tcctgttttt ctaactgagg 2520
ggttaggact tattctttct gatatgtctg ctgcttgctg cgcgttttgc agctgtctgc 2580
tgctctgaag agcaccgtac actggaggaa agctgtccct ttaagaacaa ctgtccaggc 2640
tgaagaaagt cacagtggac cagaggtttt ccttttgaac ccctcctccc ccttgcccct 2700
ttccctcacc acctcacata cagtacactc acatgacctt tctggtttgt aagggttcca 2760
cacggtccct gtttgcgcct gctggaacat gaggttttca gtaaactaaa gagcagaccc 2820
tcttcagaac atgtgggtgt ccagtctc 2848

<210> SEQ ID NO 15
<211> LENGTH: 2034
<212> TYPE: DNA
<213> ORGANISM: H. sapiens

<400> SEQUENCE: 15
ggatctggca gcgccgcgaa gacgagcggt caccggcgcc cgacccgagc gcgcccagag 60
gacggcgggg agccaagccg acccccgagc agcgccgcgc gggccctgag gctcaaaggg 120
gcagcttcag gggaggacac cccactggcc aggacgcccc aggctctgct gctctgccac 180
tcagctgccc tcggaggagc gtacacacac accaggactg cattgcccca gtgtgcagcc 240
cctgccagat gtgggaggca gctagctgcc cagaggcatg ccccccctgcc agccacagcg 300 acccctgctg ctgttgctgc tgctgctggc ctgccagcca caggtcccct ccgctcaggt 360
gatggacttc ctgtttgaga agtggaagct ctacggtgac cagtgtcacc acaacctgag 420
cctgctgccc cctcccacgg agctggtgtg caacagaacc ttcgacaagt attcctgctg 480
gccggacacc cccgccaata ccacggccaa catctcctgc ccctggtacc tgccttggca 540
ccacaaagtg caacaccgct tcgtgttcaa gagatgcggg cccgacggtc agtgggtgcg 600
tggaccccgg gggcagcctt ggcgtgatgc ctcccagtgc cagatggatg gcgaggagat 660
tgaggtccag aaggaggtgg ccaagatgta cagcagcttc caggtgatgt acacagtggg 720
ctacagcctg tccctggggg ccctgctcct cgccttggcc atcctggggg gcctcagcaa 780
gctgcactgc acccgcaatg ccatccacgc gaatctgttt gcgtccttcg tgctgaaagc 840
cagctccgtg ctggtcattg atgggctgct caggacccgc tacagccaga aaattggcga 900
cgacctcagt gtcagcacct ggctcagtga tggagcggtg gctggctgcc gtgtggccgc 960
ggtgttcatg caatatggca tcgtggccaa ctactgctgg ctgctggtgg agggcctgta 1020
cctgcacaac ctgctgggcc tggccaccct ccccgagagg agcttcttca gcctctacct 1080
gggcatcggc tggggtgccc ccatgctgtt cgtcgtcccc tgggcagtgg tcaagtgtct 1140
gttcgagaac gtccagtgct ggaccagcaa tgacaacatg ggcttctggt ggatcctgcg 1200
gttccccgtc ttcctggcca tcctgatcaa cttcttcatc ttcgtccgca tcgttcagct 1260
gctcgtggcc aagctgcggg cacggcagat gcaccacaca gactacaagt tccggctggc 1320
caagtccacg ctgaccctca tccctctgct gggcgtccac gaagtggtct ttgccttcgt 1380
gacggacgag cacgcccagg gcaccctgcg ctccgccaag ctcttcttcg acctcttcct 1440
cagctccttc cagggcctgc tggtggctgt cctctactgc ttcctcaaca aggaggtgca 1500
gtcggagctg cggcggcgtt ggcaccgctg gcgcctgggc aaagtgctat gggaggagcg 1560
gaacaccagc aaccacaggg cctcatcttc gcccggccac ggccctccca gcaaggagct 1620
gcagtttggg aggggtggtg gcagccagga ttcatctgcg gagacccccct tggctggtgg 1680 cctccctaga ttggctgaga gccccttctg aaccctgctg ggaccccagc tagggctgga 1740
ctctggcacc cagaggcgtc gctggacaac ccagaactgg acgcccagct gaggctgggg 1800
gcgggggagc caacagcagc ccccacctac cccccacccc cagtgtggct gtctgcgaga 1860
ttgggcctcc tctccctgca cctgccttgt ccctggtgca gaggtgagca gaggagtcca 1920
gggcgggagt gggggctgtg ccgtgaactg cgtgccagtg tccccacgta tgtcggcacg 1980
tcccatgtgc atggaaatgt cctccaacaa taaagagctc aagtggtcac cgtg 2034

<210> SEQ ID NO 16
<211> LENGTH: 1944
<212> TYPE: DNA
<213> ORGANISM: M. musculus

<400> SEQUENCE: 16
cagggtctcc cttgcaacct gaggagaggt gcacacactc tgaggaccta ggtgtgcaac 60
ctctgccaga tgtggggcgt ggctacccag aggcatgccc ctcacccagc tccactgtcc 120
ccacctgctg ctgctgctgt tggtgctgtc atgtctgcca gaggcaccct ctgcccaggt 180
aatggacttt ttgtttgaga agtggaagct ctatagtgac caatgtcacc acaacctaag 240
cctgctgccc ccacctactg agctggtctg taacagaacc ttcgacaact actcctgctg 300
gcctgacacc cctcccaaca ccactgccaa catttcctgc ccctggtacc taccttggtg 360
ccacaaagtg cagcaccgcc tagtgttcaa gaggtgtggg cccgatgggc agtgggttcg 420
agggccacgg gggcagccgt ggcgcaacgc ctcccaatgt cagttggatg atgaagagat 480
cgaggtccag aagggggtgg ccaagatgta tagcagccag caggtgatgt acaccgtggg 540
ctacagtctg tccctggggg ccttgctcct tgcgctggtc atcctgctgg gcctcaggaa 600
gctgcactgc acccgaaact acatccatgg gaacctgttt gcgtcctttg tgctcaaggc 660
tggctctgtg ttggtcatcg attggctgct gaagacacgg tacagccaga agattggcga 720
tgacctcagt gtgagcgtct ggctcagtga cggggcgatg gccggctgca gagtggccac 780
agtgatcatg cagtacggca tcatacccaa ctattgctgg ttgctggtag agggcgtgta 840
cctgtacagc ctgctgagcc ttgccacctt ctctgagagg agcttctttt ccctctacct 900
gggcattggc tggggtgcgc ccctgctgtt tgtcatcccc tgggtggtgg tcaagtgtct 960
gtttgagaat gttcagtgct ggaccagcaa tgacaacatg ggattctggt ggatcctgcg 1020
tattcctgtc ttcctggcct tactgatcaa ttttttcatc tttgtccaca tcattcaact 1080
tcttgtggcc aagctgcgtg cccatcagat gcactatgct gattacaagt tccggctggc 1140
caggtccacg ctgaccctca tccctctgct gggggtccac gaggtggtct ttgcctttgt 1200
gactgacgag catgcccaag gcaccctgcg ctccaccaag ctctttttttg acctgttcct 1260 cagctccttc cagggtctgc tggtggctgt tctctactgt ttcctcaaca aggaggtgca 1320
ggcagagctg atgcggcgtt ggaggcaatg gcaagaaggc aaagctcttc aggaggaaag 1380

-continued gttggccagc agccatggca gccacatggc cccagcaggg ccttgtcatg gtgatccctg 1440
tgagaaactt cagcttatga gtgcaggcag cagcagtggg actggctgtg tgccctctat 1500
ggagacctcg ctggccagta gtctcccaag gttggctgac agccccacct gaatctccac 1560
ttggagccta ggcaggttgt gttcaagaaa gggcctcaga ggacaaccca gagccagatg 1620
cccggccaag gttgaagagc caaagcagca agacagcagc ttgtactgtg cacactcccc 1680
taacctgtcc tagcctggca caggccacag tgacagagta ggggttggat atgatggaga 1740
agccatgtta tctatgaact ctgagtgttc ccatgtgtgt tgacatggtc cctgtaccca 1800
gatatgtcct tcagtaaaaa gctcgagtgg agctgctgca cagctcgtgg acagcaggct 1860
tgaagccccc agggacgggg tttgggaggc cggggatgag cagcacactc agcaggtgga 1920
gcgctagtgc aacccaggaa agaa 1944

<210> SEQ ID NO 17
<211> LENGTH: 3172
<212> TYPE: DNA
<213> ORGANISM: M. musculus

<400> SEQUENCE: 17
ctgagaagga aacttggagt gggacttgaa tgcgtgggtc ttcagaagga gaaccgctaa 60
gcatcccgat ttcccagaac aagaaggaca agtccaaaga cagtaaacaa agataggagt 120
tcacccttga atacctggaa ggaagaagga agagggtggg cccgcctctg gaatagaggg 180
ctcaggagat tggactccta gatccaggaa gaaggccaaa agacctggtc agtgggtttc 240
taattctgaa gaggagctag tcagggtctg ctcagtctga gggcttcgac tcccagctgc 300
tagaaagagg atgaggatgc agccgcaggc ttctagaaga caaggagata aattcctagg 360
tgtgagagag aagataatag gaaggcccct gcgtctccag gaggattggg acagacctga 420
ggaaggagag ggctcggctt tggactcctg catctcagca aggacggtcc taggtttgaa 480
tacttggttg gcctagggaa agagaggaag ggcatggact cctgggcctg acagagcaaa 540
gggtaaccac agaccttccc atcttctcac agcctcagcg ttctcacaca gcatggattt 600
acgcacgatg acacagtcgc tggtgacact cgcagaagac aatatggcct tcttctcaag 660
ccagggccca ggagagacag cacggcggct gtctaatgtc tttgcaggtg ttcgggaaca 720
ggcactgggg ctggaaccaa ccctaggcca actgttgggt gtggcacacc attttgacct 780
ggacacagag acaccagcca acggataccg tagtttggtg cacacagccc gatgctgcct 840
ggcacaccta ctacacaaat cccgctatgt ggcttctaac cgcaaaagta tcttcttccg 900
tgccagccac aacctagcag agctggaggc ctacctggcc gccctcaccc agctccgtgc 960
tatggcctac tatgcccagc gcctgctgac catcaaccga ccaggagtgc tcttcttcga 1020
gggtgatgaa ggactcaccg ctgacttcct gcaagagtat gtcacgctac acaaaggctg 1080
cttctacggc cgctgcctgg gcttccagtt cacacctgcc atccggccgt tcctgcagac 1140
tctctccatc gggctggtgt ccttcgggga gcactacaaa cgcaacgaga caggcctcag 1200
tgtgaccgcc agttccctct ttaccggtgg ccgattcgcc atagacccag agttgcgtgg 1260
ggctgaattt gaacgcatca tacagaacct ggatgtgcac ttctggaaag ccttctggaa 1320
catcactgag attgaggtgc tgtcgtctct ggccaacatg gcatcaacca ctgtgagggt 1380
aagccgcctg ctcagcttgc cacctgaggc ctttgagatg ccactcacct ctgatcccag 1440
gctcacagtt accatctcac ctcccttggc acacacggga ccagctcctg tgctagccag 1500
gctcatctcc tatgacctac gggaaggaca ggacagcaag gtactcaaca gcctggcaaa 1560

-continued atctgagggc ccacgcctgg acgtgcgccc acggcctcac caagcacccc gttcacgggc 1620
cctggttgtt cacatccacg gaggcggctt tgtggcacag acctctaaat cccacgagcc 1680
ctacctcaag aactgggccc aggagctagg agtccctatc ttctccatcg actactccct 1740
ggcccccgag gctccctttc cccgagcgct ggaggagtgt ttttttgcct actgctgggc 1800
tgtcaagcac tgtgacctgc ttggttcaac tggagagcgg atatgccttg caggggacag 1860
tgcaggtggg aatctctgca tcactgtgtc ccttcgggca gcagcctatg gagtgagggt 1920
gccagatggc atcatggcag cctacccagt taccaccctg cagtcctctg cttctccctc 1980
tcgtctgctg agcctcatgg accctcttct accactgagc gtactctcta agtgtgtcag 2040
tgcctattca gggacagagg cagaggacca ttttgactca gaccagaagg cactaggcgt 2100
gatggggctg gtgcagagag acacttcgct gttcctcaga gacctccgac tgggtgcctc 2160
ctcatggctc aactccttcc cggaactaag tggacgcaag ccccaaaaga ccacatcgcc 2220
cacagcagag tctgtgcgcc ccacggagtc tatgcgcagg agtgtgtctg aggcagccct 2280
ggcccagcct gagggcttac tgggcacaga taccttgaag aagctgacaa taaaggactt 2340
gagcaactca gagccttcag acagccccga gatgtcacag tcaatggaga cacttggccc 2400
ctccacaccc tctgatgtca actttttctt gcggcctggg aattcccagg aagaggctga 2460
agccaaagat gaagtgagac ccatggacgg agtcccccgc gtgcgcgctg ctttccctga 2520
ggggtttcac ccccggcgct caagccaagg tgtcctccac atgcccctct acacgtcacc 2580
catagtcaag aacccttca tgtctcctct gctggcccct gacagcatgc tgaagacctt 2640
gccgcctgtg caccttgtgg cttgcgctct ggaccccatg ctagatgact cggtcatgtt 2700
cgcgcggcga ctgcgcgacc tgggccagcc ggtgacgctg aaagtggtag aagatctgcc 2760
gcatggcttc ctgagcctgg cggcactgtg tcgcgagacc cggcaggcca cggagttctg 2820
cgtgcagcgc atccggctga tcctcacccc gcctgctgca ccactgaact gagctgggga 2880
cggcgggggg cggcactaaa agacctcttg ctcccatctg cgcgggcttc cgttatgagt 2940
gcgctccgag atgggctcca ggccccctca gtcgggctgg gcgggcggga gtgggctgtg 3000
cttaacttga gacagtaagt ggggcgggac aggggccaaa agctgaacct gggggaggga 3060
cacacacaca cctgtcactg agacagctgg atctgcactc taccactgcc ttctgctgct 3120
gtgaccgacc cggctagtcg gttttgcctt tttgtaaata aaagttattt aa 3172

<210> SEQ ID NO 18
<211> LENGTH: 1350
<212> TYPE: DNA
<213> ORGANISM: M. musculus

<400> SEQUENCE: 18
ggatgagaca gaaggataga gaggaggaga gagagagaga gaagagaagc aaccagaaat 60
aggcagccaa taaaaaggag ccgcacttat ctgaagcctc aaggggcctg agccaggtcc 120
ctgtttgatg gcagttatga aaaattacct cctcccgatc ctggtgctct ccctggccta 180
ctactactat tctacaaatg aagagttcag accagaaatg ctccagggaa agaaagtgat 240
tgtcactggg gccagcaaag ggattggaag agaaatggca tatcatctgt caaaaatggg 300
agcccatgtg gtattgactg ccaggtcgga ggaaggtctc cagaaggtag tgtctcgctg 360
ccttgaactc ggagcagcct ctgctcacta cattgctggc actatggaag acatgacatt 420
tgcggagcaa tttattgtca aggcgggaaa gctcatgggc ggactggaca tgcttattct 480

```
aaaccacatc actcagacct cgctgtctct cttccatgac gacatccact ctgtgcgaag    540
agtcatggag gtcaacttcc tcagctacgt ggtcatgagc acagccgcct tgcccatgct    600
gaagcagagc aatggcagca ttgccgtcat ctcctccttg gctgggaaaa tgacccagcc    660
tatgattgct ccctactctg caagcaagtt tgctctggat gggttctttt ccaccattag    720
aacagaactc tacataacca aggtcaacgt gtccatcact ctctgtgtcc ttggcctcat    780
agacacagaa acagctatga aggaaatctc tgggataatt gacgccctag cttctcccaa    840
ggaggagtgc gccctggaga tcatcaaagg cacagctcta cgcaaaagcg aggtgtacta    900
tgacaaattg cctttgactc caatcctgct tgggaaccca ggaaggaaga tcatggaatt    960
tttttcatta cgatattata ataaggacat gtttgtaagt aactaggaac tcctgagccc   1020
tggtgagtgg tcttagaaca gtcctgcctc atacttcagt aagccctacc cacaaaagta   1080
tctttccaga gatacacaaa ttttggggta cacctcatca tgagaaattc ttgcaacact   1140
tgcacagtga aaatgtaatt gtaataaatg tcacaaacca ctttgggcct gcagttgtga   1200
acttgattgt aactatggat ataaacacat agtggttgta tcggctttac ctcacactga   1260
atgaaacaat gataactaat gtaacattaa atataataaa ggtaatatca acttcgtaaa   1320
tgcaaaaaaa aaaaaaaaaa aaaaaaaaaa                                    1350
```

```
<210> SEQ ID NO 19
<211> LENGTH: 1418
<212> TYPE: DNA
<213> ORGANISM: H. sapiens

<400> SEQUENCE: 19

cattaattgc ttgccatcat gagcagaagc aagcgtgaca acaattttta tagtgtagag     60
attggagatt ctacattcac agtcctgaaa cgatatcaga atttaaaacc tataggctca    120
ggagctcaag gaatagtatg cgcagcttat gatgccattc ttgaaagaaa tgttgcaatc    180
aagaagctaa gccgaccatt tcagaatcag actcatgcca agcgggccta cagagagcta    240
gttcttatga aatgtgttaa tcacaaaaat ataattggcc ttttgaatgt tttcacacca    300
cagaaatccc tagaagaatt tcaagatgtt tacatagtca tggagctcat ggatgcaaat    360
ctttgccaag tgattcagat ggagctagat catgaaagaa tgtcctacct tctctatcag    420
atgctgtgtg gaatcaagca ccttcattct gctggaatta ttcatcggga cttaaagccc    480
agtaatatag tagtaaaatc tgattgcact ttgaagattc ttgacttcgg tctggccagg    540
actgcaggaa cgagttttat gatgacgcct tatgtagtga ctcgctacta cagagcaccc    600
gaggtcatcc ttggcatggg ctacaaggaa aacgtggatt tatggtctgt ggggtgcatt    660
atgggagaaa tggtttgcca caaaatcctc tttccaggaa gggactatat tgatcagtgg    720
aataaagtta ttgaacagct tggaacacca tgtcctgaat tcatgaagaa actgcaacca    780
acagtaagga cttacgttga aaacagacct aaatatgctg gatatagctt tgagaaactc    840
ttccctgatg tccttttccc agctgactca gaacacaaca aacttaaagc cagtcaggca    900
agggatttgt tatccaaaat gctggtaata gatgcatcta aaaggatctc tgtagatgaa    960
gctctccaac acccgtacat caatgtctgg tatgatcctt ctgaagcaga agctccacca   1020
ccaaagatcc ctgacaagca gttagatgaa agggaacaca caatagaaga gtggaaagaa   1080
ttgatatata aggaagttat ggacttggag gagagaacca agaatggagt tatacggggg   1140
cagccctctc ctttagcaca ggtgcagcag tgatcaatgg ctctcagcat ccatcatcat   1200
cgtcgtctgt caatgatgtg tcttcaatgt caacagatcc gactttggcc tctgatacag   1260
```

acagcagtct agaagcagca gctgggcctc tgggctgctg tagatgacta cttgggccat 1320
cggggggtgg gagggatggg gagtcggtta gtcattgata gaactacttt gaaaacaatt 1380
cagtggtctt atttttgggt gatttttcaa aaaatgta 1418

<210> SEQ ID NO 20
<211> LENGTH: 2181
<212> TYPE: DNA
<213> ORGANISM: H. sapiens

<400> SEQUENCE: 20
agagagccga gctctggagc ctcagcgagc ggaggaggag gcgcagggcc gacggccgag 60
tactgcggtg agagccagcg ggccagcgcc agcctcaaca gccgccagaa gtacacgagg 120
aaccggcggc ggcgtgtgcg tgtaggcccg tgtgcgggcg gcggcgcggg aggagcgcgg 180
agcggcagcc ggctggggcg ggtggcatca tggacgagaa ggtgttcacc aaggagctgg 240
accagtggat cgagcagctg aacgagtgca agcagctgtc cgagtcccag gtcaagagcc 300
tctgcgagaa ggctaaagaa atcctgacaa aagaatccaa cgtgcaagag gttcgatgtc 360
cagttactgt ctgtggagat gtgcatgggc aatttcatga tctcatggaa ctgtttagaa 420
ttggtggcaa atcaccagat acaaattact tgtttatggg agattatgtt gacagaggat 480
attattcagt tgaaacagtt acactgcttg tagctcttaa ggttcgttac cgtgaacgca 540
tcaccattct tcgagggaat catgagagca gacagatcac acaagtttat ggtttctatg 600
atgaatgttt aagaaaatat ggaaatgcaa atgtttggaa atattttaca gatctttttg 660
actatcttcc tctcactgcc ttggtggatg ggcagatctt ctgtctacat ggtggtctct 720
cgccatctat agatacactg gatcatatca gagcacttga tcgcctacaa gaagttcccc 780
atgagggtcc aatgtgtgac ttgctgtggt cagatccaga tgaccgtggt ggttggggta 840
tatctcctcg aggagctggt tacacctttg ggcaagatat ttctgagaca tttaatcatg 900
ccaatggcct cacgttggtg tctagagctc accagctagt gatggaggga tataactggt 960
gccatgaccg gaatgtagta acgattttca gtgctccaaa ctattgttat cgttgtggta 1020
accaagctgc aatcatggaa cttgacgata ctctaaaata ctctttcttg cagtttgacc 1080
cagcacctcg tagaggcgag ccacatgtta ctcgtcgtac cccagactac ttcctgtaat 1140
gaaattttaa acttgtacag tattgccatg aaccatatat cgacctaatg gaaatgggaa 1200
gagcaacagt aactccaaag tgtcagaaaa tagttaacat tcaaaaaact tgttttcaca 1260
tggaccaaaa gatgtgccat ataaaaatac aaagcctctt gtcatcaaca gccgtgacca 1320
ctttagaatg aaccagttca ttgcatgctg aagcgacatt gttggtcaag aaaccagttt 1380
ctggcatagc gctatttgta gttacttttg ctttctctga gagactgcag ataataagat 1440
gtaaacatta acacctcgtg aatacaattt aacttccatt tagctatagc tttactcagc 1500
atgactgtag ataaggatag cagcaaacaa tcattggagc ttaatgaaca tttttaaaaa 1560
taattaccaa ggcctccctt ctacttgtga gttttgaaat tgttcttttt attttcaggg 1620
ataccgttta atttaattat atgatttgtc tgcactcagt ttattcccta ctcaaatctc 1680
agccccatgt tgttctttgt tattgtcaga acctggtgag ttgttttgaa cagaactgtt 1740
ttttcccctt cctgtaagac gatgtgactg cacaagagca ctgcagtgtt tttcataata 1800
aacttgtgaa ctaagaactg agaaggtcaa attttaattg tatcaatggg caagactggt 1860
gctgtttatt aaaaaagtta aatcaattga gtaaatttta gaatttgtag acttgtaggt 1920
aaaataaaaa tcaagggcac tacataacct ctctggtaac tccttgacat tcttcagatt 1980
aacttcagga tttatttgta tttcacatat tacaatttgt cacattgttg gtgtgcactt 2040
tgtgggttct tcctgcatat taacttgttt gtaagaaagg aaatctgtgc tgcttcagta 2100
agacttaatt gtaaaaccat ataacttgag atttaagtct ttgggttgtg ttttaataaa 2160
acagcatgtt ttcaggtaga g 2181

<210> SEQ ID NO 21
<211> LENGTH: 3160
<212> TYPE: DNA
<213> ORGANISM: H. sapiens

<400> SEQUENCE: 21
cctcccctcg cccggcgcgg tcccgtccgc ctctcgctcg cctcccgcct cccctcggtc 60
ttccgaggcg cccgggctcc cggcgcggcg gcggaggggg cgggcaggcc ggcgggcggt 120
gatgtggcag gactctttat gcgctgcggc aggatacgcg ctcggcgctg ggacgcgact 180
gcgctcagtt ctctcctctc ggaagctgca gccatgatgg aagtttgaga gttgagccgc 240
tgtgaggcga ggccgggctc aggcgaggga gatgagagac ggcggcggcc gcggcccgga 300
gcccctctca gcgcctgtga gcagccgcgg gggcagcgcc ctcggggagc cggccggcct 360
gcggcggcgg cagcggcggc gtttctcgcc tcctcttcgt cttttctaac cgtgcagcct 420
cttcctcggc ttctcctgaa agggaaggtg gaagccgtgg gctcgggcgg gagccggctg 480
aggcgcggcg gcggcggcgg cggcacctcc cgctcctgga gcggggggga gaagcggcgg 540
cggcggcggc cgcggcggct gcagctccag ggaggggggtc tgagtcgcct gtcaccattt 600
ccagggctgg gaacgccgga gagttggtct ctccccttct actgcctcca acacggcggc 660
ggcggcggcg gcacatccag ggacccgggc cggttttaaa cctcccgtcc gccgccgccg 720 cacccccccgt ggcccgggct ccggaggccg ccggcggagg cagccgttcg gaggattatt 780
cgtcttctcc ccattccgct gccgccgctg ccaggcctct ggctgctgag gagaagcagg 840
cccagtcgct gcaaccatcc agcagccgcc gcagcagcca ttacccggct gcggtccaga 900
gccaagcggc ggcagagcga ggggcatcag ctaccgccaa gtccagagcc atttccatcc 960
tgcagaagaa gccccgccac cagcagcttc tgccatctct ctcctccttt ttcttcagcc 1020
acaggctccc agacatgaca gccatcatca aagagatcgt tagcagaaac aaaaggagat 1080
atcaagagga tggattcgac ttagacttga cctatattta tccaaacatt attgctatgg 1140
gatttcctgc agaaagactt gaaggcgtat acaggaacaa tattgatgat gtagtaaggt 1200
ttttggattc aaagcataaa aaccattaca agatatacaa tctttgtgct gaaagacatt 1260
atgacaccgc caaatttaat tgcagagttg cacaatatcc ttttgaagac cataacccac 1320
cacagctaga acttatcaaa cccttttgtg aagatcttga ccaatggcta agtgaagatg 1380
acaatcatgt tgcagcaatt cactgtaaag ctggaaaggg acgaactggt gtaatgatat 1440
gtgcatattt attacatcgg ggcaaatttt taaaggcaca agaggcccta gatttctatg 1500
gggaagtaag gaccagagac aaaaagggag taactattcc cagtcagagg cgctatgtgt 1560
attattatag ctacctgtta aagaatcatc tggattatag accagtggca ctgttgtttc 1620
acaagatgat gtttgaaact attccaatgt tcagtggcgg aacttgcaat cctcagtttg 1680
tggtctgcca gctaaaggtg aagatatatt cctccaattc aggacccaca cgacgggaag 1740
acaagttcat gtactttgag ttccctcagc cgttacctgt gtgtggtgat atcaaagtag 1800
agttcttcca caaacagaac aagatgctaa aaaaggacaa aatgtttcac ttttgggtaa 1860

```
atacattctt cataccagga ccagaggaaa cctcagaaaa agtagaaaat ggaagtctat   1920
gtgatcaaga aatcgatagc atttgcagta tagagcgtgc agataatgac aaggaatatc   1980
tagtacttac tttaacaaaa aatgatcttg acaaagcaaa taaagacaaa gccaaccgat   2040
acttttctcc aaattttaag gtgaagctgt acttcacaaa aacagtagag gagccgtcaa   2100
atccagaggc tagcagttca acttctgtaa caccagatgt tagtgacaat gaacctgatc   2160
attatagata ttctgacacc actgactctg atccagagaa tgaacctttt gatgaagatc   2220
agcatacaca aattacaaaa gtctgaattt tttttatca agagggataa aacaccatga   2280
aaataaactt gaataaactg aaaatggacc tttttttttt taatggcaat aggacattgt   2340
gtcagattac cagttatagg aacaattctc ttttcctgac caatcttgtt ttaccctata   2400
catccacagg gttttgacac ttgttgtcca gttgaaaaaa ggttgtgtag ctgtgtcatg   2460
tatatacctt tttgtgtcaa aaggacattt aaaattcaat taggattaat aaagatggca   2520
ctttcccgtt ttattccagt tttataaaaa gtggagacag actgatgtgt atacgtagga   2580
attttttcct tttgtgttct gtcaccaact gaagtggcta aagagctttg tgatatactg   2640
gttcacatcc taccccttg cacttgtggc aacagataag tttgcagttg gctaagagag   2700
gtttccgaaa ggttttgcta ccattctaat gcatgtattc gggttagggc aatggagggg   2760
aatgctcaga aaggaaataa ttttatgctg gactctggac catataccat ctccagctat   2820
ttacacacac ctttctttag catgctacag ttattaatct ggacattcga ggaattggcc   2880
gctgtcactg cttgttgttt gcgcattttt ttttaaagca tattggtgct agaaaaggca   2940
gctaaaggaa gtgaatctgt attggggtac aggaatgaac cttctgcaac atcttaagat   3000
ccacaaatga agggatataa aaataatgtc ataggtaaga aacacagcaa caatgactta   3060
accatataaa tgtggaggct atcaacaaag aatgggcttg aaacattata aaaattgaca   3120
atgatttatt aaatatgttt tctcaattgt aaaaaaaaaa                         3160

<210> SEQ ID NO 22
<211> LENGTH: 4127
<212> TYPE: DNA
<213> ORGANISM: R. norvegicus

<400> SEQUENCE: 22

agccgctgct ggggaggttg gggctgaggt ggtggcgggc gacgggcctc gagacgcgga     60
gcgacgcggc ctagcgcggc ggacggccga gggaactcgg gcagtcgtcc cgtcccgcca    120
tggaaatgga gaaggaattc gagcagatcg ataaggctgg gaactgggcg gctatttacc    180
aggatattcg acatgaagcc agtgacttcc catgcagaat agcgaaactt cctaagaaca    240
aaaaccggaa caggtaccga gatgtcagcc cttttgacca cagtcggatt aaattgcatc    300
aggaagataa tgactatatc aatgccagct tgataaaaat ggaggaagcc cagaggagct    360
atatcctcac ccagggccct ttaccaaaca cgtgcgggca cttctgggag atggtgtggg    420
agcagaagag caggggcgtg gtcatgctca accgcatcat ggagaaaggc tcgttaaaat    480
gtgcccagta ttggccacag aaagaagaaa aagagatggt cttcgatgac accaatttga    540
agctgacact gatctctgaa gatgtcaagt catattacac agtacggcag ttggagttgg    600
agaacctggc tacccaggag gctcgagaga tcctgcattt ccactacacc acctggcctg    660
actttggagt ccctgagtca cctgcctctt tcctcaattt cctattcaaa gtccgagagt    720
caggctcact cagcccagag cacggcccca ttgtggtcca ctgcagtgct ggcattggca    780
```

-continued

```
ggtcagggac cttctgcctg gctgacacct gcctcttact gatggacaag aggaaagacc    840
cgtcctctgt ggacatcaag aaagtgctgt tggagatgcg caggttccgc atggggctca    900
tccagacggc cgaccaactg cgcttctcct acctggctgt gatcgagggt gcaaagttca    960
tcatgggcga ctcgtcagtg caggatcagt ggaaggagct ttcccatgaa gacctggagc   1020
ctccccctga gcacgtgccc ccacctcccc ggccacccaa acgcacattg gagcctcaca   1080
atggcaagtg caaggagctc ttctccaacc accagtgggt gagcgaggag agctgtgagg   1140
atgaggacat cctggccaga gaggaaagca gagcccccctc aattgctgtg cacagcatga   1200
gcagtatgag tcaagacact gaagttagga aacggatggt gggtggaggt cttcaaagtg   1260
ctcaggcatc tgtccccact gaggaagagc tgtccccaac cgaggaggaa caaaaggcac   1320
acaggccagt tcactggaag cccttcctgg tcaacgtgtg catggccacg gccctggcga   1380
ctggcgcgta cctctgttac cgggtatgtt ttcactgaca gactgctgtg aggcatgagc   1440
gtggtgggcg ctgccactgc ccaggttagg atttggtctg cggcgtctaa cctggtgtag   1500
aagaaacaac agcttacaag cctgtggtgg aactggaagg gccagcccca ggaggggcat   1560
ctgtgcactg ggctttgaag gagcccctgg tcccaagaac agagtctaat ctcagggcct   1620
taacctgttc aggagaagta gaggaaatgc caaatactct tcttgctctc acctcactcc   1680
tcccctttct ctggttcgtt tgtttttgga aaaaaaaaaa aaagaattac aacacattgt   1740
tgtttttaac atttataaag gcaggttttt gttattttta gagaaaacaa aagatgctag   1800
gcactggtga gattctcttg tgccctttgg catgtgatca gattcacgat ttacgtttat   1860
ttccggggga gggtcccacc tgtcaggact gtaaagttcc tgctggcttg gtcagccccc   1920
ccaccccccc accccgagct tgcaggtgcc ctgctgtgag gagagcagca gcagaggctg   1980
cccctggaca gaagcccagc tctgcttccc tcaggtgtcc ctgcgtttcc atcctccttc   2040
tttgtgaccg ccatcttgca gatgacccag tcctcagcac ccccacccctg cagatgggtt   2100
tctccgaggg cctgcctcag ggtcatcaga ggttggctgc cagcttagag ctggggcttc   2160
catttgattg gaaagtcatt actattctat gtagaagcca ctccactgag gtgtaaagca   2220
agactcataa aggaggagcc ttggtgtcat ggaagtcact ccgcgcgcag gacctgtaac   2280
aacctctgaa acactcagtc ctgctgcagt gacgtccttg aaggcatcag acagatgatt   2340
tgcagactgc caagacttgt cctgagccgt gatttttaga gtctggactc atgaaacacc   2400
gccgagcgct tactgtgcag cctctgatgc tggttggctg aggctgcggg gaggtggaca   2460
ctgtgggtgc atccagtgca gttgcttttg tgcagttggg tccagcagca cagcccgcac   2520
tccagcctca gctgcaggcc acagtggcca tggaggccgc cagagcgagc tggggtggat   2580
gcttgttcac ttggagcagc cttcccagga cgtgcagctc ccttcctgct ttgtccttct   2640
gcttccttcc ctggagtagc aagcccacga gcaatcgtga ggggtgtgag ggagctgcag   2700
aggcatcaga gtggcctgca gcggcgtgag gccccttccc ctccgacacc cccctccaga   2760
ggagccgctc cactgttatt tattcacttt gcccacagac acccctgagt gagcacaccc   2820
tgaaactgac cgtgtaaggt gtcagcctgc acccaggacc gtcaggtgca gcaccgggtc   2880
agtcctaggg ttgaggtagg actgacacag ccactgtgtg gctggtgctg gggcaggggc   2940
aggagctgag ggtcttagaa gcaatcttca ggaacagaca acagtggtga catgtaaagt   3000
ccctgtggct actgatgaca tgtgtaggat gaaggctggc ctttctccca tgactttcta   3060
gatcccgttc cccgtctgct ttccctgtga gttagaaaac acacaggctc ctgtcctggt   3120
ggtgccgtgt gcttgacatg ggaaacttag atgcctgctc actggcgggc acctcggcat   3180
```

```
cgccaccact cagagtgaga gcagtgctgt ccagtgccga ggccgcctga ctcccggcag   3240
gactcttcag gctctggcct gccccagcac accccgctgg atctcagaca ttccacaccc   3300
acacctcatt ccctggacac ttgggcaagc aggcccgccc ttccacctct ggggtcagcc   3360
cctccattcc gagttcacac tgctctggag caggccagga ccggaagcaa ggcagctggt   3420
gaggagcacc ctcctgggaa cagtgtaggt gacagtcctg agagtcagct tgctagcgct   3480
gctggcacca gtcaccttgc tcagaagtgt gtggctcttg aggctgaaga gactgatgat   3540
ggtgctcatg actcttctgt gaggggaact tgaccttcac attgggtggc ttttttaaa    3600
ataagcgaag gcagctggaa ctccagtctg cctcttgcca gcacttcaca ttttgccttt   3660
cacccagaga agccagcaca gagccactgg ggaaggcgat ggccttgcct gcacaggctg   3720
aggagatggc tcagccggcg tccaggctgt gtctggagca gggggtgcac agcagcctca   3780
caggtggggg cctcagagca ggcgctgccc tgtcccctgc cccgctggag gcagcaaagc   3840
tgctgcatgc cttaagtcaa tacttactca gcagggcgct ctcgttctct ctctctctct   3900
ctctctctct ctctctctct ctctctctct ctctaaatgg ccatagaata aaccatttta   3960
caaaaataaa agccaacaac aaagtgctct ggaatagcac ctttgcagga gcgggggggtg  4020
tctcagggtc ttctgtgacc tcaccgaact gtccgactgc accgtttcca acttgtgtct   4080
cactaatggg tctgcattag ttgcaacaat aaatgttttt aaagaac                 4127
```

<210> SEQ ID NO 23
<211> LENGTH: 2194
<212> TYPE: DNA
<213> ORGANISM: M. musculus

<400> SEQUENCE: 23

```
gacaggctgg tcctcaccat ggccacctgc tggcaggcac tatgggccta tcgctcctac     60
ctgattgtgc tatgtctgcc cattttcctg ttgcctctgc cactcattgt ccaaactaag    120
gaagcctact gtgcttactc catcatcctc atggcgctgc tgtggtgtac agaggccctg    180
cccttggctg tcaccgccct cttccccatc atcctcttcc ctttgatggg tatcatggaa    240
gcctccaagg tctgcttaga gtacttcaag gacaccaaca tattgttcgt cgggggtctg    300
atggtggcca tcgccgtgga gcactggaac ctgcacaagc gcattgccct tggagtgctc    360
cttatcatag gagtgcggcc cgccctgctg cttctgggct tcatgttggt cacagccttc    420
ctctccatgt ggatcagcaa cacagccacc acagccatga tgctgcccat cgggtatgca    480
gtcctggagc agctgcaggg ctcacaaaag gatgtggagg aaggcaatag taacccttcc    540
tttgagctcc aggaagcaag tccccagaag gaggagacca agcttgataa cggtcaggct    600
gtatctgttt cttcggagcc aagagctcag aagaccaaag agcatcaccg cttcagccag    660
ggcctgagtc tctgcatctg ctactcagcc agcattgggg gcattgccac cctgacgggt    720
accacaccca acctggtgct ccaaggccag gtcaactcga tcttccctga aaatagtaac    780
gtggtgaact ttgcttcatg gtttggtttt gccttcccca ccatggtgat cttgctgcta    840
ctggcttggc tatggctaca ggtcctcttc ctgggtgtca acttccggaa gaactttggc    900
tttggggaag gggaagagga acggaagcag gctgccttcc aggtcatcaa gacccagcac    960
aggctgctgg gccccatgag ttttgcagag aaggctgtca ctttcctgtt tgtcctgcta   1020
gtggtgctct ggttcacgag ggagccgggc ttcttcccag gctggggtga cacagctttc   1080
gccaataaaa aagggcaaag catggtatca gatgggacag tggccatctt tatcagcctg   1140
```

```
attatgttca tcataccctc caagattcca ggactaaccg aggacccaaa aaaaccaggg   1200
aagctgaagg ctcctcctgc catcctcacc tggaagacag tgaacgataa gatgccctgg   1260
aatatcctga tcttgctggg tgggggcttt gccctggcca aaggcagtga ggaatcaggt   1320
ttgtctaagt ggctgggaga caaactgacc ccgctgcagc acgtaccgcc atcagccacc   1380
gtgctcatcc tctctctatt ggtggccatc ttcactgagt gcaccagcaa cgtggccacc   1440
actacactat ttctgcccat cctggcctcc atggcacagg ccatctgcct tcacccgctt   1500
tatgtcatgc ttccctgcac cctggctgcc tccctagctt tcatgctacc cgtggccact   1560
ccacccaacg ccattgtctt ctcttttgga ggcctcaaag tgtctgatat ggcccgtgca   1620
ggattcctgc tcaatatcat cggagtgctg actatcacat tatccataaa cagctggagt   1680
atccctatct tcaagctgga cacatttccc acctgggcct actccaacac aagccagtgc   1740
cttctcaatc cgcctaattc cactgtacca ggccactaga ctatggtaca acctagctct   1800
gctaggggaa aagccgctgg tgccactcct cggagccagg agagggcgct ccaaactcca   1860
agtcccggga cagaggtgca gaatcggctg gcgcatgcga aatcatgtat tcgtgtgttt   1920
gcctacatcc tgtatgtgtg ctctccggtg aagaggaaga tgctcgtgtc tccgtgtggt   1980
gtgcgtggac gcttgcgtgt ggtgtggcct gagggctcct cagtagttgt atgcatggca   2040
accgcgcccg ccctctgact cccagctagg cctccagatc tctttgccct gtatttattg   2100
aaactctggg caggaggccc ctgggagcag gaactccaaa gttcattaaa ggctttttca   2160
gtagagtccg ggtgtgtttc ccggtgttca gaag                               2194
```

<210> SEQ ID NO 24
<211> LENGTH: 5383
<212> TYPE: DNA
<213> ORGANISM: M. musculus

<400> SEQUENCE: 24

```
tcccagtctc ccggggtttc tctttgctgg tgcctggaag tgggggtaga tgtgaagtta     60
gaccgagttg tgagtggcgg tagccagtgt cttcctcact tctttcgatg cgatttcccc    120
agtgaaccat ttgctaagcg ccagaccaaa gtcctaggct tgcacacaat tcctacttgg    180
aatcacgtta tcctgctctt aaagaaaagt cacccatcag cccacagcaa agaggataag    240
gagaaaaaga ggggaggaga gacggagaag ctagaggcag agggaacagc agattgcgcc    300
tagccaatgg aaaaggcagg acaaggtggc accaaattct ctttggccaa tgacaagacg    360
ggcttcacag gaggcacatt agcatttatc cccaggcagg gggttggagc agcgcgccct    420
gttgatgcct tcagcatccc ggcgcctcca aggtctactc tggaatctac ttggctttct    480
ttcccgttct tggtcccgcc ctctctctct ccctccctcc ctccctccct tcctccctcc    540
ctccctccct ccctccctcc ctcacctcca cgcctggctt ccttggctag ctatctctgc    600
gctctttacc ctttgctggc agccgataaa agggggctga ggaaatactg aacacggtca    660
tcccatcgcc tgctctaccc tttaaaatcc cagcccagga gatctgtgca cagccagacc    720
gggctgaaca cccatcccga gagtcaggag ggcaggtttc caagcgcagt tccgccactc    780
gcctacacca acgggctccg gaaccgaagt ccacgctcga tctcagcact gggaaagtga    840
ggcgagcaac tgactatcat catgccggcc cacatgctcc aagagatctc cagttcttac    900
acgaccacca ccaccatcac tgcacctccc tccggaaatg aacgagagaa ggtgaagaca    960
gtgcccctcc acctggaaga agacatccgt cctgaaatga aagaagatat tcacgacccc   1020
acctatcagg atgaggaggg acccccgccc aagctggagt acgtctggag gaacatcatt   1080
```

-continued ctcatggtcc tgctgcactt gggaggcctg tacgggatca tactggttcc ctcctgcaag 1140
ctctacactg ccctcttcgg gattttctac tacatgacca gcgctctggg catcacagcc 1200
ggggctcatc gcctctggag ccacagaact tacaaggctc ggctgcccct gcggatcttc 1260
ctaatcattg ccaacaccat ggcgttccaa aatgacgtgt acgactgggc ccgagatcac 1320
cgcgcccacc acaagttctc agaaacacac gccgaccctc acaattcccg ccgtggcttc 1380
ttcttctctc acgtgggttg gctgcttgtg cgcaaacacc cggctgtcaa agagaagggc 1440
ggaaaactgg acatgtctga cctgaaagcc gagaagctgg tgatgttcca gaggaggtac 1500
tacaagcccg gcctcctgct gatgtgcttc atcctgccca cgctggtgcc ctggtactgc 1560
tggggcgaga cttttgtaaa cagcctgttc gttagcacct tcttgcgata cactctggtg 1620
ctcaacgcca cctggctggt gaacagtgcc gcgcatctct atggatatcg cccctacgac 1680
aagaacattc aatcccggga gaatatcctg gtttccctgg gtgccgtggg cgagggcttc 1740
cacaactacc accacacctt cccctttcgac tactctgcca gtgagtaccg ctggcacatc 1800
aacttcacca cgttcttcat cgactgcatg gctgccctgg gcctggctta cgaccggaag 1860
aaagtttcta aggctactgt cttagccagg attaagagaa ctggagacgg gagtcacaag 1920
agtagctgag ctttgggctt ctgagttcct gtttcaaacg ttttctggca gagatttaat 1980
attctgttga ttaactaaca actggatatt gctatcgggg tgttaatgat gcatttaacc 2040
tattccggta cagtattctt ataaaatgag aaagctttga tcacgttttg aggtaataaa 2100
tattttattt agctaggatt aaccatgcca caagacatta tatatttcta agcacacatg 2160
ataaatgcat atacaatttt gcacaacagc tttaaataat aacaataaat ttgaacattc 2220
tatacagaga ggatcaaagc caaggaacat gctgttttga tgctagggtg agcatggtgc 2280
tcagtccctg tttgtttgca tggtgtccag ctttgtttct tctctgtcat caccaccttc 2340
aggcaaatag ttgaccaacc actggcctgt gtctgtccac cctccaaagc ccaggccacc 2400
tttctgtttt ctgaaatact gatccttcct cctgaataca tccctccttg ttcctagctt 2460
caagactgct gcctcaaata gggatagagc aagtccccgc tgcaggttgt gctagatggg 2520
atggagaaat tatcttcatt tgatacagag caagtagatt gtctcgagag aaaagttagc 2580
atgcgtggta tgatttgtaa gtaaagatgg aagagagaga gagagagaga gagagagaga 2640
gagagagaga gagagaggta gccatatcta acagcctact taccaaagac cccaggcctc 2700
tctgcttggc atgcctcctt tctgtccatc ctctgaaccc cagagattag tgagatttga 2760
ataattaaat cattttcaga gtgaaggggg ttaatgcagg gtctgtgcta ggggagggtt 2820
ttagcttttg gtaactgaag atttttttcat ggaaaaagtc ttcgtgttca atgtgcctag 2880
aactgataac taaacagctg acatttgtcg ggacagata tggtgtgaaa ctatgaaaat 2940
ataagcaaaa tcttcacttg gaacatgaaa ctatttcact tagaaaataa tcgaaggacc 3000
cgaggtgttg cctgggttgc cagtttcttt cgtggctggg caggaactag tgaggttgag 3060
gggcagtgtc tgtaagtagc tgctaagagg tgcatttcca gatgaagccc ttggggaaca 3120
tctgccaggg atccgcatgg tgttggctcc atccattgct ttagtttcct ccttggattg 3180
tgtagaaact tggcttccca tggttttgaa ccttccatgc cttctttgct ttgtggccac 3240
ccagcctgcc tagtgctgcc taggaagctc ttacccacct gatttcttct gacatttctt 3300
tctttggcct ttttttcttt ctccggacat gcagctagtt gcctgagtgt atcaagagca 3360
cccaggactt gctgctgtcc aggcctgttc ctcccccagt atccgtgggt gtggaagagc 3420

```
tgtgtagctt caggaagcag agccaggtgc cacctttctg tggcttccag atcctcccta   3480
cctccaactc atgtgcctct gtcacagtga tttcaggaaa gcttggtaga ccctctagca   3540
acatctcggt tcagaaagtc tctctggttt gtgagttaac agctcagcta agtgctgttt   3600
tgtctcagtg agttaaccac tgaatgcgag ggttggttgt tgatctgtct cggtgtgtgt   3660
cggagtagac agcatatgca cttctccctg tgcgctttgc aaggtaatgt ggctttggct   3720
gatccatgca ggcaggtagt ggtacagtgc tgctgaaagg aagaagttcc ccattttatc   3780
tgttaaaaca ccagagacat gggcaagtgc taatggacct cacttcagga agagggtctg   3840
cttcctgaag ccagtgtgtg atgaaaagtg actgagacct gatatctaag gtgagacctg   3900
atacctaaca ctctgtcaca cagtccaggg ccaacagtgc tataggaaag tctagaagaa   3960
aacatcacat cagtatttta gaaccatcaa ccatctcttg tccctatagc ccaatccaga   4020
ggcctggttt ttagaactgg ctgtgtaagg tgccaaacac tcagttcact tgtagaatca   4080
gagccttttt tccccccctat gttaattgaa cacgcgctct gagctgtttt gttgaagtag   4140
aaaatctcat agaaaaatca ctgtagatct actgacctat agccctctgg aaatgccttt   4200
gagatggttt tacttttcta ggtcatagat gcctgattat aaagatgaac aataaaatca   4260
gctttctttc tttctcttct gatcttattc cccagatctg attcaggcca tgttccaaag   4320
caaggctaca ttgaggtcct ggtgtcttta agtaaaggac atctttcaga tcctctcaaa   4380
gaaggattta taacagtttc cagatgaatg tactaatagc tttgggtgcc ttatctcttt   4440
cctaatctgt agtgcctgtg agctcagtct cactccttcc cttagcccgg agacccctta   4500
gatcgagtgg gaatagtcaa gaggctggct ggagagtcat cagtacattg gtttgcagaa   4560
atcttttaca ggctacattt tggaattttt tttttttag taagtgatca aatttggtgg   4620
gaagtaattc gagtgtattc gattgtattg tcgtcctcgt tatcattgtc aaacatgtta   4680
tagacggcag ttggcactgg ggctgctaat ctctgggtgt agtctctgaa actgtagctc   4740
cagtgaggtg gtgtgaaagg ttagcaaagc caccatctgc tggtgctcca gccaaggtgc   4800
ctcttagcca ctgaattgct atgttatcct ttctcttgta acaaacccac cccagagata   4860
aagcctttaa tcaacccaag aaactcctgg gctaagtatc tgacagtctc acatctcaac   4920
agtgtgaatt aagtgtccat agcatcagct caggaggaca ctctgggaga gtgctgacaa   4980
aaaagggtta ttaatactga cctactactt caagggcagt tctgaggtga ttagagcttt   5040
ttttaaaaac caagtatttg gggatcctca gcagaggtat tcatacagac tcccaaagaa   5100
ctatatatgt tcctgagacc atcgtttagt ctacattgct cttcccagag actgacagat   5160
atgaccagtc aaagtgcaag actacctacc cactgccatg aaaaccattg caggaaacct   5220
ttcccttcct gaatgagatt tttttttcc ctttttatgt ggggtaatta tttgtgaccc   5280
aagtgtaatt tggatgattt ccattaatat caactcttga agcctacttg tactgattga   5340
gattgtattt gttcctaata aaagtggatc tggttgtact gtc                     5383
```

<210> SEQ ID NO 25
<211> LENGTH: 14796
<212> TYPE: DNA
<213> ORGANISM: H. sapiens

<400> SEQUENCE: 25

```
tctagacatg cggatatatt caagctgggc acagcacagc agccccaccc caggcagctt     60
gaaatcagag ctggggtcca aagggaccac accccgaggg actgtgtggg ggtcggggca    120
cacaggccac tgcttccccc cgtctttctc agccattcct gaagtcagcc tcactctgct    180
```

-continued

```
tctcagggat ttcaaatgtg cagagactct ggcacttttg tagaagcccc ttctggtcct    240
aacttacacc tggatgctgt ggggctgcag ctgctgctcg ggctcgggag gatgctgggg    300
gcccggtgcc catgagcttt tgaagctcct ggaactcggt tttgagggtg ttcaggtcca    360
ggtggacacc tgggctgtcc ttgtccatgc atttgatgac attgtgtgca gaagtgaaaa    420
ggagttaggc cgggcatgct ggcttatgcc tgtaatccca gcactttggg aggctgaggc    480
gggtggatca cgaggtcagg agttcaatac cagcctggcc aagatggtga aaccccgtct    540
ctactaaaaa tacaaaaaaa ttagccgggc atggtggcgg gcgcatgtaa tcccagctac    600
tgggggggct gaggcagaga attgctggaa cccaggagat ggaggttgca gtgagccaag    660
attgtgccac tgcactgcac tccagcctgg cgacagagca agactctgtc tcaaaaaaaa    720
aaaaaaaaag tgaaaaggag ttgttccttt cctccctcct gagggcaggc aactgctgcg    780
gttgccagtg gaggtggtgc gtccttggtc tgtgcctggg ggccacccca gcagaggcca    840
tggtggtgcc agggcccggt tagcgagcca atcagcagga cccaggggcg acctgccaaa    900
gtcaactgga tttgataact gcagcgaagt taagtttcct gattttgatg attgtgttgt    960
ggttgtgtaa gagaatgaag tatttcgggg tagtatggta atgccttcaa cttacaaacg   1020
gttcaggtaa accacccata tacatacata tacatgcatg tgatatatac acatacaggg   1080
atgtgtgtgt gttcacatat atgaggggag agagactagg ggagagaaag taggttgggg   1140
agagggagag agaaaggaaa acaggagaca gagagagagc ggggagtaga gagagggaag   1200
gggtaagaga gggagaggag gagagaaagg gaggaagaag cagagagtga atgttaaagg   1260
aaacaggcaa aacataaaca gaaaatctgg gtgaagggta tatgagtatt ctttgtacta   1320
ttcttgcaat tatcttttat ttaaattgac atcgggccgg gcgcagtggc tcacatctgt   1380
aatcccagca ctttgggagg ccgaggcagg cagatcactt gaggtcagga gtttgagacc   1440
agcctggcaa acatggtgaa accccatctc tactaaaaat acaaaaatta gcctggtgtg   1500
gtggtgcatg cctttaatct cagctactcg ggaggctgag gcaggagaat cgcttgaacc   1560
cgtggcgggg aggaggttgc agtgagctga gatcatgcca ctgcactcca gcctgggcga   1620
tagagcgaga ctcagtttca aataaataaa taaacatcaa aataaaaagt tactgtatta   1680
aagaatgggg gcggggtggg aggggtgggg agaggttgca aaaataaata aataaataaa   1740
taaaccccaa aatgaaaaag acagtggagg caccaggcct gcgtggggct ggagggctaa   1800
taaggccagg cctcttatct ctggccatag aaccagagaa gtgagtggat gtgatgccca   1860
gctccagaag tgactccaga acaccctgtt ccaaagcaga ggacacactg attttttttt   1920
taataggctg caggacttac tgttggtggg acgccctgct ttgcgaaggg aaaggaggag   1980
tttgccctga gcacaggccc ccaccctcca ctgggctttc cccagctccc ttgtcttctt   2040
atcacggtag tggcccagtc cctggcccct gactccagaa ggtggccctc ctggaaaccc   2100
aggtcgtgca gtcaacgatg tactcgccgg gacagcgatg tctgctgcac tccatccctc   2160
ccctgttcat ttgtccttca tgcccgtctg gagtagatgc tttttgcaga ggtggcaccc   2220
tgtaaagctc tcctgtctga cttttttttt ttttttagac tgagttttgc tcttgttgcc   2280
taggctggag tgcaatggca caatctcagc tcactgcacc ctctgcctcc cgggttcaag   2340
cgattctcct gcctcagcct cccgagtagt tgggattaca ggcatgcacc accacgccca   2400
gctaattttt gtatttttag tagagacaag gtttcaccgt gatggccagg ctggtcttga   2460
actccaggac tcaagtgatg ctcctgccta ggcctctcaa agtgttggga ttacaggcgt   2520
```

-continued

```
gagccactgc acccggcctg cacgcgttct ttgaaagcag tcgagggggc gctaggtgtg   2580
ggcagggacg agctggcgcg gcgtcgctgg gtgcaccgcg accacgggca gagccacgcg   2640
gcgggaggac tacaactccc ggcacacccc gcgccgcccc gcctctactc ccagaaggcc   2700
gcggggggtg gaccgcctaa gagggcgtgc gctcccgaca tgccccgcgg cgcgccatta   2760
accgccagat ttgaatcgcg ggacccgttg gcagaggtgg cggcggcggc atgggtgccc   2820
cgacgttgcc ccctgcctgg cagccctttc tcaaggacca ccgcatctct acattcaaga   2880
actggccctt cttggagggc tgcgcctgca ccccggagcg ggtgagactg cccggcctcc   2940
tggggtcccc cacgcccgcc ttgccctgtc cctagcgagg ccactgtgac tgggcctcgg   3000
gggtacaagc cgccctcccc tccccgtcct gtccccagcg aggccactgt ggctgggccc   3060
cttgggtcca ggccggcctc ccctccctgc tttgtcccca tcgaggcctt tgtggctggg   3120
cctcggggtt ccgggctgcc acgtccactc acgagctgtg ctgtcccttg cagatggccg   3180
aggctggctt catccactgc cccactgaga acgagccaga cttggcccag tgtttcttct   3240
gcttcaagga gctggaaggc tgggagccag atgacgaccc catgtaagtc ttctctggcc   3300
agcctcgatg ggctttgttt tgaactgagt tgtcaaaaga tttgagttgc aaagacactt   3360
agtatgggag ggttgctttc caccctcatt gcttcttaaa cagctgttgt gaacggatac   3420
ctctctatat gctggtgcct tggtgatgct tacaacctaa ttaaatctca tttgaccaaa   3480
atgccttggg gtggacgtaa gatgcctgat gcctttcatg ttcaacagaa tacatcagca   3540
gaccctgttg ttgtgaactc ccaggaatgt ccaagtgctt tttttgagat tttttaaaaa   3600
acagtttaat tgaaatataa cctacacagc acaaaaatta ccctttgaaa gtgtgcactt   3660
cacactttcg gaggctgagg cgggcggatc acctgaggtc aggagttcaa gacctgcctg   3720
gccaacttgg cgaaaccccg tctctactaa aaatacaaaa attagccggg catggtagcg   3780
cacgcccgta atcccagcta ctcgggaggc taaggcagga gaatcgcttg aacctgggag   3840
gcggaggttg cagtgagccg agattgtgcc aatgcactcc agcctcggcg acagagcgag   3900
actccgtcat aaaaataaaa aattgaaaaa aaaaaaagaa agaaagcata tacttcagtg   3960
ttgttctgga tttttttctt caagatgcct agttaatgac aatgaaattc tgtactcgga   4020
tggtatctgt ctttccacac tgtaatgcca tattcttttc tcaccttttt ttctgtcgga   4080
ttcagttgct tccacagctt taattttttt cccctggaga atcaccccag ttgtttttct   4140
ttttggccag aagagagtag ctgttttttt tcttagtatg tttgctatgg tggttatact   4200
gcatccccgt aatcactggg aaaagatcag tggtattctt cttgaaaatg aataagtgtt   4260
atgatatttt cagattagag ttacaactgg ctgtcttttt ggactttgtg tggccatgtt   4320
ttcattgtaa tgcagttctg gtaacggtga tagtcagtta tacagggaga ctcccctagc   4380
agaaaatgag agtgtgagct agggggtccc ttggggaacc cggggcaata atgcccttct   4440
ctgcccttaa tccttacagt gggccgggca cggtggctta cgcctgtaat accagcactt   4500
tgggaggccg aggcgggcgg atcacgaggt caggagatcg agaccatctt ggctaatacg   4560
gtgaaacccc gtctccacta aaaatacaaa aaattagccg ggcgtggtgg tgggcgcctg   4620
tagtcccagc tactcgggag gctgaggcag gagaatggcg tgaacccagg aggcggagct   4680
tgcagtgagc cgagattgca ccactgcact ccagcctggg cgacagaatg agactccgtc   4740
tcaaaaaaaa aaaaaaaaga aaaaaatctt tacagtggat tacataacaa ttccagtgaa   4800
atgaaattac ttcaaacagt tccttgagaa tgttggaggg atttgacatg taattccttt   4860
ggacatatac catgtaacac ttttccaact aattgctaag gaagtccaga taaaatagat   4920
```

acattagcca cacagatgtg gggggagatg tccacaggga gagagaaggt gctaagaggt 4980
gccatatggg aatgtggctt gggcaaagca ctgatgccat caacttcaga cttgacgtct 5040
tactcctgag gcagagcagg gtgtgcctgt ggagggcgtg gggaggtggc ccgtggggag 5100
tggactgccg ctttaatccc ttcagctgcc tttccgctgt tgttttgatt tttctagaga 5160
ggaacataaa aagcattcgt ccggttgcgc tttcctttct gtcaagaagc agtttgaaga 5220
attaaccctt ggtgaatttt tgaaactgga cagagaaaga gccaagaaca aaattgtatg 5280
tattgggaat aagaactgct caaaccctgt tcaatgtctt tagcactaaa ctacctagtc 5340
cctcaaaggg actctgtgtt ttcctcagga agcatttttt tttttttct gagatagagt 5400 ttcactcttg ttgcccaggc tggagtgcaa tggtgcaatc ttggctcact gcaacctctg 5460
cctctcgggt tcaagtgatt ctcctgcctc agcctcccaa gtaactggga ttacagggaa 5520
gtgccaccac acccagctaa tttttgtatt tttagtagag atggggtttc accacattgc 5580
ccaggctggt cttgaactcc tgacctcgtg attcgcccac cttggcctcc caaagtgctg 5640
ggattacagg cgtgaaccac cacgcctggc tttttttttt ttgttctgag acacagtttc 5700
actctgttac ccaggctgga gtagggtggc ctgatctcgg atcactgcaa cctccgcctc 5760
ctgggctcaa gtgatttgcc tgcttcagcc tcccaagtag ccgagattac aggcatgtgc 5820
caccacaccc aggtaatttt tgtatttttg gtagagacga ggtttcacca tgttggccag 5880
gctggttttg aactcctgac ctcaggtgat ccacccgcct cagcctccca aagtgctgag 5940
attataggtg tgagccacca cacctggcct caggaagtat ttttattttt aaatttattt 6000
atttatttga gatggagtct tgctctgtcg cccaggctag agtgcagcga cgggatctcg 6060
gctcactgca agctccgccc cccaggttca agccattctc ctgcctcagc ctcccgagta 6120
gctgggacta caggcgcccg ccaccacacc cggctaattt ttttgtattt ttagtagaga 6180
cgggttttca ccgtgttagc caggagggtc ttgatctcct gacctcgtga tctgcctgcc 6240
tcggcctccc aaagtgctgg gattacaggt gtgagccacc acacccggct atttttattt 6300
ttttgagaca gggactcact ctgtcacctg ggctgcagtg cagtggtaca ccatagctca 6360
ctgcagcctc gaactcctga gctcaagtga tcctcccacc tcatcctcac aagtaattgg 6420
gactacaggt gcaccccacc atgcccacct aatttattta tttatttatt tatttatttt 6480
catagagatg agggttccct gtgttgtcca ggctggtctt gaactcctga gctcacggga 6540
tccttttgcc tgggcctccc aaagtgctga gattacaggc atgagccacc gtgcccagct 6600
aggaatcatt tttaaagccc ctaggatgtc tgtgtgattt taaagctcct ggagtgtggc 6660
cggtataagt atataccggt ataagtaaat cccacatttt gtgtcagtat ttactagaaa 6720
cttagtcatt tatctgaagt tgaaatgtaa ctgggcttta tttatttatt tatttattta 6780
tttattttta attttttttt ttgagacgag tctcactttg tcacccaggc tggagtgcag 6840
tggcacgatc tcggctcact gcaacctctg cctcccgggg tcaagcgatt ctcctgcctt 6900
agcctcccga gtagctggga ctacaggcac gcaccaccat gcctggctaa tttttgtatt 6960
tttagtagac ggggtttcac catgctggcc aagctggtct caaactcctg accttgtgat 7020
ctgcccgctt tagcctccca gagtgctggg attacaggca tgagccacca tgcgtggtct 7080
ttttaaaatt ttttgatttt tttttttttt gagacagagc cttgctctgt cgcccaggct 7140
ggagtgcagt ggcacgatct cagctcacta caagctccgc ctcccgggtt cacgccattc 7200
ttctgcctca gcctcctgag tagctgggac tacaggtgcc caccaccacg cctggctaat 7260

-continued

```
ttttttttggt atttttatta gagacaaggt ttcatcatgt tggccaggct ggtctcaaac 7320
tcctgacctc aagtgatctg cctgcctcgg cctcccaaag cgctgagatt acaggtgtga 7380
tctactgcgc caggcctggg cgtcatatat tcttatttgc taagtctggc agccccacac 7440
agaataagta ctgggggatt ccatatcctt gtagcaaagc cctgggtgga gagtcaggag 7500
atgttgtagt tctgtctctg ccacttgcag actttgagtt taagccagtc gtgctcatgc 7560
tttccttgct aaatagaggt tagacccct atcccatggt ttctcaggtt gcttttcagc 7620
ttgaaaattg tattcctttg tagagatcag cgtaaaataa ttctgtcctt atatgtggct 7680
ttattttaat ttgagacaga gtgtcactca gtcgcccagg ctggagtgtg gtggtgcgat 7740
cttggctcac tgcgacctcc acctcccagg ttcaagcgat tctcgtgcct caggctccca 7800
agtagctgag attataggtg tgtgccacca ggcccagcta acttttgtat ttttagtaga 7860
gacagggttt tgccatgttg gctaagctgg tctcgaactc ctggcctcaa gtgatctgcc 7920
cgccttggca tcccaaagtg ctgggattac aggtgtgaac caccacacct ggcctcaata 7980
tagtggcttt taagtgctaa ggactgagat tgtgttttgt caggaagagg ccagttgtgg 8040
gtgaagcatg ctgtgagaga gcttgtcacc tggttgaggt tgtgggagct gcagcgtggg 8100
aactggaaag tgggctgggg atcatctttt tccaggtcag ggtcagccca gcttttctgc 8160
agcgtgccat agaccatctc ttagccctcg tgggtcagag tctctgttgc atattgtctt 8220
ttgttgtttt tcacaacctt ttagaaacat aaaaagcatt cttagcccgt gggctggaca 8280
aaaaaaggcc atgacgggct gtatggattt ggcccagcag gcccttgctt gccaagccct 8340
gttttagaca aggagcagct tgtgtgcctg gaaccatcat gggcacaggg gaggagcaga 8400
gtggatgtgg aggtgtgagc tggaaaccag gtcccagagc gctgagaaag acagagggtt 8460
tttgcccttg caagtagagc aactgaaatc tgacaccatc cagttccaga aagccctgaa 8520
gtgctggtgg acgctgcggg gtgctccgct ctagggttac agggatgaag atgcagtctg 8580
gtagggggag tccactcacc tgttggaaga tgtgattaag aaaagtagac tttcagggcc 8640
gggcatggtg gctcacgcct gtaatcccag cactttggga ggccgaggcg ggtggatcac 8700
gaggtcagga gatcgagacc atcctggcta acatggtgaa accccgtctt tactaaaaat 8760
acaaaaaatt agctgggcgt ggtggcgggc gcctgtagtc ccagctactc gggaggctga 8820
ggcaggagaa tggcgtgaac ctgggaggtg gagcttgctg tgagccgaga tcgcgccact 8880
gcactccagc ctgggcgaca gagcgagact ccgtctcaaa aaaaaaaaaa aaagtaggct 8940
ttcatgatgt gtgagctgaa ggcgcagtag gcagaagtag aggcctcagt ccctgcagga 9000
gacccctcgg tctctatctc ctgatagtca gacccagcca cactggaaag aggggagaca 9060
ttacagcctg cgagaaaagt agggagattt aaaaactgct tggcttttat tttgaactgt 9120
tttttttgtt tgtttgtttt ccccaattca gaatacagaa tacttttatg gatttgtttt 9180
tattacttta attttgaaac aatataatct tttttttgtt gttttttttga gacagggtct 9240
tactctgtca cccaggctga gtgcagtggt gtgatcttgg ctcacctcag cctcgacccc 9300
ctgggctcaa atgattctcc cacctcagct tcccaagtag ctgggaccac aggtgcgtgt 9360
gttgcgctat acaaatcctg aagacaagga tgctgttgct ggtgatgctg gggattccca 9420
agatcccaga tttgatggca ggatgcccct gtctgctgcc ttgccagggt gccaggaggg 9480
cgctgctgtg gaagctgagg cccggccatc cagggcgatg cattgggcgc tgattcttgt 9540
tcctgctgct gcctcggtgc ttagcttttg aaacaatgaa ataaattaga accagtgtga 9600
aaatcgatca gggaataaat ttaatgtgga aataaactga acaacttagt tcttcataag 9660
```

-continued agtttacttg gtaaatactt gtgatgagga caaaacgaag cactagaagg agaggcgagt 9720
tgtagacctg ggtggcagga gtgttttgtt tgttttcttt ggcagggtct tgctctgttg 9780
ctcaggctgg agtacagtgg cacaatcaca gctcactata gcctcgacct cctggactca 9840
agcaatcctc ctgcctcagc ctcccagtag ctgggactac aggcgcatgc caccatgcct 9900
ggctaatttt aaattttttt ttttctcttt tttgagatgg aatctcactc tgtcgcccag 9960
gctggagtgc agtggcgtga tctcggctga cggcaagctc cgcctcccag gttcactcca 10020
ttcgcctgcc tcagcctccc aagtagctgg gactacaggc gctgggatta caaacccaaa 10080
cccaaagtgc tgggattaca ggcgtgagcc actgcacccg gcctgttttg tctttcaata 10140
gcaagagttg tgtttgcttc gcccctacct ttagtggaaa aatgtataaa atggagatat 10200
tgacctccac attggggtgg ttaaattata gcatgtatgc aaaggagctt cgctaattta 10260
aggctttttt gaaagagaag aaactgaata atccatgtgt gtatatatat tttaaaagcc 10320
atggtcatct ttccatatca gtaaagctga ggctccctgg gactgcagag ttgtccatca 10380
cagtccatta taagtgcgct gctgggccag gtgcagtggc ttgtgcctga atcccagcac 10440
tttgggaggc caaggcagga ggattcattg agcccaggag ttttgaggcg agcctgggca 10500
atgtggccag acctcatctc ttcaaaaaat acacaaaaaa ttagccaggc atggtggcac 10560
gtgcctgtag tctcagctac tcaggaggct gaggtgggag gatcactttg agccttgcag 10620
gtcaaagctg cagtaagcca tgatcttgcc actgcattcc agcctggatg acagagcgag 10680
accctgtctc taaaaaaaaa aaaaaccaaa cggtgcactg ttttcttttt tcttatcaat 10740
ttattatttt taaattaaat tttcttttaa taatttataa attataaatt tatattaaaa 10800
aatgacaaat ttttattact tatacatgag gtaaaactta ggatatataa agtacatatt 10860
gaaaagtaat tttttggctg gcacagtggc tcacacctgt aatcccagca ctttgggagg 10920
ccgtggcggg cagatcacat gagatcatga gttcgagacc aacctgacca acatggagag 10980
accccatctc tactaaaaat acaaaattag ccggggtggt ggcgcatgcc tgtaatccca 11040
gctactcggg aggctgaggc aggagaatct cttgaacccg ggaggcagag gttgcggtga 11100
gccaagatcg tgcctttgca caccagccta ggcaacaaga gcgaaagtcc gtctcaaaaa 11160
aaaagtaatt ttttttaagt taacctctgt cagcaaacaa atttaaccca ataaaggtct 11220
ttgtttttta atgtagtaga ggagttaggg tttataaaaa atatggtagg gaagggggtc 11280
cctggatttg ctaatgtgat tgtcatttgc cccttaggag agagctctgt tagcagaatg 11340
aaaaaattgg aagccagatt cagggaggga ctggaagcaa aagaatttct gttcgaggaa 11400
gagcctgatg tttgccaggg tctgtttaac tggacatgaa gaggaaggct ctggactttc 11460
ctccaggagt ttcaggagaa aggtagggca gtggttaaga gcagagctct gcctagacta 11520
gctggggtgc ctagactagc tggggtgccc agactagctg gggtgcctag actagctggg 11580
tactttgagt ggctccttca gcctggacct cggtttcctc acctgtatag tagagatatg 11640
ggagcaccca gcgcaggatc actgtgaaca taaatcagtt aatggaggaa gcaggtagag 11700
tggtgctggg tgcataccaa gcactccgtc agtgtttcct gttattcgat gattaggagg 11760
cagcttaaac tagagggagt tgagctgaat caggatgttt gtcccaggta gctgggaatc 11820
tgcctagccc agtgcccagt ttatttaggt gctctctcag tgttccctga ttgttttttc 11880
ctttgtcatc ttatctacag gatgtgactg ggaagctctg gtttcagtgt catgtgtcta 11940
ttctttattt ccaggcaaag gaaaccaaca ataagaagaa agaatttgag gaaactgcga 12000

-continued

```
agaaagtgcg ccgtgccatc gagcagctgg ctgccatgga ttgaggcctc tggccggagc  12060
tgcctggtcc cagagtggct gcaccacttc cagggtttat tccctggtgc caccagcctt  12120
cctgtgggcc ccttagcaat gtcttaggaa aggagatcaa cattttcaaa ttagatgttt  12180
caactgtgct cctgttttgt cttgaaagtg gcaccagagg tgcttctgcc tgtgcagcgg  12240
gtgctgctgg taacagtggc tgcttctctc tctctctctc ttttttgggg gctcattttt  12300
gctgttttga ttcccgggct taccaggtga gaagtgaggg aggaagaagg cagtgtccct  12360
tttgctagag ctgacagctt tgttcgcgtg ggcagagcct tccacagtga atgtgtctgg  12420
acctcatgtt gttgaggctg tcacagtcct gagtgtggac ttggcaggtg cctgttgaat  12480
ctgagctgca ggttccttat ctgtcacacc tgtgcctcct cagaggacag tttttttgtt  12540
gttgtgtttt tttgtttttt ttttttggta gatgcatgac ttgtgtgtga tgagagaatg  12600
gagacagagt ccctggctcc tctactgttt aacaacatgg ctttcttatt ttgtttgaat  12660
tgttaattca cagaatagca caaactacaa ttaaaactaa gcacaaagcc attctaagtc  12720
attggggaaa cggggtgaac ttcaggtgga tgaggagaca gaatagagtg ataggaagcg  12780
tctggcagat actccttttg ccactgctgt gtgattagac aggcccagtg agccgcgggg  12840
cacatgctgg ccgctcctcc ctcagaaaaa ggcagtggcc taaatccttt ttaaatgact  12900
tggctcgatg ctgtggggga ctggctgggc tgctgcaggc cgtgtgtctg tcagcccaac  12960
cttcacatct gtcacgttct ccacacgggg gagagacgca gtccgcccag gtccccgctt  13020
tctttggagg cagcagctcc cgcagggctg aagtctggcg taagatgatg gatttgattc  13080
gccctcctcc ctgtcataga gctgcagggt ggattgttac agcttcgctg gaaacctctg  13140
gaggtcatct cggctgttcc tgagaaataa aaagcctgtc atttcaaaca ctgctgtgga  13200
ccctactggg tttttaaaat attgtcagtt tttcatcgtc gtccctagcc tgccaacagc  13260
catctgccca gacagccgca gtgaggatga gcgtcctggc agagacgcag ttgtctctgg  13320
gcgcttgcca gagccacgaa ccccagacct gtttgtatca tccgggctcc ttccgggcag  13380
aaacaactga aaatgcactt cagacccact tatttatgcc acatctgagt cggcctgaga  13440
tagacttttc cctctaaact gggagaatat cacagtggtt tttgttagca gaaaatgcac  13500
tccagcctct gtactcatct aagctgctta tttttgatat ttgtgtcagt ctgtaaatgg  13560
atacttcact ttaataactg ttgcttagta attggctttg tagagaagct ggaaaaaaat  13620
ggttttgtct tcaactcctt tgcatgccag gcggtgatgt ggatctcggc ttctgtgagc  13680
ctgtgctgtg ggcagggctg agctggagcc gcccctctca gcccgcctgc cacggccttt  13740
ccttaaaggc catccttaaa accagaccct catggctgcc agcacctgaa agcttcctcg  13800
acatctgtta ataaagccgt aggcccttgt ctaagcgcaa ccgcctagac tttctttcag  13860
atacatgtcc acatgtccat ttttcaggtt ctctaagttg gagtggagtc tgggaagggt  13920
tgtgaatgag gcttctgggc tatgggtgag gttccaatgg caggttagag cccctcgggc  13980
caactgccat cctggaaagt agagacagca gtgcccgctg cccagaagag accagcaagc  14040
caaactggag cccccattgc aggctgtcgc catgtggaaa gagtaactca caattgccaa  14100
taaagtctca tgtggtttta tctacttttt ttttcttttt cttttttttt gagacaaggc  14160
cttgccctcc caggctggag tgcagtggaa tgaccacagc tcaccgcaac ctcaaattct  14220
tgcgttcaag tgaacctccc actttagcct cccaagtagc tgggactaca ggcgcacgcc  14280
atcacacccg gctaattgaa aaattttttt ttttgtttag atggaatctc actttgttgc  14340
ccaggctggt ctcaaactcc tgggctcaag tgatcatcct gcttcagcgt ccgacttgtt  14400
```

```
ggtattatag gcgtgagcca ctgggcctga cctagctacc atttttttaat gcagaaatga  14460

agacttgtag aaatgaaata acttgtccag gatagtcgaa taagtaactt ttagagctgg  14520

gatttgaacc caggcaatct ggctccagag ctgggccctc actgctgaag gacactgtca  14580

gcttgggagg gtggctatgg tcggctgtct gattctaggg agtgagggct gtctttaaag  14640

caccccattc cattttcaga cagctttgtc agaaaggctg tcatatggag ctgacacctg  14700

cctccccaag gcttccatag atcctctctg tacattgtaa ccttttattt tgaaatgaaa  14760

attcacagga agttgtaagg ctagtacagg ggatcc                            14796
```

<210> SEQ ID NO 26
<211> LENGTH: 515
<212> TYPE: DNA
<213> ORGANISM: M. musculus
<220> FEATURE:
<221> NAME/KEY: misc_feature
<222> LOCATION: 266
<223> OTHER INFORMATION: n = A,T,C or G

<400> SEQUENCE: 26

```
ttcggatcct tggctgggat taaaggtgtg agccaccacg cccggcttga aaaaacatgt     60

ttatatatat atatgtatat atataaaaaa tcaaggaagg aaaattccag tttgtagctc    120

agtaagtatt tgcttattac tattgaggcc ctaggttcaa ttcccagcaa tacaaaaata    180

ataactttcc ttttaatgat ttatcttgcc acgatggtga tgacactagc atctcaccct    240

ggacaggcaa gcctggccct ctggcnaccc cagccccttc gtgtctgttc atcattccag    300

gcaaaggaga ccaacaacaa gcaaaaagag tttgaagaga ctgcaaagac tacccgtcag    360

tcaattgagc agctggctgc ctaatgctga gcctttgctg agataacttg gacctgagtg    420

acatgccaca tctaagccac gcatcccagc ttttccagcc agggcctcct agcaggatct    480

tagagcagga gacagtggta ttttgaaact ggata                               515
```

<210> SEQ ID NO 27
<211> LENGTH: 955
<212> TYPE: DNA
<213> ORGANISM: M. musculus

<400> SEQUENCE: 27

```
ggcacgaggg ggccggggct ctcccggcat gctctgcggc gcgcctccgc ccgcgcgatt     60

tgaatcctgc gtttgagtcg tcttggcgga ggttgtggtg acgccatcat gggagctccg    120

gcgctgcccc agatctggca gctgtacctc aagaactacc gcatcgccac cttcaagaac    180

tggcccttcc tggaggactg cgcctgcacc ccagagcgaa tggcggaggc tggcttcatc    240

cactgcccta ccgagaacga gcctgatttg gcccagtgtt ttttctgctt taaggaattg    300

gaaggctggg aacccgatga caacccgata gaggagcata gaaagcactc ccctggctgc    360

gccttcctca ctgtcaagaa gcagatggaa gaactaaccg tcagtgaatt cttgaaactg    420

gacagacaga gagccaagaa caaaattgca aaggagacca acaacaagca aaaagagttt    480

gaagagactg caaagactac ccgtcagtca attgagcagc tggctgccta atgctgagcc    540

tttgctgaga taacttggac ctgagtgaca tgccacatct aagccacgca tcccagcttt    600

tccagccagg gcctcctagc aggatcttag agaaggagac agtggtattt tgaaactgga    660

tatcaaatat ttttggtttt gctttaaagt ggctacctct ctttggtttt gtggctttgc    720

tctattgtga cgtggactta agcaataagg aagtgatgaa gggacagtgt tctctgacag    780
```

gacctgtggg ggtcggggtg cctgtgcaag gtcttggttc tgattgtgat atttccatac 840
agggctgcta atgcagccca tgggtaagtg tggttatatg tgtttgtgct gataattttg 900
tcctgatgag ttttcctacc acggggtaac ggaataaaat cacttgaaaa agtgg 955

<210> SEQ ID NO 28
<211> LENGTH: 1435
<212> TYPE: DNA
<213> ORGANISM: H. sapiens

<400> SEQUENCE: 28
ctggcgggcg tgggaaccca ggccccgccg aggcggccag gaggtgagat ggcagctggg 60
caaaatgggc acgaagagtg ggtgggcagc gcatacctgt ttgtggagtc ctcgctggac 120
aaggtggtcc tgtcggatgc ctacgcgcac ccccagcaga aggtggcagt gtacagggct 180
ctgcaggctg ccttggcaga gagcggcggg agcccggacg tgctgcagat gctgaagatc 240
caccgcagcg acccgcagct gatcgtgcag ctgcgattct gcgggcggca gccctgtggc 300
cgcttcctcc gcgcctaccg cgagggggcg ctgcgcgccg cgctgcagag gagcctggcg 360
gccgcgctcg cccagcactc ggtgccgctg caactggagc tgcgcgccgg cgccgagcgg 420
ctggacgctt tgctggcgga cgaggagcgc tgtttgagtt gcatcctagc ccagcagccc 480
gaccggctcc gggatgaaga actggctgag ctggaggatg cgctgcgaaa tctgaagtgc 540
ggctcggggg cccggggtgg cgacggggag gtcgcttcgg ccccccttgca gcccccggtg 600 ccctctctgt cggaggtgaa gccgccgccg ccgccgccac ctgcccagac ttttctgttc 660
cagggtcagc ctgtagtgaa tcggccgctg agcctgaagg accaacagac gttcgcgcgc 720
tctgtgggtc tcaaatggcg caaggtgggg cgctcactgc agcgaggctg ccgggcgctg 780
cgggacccgg cgctggactc gctggcctac gagtacgagc gcgagggact gtacgagcag 840
gccttccagc tgctgcggcg cttcgtgcag gccgagggcc gccgcgccac gctgcagcgc 900
ctggtggagg cactcgagga gaacgagctc accagcctgg cagaggactt gctgggcctg 960
accgatccca atggcggcct ggcctagacc aggggtgcag ccagcttttg gagaacctgg 1020
atggccttag ggttccttct gcggctattg ctgaacccct gtccatccac gggaccctga 1080
aactccactt ggcctatctg ctggacctgc tggggcagag ttgattgcct tccccaggag 1140
ccagaccact gggggtgcat cattggggat tctgcctcag gtactttgat agagtgtggg 1200 gtgggggggga cttgctttgg agatcagcct caccttctcc catcccagaa gcggggctta 1260
cagccagccc ttacagtttc actcatgaag caccttgatc tttggtgtcc tggacttcat 1320
cctgggtgct gcagatactg cagtgaagta aaacaggaat caatcttgcc tgcccccagc 1380
tcacactcag cgtgggaccc cgaatgttaa gcaatgataa taaagtataa cacgg 1435

<210> SEQ ID NO 29
<211> LENGTH: 2977
<212> TYPE: DNA
<213> ORGANISM: H. sapiens

<400> SEQUENCE: 29
ccgaatgtga ccgcctcccg ctccctcacc cgccgcgggg aggaggagcg ggcgagaagc 60
tgccgccgaa cgacaggacg ttggggcggc ctggctccct caggtttaag aattgtttaa 120
gctgcatcaa tggagcacat acagggagct tggaagacga tcagcaatgg ttttggattc 180
aaagatgccg tgtttgatgg ctccagctgc atctctccta caatagttca gcagtttggc 240
tatcagcgcc gggcatcaga tgatggcaaa ctcacagatc cttctaagac aagcaacact 300

-continued

```
atccgtgttt tcttgccgaa caagcaaaga acagtggtca atgtgcgaaa tggaatgagc    360
ttgcatgact gccttatgaa agcactcaag gtgaggggcc tgcaaccaga gtgctgtgca    420
gtgttcagac ttctccacga acacaaaggt aaaaaagcac gcttagattg gaatactgat    480
gctgcgtctt tgattggaga agaacttcaa gtagatttcc tggatcatgt tcccctcaca    540
acacacaact ttgctcggaa gacgttcctg aagcttgcct tctgtgacat ctgtcagaaa    600
ttcctgctca atggatttcg atgtcagact tgtggctaca aatttcatga gcactgtagc    660
accaaagtac ctactatgtg tgtggactgg agtaacatca gacaactctt attgtttcca    720
aattccacta ttggtgatag tggagtccca gcactacctt ctttgactat gcgtcgtatg    780
cgagagtctg tttccaggat gcctgttagt tctcagcaca gatattctac acctcacgcc    840
ttcaccttta acacctccag tccctcatct gaaggttccc tctcccagag gcagaggtcg    900
acatccacac ctaatgtcca catggtcagc accacgctgc ctgtggacag caggatgatt    960
gaggatgcaa ttcgaagtca cagcgaatca gcctcacctt cagccctgtc cagtagcccc   1020
aacaatctga gcccaacagg ctggtcacag ccgaaaaccc ccgtgccagc acaaagagag   1080
cgggcaccag tatctgggac ccaggagaaa aacaaaatta ggcctcgtgg acagagagat   1140
tcaagctatt attgggaaat agaagccagt gaagtgatgc tgtccactcg gattgggtca   1200
ggctcttttg gaactgttta taagggtaaa tggcacggag atgttgcagt aaagatccta   1260
aaggttgtcg acccaacccc agagcaattc caggccttca ggaatgaggt ggctgttctg   1320
cgcaaaacac ggcatgtgaa cattctgctt ttcatggggt acatgacaaa ggacaacctg   1380
gcaattgtga cccagtggtg cgagggcagc agcctctaca aacacctgca tgtccaggag   1440
accaagtttc agatgttcca gctaattgac attgcccggc agacggctca gggaatggac   1500
tatttgcatg caaagaacat catccataga gacatgaaat ccaacaatat atttctccat   1560
gaaggcttaa cagtgaaaat tggagatttt ggtttggcaa cagtaaagtc acgctggagt   1620
ggttctcagc aggttgaaca acctactggc tctgtcctct ggatggcccc agaggtgatc   1680
cgaatgcagg ataacaaccc attcagtttc cagtcggatg tctactccta tggcatcgta   1740
ttgtatgaac tgatgacggg ggagcttcct tattctcaca tcaacaaccg agatcagatc   1800
atcttcatgg tgggccgagg atatgcctcc ccagatctta gtaagctata taagaactgc   1860
cccaaagcaa tgaagaggct ggtagctgac tgtgtgaaga aagtaaagga agagaggcct   1920
ctttttcccc agatcctgtc ttccattgag ctgctccaac actctctacc gaagatcaac   1980
cggagcgctt ccgagccatc cttgcatcgg gcagcccaca ctgaggatat caatgcttgc   2040
acgctgacca cgtccccgag gctgcctgtc ttctagttga ctttgcacct gtcttcaggc   2100
tgccagggga ggaggagaag ccagcaggca ccacttttct gctccctttc tccagaggca   2160
gaacacatgt tttcagagaa gctctgctaa ggaccttcta gactgctcac agggccttaa   2220
cttcatgttg ccttcttttc tatccctttg ggccctggga gaaggaagcc atttgcagtg   2280
ctggtgtgtc ctgctccctc cccacattcc ccatgctcaa ggcccagcct tctgtagatg   2340
cgcaagtgga tgttgatggt agtacaaaaa gcaggggccc agccccagct gttggctaca   2400
tgagtattta gaggaagtaa ggtagcaggc agtccagccc tgatgtggag acacatggga   2460
ttttggaaat cagcttctgg aggaatgcat gtcacaggcg ggactttctt cagagagtgg   2520
tgcagcgcca gacattttgc acataaggca ccaaacagcc caggactgcc gagactctgg   2580
ccgcccgaag gagcctgctt tggtactatg gaacttttct taggggacac gtcctccttt   2640
```

cacagcttct aaggtgtcca gtgcattggg atggttttcc aggcaaggca ctcggccaat 2700
ccgcatctca gccctctcag gagcagtctt ccatcatgct gaattttgtc ttccaggagc 2760
tgcccctatg gggcgggccg cagggccagc ctgtttctct aacaaacaaa caaacaaaca 2820
gccttgtttc tctagtcaca tcatgtgtat acaaggaagc caggaataca ggttttcttg 2880
atgatttggg ttttaatttt gtttttattg cacctgacaa aatacagtta tctgatggtc 2940
cctcaattat gttattttaa taaaataaat taaattt 2977

<210> SEQ ID NO 30
<211> LENGTH: 76698
<212> TYPE: DNA
<213> ORGANISM: H. sapiens
<220> FEATURE:
<221> NAME/KEY: misc_feature
<222> LOCATION: 15311-15410
<223> OTHER INFORMATION: n = A,T,C or G
<220> FEATURE:
<221> NAME/KEY: misc_feature
<222> LOCATION: 15414
<223> OTHER INFORMATION: n = A,T,C or G

<400> SEQUENCE: 30
cgcggaattc cagacctcag gtgatccacc cacctcggcc tcccaaggtg ctgggattac 60
aggcgtgagc caccatgcct ggccgattgt tccaatgtat atgcacccca gtaatttatg 120
agagagccca ggtcttaatt tttaattgtt ttccaagatg gctgtactag gctttcctgc 180
aaatgacacc atagcatata ttgtggttgc caccccagca accaggccct caccctccat 240
catgggctgc ccattatggc atgaggggga ttgacactgg gccaggtatc ttttgcccct 300
ctaggattcc ccttcatcat tctctccatg ccgtctgccc caggaaggcg atctccaacc 360
tcagagacct gcttgctgtt tcccaaactt atgctaatca cacctctatg cctttgccca 420
tactgttccc acctcttgcc ctgcactcct tcccttctca gtctggaaca ttctgaagtt 480
gtcctcacag gattaacaag aattttggac aaaaatatat taatagttat aattaagcat 540
tacttaggct gcactttgac ccactttctt gtaactgaaa attacagggc actagatact 600
gaccatttgc atccccattg ttcctacaga taggtttttt tttttttttt tgacaaggtc 660
tcactctgtc acccaggctg gagtgcagtg gtacaatcat ggctcactgc agtcttgacc 720
tcccacactc aagcaatcct cccgcctcaa cttcctgagt agcccagtct acaggtgtag 780
gctaccacac ctcgctaatt tttaaatttt tttgtagaga caggggtctc cctatgttgc 840
ccagaatggt cttgaactct tgggctaaga ggtcctccca cctcagcctc ccaaagtgct 900
aggattacaa gtgtgagccg ccaccacacc tggcctatag atcagctttc tgatgctaga 960
ataataagcc ttttatttaa gataggtaga atctctgaca ttagaatcat aaggtttttg 1020
tttaagaatt tcttaagatg ttttttagat cctgaattcc agcaagacag ctgacctcaa 1080
atagtctgaa gacccactga cccctacaga ggaatggaat cagcatgaga atacagtttc 1140
ttcatctccc tgttccatga ctttgccctg tgccctttga gcaatcaagg atctccacac 1200
tttggctgat tcccaaaccc ctgaaaaccc tagccccaaa ctctgtggag acggatttga 1260
ggtttcctcc catctcctgg ttcagcatcc ctagaaataa acctctttca ctgctgcaat 1320
gtggtgaatt gacttgccac gtgcaccgga taaaggacct attatggtta caattccact 1380
catcctttaa gatagcttat atgttgtctc tggtcactgc ctccctcctc ttggtgcccc 1440
tcgcacagtt atccatgaga gcacatttgc gtcacctgct ggggcaactg tttgtttaca 1500
tggctctgtc tctcccagca cccagcccag gccagcccca cacttcaaag tccctgcagg 1560
gcaggatggc atggaaaggt cacaggtttg ggagtcagac tgaatatgac tccaccctct 1620
gtcctcagcc tcatctgctc ccccagtttt ctgtgctcta accacactgg cctgcactcc 1680
tgtctcactt catggccctt atacatgctg ttccaactgc ttagaatgct cttcctctgg 1740
ctctttttca tcctttcgtg cccagcttaa ctatcacctc ctgagacagg ccttccttga 1800
ctactgaatc taaaggcaca ccctcttccc attctgtcat tctccagcaa ttcccttcat 1860
tgatttgcca caaccctaat tatcatatta ttcatttact tgtttgctgc ttgtctcccc 1920
tgctagagct taaagtcctt gagtacatac agggactttg ccttgtttac tgctataggc 1980
ccagctctaa cacagggcct ggcatatatt aagtattaaa aaaatttaat tttagctttt 2040 ttttttttt tgtgaacgga gtttcgctct tgttgcccag gctggagtgc aatggcacga 2100
tctcgactca ccgcaacctc tgcctcccgg gttcaagcga ttctcctgcc tcagcctccc 2160
tagtagctgg gattacaggc atgtgcctcc atatctggat aattttgtac ttttagcaga 2220
gatggggttt ctccatgttg gtcaggctag tctcgaactc ccgaactcag gtgatccacc 2280
cgcctcggcc tcccaaagtc ctgggattac aggcatgagc cactgcaagc ggccaatttt 2340 agctttttc agacaagctg gagtgcagtg gcatgatcat agctgactgc agcctctaat 2400
tcctgggctc agctgatcct cctgcctcag cctcccagga agctagaact acaggaatgt 2460
gccaccaccc ctggctaatt ttaaaaattt ttgatagaaa tggagtctca cgatgtagtc 2520
caggctggtc tcaaactcct ggtctcaagt ggttctctca ctttggcctc ctgaattgct 2580
gggattacag gtgtgagcca ccagtccacc aagaaatttt tattaactga atgaggaatg 2640
aacaaacaaa atagatccaa atccttgctc cactacttac caccagattt gtgtcttagg 2700
acaaattact taccctctcc tcatgtgaag atgaggcctc tcatgggttg tgtattggaa 2760
actgtaaaaa tgcctgatac gtgaagacat tccataaatg gccgttattt tttctttcct 2820
tcatctgaaa aatgtaccct ttttgccaag cataaagacc ttactgtaca tctttacttt 2880
ttcttttctt ttttgttttt tgagatggag tctcgctctg tagcccaggc tggagtacag 2940
tggtgtgatc ttggctcact gcaagccccg cctcctgggt tcacgccatt ctcctgcctc 3000
agcctccgga gtagctggga ctacaggcat ccgccaccac gcccagctaa tttttttgtat 3060 tttgtttagt agagacgggg tttcactgtg ttagccagga tggtctcgat ctcctgacct 3120
catgatccac ccgcctcggc ctcccaaagt gctgggatta caggcgtgag ccaccatgcc 3180
tggccaacgg tacatctttt tttttttttt tttttttga gacagggtct ccctctgtcg 3240
cccaggctgg agtgcagtgg cacaatcttg gctcactgca acctccaact ccccggttca 3300
agcaattctt gtgcctcagc ctacagagta gctgggacta caagcatgcg ccaccatgcc 3360
cagctaattt ttgtattttt agtagagatg ggattttgtc atgttggcca ggctggtctt 3420
aaactcctga cctcagatga tctgcctgcc tcagcctccc aaagtgttgg gattacaagc 3480
gtgagccact gcgcccggcc tattttcctc ctctgatctg acatcatggg catgtctatt 3540
cttccttcaa accatttcag actcattcct tcctcctatt actcttctga gacctttcct 3600
aataacttta gcacacttga cctctcctac caccaaacca gaggtatcta aagtagggga 3660
tatgcaaccc agcatgtaac acacatgttt tagcacacac gatgcccaaa aaatggaaac 3720
agcccaaatg tccaccaaca gatgaatgga taaacaaaat gtggcataaa cttacaatgg 3780
gatattattc agccatgaaa atgaataaag tactgacaca tgctaccatg tggatgaacc 3840
ttgaaaacat tatgccaggt gaaagaagtc agtcacaaaa ggccacatat tgtgtgagtc 3900

-continued

```
cattttttatg taatatccag aatagaaaaa tccatagtga cagaatgcat attggtgatt   3960
gccagacgtt caggggatgg ggaagaaact gcttgatggg taaggggttt tactttggag   4020
taatggaaat gttttggaac taggggtggt ggctgtaaaa gactgaatgt actaaatgcc   4080
actaaatgtt cagtttaaaa tggttcattt cacctcaata aattttttaa aaaatgaagt   4140
agccattctt ccaggtgagc tgaaaagttt gaatgaggca caggctcctt aaatttcttt   4200
tttttttttt tttttttttt tgagacggag tctcgctctg tcgcccaggc tggagtgcag   4260
tggcgcgatc tcggctcact gcaagctccg cctcccgggt tcacgccatt ctcctgcctc   4320
agcctcccga gtagctggga ctacaggcgc ccgccactac gcccggctaa tttttttgtat  4380
ttttagtaga gacggggttt caccgtgtta gccgggatgg tctcgatctc ctgacctcgt   4440
gatccgcccg cctcggcctc ccaaagtgct gggattacag gcgtgagcca ccttaaattt   4500
ctaagatgta aagtgctggg caaatatcag ctggggatgc tgaaggaagg aataatcaga   4560
aggtcagcaa gtgtggcttc gaaactctgc ctcaagtaat aatgataatg ataattagag   4620
atagttataa tattgacttc tttggtttcc ttgtaaacca gtgttatttt agaaaaaagag  4680
ggagatagct ctagtaatta cagctaacac ttctacaatg cttaatatga ggaaggcact   4740
gttccaagta ctttacgtct aaaacttact aaatccttac aactctaaga ggtagtatca   4800
tcacatttcc attatagatg agggaatgga agaattgaga agtttaaatg agttctccaa   4860
gtcacagata aggaaatggc agagtccaaa tttgaaccca ggcaagtcag actctaggca   4920
ctgaagtctc aaccaccagg ctctgcacta agtgctctcc aggttttatc tcatttaatc   4980
ctgcaaggaa agtgttatta ttcccatttt attttattta ttatttattt atttatttat   5040
tgagacggag tttcaccctt gttgcccaag ccaaagtgca atggcacaat ctccgctcgc   5100
tgcaacttct gcctcccagg ttcaagcagt tctcctgcct cagcctcccg agtagctgag   5160
attacaggcc accatgcccg gctaattttg tatttttagt agacatgggg tttctccatg   5220
ttggtcaggc tggtctcgaa ctcccaacct caggtgatct gcctgcctca gcttcccaaa   5280
gtgctgggat tacaggcatg agccaccgtg cctggcctat tattcccatt ttaaaaatcc   5340
ccctcatgct atccacattc cacaccttct agtctttctt tttttttttt ttttttttga   5400
gacggagttt cgctctgtcg cccaggcaga cggagtgcag tggcgccatc ttggctcact   5460
gtaagctctg cctcctgggt tcacgccatt ctcctgcctc agccttccga gtagccggga   5520
ctacaggcac ccgccaccac acccggctaa tttttttgtat ttttagtaga gatgggattt  5580
caccgtgtta gccaggatgg tctcgatctc ctgacctcgt gatccgcctg ccttggcctc   5640
ccaaagtgct gggattacag gcgtgagcca ccgcgcccgg cttttttaaa aatttttttta  5700
ttttttttat ttttagtaga gaccgggttt caccgtgtta gccaggaggg tctctatttc   5760
ttgaccttgt gatctgcctg cctcggcctc ccaaagggct gggattacaa gcgtgagcga   5820
ccgcgcctgg ccagtctttc tcctacattt atttttacgt tggtccacat actcctgtca   5880
ttctcacttt gcttcacttt tcctttcttc ttcttttttta agagacgggg gcttgctatg  5940
ttgtccaggc tggagtgcag tgaggcaatc atagcttatg ccatccccaa ctccaagtga   6000
tcctccagcc tcagcctcct ccctagctgg attacaggag catgtcacca tgcacactaa   6060
ttttcttttc tttttttttt ttggtagaga tggggtctca tgttgctcag gctggtcttc   6120
aacatctggg ctgaagtgac ccccccttcct tggcctctca aagtgctggg attagaggct  6180
ttggccacca catccaacct gaattttatt atttatattt tcttttaatc tcccattact   6240
agatggcagg gattttgatt actgttaatt ttccaatatc caaaataatg tgtggtacct   6300
```

-continued

```
aataggctct caatatcgaa aagtaatagt gcacatggca ttctgtagta ttaggtaggt   6360
atcttgtgtt cctgtgtttg cgtaaataag atcatacatt atgttctgct tttttaactt   6420
aatggctttt tttttccttt ttttgcgaca gagtctggct ctgtcaccta ggctggagtg   6480
cagtggcgct atctcggctc actgcaacct ctgcctactg ggttcaagtg attctcctgc   6540
ctcagcctcc tgagtagctg ggattacaga cgcgcaccac cacacctggc caattttttt   6600
tttttttttt ttaggcggag tctcactctg ttgtccaggc tggagtgcag tggcgcgatc   6660
tcagctcact gcaagctccg cctcccgggt tcatgccatt ctcctgcctc agcctcctga   6720
gtagctggga ctacaggggc ccgccaccac acccggctaa tcttttgtat ttttagtaga   6780
gacggggttt tactgtgtta gccaggatgg tctcgatctc ctgacttcgt gatctgcccg   6840
cctcggcctc ccaaagtgct gggattacat gtgtgagcca ccgcacccgg cctatttgtt   6900
ttgtattttt tagcagagac aggtttcacc atgttggcca ggctggtctc aaactcatga   6960
cctcaagtga tctgcccgcc tcggcctccc aaagtgctgg gattacaggc atgagccacc   7020
acgcccagcc atgtcttttt tttttttttt tttgagacaa gagtttcgct cttgttgccc   7080
aggctggagt gcaatgacgc gatttcggct caccgcaatc tccgcctcct gggtacaagc   7140
aattctcctg ccttagcctc ccgagtagat gggatgacag gcatgcacca ccatgcccag   7200
ctaatttggt atttttattt ttttatattt atttattttt tcgagacgga gtctcgctct   7260
gtcgcccagg ctggagtgta atggtgcgat ctgggctcac tgcaacctct gcctcccggg   7320
ttcaagcgat tctcctgtct cagcctcctg agtagctggg attacaggcg cccgccacca   7380
cgcccggcta atttttgtat ttttagtaga gacggggttt ctccatgttg gtcaggctgg   7440
tctcgaactc ccgacctcag gtgatccgcc tgcctcggcc ttccaaagtg ctgggattac   7500
aggagtaatc ccaaaaaaag cgccgggccc tttttttgtt gtttttttaaa ttcagtaact   7560
atctagttca ttcttggatg gatgacaacc cagattggat gtgtagcagc gttctcttaa   7620
ccagtttcct attaatcttc atttcatccc cagtgtttct ccagaatgca aataatatgg   7680
cattaaatat cttcacacat agctttttgt gtatgtgtat acttatttct ctagaattag   7740
tgtctagaag tgaaactgcc gggaggaagg atatatactt ttaacatgtc caagttccac   7800
tgtgatagcg ctgcgagggc acacaacagg tttcaatata ccttggacca aaccggatat   7860
tatcagtttt tttaacttgt tgctaatgtg atgggggaaa aatgaactcg gaatttacac   7920
acaaggaaaa gaccgtttaa ggttcaggga ctgtccacat agctgtcaag tggcggagcc   7980
gtgatttggt attaaagtgc ccggagagga cgcgtcaaag ttggacactg tgccctgtgt   8040
cctgaggcac gtctggtgat cgctgggcct tgcaatgctg ggcaggcagg ccttcctctc   8100
cccttctagg cctctggcca ctcctggctg gccgaaagcc ggttcttctc gattaccgag   8160
tgcctctcct gaaagcaagt cagcgtcgcc taacctcttc agcttcgaaa tggcggccac   8220
cagatcgcta ggccacgccc cgggggcggg gcctgagttc aggccagagc gatggatgcc   8280
cgagccaagt tagaagtcga ctgccagtag ggctcgcgca gaatcggaga gccggtggcg   8340
tcgcaggtcg ggaggacgag caccgagtcg agggctcgct cgtctgggcc gcccgagagt   8400
cttaatcgcg ggcgcttggg ccgccatctt agatggcggg agtaagagga aaacgattgt   8460
gaggcgggaa cggctttctg ctgccttttt tgggccccga aaagggtcag ctggccgggc   8520
tttggggcgc gtgccctgag gcgcggagcg cgtttgctac gatgcggggg ctgctcgggg   8580
ctccgtcccc tgggctgggg acgcgccgaa tgtgaccgcc tcccgctccc tcacccgccg   8640
```

-continued

```
cggggaggag gagcgggcga gaagctgccg ccgaacgaca ggacgttggg gcggcctggc   8700
tccctcaggt aggtggcagg accgggtcgt ggatgccggg ggagccgggc ggcggggctg   8760
agggatcggc ttccagggcg accgggcctg ggtggcgctg atggagcggc cccgcggctg   8820
ccgggcagag ggcttgggcc aggccgttgt caccctgggg tagcgttggg cgggggcccc   8880
ggagtccggt gtcatggccg gcgagccgag ttcccacatc ccactcaaat ttccttgtgt   8940
ttggcggaaa cgtgccaacg ccacccttat gccatgcgca ttcctcatat ttggcagtgg   9000
gaaaatccgc ccagagctgc cccatatctg ttgtcacttg gatgggccaa ttccttttct   9060
cttgggccgc cgaatgtggg acccgggctt gcaccctttc tcagggtact tcagtcaagt   9120
gacacccttt tagagacgac gtgaggaatc gggtaagaga ggaggaaact ggccagtgcc   9180
ctaccacaaa ggcacagggg cctcttcttg ggtatcagga ctagccttgg gtatcaggac   9240
tctgggttat taatgaaagg tttgggatac ttatagagga ttggcctcag gacgctttgg   9300
aatgaagagc cagggctgtc ttttgtgtga cgcgagagcc gccgggacgc ttcagctctg   9360
cagctgctga ggctctgcga gcgagtcgat gcccaagaga gaggggtttg gacgtcgtga   9420
gaggcgaggc ggccgtgttc attcattgtt ctcgttctag ggctctgggt gtgcccctgg   9480
tattcattct gtggtgggaa gaaggaatgg aacttagtgt atccttgaga tgtgaacggg   9540
ttctaggggg tcacttaatc taagtggaaa atgaattcaa ggcacgttca ttgagcgttt   9600
ctgcttgcct ggtcctctgt gggctgagtg gagagactct gccctccctg cgctcctaag   9660
gcgtgaaaac aatgcagtgt gataagaatt ggcttatcaa gtgttatggg gatttagaac   9720
agttagtttt gcttggggag gagttgagga agcttctaca ctcgaggaga cttctgagtc   9780
gagttttgaa acacctgtga gtaagtgctc atcgggtgag gaggagctca gggaacagct   9840
ggtacaaagg cttagagcca tgtgggagtt gggatgagtt tggggagcag caaattgcct   9900
ggggtgcagg aaggaaatgg tgagagatga gagtaaaata aaagttgcta gaattgtgag   9960
ggggctgtct ttgttgtaga tagtgaacta gttgaatttg gattattgta catgggttgc  10020
cgagtcttca ttcttgctga taattttctc cctttgttga tgttgaagct gatagtgatt  10080
gaacatattt agtttaactt agttaatgac ttttaaattt tttttatttt tttcagaaca  10140
atgcaaactt tttttttttt tttttttttt tttttttttt taaaggaaca ggatctcact  10200
ctgtcgccca ggctagagtg cagtggcatg atcatagctc ggttgcagcc tctaactcct  10260
gggcttaagc agttctcctg cctttgcctc ctgagtagct gggactacag acaggtgcca  10320
ccacacatgg ctaattaaaa aaaaaatagt agagatggag tctggcagtg ttgcctaggc  10380
tggtctcaaa ctcctgggct caggcgatcc tcctgcttcc acctctccct cccaacgtgc  10440
ttgctgggat tacaggggtg agccactggc caggcagaac tttttttttt tttaaataat  10500
agagaggggg tcacactatg ttggccaggc tggtcttgaa ctcttgggct caagtgatcc  10560
tccagcttca gcctcttaaa gtgctgaaat tacaggtgtg atccactgtg cctggctagc  10620
agaacatttt tgataagtgt tttatatcaa atgttttgac ttacacagtg gtgaatgaat  10680
tgaactcata tattcctggg gattcttgca aaaaattctc ttaaagttat acttgctcac  10740
aaaaatgtta actttataaa tgtagaacac tctcctacta atttttattt tattattcta  10800
ttgtttttta tttttttgcg acggagtctc actctgttgc ccaggctggc gtgcaatgat  10860
gcgatctcgg ctcactgcaa cctctgcctc cttggttcaa gcagttctcc tgcctcaccc  10920
tcctgagtag ctgggtaggc acactccacc acgcccggct gatttttgta tttttagtag  10980
agatggggtt ttgtcgtgtt ggccaggctg gtctcgaact cctgaccgca agagatctgc  11040
```

-continued

```
ccacctcggc ctcccacggc ctcgctggga ttacaggcat gagccactgt gcctggccta  11100
aattttaaat ataagtaatg tactccccag tcttacagaa attggacgac tatagaaaac  11160
aaacatcaaa aaaagtgtag aatgtgagta tttttagttt aataagtgta ttttataaac  11220
tatttatttg tattgacttc tcggataaca acctgttata aaatctttat ccccataaac  11280
ataattttcc taaaatagct ataatattgt gattaatgtt tatgctaaag tgactattat  11340
ggaattaaca gacttcagtt gcagtttcta aatcttgctt tggttgtgat gattatatac  11400
cactgaagaa cattcaggat tattttggct tgtttttacc cttatcactc aagggctaag  11460
ctgtttaaaa tgcaacataa acatttgacc cagttgaatg ctgggatact tggaaaaata  11520
aacctgttac tgtttctgta ctaaaggctt atcttttaaa gatatgtggt gtttttttag  11580
cgcagtggtg cgatcttggc tcactgcgac ctctgcctcc tgggtttaag cattctcctg  11640
cctcagcctc ctgagtagct gggactacag gcgcctgcca ccacgcctag ccaactttta  11700
tgtttttagt agagacggga tttcaccata ttagccaggc tggtcttgaa ctcctgacct  11760
tgtgatctac ccgccttggc cttgcaaagt gctgggatta caggcgtgag ccactgtgcc  11820
tggctgatat gtggtgtttt gtgattataa attgtagtgg agttccttag ttttgttaaa  11880
gtcttgtcag tagttgtaaa aacatcagcc agttgtggtg gctcaggcct gtaagcccag  11940
cactttggga ggccgaggct ggtgaattgc tagagctcag gagtttgaga ccagcctggg  12000
caacatggtg aaaacctgtc cctacaaaaa atacacacac acaaaaagaa aaaaatcagc  12060
agggtatggt gtagtatgcc tgtagtccca gctgcttggg aggctgaggt gaaaggctca  12120
cctgagccca gggagattga ggctgcagtg agccatgttc atgccactgt actccagtgt  12180
tggtgatgga gtgagaccct gtctcaaaaa aaaaaagtgt gccttcaata gaaggcttga  12240
acgtatttta tgggatttgg tttagctgaa aaaaacagtg agaagcagat taagctggta  12300
atttctgaca aaaagtatct aaaagatgaa gtgaagaatg ttaaacatca agtattatat  12360
tacagttgct cttagactag tagcttttag tttataacat gtcatttgtt tgctctgaag  12420
attaagcaag ttcatacttc ttggaagtta aatttgactt ttccagaagc actggattat  12480
ttacgaaata aaaaatataa ttgataactt taaactacta tttcaggtag tctattacta  12540
gtaaatgtat gattctacat ttaaatttca ggtaaatctt tgttagtaac ctactgccta  12600
aaaaaatgtt acatgaggga gtacttttgt ttgcatgtta ggatcataat aggccataca  12660
taataatctt gagcttggga ggagcttgtt agccaaacag catgccttaa tgttgacttg  12720
cagaagacaa ttttaaatat tgcctttgaa aggcagtgga taatgtgaca gtgagggggt  12780
ttatgaaacc ataaaattga gctttttgac ttagtttttg tttttaagtt gttcagatct  12840
tgggagtcat ttcttcaaaa caaatgacta tgaggtggaa aattacttac cttgaataaa  12900
ttaattggaa aatcagagaa cactgggttt atttaggatg aggttgtttg gtatgtgtat  12960
gggagggtag aattcctaat tgctcatctg actgggttca aaatgtaata ctagatattt  13020
gtgttgcaat tcagttggta cttttggtat agggctaact tatcttgcgt gtaatttttt  13080
tttttttttt ttgagatgaa atctggtgct gttgcccagg ctggagtgca gtggtgtgat  13140
cttggctcac tacaacctcc gtctcccagg ttcaagggat tctcatgcct cagcctcccg  13200
agtagctggg attacaggcg ccggccacct tgcctggcta atttttgtat ttttagtaga  13260
gacgaggttt caccatgttg gccaggctgg tcttgaactc ctgacctcaa gtgatccacc  13320
tgcctcggct tcccaaagtg ctggcattac aggctcgctc aggcatcttg ccttgtaatt  13380
```

-continued

```
ctcatgatag taatggctat ttttttcttg ccttagagtt gtaagtaaaa attccttaat  13440
tacacattaa ggtttgatct ttaattttac aatgtttgag tcattttgtt acttcttttc  13500
tcccagaatg acttgcgtag ctctaaatga ttttagttaa tttcacatct gtttgccttt  13560
cttctaaaat gacccctaga atctcagctt aactaaggaa aatgtcaagt gggtgttgtt  13620
tctttgttag tggttttggc ctagactatc taaagtttgg caaattactc acaaagtatg  13680
ttaattggca tcacattcca atcagtgtac atagcatttt ttgaggaaca cttgacacac  13740
ggttttattt ttagaccaga ttctaagggg ttttactggg tggggcttaa caatcctaaa  13800
gctagtttac ggttttaaaa tctttatgat ttagaggttg tttacatttt ttgttaataa  13860
atgggaagca gcaggcagtg gcagtcaatt ttgtttgttt cttttttgt tttttttgag  13920
acggagtttc gttcttgttg cccaggctgg agtgcagtgg catgatcttt cctcaccaca  13980
gcctctgcct cctgggttca agcgattctc ctgcctcagc ctcctgagta gctgggatta  14040
caggcatgcg ccaccacacc tggctaattt tgtattttta gtagagacag ggtttcactg  14100
tgttggtcat gctggtcttg aactccctaa ctcaggtgat ctgcctgcct cagcctccca  14160
aagtgctggg attacaggcg tgagccacca cgcccagccc tcacataact tttatgatat  14220
tatgttctta taattgttcc attattaatt ataattaatc tctcactgtg cctaatttat  14280
atgttaaact tgatcatggg tatgtatgta caggaaaaaa catagtgtat acagtatagt  14340
atactgttct tgctttcagg cattcattgg tagtcttgga acatattcca agtggatatg  14400
gaagcactac tatgtgatgg aatgttactc agtaataaaa agaaggatgt actggtgtat  14460
actacaacat tggaaacata ttaagtaaaa gaaaccatgc aggaaagacc acatattgaa  14520
ttattccatt tatatgtaat gtccagaata ggaaaatcct tagtgacaga aagtagatca  14580
ggggctgagg gatgtaggga atggtcagtg actgtgatag ggttttcttt ttgcttttga  14640
cagcggtctg cattcataat tgctaatact tggaagcaac caagatgtcc ctcagcaggc  14700
gaatggaaaa actggtacat ccagacaagg gactattgtt cagtgccaaa aagaagcaag  14760
ataccaagcc atgaaagaca tggaggaaac ttaaatgcat atcactgagt ggaagaagcc  14820
aatctaaaaa ggctgtatac ggtatgactc ccaactatat gaaactgtgg aaaaggcaaa  14880
actgctgaga caggaaaaag atcagtggtt gacggaaggg agggatacat aggcagagta  14940
cagagaattt ttagggcggt gaaactactg taatatgtca ttatacattt gtcaaaaccc  15000
atagagtaag cctgggcaaa atagcaagac cccatctcta ccaaaaattt ttaaacctag  15060
ccaggcactt gtcctccaaa agcccacttg gccctcttca agtatatttt actttctttt  15120
ccttcctgct ctgaagcttt ttataacctt tcatgctgct ggaaaacttg cctcagtttc  15180
tttatcttgc ctatgcccct catccaattc cttcttctga ggaggcaaaa atgagggtcg  15240
tgcagcctgc acggatcact tgccggaaac tcgacacccg cacgcaaaat aattcggggt  15300
gcgctcacta nnnnnnnnnn nnnnnnnnnn nnnnnnnnnn nnnnnnnnnn nnnnnnnnnn  15360
nnnnnnnnnn nnnnnnnnnn nnnnnnnnnn nnnnnnnnnn nnnnnnnnnn aagnaaaagg  15420
ttaggaaaca ttaacttagc ctgcctcttt tttttttttt ttttttttttg agacagagtc  15480
tcgctctgtc gcccaggctg gttggagtgc agtggcatga tctcggctca ctgcaagctc  15540
cgcctcctgg gttcatgcca ttctcctgcc tcagcctcct gagtagctgg gactacaggt  15600
gcccaccacc acgcccggct aattttttgt atttttagta gaggggtttc accctgttag  15660
ccaggatggt ctccatctcc tgacctcgtg atccatctgc ctcggcctcc ctaagtgctg  15720
ggattacagg cgtgagcccc cgcacccaac ccttagcctg cctcttaagc tgtaagtggt  15780
```

```
cttgatatgg agatagaaaa taaaatacta tgaatgacaa ataatctaaa acttgaatta  15840
aataaagtag gtgtattttt attttgtcac tttttattaa aagttattgc agtatattct  15900
ctactgagta ccagcactat attttgagtg cctgcaagac ttagaattca ttgtaaaatt  15960
actgttcttg gactgaggtt acattttagt cttatcagtg gattcttcac caatcgattg  16020
gaatcagtca attccaatac agtcttcccc cacagttgaa tatagaataa aatctattgc  16080
aagctgggtg caggggcaca agtgtggcag gagtgcttga gcctaggagt tcaagaccag  16140
cctgggcaac atagtgagac ctcatctcaa ttgaaaatat atatctatat aaaaaataaa  16200
atttattaca gttcatcttg ctggaaaaca aaatactgtt tttgtaatta aaattttttt  16260
tttaaattta gaaatggggt cttgctgtgt tgaccaggct ggtcttgaac tcttggcctc  16320
aagctgtcct cccatctggg cctcccaaag tgctgggatt acaggtgtga acaactgcgc  16380
ccggctgaca aagtattttt taaagatgta ccactaaatg gagatttgat tcacatttga  16440
tagtttttga caggtctttt ctatttaaaa acattactgt ttttgtagca ttattctggc  16500
ttttccctta atttagtaaa tatttgagtg cctttgtatt ccagatactg agcaagattg  16560
gcagggttct gcccttatgg agcagaagga aggtaggggg actgactaaa acttgaaaac  16620
tgtctaacat aagtaccatg cagaaaatga aacagtatta attggcagaa ggagagcagg  16680
ctattttggc tagtgtggtt agggaaagcc tctctaaaga gatgtctctt gggtggagac  16740
aagatgtgaa aaaaccagct tgcctgtttt tggggtttca gccttgcagg tgaagagaaa  16800
cacgaagttc agaagtcttg aggcacaaag tctggcatgt tacgaaagaa ggcctttaga  16860
cgccttgtca gggagtttag attttattct gagttttaaa acgggagtga cacaatgagt  16920
tgcattttaa gcctgttcag gctgttacat ggattattag gagctgtatc atttcaggct  16980
agtgagatgc tcagatgagt ctgccttctg tctcttccgt catctatttc tctcttatct  17040
ggtcttaagc tcctccatct tttccttttt agttggaaaa aaactcaaag atctagaaaa  17100
aagaggagct gtatgtactc ctaaaaaggg acctcatagt aacctgggga tagagttatg  17160
taggagtgag tcagggctca ggttgaggct ttagaggcag gaggcagcga gatcttgttc  17220
tgtcatcccc tcttacagaa ataaaatatg ccgataaaag tttatagtgt aatagtaaaa  17280
tataaaaaca aaaagtaagt aatgtagaaa ataaaaaccc ttcacagtcc tgctgaaatg  17340
attactgtta acactttaat tctagagttc cccatccatt tatttatttc tagatttccc  17400
tctttgtaga ttaatattaa agggttcaga cttgttcatt ttttgttgtc ttggatatct  17460
tttcccacct ctgtatatat ggatctactt tatttatcac gtggatatta acatggttta  17520
tttaattccc tattgttagg tatttggtct ttaccacagt ttttcaaggg tatgaatagt  17580
gctgcaagga atatgcttac acatgttttt atacacttgt cttaggcttc tgtaggacaa  17640
atttctggag tagaatacta ggtcattctt taagaacatt tcaaactttt aatagatatt  17700
accgtattct ttcccaaaaa gaatgtacaa agactgtatg agaataactc catgttgtga  17760
tcttaagttg tctctaaacc tctttggttt tcttagctgt catctaagaa tactaagtat  17820
ctaacctccc tcttgatttg ggcatgtgat gtgatttagc atatagtgga tattcagtta  17880
gaaacttttg gttgaaaaca aggtttggat tctgtggtct ttaattctag gccatttcag  17940
ctctgactaa aatgatttga gtgttagtgt tatatatggg aaggtaaggg ctatggagtc  18000
agtgcagccc agttcagaat cccagtttgc cacttacaag ctgtgtgtgt gagaattttc  18060
tcaactgtaa aatggggaca taattcctac ctagagtaat actgtaagta ttaaggtgga  18120
```

-continued

```
taatgattgg aatgtatgct gtgtatcctg cctcataata gtaagctttt agtaaatggt  18180
agctactgtt aataataaaa caagtttctg aaggaggaag gcttgaaaag atgggattcc  18240
ttatcaacct caaagttttc taaaggagga aaccctaccc cccttacttc tgcatggttt  18300
ctgaccatga actgaactct gaactctgaa tgaactgaac tctgaactct gaatgaactg  18360
aactctgaac tctgaatgtt atggtagaaa attcatggac tttaaattta aacagataaa  18420
gaatctggtt attttaccca ctgctggggt gttcttgggc aagtagcatg acttctgtgt  18480
ccaaaaaaga aagggtttgc agtgactgaa cctgtaatcc cagtactttg ggaggctaag  18540
gagagtggat tgcctgagct caggagttca agaccagcct gggcaacata gtgagagcct  18600
ttctcaacaa aaaaaactgt tcttaaaaat tagctgggca tggtgatgca cgtctgtggt  18660
cccagctatg tgggaagctg aggtaggaga atcatttgag cctggaaaat tgaagctgca  18720
gtgagctgtg atcatgtcac tgcaccccag cctgggcaac agagcaagac cctgtctcag  18780
aaaataaatt aattaaaaag aaagtgtgga tggaggaagg gattaaaaat ctggctgggc  18840
acggtggctc atgcctgtaa tcccaggcgt gatttgggag gccgaggcgg acagatcacg  18900
aggtcaagag attgagacca tcctggccaa catggccaac cccatctcta ctaaaaatac  18960
aaaaatcagt cgggcgtggt ggtgcatgcc tgtaatcccg gctactcggg aggctgaggc  19020
aggagaatcg cttgaacctg ggaggttcag tgagccaaga tcgcgccact acactccagc  19080
ctggcaatag agtgagactc tgtctcaaaa gaaaagaaaa gaaaagaaaa tctttggggt  19140
tcttacacaa attaaatgag ataatttatt attattattt tttttgagat ggagtcttgc  19200
tctgtccccc aggctggagt gcagtggtgc gatctcagct caccgcaagc tctgcctccc  19260
gggttcacgc cattcccctg cctcagcctc ctgagtagct gggactacag gcgcccgcca  19320
ccatgcctgg ctaatttttt gtatttttag tagagacagg gtatccctgt gttagctagg  19380
atggtctcga tctcctgacc ttgtgatccg cccatctcgg cctcccaaag tgctgggatt  19440
acaggtatga gccaccatgc ccggcttgag ataatttata aagtgcctaa aatacatcct  19500
agaaatatta gtttttcttc cttgaagtca taaattatgg cttacacttt ttttcaggta  19560
tttctcatag tactaatgtg ttgctcacac tcaagggtag tagttgctta ggaagaagag  19620
aaatgtagtt gaaaaagtaa tagactagaa gtcttgagac ctgggctcat gttccaagtt  19680
ggcttttttt tttttttttg ggagatggag tctcgctctt gtcccccagc ctggagtgca  19740
atgacacgat atcgactcac tgcaacctcc acctcctggg ttcaagtgat ttctcctgcc  19800
tcagcctccc tagtagctgg gatgacagac acccaccacc atgcctggct aatttttgta  19860
ttttaagtag tgacagcatt ttaccatgtt agccaggctg gtcttgaact cctggcctca  19920
agtgatgcgc tggcctcggc ctcccaaagt gctgggatta caggcatgag ccactgtgcc  19980
tggtcccttg ctaaatgttt tgttttgttt tgttttgttt ttgaggtgga gtcttgctct  20040
gtcacccagg ctggagtgcg gtggcatgat ctccgctcac tgcaagctcc gcctcccagg  20100
ttcccgccat tctcctgcct cagcctcccg agtagctggg actacaggcg cccgccacca  20160
cgcccggcta attttttgta tttttagtag agatggggtt tcaccgtgtt agccaggatg  20220
gtctccatct cctgacctcg tgatgcaccc acctcggcct cccaaagtgc tgggattaca  20280
ggcgtgagcc accgtgcccc gcagttgctt gctaaatctt ttaactgctg gtcccatttt  20340
cctcatctat gaaatattta atggaagtgt actattaaag aaacttttct ttgctgatga  20400
atgcaggagg tatcattaaa aacccacata gtgctatttt cataattact ctttatgtat  20460
tgtgttcttg ggttgaatac ttttgttcta gagttacaat tatttgtgtt tcttaccagg  20520
```

```
tttaagaatt gtttaagctg catcaatgga gcacatacag ggagcttgga agacgatcag  20580
caatggtttt ggattcaaag atgccgtgtt tgatggctcc agctgcatct ctcctacaat  20640
agttcagcag tttggctatc agcgccgggc atcagatgat ggcaaactca cagatccttc  20700
taagacaagc aacactatcc gtgttttctt gccgaacaag caaagaacag tggtatgtga  20760
acattctact taggaaattt agctatttat ctgcctgtgg agcacattaa ggatcatgtt  20820
caacttaaag acaggcaaaa tattcattgt catttagggt ctttattttt tttttctaa  20880
ctgcagattt attttttat attgctgttc cttccacacc ccctattttt tcctacctct  20940
tggccttcct tctgttactc ttgcctggaa tgtcttcctt tgtgccactt catccaaaca  21000
aatagtacat tcttatgggt atatttcaaa gacttttctt tgagaagtct ctaggccttt  21060
ccaactactt attttagaag acattttatt tcttctatta aaatattcac ctaaagcttt  21120
ttgactatta caatcaagta taaagaagaa agtaaagtta catagaaaag attatttttg  21180
tatatttcat aggcccagga ccagtctgga ggcagcttag aaatcataga atcttctttt  21240
tcagggcact gacaccagcc acttagttct gcgtagttta ttttttcagt gccagtgaca  21300
ggttcatatt ggcatcatgg caggacactg ccactaggtt ttctgataga aaatttcttt  21360
ttctttttct tttcttttt tttttttga gacggattct cactctgtca cccaggctgg  21420
agtgcagctc actgcaacct ctgcctcctg ggttgaagtg attctcctgc ctcagcctcc  21480
caaatagctg ggactacagg cacacaccgc cacgcctggc tgattttgt tttttgtatt  21540
tttagtagag acggggtttc accatgttaa ccaggctggt ctcaaactcc tgacctcagg  21600
taatccacct gcctcggcct cccaaactgc tgggattacc aacatgagac accacgccca  21660
gcctgataac aaaacttcaa tttttctaag aatttagctc tcaaaaagtt ttctggctgg  21720
gtgtggtgat ttatacctgt aatcccagca ctttgggaga ccgaggtggg cagattgctt  21780
gagctcagga gttcgagacc agtcgggcaa cgtggcaaac cccatctcta caaaaaaaaa  21840
ttcaaaaaag taggcctggt gcagtggctt acgcctgtaa tcctagcact ttgggaggct  21900
gaggccagct cattacttga ggtcaggagt tcgagacaag cctggccaac atggtgaaac  21960
cccatctcta ctaaaattgc aaaaattaca gccaggcatg gtgttgcacg tttgtaatcc  22020
cagctacttg ggaggctgag gcaggagaat cactcgaacc cgggaggcag aggttgcagt  22080
gggccaggat tgcgccactg cactccagcc tgggcgaaag ggtgagacta tattaaaaaa  22140
agaaataaca acaaaaatgt agccgggcgt ggtggcacac gtctgtagtc ccagctactc  22200
ggtactcggg aggctgaggt gggaggatgg cttgagccca ggaggcaaag gttgcagtga  22260
gctgagattg caccacttca ccccagcctg ggtgacagag agccagaccc cttctcaaag  22320
aaaagaaaaa caaaaaaagt tttctactat tatggataaa acaaacaaaa ccaaccacct  22380
ggccaaaaca gaaaagtgaa attgcattgg ttttgcttgg tggaactttt gagaaaactt  22440
gggttcaaaa cttccatgcc tcttcctttc ccatcctctg ttctttgtgt aaaatcaatg  22500
cattgtgttt attccatata gtcaggtgaa gcaaggttct gaggtgggga accccagtcc  22560
agagttttct gtttgcttct aacagttcca ctcttcccaa tttgttaata aattgtttat  22620
acttttttg tgaacctaag gagcctccca agtgtagtgt tgaatactta ggtgcatttt  22680
gaactgaagg caaaactcaa aagtctaact ttaattaaag tttgagtaag tttatctttg  22740
tctctcttcc taaaaatgaa aattttatgg ctggcaaaat aagcagtaat aatcccctat  22800
atctgaacaa tggtcttcca tttgcaaagt aattttgcct actgtttctc attaatttc  22860
```

-continued

```
tttgtgacct taaattgaga agtcagatag gaagtgtgtg ttatgagaag ctgaagacca  22920
tttggtgctt cttcaaagtg ttattgagac tatcttctcc atccccatct gctaccagtt  22980
tgcccagaag gctgggaaac ttaatttggc atagtgatta agtgtatgaa cctttaaaac  23040
aagaaaatcc caatttaaat cctcattgcc ttttattagc tgtatcattt agacaagttc  23100
tgtacttttt tgatcctctt tcctgacctt tatgaaatga ggcttgtact tagcacagtg  23160
gctgattcat aagtgaagtg gtagctatta ttattattat tatatgtatt ttttttagat  23220
ggaggctctc actgtcaccc aggctggagt gcagtggccc aatctcggct cactgcaacc  23280
tctacctccc aggttcaagc gattctcctt gcctcagcct cccaagtagc tgggattgca  23340
ggcacccgcc accacgcctg gctaatttgt ttgtattttt agtagagaca gggtttacca  23400
tgttggcaag gctggtctca aactcctgac cttctgatcc gcctgcctcg tcttcccaaa  23460
gtgctgggat tacagacatg agccactgca cccggctgct atgattattt cttagctttt  23520
tatacatcta tgtagtcctt gatcccctcc atttgagcac agctggtggt tggaagccaa  23580
gcttgacttc tcctacagct tatgagaagg ttgtagccta ggttagtttt gcctgtttct  23640
ttgggtaaag atgaactaac tgtggaagaa ctagctgctt tcaccaggca cgcagcttga  23700
ggaaagcggt agaagaggga agagttgctt agctaggcca gcaccatcag tcagctcttt  23760
ttactcctcc ccaggttgct ttacttcctg aacccagaat gactctcata atcactcagt  23820
gggttctaga aattatttaa ctgatttcag catgtatcca tggagggctg taaagaggag  23880
aatgagacag aggacgcgta tctgatttaa ataattttag atgtgataat taggtttttg  23940
aatgtttctt ggaattttta ttttctaaat gtgtgcctct ttgacttcct cctgctgctg  24000
ttgctgctat tgctgctgct gctactgctt ctaattatta ttagataagt gattgactgg  24060
agccgaggac cactactatt agagtcagct gaccagcagg ttaaaataca gattcattct  24120
gtatgaatgg gctttattcc atactaactg aatcagaatc cttggatgtg ttggacaggt  24180
agatggaatc tatattttct caagcttctc tgaggattct aatgccagct acatttggga  24240
atctgactgg attagatgat atttaaagaa ctgtccagct tgcagtatga tttagtgaag  24300
actgataatg taacagatat cactttatag cttagaaaac attgctatac agtatttgat  24360
gcaggtcatg attccgttag gtatgtttat tactctttgt tttcctcatt cttagtgtct  24420
tagtagttca catcagtata gcttacttgt tttgtttctg aaaagctgga agttggtggg  24480
tatcactgcg tcaagaaact tttaaaataa acttattttg gaacattaaa aaatatatac  24540
aggctgggtg cagaggctct tccctgtaat cccagcactt tgggaggctg aggtggaagg  24600
attgcttgag cccaggagtt tgagaccagc ctgggcaata tagtgagatc ttgtctctac  24660
aaaaaaaaaa aacattagct agaagtggtg ctgcccacct gtggtcccag ccgaggctga  24720
ggcaggggga tcacttaaac tggggtggta aagggtacat gtgtcatgat catgccattg  24780
tattccagcc tagatgacag agcaagattc tgtctcagta tatataatat agattttaca  24840
cacacacaca cacgcacgca cgtagagaaa ataacaaatc tgatgtaccc cttacccact  24900
ttcaacactt agctaaccat ggcaggcctg cttaatctgt tttcatccac tcctttccca  24960
gtgttttgac acaaatccca ggtatcattt gtctgaacta ttttggtatg tacaagaaac  25020
ttttaaagaa tgctaatttt atttattttt aaataggtaa agcattcata tgagccaaaa  25080
gtcttgggtg acccctgccc ctgtatcccc atttcttttc ctcagaggtt tcttatgatc  25140
aatctttatc tattcgaaga atcagttggt ttccccttac cctgttgttc acgacctttc  25200
ctttcttcca catctctgaa ggagaggaaa aaccatcggt agctaaggag gctatcacaa  25260
```

actccaaagg aactttttttc gtttggagaa tcttttcctt ctcccagatg attgatcctc 25320
ctggagaata ttccttcccc actcccatca ccttctcgac taatctgtta caagttcaaa 25380
ttcttctata ctgtactctc aatgtggagt ccatctttgg gcttcaaaga atgattactg 25440
ggcagataag tccccttcag tccctggtga tagcaaaata aagccttgtg aaaaacttct 25500
tacgttgccc ctctctgatg ttttcaaatt ccttatgctt acatgcattc ccttctttcc 25560
tagattgttt tctctgcttt gcatccacat actatgccct agtttggagc ctggtaacta 25620
gaagggccca gataactatg tcctctttct taagactttt ttctgttgta aaccagctag 25680
agaaggttgg ctggattggc attgaggtgg ctggagtaag agccaagatt aagaacactt 25740
tgggcctttt gcagccctgc tttacttcct tccccctccc cgtgtaccca cataggtaga 25800
tatatgcata cactcaccac cttctggggg cggggtgtgg ggggggatgg cggggtgggg 25860
gagcggttgg ctggctgctg tcagctgtta gcactttcaa tcagaggagg aacctggtag 25920
gcagttcaca agcactgcaa atctctgttt tgccctcctt gctggccata ctgactctag 25980
ttaccttact tttgattaat tcttggcttt gaagttaaac atggagggct tttatcaaaa 26040
ctctgaaatt ttcattcaaa tttttttaca gctgccatta attgtgagta tcctgggcac 26100
tcacacttcc cagtagggtt ctgagtacct gcctagcttt ttgaggattg agtacagggg 26160
aatatagaga agtatgtgcc actaaggctg cttggtatgg tgtgcacata tatttaaact 26220
aagattggtg tttgtcccta cagcagggct ggagttctat atcttccact tcctgctttg 26280
ccttcactag tgttaagtac ttgtgagatg gaatttttgt tagaatcatc agtcattttt 26340
gttgaaagag gttgaagtac aaattttgat cataaaaact cgtttgttta tagatcagat 26400
tggcttattt cctctctaat gaatctagtg aacatatatg tgtatacatt ctaatcacac 26460
aaaattagag acgtataaag gaaaagttta tcattttatc tttcttaacc actttctaac 26520
cactttctta actgtctctt gatgtgaaca gctaggtgta aatctttcca cttgtataac 26580
atatacagat ttcttcactt tttttttttt tttttttgag acggagtctc gttcttgtca 26640
cccaggctgg agtgcaatgg tgcgatctca gctcactgca acctctccct cctgggttcc 26700
agcaattctc ctacctcagc ctcccaagta gctgagatta caggcgtcca ccaccatgcc 26760
cggctaattt ttgtattttt agtagagacg gggtttcacc atgttggcca ggctggtctc 26820
gtactcctga cctcaggtga tccacccgcc tcggcttccc aaagtgctga gattacaggc 26880
gtgagccacc gtgcctggcc tcttcacctt taaaataatc ttactctatt attctgaagg 26940
atattttccc ccaattaata tatcatggac tcctctccat ccaggtcatt ataagtaata 27000
taatagctgc ataatgtgac ataatacaga tgtctcacac tccattcaag tactttccta 27060
ttgctggaca ttcaggttgt ttcgtatatg tgtgtgtgcg tgggccatca caagcaatac 27120
agactggtgc atttatttct gtgcccacct ttccaagggg tgctgcagcc tgtgttggtc 27180
ctaaaggtgg tcctttgttt gtaggtcaat gtgcgaaatg gaatgagctt gcatgactgc 27240
cttatgaaag cactcaaggt gaggggcctg caaccagagt gctgtgcagt gttcagactt 27300
ctccacgaac acaaagggta agagctcaaa agtcaattga cttcttcaga ctagtaagga 27360
tcttctagct tcaaatagct atgtttgtat taaattgtac tagcttccta tagaatattg 27420
tatatttcta tacctttctt tataaagaga taattcagaa aaataggtat taagaaattg 27480
aaattattgc ttggacattc tcttgaaaag ttaaatacac gttaagctgg gcctgatgac 27540
caatacctgt aatttttttt tctttttgag gtggagtctt gctctgtcgc ccaggctgga 27600

-continued

```
gtgcagtggc gcgatctcgg ctcaccgcaa gctccgcctc ccgggttcac gccattttcc  27660
tgcctcagcc tccggagtag ctgggactac aggcgcccac caccgcgccc ggctaatttt  27720
ttgtattttt agtagagacg gggtttcacc gtgttagcca ggatggtaat acccgtaatt  27780
ttaacactgg gaaactgagg caagagggtt gcttgaggcc aagagttcaa gaccagcctg  27840
ggcacatagc gaaggcccat ctctacaaaa gatttttaaa aattagccag gcatggtggt  27900
gcggccctgt agtcctagct gttcgaaagg ctgacgtgag aatattgcat gaccccaggg  27960
gcttgaggct gcagtgagtc atgattgtgc tactggactc cagcctgggc tggagcaaga  28020
tcctgtctat taaaaaaagc caaaaaacaa aaaaacaaaa acaaacacat gttaggtatt  28080
gataatgttt ccatggatgg aaacagtgat gttagatgct gtgttttttt gagacaaaga  28140
tttttctttg tgtttactct aatgcattat atagactggg cactcagaaa gtgcattatt  28200
ttatataaag aatgctatcc tcgggagatt gacttttctc attcactaat tttttttttt  28260
attcagttaa atgtgtacta atccctgctg tttgatagat tgtttaaaga tgcagaagca  28320
tttctgcttc agggaagatt catggtttat cctattccta atggtggtgg caagatagag  28380
gcatcccctc aaaggctagg agtaatacct caaagcagca gagctgtcca taattatcca  28440
ttatccatta ttccctccac cccgaaaata tagggaaacc tttaaagggt tctttttttac 28500
cctcttcttg gaaagcgtca cttatgttat tcatcgttag cttacatttt ttcatgtttc  28560
aaagagttct gcagtttggg agaatagccc agggaatgaa tctactcgaa ggggtgagtg  28620
taattctcaa tttaggaggc gtttgttgaa gtgcaaatct ttgaagcaga cgttaacttt  28680
tgctgaaggt agcccaggtt gggtccctaa gccaatccat agtgttcctt aaggactaga  28740
gagattctga gacagggagg gcttggtcta ctctcatcca aggctgcact ggtttggagc  28800
tactctggag tctctaggac agacagcaga ttgtcactag gatcagtctg cagattgatg  28860
agaaaataag gcttgtcctc cttctcttca taagggcaaa atagtccttt ggagttatag  28920
gaagttttcc aggtgctgta taggtaatta tattaaggaa tgtattgttt actgttggat  28980
agtgagaaaa atggcttgac taggcttctg gtagataatg gagaggcttg aatggtgcta  29040
tacatgttat tttctcttta cctgagaata ttcttccttt ggaaaatggg ccagattaac  29100
tggataaaac ataagaaagg aattgggcat tactttttac ttatgtatct atttttttgtc 29160
ttatttatac tgtaggcaca gaaagtgtgg tttcagagta gattttaaga cagttaagtt  29220
tctcattgac ttatagaccc tacaactaca gatttgagtc tgttattaat taatagaaaa  29280
gtacattttt catttgtggt tcctttctat ttatctagat tgaaataggc tactgaagac  29340
taaattttgt actgcagcaa tatttataat ccattttaca ggatttgggg atttttgtaa  29400
gattttagtg ttacaaattc caatttaacg tatattgact ttattgtgag attttatata  29460
tcattgttta aagaaaactt tattctggcc agacatggtg gttcacacct gtaatcccag  29520
cactttggga ggctgaggca ggaggaccgc ttgaggccag ggattcaaga ccagcctggg  29580
caacacagca agactctctc tctaccaaaa aacatttttt taagtaaata aagagaaaac  29640
tttattctga gaacatgggc tttggagttc aacagaccta gattccaaca taggccctta  29700
aacttgctgt gtggccttga gcaaattacc ttcttagagt cccagttttc ttatttttca  29760
gatagaaata atacctactt cataggtttg ttgtatgaat taaataaatt attgttgtat  29820
ggattaaata aagttgtgtt tatatggcat gtgataaatg gtagctgttg ttatttctat  29880
tgaactttga tcttgtttaa acatttcatg ttttttttaa atcctttcta gtaaaaaagc  29940
acgcttagat tggaatactg atgctgcgtc tttgattgga gaagaacttc aagtagattt  30000
```

cctggatcat gttcccctca caacacacaa ctttgtaagt tgcagatctc ttctctttct 30060
ggcatgttga gggctttgcc aggcataaca gagatttctc aggtaatatg cgtatgtata 30120
tatatatata gttggattgt ttaaagttct ttatgctgtt gtttacagta aggcaattta 30180
gatttcatta gtcagagata tactctaatt tgtgattatg aattctgtac atgctggaag 30240
tatgattcat tttgtaaaaa ctttttttgga ggccaagaaa tgatgttgtc ttttgtcatc 30300
ttttatttat tcagcataat ttacacctgt gttcttgttg taggctcgga agacgttcct 30360
gaagcttgcc ttctgtgaca tctgtcagaa attcctgctc aatggatttc gatgtcagac 30420
ttgtggctac aaatttcatg agcactgtag caccaaagta cctactatgt gtgtggactg 30480
gagtaacatc agacaactct tgtaaggcat tgttctttta tccaaggaag atagggatga 30540
ggagtataca tactttaaag ggtatttgtt gtagattttg actgacaggt ctggattcta 30600
gactcattta atgaattgtg atccagaaac tactttagaa acagtgataa ttctgaaact 30660
agctaggttt ggtggcattc atactccaga atgagcaggt aggagtagga cttgttatct 30720
gtcaaattga gattgacata ctgtgactgt gattcagtaa ggaaaggagc aaaaggatat 30780
gaaaacaaga agatttttttg cttttcgctc ttaatagtat tatctactag ggttgctagt 30840
agacactgct ctgtatttttg ttgaatatgc tgaatgagcc tttgacattg agaaggagca 30900
gaaagcacgg ttgatgctat tttcttcact tcaaactgga gaaaacttag ttgtttggac 30960
ttaaaattgt ttgaatataa aatcttgaaa gattcttgtt tctttcagga gacaatatat 31020
ttcatataga taaaatgtta ttaaagaatt taaagtttac attaaaagta catggtccaa 31080
actgcctttt aaaaactgta actaggtata tgaaaagttt aaaagttttg tcctttttttg 31140
acagtactag agaaaccaag ggagtgttat tattagacca tgatgaaaac gtttttgctt 31200
tcatggtcac ttacgtattg attttgtgat gagagcttga gtagcacaaa tggcacaagc 31260
ttttaaaatt tatcttattt ttgtccccca ccctttttttt tttttttttt ttttggagac 31320
aagtctcttt ctgtcattag gctggagtac agtggcatga tctcggctca ctgcaacctc 31380
tgcctcccag gttcaagtga ttctcctgcc tcagcctccc gagtagctca gactacaggc 31440
acacaccacc acgcccagct aatttttgta gttttagtag agatgaggtt tcaccatctt 31500
ggccaggatg gtctcgatct cttgacctca tgatctgccc acctcggcct cccaaagtgc 31560
tgggattaca ggcatgagcc accacgccca gcctttttttt ttattattat tttttaaaga 31620
cagggtctcg ctctgtctcc cacagtggag tgcagtggca tgatcacagc tcactgtagc 31680
ctcgacctct cgggttcaag taatcctcct acctcagcct cctgagtagc tgggactaca 31740
agtgtatgcc atcatgccta gctaattttt gtatttttttc tagagacggg gtttcagcat 31800
gttgcccagg ctggtctcga actcctgagc tcaagcaatc tgtccgcctt ggccttccaa 31860
agtgttgtgg ttacaggtgt gagccaccgc atccggcggc acaagctttt gagtctaaca 31920
gacatatgtc aaaatctcag tgttgtcatt aaccataacc acatctgagt tttcgttcat 31980
gcatctgaat aaaggggata ttaccttcct tgcattgttc ttatgaggct tgctgacata 32040
acctgtgaaa ttactaagca caagtgccca cctcatggaa aaaaggtgcc taattactca 32100
cttttctgtg atttattcct tctattttag tcttttatct atgcattttc aagatggaat 32160
gtttccagag aagctgtgtg tgacatagtt tgtgaaatgt tatactgtag tttgaaaaat 32220
attattttga tatagctaga cacaggacca gtatttccta gaaatgcaca ctgggccggg 32280
cgcggtggct cacgcctgta atcccagcac tttgggaggc caaggcaggt gaatcacctg 32340
aggtcaggag ttcgagacca gcctggccaa catagtgaaa ccccgtctct gctaaaaata 32400
caaaaattgg gggaagggat agcattagga gagacaccta atgttaaatg acaagttact 32460
gggtgcagca caccaacatg gcacatgtat acctatgtaa caaacctgca tgttgtgcac 32520
atgtacccta aaacttaaag tataattaaa aaaaaaatac gaaaattagc tgggcatggt 32580
ggtgtgtgcc tgtaatccca gctactcggg aggctgaggc aggagaaccc gggaggtgga 32640
ggttgcagtg agccgccatt acacctctgc actccagcct gggcaacaga gtgagactcc 32700
atcttaaaaa aaaagaaaaa gaaaaagcac acaggagcct gtatgtttat tggcaggtca 32760
gtattattca cattcaataa tcattcaaat ccagttattt ggaatattgt tccctttatt 32820
ctaggtaatg taaaacagtt gaggaaaatg tgactgggaa aagttcagtt ttagtagctc 32880
tgagtttgca aaagcaaggc atgctgattg tctctgtaag attactgcaa gcctaaaaac 32940
cagtctttcc ctgcttttgt ttagattgtt tccaaattcc actattggtg atagtggagt 33000
cccagcacta ccttctttga ctatgcgtcg tatgcgagag tctgtttcca ggatgcctgt 33060
taggtaattt tttacctata gcttttcttt tagaaagtta tttggggtgg tggggttgga 33120
agcttgaaga caaaaaataa gagtttcttc gcattccctc ctctctacgt ggaaacccct 33180
tgctgcttct gtggaacttg atactggtgg tacagcaaaa ggtagaaatt tctgtttatg 33240
gacctgtagg tcttacattc tggaaagtga ctttgactgt agcttcttct gttatcatag 33300
catatttctt aatatgtcat tacattttaa agagcttgag attctgcttt cctcagtatg 33360
tactgagttc aacctcaatg gaaagggtcc taaaacttaa tacagtgatt tgataaaaat 33420
aaaaccctta actttgaaat gcatgttgtg gccgatgcat ttgctaaaac catgtattta 33480
aatagactag tgtctttaaa aacatttaat tagattttca gcataaatat tgtttctcat 33540
gtgtctctga gtttgcatat aacttgtctt tctttactct gttttccagc tttataatca 33600
gttttgttgc gtttatctac tgctcagtgt taacacacat gaatttgaaa cctaaagtaa 33660
aatctacatc caaaatatct tactttaggc caggcacggt agctcacacc tgtaatccca 33720
gcactttggg aggccgaggc agatggacca cttgaggtca ggagttccag actagcctgg 33780
ccaacatggt gaaaccccat ctctactaaa aatacaaaaa actgggtggg tgtggtgata 33840
tgtgcctttt ggcccaggta cttgggaggc tgaagcagga gaatcttgaa cgtggtaggc 33900
agtgagctga gatggcacca ctgcactcca gccttggtga cagagcaaga ctctgtctcc 33960
aaaaaaaaat atattatgta tacacacaca cacacacaca cacacacaca cacacacaca 34020
cacacacaca taatgtgtaa tcagataatg tttaatgtga aaatactatg gaaatattaa 34080
acgcagcata tcttagaata aggaatttgc atatatctgg atatatattt ctgtatggct 34140
tttatttttc ttgataattt gaaaagcaaa tctgaccaag aatttgtagt tacctctgaa 34200
gattagaaga aaccaggcct ctgaagccat aaaacagagg attatgtggg aaggcatttt 34260
tttcaagaca atagaacaat ttcccttaga aaagctggcc tttttccctt taattcatac 34320
atgggtgtta cctgaatctg aacaaacctc gaacgaatct ttagagcaaa taatgaaaat 34380
gttatacctc ttaatgcatg ttcccagttt ggttggtggg gttggtggtg actggaagag 34440
gccagtggtt aatttcacat ttaggtattt ccatctaaaa actgaattcc catttattta 34500
ctttgtttgc tggttgtagc aggtaaggac aaacagaggg taaaatcctg gcctttttac 34560
agacatgctc agcacgtcta cttatctgtt taaataaatt ctcaaattta gtctctaaac 34620
tgggcgtgtt ccaactagct taataggtgg tagcgtggtt gtcaaatgtt aatctgttct 34680
ttcctggaga tgttgtaaaa atttggagta gagtggtgct ttatttaaaa aaagaaaact 34740

```
tataatgcac tctccttttc attgaattcc caatacatgt attatttcct gttccaaatt  34800
ttgtatgcaa aagcacctag acttaagata atttttagat gtcacacatt tgaaagaatc  34860
aaacattttg tcaaaggttg tacaggtaga gtttgccctt aagcatctta cttagtcaaa  34920
tatgtacttg aaagacttca ccagtatgaa agcctaagtg ccaatcatgg aattttcttt  34980
ctcctcctag ttctcagcac agatattcta cacctcacgc cttcaccttt aacacctcca  35040
gtccctcatc tgaaggttcc ctctcccaga ggcagaggtc gacatccaca cctaatgtcc  35100
acatggtcag caccaccctg cctgtggaca gcaggatgat tgaggtaata gggcaccttg  35160
ggggtggtaa tgtcagtcaa ttaatggggt gaggttgata cttatttcag agttttgggt  35220
ttcaaatctg atcaaggaat gttgcaacac tttctcaggt ctctggactt ttacagttta  35280
ttttatatcc ataatatctt cagactggct gaatagtctg gttagtatat cattcaactg  35340
gagaactaaa acttcctgaa aaaatgttaa catttgaact cttcccatta tcagatttga  35400
ataggctatt aatgaacaag tgtctaagat atttaaagag cagtttagtt ttggtgtggg  35460
acagaaatta acagtgatgg agaactacag attctctgga agacttttgt gattttattt  35520
agaaataaaa gggtggagtc ctaggacttt aataagcagg tgtttgggga gatgtcaaag  35580
tgcccaaagc tagtgttttt gaactgcttt ttcttctctt ggctttttgg ttatgtccta  35640
ttggtttaat ttgctttctg cttcatcttt aataacaact gaatacactt aaatacttcc  35700
tttgttcttt attcttcttt atttctcatt gctttggact agaataacaa cctgagtgct  35760
tctcccaggg catggtccag acgattttgt ttgaggggaa gagtaggtat ttttcttcat  35820
gcctttgctt tcttgtaatt aacaggattg ctaaaactgt cagacagcag actaccaaaa  35880
atgaaatagt tgctaagtta aatttatatt tcttgtcact tgtttccatg ttttcttttt  35940
ctttctttct ttttaaaatt ttttttggca gtagagtata tagaagtaaa aaaaatgttg  36000
tatgtggtat tgatgatagg tgaaatgaat ttctgaagtt aggccaggca tgacggtgta  36060
tgtctgttgt cccagctact ccagaggcta aggcaggagg atcactggag cccagaagtt  36120
ctaggctgta gggagctaca attgtgcctg tgaatagcca ttgcactcca actggggcaa  36180
cataataaga atccacctta aaaacaaaca aaaaatgtta agttagattt tgaggccaag  36240
ggcattaaaa agtttttttt ttaaatcaat tccaaccaaa ggctaatgtt agacttactt  36300
agttggtgct cacagcattg gtattctgtt tatacattag taaccaaatg tgtttttggt  36360
tgataaaccc tagaataaat attctttatt gaaagcttat cagagacaac tatgctctct  36420
ctcatcatgt agacacctgc tgcgttaggc acagtttatc tcattcagac ctcaaatcac  36480
tttcaacata attgtcctgc cactattgtg aggagatcat gtataagcta taaattttat  36540
tattttgact ttatcattat gattagtcct gataatacaa taatatacca gttactgcta  36600
cttctattaa atggtttgtt cctgtatgaa cactgtaata cttacaggga acagtaaagg  36660
tcagaattgg ctgggtggga agatcacttg cgaccaggag ttcaagacct acctgggcta  36720
tatgtagcaa aaccccacct ctacaaaaaa aaatgtaaaa attagctggg cttggtggtg  36780
tgcacctgca gtcctagtta ctcaggaggc ttgggcagga ggattacttg agcccaggag  36840
tttgaggttg tagtgagctg tgtatgattg tgtcaagtaa gaatttttga gtttttatta  36900
taaaagaatt agcacaattg ttgtgcctaa tcattttttta ctttagaagc agggtaaatt  36960
ttgattcctg ttaatttaat cacatataag tcagcatttt taaagtagac taattgttgc  37020
tttattcaaa ttatttgtgg gtctcaaatt attcatagtt ctcttgagta tttagactcc  37080
```

```
aggaacaata ggaaaattct ttctagaata aattgatcca actatagaaa ttagcacaga  37140
ataaaatatg ggatatttaa ttgatacagg gaagaaaatt accataacat taaggaaaat  37200
attctgctac ataggaatat aattgtggtt aataaaaata aattgtgctt tgctttaaaa  37260
acaaagaaca gcttagttgg ataatgaaat tacagctgcc gatttctatt gaaatccaca  37320
ttattttttg ccagtgtttt gcccacctgg cagttatcct gctgtactta aaaacacaca  37380
ttcctggact tctcacattc ccctccaaaa catgctcagt caatcgtggg tcggggatta  37440
ggggtggatc ttcattcttc tttccagagt cagaatcact ctccaggtaa ttctgaagac  37500
tagctagttt tgggaaccag aactaggctt tcttgttaaa ttccgaatta tgttttggga  37560
gcaggggaac agcttggttt gattcttttt atctaattat ataattagat atataatttt  37620
atctttttat ataattgagt gggagcattc tagtaatagt tgtgtggaac aagtatcttg  37680
tctatactgt agttacacaa agagaatata gtaggacttc cccccaaaaa atgtcctttt  37740
ttaggatatg ggggccaagt ggtttcatat tattctatta tactgttcta ttccaagcga  37800
tgaattttag attggggttt aggtctcatg gagccctctg caatttaaac tattttccaa  37860
acagtttcta ataaattcta aagatagcct ttgctttctc ccatgaggag aatgtaaccg  37920
atttccaaat ttacccataa ggcagtgttt tgtggtgaaa gagctgaggg ctgagatcca  37980
tatatgatgg tttctggttc tatttctgcc acctactggt tctgccaagt gaccctgcca  38040
agtctctcta cctgttcaga tgtgttttct tatatgtaaa atgtaggttt tgaacttgga  38100
tttgtggtct ttccagcttt ctgtgatttt aggcttggat aaagtatata ggctgcttac  38160
ctttttcaaa tccaacttct agtcaattta gcctaactcc ttgtggagta agagtgagct  38220
tcccccagaa tccacctccc caccctggct ttttaaaaaa agttttgagc ctcagtggaa  38280
caagaatccc aatctttgga agggtctcag ctgagagtaa ctttgctagc ttcccttgaa  38340
agagtatgtt tgttgtgtac attgctttct tttgagaaaa agaatgtggt tttcattata  38400
tatgaaaaac taataccagg cttggcacgg tggctcacgc ctgtaatccc agcactttgg  38460
gaggccgagg cgagaggatc acctcaggtc aggagttcaa gacgagcctg gccaacatgg  38520
cgaagccctg tctctactaa aaatgcaaaa attagccggg cgtgctggtg cacacctgta  38580
atcccagcta ctcgggagac tgaggcagga gaattgcttg aacctgggag gtggaatatt  38640
aaatccttct aatatttaat gaaaaatcag ccttggagat actggccact gatatttgct  38700
gaatttaatc aaggaacgtt gattagagta tgtttaggat ttctatggtt tttagaggtt  38760
tttataatct attttgttct tgcacatcct cctcctcttt tttccctccc ccagagaaaa  38820
tcttttgtgt gtaggagttg accagctttc cttttctgtt tcaggatgca attcgaagtc  38880
acagcgaatc aggtactttt ccatagtcat ttagccaaca ataatgggct ttttttcttt  38940
atgcggtgta tcttctgttg gcttatcctt gtgtggcttc tgtttgtctt gtctattaag  39000
cctcaccttc agccctgtcc agtagcccca acaatctgag cccaacaggc tggtcacagc  39060
cgaaaacccc cgtgccagca caaagagagc gggcaccagt atctgggacc caggagaaaa  39120
acaaaattgt gagtatagac aacagtacct cctgccaatt agggttcagt aagaaaaacc  39180
tcgttggaaa ttagaatact taaacttatt ttgggagaag attctaataa aatacattca  39240
atgaaggaga ttataaatgt cactgtcatt tttggcacac ttgcatcaga cagtttgcca  39300
gtgctataac taaaatggta tttctcaaaa gacaaaaatt ggaagtatgg ttaatatgtt  39360
tatctttaaa agatatggaa acagatgaca tgggttgatc ctttgatgcc ctcattatca  39420
aaagattatt accattgcat ggagtataat aatgatctct acttgtttca gaggcctcgt  39480
```

ggacagagag attcaagcta ttattgggaa atagaagcca gtgaagtgat gctgtccact 39540
cggattgggt caggctcttt tggaactgtt tataagggta aatggcacgg taagcttggg 39600
gccctccctt tactaactgc agggctttgg tgtgaagtca agtttcagcc caggggggcca 39660
ggaggaggag aggactgagt gctcctgggc ttatagcagt actctccctt acatacttga 39720
ttatacctga agattgaact taattctttt tagactaagt tcttataaag ctcccaggat 39780
aattagaaat tagtgaataa gacttgagcc ctataatcaa atgtcaggag tacttctcct 39840
ttaaactgat taaatacagt ctgcacatgg gtcatgcttg gaagctcctt aagtgagcaa 39900
gagtctgctg ctatggaggg agcatgggtt ctagaaactt taagctggaa aggaccttag 39960
agattgaaat ggggactgat ttgcccatgg tcatgcagtt aggcatagga aagctggaaa 40020
tctcctgaag taacttctct ttgtcctgcc ctaggattag ctgtgggtgt ccctatcaaa 40080
cagggaaggc attgacttaa ttcttgaatc tatgtggaat attaatgttc tgattttaat 40140
ggaaacactt tgtcacttgg aagaaaggta ctatttaact tatgtagtta cagcttgtgt 40200
attttggcaa cactgaacat tttggcaaca tacttagcat ttctctgtta ggtttttaat 40260
gcctctggct ttaggacttt gggaaataat aggtatttcc ttgaaaatgc tgcatgttcc 40320
caaaaagtca tctcttctaa attcagatta taataaagca aaaatcacag agtcccttgg 40380
tgcctatact actttggatg acactggaat tatctttaga gataaatgtg caaagattga 40440
gagaagttaa aagcatcaaa tgaatggagt attaaaattc aaggtactga aaatatcaaa 40500
cccccccat ttttaggacc tgggggtttt tttttttttt ttttttttt ttttttttt 40560
tttgagatag attcttgctc tgttgcccag gctggagtac agtggcacaa tcacagctca 40620
ctgcagcctc caactcttgg gctcaaacag tcctcctgcc taagcctccc aagtagctgg 40680
gaccacaggt gaatgcccag ctaatttgtt ttaccttttg tagagacaag gtctcactat 40740
gttgcccagg ctggtctcca actcctggac tcaagcagtc ctcttgggtc tctcaaaatg 40800
ctgggattac aggcatgagc cactgtgccc agccttacca tgtgctcgtt aatgcatggt 40860
ttttaccact tgtaattaat catctgacca atttctagtt ccttaagagg attggcaccc 40920
gactgaacat ttgtaaagta catgtggaat gattcctttt cctttgaaaa ttgcatctgg 40980
ctgggcaggg tggctcacgc ctgtcatccc agcactttgg gaggctgagg caggcagaac 41040
acttgagcct aggagttcaa gaacagcttg ggcaacatcg tgaaacccca tctctaccaa 41100
aaattaggta gatgtgatgg cactcgcctg tagtcccagc tacttggaag gctgaggcag 41160
gaagattgct tgagctcagg aggcgaatgt tgtagtgagc tcaatacagt gagtacacac 41220
tactgtactc cagcctgggt gaaagggcaa gaccctgtct cagaaaaaaa aaaaaaaaga 41280
aaagaaaatt gcatctagta tgtactactg ggctgtctcc tgggtcccag agaaatgata 41340
ctgttgtaga atatttattt atatgtattt agagacaaga tctggctctg ttgcccaggc 41400
tggagtagtg gcacaatctt ggcttactgc agtctctgcc tcctgggctc aagctagcca 41460
tcctcctgcc tcagcctccc aagtagctag gactacaggc acatgccacc acacccagct 41520
aatttttgta ttttttgtag agatggggtt tcgccatgtt tcctagactg gtctcgaaat 41580
catgagctca agcgatccgc ctgcctcggc ctcccaaagt actgggattg caggtgtgag 41640
ccactgtgct cagccagttg cagaatattt tagatggcat aaatatctcc aggatttctt 41700
aggaaagaac acaagcactt tgtgggatag agcacttgtg tctgagataa caaggctgct 41760
agtagttgta ggaggcagag caatggatat tgcatttatt gcttctgtta gcattagaac 41820

-continued

```
atttttatat cacattttaa aagccccagc taaaagccag cggatgaagt tttaagttgt  41880
acccaagttt aattttcctc tggttgcgca ctttcatttg gggattcata atttttcaag  41940
gcattggtac gtggtactgc ttctgagctt tgtcttctct caatagagtg agctttcaaa  42000
ctgtgataaa gattatttgt tacagtgtta cttccataaa gactgctatt agaatgtaga  42060
taacttgttt ttaagattct aggtttttta ggccaggtgc ggtggctcac gcctgtaatc  42120
ccagcacttt gggaggccga ggtgggtgga tcacgaggtc agtagattga gaccatcctg  42180
gctaacacgg tgaaacccca tctctactaa aaatacaaca aattagccgg gcgtgggggt  42240
gggcgcctgt agtcccagct actttggagg ctgaggcagg agaatggcgt gaacccggga  42300
ggcagaactt acagtgagcc gagatcgtgc cactccactt cagcctgggt gacagagcga  42360
gactccgtct caaaaaaaaa aaaagattct aggtttttta agtcagaaag tctcaaaagt  42420
cagaggagtg aggagcagtg gacttttatg ccatgctttc agaaagcaag ctctggtcta  42480
tgaatgaaga agaaaaatga gtggtccagg aaacataact tctagattgt tttgtgcaat  42540
actttttcc gccatattct ggttcctgta tacagtatat ctgttcagta tcttaaaaat  42600
tacaactgtt ttcatgattt tgattgaaga ttttttaac tcagcccacc cacttatgga  42660
agtaaagcag aaagggtctc aaagcaactc agaagcctca ggtgcatgat ttaaaactca  42720
acatatttat ttaaagcagc atctgtcagg cccaaagctc acaacctcct tttgggcatt  42780
aaatttggca tcaaggctgg gtgcggtggc tcatgcctgt aatcccagca ctttgggagg  42840
ccaaggcagg gagatcattt gaggtcagga gttcaagacc agcctgaccg acatggtgaa  42900
accctgtctc cactaaaaat aaaaaaatta gccgggtgtg atggcatgcg cctgtaatcc  42960
cagctactta ggaggctaag gcaggagaat tgcttgaacc caggaggcga ggttgcagtg  43020
agccaagatc ataccacagc actccagcct gggcgacaga acgagactct atctcaaaaa  43080
aaaaaaaaaa agaaagaaaa attctttctc taggccaggt gtggtggttc acacctgtaa  43140
tccctagcac tttgggaggc tgagttggga ggatcacttt agcccaggag atcgagacca  43200
gcctggacaa catagtgaga ccctgtctct acttaaaaca caattagctg accatggtgc  43260
tgtgtgtctg ttgtccccgc tactcgagaa actgaggcag gaggatcact tgagcctggg  43320
agatagaggc tgcagtgagc cgtgataaca ccactgcact ccagcctggg caacagaaca  43380
agaccctgtg tccaaaaaaa aaaaaaagaa acttaaggag tttatattct agtggagaca  43440
gtaaacagga aaagtagaat atatagtatg ctgtaattgc taaggagaaa aatggaggaa  43500
aggagatatg gagtggcagt cccagttcaa tgtttttaat aggttggtca gggaggaatc  43560
tgccaagaaa gtggcatttg catggagggc gagggtgggt ggtgcagata tctagggaag  43620
cagtaacatc aagtgcaaag tggaccactc acctggcctg ctccgagaac tcaaggagat  43680
cttatggctt catttagagt gagtgagagg tatactaata ggagtgaggt ccagtggtag  43740
ggtgttttag ggtcctgtaa agactatcat ttgggttaaa tgggatctgg ggttgtacga  43800
gacctttagg aggtttggca agcctttgtt tgaaaatgag tgtgatgaga gagctcatta  43860
tctgtctgag agcccattct aactccaggt agttcctact agtagaaaat agtttgattg  43920
ggtgcagtgg cccacatcta taaccccaac actttaggag gctgaggtgg gagaatcact  43980
tgaagtcagg aatttgagac cagcctgggc aacatgagac ccttgtctct acaaaaaatt  44040
ttaaaaatta ggtgggcgtg gtgatgcaca cctgtattgt agtcccagtt acttgggagg  44100
ctgaggtggg aggatccctt gagcccagga gtttgaggct gcagtgagcc gtgatggtgc  44160
tgctgcactc cagcctcggt gacagagcaa gagccagagt ggggcgaggg gagggcatgg  44220
```

aatagttctt tattagagtt gaaatccgtt ttcctataat gtttgctcat tgatcctagc 44280
agactgaatg aatccctttc atggcagtcc ttgggttatt tatatgtaaa tgaggggaat 44340
gctgcagtat agaacattcc ttctggattt cataagaaat tgcaaataat ctgttaccat 44400
aactgtgtta acgagagctg gctggcagat ggatccctgc aagtaccatg ggcactgtct 44460
ttggttgacc ctgttcagtc ttcccatcag tgacttaatc agaggtgtga tatgtatttg 44520
catagtagtg cggatttaga aaagcgagaa gagttcaact ggctaggatg atggaaaaaa 44580
gaaaagatca ccttttaaca gagataagtc atattcattg ttccaaaaag tagaactgga 44640
gggggaagat gtggcttaat gataacgtgt gtggaaactg ccaaggaagt tcagccgact 44700
gcaaggtcag agtaagtcac tgcgtgggct tggctctgaa ttctgaggtt atattactga 44760
ttagggccag aacaggtgac accaaagggt gggttcagtg acaactagag catgcccaga 44820
ggagagctat aagaaaggga atggactaca aaacgaggtc catgaaatag gaaggtcctt 44880
agaagcagtt ccccctgagc gatcatccag catctcccaa gccacatgcc tgaaccccta 44940
gccctgtcct gtcccctccc gttaaaggct ctgccctttt ctgggtcctg gagcctgggt 45000
catagcgttg gccattttcc cagcacttcc actcagttga ctgcctcatt gggtcagttt 45060
accttcacag gatttcttat cttcatccct tctttctgag tccccacagt caaccattct 45120
tcttgtacct ttcctgagct attgcagcag attcctctct ggtctccctc tttctctcct 45180
acaggtgtcc aaatcctacc ctagagttta ctaaacacag ctcaggtttc tctcatcccc 45240
ctcacctcac ctttatttct gatgtgccca gtctgaaaca ttctctgtcc tatttactaa 45300
aatccttccc ttggtttata gcccatttcc ttcagaaaac ctttctgtat tctctttgaa 45360
aagagattta cttaggcacc tgtagtccca gctgcttgga aggctgaggt tggaagattg 45420
cttgagccca ggagtttgag gccagcctgg gcaacatagt gaggccccat ctctaaaaaa 45480
gaaaaaaaaa aaaaaaaagg atttactccc ccatcttggg gaactcccct tctgttccag 45540
cactcctgtc ttggctccaa ctgtaccaga atggacactt atgcaaatga ttgttgtcct 45600
cctactcagg gctggttata cacgtttccc atatggtgtc ccatatggat ccatttttct 45660
agatagaagg tagctccaaa catagtgtgg atctctccca tccagtcaac agcaccttca 45720
ccggcagccc atggcaaaca catgtgcagg ttaactggat gagagccact ttggaggctg 45780
ctgttaaaac atggggactc gttgaaactt tagatgataa aaccagagat cacagggaga 45840
cagtttgggc ctatcgtgag gaccatctct ctaccaattt tcttcccaaa aatgaaatgg 45900
ggagggctgg gtggggtggc ttacgcttgt aatcccagca ctccaggagg ccgaggcagg 45960
cagatcattt gaggtcagga gtttgagacc agcctgggca acatggtgaa accccatctc 46020
cacccaaaaa tacaaaaatt agttgggcat ggtggagcat gcctgtaatc ccagctactc 46080
gggaggctga ggcaggagaa tcgcttgcgg aggttgcagt gagccaagat tgtgccactg 46140
cattccagcc taggtaacag agcgagtctc catctcaaaa aaaaaaaagg aaggaggaag 46200
gctccaacag agaggctcca gaaacacttt taaaagtggc ttttggccag gcacggtggc 46260
tcatgcctgt aatcccagca ctttgggagg ccgaggtggg aggcctcaca aggtcaggag 46320
atcgagacca tcctggctaa catggtgaaa ccccgtctct actaaaaaca cacacaaaaa 46380
attagccaga cgtggtggcg ggtgcctgta gtcccagcta ctcgggaggc tgaggcagga 46440
gaatggcgtg aacctgggag gtggagcttg cagtgagccc agatcacacc actgcactcc 46500
agcctgggtg actgagcgag actctgtctc aaaaaaaaaa aaaaaaaaaa agtggctttt 46560

-continued aaatttatag cactctaaag tggaatggat ccctggatgt gtctaaagtt atatcaagag 46620
gctggtttta cagtgcttga caatcagttg tcagtgttat aggtagaata gcaattggag 46680
tcagactggg gttttgatcc tggctgcagc gttctttgtt ttttggctgt atgaccttgg 46740
gcaagtgact aaacttctca gcttgttgtc tgtgaagata aattatttac gtcagagggc 46800
agctgtgagg attaacagag ataaaagtat acacagtgcc aggattcagt attattagaa 46860
ttacttttta atggtattga aggcagagaa gcttaatttc aatatatatc tctgaatttt 46920
tactagggac catcttaggt ctcactgaaa tgtggattca gagttcagcc tcaatagttg 46980
ctaaatggcc tgcttcctta caccagcaac cagccccagt cattctgtat ttgccaggcc 47040
attcatatgt atgcactgat ttcatcccca caggacaagg ttttgacctg tcacacatga 47100
cctcacctct gtggcttgcc agggttggtg tgaatagttt aaccaaggct atcgaaggcc 47160
taactgtagc gatagcagtt aacctatgta actttttga gtcatttgaa ttatgtagag 47220
attggacctg taatcccagc actttgggag gccaaggtgg gaggattgct taagccctgg 47280
aggtcaaggc tgcaatgtgc cactgcactc tagcctagac aacagagtga gaccctgtct 47340
caaaaaaaaa aaaaaaaatt ggaaatttgc cgtatctgtg taggtatgtg attctttgga 47400
taaatgattc actgtatctt cctcaaaact aggttatttg aaagactgag atcattcaac 47460
tgattgcact gactgccaac taattttgca ggagatgttg cagtaaagat cctaaaggtt 47520
gtcgacccaa ccccagagca attccaggcc ttcaggaatg aggtggctgt tctgcggtga 47580
gtagaaagct ggcggtccag tccctctgga gtgctggagt ggggagtaca aggactgtag 47640
agttagtgga ctgtgccgca ggttgggacg ggcaggcagt taggactcac tgtggagttt 47700
ctgtggttgg atgctcctcc cttgagagca aagggatgtt tcctttagtt tatgtggttg 47760
tcaagccttt cgaagagccc ctttttagga gaataccctc ctctgggcac agtaaactca 47820
atagcccaat ttctgtctct gggttttggt ttgaggtggg cagaaatagg ccctattttt 47880
acctttattt cccagaaccc ttttttttat agctgagttg ccttatttta gacttcagaa 47940
cagtcagctt tccaatcttt cagtcactat ttagacttgt aggaataagt catataatgg 48000
agacttctac aaggagtcct tgtgacctcc acaggagggt catggagtgt acattgatga 48060
aagagaatgt cctctctgta agcaaggctg gcactgaact gatggcccag tgaactaatg 48120
gtgggcttct gtttgctcag aatgccaccc gggttatcag ccgtgccatg tgtttgtttt 48180
tgggactggg ggtggtgttg ggactggggg tggtgtcgac agcacagaac ccactgtcca 48240
cgggaaagca cagtagacct ccctgagcac tttcctcctc cctctcctct cttcccctcc 48300
cctccccagc aaaacacggc atgtgaacat tctgcttttc atggggtaca tgacaaagga 48360
caacctggca attgtgaccc agtggtgcga gggcagcagc ctctacaaac acctgcatgt 48420
ccaggagacc aagtttcaga tgttccagct aattgacatt gcccggcaga cggctcaggg 48480
aatggagtga gtagatggtc tgatgcctct ctgggaccca ggcatcaaat ttgtccctaa 48540
attggaacca ggatcaggaa aagccttcta gtccattaag cgattctgtg atatctttgc 48600
acaagcctct ggcctgggct ggagggggcca attatcagga atgagttgtt caggttccag 48660
ctgggtgggg tggctcacac ctgtaatccc agcactttgg gaggccaagg ccagtggatc 48720
acttgaggcc agtagttttg agaccagcct tgccaatatg gcaaaaccct gtttctactg 48780
aaaatacaag aatgaaccag gcctggtggc acatgcctat aatcccagct actcaggagc 48840
tgggacagga gaatcgcttg aacatggaag gcagaggttg cggtgagcta agatcacgtt 48900
actgcactcc agcctgggct gcagagcgag actctgtctc aaaaaaaaaa aagagaagtt 48960

-continued

```
caggttcctc cttgggactg aacttccccc ttggggctca gatttgggct ctgcctgcta  49020
ccctggcttt atcagaaacc tgagaatata gtggggtgca tgtaccttct gcttggacag  49080
ctgtggcaat gccttctgct cagctgtctg aggcatggct gtcccacatg agggtttaag  49140
cagatgttgt ttttgggata attttttttt tttaattaaa aactttttcc tggccaggca  49200
cggtggctca tgcccataat cccagcactt tgggaggctg aggcgggtgg atgacgaggc  49260
caggagttcg aaaccagcct ggccaatgtg gtgaaatctc atctctacta aaaatacaaa  49320
aattagctgg ttgtggtggc aggcgcttgt aatcccagct actcgggagg ctgaggcaga  49380
agaatcactt caacccggga ggcggaggtt gcagtgagtg gagattgtgc cattgcactc  49440
tagcctgggt gacagagcca gactccatct gaaaaaaaaa aaaaaaccca aaaaaaccac  49500
actttttcc ttagagacac aggttctcac tctgtcacct atgctagagt gcagcggcgc  49560
aatcatagct cactgcatcc ttgaactcct gggctccagc tatcctcttg gctcagtctc  49620
ataggttgct gggactgcag gcacatgcta ccgtgcccag ctaattttcg tgtattttgt  49680
agagtcggag gtctcactat gttgcccagg ctggtctcaa actggactca agtgatcctc  49740
ccacctttcc tggctagcct agggtagtgc ttctcaaact tctcctctga agtagaggag  49800
ctcctcgtac ccctagacat ctgggagtta ctaagctata gctgtgcttg caagtcctac  49860
ataaattctc acactgtctt taaaattcat atggaagttg ccttctgtgt attttaagaa  49920
atggaatgac ttttcagaaa aattgagata taattcatac atcataaaat tccccctttt  49980
aaaatgtaca cctacctcag tgtttttctg gtattgagtt gtgcagccac caccactatc  50040
taattttaga acattttcat tatcccggaa agaaacacat gcccattgta ttagtctgtt  50100
tgggttgctc taaaggaaga cctaagggtg ggtaatttat aaagaaaaga ggtttatttg  50160
actcggggtt ctgcagactg tacaaaaagc atgacaccag catctgtgtc tggtgaggcc  50220
ctcaggaagc tttcactcat ggcagaaggc aaggggagcc acgtgtgatg tggtgagaga  50280
aaggagcaag agagagagca tggagggagg tcccagactc tttaataacc aggtttcatg  50340
tgagctaata gtgtgtgaac tcactcgtta ctgcagggag gccaccgagc cgtttgtgag  50400
gaatccatcc ccatgaccca aacacctgcc acttaggtcc cacctccaac actggggatc  50460
acatttcaac ttgagatttg gagtggacag atatccaaac aatataccca ttagaggtta  50520
cccaatacct cccacccact tgcagtctac tttctgtttc tatggatttt gcctacttta  50580
tagttcaata taaatggaat catgtaagat ataatatagt caggtaacat ataatgatgt  50640
ttcggtcaat gaccacatat aggaaggtgg tcccacaaga ttataatact gtatttttac  50700
tgtgcctttt ctatgtttgg ctatgtttag agacacaaat actcaccatg ttacaaccag  50760
ctacagtatt cagtacactg agggccatac agttttgtag cctaagtgca acacgttata  50820
ccatttagcc agggtgtgta gaaggctgta ccttcttggt ttgtgtgaat acactttatg  50880
atgtgtgcat gatgacaagt tggctaacaa cacatttctc agaaggtatc cctgccgtta  50940
agtgatgctt ggctgtatat aatacataag atatggtatt gtgtgcctgg gctcttagac  51000
ctagcatagt attttcaagg ttaatgtgta gcatgagtca ctacttcatt cctttctgtg  51060
tctgagtaac attccattgt atggatatgc cacattattc attcatcatt tatggacatt  51120
gggttatcag aattacttta gagtaaaact gatgcttgaa gaagtgtcag caatggtcag  51180
gcgccagggg cccatgcctg taatccaagc attttggagg ccaacatggg aggatcactt  51240
gagcccagga gtcaagacca gcttgggcaa cagtgcaaga ccctgtatct acccaaaaaa  51300
```

-continued

```
aaaaaaaaaa aaaaaaaggc ggcatggtgg cacatgcctg tggtcccggc tactgggagg  51360
tgggaggatc acttgagccc aggaggttaa ggctgcagta agctattgac tgcactccag  51420
tctccaaaaa aaaaaaaaaa aaggtgtaag catgtttgtg ctgtggcctc accttcaggt  51480
aagcagtgat gtgaaccagg ctgaacagca cagggtctat ccctgtgtgt aacactcctt  51540
ggagccaggc cttcagtggc tttacttctt agctgtagtt taaaactgct ttctactcat  51600
gcccctcaaa cttattttta ataatttctt ttcccttcac agctatttgc atgcaaagaa  51660
catcatccat agagacatga aatccaacag tatcctttgg ttgttgagtt catttgactg  51720
ctcggttcta aatttaggga aacagaaggg aggctttcta tcacaagtgg ctctcggtgc  51780
caggggatat ctttttaagg aaagaggcag aggacaggaa aacagaaaag tcagaaaatt  51840
agtaggcttg gcctgtccct cagcagctta tgcctcacct ggactgatga gagcgatgtt  51900
taggttaggt tcctttctga gtttatctca gcaaaagtga tttggagaga tttccgtaag  51960
cttgaaatag gcataatttt atcacactat tagtaaatgt aacctgacgg ggattgggct  52020
tttgtcttaa gtttatttct agtttgtggc cagcgtgtgt atgtctatct gcttgttatg  52080
tggatagcaa gtagctacaa gccaaatgtt gaaaggtttc caaaatcact aattaaaata  52140
gtctttcttg actgggcgtg atggctcaca cctataatcc cagcactttg ggaggctgag  52200
gcaggtggat cacttgaggc taggagtttg agacttgcct ggccaatgtg gtgaaacccc  52260
atctctaaat ttaaaaatta gctgagtgtg gtggcacgta cctataatcc cagctactca  52320
ggaggctgag gcacgagaat tgcttgaacc tgggaggcag aggttgcagt gagctgagat  52380
cacgccactg cactccagcc ttggggacag agcaaggctg tgtctcaaaa aaataaataa  52440
ataaaatggt ctttctcaaa ggtacataag tgggttcttc agaagtcact attagaagag  52500
gagaggggtt gtttttatag aagagtaaat gaagaaaggt atttttaatg ctgtgaggcg  52560
tgaaatttaa caattttgaa tctgccaccc tccacgagcc tttccttgtg aaagaaagat  52620
ggcattacaa cccacgtttt gcctcttgag cagtgagagg catgatagtt gtgttggatt  52680
atgggacatg gcctatttta ggtacatgtc tgaggtgtgg aacacctttc agtggtgggg  52740
tttttagcag ccaaacatta taccatgaaa gcagacacca cagatttaag gaggtgtgaa  52800
ttcctgggca ccaacatcac aagttacttt gtgtgtgttt tgttttttaa tttttgttc   52860
tttttaatt tttttttcct cacaagtttg acttaaactg tatgacttct ttacccagaa  52920
gcgagccgac ttcagttctc attttgaagt cactgagtgg taccgattct agtgaggaat  52980
ttcttactac aacattgaac actcagtaag ggatttgcta ttttgttaac cactcaagtt  53040
tcagatggtg atttgagggc agaatacagg cagaaacgac tgtaagctgt caggccatcc  53100
ttggccctct ggggagcact ggagtgtggc ctctgctcat cctgttaggg tttcaagtac  53160
ctgtattatg tggaaaggtc acaaggccag agacccagca cctagatgtg caaatgggga  53220
gaagaagcag ggaagaaacg ctggcttgct tttggctagg gccaaataat ctggcacatt  53280
gaccaatccc tgcctgtctt ctggaagaag gtgcatttca aaagcacttt aaagaacttc  53340
agaaacctta ggaagttcag tgcagagagg ctgtgacaga ggtaaggtgg agagattacc  53400
gtgttataaa gaactttggg atatttttca aaattaacct gaccattctt ttgaaaccag  53460
agtccttaac aagcattgag atatatttct ccatgaaggc ttaacagtga aaattggaga  53520
ttttggtttg gcaacagtaa agtcacgctg gagtggttct cagcaggttg aacaacctac  53580
tggctctgtc ctctggatgg tgagaatctg ggctcccacc agcagtctct ggtatagggc  53640
aaaaggaatg ccttggagat ttatgtgcaa acttaaagcg tttctgtaca tttccccgaa  53700
```

atccacatga cccctagtga cagccagcct cagggcaatt gtagattttc ttgaggaagc 53760
tgttgatcag aaccactgtg aagcttagtg tggagaggag ttaataagct gggtgacaga 53820
aatgctgggt cttggtcctt taaagacaag gattcctgag ctgttttaac cagtgcctga 53880
gttggagtcc tttgggggaa aagctatgtg gggactgaag aatggactca ttcataacta 53940
atgaaaggga cagcctggcc cctagatgtc tgtgaggcct gtcatatggt gataaatgca 54000
cttttgtcat atggtgatac atgtaggccc cagaggtgat ccgaatgcag gataacaacc 54060
cattcagttt ccagtcggat gtctactcct atggcatcgt attgtatgaa ctgatgacgg 54120
gggagcttcc ttattctcac atcaacaacc gagatcaggt aagtctgtgc tggtgcgaaa 54180
ggacccaact cgtgggagcc cctgggcctc cgccagccta agcagctaga gggttaggac 54240
ttgttattat ctgttgttca ttcacccccc attagctcag ctgtttcctt tcccttagat 54300
catcttcatg gtgggccgag gatatgcctc cccagatctt agtaagctat ataagaactg 54360
ccccaaagca atgaagaggc tggtagctga ctgtgtgaag aaagtaaagg aagagaggcc 54420
tctttttccc caggtaaggc tcagggctgc tagaatgtga ttaaagcatg ggttggttcg 54480
taaagatggc aatataaggt gggagtgttt tgttttgttt tatagggagg ggacccaggt 54540
cctctacaag atggtggggg gcagggtaca tcctgtgtct ttgagacaca gctaatgaga 54600
gcattcttgg gctttgtttc agatcctgtc ttccattgag ctgctccaac actctctacc 54660
gaagatcaac cggagcgctt ccgagccatc cttgcatcgg gcagcccaca ctgaggatat 54720
caatgcttgc acgctgacca cgtccccgag gctgcctgtc ttctagttga ctttgcacct 54780
gtcttcaggc tgccagggga ggaggagaag ccagcaggca ccacttttct gctccctttc 54840
tccagaggca gaacacatgt tttcagagaa gctgctgcta aggaccttct agactgctca 54900
cagggcctta acttcatgtt gccttctttt ctatcccttt gggccctggg agaaggaagc 54960
catttgcagt gctggtgtgt cctgctccct ccccacattc cccatgctca aggcccagcc 55020
ttctgtagat gcgcaagtgg atgttgatgg tagtacaaaa agcaggggcc cagccccagc 55080
tgttggctac atgagtattt agaggaagta aggtagcagg cagtccagcc ctgatgtgga 55140
gacacatggg attttggaaa tcagcttctg gaggaatgca tgtcacaggc gggactttct 55200
tcagagagtg gtgcagcgcc agacattttg cacataaggc accaaacagc ccaggactgc 55260
cgagactctg gccgcccgaa ggagcctgct ttggtactat ggaacttttc ttaggggaca 55320
cgtcctcctt tcacagcttc taaggtgtcc agtgcattgg gatggttttc caggcaaggc 55380
actcggccaa tccgcatctc agccctctca gggagcagtc ttccatcatg ctgaattttg 55440
tcttccagga gctgccccta tggggcgggg ccgcagggcc agccttgttt ctctaacaaa 55500
caaacaaaca aacagccttg tttctctagt cacatcatgt gtatacaagg aagccaggaa 55560
tacaggtttt cttgatgatt tgggttttaa ttttgttttt attgcacctg acaaaataca 55620
gttatctgat ggtccctcaa ttatgttatt ttaataaaat aaattaaatt taggtgtaat 55680
ggctggctgt tacctccttt taaagtaatt ctgagctcac aacttgaatg ccccatttgt 55740
tcaccctctt caggagcaga attcaagaac aggaaatgtg cccagagcct aggctgggaa 55800
tgaatttgta atttaacctt tgtactcttt gtaaacctct actgaagagt taagtataaa 55860
aattaattaa gcagaaagta ctctaaactc agctaatacc ttaagtaata cattttataa 55920
actatttatt tatttggtag gtacagcttt tttaaacaca aaaatagatt agataaattc 55980
cagcttggaa caagctagtg ctggttcaca aggttatgct caccccttcaa ttaaaatcaa 56040 aatgactaca agacttgcca tcagctctct tcaggaccac tgctgggtca gaatcagaaa 56100
ccttgggtgc catgaaattt ttacaaaatt tcaaatcaaa gccaggcttt gcagctagat 56160
aatagatcac ttgagtacga accacacatg taagtgcacg tatatttgag ttctcaatac 56220
aattaccctg atgggcaaga acccacaggt gagagcagag gcttggttcc cctagagggc 56280
cctggctgga ggccccaaca ccaaccagac gacaggaggg ccagactgct acccagtact 56340
gtacctcctg ctccttcaag agcctcccta agggagaaga agatctatac ttccactttg 56400
tttgctgcac atgtggcaac aagattgcta ccctgatttg ggacacttga gagaacttga 56460
aaaaaatgac cacccttaaa gccctagaaa aaagttgtat gtttgttaac agctatgctg 56520
cgctcacttt gcattgtgtg ttcttgaaag ctctgtataa atcaaaattt tgacgacaca 56580
ctaaatacac tagagaaata cactatagag gaatcctttt atagggctga agactccttt 56640
ggtaagaaaa atatgctgca ttaggggcag ctgcaagttt actatttctg ggaagaaaa 56700
gatcaaaggt aagagccagg tttgtttttt aaagcaatca atccaaacag tttgggtgtt 56760
tgttagttgt taccccctgag gggcttgagg tgtaactata tcagctataa aaatagcaat 56820
tccatacatt taattaggtt actttatatc tttcactctt ccccatggct gtaataatgg 56880
agattgaatg agactaaggc taagcccaac tccactcaaa tccaagtcac acgtcacctt 56940
ggctgcagta cagggaagct ccgcacaccc tggcttggga aagtttcggc cgatggagcc 57000
caagatgcag ggcaaccatc tactctttag ggttctgatg attccactcc agaaaggtgc 57060
atgaagaggt ccccgagctc tgtcatgtcg acatcttcat tgttggggac atgccggctt 57120
tctcggttct cgatgaaatc ccagagccgc actgaattaa agaactgcaa aaacagccag 57180
tggacatgcc tggttactgc taagagcaac aggaaggctg cgttccttga tcgttctttt 57240
gcctacccca tttctctgcc aggaacggta cctggaaatg cccacagctg ctaagtgtcc 57300
ccaactagag atggctaaag tccttaccct cacagtgcct tgagaactga gctgtttccg 57360
aggtttctca ggctctgcta gccgcccatc ggggtaagca tggcgataaa gacatttgct 57420
tccaaatggg caggtcccct tgccttgctc aaagtattta caggcttttt tcctgaaaag 57480
cagaaagaaa aagtcaagag gctggtggga aaatgagggg tccaaactgg gccactgcct 57540
gcctccatcc ttaccaccct tacgccagag gtaggtcagc ctcacattct aggtggggca 57600
gctgaggctg ggagaggttg agtgatttgt ctcaggtcac acacagctgg gattctgatt 57660
tccaagcagg ataggaagta tccccactta cctgcagcct tgcaaaggat attaacctgc 57720
ctggggactt gctgtgtgga gactgcagtg ctccacaggc cctccggcag ctccagagca 57780
cctcctgggt caccacagag ctaagccagg cctggtcact cctctgggca ctaagctctg 57840
aagctgggcc acttgtctct gctcaaagtt ccctaggtac ccccaccaagc caactctccc 57900
cttcctcctg gccgcagtgc tgtcaaggtg gctacaggga aagcagaggg ttttagcaac 57960
tgcctaaagc cataggtctc cttccagttt tcctgtctcc aacctcggca ccagggaggg 58020
cttcttcacg ccttatgtgc tttggacccc ttctctgaac agtgtttttc aatgcataaa 58080
acatgggtct acagcataca gtgaccaaac agttcaaaat gttttccctc tctcttaatt 58140
ctaccattct ccccacagac ctctatgtta agaaccctgc ccaaggaaac tcaatcaaat 58200
gaattcccat tttgctcaaa tgaactctgg tttatccaat cataaaggat cccaaactga 58260
agttaaaaaa aaaaagatac ccaagaatcc agagggccat ctcggagtac agaggaaggg 58320
gaaagtcaca gaaataaagc caaacaacag aaagggcacg ctgctgtcag gggcagctgg 58380
ggtgtgtgac agcgggagac aagaacaggg aaaggaggct cctgaatcca gtggttttcc 58440

```
gtcttgtcag atgggatggc cgcaggccgg tggtgaagtt ctctgaggac ggcttcatag  58500
cagcataaag aaaagccctc tggccgggtg tggtggctca cacctgtaat tccagcattt  58560
tgggaggcca aggtgggtgg atcacttgag gtcaggagtt tgagaccagc ctggccaaca  58620
cagcgaaacc ccatctctac taaaaataca caaatgagct gggtgtggtg gctggcacct  58680
gtaatcccag ctactcggga ggctgaggct gaggcaggag aattgcttga acccaggagg  58740
tggaggctgc agtgagccaa gattgtgcca ctgcactcca gcctgggaga cagagtgaga  58800
cttcgtctca ctgggggtgg tggcgggggg gtagggtggg gggagagaga acaagctccc  58860
tggccagctg atctgatttg agcacaggtg gctggagagc aggtgtgtgg acgacacatc  58920
ctccaggccc ctgcttgcct ggagttctga gcggacttca aatgaccgtg agcagtttgc  58980
tctcaccaga gcctgctgga caactccaga gcatcctagc acactggcta tgaactcgat  59040
caggtcaaac acattatata ctggtccccc actctcacaa gaatattact ctttttcctc  59100
ccccaggctt atctggtcac caaggccaaa agcctccagt tcactctgac tcactctgtg  59160
tcctcggctc tcacacccaa ctgtgttcat tctgtttaca aatcacttcc caatctcccc  59220
ttcctttggg ttcccacact tgtggaagcc tctggggcct gcctgccagg gccacttcct  59280
cactggcctc cctcccactc ccaccagttt ccaccttcag agcagcacgg aggagcttcc  59340
caaccttttt tttttcttta aagagatgag gtctccctat gtctcccctg gacttaagca  59400
atctgccctc ctcagcctcc caaagtgctg ggattacagg cataagccac tgcgcctggc  59460
cccaacctgt tcttaaagac catggtcaca ctgggattca agtgtccctt agattccagt  59520
ctgtaggtcc caccacatcc ttctacacac ctgtttcaat gccaggagcc actcccagtg  59580
tcccccagac acaaaaccta caccccttctg tgcccatgtc cttccatcac ttcccccctac  59640
agacaggtgc ttcctgcttc atggttcagg ctcccatgct gcttcccctg gcagcccccg  59700
gtggatccaa gtgctttctc tgttgtgata gatggtccct catgaagaac tggtcaccag  59760
caaacctgta tcataattgc ccttttgcag tttcccatga agttgtctta cttggcgggg  59820
cacagtggct cacacctata atcctagcac tttgggaagc tgaggtgggt agatcatctg  59880
aggccaggag ttcaagacca gcctggccaa catggcgaaa ccccatccct actaaaaaaa  59940
tacaaaaatt agctgggtgt cgtggcgcac acctgtaatc ccagctactc gggaggctga  60000
ggcagaagaa tcacttgaac cctggaggcg gaggttgcag tgagctgaaa tcatgccact  60060
gccagcctgg gtgacagagc gagactcgaa agaaaaaaga aattgtctta ctaatctcta  60120
catcccccag tggtgcttag ctagaaggta cctgacccat agtgagtact cagtaaatgt  60180
ttgtggattg caaaaaacac agtcattaaa ggaaagcaaa gcaaggaaag atccaaatag  60240
caataacaat ctccagactg cttttcagca gagccccttt ctacaggctg ggaccctttt  60300
ctacaggctg gggccctttt ctacaagctg ggacccctct gcttgccacg ccttgccctc  60360
ttgtggacac acaggaagat tgtatgagga aaaaatggta aaaaaaaaaa aaaaaaaaaa  60420
atcaagcttt agtaaactaa tatgcaacat aaaggaacca ttaaaaaagg taatgcatag  60480
tttcactttt agtatgacaa gtaaacgcct gccataccca accctcctgc agataagtct  60540
taacacaaat atttcaagaa gacctgaagg caccagagaa tgaacaaacg cagttagatt  60600
ctttggagga gtaaacacaa agaagaatag caatggcaaa ggctaagtta cctttttttaa  60660
aaaaggtagc ttttgtggct cacatctgta atcccagcat tttgggaggc cgaggcaggt  60720
ggattgcctg agctcaggag ttcaagacca gcctgggaaa cacagtgaaa ccctgtctct  60780
```

```
actaaaatac aaaaattagc caggcgtggc ggcatgcgcc tgtagtccca ccttcttggg  60840
aggctgaggc agaagtgctt gaacctggaa ggcggaggtg gcagtgagct gagactgtgc  60900
cactgcactc cagcctgggc tacaaagcaa gactccatct ccaaaaaaaa aaaaaaaaaa  60960
aaaaaaagaa gtagctctta tcctggagca ggccaaaatc ataaccacat ggggtggcta  61020
aaactccaag gggaaatcca atctttctgg cctgaagaac taaaagacaa gagttcaagg  61080
aaatcacagc cattggaaag tgaggaagca atcccacaaa gtaaggggcc tgtgaaaaag  61140
tgctcaaagg ctgtgtataa actctgccca aatctgacta actcccaaac cacacaggaa  61200
tgcgacaaag tcagctacga atgcaaaacc agaactgaga tctgaactgc tacctgggtt  61260
tgagttcaaa caatttacct gcctgttaaa aacagcaaca cttggccagg cgcagtggct  61320
catgcctgta atcccagcac tttgggaggc cgaggtgggc ggatcacctg aggtcaggag  61380
tttgagacca gccaggctaa catggtgaaa ccccgtttct actaaaaata caaaaaattg  61440
gccaggtgca gtggtgcatg cctgtaatcc ctgctactcg ggaggctgag gcaggagaat  61500
cgcttgaacc cgagaggcag aggttgcagt gagccgagat tgtgccactg cactccagct  61560
tgggcaacaa gagtgaaact ccgtctcaaa aaaaaaaaaa tcatcacttt acagataaac  61620
cataacagaa tcctaagtct ctctacaatg taatatttac aatgtcaagg ataaaatcta  61680
aaattactag acatacgaag aatcaggaaa atgtgatcca ttcttaaaag acaacagagg  61740
tcaacttcaa gataacaagg atttcaaagt agctgctaca actatgttca aggagatgaa  61800
aagaaaaaaa gattgaaaaa gaatgaatat ccccagagat ctatgaacaa tataaaaaaa  61860
ctatcataaa cggaagtaga gtcccagcag gaaaagaaaa aaacaagaca gaaaaaaagt  61920
taatgaaaca atagctaaaa tttcgctcat cttggggagt gacataagcg tagagaaaaa  61980
ccactccact cctaggcaaa atatcaacat gctgacaacc aggataaaga ggaacatttg  62040
aggccgggca cggtggctca tgcctgtaat cccagcactt tgggaggccg aggcaggagg  62100
atcacttgag cctaggagtt caagaccagc ctgggctaca tggcgaaacc ttgtctctac  62160
caaaaaaaat tagccaatta gctgggcatg gtggcgcaca ctactggtgg ccccagctac  62220
tcaagaggct cctgcttgag cccaggaggc tgaggctgca gtgagctgag attgcaccac  62280
tgcactccag cctgggcaac agagtgagac cctatctcac cgaaaaaaaa aaaaaaaaaa  62340
aaaaaacacc aaaactaaac aggtccacat caccatgtcc ttgctcattg ctgcatccca  62400
gagcccagca tggtgcctga gagaaggaag agaggaagag gcccctaaga ccacactcct  62460
gggaaggaga acgaggacac gggctgacag cagagccagg caggcagcag gggcacgtcg  62520
aaactcaaaa gcacttaccc catcccctgt ttgaaagctt caatcaactc gttcttttta  62580
ttctgatctt ccacccaata cacacttgga attacaaact ctgatatcac acggcattct  62640
ggacaagacc tgaaataaga attagattac taagggagaa gtcatgttac gaagcctggg  62700
cacactctct gctaaacctc ttgctcaact gcctcaccac tacaggcatt tccttcacca  62760
gaaattccaa aagatgaaat cacaatcatc caagaacctt atttactatt aacaaaatag  62820
ggtttcccaa tgagaacaca tggacacatg tgggggaaca tcacacaccg gggcctgtcg  62880
gtgcaggggc aaggggaggg agaacatcag cacaaacagc taatgcatgc atggctgaaa  62940
acctaggtga tgggttgaga ggtgcagaaa accaccgtgg cacatggata cccatgtaac  63000
aaagctacac attctgcaca tgtaccccag aacttaaagc aaaaaaaata cacacacaca  63060
cacacacaca cacacacaca cacacacaca tatatggttt cctcaacaaa aaagacagat  63120
gaaataaccc tcatacattg ctggtgagaa tgtaaaaggg tgcagccact ttgaacagag  63180
```

tctggcagat tctccaacag tttaatgtag agttattata ccataaaacc tagcaatccc 63240
acgcccaggt gtatacccaa gagaaatgaa aacacatgcc cacatgctgt gttcacaaat 63300
gttgacagca gcattattca taatagttgc aaagttaaaa cagcctaaat gtccactagc 63360
tgaggaatgg ataagggaaa tgtgctgcgt ccatacaatg gaacatattc cgccaggaga 63420
aggggactct ggcacatgct acagtcggga tgaactctga caacactatg ctcagtgaaa 63480
ggggccaggc acaaaaggcc ccaaattcta tgattccatt tataagaagt gtccagaata 63540
ggcaactctg tagagacaga aagcggatga gtggtgagtt aaattgtggg cttttatctc 63600
aatagagcag ttgtttcacc acacgatttt aggcaaatta cttgaccccc gcaccccagg 63660
cctgtttcct aatctgtaac tgaggagggt ctttgaggga atgagatgag cggacagatg 63720
tggagttctg aacagtagaa cgcgtgcagt aacctctcca catgccagct cttcccctgt 63780
cctgctggag aatttgagac tcctatgttg gccacattga gcacatccca tgtgccaggc 63840
atcatgcaga atgttttaca tgcattattc cacttcatcc tcaaataacc ctattttcgt 63900
ttttggtggg gggaaaaaac gaagctcaaa atgattaaca ggcaactggg ctacaggcag 63960
gtactactgg atttcaaaca caaggctagg agatgaaaac aggtcagtgc catttaacac 64020
ctttttacac agatcatctt tgctgagttc ctccccaaca cccagaaagc ttggtaggaa 64080
ttgttgccca tcttttatag gaacaggcac ttaggctcag gaagagtaaa tgacttgctg 64140
aagttcatgc agccaggggc cagaactcac cagttactct tgagggtaac ggagggctta 64200
aaagtggacg gaataaagtc tcaaatcaaa cattctccta gctcccacag ctaagacccc 64260
tggctgtact tacttaatga ttgggttttc aaactgtttg gcacaccgcc actgccggat 64320
gcaggacaaa cagtacgtgt gattgcaatt ggagagaatc ccaaatctcc tctcagaagc 64380
agaggccttc tccaggatca cttccatgca gatactgcac actttgtcct ggcttgcctg 64440
gaaggcaaag gccttttcca tctcgtgttc gaacgtcaac atgcagatct gaagcacaga 64500
caggaaggaa ggctttggtt gtgggccact gaggagtggc aggagcccta ggagtagctg 64560
cagccacact gccacagctg agatcaggaa ggaacactga cagcgactgc tgtgagcaaa 64620
ggcccaggct cccccaagtc aggacactga catctccctc agaccacaca aaggacttca 64680
aaccatcact ggtccagccc cttgctttcc taggaggtga catggtcacc acccatttag 64740
gactgagaac acggagatcc aaaaaggtta aactgcagtg gagtcagagt ccgtaaggac 64800
tgcggcccta gtcccccagc tcctctgggc actgtttccc ccgactctga gccatgtcta 64860
catcagagat gctgactcgt ccttaccatg aggcttgagg ctggcagcct agtcctatgt 64920
aagaagcacc acttctcccc aagaaaatga ttcaatgaat tcattcattc actaggcatg 64980
ccctgaattc cttctatgtg ctggcatttg agcaagagtg agaagaccta ggcccagccc 65040
ttgtaagctc agtctgtcca gatctgagac aagccaacac tcaccgcaga gacctcacac 65100
acttgcataa agaagacagc tctaaccctc tgcttccctg gaagacaatg gagagtgtct 65160
ccttgtccgc tgccacatgg agtcagtact aatttacctc ttgattatct aggaatacgc 65220
tgtccattta aacatgcctt aggccaggtg cagtggctca cacctgtaat cccattactc 65280
tgggaggcca tggtaagagg actgcttgat ctcaggagtt caagaccagc ctaagcaaca 65340
tagcaagacc tcacctctga aaaataaaat aatttttttt ttttttgag acagagtctc 65400
tctctgtcgt ccaggctgga gtgcggtggt gcaatctcag ctcgctgcaa gctccacctc 65460
ctgggttcag actattctcc tgcctcagcc tcccaagtag ctgggactac aggcgcccgc 65520
caccacaccc agttaacttt ttgtattttt agtagagacg gggtttcacc atgttagcca 65580
ggatggtctc aatctcctga ccttgtgatc cgcctgcctc gtcctcccaa agtgctggga 65640
ttacaggcgt gagccactgt gcccagccaa aataaaataa aattttaaaa gttagccaag 65700
ccaccacacc tggcattttt aaattttttt attattattt ttcttgagac agggtctcac 65760
tcttattgcc caggctgtag tgcagtggca caatcttggc tcactgcaac cttctgcttc 65820
ccaggctagg gtgatcctcc cacctcagtc cttgctgagt agctgggact acaggtgtgc 65880
accaccacac ctggataatg tttgtatttt tttttttttg tagagacggg gatcttacca 65940
tgttgcccag gctggtctca aactcctggg gtcaagcaat ctgcctgcct tggcctgcca 66000
aagtgctggg attacaggtg tgagtcacca tgcctggccc tcccccgcct cttatccagc 66060
ttcgtaccct ctgcatcatg catagggcct agcataaggc aaagcctccc aaaacactgc 66120
agacattaat gactttaaaa ggcccttcca acaagtggct cctcagattc tatgatttgg 66180
gctcaaatct tccaaaactt cacctagctg gatcccaacc atgaggaagt gtgaacccag 66240
ggagggagga tgctgtatct gcatgtgata gagacataca cacagacgac ataccatggt 66300
cctgagctag atctgttctt tgaacttagc atgattttat atttcagata cgacttcttt 66360
ttctctttat tctgagtaat taaaaattgg caaaataggc cgggcatggt ggctcatgcc 66420
tgtaatccca gcactttggg aggccaaggc aggcggacaa cttgaggtca ggagttcgag 66480
accagcctgg ccaacgtggt gaaaccccat ctttcctaaa aatacaaaaa gtagccgggt 66540
gtggtggtgg gcgcctgtaa tcccagctac tcggtggggc tgaggcagga ggatcacctg 66600
agccagggaa gcagaggttg cagtgagccg agattgcacc actgtactcc agcctgggtg 66660
agagggagac tccattaaaa aaaaaaaatg gcaaaatgac tgcaggaaaa agaacctgaa 66720
aacaggatgt aaatatacca gatacataat atgggtatta ctggcagggg gatgcctgtg 66780
gaaataccaa caattctgtc acttagtaca tttcagattt cttgagtgta tatggatggc 66840
cttccgtgtc ctgttcagta catttcagat ttcttaacat gagttcatgc aaaggtttgt 66900
gactttacct tttcatgagc cttcctctgc tctgggtcga atgggtgcaa gacttgcagc 66960
ctacagattt cacacacctc cccgtgcagg tagacacagg catccccaaa ccggcactcc 67020
ccagcagctg cgtaggggca cagctgctgc tcgttgctgt aggagctgct ggcctccacg 67080
tcatcaaggc cactcctgat ggcatccagg taggaatgcg gcttcatctc ggggctgggc 67140
tgggggtcgc tgcagctgcc tggattactc accatgctcg gctgggtctt cctttcagcc 67200
atgccagaga gatctgaaaa caacacacag cacacatgca catgaaaatg gccccatttt 67260
tctggtatgc cgttagccaa agcctaacat attaagctac tctgacctaa gaattccact 67320
cttgagaaca tatggcaaaa aaaacacacc gaaggggaaa aataaaagga atagtataaa 67380
atgttcatag tgacattact tataattact taaaaaaaca aaaaacaaaa aacaaaaatg 67440
gcaagacagg gaaatagcaa aacaatagga tatacttata caaaagaaca ctaaagccgt 67500
ttaaaatggc aaatatggaa atgttaacac atggaccagt taacactaaa acaaacaaaa 67560
aaacagtgag agcactagaa cacagtgttt ccttcatacc agcaaaggta aaatcatttt 67620
aagtgaacta gaatagatgt ctagagcaaa tctgtgggtc ctgaggccag tgtaaactgc 67680
cccatggtca ccccttctca cgccaggagc tgctgccttc ccactgcaca cctccgagct 67740
tgtttagagg tcacgtattc tcacaggatt actcatttgc tgaggacaga atctgcctac 67800
ctcatggtag ccaattccaa gaactagaaa tctcttcacc tggtgaggac cagccaataa 67860
aaacaacttt tatggccagg tgcagtggct cttgcctgta atcccagcac tttgggaggc 67920
cgaggcgggc ggatcatgag accaagagtt tgagaccagc ctggccaaca tagtgaaaca 67980
ctgtctctac taaaaataca aaaattagct gggcatggtg gtgggcacct gtattcccag 68040
ctactcagaa ggctgaggca agagaatccc ttgaacccgg gaggtggaga tcatgccact 68100
gcactgcagc ctaggcgaca gagcgagtct ccatctccaa aaaaaaaaca aaaacaaaac 68160
aaacaaaaaa cacaacaaaa aaacttttac aatttgtagc tttcttcctc atcaaaccct 68220
gttttaaggc acagaccatg ccccaaaccc tagtgtgcta ttcttttccc aaaggtgcaa 68280
tctaaactgt caaacactgt cagcataaaa actaagacca ttcactggcc taaaagtcaa 68340
acagtgaaac atgctcttta gcaaaatatt tagttttctt tttttttttt ttttttttga 68400
gagggagtct cactcttgtc atccaggctg gagtgcagtg gcgtgatctc agctcactac 68460
aatctttgcc tcccgggttc aagaaattct cctgcctcag cctcccaagt agctgggatt 68520
acagacacct gccactacac ccggctaatt tttgtatttt tagtagagac agggtttcta 68580
ctaaaccatg ttggccaggc tggtctcgaa ctcctgacct caggtgatcc acccgcctca 68640
gcctcccaaa gtgttggggt tataggtgtg agccacttta cccagacaaa atatttacgt 68700
ttgaaatgaa gagcttgatg cttctcacca gctggacaac caccatatga agatggaagt 68760
tacatgttga caaaaagatt gtgtttttat gttttaccag gccagtcttg gagctcaacc 68820
cagccttggg cacgagggcg aatgtatcat ttgaatgatc tgcagccaca tggagcctct 68880
tcagaacagt tctgaagtct ctccgcgcag acaatctgga ggtgtattag gttaggagtc 68940
ctcttgacaa gaggaggcta gaaaggagca ccaagcatta acaagagtgc tatgcaaaaa 69000
gacgcaacaa aaggcttccg cttactcact tcggtctcta agaaccaatg ttctcttttc 69060
acgctttccg ggttcatgtg agttagtttt cacaatggat gcagtgacct cggaaggagg 69120
gtgaggactg tggaaagctg gggagggcac actgtgggcc atggtgccca cagcacctcc 69180
agctgcagca gagggcctcg tgtggtcata tctaaacaaa acacacagca gatgcattac 69240
agacatgcca cccacacaca tctcccacac tccccagatg ccaatggccc tccttctgct 69300
gcacttgttg aggtgaagaa ggcggccatc ttttccaata tttaaactct aacaggatta 69360
tcgattatta acagatgctt ggcaattcat tgtgaggggg acatttgcta tctatcacct 69420
atgcttaagt gtctctgtgg gacttgagtg ggacagacac acagcaccag accacacaga 69480
gaacctgaaa gttccaaaca gatgttgagc taaaatctcc tgatgcctga ctgacccagt 69540
attcttttga gcaggagtcc ccaaaatgct gacaagggcc aatgatctct ccctgactgt 69600
ctctcttggc actcattgac aggggaagac caacgtgggc ctacttccat catctcccac 69660
tgcactgcag agaaaaagga gggaaggaag ctttgcagtc tagaaagaaa agatcggctc 69720
tttgctacaa aagcatgaac aagtttccgg aattgtgtac aattttataa ctatatattc 69780
ataagaataa ggctgaaaag tagttttaaa aaatgaaaat taggccaggc acggtggctc 69840
acgcctgtaa ttccagcact ttgggaagct gaggcgggag gatcacgagg tcaggagtta 69900
gagaccagcc tgaccaacat ggtgaaaccc catctctact aaaaatacaa aaaaaaaaaa 69960
aatcagccag gcgtagtggc agatgcctgt aatctcagct acttgggagg ctgaggcagg 70020
agaaccctgg aggcggaggt tgcagagaac tgagatcgca ccactgccct ccagcctggg 70080
caacagtgag agactctatc tcaaaaaaaa aaagaaaaga aaattagttt tagggtactg 70140
aaactgaggt tttaaactta tttgccatac tttttgtgat gttgccatat tacttttaca 70200
ttaaaatttc ccccttatca agacccattc tccaaatgaa atcagtgtca cagctggaat 70260

-continued

```
ctgttgcaga gtccttgcct gcaccgagtt ccataggcac agtagccctt ctggtagtac  70320
ttgcagatgg tggacggttt gctgtttgcc aagtcatgtg agaataggca ctgacttcct  70380
tcccgacaca caccatgcat aaaatacctg cagagacaag cacaggcata caacttttag  70440
aagcacattt tgctttataa aatcagctta ttcttgaact tagcatacaa acatttacca  70500
ggcatatatt atgtataaag gctctattag gcactggaga gagatctata tatttccttg  70560
attctacaac agtgatttca gaggcactac aactgattca atgacagctt ttctgaaaga  70620
aaaacaaatg atcccatata tttctatgtg aagatatatc ttcctgattt gagatatgtt  70680
caatgtgagc cacataattg agaaaacact ctgtgaaaaa ctgttctctc tgttctcaag  70740
gagcttaaag ggcatgacta acgaaaccag aagatctggg ctcaagaccc agctctgcca  70800
cttaagaaca tgtcacaaaa ccaacttccc tgggccttgc tacctttccc tataaaatga  70860
agattatact acccacttaa ctggtcgtgg tgaggatcaa ataccatagt gtggtatcaa  70920
aagatataca cagatgctcc ttgactaatg atggagttac atcccaataa agccactgtt  70980
ttttgttttt tgttttgaga tggagtctct ctgtcaccca ggctgaagtg caatggcaca  71040
gtctcagctc actgcaacct ctgccttccg ggttcaagcg attctcctag ctcagcctgg  71100
gctaccttac ttatgcttag aacacttaca tcagcctaca gttgggccaa atcatctaac  71160
acaaaatcta ttttacaata aagtgtagaa taatctcatg caatttattg aacaccgtac  71220
tgaaagtgag aaacagaaag gttgtatggg tacttgtagt ttttaatgaa agctgtttct  71280
catacattgt ttcagatgtt tcagaatatc agatgtatca catgttctgt atcagaatat  71340
tccactgaga tatcagatcc tggccttgaa gaataagtgg tacaggaata cctgggaggc  71400
taactctgtc cagacagggt agagagacct gagtgaatac tcaaacagta gagaccctag  71460
atgaacatgt cttgatatta aagataaact aggctgggtg tggtggctca cacctgtaat  71520
cctagtactt tgggaggcca aggcgggcgc atcacctgag gtcgggggtt ccagaccagt  71580
ctgaccaaca tggagaaacc ccgtctctac taaaaaaaat acaaaattag tcaggagtgg  71640
aggtgcatgc ctgtaatccc agctacttgg gaggctgagg caggagaatc gcttgaactc  71700
aggaggtgga ggttgcggtg agccgagatt gcgccattgc actccagcct gggtgacaag  71760
agcaaaaact ctgtctcaaa aaaaaaaaaa aaaaaaaaaa gataaactag ccagggcaac  71820
aaagggagac cctaaaattt aaaaattagc ctagcatggt ggtatgcacc tgtggttcag  71880
ctactcagga gagtgagaca ggaggattgc ttaaacccag gagttcaagg ctgcagtagc  71940
catgattgtg ccactgcact ctagcctggg tgacagcaag atcctgtctc acaaaagaaa  72000
aaaaaaaagt aaactagtgt tagagtagaa gtattttaga cacaccctaa taaggcttaa  72060
aaaaaaaaaa cacaagctga tagcaagtat ataacttact gtcagccaaa acaaacttta  72120
aaggaagaca atacaatcca aatgctcaga aactcacaat gcttggcatc caatcataaa  72180
ttactagata tgccaaaaag cagaaaataa tgtgacctat aaccaggaga aaaataaaga  72240
acaggaatta cagagatgat ggaatcagca aaataagacc ttaagaacag ctattataca  72300
tatgctcaat atgctgaaag atttaaagaa aaacataaac ataatgtgga gagaaatgga  72360
tgatttaaat aagaccaaat actaggtgtg gtggctcacg cctataatcc cagcgctttg  72420
ggagactgag gtgggtggat gaccagaggt caggagttcg aaaccagcct ggtcaacatg  72480
gtgaaacacc atctctatta aaaatacaaa aattagccag gtgtggtggc aggtgcctgt  72540
aatcccagct acttgggagg ctgaggcagg agaatcacct gaaccctgga ggcggaggtt  72600
gcagtgagcc aagatcgcgc cattgcactc cagcctgggc aataagagcg aaactccacc  72660
```

-continued

```
tcaaaacaaa acaaaacaaa aaacaaatga aacttctaga agtgaaaaat acaatgtctg  72720
aaatgagaat tacattagat gagtttagta gatgggatac tacaaaggaa aatatcagaa  72780
tacttgaaga cacagaatag aaaccatctg agagagagag agagagaaac aaacttgctt  72840
ctgactacca aggagcatgg atcttggctt ctcactgtaa aaaaacaaaa caaaacaaaa  72900
caaacccaac tgaaaaatga aacaaaatat gtgaaacaac tgctttcaga caatagaaaa  72960
aaggactggt ccttaagaga agggaaacac aggaagtaag ccccacattt agtctgactt  73020
cctacctgga ggcatattct aggtcttggt actgggagta gaacctcagg caaatcacag  73080
agattgagtt tagggaggct gcagggattc tttaaagatc cataaatagt ctgggctcag  73140
aggctcatgc ccgtaatccc accacttcag gaggccaagg tgtgaggact gcttgaaccc  73200
aggagtttga ggtcagcctg ggcaacatgg caaaacccaa tctgtataaa aaatacaaaa  73260
atcagccgtg catgatggct acttgggggc ctgaggtggg aggactgctt gagcccagaa  73320
ggagagagcc tgcagtgagc tctgtttgca ccactgtact ccagcctggg tgacaaagca  73380
agaccctgtc tcaaaacaaa caaaaaaaca aacaaaaaac cctgtaaata gaaccacaca  73440
taggccgcat gcagtggctc atgcctgtaa tcccagcact ttgggaggcc aaggtgagtg  73500
gattgcttga gctcaggagt ttgagatgag actgggcaac atggtgaaac ctcgtctcta  73560
ccaaaaaata tacaaaaaat tagccaggca cggtagcgtg cacctgtgct cccagctact  73620
tgggaagatg aggtaggagg atcgattgag cccaggaggc agtggttgca ataagccaag  73680
atcatgctgc tgcactctag cctgggtgac agagtgagac cctgtctccc aaaaaaaaaa  73740
aaaaaaaaaa aaaaaaaggt aagttgggga aagaatcttt tcaacaaatg atgctggacc  73800
caaaatcgac ttggaaaaaa cttaaatatg tacctgctga tatgacccaa aatgaagtat  73860
aaaacaacct atgacgtatt ctagccagaa acaattaatt tgaatccaca aaactccaga  73920
tctaacatcc agttcataga aaatacagga gactggggac aacctatgaa agacatctcg  73980
agaaaacaac caaataaata caaaagaggc tgtacgtggg acctaggcct actgtcttta  74040
taagtgccat gtaactaaag gaggctgagt ttggaagaca gtttgacagt ttcttaaaaa  74100
atgtaaacat aaatctacca tatgacccaa caattctacg cctaggtatg tacccaagaa  74160
aatgaaaatc tatgtccaca caaatacttg tacatgaatg tccaaagcag cactatgcat  74220
aacagccaaa aagtggaaac aatccaaatg tccatcaact gatgaacaga cagagaaaat  74280
gtgatttatc catacaatgg gctcttatcc agccataaaa aggaaagaag tactggcaca  74340
cactacaaca tgggtgaacc ttgaaaacat tacgcagagt gaaagaagct ggacacaaaa  74400
gaccacatgt tgcatgattc catttatatg caatgtcaga aaaggcaaat ctacagagac  74460
aaaaagtaga ttaagtggtt gcctagggtt gggaggagag aagtgagggt gactgttaat  74520
gggcacaagg gatcttttgg gggtgataga aatgtcctaa aatttaactg tggtgatggt  74580
tgtacaactt tgtaaattca ttaaaaagtt ttgcactgta cacttcaaac aggtaaattt  74640
tatggtatat aagttatacc tcagaaaaag ctgttaaaaa agagaaaaaa gggaagggac  74700
aatgctaggt tagcagacag aacacaaggg acataaccag atgcaatact tacctctgga  74760
ctagaatctg gtttcaacaa accagataca aaagacattt ttgaaaccag atattttgaa  74820
agatattttg aaataaatgt gagtatggac taggtataaa atgaaaattt attaatatgg  74880
aaagttaaac acaattaact gagaagagta gattataaaa cagctaatgg tgcagcttct  74940
atagaaaaac agtacggaag ttccttaaaa aattaaaaat atatttacca tatgatccgg  75000
```

caattccact tctgggtata gacacaaaat aattcaggcc aggcccagtg gctcacgcct 75060
gtaatcccag aactgtggga ggccgaggtg ggtggatcac ctgaggtcag gaatttgaga 75120
ccagccggat caacatggtg aaaccccatc tctactaaaa atacaaaaat tagccgggcg 75180
tggtggtggg cgcctgtaat cccagctact ttgggggccg aggcaggaga atcacttgaa 75240
cctgggaggg agaggttgca gtgagccaag atcacgccac tgcactccag cctgggcaac 75300
agagtgaatc tgtttcaaaa aaaatagaag acttcaaagt agggactcaa acaaacattt 75360
gcacacccgt gttcatacca gcattattca caatagccaa aaggtggaag caactcaagc 75420
gtgcgctaat ggacgaatgc ataaacaaga tgtggtctat ccatacaatc agccttaaaa 75480
agaaaggtga ttctggccgg gtgtggtggc tcatgcctgt aatcccagca cttagggagg 75540
ccgaggcagg cggatcatga ggtcaggaga tagagaccat cccggctaac acggtgaaac 75600
cccgtctcta tgaaaaatac aaaaaaatta gccgggcgtg gtggcaggcg cctgtagtcc 75660
cagctactcg ggaggctgag gcaggagaat ggcatgaacc cgggaggtgg agcttgcagt 75720
gggccacgat tgcgccactg cactacaacc tgggcgacag agcgagactc cgtctcaaaa 75780
aaaaaaaaaa agaaaggtga ttctgacaca cgctgcaaca tgcatgaacc ttgaggacat 75840
gacgctaagt aaaataaacc agtcacgact ccacttctgt gaggtcccta gagtagtcaa 75900
attcataggg acagacagtc gaatgccagg tgtcagaggc tggggatggg agaaatggaa 75960
gttttttaat gggtagtaca gagtttcagt tatgcaagat aaagagctct ggagattggt 76020
tacacaacaa tgtgaatgca cgtgacagaa ctataactta aaaatggtta agatggtaaa 76080
ttttatggaa attttacaat gatttttttt ttttttttga gatggagtct tgctctgtca 76140
cccaggctgg agtgtagtga catgatcttg gctcactgca acctccgcct gccaagttca 76200
agcgatcacc tgcctcagac tccgcagtag catggaaggc acactccccc aacaccgtac 76260
cagtaaaata atctcctctc tcctcccagc gcatattctc atacatacca gccaccagat 76320
tctgatactt ggaatccata ttaacccccg ccccctccgc gaacgatcgc tctccctacc 76380
cttccgcaca ccaccaccgg tgaccatccc tctacacccc cgttacccaa aactctcatc 76440
attcacggct tctgcccagt acgatgcata cctcactccc tacccaacac gagcccttca 76500
gcctccgagc atcgcctaca tcggcacttc catgcattgt ggaccaatgc tctctaattc 76560
cctccaccaa caccgaacat tctcacctct cctgtataac ccttccttcc gctatcccca 76620
tcataaaccc cgcgttgccc tctgaacggc ctctcacttt aacgagaact cttgctctcc 76680
ccatcgtcct atctcgcc 76698

<210> SEQ ID NO 31
<211> LENGTH: 4878
<212> TYPE: DNA
<213> ORGANISM: M. musculus
<220> FEATURE:
<221> NAME/KEY: misc_feature
<222> LOCATION: 4765, 4766, 4769
<223> OTHER INFORMATION: n = A,T,C or G

<400> SEQUENCE: 31
attgaaataa acaaccaggc agcagttatt aacacgggaa catggcggcc gcagcctggg 60
ctcccgcggc ggcggcggag gtcagcgccg acggcagccc gcacctgacg gcgtgacggc 120
cacattgatt ttcctcgcat ctggcttcac tgcattggct cttctgcact gtgtacaggc 180
acagttgctg atatgtgttc aagatgagtg ggatgggaga aaacacctct gacccgtcca 240
gggcagagac cagaaaacgc aaggaatgtc ccgaccagct cggacccagc cccaaaagga 300

-continued

```
gcactgagaa acggaaccgc gagcaggaga ataagtacat agaggagctg gccgatctga    360
tcttcgcaaa ctttaatgat attgacaact tcaacttcaa acctgacaaa tgtgccatcc    420
taaaagaaac tgtgaagcag atccgccaga tcaaagagca agagaaagca gcagctgcca    480
acatagatga agtgcagaag tcagatgtgt cgtccacggg gcagggtgtc atcgacaagg    540
atgcactggg gcccatgatg cttgaggccc tcgatgggtt cttcttcgtt gtgaacctgg    600
aaggcagtgt ggtgttcgtg tcagagaatg tgacacagta tctacggtat aaccaagaag    660
agctgatgaa caagagtgtc tacagcatcc tgcatgtcgg ggaccacact gaatttgtca    720
agaacctgct gccaaagtcc atggtgaatg gaggatcctg gtctggagaa cctcccaggc    780
ggacgagcca taccttcaac tgtcgcatgc tggtgaagcc tttgccagat tcagaagagg    840
aaggccatga tagccaggaa gcccatcaga aatacgaggc gatgcagtgc ttcgctgtgt    900
ctcagcccaa gtccatcaaa gaggaaggcg aagatttgca gtcctgcttg atttgtgtgg    960
cacgaagagt ccccatgaag gaaagaccaa ctcttccctc atcagaaagc tttaccaccc   1020
gccaggacct ccaaggcaag atcacttcac tggacactag caccatgaga gccgccatga   1080
agccgggctg ggaagatctg gtaagaagat gcattcagaa gttccacaca cagcatgaag   1140
gggagtctct atcatatgcc aagaggcatc accatgaagt tctgagacaa gggttggcgt   1200
tcagtcagat ctatcgtttt tctttgtctg atggcactct cgttgctgca caaaccaaga   1260
gcaaactcat ccgttctcag actactaatg agcctcagct tgtaatatct ttacacatgc   1320
ttcacagaga gcagaatgta tgtgtaatga atccggatct gactggacaa gcgatgggga   1380
agccattgaa tccaattagc tctagcagcc ctgcccacca ggccctgtgc agtgggaacc   1440
caggtcagga catgaccctc ggtagcaata taaattttcc catgaatggc ccaaaggaac   1500
aaatgggcat gcctatgggc aggtttggtg gttctggggg catgaaccat gtgtcaggca   1560
tgcaggcaac cactcctcag ggtagtaact atgcactcaa aatgaacagt ccctcgcaaa   1620
gcagccccgg catgaacccg gggcaagcca gctccgtgct ctccccaagg cagcgcatga   1680
gccccggcgt ggctggcagt cctcgcatcc cacccagtca gttttcccct gcaggaagct   1740
tgcattcccc tgtgggagtt tgcagcagca caggaaatag ccatagttat accaacagtt   1800
ccctcaatgc actgcaagcc ctcagcgagg gccatggggt ctcactcggg tcctcgctgg   1860
cttcaccgga cctaaaaatg ggcaatttgc aaaactcccc agttaatatg aatcctcccc   1920
cactcagcaa gatgggaagc ttggactcca aagactgttt tggactttat ggggagccct   1980
cagaaggtac aactggacaa gcagaggcca gctgccatcc tgaagaacaa aaggggccca   2040
atgattccag catgccccag gcggccagcg gggacagggc tgagggacac agccggctgc   2100
atgacagcaa agggcagacc aaactcctgc agctgctgac caccaagtcc gaccagatgg   2160
agccttcacc cttgcccagc tccttgtcgg acacaaacaa ggactcaaca gggagcttgc   2220
ctgggcctgg gtccacgcat ggcacctcgc tcaaggagaa gcataagatt ttgcacagac   2280
tcttacagga cagcagttcc cctgtggact tggccaagct gacagcagaa gccacaggca   2340
aagagctgag ccaggagtcc agcagcacag ctcctgggtc ggaagtgact gtcaaacagg   2400
agccagcgag ccccaagaag aaagagaatg cactactgcg ctatttgctc gacaaagatg   2460
atactaaaga tattggttta ccggaaataa cccccaaact cgagcgactg gacagtaaga   2520
cagatcctgc cagtaacaca aagttaattg ctatgaaaac tgtgaaggag gaggtgagct   2580
ttgagcccag tgaccagcct ggcagcgagc tggacaactt ggaagagatt ttggatgatt   2640
```

-continued

```
tgcagaacag tcagttacca cagcttttcc cagacacaag gccaggagct cctactgggt   2700
cagttgacaa gcaagccatc atcaatgacc tcatgcaact cacagctgac agcagtcccg   2760
tcccacctgc cggagcccag aaggcagcac tgcgcatgtc acagagcact tttaataacc   2820
cacgaccagg gcaactgggc aggttattgc caaaccagaa cttaccactt gacatcactt   2880
tgcaaagccc aactggtgct ggacctttcc caccaatcag aaacagtagc ccctactcag   2940
tgatacctca gccaggaatg atgggtaacc aagggatgct aggaagccaa ggaaacttag   3000
ggaacaatag cacaggaatg attggcagca gcacttcccg gcccagcatg ccttctgggg   3060
aatgggcacc acagagtcca gctgtgagag tcacttgtgc tgctaccact ggtgccatga   3120
accgaccagt ccaaggaggc atgattcgga acccaacagc cagcatcccc atgcgagcca   3180
acagccagcc tggccaaaga cagatgcttc agtctcaggt catgaacata ggcccttctg   3240
agttagagat gaacatggga ggacctcagt ataatcaaca gcaggcccct ccgaaccaaa   3300
ctgccccgtg gcctgagagc atcctgccta tagaccaggc atcgtttgcc agccagaaca   3360
ggcagccctt cggcagctcc cctgatgacc tgctgtgtcc acatcctgca gcagagtcgc   3420
caagcgatga gggcgctctt cttgaccagc tgtatctggc cttgcggaac ttcgatggcc   3480
ttgaggagat tgatagagct ctggggatac cagaactggt cagccagagc caagctgtgg   3540
atgcagagca gttctcaagt caggagtcca gcataatgct ggagcagaag ccccccgttt   3600
tcccacagca gtacgcatct caggcacaaa tggcccaggg tggctataat cccatgcaag   3660
atccaaactt tcacaccatg ggacagcggc caaattacac cacactccgt atgcagccac   3720
ggccaggcct caggcccaca ggcattgtac agaaccagcc aaaccaactg agacttcagc   3780
ttcagcaccg cctccaagca cagcagaatc gccagccgct tatgaatcag atcagcagtg   3840
tttccaatgt gaacctgact ctgaggcctg gagtgcccac tcaggctcct attaatgcac   3900
agatgctggc ccagaggcag agggaaatcc tcaaccaaca ccttcggcag aggcagatgc   3960
agcagcaggt gcagcagcgg actctgatga tgagaggaca gggcttgaat gtgaccccaa   4020
gcatggtggc tcccgctggc ctaccagcag ccatgagcaa tccccggatc ccccaggcca   4080
atgcccagca gttcccattt cctccgaact acggaataag tcaacaacct gatcctggct   4140
ttactggggc tacgactccc cagagtcctc taatgtctcc ccggatggca catactcaga   4200
gtcccatgat gcagcagtct caagccaacc cagcctacca gcccacctca gacatgaatg   4260
gatgggcaca ggggagcatg ggtggaaaca gcatgttctc acagcagtcc ccaccacact   4320
ttgggcaaca agcaaacacc agcatgtata gtaacaacat gaacatcagt gtgtcgatgg   4380
caaccaacac gggtggcttg agcagcatga accagatgac atgccagatg agcatgacct   4440
cagtgacctc cgtgcctacg tcaggactgc cctccatggg tcccgagcag gtcaatgacc   4500
ctgctctgag gggaggcaac cttttcccaa accaactgcc tggaatggac atgatcaagc   4560
aggagggaga tgcatctcgg aaatactgct gaccctggag aaactgtctg catctttctt   4620
caacccactg ggcttacaaa catttaccag tctggagagc tgcgtctctt tgtgttgcca   4680
cctgacatgc cgccagttct cccaggacat agcagcagac agtcgggccc tgggcccgca   4740
gcatagagcg tgctggcttg gctgnnacng gaagagttgc ctctcccgac agcctgcagc   4800
tcgcctccag accaacccgc agtctgttca ctgcattcac cgtagtgcaa cttagatctc   4860
ctgcagagta actgtccc                                                 4878
```

<210> SEQ ID NO 32
<211> LENGTH: 240001

<212> TYPE: DNA
<213> ORGANISM: M. musculus
<220> FEATURE:
<221> NAME/KEY: misc_feature
<222> LOCATION: (1)...(240001)
<223> OTHER INFORMATION: n = A,T,C or G

<400> SEQUENCE: 32
tgtgctgggt ggtgaacttg ctatgtagcc aaggatggct ttgaactcat cccgtgcctc 60
tacctcccca gtgctgcaat tagaaatatg agccatcata tcaagttgat tctgaggtct 120
caggaattga tacttcagaa acagggaaag cctttttttat aagaatgttt tatagtgtac 180
tcatgtaaat aaaataaata aaatttttaa taaaagggga gctgaagaga tggctcaatg 240
gttaagagca ctgactgctc ttacagaggt cctaagttca attcccagca gccacatggt 300
ggctcaccaa ccatccgata atgagatctt gatgccctct tctggtgtct gagacagctg 360
cagtgtactt atgtaaataa aagcaatgtt tgatgatttg gaccctggca aaagaggtat 420
gaaaggccac gaggcctcgc cagatacagt tgtccctttt ctttctgtag cttcactggt 480
ccatgctcaa ctacaatttg agaatagtaa gtgaaaaatt tcatagataa ctcacaactt 540
ttacattgct tgccactatg tcatgtaatt ttacaatgtc ttcttcagtc ccactttgta 600
ccaaatccac ccctttgtgt agtctctgct tactatctgt gctttttggc taccaagaaa 660
atctataaag tgttcccttc aagcaaaaca attcaagtac agagagatgt gcgtgggaaa 720
gcctacagat atttgtgtaa cactgattat agtatagctt tcattgtttt gtagtattag 780
ttacaacctc tcactctgct taatatataa actttatcat tggtatccag gtaaagaaaa 840
aacatgttag gaacttggta ctctatgtga tttcaagggt cactagaggg tattacattg 900
gctgaggtgg gagggtcttg ggccctagga gcttagtctg gagaatgaga agggcaaatg 960
cacaaacaag gccacacgct ctgtacaaac agaacacagt aatacttacg tgttgttgaa 1020
ctggcacagg acttaatagg caaatacaaa aatagttttc tgcaacccgg aaatcattgt 1080
tcagtatgag tcttgataca tacaggagag attgttactc aaggcagctc aaagatgatg 1140
tattgataat acggctggtt ctaagaatac aaagttaaac atataaaagc aaaataaata 1200
aataccacag ttataacatg ggtgtgacgt cttgacacta tttcagtact ccaaagtgac 1260
atgattcttc caggtcccgc tggagtgagg cagctgggca tggagttctt tacgctactg 1320
taagagctgt ttggtttgtt ttattgttta gagacagtcg tgtgtcttga gcattcagta 1380
agaaggtgca ctgagtaaca cagcatggaa gcagggatgt gtttgtctgc acgttcagca 1440
caggtagttt tttcatgtta attctgttgc cactgagcac tgatggactc tggatagctg 1500
cctctcccct caagagttgg aatagaaagc aacaagagtc tttcttaact cttaagaatt 1560
taggacagga gaagaaatct aagtggcaat ggggacattc ctgcgaggaa cccaacctcc 1620
ctgcaaaaat attatgggtt aagagtggag gaggacagat cagagggaca ctctgtatct 1680
ccttgttctg tccctaagct gctgaaggct tttgagtctt cggggaacat aatttattct 1740
agctaattaa aaaaaaaatc cttaaaattt actaacaggt ggtcaaaacc aatcattcca 1800
aacagcagac acttccctga aaaacgtgaa gtagcctatt gcagacctcc ttccgattcc 1860
actcaccaat gttaacattt gttacagctt tctaaatatt ttctagctat agccaagtag 1920
gcatatactt ttctttttct ttgtcataat aaactggagc taaaaaaaaa atacgatcaa 1980
aaagcatgtt ttgcaattaa tggacctggg ctcaaatctt gcccaccttg cttactgtgt 2040
aactctacaa aaattacttc tttaggtttc aatgttttat gaggtataaa aatagcaatt 2100

-continued

```
acttcgtaag gtttgaggat taaaatttgg agtgtgtgtg aatcacttaa tgcagtgcca   2160
agtcgttaca gttcaataaa cacttattgt ctatggcaag tgacctttca taagagttaa   2220
aataaggaaa cgtgttcctg tcatattttg ataacttccg ttaagcaaac aaatgttgct   2280
catttctttc aactaattat atctaaatgg aaaagaagtt gcttttccag ttaaaaacca   2340
aacaacattt aaacgtgaaa actcctccac gtctccttaa tcccaatact ccattgagga   2400
tttgataatg gattccccaa ttaaaaaaca aaacaaaact tttgttgtct cactgcgtgc   2460
ggagaacact cccctcggtc tttctaaata ctgagcagcc tttgctttgt caggcaatcc   2520
cggggtggta ccccggtaag ttcgcctccc gcggtcacgc ccctctatcc cctccagaga   2580
cctcagggac agcaattggg gaggcgtatc cacgaaaaaa ccgaggggac atggtggcca   2640
aggagtgcgc cccggaacag cgtctgggtg cagaggtgcg cccgaggggt gcaggctgcc   2700
ggctaccggg ccctgcctga gcgcgcgcgg gaggcacctc tgggactagg ttttccgcga   2760
ccttctcgcc gcagcgtccc tgccgtcgga ggcgcggcag tcccttggcc tccaccccca   2820
ggcccgggcc agtcccccctt tttagctttc ttttgggcat tgccctttgc cctcgcatgg   2880
agtcctctgt tgactctccc ttcacttcca gtcacccata ggtcacggtc cctagaccac   2940
agccacccat cttgtccaac tccccgagct ctgaagtctc gccagccagg gagatgctga   3000
ggaccccgcg ggtggggtag ccccggtgtt cccgggccca cgctcggggg gcgcgggacg   3060
caagtttccg cccggtcccc tgagcggtga cagcgttcgc tcggaggcgg cggggaggcg   3120
gagggcgggc cagccccgtg cccgagcccc ctcccctgct cgcgagctcg cgcggtctgt   3180
gtctctctcc gcaagtgcag agccgcggag gaggaggggg aggaggagga gggagctggg   3240
ggaggatctc cattgaaata aacaaccagg cagcagttat taacacggga acatggcggc   3300
cgcagcctgg gctcccgcgg cggcggcgga ggtcagcgcc gacggcagcc cgcacctgac   3360
ggcgtgacgg ccacattggt aagcgcgcct cccctggggg ctcacgggcg gcgggcgggg   3420
ggcgccgcat tcccacccgg gccgctgccc ttggtgcgcg cagcccggcg gagccgcgcg   3480
ccggccggcc gggcaggctg ttgttgtgtg cgggcaccgc tgcccaggcg tgcggagccc   3540
gcgacgccnn nnnnnnnnnn nnnnnnnnnn nnnnnnnnnn nnnnnnnnnn nnnnnnnnnn   3600
nnnnnnnnnn nnnnnnnnnn nnnnnnnnnn nnnnnnnnnn nnnnnnnnag aacctggaaa   3660
gtgccgaggg tgtgtgaagg tgacgcggcc ggcaggggcg gcggcggggg ctcgggcgtc   3720
tggggggcct cgggcttggg tggcttcggg gcggtagcgc tcgggccgcg caggccgggc   3780
cgcggtgggg gcggggagcc ggggtcgggc ggcggcggcg gtggcggcgc cgcgccgggc   3840
tcgcccctga cttaactttc tgggtgcggg catgtgtgcc ggaggcgcgc tggggccgcg   3900
gccgggggcg ggaggcgggc tgcgggccag gaggttccgg gttggctcgc cagcgccccc   3960
tcttccgtac cccttctgcg gcccctgcag ggacaggccc tcgggggccc cccgcgggaa   4020
gcgggagggg tcctggcggc cctcgcgccc cggtcacgcc ctgggccggg gaccctcctc   4080
tccgggcccc tggaggctcc cggggaggcg tccagggtcg gcgccgcggg ctggagtgcc   4140
cgcaccccgc ccctgggggga gtcctggagg cgccgcggcc gcgctcgggg gtggctcggt   4200
ccctgcttcc atggtccctc cctttcccct cccccaagtg gcttccgggg cctgcggact   4260
gaggggcggg aatcggggac ccgagcccct tactctccgg gagtgacgtt gggcctcaag   4320
cctagagggc ctgtcactgg caggggaaac tttcccaaac ccgagcctga gctcgagcac   4380
cctcctccgc cacctcgtcc tctaatccca ctcccactcc acctcctccg actccttccc   4440
ctcccaccga cccgaatctg gctgtgcctg actgatgggg cagtgagcca atggaaggca   4500
```

-continued

```
ggaactgacc tgccgggtac cggtaagcca atggtgggag ccagaggcag gaaggaggcg   4560
gggtttcttc cgtccagtta gggctgagtt gcaggcgggg cgggggagcc ttggagacgc   4620
cgcgagccct ccactctggc gcgtcccttg gtcacccgca cctgggtttg tggaatagtg   4680
tcactcacag aatctgtgac ccggggagac ctgcataggt gcgcgaagat attgcttttc   4740
tctggtgctg cgagaggcgt tgttttagac atgacaaagt ctaaagccac ttcaggatgt   4800
ggcagtaact gcgaggcccg gttttaaaat ggcatatgtt gatagtgacc gcgttctgga   4860
tctcagcacc aggtgagatc tttgaaggtc tgcgttagtt tcactgggct tctgtccagc   4920
acccggacga tggtgaattg aaagggcacc ctgagagtaa aggcgcgggg tggcctcttg   4980
tgaggtgatt tttaggagtg ctaaagcatt cttgtttgga attggcctca ctgggatctt   5040
gtttaatcag accaacacca atttcccaag tctccttgaa agtttcgtgc ttggtctggg   5100
tgtgacattt taacaaagtt actggttatg ctgtgcatat ttttttgtct tgttcttggg   5160
taaacaaaat gaagttttga accaaagcgc cactaagata ccaagcgtgg gtacttagca   5220
aaagcagcta aagaatattt gttggcagaa aacaaaagga ataaagtata gcagtatagc   5280
tttccatatt actcccttac aaaagattcg taaaacattt tatctattta tttatttatt   5340
tatttattta tttttagttt ccttaaacac ggatgaattg tacagtatgt ggctacttct   5400
ctgatgtgta agaggtcaag agctatcttt ggttgtttgg gtccagtgaa ctgactttct   5460
tgactcctga gttttaggaa aggggggcgg gggcggttcc cttgaggatc cctggttgct   5520
cagcgggaat tgcggtctgt taaaaagacc gccgctgctg ctgcagtgct tttgtgtgt    5580
gtacatgctc tgttctttgt tggtgaggtt agtccaaccg gagggcagca acacattcct   5640
tttcccaatt ggaatctttg ggagttcaaa ggatgagaaa tgttaaactt aaaatccatt   5700
catttttgga atctgtcacc catgaattta attttgggat ttaaaaaaat atctaatggg   5760
cacgaaccac actgggttct ccagctttta ttactattgg attattaaga aaggacttgc   5820
gagagactaa tgtaaggaaa gagtagtgtg taatatgtga ctttcaaatc tatagtgtag   5880
attcccaacc tgtgtaattt tagacgttct tgtagaagta aattgctttt tttttttttc   5940
cttcgagaca gggtttctgt gtatagccct ggctgtcctg gaactcactt tgtagaccag   6000
gctggcctcg aactcagaaa tccgcctgcc tctgcctccc aagtgctggg attaaagctg   6060
tgtgccacca ccacctggtg taaattacgt ttttctgtag cttttgaagt gttattttgg   6120
tgataaatga gtcaagtgaa agataagcac ttatttcaac tgacagaagt agggagtatt   6180
gtaaattaat gttcagaacc cagcaacatt cagagactcc cactgctggt taatttggga   6240
ggccactctg atgcaggccc tttctctttc ctgaattctt aaaagcaacc cattatttca   6300
cttcattctc cataaggatc cttcaaagcg ttcttagatt cttggtggca gagaatagca   6360
agtcgcctaa tgcctggtga ggggaaaaac ctcgcaagca tatggaggca tctagaaaaa   6420
gatgtgcatt gtcagcggcg gcgattccat tgtgtgctct cttgctggag ctgaaccttc   6480
ttcctcctgg gaatttccct cttaaaagag aggatttctt tgactttaga tgtcagggtg   6540
ctgaggccca ggtttcagga cagctcaaca atcattcatg tgagtttaat gcttttgagg   6600
acttaatatt tttaaaaata tttttaaccc ctcatcgatt aaatataatt tagatgactt   6660
tcagcatgag agacatctta ctgaaaatac atataaaaga tggagggtcc taggattgca   6720
taaagggtta atggttctcc ccttacctct caatagatgc gtcttattaa agctttccag   6780
tctccatgga atccatgatc tctgattacg tttctatttt acatgtagaa gttaaggact   6840
```

```
cagtgcctta gctgtttcag gccacagtag gttgctattt gacccatact ttgacagctt   6900
agatctctag gaaaaattgt ttttgtcgta ttgaatacaa aggcagtccg tatattgtta   6960
gaaagaaaaa gcatgaagag tggcccttta aagcattttt aatagaagac taattttctg   7020
gtatgcatgg gtgtctttga tatcttggtc attgttgtgt tgtggttgaa attatattta   7080
aaagtttaac tatttttagt tgttaatatg ataaaaccaa tgtttaagcc ctattagctt   7140
tttaatttgt ttattttttta agatttattt attatatgta agtacactat agctgtcttc   7200
agacacccca gaagaggaca tcagatctca ttatggatgg ctgtgagcca ccaagtagtt   7260
tctgagaatt gaactcagga cctctggaag agcagtcagt gctcttaacc actgagccat   7320
ctctccagcc ccatgatact gatttttgaa tgaagaaaag ccatggaatg gaaaacacaa   7380
tgttgagttc tttttcccct tttctatcac acgctccttt gcctccatgt cttctaagtg   7440
gaaagaaagg aggcactcag tgtttatgcg cttctttctt tcttttgttt ttgttttgat   7500
tgtttcctac tttttgattt agactagaga agcaagaagg ggtgccatgg cataccaccc   7560
tctgaagcct cttaaagtat cctacctggc aaagctgtaa agtgcagttc agtgtcacag   7620
gccctcactt cagagagcac gagggaaact ttacaggttc cagatgttct agatagaggc   7680
gacagtatga cttgcgtggc tgttatagca gtctatgcga cgtcctagct gctgtgaaag   7740
ggagagtaca gagttggcag cttacagtga aggtaactag gtgttctgct ggtctgcagt   7800
agagcacacg acttggcttc aagagcaaag agtctctgtg tttactaatt agcgatattc   7860
attcccattt ctagggtcag aggcagtggt ggaatgctag gatttgtttt agaccggtgt   7920
ttatttggtt ctatggttgg gaatttctag caaactcgaa tgagtacagt gcgtacggta   7980
atgtttctca cagctgcttt ggaacttctg gacatagtgt cagtcatcag gaggaggttg   8040
caaatcggga gacgttaagg ggcacttgac agatagatgg aaactgaagt ttgcggtaaa   8100
ttctggtggg acttatacct caagccagcc agttcttatt ctgtcctggg cccatgttta   8160
gcagaatctt tattttgggt tttggaggtc ttttctctgc cttttttttct tctttagcaa   8220
ttgtttcatt gatttatttc atcattattg atggaaattt gactcttcta gtcttgacag   8280
tgtatttggt aataaaatct tcaagttaca gagccaggga ctaaagggag ggccacaggc   8340
tgggggtgat gggcgatggt ctccttcctt cctccttttc ctcacacctt ggtggtaggg   8400
aaggaaatat ttgccttaat cttatcttct gtgtgagtgt aatttcaagt atgtactatc   8460
tagcaaattt tgcatggatt tgggattctg ctatttttcc tgagaaagga attatgttta   8520
gaataaagaa gttgtggggc ttggggggtg gctgagtcag tagtgtgtct gcactgcagg   8580
actggagttt aagcttctag cactcatgta gatgcctggc atggctacgt ctgtagtctc   8640
agtgcttggg agcagagaca ggctgacccc agagtgcact aaccagcctg cgtagtcagc   8700
tgtgggcttt ggggtcaggg agagtcgttg ttgttttaaa tgagatggag aacaaagtgc   8760
agggcacctt gagctctggc cttcacatgc acacactgat agacatacac ttcgtactct   8820
cacacaccat cctcaagttg tttaaatgtc acacactgat agacatacac ttcgtactct   8880
cacataccat cctcaagttg tttaaatgtt cccttgatag atgagcttaa aattaattag   8940
attcctcttt atgaaaatat ggacgcttat gattggttca gttttgtttg gcttgaagct   9000
tacgtgctgc tctaggcgcc ctgtgtggta tggtacatgg ttacatggtc agagtggtcc   9060
tatgcagctg gtaggatgtg acagggtggc ttggcaggtg ggccccatca tctctgtccc   9120
accccctctc ctatggccat ttcttgtgct gcctcctctg ggcctctgta gcctggcttt   9180
agctctgtat gcagccttgt gttctgctgt ggctatgggt cttctggaaa gagctcattc   9240
```

```
ccgtcaggcc cacagtgtct gtgtcaggga tagtgccagc cactttctag actttcttat   9300
gagtggtcca ttcttttgat tatggccaca aacacataaa tacatgctgt tatcctcatg   9360
ttccaggagg ttagaggtta aggggaagtc tgggatggct gtccatcaag agtgggatat   9420
aacaaatgac cttaggactc tgagctgttc agtctaagaa ggaacagatc tgaatagctg   9480
aggttctgcg gacgttccca gtcaggactg agaagttaac tcctgtaagt catatacaac   9540
acatacctca actattcttg aaatttcaag atccccttac ctttaaatgt caagaagcag   9600
gacaagcagt gaagtaaact tgatggagtt tactaaatgt gtctggggtg agggacattt   9660
gttatgcact tgggtttttc acttagatgt gtgaagcagt tgtagcatcc tcctttggct   9720
gctcaggaag gaaatggaca cacagggatc agataacttc caggctcaca cagttgggct   9780
actgaagcac attagaaccc caggcttctg gcctgctgag ctggggttcc tattggctga   9840
ctgttaggct cttgcgtcag cctttgttaa gacaagacaa catcaatcca tttattctgt   9900
gaaaagcata ctcttgtctg ttgttctctg tatggaaaat ttgtttgtgg gggatcagta   9960
gaaaatgtac ccagggaaca ctttccggga tacagatttg gaaaagacaa ggagttgacg  10020
tacatatgtg gcttcttatt tcttcaatat agatttaatg ttgtctgttt aactgtcgga  10080
cacaggttgt gtggtgcctt ttggtgagtg ttgtgcactc catgtagagc ggatgactct  10140
gctgagatac catagaccca aaagaaggct gataatatat tccgtcatct gacttctgct  10200
atgctatttg tggaattctt ctgtctgctc aattgtttgc agggagcagg cgcgctttca  10260
ggaaactcgc tcctgtgctc tgccaggatc tgcacgcatt gcttgtaatg ttccagctgc  10320
caggacccag ggcctgttgt cagagatgaa aatgatgcat gggatttttt gttggtcact  10380
tatgtcccca aaggcttcac ttggagagtg agtgagttcc ggaacgtgct gctcgctgcc  10440
ctctgcccat tagaggccac aactgaagga gggtaggccc ttccagcagc tccatcttgc  10500
tcataggatc tgctcgtgaa caaacttcct ctgcctctga tgtcacccct gctttcgtaa  10560
gaacatttaa taattatctt aaaatttcta attatattgt taatatgctt aagatgaaaa  10620
actttgagtt gttttgaaaa tgtaagttag aatattgaat cgtgccaggc ctggtggtgc  10680
agttctttca tgaaatcttt agggaggtaa agagaggggt gtctctgacc ctgagaccta  10740
gttcatgttc aggatagcca tgactaagta gagaggcctt gtttcgaaaa ccataaccca  10800
acacaaacaa caaatgttgg gttgtgtgta tgtatgcagt tgtgtcttga tgatgttact  10860
cagtgctgga ctgcttgctt agcatgttca aggtcctggg ttcaagctca gagagatgac  10920
ccctccccaa tgtaattgtg tatttccaag gacccttcag catgtctcca gttattttag  10980
gccatcttta gagtctgtgc aaatggagac tttagataat tacataagta atattttta  11040
agaattagtt ttattttgtg tatgagtgtt tgcctgcatg tttgtccagg caccacatgc  11100
atgtctggtg cctacagaat ccaaaagagg gcattggatc ccttaggact gcagctgtag  11160
ctggttatga gccactgtgt gggtactggg aatcaaaccc aggcaattct taaagtgcaa  11220
ccagtgttct taaccactga gccattgttt tctagtttaa ggaacaaaat tttaatgata  11280
cttttaatgc actaagatgt gtgtgtgtgt gttattattc tctactatta tttcattcat  11340
atatttttgt ggtgttgtgc ccagggcctc cagtatgcta aacattagat caatattata  11400
tataaaatcc taacatgtat ataattagaa ttactcatag ctgtcacttt catctaacat  11460
gtaatcactt ctgagcagtt attgttggga tgtgagaagg aaattcttcc acatgcactt  11520
ggtaggtccc taagtaagga ttatagaaac tcattaaaat tcggagttac cacagtgcca  11580
```

-continued

```
tgtcctcaag ttgctgtcct gggctggggg actccctggc ccagaggtga tctttttgcc  11640
tgtccctgtt gtgtgtgctg cagaggagga cgcggagtga ggcaggcacc agagtgagat  11700
gtgagaagag ctgctctcgg gttccaccag gaatgctttg cacatctttt ccctcttttt  11760
ttccttctgt ctttcttccc tcaaccccac ctcccacccc aagtagaatt ggagatgtaa  11820
agatgaatat gggcagagga caaaccagaa ggatttcgtg tgaatgagca tggtaggcag  11880
tgtcccttct tggtaggtag gtctaacctg tttgcagcac ttagtgagag aagtagctct  11940
ctctctgtta ggaatgtgac atgtaaaatc attgctgttg ttcagtgttg tcgcagcagt  12000
aggggcactg atgtgtaatt tagttggatt gttatattcc atgccttttc atgtttctct  12060
gcttagggat attattacag acttgacaat gttaggtgat ccaagtggct cacatgttat  12120
aattgaaaat attgaagtta tttaagatgg ttcaaaagtg taaccaaatg tttaagacct  12180
taagaatgtt tgcctctaaa tttttttgcc agctgtgttg gcgcacgcct ttaatctgtg  12240
atctaagaaa gcagagccag atgggcctct gagttcgaga ccagcctgac ctctacatag  12300
tgtgtttcca ggctatccag ggcttcaaag tgagatcctt actaaaataa gcacacacat  12360
aaataagtag aaaagaatgc aaagagagag agagaaagaa tccttgcctg tgaggtcaga  12420
ggatatagct caggctgtca agtgcttgct tagtgtacag gaggctctgt gttcactagg  12480
caagcactag taacctaggg ggttcccagc agcagtaaac caagtgtccc ggcacacctg  12540
caatcctagc cctcaggagc tggagccctt gggtcagagg ttcaaggcca ttctcagcta  12600
tacagtgagt gtaaggttag tcaggaatat gtgactgttt tctgttcctt ccttttccca  12660
aaggaaaaga atgcattttt ttaaaaaaag atttatttat ttattattat atgtaagtac  12720
actgtagctg tcttcagaga ccccagaaga agacatcaga tctcattatg gatggttgta  12780
agccaccatg tggttgctgg gatttgaact caagacctgt ggaagagcag tcagtgttct  12840
taaccgctga gccatgtctc cagccccaag aatgtatttt ttataatttc cttctgagcc  12900
ttggttttct tagttgcttt cttaagttgt gttagttttt tggtttttta agacttttcc  12960
atttaagggt gatagaaaaa ttccttgaaa atgttagttt tcgtattcac cgcatcagag  13020
tcttggcaga acaaacaggt ggtggagagg agagccagca aggaagtccc aggaagtgct  13080
cgctgctctg tcgtggactt ttatcttcag caagaggcaa tgcggaagct tagtcttcaa  13140
gtttccactt cacacatgta attatgaatc atagcataat ggaagaccga gatattagct  13200
gtaatacaag aaaacaacac agtcatcact tcagacacag aactgaccat tttagtcagt  13260
attgacagct accctcttac cctcccagcc cagcattgtg cttggacatg aagtggattg  13320
gaaaacaaaa cgagagcttg gggtctcagc atagcaggaa gcacatgggg ctggtctacc  13380
tggactgggc tggccctgtt cccttcaggg tcctgacacc atcactgaga gaggactctt  13440
gtttcctgtg agggctgtgt gggtgggcta gtggggaggg aaggcgagaa tggctgacct  13500
tgctggttgg gggagtaagt cagacccctg atgatcacca gcaaagcagc tgtctgcacc  13560
tggatcttcc caggagccaa cctggactgt gctcaggtgt caggtgcaca ggattctaat  13620
gtgcacgttc atggaggaca ccagtgtaca gaggggctgt gcagagagag gaccctactg  13680
aggcagagag taaagcaaga gtgttatgtc cgtcctcttg catcttagag gatgctaaag  13740
gatgttttaa tagttttccg agttatcaaa agtgcaggtg actgatggtg ttgccagtgc  13800
atggaagaaa gaactactgc tacatgatac atcagcatca gtgtatatta agatggtttg  13860
ttctgtgtcc tgtaaataaa tatagtcttt acatctaagc aactcaggaa cttgcacttg  13920
ctctctcatt ggttcagaat acatgtgcct gtgcataaac atagcataca tacacataca  13980
```

tgctatacac acactatatg catgcagaca catactacat gtaattacat atcatatata 14040
tatatatata tatagtacat gtgtgtgttt attttcaccc cagacagtgt gtagaacagc 14100
tgaacagcat agaagacttt gtttttctaa actttctatt tgactgacac ttaaatcttt 14160
ctctactgca agccattaat aggttgatct tcccacggta ttcctttcct aataatgtaa 14220
tttcccactt actatagaac gatatcttta aacacttacc tctgagtctt tgatgaaccc 14280
acccttcttc tatttctgct ggcacatgtt gtggtatacc ctcttgttct cttgatttgc 14340
ctagagaaag tagatgagtt aatctaaaat ttaggaagca tgcctttgac ataagaatta 14400
ttttaggaat tcctactgct aatttaaacc tgaagtaatg aaccagaaca aaaggaggag 14460
tccaaaaata ttccaaagtc attactaagt agcttaatga atcaattatg gattaaaatt 14520
gtcctacagg aacggaagca aatctaactg tgttctcctc agaaacaata agcacagtgt 14580
gctttgtcgc tgtgatatga tcacacagtc cttcagtgcc agggtttagt ggtttttcct 14640
ctgcatagta tttgacactt tagagaaaat ggattttagt ttatagtgga gaggagaaaa 14700
aaaatgaaga aaaccatggg gatagttggt agtgctagga agttaataaa ccagacactt 14760
cagagatagt gtgccagggt ggttacttga gtacctgcat tgaagaagca gtaacaagaa 14820
cgaacggaag tgtcaactga aggactaaaa cctcaagaga tgatgaaatt ctacaatata 14880
cattaatata gactgtatta acacttataa aaatatcctg attctccaaa ttttacttac 14940
atatttttat tatttttaat tgtgtgtgca tctgtgttcc tggaggccag aggcatgaga 15000
ttcccgcagt tggtgttgcg gtgcttgtga ggcatctgac atacgtgaca tctgacatgg 15060
gtgcctcaca atagaactcc agttctctga gccatctctt catccctcac cccctaattt 15120
aattttttgt tttggacagg gtctcactgt aatcctggct agcatggaac tttctgtgta 15180
gaccaggctg ggctgctcac tcttctcttc tctctcttta tccttctatc gccatctctt 15240
tgtatctttt cattgtgaaa gattacaaac attcagaaaa attccagtga gtgcctgtgt 15300
gcagtgcatt tccatctatc tgtctgtcca tccacatacc catctatcta tccacccatc 15360
catccattat acatacattt attcactccc cctctgtctt tgccccccccg cccccccctct 15420 cgtgtgtgtg tgtgtgtgtg gggggggggg tatgtaggta ggataaatca taaataaagc 15480
ggtagatagg attcttcatc cgtaaagaac aatgtcttag gagcactgcc ctgagtccca 15540
tcacctcaga actaatctct tcttgctgag ttttgatttt tcaaaactag tccacctcat 15600
agttaaccaa gtccactccc tgcatctcct ttccaggctt ttctcctttg aatggctcta 15660
agagtccagg tcagttgtcc tgagggtttg tgcttatcct gctagctttg gggtggcttc 15720
tgttgcttgt tggtgaccat ggcgtggtcc acttgggcgg ttctccctga gtcttcctgc 15780
agtctgttta gattgggcct acacaaacca tgctgtggat cacaagggaa gacaggaagg 15840
tcaggactga cctgaaggac gctcatcacc cattaatctg aggtatactt tttaccttta 15900
agaagaggta gattttgttc aggcacagac cagaagaagg tgagtcctga ggcattaatt 15960
gtatagtcat ctggacaaac aggaagtcta taacgggctt tctctgacct gccagggata 16020
gaggtaagca ggcgcttcta gttgagttga aagcttaggc cttctgcttg ggcagtctcc 16080
agctactcta acttaagcat ccttagagcc tacggcctgc tgtgtggctg gctctatctg 16140
tccctttctc tgctctgctc cagtccatgg ttgttcctct gcctgctctc tgtagctccc 16200
tctgctcctc cttctcccag ctccccctcc tccgccctgt ctgaaagttc caccctctac 16260
ttcctgctca gctattggct gtcagctctt tattaccacc aatcagaacc tcagataatt 16320

-continued

```
ctaaattccc ttaggcaagt gagaaaggat gaatatttac aaaatataag gctggtggtg  16380
ggtcataaaa atgacaatac caatataatg ccagcagaga cacatcttca cacaatatga  16440
agaaaagatt accccagcag aagcctttgt ttgaaattct tcccgtttct tgttctgtgt  16500
tggagaatgg taatttacat ttcttgcacg cttgactaat ttcgttttta atgtttctga  16560
ttttcttctt tctttatagt cttcatttgt tctctcctcc aactttccca accctgaaac  16620
tcttcctagt gtctttagtt tctcaagctc cttcagaact gtctggaagg ggtggtggga  16680
gcttcactcc ccaccactct tgagggtgtg gagcttcatt ctcaccttga caaaaggact  16740
ttaaaggtga gaggcattcg cagggactgt ctgggcttct gcttttgcca cgcacctgcc  16800
taatacggtg tagagatagc aattatcagt agatatctgt ttacttttag ttgatgtgtt  16860
taatgcttag gcgaggacag aagtcaccac tgttttgttt tgttttgttt tgttttgttt  16920
tgttttgttt tgttttgctt tgctttgttt ttcgagacag ggtttctctg tatagctgtg  16980
gctgtcctgg aactcacttt gtagaccaga ctggcctcga actcagaaat ccacctgcct  17040
ctgcctctcg agtgctagga ttaaaggtgt gtgccaccac gcccagcaga agtcaccact  17100
tttaacaact atattttatg tatctataac aacaaacaaa ttacatttga ttgttaatgc  17160
aattttgcct gatttcatac ccaacaaatg aattattctc atttctgacg agaaggaaaa  17220
cagcaattct gtctttaatg tgaatctaca ttcatgtata agaattggga ggcggaaaga  17280
taccatcacc taaaatggag aggtcactga agatatcaag atttactcca gagtcaatcg  17340
gagttaccaa agacttagtt actgagactc ctgtcttttg gcacggcctg gctctgctag  17400
aggtggagtc tgatggcctg ggtcacacct gcactgcttt caaggggcac tcccacctga  17460
gacaagaaat gctgtctagg aagctggagg agtgttttat tatattaata gttaatattt  17520
aaattgagaa agaacatatt taggagacca gagaaattaa gaaaggaaag aaaaatgagt  17580
ctggtgacca gattttcaag actgtagttt tcaaggtgta gttaacaaat cagggttatt  17640
ttattaagca gagaagtaac aaagatattt aataataata aaatatttta attgatttta  17700
tagaactttc cagaagtgta tattattggt atgttacata atcttgtttt gtcattgtgt  17760
gttatatata tgcgcgcaca cacacacaca cacacacaca cacacacaca cacacacatc  17820
cctagtgccc tgggcccctc gtgataagct ttcattgagg tctcccatgc gggagcctca  17880
tgcaagagcc ttgctgcatt ttacttgata tggctgcttc tctaaatgtg gtgtcatgct  17940
tgcagatgtt gggagtaagg acatgcttct gggttccatg acagaggcag gcctgatgca  18000
ggtctgtgac aagatctaac tggggactat gggctgggat ctcggcacat atcctctccc  18060
cacagccttg gcaagctggg gttaaaacca gttgtcttac ataagacaga tttcactttg  18120
tgaagcctca gaagttgtgt agacacttta agcatgctgt aaccctcttg taatggaggc  18180
tcagcagagg gagtgtaagt gagcaggtga ggctagaagt ggagttatcc tgtttattac  18240
aggctaaggc agacaacaga agtgttagga gagaggaata ttgacataca agtgatccat  18300
tcattatgag atttaagcag ctcttccttg gttaacaaaa ccctaacact atatctatcc  18360
atgggtatag taagacattt agatggtttg gagaccctca aatgcagtag ttcgcttgct  18420
tttcaagtct gtgaaagcat tttggtcaac gccatgcact gctgtttaat aatgcatttg  18480
tatatgggtg gcctcatgtc ccgtttctgt tactgcctcc tattgttatc cttcctttaa  18540
tgctgcgatg atcagcattg acccatgttg atgccctgtc agtcttagct aggtctctgg  18600
aattttaatc taaagtaaat tgttttaatt tttaaaatga ggattttcta aagggctggc  18660
tatttaagaa gttagtcctg aagacgagaa ctgcctgtat gttgggattc tctgtggtct  18720
```

ggcttttgat ttagcctccc ctcttttgac agctaatgca ctgtccagga gtgcgaagtg 18780
tcactgggac tcttcagtct atgagacgct attttgaatg ctctttgtca actgtttaga 18840
gcaaatatgt tcccattttg ttacattaga gaatgttttt gataatcttt ttagcaccca 18900
gtagatttaa tgctatgatt ctcaacaggc agattatttg atgtatagtc tcattatgga 18960
gtgtctgtcc ctctgtgttc atgtggctcc acacaatggt tggtgaggct gggagtcatg 19020
ttttgtgcag aagactgaga acagggtaat ttaaatcagt aaagtgcctg acttttaagg 19080
gaaaaaaaaa agtagttatt ttaactactt ggaggtggta gaacatttaa attatattga 19140
aaatagctga agaataaagt acatagaatt cacatttcct taactcggaa gattgtctgc 19200
ttgcttgaca tatcttaagt gttggtctta gaagcagaca ctgttattct ccacagagag 19260
attatacttg gatctgtcag agaactatct aatgggaact cactgttaaa atcatttggg 19320
tgagccgggc atggtggtgc acgcctttaa tcctagcact cgggagccag aggcaggcgg 19380
atatctgagt tcgaggccag cctggtctac aaagagagtt ccaggacagc cagagctaca 19440
cagagaaacc ctgtctcaaa aaatcaaaaa aaaaaaaaaa tcatttggat ggtttgatta 19500
tagtttaaaa caaaaccacc tgtcttttgg gaatattaat gcataagact agatgctact 19560
tttgactagt tcaatctgtg gcttattctt caatactttt ctcaggggaa aaaatgcagc 19620
tcttgctatg agtggtcgga ctaattcacc agagtcaggc atctgcgatc gttttgggtt 19680
tggaagatgg tctggtacag tgggcttcgc aggtagcata agtaaacctg atcactagca 19740
acgcggaggg gaggcaggga gaagctgact cagatttgta ctgtatctcc cagttgcaga 19800
taaaagtccg tttcactgaa gatagaggat ggccgtggtc aggcgtatta gcctgtgttt 19860
acctggggaa tagaatgtgc ttaatagctt agaagtggtg ggaaagttta tataaaaatt 19920
gtttggtggg gacttggcag atctgcaggg acagatgaga tatttagata tagttagcag 19980
ataataatgc ttaggagctg gttatgaagt ttacaggaac ttctgaggct acacagtact 20040
agaaggacat ttataaatac ctatcactga aagaaatctc taaggtgatt ttggtgtgta 20100
cctcataaaa cataaaccct ttagaaactt ttggatttcc aacagttata tttaaatatg 20160
attgataact caggagcact gggtgtgtca gactgtcacc cgtgcttcac tctggacaca 20220
ccgtgacaat gtgactgtga ggaattactg gtgaggtgta gcacactcat ggacagagga 20280
tctccgcccg gtcctatcat gcttgcctgt taccctgcca cacagcatgt tcaagagcta 20340
gggtgtgcta cgggtgctgt gctggttggt gttttagggt ctacctatct agccacacat 20400
gcactgtctt ttttttgttt tcatttcctt agtatttcat atttgctttt aaatcttgaa 20460
ataggaatgc atattagtga acttttccgt cacagtcctg gggactgtag agggccatct 20520
gtgtcgttca tgatgtgcca tatcaactca gatttgagct tttagcagga aagtaaagca 20580
ttactgagac agccaatccc acagtgagtc agggtgagag gaccctgcgt tacagcggag 20640
tccagcacag tttactaagc ctgaagcatg tgataacagt taactgaaag agattagtat 20700
gttaactaag aagtgtccat gctctgactt ggatagatta aatcaaaact atagtgttca 20760
ccgggaatag gcacattgct gtcccctccc attcgtggtt cactgactag aattcctgaa 20820
cacaatgctt aacagcttca ggttgttttc tagacatgaa atgaaccgat ctcagccttt 20880
ctcaacagaa caatagtttt tatgagctct ggaggactaa gtcctatttg ttttccttca 20940
tttctttagg cataaaatgt tttagataca aacttctatg tgcttttatg attctttgtt 21000
ttagccagtt ggtttattgt taggaacatg gaaatttcat ggttgtaaaa gtttcctgga 21060
ggggctggag agatggctca gcggttaaga gcactgattg ctcttctgaa ggtcctgact 21120
tcaaatccca gcaaccacat ggtagctcac aaccatccat aatgagatct ggcgccctct 21180
tctggtgcgt ctgaagacag ctatagtgta cttacatata ataaataaat aaatcttaaa 21240
aaaaaaaatt ccctggagac tgaaggccac ctctgtcttc ccctgtcagg tgagccggtc 21300
cttgcttggg tgacatcagt tctgaatgcc ttgcttattg atggcccttt ccctctatga 21360
tcttcatggg cactcccctt ccactgcatg catgcctgtg gtgtcttctg accttataaa 21420
gctttccctc ttcctcctgc tcctcctctc cctcctcctc ctcttctctt cttcctcctc 21480
ataggtggta gttggggctt tgtatcttta atgaagaaac aaaccgcttc agtagtagaa 21540
ggaagagatg ttggagttag aggatgcctt aagttggcaa tgggcagagt attagctttt 21600
aaaggattct tttatgatat agtactcaca tgatcttgta taaaaaacaa gattacatgt 21660
tttttgtttt gtttttgttt tttaacctac aagaagccat gtgttgggac tgtgcatgaa 21720
cctttattcc aagcactcag agacagacac agaatctgtg tgttctaggc cagcctagtc 21780
cacatagtga gccccaggat agccaggatt atatagagaa cctgtctcaa aacaccaagg 21840
cgtgtgtcag gagaagacat gcatgtttgt acttaacggc tgttggccag gacttgaatg 21900
agaactgaga ttctcgagaa actgtagatt aaaatctgtt atattctcag ttggttagtt 21960
ttcatctcca tatcatcaac ttcattatgt caagttcgtc tttgcgtttg ttatcacctc 22020
tgtaagcttg aataacatga taaaattgtt ttacatttgg caattatgac ataatagctc 22080
aacgagtgtt agtctctaca gtcttcactt cgtaccttcg gaggcttcct gttctctctg 22140
atgtccttag atatttctcc tgtcagtttg gagcacttta aacaataaga agttaaagag 22200
atcgtgtcct gggatggcct cttgtttcag taccttctga aattcttcat agtttctagt 22260
tctacaggat attcattcat tcattcattc attcattctc tctctcttcc ctcccccaca 22320
gctctccccc atccccccat ctaacagagg caggtgcatg cttgtaatct taggatctgg 22380
gggtgaaggt aagaagatag gaaggtcaac acttgggtca gcctccactg cataccagtt 22440
cactgcccat ttgagctagg aggctgacta ggaggaaagg gaagcaatcc caaacagaca 22500
cccaaaacct aaagagcagc aagagtttga agcaaattcc aagtatcatt tcattttgtg 22560
ttaagaacga ggcaaaaaaa aaaaaaaaaa aggcctggtg tggtggtgca cacctttaat 22620
cccagcactc agaaggcaaa aaggcaggtg gatctctgaa ttcgaggcca gcctggctta 22680
tgtagtcagt tttgatggtt ctgaaattac aaatgcaaag agaagacaca aagccttggt 22740
ttctagccct cgcagtgctg tgctcagcga cagagcactg atgtgttgtt aggtgcagag 22800
ctgatgcttt ttcctgaagg tgtgccaatg gacagtgcag cctgggcggg gtctcagaca 22860
tttaacttag gaggcacgta aaatcccaag ccctggggtc agaaatcttg tccgtttttg 22920
cctagcatgg ggcctggaac cttgagtact aatagagaat ggaagtggat tcttgtgaag 22980
atgaatcttt cttagtgact ggtatctttt aggacttaaa gtatgggaaa tgaatgaagg 23040
gcaggagaaa cagctcagca gccgagagca ctggctgctc ctgcagaaga cctgggtttc 23100
actctcatca cccaaatgga ggctcacacc catttgtacc tccaggaggg atggggcatc 23160
tgatgccttc tgctctcttc caaggtcact agccatgcac acaatgcaca tatatacatg 23220
caggcagaac attcctacac ataaaataaa aatccctcat atacacagaa ttattagtta 23280
attaaaaaag aggagatgaa ttaagaattt gctcacagtt cctgcagaca atacctgaag 23340
tgcggggtgt ggtcagcggt gtcgcctctg tgaaatctga ttgagagaac tctgaagctt 23400
gcaggtcagt atttcctagt gcacagcagc actggttctt gtttatgttt attttctatc 23460
aagaacctgc ttgacatcgt ttctgtctta tagaagaagg caggctatgc ctcaagtagc 23520
catgtttgca tattcaaaac acttaaaata atctaccttc tcttgaacca gagtgagcta 23580
tttataaact ttgtaatcat tgacacactt ctatatcctt cactaagaca attaatgtgg 23640
gaagacagta tttcagtgca taaccagctg ttgatcatct ttgtagctat tttagttgct 23700
ctgtaagact ataacaaaac tatcttcaga gacagttgat agaatgagaa atttagttgc 23760
ccaatgtttt aagtaggaaa aaggcaaatt acttggttac tttactatat acataataaa 23820
ggttagaatg aacacaagtg tgtcccttac cccctcattg tgggtatgct gtatataacc 23880
agtacatgga ggggttttga gtcaggtctc tgctggtgtc tgttttgact ttgaatacta 23940
tgtggtagag gctatcttta aagtactgct cctgcctcca cctaccaagt tctgagatta 24000
ctgccatggg ttatctactt agctcgagtt ccttttctca gctactgtct ccagcaaact 24060
gaaattacag cagatactgt tgtcattgac agtataagct agcaggcaga cttgtgacac 24120
agctgccaag cagtgatgtg tgtgtctaga ccattcttgg aaaagggaga ctgccaggga 24180
cttagaaagg ttgtgtacag ccaaatgata attattttc agtgatcttg agcggcttgg 24240
atctttcttc tcctgtcatg tgctaaatgc atttaattaa tatttccaag acactgaatt 24300
tctcccgtac ttctcaaaaa atgattagag gtggaagatg gtggctgtct agacagtagg 24360
tgggtagaaa gctttcaagt ttacccaaat cttttagaaa ccaggtaatt gttctaacta 24420
tttttgagaa tttagtcttg catggtatta aattctagct aaaatgtgga agaatagtgc 24480
tggcaagatg gctcaggagt tctaggcaat tgttgtccat cccgagttct atcctcagga 24540
cctacctggt ggaagaagag aatgacaaat gcagattgtc ccctgacctc cacatgtgca 24600
ttgttgcata tatgcacaca tacacacaga gaagaattac catatagtat gtattctcta 24660
aaatgcatct taaaacatta agagacctat aaaagacttc ccacatcacc tgttaactgt 24720
ttggctctat gagaggaaca tagcctgctg gttaaaggta tatagactgg aaacattgcc 24780
tgccccaatc ccagctcatc cactggggag ttctatagac cagtaagtaa tacagtaagt 24840
tggtctgact gtattaacca agccactaag aacatctgag agcattatca gactgcttct 24900
agtagagctt acttaaacag catcttgtta acttcatgtt gtcttttcag tattgttcct 24960
gtaagagctg ggcctatgta agttgttttg ttagtacttt gttgctctta ggaaaacatt 25020
ctaaatttat aaggtcttta tttttgaata gtacatcata gacttatggt aagaaatcag 25080
tgggttggtt tttttgtttg tttgtttgtt tttgtttttt taaattacaa gagtcctttg 25140
aaaagccaca caccatgttc cttacacatt tacccttgtc tctagctctg attttgcaca 25200
gttaggcctt gtagacagac atgtggattg cctagtctgt aatggcagtg gctagtgatt 25260
caacagctca cactggaggc taagttctat gatgttttag cttttagaaa taattgtaca 25320
tagcacctaa aatgctcaga atggtattta aactgtactg cactgacagg tctgactaga 25380
taactgcttg tctaattgtc acacagccta gttgggttgt attctgaccc agttgtggca 25440
gttatattca agacctggta tgtgacatga acagtgtctg ttaggctgcc tcactgaaaa 25500
gtggaaggaa tcagtccgtg ttagttgatt gcctggttcc aacttaaggc gaacctttct 25560
gcttcttaaa gatttattta tttatttatt atatgtaagt acactgtagc tgtcttcaga 25620
cactccagaa gagggagtca gatctcctta tggatgattg tgagccacca tgtggttgct 25680
gggatttgaa ctccggacct tcggaagagc agtcgggtgc tcctacccac tgagccatct 25740
caccagcccc ctttctgctt cttatcaaga gccagatgat gggacggacc ctggtgccta 25800
ggccagcttc agcctgtgga acgagaggca aacttaccag gttagttgtg agactgaagc 25860
actatcagaa ccccacactt tcctgcctgt ttagtttggg attgtgggct ccagtaatag 25920
cagctgcctc atttttagat tttgtggaag aactgtcaga tttggggttt ttaatttgtt 25980
tttctgaaaa ctttttattt aatgactcta cccgtaaact aattttcata tttctgtttg 26040
cactgctgtg gaaatgggag ccattctttt caactcagtg cctggaatgt tggactgaaa 26100
attccatttt attgtgtgtg tgtgtaaaaa tgtgtgaaag cttttgttcg tttgtttaag 26160
taattccgct tatttttcat ggaaagatgg gtggctcaaa attgccagat taattaaagg 26220
tatgagaagt gttcaaagat ttaattttgt agtgaaactg atcagtgcaa cataataaat 26280
actaaatttt gatgtgctta tttattcact attccctcta tcttatctca caggagtaga 26340
aatatgtccg atttacaggt catttctaat agaccagaac taagattttc tttggaagat 26400
ggactgatag tctttataga gttttcatca atcaagatgt taagaatacg tatctacaaa 26460
ataagaacta ttagaggact ttcatttgtg gttttgtttg cttgtttttg gtttttcatt 26520
cattgaaaga gttttgattt ctaagtatta aaaaataaat accaccgtgc tttttttgatt 26580 cctgcactgg ccattgtcac ggtgtacaga gcacaagatt gtgtgagccc atttgctgca 26640
gaaagccatc ccatcatgat cagtggaaaa atcgattgtg tagttttgaa aatttagatg 26700
gatggttgtg ctgctggtgt cagctggagc tggggtcagg agcgggccag cccagcatcc 26760
gcacggtgga ggactgaggt tagcagccct tcccagcatg agccccaagc tccctcgtgg 26820
aagatgagag atatacctga acaggaatac ctgatttgaa caggaaatca cattaaataa 26880
gtgttggact gatctgcccc ctaacatggt caccttgggc aagtgagtag actctgcctg 26940
tccactaaca ttggagctca ttgttctttt ttgttttttt gtttttagtg gaagtttagc 27000
gtaagataaa gcacccaacc acaaaccttt aaggtaatat tatatccgtg tgtgttttat 27060
aacctcacag cgttcagaga tgttccatcc attcacctct gctctcattg ctttagcagg 27120
ttgttgtttt aaactgaatt ttttaaccca ctagtaagtc ctgaaatcac tttagttagc 27180
tgtagccagt ataaaaccaa aacaaagcta atgaatataa aagaaaactt tagggtgtga 27240
tgcagagttc agtaaaggca aagctaaacg cacagttgtg tgcgcctaca gctttccctc 27300
cacaggactg acggtggtag agtgttttgc ctaccttgtt caaggccgct ctgccttcct 27360
gtgagtgttt tctctctctg actgtactct tcatctctac ttttcagatg gagagccttc 27420
tggtatagaa ggctaactat caatatttca tggctcccta agggcagagt tcctaaagga 27480
agtactgtga cttgtaggtc ccgtgatacc tgagcatgtc tgaggtgctc cttggtgggt 27540
aacatagaag gcccatcttg agctttcatt ggctctcagg tctaagcagt gtcgcagtgt 27600
gatctaagca gccgcctgtg caggtgctct gtctctcaac accattacag acggattagc 27660
agggaaccct tcgtcttcta catcgcattt tagttgtatt ttaattgttc attttgcaaa 27720
ggctttgctg aaatagcata ttctgcatcc ttctgatttt caagtatgcc tacctctact 27780
ccctgtagta aatgcacata tgtgtgcaca cattcataga ggccagaggg gcattattct 27840
ctcctccgga tgttctggac ctggagttta gtgctaggac tgtctacgct gcttggtcca 27900
tgtgctctgg ggatctttct gttagtgtct gccatgctag tgctgggtta cagttttcat 27960
gtaggtgttg caggtctgaa cttgggtctt tgcacttaaa cagagtgagc catctcccta 28020
gcctgtgaat ccttttgggg tttctaaaag agctattcca ccctgcaaca taagcaaact 28080
cctaacgaag caaaaaaact tttctttaat tcaaaattca aataacagac agttggtatt 28140
tttgaaataa tggagttgga tacttatata actctatttt cctcactgag tgctttatta 28200
agaaaagaga ggagctgatg agatgaccca gtggtttaaa gcactggccg ttcttccagg 28260
agacccaggt ttgattcctg tcactacatg gtgacaccct atctggcttt cacaaggatg 28320
caagtgatgt acatgcaggc aaaacaccaa tacgcaaaat aatatatatt ttaaagaaga 28380
tagttatcta ggtcagcaag caagatccct tggccattgt tgaggacctg cggctaatgt 28440
catcacaaaa gtgggaatat gtgctgaggt gtcatatggt gagccaggaa gccagagagg 28500
ttcaggggcc acccttgcta ttttataaca tcttgctttt gtgaaaacta actcatttca 28560
agaaatgtgg ccttaaactc agagatcgaa ttgcctcttc ttccaaatgc tgggattaaa 28620
ggtgtctgtc agcatactta ggcactgtaa tggctcttcc tggttgtcaa cttgactgta 28680
tctggaatga actacaatcc agaactagaa ggctcacctg tgatcctaac ctggaggctg 28740
ggagatacaa ggttctgccc tggatctcag catggagatc tggaggcaca gtggctatga 28800
atcccatcca gaagattaag taagacaggg agatctctga gttcaagggc atctggaaca 28860
aagcaagtcc cagatccagg cttgttggca cacaccttct gctggagccc tacataagga 28920
cattggaaga aggaagatat atgctctctt cttcacctgc ttgcctgtgg ggctgagcaa 28980
ctgctagatc cttggacttc cattcacagc tgctgctgac cattgttggg agttggacta 29040
cagacctaag tcatcaacag atttccttac tatatacaga ctacccgtaa gttctgtgac 29100
tctagagagc cctgattatt acaggcacat acagatttta tttttttatt attttttta 29160 gatacggttt ttctgtgtag ctggttgtcg tgaactcatt ctgtagatca gactagcctc 29220
aaattcagag atccacctgc ctttgcctct ggagttctgg gatcaaaggt gttcactacc 29280
actacctggc gatttgattt tagcttaaat ctacatagac agaatagtta gaattgcaca 29340
cctagtgcag gggaagagag gtgaccagat gttgccacag cttgccagct ccatagagag 29400
tgtctgtagt gcagaataca cttggcatag tgttcagctc ttctctcagg atggaagcta 29460
agcatgtgtc cacaacactg tgtgtgtgga tgtttatagt ggcctagtca tgcagccaga 29520
gataagagaa gctcaagtgt ctgtccacgg ggaaagtcac ccaacggaat cctgttaagc 29580
tgtaaaagga agcagtgaat gagaaaggtg acagtcacgt ggatggggca gacttgctgt 29640
gtaagagacc agagcatgca ctttgtcttt ttctctgaaa cttgggaact agaacaagag 29700
aaatcagacg gctgttgctt gaggctgggg tggagaaaaa gacccatcta gaatggtaag 29760
cgtagcttgt atgttgtagt gcaccacctg tttggtgtgc gtcagttgtc aggaagtgga 29820
cccaccttgt gtataagcgg tccttgtgcc cgccggtgtt ggttgcttta tgtaaagtag 29880
aaagcagcct ttcttggtgg accgcatccg tccccagctt atacacgtgg cctcagttaa 29940
atcttaaagt tacccaaatt aatatttgtg gcacttggtt tggggacatt tttgggaccc 30000
gaagggtgta ttactctgca taatctccaa ctggtctcag cagttctggg cactccatac 30060
tgtcttcccc ttttctgata acagagcttc gggacatgtt ttttatgggc agatgatttt 30120
tgagcttctg agaattttag aacagattct ggtttccaga aatactgttt gaaattgttt 30180
ggaatctttt cctttgtagg atttcaaaat gaatgcactc ctatgtctgg gttgtattgt 30240
ttgttgtttt gcttttcttg cctattaatt ccgtgtctga gtcactgagt ttttactttt 30300
ctggttaggt tgacttatag ttaatgtgac ttggcctgat atttttcaaa agacttacac 30360
agatatgtag tgtatttgtg aatatttata ttttgttaat cactggattt tacttgttta 30420
ctattaatag actctagtgt ttaccaccag ctccttagaa agctccaggg ttagactaga 30480
cttctcagag gtccctgtga tgatggccaa aaaggacagg gagtttccat ctcaggtcgg 30540

-continued

```
gtccggtggg agactgcagc gggttctcct tgatcgaagt gttctcacag tactcgtgat  30600
tacagggtca taaaacaaac catgctttgt atgcacactg gaagttgttg ttttgttttg  30660
tttttccttc aaaacagggt ttctctgtgt agccctggct gtcctggaac tcactttgta  30720
gaccaggctg gcctcgaact cagaaatctg cctgcctctg cctcccaagt gctgggatta  30780
aagacgtgcg ccaccactgc ccagcacact ggaagttttt acaagcctta gtactgccct  30840
tgtaaatttg atattgctgt cttaggtata ttgtgaagaa atctagattg tcctgtgctt  30900
tttactctat attttttatt gtatgatata gaatacattt caaaatttat caccttagca  30960
catggttacg cttatcttta tttttgttgc aacaacataa agaacattac ttactatgac  31020
aaaggttaca tgcatttatt tagcttttttt ttaacctttt tgttttgtat ttgagtcggt  31080
gtctcactct gtaaccctag cttggcctgg aactcacaga gctccttcct ctgcctccca  31140
gccctgaggc tcctgcccgt tcttgcgtgg caggggagat gagtgagtac acgctctaaa  31200
aatctctttt ttaaaattta aatctcttct caattactct ccagtgttgc tggtcagagc  31260
ttgtgcactg tttggctctt ccatgccttt tcttgccatc acagcttctt ccagcttggg  31320
gtgggcttct gtccagtccc cctcccccttt ctcctattag agcagttcta tttgcttggt  31380
ttttttgaga tagggtttca tggtttctgg ttccattccc tatgtggctg tggttggcct  31440
tgagtgcctg atgctcttgc ttctacctcc ccgttgctgg gatcacaaga gcatcccacc  31500
ttgtttgctt agcagtgaga ctcctgaagg gtgtacttag gtgtacaata aaggtgctta  31560
cttcacagtt gttatttgaa atgtaatttg ctcacacagg gagtaataaa tttggagtgt  31620
ctcaggagag aaagcctggg atttctgac aggcagtttt gctctattac tgtctccact  31680
ctgtactgtg tgaccagata tgtgtagagt cctgcaagaa caccgagtgg cttctgtctg  31740
tattttatag tttcttagtt cactccttag gcaaagcaaa cacagtaatc cagggcctga  31800
ggtccagaca gcccatggac ccagaacaga ttccctatct ggtttatgcc tccagctgtt  31860
accgttgcct ctacagcact ggctcccgtc tttccatcgc tgcgaccctc taatacggtt  31920
cctcttgctg tggtgaccct cagctgtaag attatcttca ctgctacttc atagctatga  31980
ttttgcataa gtatcagtat tttctgatgg tgttaggcaa cctctgtgaa agggctgttg  32040
gaccactgtg gaatggttgg ccctacctca gcctgataac cctatgatgg taaacgtgtt  32100
ttgttctctg ctcttgtcct gaagagccaa ccagggtgca ggatacagta gattagttgt  32160
gtatgcttct ctaacaaacc tgaactccag taaatcacac ttttctgctc caggctcata  32220
agagttgttt tggtaccatc tttctttctt tctttctttc tttctttctt tctttctttc  32280
tttctttctt tctttctttc tctctctctc tctctctctc tctctctctt tctttctttc  32340
tttcttttaa ttttaaaaaa atttttatgt ctgtgggtac actgtagctg tcttcagaca  32400
ccccagaaga gggcatcaga ccccattaca gatggttgtg agccaccatg tggttgctgg  32460
gaattgaact caggaccttt ggaagagcag ccagtgctcg caagtgctga gccatctctc  32520
cagtccggga ccatgtttct aataggcctt tttgttcact tgtctgcttt gattttgaaa  32580
tagggcctgc cctgtactct agatgtacct acgacttgcc actctcctgc ctaagcctct  32640
ggattgctag gattccagtt ctacaccacc tcacctggcc tggaaggtgg attttagaaa  32700
actgtcaaag atgaacaaac tttaaagaaa tccagagtta gaaaaccaga ttaatcaggg  32760
ctgatttatt cattttatgt tggtgtatgt tcaattttat acactcaatt acacattcaa  32820
ttctatcaaa gaaccagtta tactaatgat ttcttaaatg aatattttcc aaaccttgtt  32880
taaactcttt gagttacaaa agttgaatct gcatataatc tttcagtttg tcaaatgagc  32940
```

tgtgagtttt caggaaatct atccatttgc tagtgatagg aatgttacaa catgttcaaa 33000
ctgttactta agtttattat tttagcaata ctgccacata tgaagagata taagggaagt 33060
ggtaaattat aatgaggaat agttaatgtg acaggaccca aaagtgtatt tcagtccttg 33120
tccctggagg tctgtcatgg tagtttttgg aagacatcta gtgagtcact gttttattta 33180
gttcagtggc cattatagca atgatactga ttttgtttta tatggcagat ttacggggca 33240
catgaaaaat agaatttgca ggctagggat gtagctaagt tggtagagtg cttacttgtg 33300
gagaggcaag ttcgatcccc agcacctcat aaagtgggtt tagtggcttg tgcctgtaat 33360
cccagcactc aggagtgggg aggcaggtgg acccaatatt atcctgtgtt gctattaata 33420
gcaaagtcaa ggccaggttg ggttatatga gactatgaga ctctatcaga aaaaaaaaat 33480
aataattagg ggaaaaaaag aaaaagaaag cagatcctgc ctccaggaat gacaggattg 33540
cagtttgggg agggtcactg gtcaggaagg gactgactta gtaaagtgca gtctggccgt 33600
ctccttttga gggcctcagc cagtgactgc tgtcctaatt aacatatcag taaaacttat 33660
tgtgtgatac ttgaactcag tgaaagatta tagtaaactt actcacgcta gactttgcca 33720
acattgtaag aaaaatggaa ttgatgactt tcaggatatt gtaatggatt gctttagctt 33780
tagtagcaga tttttaaaag gaatgaatca ataaagccat tattctgtgt gtgtgtgtgt 33840
gtgagcatcg caagcatgtt cgtgccatcg tctgtctgtg gtgttgcaat gcatcagccc 33900
acattgagat cagaggatag cctgagagag tcaggaatgg cactcagacc caaggccact 33960
cagacccaag gtagccgctg cctttaaccc tttacctgct gagttcttcc ttgctgtcaa 34020
aggataggta atgactgtgt ttttcttcca tctggtcact tcttttgggc tcctgtttac 34080
cttcacttcc cttagagacg aagttctgta aaactacccc atttgtctga gagcttattt 34140
gtgtcctccg agttgcctgt tggaaaaagt cctggcctag aggattccac agcctcccct 34200
ctgagtgctt cctcatcaga cttgtggttg ctgagggcag aatgtagaac tctgcagaat 34260
gatgtcctgt ctcagcctcg ctcatgtctt agcgctgaag agtgacccca tggaccatcc 34320
atcagcctca catctcacat tgttgctgct gactcccttt accttgcatt cgggttgtca 34380
gactctgcac tgtcctgagc accatgaaac ccttgcagtc tcttgtactt cccagtcctc 34440
atctggagat ggagcaagca cagtggctta tagatcttcc cttgtgagtc cgtggtatgt 34500
caagtttctc ttcttaatgc gttcagaatg tggtcagtgt tgaggagcgc tgcactcaca 34560
cagacaggaa ggaagagctg gagtctgcac tctaacatcc ttagacccaa ggtcacttct 34620
gtgtctatgt tcactagacc cacctgaaga ccctcgtttc ttatcctgaa ggctcagctt 34680
agacaagctc acagctcttt tatttcagcg ggtctctctg taatagggtt tagttttttt 34740
gttttttac ttttagaaag taggtgttaa catctttagc atttagattt ataattactg 34800
agaattttct gacattttga atagtaccac ttaatacatg gagactaata atcaaacatt 34860
tagactggag ctgtttgtgg caggagccag ttttccctca aagctggcgg actgtgatta 34920
tctgtcccta tgtacagcag ctccacaagc catgctacac tctccgcagt cccatttcta 34980
tatggtgttg gggtaactac cactctgttg gtagtctttc actgtatgtg gaaatatagt 35040
ccacctcctg aggacgagag agaggaaaca gtagcaatta atgctttatt cccgcagtgc 35100
ttcagaaatc ggcatgcaag ttctcatgct agtcttacta atgctgttat tttgaatttg 35160
tttaatttca aaacagtgtt cagtgtctcc taatgagaca tagcccctga aacaaggtca 35220
gtgtgataga agagggagcc tggtctgtca ataacaggtg gattttaaaa gcctctctcc 35280
aagctggtgg agctctgagg gctaggtgtg cagtggatgt gatgcggatg ggtgcttcca 35340
ctctcccttg ggaacactgc agaggctcct tctgtgctcc cctgggatgg atggctactg 35400
cctgtagatt tgggttatac ccactccggg caatcttcag gagtcttgcc ttcacacttg 35460
gtctttctag cagtaagact gcttctgtgt gagagtgtct gttttgacta gcttctgcaa 35520
aattggggtt gcctaggaat cctgtctttg cctaaaaatc tgaactctag attttgtaag 35580
tacaccaagc ttccacataa tactggatat tggacccagg gtctggtgcc ttcgaggtaa 35640
gccttctgcc tctgagcggc acccagctgc tggttttgtt tgttcggttt tcccgagatg 35700
ggttttgctg tgcagcctct gctgtccttg aactcactgt ttagaccagg ctggcctagt 35760
gctgagatta aatgtttgta ctaccatcac cctgctcttt ccttttgtgc ttagtcaggc 35820
ctaagttgtt cactctgtat gccaggccgc ctttgaactg gagctctgcc tgtctcagcc 35880
atccacatcc atgctgcctg caagacaagc acaggccaca ggcttggctc caagttaaaa 35940
aagaaaaggc tacagaactt tgtaggcttt tgtatttttt taacaaacac aggctatata 36000
tgtgtgtgtg tgtgtgtgtg tgtgtgtgtg tgtgtatttc tgaataaagt gcttaataaa 36060
aattaagaaa aagattgcta atttattcag taccattgta tactgcagag ctttatcaag 36120
tattttcctt ctttattttt ttaaaacttc ctttggccaa cctttgtcct acctcaatcc 36180
tcaaacttgt ctccttgtgt agatacagtc cttggagcac tgcagcaaga ggcccttgta 36240
ggatcttgga gctctgtgta aattcaactt ggaagccaga aatggttctt ggcacttgag 36300
gccaggaaag ggcagtgtga gcagcggtga atggaggtgg cggtgaatgg aggcagtggg 36360
atgctgttta gtctgtttcg gttgactagc ttggtgctta cgctcgctct gttctgtctc 36420
ccattgttgt atcactaaca tgaaggaagg tacctgtggg cctcggatgg ctcacagcct 36480
acccagtcct tttacttcat ggttttgctg aacacttttt taaaaatcct ttttattgtt 36540
ttttgttggc attcctcacc ccgtccttgc ttttcatttc cattttgaag gacagcttaa 36600
agaaatgtcc atgtctcagc acccgtgtac cttctgtccc catgtggaac tcaacaaatt 36660
tggaagacat ttgcttggaa ttccaaaggg cactgtggaa actgaacttt catggtaaac 36720
attctggaaa tgacagaaaa tgggggtatt ctcttctgaa agaagacctg tggtcttgtt 36780
gaagataaag ctgagaataa cagcatgcgg taaaatctgg ctttgagtta gagatttaga 36840
tgagcggttt ctatgtcctt ggtttgttaa gcctgtctac aatattgtat ctgttcagaa 36900
atatttatta ggttgaaatg aaggtatttt tttccagttg tttggtaagc aactattata 36960
tatcgctacc aaatacaaat gtctcaagtg catgttaaat taggaaagca aagctagaaa 37020
gacttcgggc agcataaggt gtcgcagaat aaatgtacta ttcggtttct tctcatgaac 37080
cccttctaga ctcgcccaag atgggaatgg tatatccacc cagagttccc acgctgtcag 37140
cacggacaga ctggaacaca gctgttgatt tctataggac ttgcctggct gtttcagaag 37200
agttggtctc tccttcagca cattgagtag tgctcatttt gtagtgttac tgggaactag 37260
agagtagagg gctgagagac tgatgtccca catatggggt cttgagttgt acctcctaat 37320
gtggccctgt gtctgtgata atctatgtgg ttatcattag tttttagcat agagagggtg 37380
tgatgaaact agtcacactt ttatacttag gacttcaata tgcgtcattt gatttagttc 37440
tcccaagatc tagcccttca tggtggtgca tgcccataat cccagcactt gggaggcaga 37500
aggttgatat ctgtgatttt gatacaaatc aagttctggg acagccaggg atgcataaaa 37560
cagactgtct cgttaaaaaa cttaaaaaaa ggatcccttg gtgctgtttc tatttttgac 37620
ttaacatggt ttctctttga aagaataaat ttctcttaag aagtcaacat tactgttaac 37680
aaattatcag ctgattaact atttcccttg agtgtctcaa agcttttttt cttgcactgc 37740
tttttctatc atctcctctg ttttataccc tcctgccccg gcagactgtt tcctgcccac 37800
ctcccccccc cccnnnnnnn nnnnnnnnnn nnnnnnnnnn nnnnnnnnnn nnnnnnnnnn 37860
nnnnnnnnnn nnnnnnnnnn nnnnnnnnnn nnnnnnnnnn nnnnnnnnnn nnngatgcag 37920
caaacacccc tttccgtgtg ctcttggatt aacagtgctc tccctctgtc catatttttc 37980
ctggtctagg agatcggccc ttgcgccttc tgtgcttcga ctctgggttg agccatgtgt 38040
catccagcac tatctccctc attttcatgt cattcttaga gtctcctcca ctttcatttc 38100
tgttttattg ctatccccat cagcactgta cattatattc gttgtgggag aaacatttta 38160
tgtttgtttg ctttttaaaa caaagtctga atatgttgcc ttgtctggcc tgtatgtaat 38220
tccttgtgta gaccaggacg ctacacagat ctgctggcct ctgggttccc cagagtgctg 38280
gaattaggta tgtgaactac catgcctggc tccaaaacat tattttataa taagataaag 38340
aacattttgt ctctagagaa ctctaggtca taaccagtat tttatttctt ttgagcatta 38400
aaaaatacaa ttacattttt actaaatata acacgacata aaatatataa tgcaataaat 38460
aatacaatta tatgtaatat atgtgtccac acacacatac atcaactttg taagtataaa 38520
gttgcaaact ttgacaaatg tttgtaataa gctacttaga cacaagtgta tataattaga 38580
aaatttactg tacttttaag tcacccttgt tttcaccctt agactggccc cccacctggg 38640
tcctctcagg tgtaaaggtg taaaactgcg aattgatttt tacaccttta cacctnnnnn 38700
nnnnnnnnnn nnnnnnnnnn nnnnnnnnnn nnnnnnnnnn nnnnnnnnnn nnnnnnnnnn 38760
nnnnnnnnnn nnnnnnnnnn nnnnnnnnnn nnnnnnnnnn nnnnnnnnnn nnnnnnnnnn 38820
nnnnnnnnnn nnnnnnnnnn nnnnnnnnnn nnnnnnnnnn nnnnnnnnnn nnnnnnnnnn 38880
nnnnnnnnnn nnnnnnnnnn nnnnnnnnnn nnnnnnnnnn nnnnnnnnnn nnnnnnnnnn 38940
nnnnnnnnnn nnnnnnnnnn nnnnnnnnnn nnnnnnnnnn nnnnnnnnnn nnnnnnnnnn 39000
nnnnnnnnnn nnnnnnnnnn nnnnnnnnnn nnnnnnnnnn nnnnnnnnnn nnnnnnnnnn 39060
nnnnnnnnnn nnnnnnnnnn nnnnnnnnnn nnnnnnnnnn nnnnnnnnnn nnnnnnnnnn 39120
nnnnnnnnnn nnnnnnnnnn nnnnnnnnnn nnnnnnnnnn nnnnnnnnnn nnnnnnnnnn 39180
nnnnnnnnnn nnnnnnnnnn nnnnnnnnnn nnnnnnnnnn nnnnnnnnnn nnnnnnnnnn 39240
nnnnnnnnnn nnnnnnnnnn nnnnnnnnnn nnnnnnnnnn nnnnnnnnnn nnnnnnnnnn 39300
nnnnnnnnnn nnnnnnnnnn nnnnnnnnnn nnnnnnnnnn nnnnnnnnnn nnnnnnnnnn 39360
nnnnnnnnnn nnnnnnnnnn nnnnnnnnnn nnnnnnnnnn nnnnnnnnnn nnnnnnnnnn 39420
nnnnnnnnnn nnnnnnnnnn nnnnnnnnnn nnnnnnnnnn nnnnnnnnnn nnnnnnnnnn 39480
nnnnnnnnnn nnnnnnnnnn nnnnnnnnnn nnnnnnnnnn nnnnnnnnnn nnnnnnnnnn 39540
nnnnnnnnnn nnnnnnnnnn nnnnnnnnnn nnnnnnnnnn nnnnnnnnnn nnnnnnnnnn 39600
nnnnnnnnnn nnnnnnnnnn nnnnnnnnnn nnnnnnnnnn nnnnnnnnnn nnnnnnnnnn 39660
nnnnnnnnnn nnnnnnnnnn nnnnnnnnnn nnnnnnnnnn nnnnnnnnnn nnnnnnnnnn 39720
nnnnnnnnnn nnnnnnnnnn nnnnnnnnnn nnnnnnnnnn nnnnnnnnnn nnnnnnnnnn 39780
nnnnnnnnnn nnnnnnnnnn nnnnnnnnnn nnnnnnnnnn nnnnncctgg ctgtggagtg 39840
tagacagtac tccagagtac agccacaccc cattctcttc acccgcacac caggggaagg 39900
aagttttgac tgtctctgtc acaaagctgc catgagctct tgcttgctgg ggtggcccta 39960
ctcagggcag gcatttgaga gagcacttag ttggacagtg gttgggaagg cttaaatgtg 40020

-continued

```
cagccttgct ggacgaggca ccgcgctctt tcccttcatg ttttcccctg aagcgtgtga  40080
gcgctcagcc tcttgcagcc ttccatgcct gcctctggct gccactctgc agtgcctaag  40140
ttgtgttagt actgaaacag aaaaaagtat tatagctact aaatgtctga caaacatttt  40200
catttcatat tgggttaata cctacgaatg ggtttgtggc aaattttcac ttgtttactg  40260
ttcttgttca ataaactaca gaagtttgga aagaaacttt ccaactaaag gctcggtgcc  40320
tttccagaga gaaagtcagt tcgactgtgg tttgattgtt gagctgatga ggagctgcct  40380
tgttgattga cagctttcct tagtttccca cttcctcatt ctcacttcct gcccacacaa  40440
tcaccctctg ccccacaaat ctgttgtgtt tattttaaat tagattcttt ttttgtaaga  40500
tagtaaatat gtgctggaaa ctcagccctc gttgtatggg tgctaatgtc tctcagccag  40560
ccacgctgtt ctcaggccgg tgctgagtga aggtgcaagc attaggtcag cccacgtggc  40620
ttgttcagtc aaactcggta tgttctgggc tttgctttga aatacttgga attttccaga  40680
agttactttg gttgttcttc tttcaagaca gagtttcttt ctctgtatag ccctggctgt  40740
cctggaactc actctagacc aggctgtcct cgaactcaga aatccacctg cctatgcctc  40800
ccaagtgctg ggattaaagg cggaacggat gccaccactg cccagctttc ctttggttct  40860
tcttaagggt gtgtttctga ttcctgctaa cttgcccgcc acatggtctc tgaatggact  40920
cactgctcct ttggatgaag gaatgcactt cccagatact ggcattctgt ttggagactg  40980
gacatttagg gatgtgttta ctcgtaatta aactgtttga gattttgtag tagtggacgg  41040
tttggtttta agatctattt aagataaatt cttttaaaat catttccttt ttaaaaaaga  41100
tttatttatt ttatgtatat gagtacactg tagctgtatt cagacacacc ggaagaggga  41160
atcaggatac cattacagat ggttgtgagc caccatgtgg atgctgggat ttgaattcag  41220
gacctctgga agagcagtca gtgctcttaa ccactgagcc atctctccag ctcctcttta  41280
agataaatta taagataaag ctagaaaata ttttttgaac atgtatatat atatgtgtgt  41340
gagcgtgtat gtatgtgtgt gtgtatatat tcattttttt tcttgagtta aaaaatgtat  41400
atacacatga tttaaagtga attaagcacc ccttgctgct actgaagatc aaatgtaagg  41460
cctcacgctt tctgttcttc cctgagctat atcactaagc ccagattagg cttttttttt  41520
ttttctttcc attttttatt aggtatttag ctcatttaca tttccgatgc tataccaaaa  41580
gtcccccata cccacccacc cccactcccc tacccaccca ctcccccttt ttggccctgg  41640
cgttcccctg ttctggggca tataaagttt gtgtgtccaa tgggcctctc tttccagtga  41700
tggccccaaa ttaggttttt ataaccacaa ctttatttag atttttgtat taaataattt  41760
tgatgaagct ccaattttca tgtatacatt tcctctatag acaaagtatt cagtgatggg  41820
ttagtgctag aagctcttaa gaacttaaga ttagattctg tgcttcaaaa ccacccagag  41880
tcgttttaga tacaattttg aatcctctta ttttttaact tgactcttaa aaaggtttat  41940
ctttagtgtt tgctttgaca atacatatat taaaattgga acaatgcaga ggtgattaga  42000
ataccccccca gaaggatgac atgcaaattc gtgtcataga aagcattcca tacttttaca  42060
aatgctaatc tttattgttt aaatgatgtg tttggcctgg gcgcacactg ggatagtatt  42120
ccataagtaa taccttaact ggcagagata tttcaattct ctgatcacat ggaaaggggg  42180
ctagcaaacc tggctgtact ggcaatggct agtgccttgg ctattcttgg ttgtcactgg  42240
actatatctg gaatgaatta caatccagaa atattgggca catctgtgat tgagatggtg  42300
agacaggaag acaacatgct tttgatccag atcttgaggt ggtttggaac aggcctttaa  42360
tccagatctt taggcacacc tttcctctgg gccacacaca ccttctgctg gaggcctatg  42420
```

gaaggagaat ggaaggaaaa gggtttgctc attccttgtt tgcgtgtact cactctgtct 42480
gtcagcacat ctgtgggacc ctacttcttc agtggagttc caccttacac agaagaccac 42540
tgagacaccc agcctcacgg gactgagcag ctgctgggct tttggacttg gcattcacaa 42600
cccccattgt tgggttagtt ggattgctgc ctctaagtca ttcaataaat tacacacaca 42660
cacacacaca cacacacaca ctatttgtat atatttcatc ctgtaagttc tgtgactcta 42720
gagaaccctg attaatacag ctagggatgg gctggctggg atgatgagag catcaaggct 42780
tctagtggcc tcttaacaat gtgtaatgaa ctgtccttaa atgcaagggt tctgttttgt 42840
gctattaatt aaattcacag tgaatactgg taggacagct tgcaatttat gtgttttgtc 42900
ttgggacttt agtaatttgc aaggtgagat gaagggacag atagtgaatt ttcagtaaat 42960
tgtaccagga aaacgtgtaa cttcttggat tataaccaat ttgttggaag acagtggctg 43020
tgcagcacat gccaattcat tgtttctctc actgattact gcagtttaac tcaggtacca 43080
tgctttcctc attggtctaa gctgactttg gaggtattaa aaatgtacta cggtttgctt 43140
gatgattcta gatgggtcac ttgcttagtg tgggctgctg cccctgtgtt taatgtgcat 43200
taggtttttc ctacaatcct gccttaaaat ggagcatctg tttgtcatag acactcacgt 43260
atctctggtt gcttgtcatc ttctcagtgc tgccttttga taaacaagca cttttaattt 43320
tgataaattt aaagttaaat ttgttgcttt tagagccata ctcaaggtta caaagcattg 43380
tggaaatttc tgtatttggt aggagctagg taggggttca cctctattcc tttccatgtg 43440
actgttcagg catggttgga agtcatttgg ccacaggcat ccagtcttac ttttgttctg 43500
taatccagta caattgttga ttgtgctgtc ttggtgcagt tttaaggctg agtagtgaag 43560
gtctttcacc attgctccct tatactattg tttgattatt ttgaattctg gcatctctat 43620
gaatttgagg attcgttctc catttctata caaaagatca ttgtcatttt gacaggaact 43680
tcgctgactc actagttgac tttgggtgtt tgtccttttg acagtatcct ggtgtcttcc 43740
cgtgctcagt ctctggttcc tgtcagcagt gggcgtggtt ttcagtgcct agtcctcacc 43800
tccttgactg tcagtcccga gtagtgtagt ctttggattg ttccttattc ttacattgat 43860
agcatggcaa gcacacatca agcagaggga gcacactgag cacacacact gagcacactg 43920
aacacactgg cttcctagga ggaggcagat cacagcactc ctaaagtgca ggatgaactg 43980
ttttcagact gtgcacataa ccttaaggaa agcacactga tgccgagggc cccaggagaa 44040
ggtgactgga ggccagatgg cccatgatcc cggtttagtg agctcagcta gctttgcagc 44100
gactccaatg agatgtttca cagtgcagtg atgggttgtg gatcctgatg cctcagtaag 44160
ggtctaagga gggaaaagcc ctcctgcccc ctttacaggc gaaacaggca actgatagca 44220
aactttgcct tctgttctta agtgtttctg ctggtttcaa aatgttaagt aaccagaatt 44280
gatgagtgcc ttacttttga ggaagaaagg tatttactta caacaattaa acacaccttt 44340
cacactgaaa catgtaatgg ttgatatttt ctaggtacct ttctttgctc ctttactcgt 44400
ttgtctggac tgtggtctcg agacagtttt agtttgcaag tggtgttttt gttttttgt 44460
tggggacggg aggtcctgtg atctctggtg ctgggctttt ataacatcat tggtgggaga 44520
ctgcattgct gcttcaggag tgcttggcag taaagctccg tgtgcacagg agacagggct 44580
ttcaggcctc tcctgtggtc tttgtgatca ttatggcaga tagatggtct gacctagtta 44640
ggttgcttgt gagcatgaga gagtcagtcc taagacacag tatggcagac tatttcttct 44700
gttgttgact atgtctgtgg acactgctgt cagtggtagg tttcctgttg aactttgggc 44760
atggcttggg gatatttctt agctgagggc ttcggacagt attttggagc tagagtatga 44820
caggaaacga tttagtctct agtagattaa agattctgtg ggaatagttt ttgtggagtt 44880
ggggatttag ctcagtgata gagtgcttac ctggcaagct cgaggctctg agttcagtgt 44940
tcagctgggg gagggggggt caggtaactg ggattttttt gtttttcctt tctccggtta 45000
tttttactca ttgcttggtc tctaggacca gaatagtgtt tggtgtagca gagcctcagt 45060
aaataaatag ggactgacca tgtgtcttca gaagtatcct tggaactcca tgttggttta 45120
tgtttaaagt caccccctta gaggattata tagtttgact agtgagggac aacatatgtc 45180
ttgcttagtc ttctttatat tgatcatggc tgatttggcc atgtgccata cataacagct 45240
gatgtagtaa tagagatata agtacatcag ctagctcaat cagcactcac ttcccagtat 45300
ataatagctt aattttgttg aatttgcatt tacaatatta taaacagtgt gctaattgcc 45360
acagtgtgag tatggattag acagctaaca aagctggcat ttgaagacca acatctgtgc 45420
caaacacctt taattacagc aggctttgat tgccttgatt tgccccataa ataaattcat 45480
tctattggaa ctgctaaaat ttctgataat aatcgccctc ttttccagaa tctgccacct 45540
acaatataca tcttctactc ttacgcaaac ttctgttatt ttcttttaaa gatatacatt 45600
tatttatata attttatgtg tgcttacatg tatgcatgcg tgtagacatg ccactgtaca 45660
tgtgtggtgg tcacaggaca acttatggga gtcagtacct cattctcata tcgtgatccc 45720
atgaataaaa cacaggttgc caggagcagt caaatccaac cggagacatc tcagcagcag 45780
acagaagtcc tgttagtttg agagattgct attctgcaaa cattctttat aggatacttt 45840
agttgatcaa gcttgttgtc gctgtccata tcattgaact cttcgtgagt accgaagaga 45900
ggcagagatt tccctgacgt tgcctagatt tttacttgaa taggaacaca ctgttacatt 45960
ttcttccttt ctgtttttta ttgtatttat gagacagggt ctgtgtagct caggctggcc 46020
tcaagcttgc tttgtgaggg tgaccccgaa gtcctgctcc cttctagacc tatataggtg 46080
ctgtttccta tggtgctggg gctgtgcact gggcttctgc tttgcctgct gagctacagc 46140
ccccgttctt ctttttcttt tcttttaatg atgtcattga taggggggggg agttagagag 46200 agagagagag agagagagag agagagagag attgagagag agagaaaatt gtgtggttgt 46260
gtatttgtgt ttgccctcgt atgtgcgtgt gcacatgcgt gtctgtctgt cttggaaagg 46320
ctgcttctga gggaannnnn nnnnnnnnnn nnnnnnnnnn nnnnnnnnnn nnnnnnnnnn 46380
nnnnnnnnnn nnnnnnnnnn nnnnnnnnnn nnnnnnnnnn nnnnnnnnnn nnnnnnnnnn 46440
nnnnnnnnnn nnnnnnnnnn nnnnnnnnnn nnnnnnnnnn nnnnnnnnnn nnnnnnnnnn 46500
nnnnnnnnnn nnnnnnnnnn nnnnnnnnnn nnnnnnnnnn nnnnnnnnnn nnnnnnnnnn 46560
nnnnnnnnnn ncccgaaggt cattggagag ctggggtgta ctcccagaag tgatcagact 46620
atagtcacat actgttttta tattatagag ctcacaccac agtgaccttg gcactggggc 46680
aagggagagg ttggggctgg cggctgctgg cactgatact cagcagtggg cagcagaaag 46740
agtggactgg caggctcttc tccaggttct cccataggcg acatgcctgt ctttggacag 46800
tccgctttca ctctgcgtct tcagactgtt tttcttttgg gctatgttga gattgaacag 46860
agagccttca ggatactaag caagctttct accaccgacc cactgacctg catttcccgc 46920
cgtgtagacc atttatctct ttaatttcca aggtctctcc caccaattct gccaaagcag 46980
gttttccatt ttatttgcca acttgctttt taaaacttcc tgttaatcat cataatatta 47040
aaggtttttt tcttcaaaca ctagggtggt tggcttactt aacttggtga taaattctct 47100
gatctcaacc acaagtcaga ttgctgcagt tgtcagaata gtttgcctta ataatttgag 47160

```
tccaacaaca taatgtgttc taaggggaag aaatagaaac tcttaaaggt aaacacacca  47220
ttaaacagga gggtgttttc agtctagggt ggcttggatg atctgtaata ttgacattat  47280
gtgcagaagg aaacctgcct ctgcctaacc tcctgtgagt gcttcatcta cagaggatgg  47340
ccaagttcaa ttagaaacac ggtccaggtc catctggcta gcctgtttga ccagggagaa  47400
ggaactgtat gtagattgtc attttacaaa aatgtagaag agaacaggaa atatgagagt  47460
atatttgata gagcaacaat aattactttt aggggaaaac ttggatttca gttattatgt  47520
gctctggtcc attactaaga tgtctttcat tcttaactgt tcctgtcttt gctgtggaca  47580
cctcatgtac ttcacagtgc agtcacagtg ataggcagta aatagtgttt agttatacag  47640
aaactcagta cagttacatg gggaaaccca tacagctttg gatgactggg atactattta  47700
gaaaattaaa ggaattgaca tgtcataatt ggttttgtta catccctgca acctttgtgg  47760
gcatagggaa ggtgctctat gtagtttata tccgtgtgca tggtgagagc cttggttttg  47820
gggctagcaa tactggttcc agtcttgtga cccacataaa cttggggcat tggtgatttt  47880
cttttcaact aggttggact tcctcattta aaaaggaaag cagtcaggct ggagagatgg  47940
ctcagcagct gagagcactg actctgatct tccagaggtc ctgagttcaa ttcccagcaa  48000
ccacattggt agcttacaac catctgtaaa gggatctgat gccctcttct ggtgtgtctg  48060
aagacagcta cagtgtgctt gtcatatata taaaataagt aaataaaaat ctatttcttt  48120
ctttttaat tttttaaag gaaagcaatc gtactacctt catggtgagg ggaaatcata  48180
ctgcaagtac ctagagtact ttgtaataga gtagatgttt aaaaatgttt attaaataag  48240
ttaaaaggct gttaaatcat agcaaactag tagtgattat tttaagtatt ttgttaaaaa  48300
aataaattat aaggctaatt ggatcctatg catggagaaa ttccttgtga cactctgaaa  48360
acttaaaacg aactgtagtt agagaagaag gcattcctct tgtgttccag aaatgtctgt  48420
gtacataggc agactgtatg gagaccagag gccatctctc actagcttag aactggctga  48480
agagacaggg ctggctggca agaatccctc cctccctccc tnnnnnnnnn nnnnnnnnnn  48540
nnnnnnnnnn nnnnnnnnnn nnnnnnnnnn nnnnnnnnnn nnnnnnnnnn nnnnnnnnnn  48600
nnnnnnnnnn nnnnnnnnnn nnnnnnnnnn nnnnnnnnnn nnnnnnnnnn nnnnnnnnnn  48660
nnnnnnnnnn nnnnnnnnnn nnnnnnnnnn nnnnnnnnnn nnnnnnnnnn nnnnnnnnnn  48720
nnnnnnnnnn nnnnnnnnnn nnnnnnnnnn nnnnnnnnnn nnnnnnnnnn nnnnnnnnnn  48780
nnnnnnnnnn nnnnnnnnnn nnnnnnnnnn nnnnnnnnnn nnnnnnnnnn nnnnnnnnnn  48840
nnnnnnnnnn nnnnnnnnnn nnnnnnnnnn nnnnnnnnnn nnnnnnnnnn nnnnnnnnnn  48900
nnnnnnnnnn nnnnnnnnnn nnnnnnnnnn nnnnnnnnnn nnnnnnnnnn nnnccctctc  48960
cctctcctct ctcttcgtca tggcagcagc agcatttgaa tttctttaag ggaggtttca  49020
ggttagaact ctggtcctag gagttgctta cccagcaggc agatgcttca ctcagtgagc  49080
cgtctctcta gcctacaaat cactcttttt tgataaaagg caagcattaa tcaaataaga  49140
aattataata tgcaagatag aaactagaga gtaagtagac caaaatcaaa tcactgactc  49200
acttgccaag acttcaaaga actccaaatg aatcctctga agaagcacac ccaagtgaag  49260
aagagccatg cgtaatccac ttgacctggc tgatgctcgc atggtggaga catcacatct  49320
actcaggaat gaaaaatagg agtatgctta catgagacct accttttgcc tagcttgtct  49380
tctatgctta ccagcaggaa aaaatgttaa atattctgaa tattctgcct taattagcag  49440
agccagtggc tgtccagtaa tgggctataa cagtttgctt tgctgttagt tttcagaaaa  49500
```

-continued

```
ttgaaaatca tatgctggtt aggcttgcta cattttaagg aattttgaac aaatgattga  49560
ctttggtttt ataaaagaaa accctttatg agaacatgct agctgctcag tctctgaggc  49620
tgccacactc agcagtccca tgctggtgct gaaggcatgg aggagccctg gagagctgct  49680
gctctttagt tcgtgttgga atgccaaaga tggtggcaga gaagagcata ggaacagcaa  49740
cgaagcagag gctgccaggg aggcgtgaag gcggtagaca gagccatagc ttttccttgg  49800
gatcttctcc tacggagcca cccaccacat gccgctgctt ctccttctgt taagcaaacc  49860
cataggaaat accctggccc acctaaatct agccatgttg acaaccgagt tagccgtcat  49920
agccactgca gagcagattc cccttagata tctgcttaag tcatcgatgt gctaggcatt  49980
ctgtggaggt atggaaacac ttgatcttgc cattacccaa aatcaggctt tatatgcatc  50040
tgagatagat gctatatgat atgttaaata aaagtgcctg gacatacagc agtgtactaa  50100
tatacgtatt ccttagggct gaatattaag aaaggtgcaa tcggtgtgat gctaggtgag  50160
accgagggag agttagtttt ataaaagtta gtttgggata aagaactccc tatgcatcta  50220
ctggagtggg aacttgtaga actttgtcct gccacatgtg gtgcagatgt agaatttgct  50280
cacgatggcc cattcagaat agaacatcaa agaggcagtg accaagccag gcatggtggc  50340
acaccccttt aatgccagga ctcgggaggc agaggcaggc ggatttctga gttcgaggcc  50400
agcctggtct acagagtgag ttccaggaca gccagggcta cacagagaaa ccctgtctca  50460
aaaaaaaaaa aaagcagtga ccacgtcgta tttcatttgt aagatcacat gaaggaattc  50520
ctaggcgtca gaattcagca tctgactgag tgctggcatg ggacacatag tcacttcttg  50580
aactgaaagt acagttattt ccagtggatc cacacagagt gttgggacta cctggctctt  50640
ctgttagtcc ctttctgaac ctttgctaac cattcctttt ccttcgattt gcagctatcg  50700
actttatctg ttagagactc gcagatcaat ttgtttttat ggttattaca tgttttaaat  50760
ttattattga ggcaatttca ataacatata cttttctaca atattttgtt atacatcatt  50820
ttcaactatg agttctgagt tctcttttgt tcccagtgct ctgcactgct tctgcagtac  50880
cggtaactat acttatgtcc tctgactgtt tacagctgcc ccactcctgg gtctccatct  50940
aggcaagagc tttttaattt ccctacagcc cgtttgactt ccttgatgtg atgtgtttaa  51000
cccatgttgc tgctttaccg ctattactat gatccaactt cagaccttgt gtacactaga  51060
cctaaatact ctcccatttg gataaacaca caagttggca tcatacgctt aatgtttgcc  51120
cctgcatagt gctcatagcc accagctcct gatgagttct gttagactga gagtctcgtg  51180
ccagtctccc atggctgggg ttagctttcc ttctggcttt ccttcacccc ctcagccatt  51240
tttaaatgac ttttcctctg gaatctgcca gtgtgctctt tttcaagtgg tcttatttat  51300
cttattcatc cagtatcacc acctttgagt agcttctaaa tccacagatt tcagcctgac  51360
cttgcttgaa gcgctgcttg cttgacacag tgtcacacaa ctgagtgaaa ccaagtactt  51420
cccccaccca aaccagttct tgcccaggtc tcctagtttc tgcgtgcggg cactgctgca  51480
tacctatctg ggagcaatcc tcttgcttct tttgtgcact ttgtctcttt ctgtgctcac  51540
ctgccctctt cctgcagacc acttcccagg ccctcccaga agaggactgt gatccagnnn  51600
nnnnnnnnnn nnnnnnnnnn nnnnnnnnnn nnnnnnnnnn nnnnnnnnnn nnnnnnnnnn  51660
nnnnnnnnnn nnnnnnnnnn nnnnnnnnnn nnnnnnnctc ccagaagagg actgtgatcc  51720
attgtatgcc ttcggccgcc tgcatgccca gactctccct taggatttag tactctgact  51780
acaattagag cagaaggttc ctcactttgc cagacactgg ccaggcaccc ctgtgggttt  51840
gctggccttc tatgacctca ttggtcagtg atccaccata agactttggg cctggtctgc  51900
```

cctccccagg ttcagctctt agggagcccc ctctgcctac atctcctctg tggaaaggag 51960
tgaagggccc tctcctacag cctttcctaa tcacacagag tatgtgtctt tggaggtctt 52020
gccattcacc taacttctgt ggtgtgcagg tggcaggcag cttggagtgt tgaggctcct 52080
actgggcgga gcctctctta ctcatccttt tcttgttgtc taagcagtta gcacagattg 52140
gaaatattga ttgagaataa ttaaactgat tgcagatggg tttagtttcc tttaatgagg 52200
ctgctaacca ttttcttcct aagaaacttg attaccctgc cttttctttt tttttttttt 52260
tttttttttt tttttttttt aaatttattt atttattata tgtaaataca ctgtagctgt 52320
cttcacacac accaaaagag ggagtcaaat cttgttacgg atggttgtga gccaccatgt 52380
ggttgctggg atttgaactc tggaccttcg gaaaaacagt cgggtgctct tacccactga 52440
gccatctcac cagccctacc ctgccttttc aaagggcagc aagcttaccc atgccaccga 52500
cacagccact tctatgcaac cctgctcctg ggtggccggc atcctgggct gttgtgactg 52560
caatggtata atgaggcttt ggcttgagtg gacattcatt gattatgcgc tagcaggcct 52620
agcttttata tattttcctc ctttaaaaat tattcttttg gtacagtatc tcaacaactc 52680
atgatagtat tataaaattt aaggtaagag ctattgtgtg tgagtagatt tgtaaacatc 52740
agaagcaaat ccccttgccc tggctttttc ttcacctgta gaaccaagga ttcaaagagc 52800
gagcagtacc ttactcacag ccaggaaagc ctttctggcc agttggccat gagtctgcca 52860
ttgcatctta tgctgatggt atctacaatt attaaagtgg tagttttgaa ggggaaatca 52920
tgattagtct gtcagcaagc tgagcctagt agaatcccac cctgttgaaa gacttgggcc 52980
tagttgggaa tggatagcca ggagatgaca gtgagtggta atcagcccca ggtctcatgt 53040
ttgtttctcc tcattcccag ctctacttct gggcacctgc aggatacgcc tggctggtga 53100
cacttctact ccctctcatg ggcctcttgt gataacacag tgtcttaatt ttgtgaaagg 53160
aaacaattgc cttattggca ttttagagaa gaggcaggca gctcaggttc agattgataa 53220
gtcatttcag gaacaatctg aaatttgaac attgcagaca aaccagtatt gtgctccttg 53280
cagacccagg cctggaccta tcaacaggga tgttgcaaga agatgtaatt atcattcagc 53340
agcaactttg atacttacac ccagtggctg taaacagtta gtaagagctg tgacacaggt 53400
cacaatggtg gagccagggc gaaggccaga aaagcaggct tctgtgcggc tttgaatcca 53460
cagggaagtg tactcctgct gaaatgttgt gtgcttaaat gggcagtgct acatttttgt 53520
ctgtacctgt gtgtggtggt atacatcttt atttccagca gaggcaggtg aatctctgtg 53580
agtttgaggc cagtctggtc tacatagcga gttccaggac agcaagagct acatagttga 53640
gactctgtct ctaaaaccaa aatcaaaacc agacacactt tgttggtttc tgcatattag 53700
gaggcatctc aggtaaccca tctctgatca ctgctaggac acatacctgg acacactagt 53760
ccctagaggc cccggaggga aggccatttg agggtaggca gtctgtgctg cttgggtttg 53820
caccccaagg cggggacttg cagtgcgctg ggagatggtt ggatctgggg ccctggttgt 53880
caggcttggt caggtctgtg ctgctcctgc agctctgtga acttggagtt gccccttgtt 53940
ggcccagcgc tgtcttgtgc tctctggcaa aagcaccttg cgatcttttt tatttgctta 54000
cttaaaagta gttgtgtgtg tgtgtgtgtg tgtgtgtgtg tgcgtgcgtg catgtgtgta 54060
gaggggttag tggatgggaa aactctcatg tgctttggag aaccttggca gagggtggta 54120
ggcacataac gttagtgaga aggcctgtgc tgcacttaag gtcttgtagc taaaacgaac 54180
ccaaattaag agtgtttctt ggtatgaata taatttcaca aggtacctga aggagggcca 54240

-continued

```
ggtctgggtt gcatctgact actgcagact gttttgtagc tcctgcttga gttgcttgtt  54300
tctttgtccc ttagatttgt ttgctactgt cctgcacatg gtcaccggct gtgtggctac  54360
agttacagta actctactta cttctttaca aatgctttga aattttatct gcctgaaaac  54420
tgacatttct gaattgaaga acacnnnnnn nnnnnnnnnn nnnnnnnnnn nnnnnnnnnn  54480
nnnnnnnnnn nnnnnnnnnn nnnnnnnnnn nnnnnnnnnn nnnnnnnnnn nnnnnnnnnn  54540
nnnnagaaca ctcctggctg aagaagaaag ttatgagcca catgggacac atttacaagt  54600
tctttgatag aactttgaat gaaggccttg gaggtcatta gccctgtgtc cctgcgtgtc  54660
actgcttcca tttaactcct cgggagcaac cgtattactt tgttggtgat cctttggagc  54720
tatatgaaat gataatttaa ctttcagatg tggttaatct ttaggtctct cttctaagta  54780
ctaatgtcca tggcatgaca ggcttaaccg tttccaggag tgggtgtggc tgaggcgctt  54840
ggctgagaag tggctcgtcc attacctagc tgctgctatt ccccagccgt ttggcactgg  54900
cactgaatgg agcatgtaag cctcaacccc acttgagaca ggttttacat taaataaatg  54960
cactgccttc ttgaggtggt ttagtgtgtt tatcatcttt tataatgcag tttagaactg  55020
tgttttgtct tctgaacgct taagtttgtt aataaacaga ccttgacact tataatccca  55080
actttcccgt cagcatatga ctgtcctgat gtcttttccc acttctcttt tcctctccgt  55140
gccttgcttt gatccctccc tagaatcaaa gagaagctgt ctgtgtgggt gccggtctgt  55200
ttgcttctct gctctctagt gtgtccacca gtgctctgtt gttggtgtca ctgttgggtt  55260
gtgggtgggg acagctcttg ctgtgctcag gactgatgct ggaggctttt gtgccacctt  55320
ggaaactgtg gcggttttag aacaggccgt ctattagcaa gttttaatat ttgagtaagg  55380
atgttaaata tcacagaata aaactttagg gaaaggcata agtaggtatt ttgcaccaat  55440
ttcattagta aaaataaaca ttttatagaa atacttgagt atcttcagtt cttgtggttt  55500
tgcatcttgc aagttattcc cagtgcccag attcataggt ataggtgctc agtaatgtat  55560
agacagtcat tcttggagta actcaggctt ccttgactat ctggggatag tggttgttta  55620
cttttgctgg gtgcttgcag ggagacagtc agtatacaag gaaacagtta atgaccgagt  55680
tgctagctca tgtaatttgt ccggtgatgt cttttatatt ttgtctgtga tacacatcat  55740
cttttgaatc cacattattc ccaaggaaac ataaattctg aaagatgcat tacagctacc  55800
taggttgtgt gtaggaatct acaaaggttg gagaggatgt tgacttgtag cctatgaaga  55860
attggtttct tttaaaccca aatagaatac aacaagaata tatcattagc ataaaatgtc  55920
ttctggtacc ctagcagtat ctagtgcttt caaaaatgtc taatgttgtt gtcaggaggt  55980
tacacataag agtgtaggtt ttcaaaggat gaccaaataa aattgtgcaa agaggctggg  56040
ttagtttgca tttttcttca gcatattaaa ctagaagtgt cttaacatta ttggtcttat  56100
ttgaattgga caaatgttag gaaaaactaa aaatcttttt attctttaaa ctgagaaaat  56160
aattcatttg attatttcaa attttataaa agctgaaaaa attatcccgg aaagccagtt  56220
attaagtctg atgtgtctgg acctaaaagg cagtcttggg ttttcattgt gttttgctag  56280
tttctgttca gtcagtcttc aggatcctga agctggctgc ctaagggtgg aagagctcca  56340
ccaccaccaa aaagcagcag caacaagaac gctccagccc aggactgtga atttcaaagc  56400
tataagaagc tcagttagtg tcacagcaca gataacttag aaatggctgg tacattacgt  56460
aatctcacac aaagtgaggt tgatggattt tgtaatagtg ataacaaatt tataaaaatg  56520
ctttagagtc tggcagcagt tttcagtttt tcttaaaaga aaagaatcct aagagtttct  56580
tataaagtcc ttcacactcg gaagacagtg aggttaaagc gtgttgtgtt aaaagtcttg  56640
```

tgtgatagag tacaaaatgc acgtatggac aacacacttt taaaaatatc tgtatgaatt 56700
catttacaat ttggtttcat tgtaaagagc aatctgatct taacttaata ctactttgtt 56760
tacattcaaa ggtgttcccc ttcattgtgg gttgttttac atctttgaag acatggaatg 56820
ggaagagtat taattacctg gctcatattt atagcgtaca tttctataag aggttattca 56880
tgcatttgaa aacaacagga agaactcaga gcctctgcac actaattgca ttcacaaatt 56940
ttgctatcat cagagtaata ctacatctgg aacatgaaca aatgcaaaca ggaaaaaatt 57000
tctacttccc ttttcagcag tgtgaattgg taaatgtccc caataatgtt gggaaagtag 57060
ttatttatga acttatagca catttagaat gtctactcaa agtggggtgt actgcatatc 57120
ttctgattgc tttggaaaag agaaagggat gatgcttctt tcagtatccc tatgctcaca 57180
tggcttgtct ccatagtaac ctatgccatc catatcacaa gaagaataac aagtgaaaag 57240
gttccacatt acattcacac agttgacttt ttttccctca tagacatgtg gtacagggat 57300
taaggtttct ccagaaaaat cattcttgaa tcttataaac tgttcatctc tctaaattta 57360
tcaatgttgt tacaagtata tcattaagca catatttact atgtattatt tgcttattac 57420
aagtttttgg acatacactt atcacctaat caaagtgttt cccttttgca atagctaagt 57480
ggtatgagac tgaagagact tgcacttcta cagcatggct ctactgggct tgatttaagc 57540
agagacctat ctgttaagcc attccttctg tgtctttgaa cgtactggaa tgccttgcaa 57600
acaataatta catacctgcc atagacatgc atggttttgt gagatttaat aatcatccat 57660
aactgaaagc agtgcttagt gtatgctatt gattttcttt acaactttgt agcacatatt 57720
aaatttcttt cttaggcatt ttttcatcag cttgcacagg aaaattacct tccatgactt 57780
ctagaacttt gaaaatggtc ttcaatagta tgttcttcct aaatgtagcc tatagctgtg 57840
agattcctat aggtctctaa catcacacct ttgtagagac tcttgtgaga aggaagcatc 57900
cagcaaagcc cactcttctc gagtgaagtt ctcaagcccg tcatcatagg tcgctctatc 57960
caagtctgca tgcacgtcat cataggtcgc tctatccatg tctgcatgca cgtcatcatg 58020
ggtcgctcta tccatgtctg catgcacgtc atcataggtc gctctatcca tgtgtgcatg 58080
cacgtcatca taggtcgctc tatccatgtc tgcatgccca tcatcatagg tcgctctatc 58140
catgtctgca tgcacgtcat catgggtcgc tctatccatg tctgcatgca cgtcatcatg 58200
ggtcgctcta tccatgtctg catgcatgtc atcataggtc gctctatcca tgtctgcatg 58260
cccatcatca taggtcgctc tatccatgtc tgcatgcacg tcatcataga tcgctctatc 58320
catgtctgca tgcccgtcat catagatcgc tctatccatg tctgcatgcc catcatcata 58380
ggtcgctcta tccatgtctg catgcatgtc atcataggtc gctctatcca tgtctgcatg 58440
cccatcatca taggtcgctc tatccatgtc tgcatgcacg tcatcatggg tcgctctatc 58500
catgtctgca tgcccgtcat catagatcgc tctatccatg tctgcatgcc cgtcatcata 58560
gatcgctcta tccatgtctg catgcccgtc atcataggtc gctctatcca tgtctgcatg 58620
cacgtcatca tagatcgctc tatccatgtc tgcatgcacg tcatcatagg tcgctctatc 58680
catgtctgca tgcacgtcat cataggtcgc tctatccatg tctgcatgca cacgtcatca 58740
taggtcgatc tatccatgtc tggaggtctg agtttgacga gctcccctca cagaacccag 58800
cagggtctct cagaacatag ctcacagaaa tcctcacagg cttgacccag aagagctgcc 58860
gccaacactc ttcattgagg tgttccaggg gctgggtacg tacgtagggc taaggtccac 58920
tgcttaccct gtaactatat ctcctgggca aagtcagaca gattatccct tgcatttcat 58980

-continued

```
tgaacagaag gttactaatt aataaattta agtgtgaggc cggcaagtgt gcacgtactt  59040
aaatagaaat ctttttgggg ttgtgtctgt tttatttgta ccacggaggt cattagtagt  59100
tctcaaagca gtcaaggcca ttgttgggga ggtcacacac cactgcaaga gttttactga  59160
ctactcctag ataattaaat tttgtgttat aagagtgttt atcaaggaat atgacagtga  59220
agaattgtct gagattagag tgtagctcag gttagagatc tctacctctc atacagaggc  59280
catgtatcct aattgcagct ccagaaacgg caaaacaacc ccacatttgt ttgaggcacc  59340
gagcatcatt aaattcattg atattttgcc catcctcgag cttaagttac ccctccttca  59400
gttcttctcc tccccttcc tccctccctc ctttttggtt tttcgaaggt tttctctgtg  59460
tagatgtggt catctgcgac tcagtgtgga agtcaggctg gcctcaaact cagaggtctg  59520
tctgccctgc actaccacca ctgcctaata tttctttcat aaaaacctgc agtcctcatc  59580
acaaccagac agtgccactg ttgttgctac tggtccttgg ctgagcgtct agaagcagta  59640
ttgggacttg gatgtgactc tttgtgtctt tctttagcac aaaaaggcca ggtaccaaac  59700
ttgctgaagc tagctagcat caccggcaag tggaggccta tctttagtct cctagtcagt  59760
ttcttgcagt gggaatcctg accactttgt tgctatttag aaagattgct ctgggcaagt  59820
ggagttcaca tttttttgtg actctgaccc cttcctctca aggtttcact gaccagaact  59880
ggactgagag gcacatgttg ccagtgattt tacagtggtg gtgttctggc cacaggtcag  59940
ccatgtggtt gtggcagctt ctgagagctg accctgattg gtttccagaa aggccctgac  60000
tatcctcatc ctaaaccaga ggctgtcctg tgtccggtgg agaggcaggg taagcatctc  60060
caccttctgg caggagctca gcagagagaa tgaatggcct agcgtgagtg tctccaaagg  60120
cccagatgct gatggcttgc tcttcccttc agtgctgttt tgaggtggtg gagggactgg  60180
gtggttcaag aaaacattgt ggtcacttga gggtaggtgt agtgctttgc ctgtgccccc  60240
ctcgattgtc tcaatatctc agctgtgaag taagcaaatt tgtaccacac acatacacac  60300
acaaaataaa acatctaaaa agggtgccta gtcaactatg tagaggcaaa gagtagaatg  60360
ctggcagcca gggtttggaa gggacttgga gttgttcagt acccagtttc agttttgcaa  60420
gatgaaaact tgaattgtca gatacgtctc agcaacacca cagtggtgga gaataactag  60480
ctgggttgtg cttcctagat tccattatgg tacccagtga atgttttttt gtttttgttt  60540
ttttctccga gacagggttt ctctgtttag ccctagctgt cccggaactc actctgtaga  60600
ccaggctggc ctcgaactca gaaatccgcc tgcctctgcc tcccaagtgc tgggattaaa  60660
ggcgtgtgcc accatgcttg gctcccagtg attgttttta tatctgttta ggaagagctc  60720
atggtgcatg ctaagagaag tgagggagca gagaccatag tgacagggac agtgtccata  60780
tgtcccaggg aacatatgga agcttgtgga ttgaggcaga gatggctgac atagctccat  60840
cttccgtgac gtgctgccag tcagctttcc ctctatgtcc catctggtca gcaagcacat  60900
ctgtttggta gcctctccag aggacggaac ccgtgacccc gacttcaacg agagcactgc  60960
cgggaagtat taagattgat ttggtttttc atcctgagta tcctgtatct gacatgcttt  61020
ggcttagaac tgcgttagat tctggaatat ttgcacagac atgggattca tgtatgtttt  61080
atatgcatgt gacttatata catggcctga tggtgatttt gtccaatgtt gtaaataatt  61140
ttttgtgcat gaattgtatt ttattttttg agataaggtc tcactggcag gcctagaact  61200
tgctatttaa accaggtagg ccttcaactc atcgatatcc tcctgtctgc cttgcaagta  61260
tgcttggaat gaagtgaagt tttgtggtgt gaaattttct acttgggatc tcaaatacag  61320
gttttggtct atgccagacc ttaaagtttc aagttaagat agtcacagtg tggagttggg  61380
```

```
tagagaggat gtttagaact gatgttttaa tctatctgaa aaaggaaacc agcttatgta  61440
agtcaatgta aaggtataaa ctgtcctaag aagcaagagg tgaaaacaac aacaacaaca  61500
acaacaacaa caccagcctt accatcaaga gccaccaaaa gttgtcagtg catcagacac  61560
gacggttggc tgtgaacctg acttttaata gttgaaccat ctttccaggc aggattggca  61620
tgatggggac tacgttcata tttgatggct agcagtggat agtgcagatt gtgtagatag  61680
gaagccactg gacaggtcag gactcacaca tgagaagtga gaacactgag ctgacataga  61740
tagggtgcaa ggggggacag ggacagttag catgtgtgct gcttgtacag agcacttccc  61800
agggctgtga cccacccatc catgtccctc tataccttca ggcaagctgc cacagcctcc  61860
cttatgctgg aacatctctg ctagagcatg atggggctct gtggtgagga gacagaggtg  61920
gcaagctctg gatggtgatc accagcatgt cctggctctg ttacaagacc acagagatgc  61980
caggcctttc cagcttccat gcctctgcac acgggtgtgc actacacact cggaaggtta  62040
gagtatgtaa gctttttttg taaactgtca tctgtagttg cccagcagtt tctggaggag  62100
gctgaaatac agcaggtcga tacagtgatg ctgagccggg cagcggtagg tgttagagag  62160
gaaaaggccc acggccagca ttgctcagtg ctccattctg gagcgtcaga gtggaaagcg  62220
cctgcagctg aggctgagac tgaagctgct gtgtgctgtc tccatgtccc agcacccctc  62280
caagcacatc agtagatgtg tgagaatttc aggttattat ggacttggtt gagttctgat  62340
ttaagttaat tctttctgca aatataaagt cctttaaata tggcatgtaa gcacctgtaa  62400
aaagcattgt ccagccatca ctttgtgaaa tgatgctgct agctccgggt gagttggggg  62460
tagggtgaag tggaaacagg gttgggtctc tgctctgggc cagccgaggg ttttagagca  62520
gctattgagc tgagtctttg tgaagtgagg catgtagccc acacaagtac tctgacgact  62580
taggctaatg attaaggcac aggcactgtt ctttgtcgta aaaagaatgt gtttttcacc  62640
tccactgtgt gaggcctcag gtgtacgaaa cagctccctc cacggttgaa gaagcatgtg  62700
gctgctgaac tgtgaactcc tggagtttga gctttcaaga ttaaataggc tctgagccat  62760
caatgaagac agtaagggtg cagccacttt gagctatttc taggggaaac tttaatttga  62820
tatacatatt atatggtaaa tatgcttaaa tagtgacatg ccttgtgcac tcattcactt  62880
acacaatgtt cacctcacca gctacagaat ttgtgtctca gatagtcaca ggggttttgg  62940
cagactttgt caacgtccac agaggaagac ccaccttcat ggagttagga gttgcttggg  63000
aagaagtttc cttaagaccg ttattgtaca cagacttaga aatacatgca tcctgtaatg  63060
taatgtcctg actagtcaaa tgttggtttt cttttagtta ttaagcatag tttgaaacct  63120
gcttgtactg tagccatttg aattcacagt ggacagaact tggcacggat gccctgaaat  63180
catagtgtag ttgtcttgct gaaaacttgg acccttaact tcctagacat tgaaacgttt  63240
tgaatcacga gcactctgcc ctgcttttgc tctaagcaat tgtgttggct tctccccagc  63300
ctctgtaatt gtagttcttg tgggtggcag cttctgtttg ggaaaagctg tgggtttaca  63360
ggtccttgct gagcccctgc ttttcctaag atgagctctc tgaagtctta taggagatca  63420
ggagacattc ctttttcata aaagaatgga gctagagcaa tgcctcagtg gttagagccc  63480
tcactgctct cctcgaggac cacgtttgga tcctagcacc atggcagggg tctcataagt  63540
gcctgttgtc actccagttc aggaaatttg atgccctctc ttggacttca tgggcaccct  63600
cattcatgtg ctcattccac ccaaactccc tgtcattaaa aagaataaag tatcaaaaac  63660
aacaaaaaca aaaaacaaag actaaaggag agttgcccat gaggggcttg tagtctgttg  63720
```

-continued

```
tgtgtcttga aagacatggc ttgctgttta aaccatggtt aaccctgtct gtgagaatct  63780
caacaccttg gccaggactc cagtccatca caaggctttt attttgttca caatatttgg  63840
ttgccacttt actcaataat gagagtattg catttaaaag taaagtttaa gtcatgcaca  63900
ggcctggaag ctcagggcca gtaggagagg gattcctcgg aaagactgaa ccggaagcag  63960
aagccagaca gcccaggtaa tgctgagctg gggcttcagg ggcacgtggc caaggctgag  64020
tctactgtgg ttcttcagac agtgggcagc tcagggcctt taagtatagc tctgaatggt  64080
tggcacaaag tgccacaatg gcgacggctc tgtcacctcg gctgctctcg ctgtgtaagc  64140
cgtagacacg tgtaaaaagg agactgcctt gcataatgtc tgagctggag ttgactaacc  64200
aggtttgcaa atgactcgga ctttgttttt gtaagatttg tattctatca ggacccagag  64260
acataaaagt gggtgttaag atggagacta aaaagtcctg tcctggtcct ttgttgtgct  64320
tctctgtcgt ctcaggggct tctgaccttc taaaggctta ttattgctca gtcatgttag  64380
acgttttgtg gtttttgttg ttgttgttgt tgttgttgtt ctcttaagag atctcagtag  64440
ttttagtttg aactattatc taaagattca taaacagcat ttgtagagaa cacatagttg  64500
aaattgtgaa cccagacttt gccttctgta gctaaaagct ttccagtgtg ggcacccctg  64560
taaaccccctg tttatcttaa aacttctttt ctgtgctgag ggtccttacg tcagagaacc  64620
tttcaaacag agtcactaat taagagtaga gatagagaaa aactactgta ttattttctc  64680
atcatgtagc ccagactggc ctggagcttg tgatcctcct gcctcagtct ctggagtagt  64740
ggcattcacg ggtgtttgcc acagcagctg ctagcctttt gtctgttctg cacagctgtc  64800
ttctgagtaa ctggagagaa ccccctcttc tgagtgagag tcgctcttaa aagcacttca  64860
aaggtgaggt ttgttcctaa atgtgttgtg ttcaagcctt ttaagattac acaaggtgat  64920
tttttttttc ttgtgacgtg aggaaacaca cctatggctt ttgttgctgt gttgagcatt  64980
ttgctctgag acatcagact tgtccaaagc ctgtgtttct gttcctgatt tttgctcata  65040
gttgtcagct gttgcttctt actgccggca ttcagatgtc ccgtctccac actccttgtg  65100
tggtgcaata acatcctagg aaagaacaca tacacactgt gtgctttaca gtcttactgt  65160
cagcgctgtt tcacaagtgc catccttgac atgcagagga agagagtcag gtgtagctac  65220
tgcattatcc tgctcaagtc cgaaagtcac tgagtgacga tggatgccat gcagatgact  65280
attcccatag ttactggagt aagtggacag tgctgcccat gtacactcgg ggcattgcta  65340
atgctcaaaa ttccctcttc tccctcccaa agacaaccac cacctcgaca ttcttctcta  65400
tagatttgtg tctctgcccc ccaaggatga cattttttaa atcaggcttt tagcttcata  65460
aaaatagaat cagggcgaca ctgtttttgt gtccagcttt tttcatacca ttaaatctgt  65520
gagctccatc catctttggc ttatagtgcc ttcattgatg tgggctgaat tattaatgtt  65580
tgtatgaata tttggggcct acctgttagg gaagaactta ctgtgaagat tactatatat  65640
gttgttagag gatgtgactc ctcctaaatt acttagttta ttgaactata tagtcagtgt  65700
aatccaggtt attagtcact tttatgctgc tgtaatcaag gcagtgtgta tcttgagttt  65760
ctggaataat ggagaagatg ggggcaggag ttggaggcag aaggagatgc atgctggtgc  65820
ttaccccagg cttcttttta tacagactaa gattccagcg taacaaatag aactacctac  65880
agtggctggt tgggtttccc acctcagtta acctaatcat gataaccccc agaggcacgt  65940
ctcccaggtg attcaaaagc tcatctagtt gacaattgag acatatccca gctaccattc  66000
tttctgtagt tacaggttct gccagatgcc ttgaaagtat gtgaagcaaa aagtgccctg  66060
ttgctgagta tgtgcaagtt taccacgcag acacagcatc tgtaccgtgg tgagcattgg  66120
```

gagtaatcta gagatgcttt tgcgtatgca ggaggagttg gggctgtgca aacagtggtt 66180
ggctttgtag aagaacctga actgctacaa cattttctgt gcacaagggt cctgaaacct 66240
accccttct acattcaggg tcaactttgt caccagttta actgtggtga cacttgtctc 66300
atcagcagtg caagagggct ctgggagcta catcacttcc tgactaatgc cagggttggt 66360
ttccctgttc tttacattgt aattcattag caagaaattt agtttgatac aggggaaatg 66420
caaattataa gctatatttc aaaataaaaa tatttaatgt gcagttctca tgcatagaga 66480
ttaatagttc tatattatat actgatgatt cttttcctcc cagtatgttt ccattgtttt 66540
gttttggagt gtattgtagt aggtatgttc atgagtgtgt gcaaatgtgt atgtgggcca 66600
gagtgttatc ttccatcacc tctctccctt gtctcttgag atggaatctc ttactgaact 66660
cggagctcag taagtcatct agttagctgg ccagtggggt cagctccagg gtctgcagct 66720
atgattttca catgggattc aagctcaggt cctggtactt gtgcagtgtg tttaactgcc 66780
ctagcagtcc ctagtctccc aatccctact tttttttttt ttttaaaggc agccttgatt 66840
tcttctttga gcactgatgt taacacaggt ctgtgggagt agaaaccatc gctcagtatt 66900
ctagaaattt gtttagattg tgggatgggg gctggccaga ggagaggaag agcacccagc 66960
ctggccacaa gctcaccatg taagcggttt ggcctctgcc tcccatatgc tgggattaca 67020
ggtatgctac caggaatagc tattttagaa ttttagttaa gaaaattaaa tggtgactcc 67080
acacacacac acacacacac acttgtctgc agcagcagat ctcatggaac ttggagccct 67140
gcacacttaa gttccttcca ccacaataaa gatctttatc tgtgggaaca aattcaaaag 67200
atccaaggaa ggtgttggta tggttgtgag ctagctgcca tgtaagaaat caaacccagg 67260
tcttctgcaa gagcagcgtc tgatcttaac cagtgagacg tttctaagga gttaagttta 67320
aacagtacat acaaaggtgg cttggaggga ctaaaacatt atattaaaaa atgtcacaaa 67380
ttatagccaa agatgtaaaa ttgtctttaa aagaacacag taaagaactt tatagctgga 67440
aaaatgaaac gtggtttttg ttttctgttt atttatttat tttttgtttt gtttttttac 67500
agaagtctag cagttaacaa catttgggtc tttatcatct ttgttaaatg acttactagg 67560
ttcaagtgtg gtcgaattga ttagttctta ttgtcccaac tctagctact tatgttccac 67620
ttttctgtgt ctcaggtatg ctaattagtc aggcggtctc atctgaaact aggaaggtgt 67680
gatagtgcta ggttgtacaa cttgccatac cagttttaca gtgtttttgt tttgctccga 67740
ctagatgaaa ggtttaagtg tggccacact ggtactgcat tcctggtgat cttggagggt 67800
taatgacaat ctttgtcata gacatcagga aatgtgggtt gagtctctgg gatgcacaag 67860
gctagttcat tagcatgctc cttccggagc actggggatt gttggaggta tccggtggta 67920
ggtaggtgat gcagcttcag agaactttca tctgtctgtc atcagctgtc atttgtccgt 67980
ttacccttct atctttccat ctatccatcc agcctgactg tttctatagt catcttggtt 68040
tttaaaaact gtttttaacg tattggtgtt tggttaaatt accactgggt ggttgctttc 68100
tctagcaaga cccagcaggg aaaccaggta ggttttgtgc cacagtcagg cttgtttcct 68160
cggtgttgtt ggcttggttt cgaggacagg catgtgagag atcatcgctg ctgttgaact 68220
ggttgccttt tagctgagta aactatcagt cagtgctgtg gtctatgcct cagttgtttt 68280
ctttttttaat tagggtagct ggaagagctg cttaaaatag gtatctgtga gactcgcaga 68340
cgcagctggt ttggacttag cacgctttca ggcaggttca ctgaacgtgg ttctggttgc 68400
tctggtttct gtaaaagcct gcgcttgtgg tgactgtgcc aatataggtg agcatttagg 68460

-continued

```
agagcgacac actgctgttg cctttttttct taagaggtgt acttaactta tttcagatag  68520
attccttaat aataccatga tccaaatgta actaaataca aagcagggtg cttcatttca  68580
atactcttca tgtacaagtg ctatagatgc aagcagaatg tacttagttt cctggagcat  68640
tcaaagactg tatgccacca tcggcaaagg cattggagtg ggctagtact gttgagtcac  68700
tgattgtccc atctggagcc ttagtgaagc ctggagagta agttatttat tagaacccct  68760
gaggatgtgc tgagctgata atgcactggg gtcttttctt ttaaaggtat ctctgttgtg  68820
tgagactgtt ggcagtctcc agagttcagg ctgcgaaggt taaatagtga ccaacctttt  68880
catccacctc tgcatttgga gcattgtgag ggttggagag gagctgagag gcccagccaa  68940
catgttcagg attgaatctg cacctccttc ccaagtagtg agctttgctg gagtttctac  69000
atgttcaatc tgagggtttg aggctgtgat tggccatctt catgattcat tatatacata  69060
agtaacataa aaaattaaaa tctattaaat atgctgtgat ttgagtaaaa gaatatgttt  69120
ctattaaata aataaataaa taacaagtta tctaggcatg attgtgtatg ccttgaattc  69180
caaatcatgg gagggagagg caggctggta tctataagtt ccatgccagc taagggtaca  69240
caagaccctg cctcaaataa gaatatgtaa ttacaataaa aaatttaaaa cttgttcatt  69300
ttcctcctgt agagttgcat atttaatgaa tgaagtatcc tacaacttaa gtctatgtat  69360
aagtctgaga atcaaaaccc cagggttttt ccttggcttc gtttgtattg atttattttg  69420
tgatcttgtt ttgaactaac aacagggaag tggctgtgtc atttcacatg tatgtgggag  69480
actgtaaata ggaataggga catgttttct gcatccaggt gttattcaca gactcggtta  69540
atgtggtaag tagctagcta ccttgaaaag aatatgtgga gccatagctt ggcagcagga  69600
agaactgaag tgttgctcag aacttggagt ttcggtggaa gtcagttaaa acctcagctg  69660
ggtgttttgc ttgtcttgcc agttgctggg aggtggggag tagcttcctg gtggctcctt  69720
ctgaactcac agttgctaga atggtaggct tgtcttagcc agaatagtca actgcctatg  69780
gtgatggttc tggcctcagt ttatgagccc atgaggcagt agtgtctgag ctttggccag  69840
aaagatcaga atgccagacc acattagtgg gttacctgtg tcatctgttg atgggcagag  69900
accattttag agtatataaa gaatagggtc ttaaattagc agctaacata ctattttctg  69960
ttaaattatt aaatgattga taaaataaag gggtgatttc attaagggtg tcatcaaaac  70020
aaaactttta gaaaccactc tcgtgcaaat tgattttatt tttctgaaaa atcattggtt  70080
ttgtaattca aatctttaca actcgtctct cttggcccag taatgctttg tgcagacttt  70140
gcccacatat gatggaggca tttggttctg tgaaatggaa gcactgttta ggtagcaaga  70200
gcagagccag ggaagcagca aatggtaagt gttctgtaga tttatgccca gctaagtcta  70260
ctaaagcaac cacaaagcag ccgacaaagc cagcgaacaa gacattattt aaaatattgg  70320
cagagtttcc ttcatggtgg ggaacagtgg gcatcttcct tttttccatt ttctgtaatg  70380
attgcttact tattttttaa tctttaaagt tgaaagggaa cagggtgacc taagggagac  70440
atggccagat cagcaggcca caggaaacaa ggtcacaggt tcgagggata gcagggcggt  70500
ttggggatga gtaagaaagt gggttaattt ttctaaagaa catgctatgt gggaaaggaa  70560
accatgaaca catttctata cctctggctt gataaattca taggaagagt gggtgaatga  70620
atgactgtgg cacgaattga caagatcaag ttggctatat ccacttggca gcaatcgtat  70680
gtttgaagag ctacagacaa cagagatgtt tgaggtggaa tggtgaccag cttagaatgt  70740
gatatcctga gaatatgtgt ccttgacgga tgtgtgccag gggcagcaga ggttgggatg  70800
gagccagtct ggggggggctt agatgaggct agggctcaga actcaacctt cccctctgga  70860
```

```
gatcaggatt tccttggaca tagtgagcca gttcactgga tagtgttgag tgattgtatt  70920
tacacatgct tattattttt aagtattgaa ctcttttaga ggcttacttt atttaatttt  70980
taaaattttt atttatttta caacttcctc ttacccagct aaattcatgc cgtcctgttg  71040
tgtggcaaaa tttcaaaaag tagttgggtc acagtatttg agtgggacgg tgttagagct  71100
gtagctttgg caatatggca tacttgttct ttgtagggac agcgacagca acagcatcag  71160
cacaggatga gcagtgagga cctagtgcag tcaacactta ctcacaagct cctggtacat  71220
tcctcgtgag tctttcctgg tgtttattag taaccttgtt gaagttggct gtttttgtta  71280
ttttcctacc ctgataatgt tgctttttaa ctgagaaaat tatttcatgc agcactgatg  71340
tgagttctta cagttgccgc acatgctatc taaatgtagt ttgtatttat agccatctct  71400
cttctgtgag tcactcttga tagtctcccc tatttttagg tttttccttt cctaagcttg  71460
tgtgcctgtg acacacccag cttgtcctct gccactgagc tgtacccccca gccccacttg  71520
aacgaaactg ttgaagctag tagccactcc tgttttctgc taactggcat actaaaggat  71580
agcatgtttt cttaccattt cctttgtgtg catgtctttt gagagagagt acaggatttt  71640
aaggataggt ttgtgtctga ttgttggagt gcgccaggtt tccagtacac acctctgatc  71700
tccatggact ctgttcactg actaactatt gaagattgct gcatgctccc ggggtgtttg  71760
cagtagcctc agtagtttct gtgtgagtgt cctctgagtc aggagttggc agtctagctt  71820
ccacataata atgagatatc tgcgtcaagg tggcacctgc agagcctcct gccagtctat  71880
ctcatgcata acaagaggcc acttggactc tgccaacccc agaattcaac cctagtatct  71940
atcatcttta tttttctttt ttttttcttt tgctcctgga ggttgaaccc agggactccc  72000
aacatgctat gcacatgctc tgccccctag tcatatctcg gtccctacag acattttaaa  72060
aattaattct gtgaagtatc tccgaaggtc ctgtggtttt ttttgggggga gggggggttaa  72120
gtagcagtaa ctgtagcaat tattgtaact ggtatcctta ctcattacag tctctatcac  72180
cgggaccctt ctcgggatgt ttccttattt gcatttttaa caactcagat tacaggtgaa  72240
gtaactcagg caatgggaga tgagctggct tacgtggggc aggtagtaga tgtcacattc  72300
ggagctgtgg tttgtcaggt cccaaaacat gtgtgaattt taagtatgct cgggggtgag  72360
ggtcctggaa gaactgtatt aagagcacag gttgctgtta cccattaacc tgctgaatac  72420
tagcaaatac ccacattgtt cttacagcta cttataacat gcagtagttg gcattttaca  72480
tagaaaccta aggttccctt acctaggcaa accctgctat ctattttttg tttgttttca  72540
gcttttcaag acggggtttc tctgggtagc ccgggctgtc ctggagttca ctctgtagac  72600
cagggcggcc ttgagctctg cctgcctctg cctcccaaga gctgggatta aggtttgtat  72660
cactgtagtc aggcaaaacc tgctatcttt atgaaaggcc actcacaagg catgtctgtg  72720
ttgtgcacac cacacggtga ctgctgttta tcttttgaca gggtttctct gagtaataga  72780
atccaggctg gcctaaactc gcaaggatcc cccagcctgt gcctcatgag tgctggaatt  72840
aaaggcacgt gccgccatgc ccagtgactg ccgtttatct ttaggcatca gtaaatcttt  72900
gtaataggaa cacattccta ttaataatgt caactaagtc ctagagacaa gtgtagcagg  72960
tctcagtaag agccacgtcg gaagtatggt ttgcatactc tcagagtccc caggtttaat  73020
ggcagcgttg ctagatctga atttaggtga gtggtgagga agtagcctcc cggcagttgg  73080
agatagtttt atatgctagg tcagtgaacc aaaaatctct attatgtagc ttagggaaga  73140
gtttctagga atcagatttc tgaggtctat tatagctgag aaaggttttg ttcttgatta  73200
```

aagaatcgta tatttcaaag ctcacagaaa ctggaaggtt aggaaaggct ggaacaggag 73260
ggctgcagtc tccagacctg acagggcttc atagaaaacc tgcctcagaa accaaagcat 73320
gttcatgaga aaaactgcag tgttggtcct gattagggaa gagtggcctt gctaaagcta 73380
tgaactctat gtgaaggaaa atgaatgtcc cttccctggc ccctccggca cctacttggg 73440
ttgcctgagt agtttcacat aaattatgta tgtgatatgt ctcctgtctc atgtcagata 73500
tgtctgtctg tctggtggag cttttatctt ttatgtaaga tacgtatctt cctgcagctc 73560
ataccgtgtg tgtgtgtgtg tgtgtgtgtg tgtgtgtgtg tgtgtgtgtg tgtgttgctg 73620
atagttgaat ccaggtttca tatgtgccat ataggggttc tccactaagc tgcaccccta 73680
gctctctctt ttttcttctt atatttttat ttttatagat aaatgataaa ctatctattt 73740
ataattgtgt cggtggggga caaatgacat tatgagtcat taaagcaatg tagaattgtt 73800
aaaataatgg agatatccgt cacctcacag ccttacctgc tttatggtga gaatacaaca 73860
tttactctta acaattttga aattgtcaac acatgtttag tagctgtgtc cctcatattg 73920
tacagttctc caaatcaacc cacaggcgtt ttcctcctaa gggatttgtc ctccgagcct 73980
gtcatcttcc tttccctaca tccgtggcct ctggaaccac tgttcacttt gagtgtcctg 74040
ggtccccttg tttctgattc tgtatatagc atttatgttc ctgtggttgg tctgtttcac 74100
ttagtttgcc ccaggctgac agaaacaata gtctggtttt aaggctgagt gtgtgctgta 74160
catgcatctg tcagttcaag gccactgtct ttcaggctga ttgtacaccg tagctttagg 74220
gcagtgctgc agtgaatatg aggatataga tatctcttaa aaatttagtt tatgtgtaga 74280
gcagtctgcc tgcgtgtaaa tctatgcatc gcacacttcc ctggtgcttt ccgaggccag 74340
aagacagtgt tagatccctt gggatcggag attatgggtg attgtgagcc accctgtggg 74400
tggtgggaac tgtacttggg ttctctagaa cagccagtat tcttaaccac aaaacctcct 74460
ctccagcctc ctgcagatat ctcttgacaa gatgatttca aatcgtttgg taaatgacta 74520
gtgttggggt tgctggggct ggagagtagg ttcgcagtga tctggaaacc aggccgcagc 74580
ttcactctta gatgtttaca gcttcgatac tgtgttggaa ggtgtctagg ttcttggagt 74640
tgtgctaagt tgtttgctgc ggcacaccca gggcttggta aagatgtgtg tatttaaaac 74700
agctcattaa acagcccgga gtccttgtaa accaagttca gtctctaaca gtctaacaag 74760
actctccttt atccttaggt gttttgactt ggagaggaca ctaggttcac atgtagactt 74820
taccgagagt cggcatgtcc ttgaagccat gtgtgaaggc gctgttctgc ctctgggtga 74880
tgccccatgg gaaggacatg cactgctagc tattgcaggt gctttctgct gaccattcaa 74940
cacgttacag ttctgagcct cactagtttt gtagcataat attcccccag tagtgacctg 75000
tttcagcagg cagggtgtgg gccagctcag tcagacccag gtctgtttgt tttcatgcag 75060
tcttggctcc tcactggagg ctctctgctg ccaactgtgg gctttggttg aggcttgtgg 75120
caagattgtg ggtttaaccc aggagtattg cagcatcact tgtcatggag gtatcacact 75180
gttcagtggc ctcctatggt ttaggtttag atcatttgtc atgtggctta ggtttgtgtg 75240
tgttcatggc tttctcctcc tttagtcctt tcctgggtca cacagacatg cgagcgggga 75300
gtaaaccctg ctgatgactt tgcccttgct tacagtttca gtttccaggc agctttcttt 75360
acaatcgctc acatacagac ccaagctaac tggacactga ccctttagat tagcccactt 75420
tcccaacagt tctcatgtga ctttgatatt aagtggaact gttaatagag ttagtagttt 75480
agtgtggaca gtaaagacca tgctcaccca tgctcagtgc atgtgctctc agcgagctga 75540
gacacatggt gtgtttggtt tgtgagtgct tttctttgga atgctgctca aaggttggga 75600

-continued

```
ttttaccatc ttttctttcc ctcagaggtg ctggatgcca agatgatgca caggtaaagg  75660
gtaagccaaa catggaggag gctgggcaag ttgtgtgctc actgctcatg gttggcgtgc  75720
aggccctccc tgttactggg agaccgtcag ggcttccttg gtgtttcctc accatttctc  75780
ttagggtctc ttagaacatg ggccttggac agctccacct tttccgagaa cttccagggg  75840
tggactcttt ccctacttcc tcagtgaatt cagactcaag ttcttcgccc taacccactt  75900
gtgcagtcct ccacagcgca ctgcagcctc ttcagctccc catacttgta tggaatgcat  75960
gtacttctat gcatttcaac tgtgcaaatg ccggaaaaga ctcaggttgt caaggtgact  76020
ggagctaggc atgccactgt cactcaggaa ggctctgctc tgccattgac ctgtaggaaa  76080
cggctctatt ctcagaagtt aaaaggtggg ctggtgaggt ggctccatgg ttcagagagt  76140
ttactactgc acagcagagg gctcggtgcc acgcatgaag gtgttggtat gcatttgaca  76200
tcttttaatt acattgcatt ttgtagtgga tgctgttgtg tgtcctgttt aaagattaaa  76260
gaatgttcca aaaccactta gagcagtgtt ccttgaagca agctgacagt gaagaggtgt  76320
cctccctcct ccttcttctc caccttcgtc catccgtccg tccgtccgtc cttctgtgtg  76380
tgtgtgtgtg tgtgtgtgtg tgtgtgtgtg tgtgtgtgtg ttccagttat aatcgtctgc  76440
agagtgcagt cttatttctt ggacattcag acatgccttt tcgatgccgt gagctttggg  76500
tagtttcatc atttagtgtg tgtggttttt ttgtttttttg ttttttccaa acaatgcctt  76560
agttacatct atctcaagtg gctctggatt tgtgtcctca cttacagagc agtcatttta  76620
tagaattttc cttcatgtca ggaaacacgg taattgtgca ctggtggaat gtgccgtgca  76680
tatgcacact ctgtactgtt ttctgtgctg ttgttttcct ggggtcttgg tgggatgctg  76740
tgctttgttg agataggact tgctatgtat ttgtggagaa cactgttgct gttgaaatgt  76800
atattgtatt tccaaatgtt tgtggtctgt tgggagagtc accccctcaa ttctaaaacc  76860
gatatgatgg ggggagggcg ggagactgat atgtgcttaa ggaccaggaa gttctggagt  76920
gtctgaaatc tagccagcac agactgcagc tattgcttta aacacttgtg tatctttaga  76980
aacaaacgca tactattttg ttatagttca ttctccttta aaagcagaaa tgtgtgtatt  77040
gcataaacct taatacttgc atgtctacat ctatgtataa atgaggagga ggtttgagac  77100
tacatcacaa tctcttattg tcttcccaca gccctgtcag cctcaaggca ttacgtcacc  77160
aagtgagaag ccatgcctct atcctgaagt ggtaaagatg ctattcctga aaacagcttg  77220
aattactaag ctgcttttta ctttcaaaag cttttgaagt attttgggac ttgccaacca  77280
ctattagttg gaagtgtgtt tggtttgttc tgggagctga tagttgtctg aaagaagggt  77340
tagaaatgtc tcgtttcttt gggaattgtg ttataatttg gattaattag ctttcgcctc  77400
agagttttct cttttataaa tagggcaaac cccatatttg tcaggagttc tgggccccag  77460
ttagccagct gagtttttac acaagctttt acgcttggac ctggatgctg gctccaggtg  77520
cagacacagc accatggatg ctgaagatgg cgttacttcc ctggtgtcat cccttccacc  77580
ttctgcttga tgtgtgctaa gtgtgcccac ttctgatgaa ctgagggccc cttggttcct  77640
cagcattgct ttaatgtagc tacagaccca tggagtggag agctgcagtc tcatgttagg  77700
agtctagtgt ctatgagcat ggcaaaatgc ctaccgtccc ttgccgaatt atctgcaggg  77760
tctctggggt ttttaaccta gctcaaccag aaaccaggct gcctttaaca gtcccacata  77820
gcaaaaagca tatagtgtta aaggggaaat tgcaaagttg tgttaaaggg gaaattgtag  77880
taaagttaca tgatttttaa taaaataaaa aaagaggatt tttaggaagt ataaaccagt  77940
```

cattgtgtca tccatctatc catctatcca tccatccatc catccatcca tccatccatc 78000
catctatcca tccatccagg tggtggggat gaagtgtgtt tgtgtagccc agactggcct 78060
tgaactcaga gatctcttgt ctctgtcacc taagtgcttc tggggtcaaa ggcgtgtacc 78120
accatagcct accattctga tttgttattt tagaaataaa accaccccc cccccacaga 78180 gtttctctct atagccctgg aactcactct gtagaccagg ctggccttga actcagatat 78240
tcccctgcct ctgcctctgc ctcccaagtt ctgggattac attgctgctt taaaacaccc 78300
acgttcacta cagacccttt ccctcaacca agaaaggcac caattatcaa cacttgataa 78360
cttagtagcc acttgagcct ttctgtacct gaaatcttga caaaaaattg agacataaag 78420
gccccaaact gtgttatttt aggaaattta agatataaca ttttaccaga tagtggtgac 78480
aggcctttcc ccgcactcag gtagcagagg caggtgtttc tgagtttgca gggagcctcg 78540
tctacaaagt gagttccagg acatgcaagg ctacacagag aaaccctgtt tggaaagaac 78600
aagcacaaca gtaacacaca aaaccaaaag atacggcaat gtaacttcta gaaacaatca 78660
attaattaaa aatgatgcaa tgtttttctt agggctataa aatttatttt gtagctcttg 78720
tgtatttgca agggagccag aaggcctcag ctctagactt ttgtgtctga atgatttctt 78780
tttccaatag ttgaatggtg cacagcagtg tcttcccaca cgcctttgag tgcccaccct 78840
gaacccttgt ctccttcctt gctcctacac tcccatgagt cttctacttt caggtcatat 78900
gtgttcacgt gtgttgtgtg tctgtgtgca ctccatgatt tagtggcttt ggtcacatcc 78960
agtgccatca gagcatttac agggcataat taaaagctca tgatacctca caattgtagg 79020
ctgcaatgaa acagtaagag ggggtattgt tgtttagggt gtggttagag aaatagttgt 79080
atcttttaat taaacaaagg atggctaatg cctgaaaact agtctattga acaggaggga 79140
ctgtgagctt tcaaacaaat caggaacttg agaatcacgg tgtgtaggtt cttttgtcac 79200
tgatgaattt gagtcttagc gatgctcagt ggtgatctca ggagcccaga tcgttgcttg 79260
gcatctgtac ccctgnnnnn nnnnnnnnnn nnnnnnnnnn nnnnnnnnnn nnnnnnnnnn 79320
nnnnnnnnnn nnnnnnnnnn nnnnnnnnnn nnnnnnnnnn nnnnnnnnnn nnnnnnnnnn 79380
nnnnnnnnnn nnnnnnnnnn nnnnnnnnnn nnnnnnnnnn nnnnnnnnnn nnnnnnnnnn 79440
nnnnnnnnnn nnnnnnnnnn nnnnnnnnnn nnnnnnnnnn nnnnnnnnnn nnnnnnnnnn 79500
nnnnnnnnnn nnnnnnnnnn nnnnnnnnnn nnnnnnnnnn nnnnnnnnnn nnnnnnnnnn 79560
nnnnnnnnnn nnnnnnnnnn nnnnnnnnnn nnnnnnnnnn nnnnnnnnnn nnnnnnnnnn 79620
nnnnnnnnnn nnnnnnnnnn nnnnnnnnnn nnnnnnnnnn nnnnnnnnnn nnnnnnnnnn 79680
nnnnnnnnnn nnnnnnnnnn nnnnnnnnnn nnnnnnnnnn nnnnnnnnnn nnnnnnnnnn 79740
nnnnnnnnnn nnnnnnnnnn nnnnnnnnnn nnnnnnnnnn nnnnnnnnnn nnnnnnnnnn 79800
nnnnnnnnnn nnnnnnnnnn nnnnnnnnnn nnnnnnnnnn nnnnnnnnnn nnnnnnnnnn 79860
nnnnnnnnnn nnnnnnnnnn nnnnnnnnnn nnnnnnnnnn nnnnnnnnnn nnnnnnnnnn 79920
nnnnnnnnnn nnnnnnnnnn nnnnnnnnnn nnnnnnnnnn nnnnnnnnnn nnnnnnnnnn 79980
nnnnnnnnnn nnnnnnnnnn nnnnnnnnnn nnnnnnnnnn nnnnnnnnnn nnnnnnnnnn 80040
nnnnnnnnnn nnnnnnnnnn nnnnnnnnnn nnnnnnnnnn nnnnnnnnnn nnnnnnnnnn 80100
nnnnnnnnnn nnnnnnnnnn nnnnnnnnnn nnnnnnnnnn nnnnnnnnnn nnnnnnnnnn 80160
nnnnnnnnnn nnnnnnnnnn nnnnnnnnnn nnnnnnnnnn nnnnnnnnnn nnnnnnnnnn 80220
nnnnnnnnnn nnnnnnnnnn nnnnnnnnnn nnnnnnnnnn nnnnnnnnnn nnnnnnnnnn 80280
nnnnnnnnnn nnnnnnnnnn nnnnnnnnnn nnnnnnnnnn nnnnnnnnnn nnnnnnnnnn 80340
nnnnnnnnnn nnnnnnnnnn nnnnnnnnnn nnnnnnnnnn nnnnnnnnnn nnnnnnnnnn 80400
nnnnnnnnnn nnnnnnnnnn nnnnnnnnnn nnnnnnnnnn nnnnnnnnnn nnnnnnnnnn 80460
nnnnnnnnnn nnnnnnnnnn nnnnnnnnnn nnnnnnnnnn nnnnnnnnnn nnnnnnnnnn 80520
nnnnnnnnnn nnnnnnnnnn nnnnnnnnnn nnnnnnnnnn nnnnnnnnnn nnnnnnnnnn 80580
nnnnnnnnnn nnnnnnnnnn nnnnnnnnnn nnnnnnnnnn nnnnnnnnnn nnnnnnnnnn 80640
nnnnnnnnnn nnnnnnnnnn nnnnnnnnnn nnnnnnnnnn nnnnnnnnnn nnnnnnnnnn 80700
nnnnnnnnnn nnnnnnnnnn nnnnnnnnnn nnnnnnnnnn nnnnnnnnnn nnnnnnnnnn 80760
nnnnnnnnnn nnnnnnnnnn nnnnnnnnnn nnnnnnnnnn nnnnnnnnnn nnnnnnnnnn 80820
nnnnnnnnnn nnnnnnnnnn nnnnnnnnnn nnnnnnnnnn nnnnnnnnnn nnnnnnnnnn 80880
nnnnnnnnnn nnnnnnnnnn nnnnnnnnnn nnnnnnnnnn nnnnnnnnnn nnnnnnnnnn 80940
nnnnnnnnnn nnnnnnnnnn nnnnnnnnnn nnnnnnnnnn nnnnnnnnnn nnnnnnnnnn 81000
nnnnnnnnnn nnnnnnnnnn nnnnnnnnnn nnnnnnnnnn nnnnnnnnnn nnnnnnnnnn 81060
nnnnnnnnnn nnnnnnnnnn nnnnnnnnnn nnnnnnnnnn nnnnnnnnnn nnnnnnnnnn 81120
nnnnnnnnnn nnnnnnnnnn nnnnnnnnnn nnnnnnnnnn nnnnnnnnnn nnnnnnnnnn 81180
nnnnnnnnnn nnnnnnnnnn nnnnnnnnnn nnnnnnnnnn nnnnnnnnnn nnnnnnnnnn 81240
nnnnnnnnnn nnnnnnnnnn nnnnnnnnnn nnnnnnnnnn nnnnnnnnnn nnnnnnnnnn 81300
nnnnnnnnnn nnnnnnnnnn nnnnnnnnnn nnnnnnnnnn nnnnnnnnnn nnnnnnnnnn 81360
nnnnnnnnnn nnnnnnnnnn nnnnnnnnnn nnnnnnnnnn nnnnnnnnnn nnnnnnnnnn 81420
nnnnnnnnnn nnnnnnnnnn nnnnnnnnnn nnnnnnnnnn nnnnnnnnnn nnnnnnnnnn 81480
nnnnnnnnnn nnnnnnnnnn nnnnnnnnnn nnnnnnnnnn nnnnnnnnnn nnnnnnnnnn 81540
nnnnnnnnnn nnnnnnnnnn nnnnnnnnnn nnnnnnnnnn nnnnnnnnnn nnnnnnnnnn 81600
nnnnnnnnnn nnnnnnnnnn nnnnnnnnnn nnnnnnnnnn nnnnnnnnnn nnnnnnnnnn 81660
nnnnnnnnnn nnnnnnnnnn nnnnnnnnnn nnnnnnnnnn nnnnnnnnnn nnnnnnnnnn 81720
nnnnnnnnnn nnnnnnnnnn nnnnnnnnnn nnntagcata gactcttaag gcatctcttc 81780
cagatggcag gatttggggg agagcggggt gatagtttac taagtcttag tgtgtgtgca 81840
catgcgtgtg tgtgtgtgtg tgtgtgtgtg tgtgtgtgtc cccatgtgca cactggagcc 81900
atggcactta tgtggaagtc agggctgcta cagagagtag tttttctcct tcctctattt 81960
gggtcccagg gatcaaactc aggtagtaag gcctggtgcc tcccatatta taatgggtga 82020
gccatctcag caggtccacg tgttactttt catacttgaa ggctattgtt ttgacttttt 82080
cagtattttt gaacaaagta ttgatgagct aatagttagc attgtgaatt ttttcttatt 82140
ttaaaaagga agttgacata gtagcaagtg ttgtgcttta agcgaaatga taagaggaag 82200
gcaaaccagc ctgagtgact tggctggcaa gaggctgtct ctttgcaggg gatttagagg 82260
gacgattagg aaaagaaaga aaagagacaa gtgtagagct ccacagccag cgatcttgga 82320
caccgtgctt acctgatgac tgttttgttc tttcacaaca tgggatcaag cagttttctt 82380
aggtttaaaa atactttgtt gaatattgac tcttatttgt gttccctttg gtatcatatg 82440
acatttgaag agagaaagct acaaatagaa gaagtttgac taattttagg acctagagaa 82500
tagtattatg aaaggttaca ttgtgcttct ttaataaaag aagcagttag aattatttta 82560
gccactggca tagtgtgttt aaactgcaca cacacctaga cagacataaa tccccgaaaa 82620
agcagcagct cactgctcgc ctgtttccca ccccatgtcc tggagtcaca gctgcagtaa 82680
agcagggcag tcctatagct ggtctagaat gcatcttaga cgtgtctctc ggccatactc 82740
agtgacgaaa acgtgaaggg gattagttac gcgtgccttg aatttccccg tctgaaacga 82800
gaacccaaac attataccat ccaggagagc taactatggc ctgggtaacc tgcagacctt 82860
ctgtggatgc cggtgctgcc ttcacctcct tctcgtggag gcactcagac tcgggtgaca 82920
ctgagactgc tctaggtttt acgacttgga caaatttggt tgatttctta attatgctcc 82980
tcatggctag ctatttttgt gagggaggaa aaattaaaat atacaggaag acatcatgaa 83040
gcattcttca aatttaagtt tcttataatc ttttggttgt gaacctagcc tttaacagtt 83100
gagccatccc tccagcccca aatttaaaat ttttaaagnn nnnnnnnnnn nnnnnnnnnn 83160
nnnnnnnnnn nnnnnnnnnn nnnnnnnnnn nnnnnnnnnn nnnnnnnnnn nnnnnnnnnn 83220
nnnnnnnnnn nnnnnnnnag gctgctgcta tgaggtgtgg ttcttctatg atctgggcag 83280
agcagtgagt tgtagcccca gacagccatt ggcagaagca gaagcagaag cagcaggcag 83340
tacacagtca ctgtgctact aagacattag acgtgtggga agtgagttgt agggtatgtg 83400
tggatacagt ctcgtgcaaa gtgataaaca cccacagatt cccagagcct gcctttggaa 83460
ataaaggaca gataagtggt cactagtcac tgtgggcctt tttgtgcttg atgccattct 83520
ggctggctcc tctctgatct tgagaaatgt ggggtttttt gtttgttcat ttgttttgtt 83580
ttgttttgtt ttgctttgtt tttaacttta aaaccccttac tgaattacta tatatacagt 83640
ttgctggttg ttactcggtt gtgtctctgt taggaacttg gacagagtag accacatcga 83700
acagctgggc ctggcttggc tgttcccata gttttggaca tggcctccgt gacttactgc 83760
cttccataac ctcaacagag tgccaccggg aaccatagat aactcaggac actgacacag 83820
ggctctcaag tgaatgtgtg aggttcacca gttcctgctc tttgccaaag ctgcccagtt 83880
tcatgggagg gcatttagcc tcttgtatcc agggaagaag tggccaaggt ccttgccatc 83940
tatagtctcc aatggttcca ttcagggatc atgttcttct gtaacacttg accttgcgag 84000
tgacattacc ataactgcca cttattcagg tgaatacata cttcaatctg tagggcttaa 84060
agatagtttg ctgtcttcct tctgtggttt gtggctgcct gcccatagta cttgttgttc 84120
ttggtggatt ggagggtgtt gagcacagag gatgtttgct cattgtgaat ttgccctgga 84180
gagctagagt ctcccaaaga ggtcccggca tttgtgaagt gggtgccttt gcttgatnnn 84240
nnnnnnnnnn nnnnnnnnnn nnnnnnnnnn nnnnnnnnnn nnnnnnnnnn nnnnnnnnnn 84300
nnnnnnnnnn nnnnnnnnnn nnnnnnnnnn nnnnnnnnnn nnnnnnnnnn nnnnnnnnnn 84360
nnnnnnnnnn nnnnnnnnnn nnnnnnnnnn nnnnnnnnnn nnnnnnnnnn nnnnnnnnnn 84420
nnnnnnnnnn nnnnnnnnnn nnnnnnnnnn nnnnnnnnnn nnnnnnnnnn nnnnnnnnnn 84480
nnnnnnnnnn nnnnnnnnnn nnnnnnnnnn nnnnnnnnnn nnnnnnnnnn nnnnnnnnnn 84540
nnnnnnnnnn nnnnnnnnnn nnnnnnnnnn nnnnnnnnnn nnnnnnnnnn nnnnnnnnnn 84600
nnnnnnnnnn nnnnnnnnnn nnnnnnnnnn nnnnnnnnnn nnnnnnnnnn nnnnnnnnnn 84660
nnnnnnnnnn nnnnnnnnnn nnnnnnnnnn nnnnnnnnnn nnnnnnnnnn nnnnnnnnnn 84720
nnnnnnnnnn nnnnnnnnnn nnnnnnnnnn nnnnnnnnnn nnnnnnnnnn nnnnnnnnnn 84780
nnnnnnnnnn nnnnnnnnnn nnnnnnnnnn nnnnnnnnnn nnnnnnnnnn nnnnnnnnnn 84840
nnnnnnnnnn nnnnnnnnnn nnnnnnnnnn nnnnnnnnnn nnnnnnnnnn nnnnnnnnnn 84900
nnnnnnnnnn nnnnnnnnnn nnnnnnnnnn nnnnnnnnnn nnnnnnnnnn nnnnnnnnnn 84960
nnnnnnnnnn nnnnnnnnnn nnnnnnnnnn nnnnnnnnnn nnnnnnnnnn nnnnnnnnnn 85020
nnnnnnnnnn nnnnnnnnnn nnnnnnnnnn nnnnnnnnnn nnnnnnnnnn nnnnnnnnnn 85080

-continued nnnnnnnnnn nnnnnnnnnn nnnnnnnnnn nnnnnnnnnn nnnnnnnnnn nnnnnnnnnn 85140
nnnnnnnnnn nnnnnnnnnn nnnnnnnnnn nnnnnnnnnn nnnnnnnnnn nnnnnnnnnn 85200
nnnnnnnnnn nnnnnnnnnn nnnnnnnnnn nnnnnnnnnn nnnnnnnnnn nnnnnnnnnn 85260
nnnnnnnnnn nnnnnnnnnn nnnnnnnnnn nnnnnnnnnn nnnnnnnnnn nnnnnnnnnn 85320
nnnnnnnnnn nnnnnnnnnn nnnnnnnnnn nnnnnnnnnn nnnnnnnnnn nnnnnnnnnn 85380
nnnnnnnnnn nnnnnnnnnn nnnnnnnnnn nnnnnnnnnn nnnnnnnnnn nnnnnnnnnn 85440
nnnnnnnnnn nnnnnnnnnn nnnnnnnnnn nnnnnnnnnn nnnnnnnnnn nnnnnnnnnn 85500
nnnnnnnnnn nnnnnnnnnn nnnnnnnnnn nnnnnnnnnn nnnnnnnnnn nnnnnnnnnn 85560
nnnnnnnnnn nnnnnnnnnn nnnnnnnnnn nnnnnnnnnn nnnnnnnnnn nnnnnnnnnn 85620
nnnnnnnnnn nnnnnnnnnn nnnnnnnnnn nnnnnnnnnn nnnnnnnnnn nnnnnnnnnn 85680
nnnnnnnnnn nnnnnnnnnn nnnnnnnnnn nnnnnnnnnn nnnnnnnnnn nnnnnnnnnn 85740
nnnnnnnnnn nnnnnnnnnn nnnnnnnnnn nnnnnnnnnn nnnnnnnnnn nnnnnnnnnn 85800
nnnnnnnnnn nnnnnnnnnn nnnnnnnnnn nnnnnnnnnn nnnnnnnnnn nnnnnnnnnn 85860
nnnnnnnnnn nnnnnnnnnn nnnnnnnnnn nnnnnnnnnn nnnnnnnnnn nnnnnntgcc 85920
cccaccccc gccccacaat tgtttaaact gtagcatctc tgttctttat tatgctttag 85980
ggcacagcat gaaggtacca ctttggctta aatttggtgt gtcagtaaag tttttgaaaa 86040
acacccgtac atgaatgatg ttttaaaccc cccattttat agtcatgtct attttttgtg 86100
aataatgggg acattttagc ttatagtagc ttctatgaaa agcaacagag ttctttgtgt 86160
cactctcgcc cttgattgtc agtggaacct atgatataag gccaggccac taaatccagg 86220
tccacaggga ttgaaatggg ctcttcgcag atggctctgt tgcacttttt cagtgtgcac 86280
ttttttttc ttgagagtgt cacacatgtg cggtgtactt acatcatttc caccctcttc 86340
ccaggcaccg cattagtgca tgcatgtgcc ggatttccaa tcttacttgc tttctgtact 86400
taaccttata gagacctttg tcccccagag cttgatatca agcatcaata tttagtaagg 86460
gcaaatgcaa ggctgagact gaagtgactg ttggttgttc caggtgacaa cagttctcaa 86520
cctgtaagtc acaaccatta gcagacacat atttccaacg gccttaggaa ctgttaagat 86580
atgagagact gctcatttgc aaaattacag ataagaagca gcaataaaaa caaatttatg 86640
gttgggggtc cctaaaactg tcagaaataa tgtgttttcg aatggtcatg acccacaggt 86700
tgagaaccac caccttagga cttagcagat ttacctgtgg gtcactttgc attctcatgt 86760
aaggtatggg agggaactaa catctagcca ggatatatgg gacatttatg cgcagtttgc 86820
atcccagcaa cctctggttt gaaggaagaa gagaatgatg ctaggttatt ttccagtgct 86880
tgctttctac ttcaagtttc agaatggttt cactttcttt ttaaatacca tatcctgtgt 86940
ctgataaatt ctttgtcaga gccttctccg tgttccttca cctctgttgt aatgtgatgt 87000
tatatcttct agtttccttg cttttgttgg cataagcaat tgggcagtct tgttcgggtg 87060
ataaggtgca gctccttgct aggcagctgc tggcggctgg gttaggctgc acgtggcaaa 87120
gcatctttgt ggtgctcagc tgcgctttct gagtggagaa ggaagtaggg gagagccagg 87180
gaagcaggga gggctttcgt tcttctgatt taacgtgaac accgtttact ggcactaacc 87240
tatttgtgag aagtaattaa aataattcat gtaaaagtta cagcagagcc attggtattt 87300
gttctcagca atcagtaggt cttgtttctt tatgtgtgaa tagtacagta ccgttttatc 87360
tgcttgtaca ggtgggtacc tgagttgatt ctgaatcttg gaatcagtct ttgtgtatat 87420

-continued cgctgcagtg cacacaggtg tgcacacatc tattgtcaca ctgatttatt tttctttgga 87480
catatcacat gggactggtg tgacatggat gagcccagag gacattatgt tatgtagtca 87540
gatacagaac aaatactgta tattctcact tatatgtggg aattaagacc ttgatctcat 87600
gatctggaga atagaatagt ggctcctgga aaagagagct tagtggcaca gctgatagga 87660
ataataaatt cctatagcac tgtaagcttg ccgtgttagt cagtcctata catttcccag 87720
gggcgtagga agaagatcca gactgttcca gtacaaacag atgatacacg tttgaggggt 87780
tggatttgcc aggggccctg ttcatggaca tgcccattgt gggcctgtac tgctctccat 87840
cgctttgcat acatagctgc tctccatagc gctgatagcg tgtatcatta cctcacacca 87900
attaaaaaaa gagtgcaaaa gcagttccca taagtatgtg cttcaaatgc tagaccaatc 87960
atttccagat ctgtccagtc tctcttatac tttctattgt tagctatttc atccatgcat 88020
tttatatttc gaggcttcat gctttctttg taagcataat actcacccag gatgggaaag 88080
ttggtgaaga tagggcgttt caaccaaaga gcttagagtt cattgttcct ggactcataa 88140
aacactcagg atgagtggag aaagtatatc gcccacaggg cgacatgagc acctggactc 88200
ggaagggtgt ggggaggtgt ggggaagaga tgctttcctc ctcgtcgacg gccagcgctc 88260
tggcatgcgc gtgcagcttc tggtcatcat actgaaatga tgatctgaat gtggtgacaa 88320
tcatttgaca gaggcacctt tggtagacag atgtctgctg cctgttgagg gtgcttttgg 88380
gtgttaaaga ctgtttctga cctgtgtgga cggatcatta agtttaaata ttacttttgg 88440
tccaattgct tagctcattg tctgacgatg ttttatatat gtcttgggca gtcctaaagt 88500
gtcttacagg cttgtctacc ttaaactcaa gaatataaac ggaagggtaa aggctcattt 88560
atttttcagt gtgattgatt tcattaacaa taattaggaa ttaaaaaaca aaaacctaag 88620
agaaggtgaa tgtctgaagg gagtttgtaa tttgagattg tccactgcgt gactgaagta 88680
aggacagaaa aacttcactg tgtttgagga attttaacat agcctttaat ttgaggaact 88740
ggttggtgtg agaggccaca tgacctgttc tagtcttggt aggaaggtga agctgagcct 88800
tgtgtgtata tttcagagag cttctagcct aagtgcaggg tgccctgctc tactcagagc 88860
tggctcactc cttagccctg ctctcccaag gaccaccgtg gccttactta ctcttgccct 88920
caaagaactc ccacgaagat agcaaggtac agtttagttt aaggtaatga tagttgtcat 88980
tttcatgtgc taaacctgaa tccttatttc ctattcactt gtcagcacct cagccctttc 89040
cagcctaata tatatctttc tctctttgtg tgcttttaaa gggtccagca tttctgatta 89100
cccaatcaag taggagcctg ctcgtctcac ccgtggaatg gaatgctatg cctctcctct 89160
tgcattcctt tccccagact ttgctggcct tccacctgnn nnnnnnnnnn nnnnnnnnnn 89220
nnnnnnnnnn nnnnnnnnnn nnnnnnnnnn nnnnnnnnnn nnnnnnnnnn nnnnnnnnnn 89280
nnnnnnnnnn nnnnnnnntt tgagacatat agtggtatgt tattgtggtc cagggacttc 89340
aggaagctgg ggcaggaggg tcataaacaa attagagacc aacccaggca cctatctcaa 89400
aaggccctcc ccattacccc tcctcacacc cctgtgctgg gcaagtaggt gacatggagc 89460
tgcgttcctc gccctatgtg tgttagtaag tcttaggatg cagtactgga ttttcttatt 89520
cactgaaatt tatactactg ccgctgcatt ttaggatgta tttatgttac ttaaacagta 89580
tacacacaca gatgtgcacg cacacagacg cacgcacaca gacgcacaca cacagacaca 89640
ttctatcgtt aaggtgattt gaagcaatct tgtgatttga agcaaactgt taaaattgat 89700
tttatgttta actatgtggt aggttctgtg tttttaagca aaatattatt attattatta 89760
ttattattat caagtgctga cagtagtaca tcatgactgt ttgaccatat attataggct 89820
gttggcatcc atattcatgt atggtttaag gaatttgaag attcctttgc agctttccct 89880
atccctatat agtcctcagg gcttcccagg ctgcctgcct ggaggtgggg gtgggggtgg 89940
gggtgggggt ggctggagtg actctagcct aatggaggcc agtctctgtc agccagagca 90000
tgcgggctgg cagtggcctg gttcctttgt ctggccagtc agtcatcttt ctaacagaca 90060
cttggcttct ccagtgtatg tcagagatgc agacagctgg ttcaggatgg cctgcctggc 90120
ttcccccagc accacactct gctgtatagg acatggcttc ttttgatcgg tgacagcttg 90180
aactgagaaa atcacgtggc tcaggccttg ctctcagcct gtatgtgcca gggctcgaag 90240
gggccatgca cttctgctgt tcttattagt gtgacatcag agatcagaag gcagttttca 90300
gggggtcaca tctctgcctt cttggttagt tggcaaaaaa ttatagcatt atcaaaactg 90360
gccttccctg actgcccgga aggtatggtg accatacact gtgaatctgg tcagccttgt 90420
caacctttcc agccatgagc tctacagctg gaccttgctc cccaggcatg cctcggggac 90480
aatatggaca tgtggcagaa cacctgcctt aggtgtgtat agattgaact gggaacaccc 90540
gtgccttcta ccccatgctc acccagtaag cttccagtgg atgatagctg cttgtgcgtt 90600
ggtatttcag tttgacacta tgtacagact ttaaaagaaa aacaaaacaa aaaccaaaaa 90660
aactccttca ggcaaattaa atgccctttt ggtaggtagc aaagctgccg cttccttctt 90720
ttcccaactt tattttctct ggctctgttt ataatcactt attaacaaaa tctgagaggg 90780
tcctgagtgt gactgttcct tacctatgcc ctcaacgtac ttgttctcat gtttctcgca 90840
gagtgcacat ggagcagact tggtgctgca gggagtgacc tgctgctaac tgatgatcta 90900
ctggcaaggt gcacattgtt ttagaaagac ctttctcgtg ctgcctttat cctagaacag 90960
ggacacagaa caatcttgta gaaaccattc actcttcctg gtcggggtga gagagaggat 91020
aacttaaaaa cctgagcatt ttaaacagtt gcatgggagc tagtgagagc tcagcatctg 91080
agagcacttg ctgcatctct gtgaggacaa gagcttgact cgtgctaccc agtgttggtg 91140
gccgtgggtg gagggggctg actgtcagcc tagctgacaa acagatgagc tgctgaagtt 91200
actgcctccc ctcagaggaa taaggcagag agtgatagag ggagacgccc ttctgtggct 91260
gccttgcaca tacatgcatg tacactacat atatacatat ccatgcacac atgcagcaca 91320
cacacacaca cacacacagt agggggagat ttaaaatagc tggatcttct tagaccaaga 91380
tcctaatatt gagcaaatgt gtattttact tcttctaaga aactgcctta gtggttagag 91440
agatcgttct gtagttaaga acatctgctg cttcgcagag gcctgaagtt cacagcctgt 91500
aagacatgtg atagaggtgc taaatccctc taagggatcg atgcctctat agtcacctac 91560
atatacacgg gacacacaca cacacccagg atacctacat atacatagca tacacacata 91620
caggttacct gcatatccat tgcatgtgca tacatctttt taaagctcct tcttaatgat 91680
ttatttgtat cttatgcatg tgaatgtttt atctgagttt atgtctgtgc accatgtgta 91740 tatcaggg at ctgtggaggt cagaagaggg cactgaatgg accattgtga gctgccttgt 91800
gtgtgctggg tctcaactcc tgggccatca gatctccagc cccacactat tttcaaaatt 91860
gtttttaaaa agttattttt cttattagtg agtggtagga gctcttggtt tttctagaca 91920
ctgccttttt ccagatgggt ccctcttggt ttccagtgag tttctgtaca cgatgcacta 91980
ggctgcttct ctgtgcactt gtgcagccag gcttgaccat ttctgcaaag accagccttc 92040
ccagttgaat gactttgacc tattttgttc agtgtgaacc tacacagaag tcagttccgg 92100
gactcgattt tgttctgttg cttggtttat atggatgccc cactgctctc tgattatggt 92160

-continued

```
gactttccag taagtcggaa atgggtcagt gcaagtttaa agtaggtggg ttcaagggta  92220
aatacatgaa gatctgctag gtggacttgg ggtggatggg cctgcccaag ctctgtgtct  92280
tctagatgct tctctcaaga ttacgtaaag aactgtgtta gtttcctttc ataatgaagt  92340
ctgtgatgga tgtgctaggt tgtggtatta gtctcatggt aatcataatc tatagatagc  92400
agtagtcttt gtgggggtga gacctagtct gtataaggaa tgtaacctcg gctgcttcac  92460
ccgtcccacc atgcttttgt agacctacca tgcctaagtg acacctggaa atgcagtgaa  92520
cccacagtgc agcccctctg ccctatgtgc ctatgtgctc ctgtcttctg acctatgtgc  92580
cctctgccct atgtgcctat gtgctcctgt cttctgtcct atgtgccctc tgccctatgt  92640
gcctatgtgc tcctgtcttc tgccctatgt gccctctgcc ctatgtgctt atgtgctcct  92700
gtcttctgtc ctgtgtgccc tctgccctat gtgcctatgt gccctctgcc ctatgtgcct  92760
ggctcctgtc ttctgtcctg tgtgcctggc tcctgtcttc tgtcctgtgt gcctggctcc  92820
tgtcttctgt cctgtgtgcc tggctcctgt cttccccagc tctccccagc cccagtcggt  92880
ggctcctccc ccaggactgg cacagcagag ctggttacta gttgcagtct taccttttat  92940
gccatgcact gttgcttttt aagtagtgtt aaacttaaaa cttgagtttg taactcttta  93000
taaattttgt tagttttctg tttggaactt gcactaagga tatctggaaa cctattggtc  93060
tcctatgtat ctgtctttaa ctggaatgaa ttgataggtg gcctcatgtt gtttttacat  93120
ctgatcaaag catactgaat aggatagagc aagcaggcag tgtcctgtcg atactgcagg  93180
ctttagctca tagttgttga ctgcttgatg gctttgagca gaggattgga tggggtttgg  93240
agtggctcac gaaggctagt gcacgtaagg catggtttaa aatctgcctg cgtctcagga  93300
aaggatggag agtgctcctt tatgggtgtt attacccctg ccactgactg ccactcactt  93360
tactaggata acttgtttgc atatacattt tctgttactt tcgtccaact gtttctgata  93420
cccatgttac attttattat atatgatgat ttcaagacta tgttctggtg taaaccaaac  93480
ttcatccttg tcagctgctc tactatatag acattatata gtcaaatgtt tccagtgttc  93540
tagaaaaagt gcagtttgaa tattaatttg gtgttagctt cttcaccttc tgttttctct  93600
tctaaaacaa aactgaaaag ctttaaatgc attagcactg ctttaggttt ggtaatgaat  93660
acaatgtcat tggcaatgtc actgatgtca catgaagaaa atacaaccct tgaagctcac  93720
ttgcaagaac atttccttga tgctaagtct gtaacgttaa tgcttttcca aaagacgatt  93780
ttagaactgt tgccagcaac gagcactcgg gctttttttct tgcatccata acatatacaa  93840
ttaatctaga taaaatagca taagcgtgca ttttaggtct tgtgtttctc agtatgcgtc  93900
ttgtatgtcc aggcagcagc ctgccagctt gcgcttgcgg cctgtgttct gagatagacc  93960
ctgagggaac ttggggctgc tttctggcct tgcacttctc tctagcaaac tatgatggct  94020
gttcctcatt gtgtgtgctt tgctccaaca gacttttctt cagagaacaa attgctctga  94080
catctttgtt cttttaaaca cttactatat agatttttgt tttattttag taattttaag  94140
catctccatt gtaattatga gaactcaaaa tcttgtacat gttctgatgt tcataaggaa  94200
atatctcgtg caccttttgt actgcgctcc acaagcagaa gccatgcctt ggccattctg  94260
cctcttgcct tgctatgcat ttcagtgcag agtggtccct ggtgactggt gctgtgcatt  94320
gggagcattg agcgggcatt agctatatag cgattacaaa aatggcatct gctcggagca  94380
gtccagcagg gctcggcatc ctcactaacg tctgggtttt gttcccattg cagattttcc  94440
tcgcatctgg cttcactgca ttggctcttc tgcactgtgt acaggcacag gtgagttaat  94500
ccttgggtct ttcatgttgc gctatgttga ctattagatt aaatatttta aattgcctaa  94560
```

-continued

```
tacattagaa acaataagca aataagagga atgtgagtaa gaacagaata aaacttacta  94620
ttttcctgca tgtttttgtt aagagagttc ttttatgaaa ttgttgaaat gacattgaag  94680
gtgacacacc agatatcttg attggtggtt attgtttcta tttggaaagt gtgtgtcttc  94740
agtgtacctg ctggacaagt tgagttaatt cattaagttt taacctcaga gcctggaaaa  94800
aaaatttttc tacttatttt catatgtcac atatttttga gtggttgtat tatttacctg  94860
ttattaaact ggtataatgt aggagaaaag aaaacttctg taggttttac cattaactct  94920
caggctgcat gtacaggtgc tgtgcaatac tgggcttggc ctctgtgcca gtggcgttcc  94980
ccactcatcc actgatgatg tccatgagat ttatgaaaca tgttagtaac atgcgataca  95040
cttttcttca tttgtaactt acccttggag aacttcagct cccttagcat tgggactgct  95100
tgtactcaaa gacatagcct tagttcttag agcacggaat gctttgcagt gaagactaaa  95160
gcctgctgag tgtgagcatc tgtaagtaca cagtagaagc gagaattatc tgtacagagt  95220
gtataaggct ttggaacatt atgagaagtc agtatgttgg acctgttcct tcagagatca  95280
gggtagagtt gaggggatgt ggcttctgac tcctcactct gtcaggtgtc tgtggtctta  95340
ggatgaagtg caaacacctt aagtttggta ttttttaccc tcttagcatc ttgggtatgt  95400
tttgtgatac caagttttga tgtctgaaga ttggatgaat taaatctttt ctactgtctg  95460
tcgctggatt taccgttttt catttagttc ccagcctggg agacttgtct gctcattttc  95520
ctgctgtgtg cactcatgtg ggcactggtc tcagtggctg ttgacctcac aggacacctg  95580
atgcccatgt gctcttgacc acgccaccct tcttcaagtg ttgagatact agccatctct  95640
cttgggtact tgtctgtttt acttaaagtt gttactgtat ttccttattt attgagtgct  95700
gcactggaca tttgtggagg tcagaagata gcctgcaccg agttggttct tttcttctac  95760
catgtgggtc ccaggactca aactccactc atcaggacta gcagtaaacc ccttagctgc  95820
ccagcctccc tcaagactcg ttttgctttt gctctgtctt catgcatatt tgtctctcgt  95880
ctttacaggg gctatttttc ctcctaggac ctttaatttg cttgtaatta aataaaacgt  95940
tagctgttgt acactatttc ccattcacac atccttacag ggttagtctg cagaagcacc  96000
attgctcttt cagcagctct gcagtgctcc tctgagtgcc cagcagccac agttgctctc  96060
tggttgtgtc tggattagca gatgaggaca cgcatctggt taagtgactc tcccaaggac  96120
atatcacctg agtggtggtt tgctgctctg aggaccgtga tcttaaccat gaagcaccat  96180
ttctgcctaa acagccctgc tggctctcat gtttgtggca gtaagtgtaa tatatgaaaa  96240
ttattttcat gtttgaagac ttcaaaccta atttgaaaaa tcagacatta tttacttgtg  96300
ttttattaac taggcctaac ttttaacctg taatcttcat ttcaaactgt ggaacacgat  96360
ggcttacttg aaaaccaatg actgcattag tgataaaagc tctgcagctt gtctcagatt  96420
gactggtgac tggagcgagg gtcgcagctc cagcctcttt tgttttcatt atttgttttt  96480
taagcatggt atgctaggaa ttggcattct ttccccctta gacattttag attataggta  96540
gcatctgtgc ttcactggat aaattgcaaa acatctgggt gtggtggcac atgcctataa  96600
ccgccagcat ctgcagggtg ggaacagagg gaggagggcc tggagtccaa agacatctgc  96660
agctgtacag tgagttcaag gccaccctca gtacttggtc ctgttcaaaa aatcccaagc  96720
acacaaaagg aatacacatg taatacacat gtctaaatac acgtgtactc acagaatagc  96780
tggatatgta gctcagtggt gattctatgt ctatgtaata taatgcatac ataattattt  96840
atatatgaaa tatagtgact atattttata tagtgaatat attatatatt tcatatatag  96900
```

-continued

```
atttttgcct taaaacatgt agtgagagag ctgccatttc aagacaggaa taaaagccta  96960
ggagagtgtg agtattgacc tgcctcatta gtgagctgcc attatctctt gcacatttat  97020
actgctcact gacaagctca caggccagag cttggaaaga ccatctttat atgcatttct  97080
tatttgtcag gacactattt aactcctatc ttctggttct gaagatatct cactacttgg  97140
cttggaggac agagtagaca caagtcttct taatattgtt agtagctttg atagcttttt  97200
aagcttaagt tcttgctatt aaagacagta agatacagtg actgcatttc aacaaagggt  97260
ccagtgcttg aggtttaatt aaagaagtca acatgcacat atacatctgt agggctctct  97320
gcactcacgt cacccagtca taggtcagtc ttgtctgctg agtgctctag agtggctttc  97380
caaagcaccg aggcatcccc ctattctgta tatgtactct gaacagaatt accgcactgt  97440
aatgcaccat gtaccttgtc agaatgcaaa tcgaagagca ggtaagggat ttcttagttt  97500
atttttttaca tgactaaacc acctcttaaa ggctgctagc atggtcgcca gaaaactgat  97560
tttgaagttg cagagctcct caacaaggga ttgacagtgc acttccagag cctggagctg  97620
ccgtcccagg ctgtggcacc gtatgccagg gatggagggc tttgcctctg tagtagttag  97680
ctgctttcag gctcaaaatt aactcttgta gttgatactt cacttattga aacagacact  97740
tatttctagt aacatgtctt tgaaaaaaca aagtagatta cttaaattgt gctacagaaa  97800
gtctaatatt gtcttgaaat gtttaaatta taaataaacg atttcccctt aaggaacatg  97860
atgacatatc ttcaggaagt tttgtttatt taagaactga catggtatca ccggtgttta  97920
ggtagagcat acttagactc tctcttagcc ccttcatgct tagttgtctt caggactgaa  97980
cagttcattg tataaaggta ctttgggtct taattgcata atattggttc aatatacctt  98040
aaaattttca ttggaaaaca aacttaattg tattttcttc aactttctga aaagactgta  98100
agagaattcc tggtctgaat tatgggatgg agaattcttt agtttgaatt caaaaggcaa  98160
aggactatgt gccattaaaa aaaaagtctg tagcaagcta ctggttccag tctagatcac  98220
acttttaaca tcattaaacc taaactggct ttgtccacta aacagcagga tttaggttag  98280
ccttgacatg ccattgaatt taaatacatg actagtgctt cactactgct gtgtgtgtgt  98340
gtgtgtgtgt gtgtgtgtgt gtgtgtgtgt gtgtgtgtgt ttaaggcttg tatgataagt  98400
acattctaat gttttcgtca tctcatgatg ttccttttac ttgagccact gttttgacag  98460
acatctgtgt tgatgaagcc tcttgttttc tgcaggtttc caaggactga tggtgatagt  98520
gacacacctg gtgtgtttgt tacatgtcac tgtgtagttt cctggttatc agagtcatat  98580
aaaggctaca gagaaagaca gagggaagag aaagaacaaa ctttggcaaa gcgcagctct  98640
tggacatgta ctgtgtcaag ttaaactaga tgattctttg tcagagagtg aagtgtattt  98700
ggattttacc tgatcaattt tatttggcag acttacactt tgcatcctag ccggtggctt  98760
aggtggtaaa gtatcagaac tgtgtcctgc aagctgtcat ctttagtttg atctgtaaga  98820
gtcccagaga tgctttacgc ctcaagctgc aagtgcaaga gctactctgg aggctgtgac  98880
aggacctgag ggaaagtgtg cgtgggagtt cttacatgtc tgtctcagca gtatgtgctc  98940
tgctcgctta tttatgggac attattagtg ttacagctgc ccacacgtgc atgcctaacc  99000
ttagttatgt ccttgaatag aaacttactt atccaaaata gcattattgt attataaaag  99060
acgaatactg attgaagcgc caatagtagc aaatgagtag aaattaatgc atgtatacta  99120
aagttaccta aatgtgtgtt tatttacgtg tgataacgtt tgtcagaact gaccgcactg  99180
tagtttgagt agagaggcat gaagggaagg cacgtgatgg caatagtgtg ctcgcctatc  99240
atacccacaa tggaatggaa tggagagaat cctgtgcaca ctgaggcagg taatgtccta  99300
```

-continued cggccttctc ctatcagtca gataatcatc agaagaaccc agggactcac tattgtggtc 99360
ttaaggcttt gtttggttga tctgtggatt ttgggttttt tgtttgtttg tttgtttgtt 99420
tgttgagata gggtcttcct gtgttcctgg ctgtgctgga aattgatatg ggaaccagat 99480
tgacctcgaa ttctgcctgt ccctgcctcc tgaactctgg aattagttgg ccccaaagtg 99540
gagccaatga tcacatttta aaatgagaaa tgaagtaact gttgtgttaa atgaccactc 99600
agtgatgtat ccaagttcac aagctattta gaggccaaac tcaggttgat ttttgtggtg 99660
tttggctctt tagaaacgaa acagcaaatg cagacagttc ttatgagatg cagttgcttg 99720
ctgttcaggc cccatgatca gggcaatatg gaacacatgt aaaggtatac agaaagagcc 99780
agctccacag ggtgggtctc tctctctctc tctctctctc tctctctcac tctcgctctc 99840
ccccctctct ttctctcttt ctcaccacaa agttcatttc aagctgcctt cccccacagt 99900
gagatgtgca ggccctttac actggctatt tgagaagttg aaggcctgtt ttataatcag 99960
aaactatacc tgtcggtgat tagtacggga aagcacaatt caagtgatgt ttcattttca 100020
aagattgaaa aaaggacacc aactttttcc ccccatttc ttctgtttac aaacaacttt 100080
aaggctatgg agttatataa aataaagcta tacaggggct ctataatgta cttggtagat 100140
tgcttgccta gcatgctcga gcaccaggtt tggtttcccc tgttataaac tgtgtatggt 100200
ggcacaacct ttcatcctat gactcaggaa atgcaggcag gaacatcaag agttcagagt 100260
cagcctctgc ccgacagcga gttcacggcc agtctcgcta tgtgcagccc tgtctcaaaa 100320
caaaatgaga cttattttta cttgataaat attgtaaagg aatgtcttag aattcatata 100380
atcagaaatc aacacaggac tctctcacag agaagaaatc ttcagaaaag attttggctt 100440
ttagttttta aatgttaaca ttttgaggac tgatgagatg tcttggctgc tgagtctgat 100500
aactgaattc aactctccca cctctgagct ccatttaaag gaatagagaa cctcttcctt 100560
cctacaagtc gtcctatgcc cttgaccgtt tcaccctctc cctctgtttc tctgtcctac 100620
aagtattagt tggatggaga acccttctag ttagtttaaa aagcatacat ttatgttagg 100680
ttttatatta tgacgtctta acagacatta cactttaccc tggtaaaaaa tgaggctatt 100740
tttcgccatg ttgtttcttg agttgttaag gggccgtgta cagtggtagc tgaggagcgc 100800
tgaggtctaa ccactgcacc atctaaaata gacacagagg gcttccatca cttcccctaa 100860
ggttcctggc ctacacctgc catttcagct cctcttctct tttaaaacca ttttcaagga 100920
gattcataat agagctataa ttttatcagt gctgtcaaag gttttcctgg tatctcaata 100980
attcatgctg tttctcaact tactgattga ctttgaatct ttatattgtc caaatatttt 101040
tttataaatt agaatgtgaa gcttattagt aaattatatg taacataact atttgaagat 101100
gactctagtc gaggcacaat gaccgggcag gaagctgatg agatttttgg gaatgggagc 101160
tgtccagtga ggctcctctt tccagcattg ggcatcgccg cgccacatgg gaagagcagc 101220
agagttcact ttgcttgagc tgtgacactt acctccaggc ctcattcatt atctgtgaca 101280
gacgttagcc ttggctagcc tgcctgtgtt cctgttcacc taggtgtcca tttgtttttt 101340
cttatactgt gggtttttag tattgatgga actcataaag tatacagcac atagattatt 101400
acttttatat ttccctcctc cactctatcc caccctccct cctctcttcc cccccccccc 101460
atcctcctcc cttctctcct caattcttat cctacaccta ggttacatat atctcttttt 101520
ttcacccctc cctctccctc ctatttcctc ccctcccctc ccctcctccc tctgttttgg 101580
gacagggttt ctctgtgtag ccctggctgt cctggaaatc cctctgtaga ccaggctggc 101640
ctcaaactta acagagatct gcctgcctct gcctctctgc ctcctgagtg ctgagatcaa 101700
aggtgtatgc caccatgcca ggctggttat atttatgtct acaggttcag ataatgtgtc 101760
aatagtggtt cccagctcag ctctacctgt tacataagta cctatgctta gtcccaccac 101820
caccctggcc accctgcctt cactggacta tcaggactga gacaaactta ttccagaata 101880
gcaacccatg atacttagca gcagccttca ctgaccagca catcctttgc tgtcctcact 101940
tctgaaagtg cacacacatg ctagctgtgg attcgactgc agtgactttg tcagagacag 102000
cagatggctg agagactgtg gtcccttccc aacaaatctt ttctttgcaa acctcttcag 102060
aactgatgaa atgctctgag agctgcagac cttcaaagag cagttctaac ctgaaaaacc 102120
agttctgggc ttgcattctt gccactgagt atttctatgg catttttctt taacatatat 102180
ttctttgtga cctccttact gttcttcttg tccctggtca tgcctcagta tggtggaaaa 102240
caaaaatagt aaagcaacaa aggaaaacat gattttaaat gtgtacctac ctagctaggg 102300
tttatacaga tagagaggta taataacagc cacttaaggt cccttgaaga tccaacaggt 102360
ggtcatttta ttttagagtc tctttcataa gccttctgat gatcaccctg tgttgtaaga 102420
ggcaaatcag tcattggtca tctggtagag atgggtgtag cagagagctg gctatgttgt 102480
aagaggtggg tcaggcattg gtagtcatta gtagagaggg tggggataat ggagagctct 102540
atggctcctt ctcttaaaag ggataccttt gaacatcctt gtctataaat ttgtgatagt 102600
aacctcccat gagaagagta aaaatcaagc agataccaga cagatgagca tgtgcattcc 102660
cagatgcagt tgctgcgtta ccagaatgag cgtgtgtcct tacagttaac atatccccag 102720
gaggtagcat ggagcctcct aatgcctctc ttcccagttg ggtggccggc tggtctggtg 102780
tagcagaagt gcagagccca ggcttccttc catatctgtg cttcctgctg gaaaggacat 102840
gggaagccgc caaaatttca ccagctcagt ctcagactgg tggctgtgag attttaagca 102900
ggtagatttg tcttttacct caagtctcct cttgattcca ttagatgaac taagagtaag 102960
ccatcaatat tgactatgaa tcacggtatg gctggtccct caaaatgttg gtggatcccc 103020
aaatccagga cctgtcaggg aagctggtct gccttcccca gttttattct cagtgcccag 103080
cccttcttgg aagctgtcag cactcagatt taggtacact agccctataa actgtgtgca 103140
gatagtccaa atcaaaacag gagatagaag atggctcagc agttaaaaca ctcaatactt 103200
ccacagagga cctgaggttt tcccagcacc catcagggga ctctttcatt gtcagagttg 103260
tcccattgag tccctggggc atggatacac acactcaaaa agaaaaagaa agcatttaaa 103320
acacaaaaca aaagccctct aaaatctgag acattgcccc aagcatttcg aatatgggct 103380
gggaaggtgc tatactgttc tgtgcctggt ataaaggttt cttggtctta gtaacaagtt 103440
tgtgcacatt ttgtgtgcat gagccctgtg ctcagattct tacgtgcata tttactttca 103500
gttttcatgt gtatatctgt cttatatctg tgtatctgtg tatcatgtgt gttcctgggt 103560
catggcagtc acaacagggt gtcggattcc ctggaaatgg agtttcagat ggttttgggt 103620
gagcactcca tggaactggt gaattgaacc caggtcctct agaagagcag cagctcctaa 103680
cagctgagcc atttctccag ctaccccttt gtcctctgaa agaaaggaag aaagcataca 103740
gctttgtact caggcatgtt aggaggttaa ctcctaagct gcaaggcctt ccactgtcat 103800
atattagtag catatattca gaatcaggac tgtaagactc caagtcacag agagtgaaat 103860
tatctttaga atgttaaact tagcaagata ggggattatg gtaattttta atttatttta 103920
ggatagcttc aaatgataat ttaataattt aatgtggttt tgttttgttt tgtttctgta 103980
actgtgtgct gataggttac aggttctgtt gtgttgtggc aatctcagtt gaaaactcag 104040
ctctgcagca tgtgctacag agacactggc agtaggtggc cacactgtga aaggcaggcc 104100
atgaggagag agattttact tggtggcctc cggtgttaat gttgcttggc agctgtcatc 104160
tattagtact gtgaggattt cccacgtcag tgtcactgct tgtgacacta gtgttctgga 104220
tctgggatct gccagagtat ctctgtgtag ccttggctat cctggaactg agtttgtaga 104280
ccacgttggc ctcaaactga actctgagac ccatctgcct ctgccttctg agttctcagt 104340
gctgagatca aaggtatgct ccacagtgct aggctgtacc cggggtttct aagttacttt 104400
tcccaagttt taagggctga cgcaagatga cacaagaaag catctttctt ggaagtttcc 104460
agggccagga tacctgcaca taggccacct gctttcatca tgggtggctg cctttccaca 104520
agatcatgct gccttccctg cctttggaca atgagaagcc actctgtgca gatgtggatg 104580
cagatgcgga tgtgggtgcg gatgaggaag cattgtttag ggttgggtag ctgtctgtgc 104640
agaaccacta gctggaagga cattcctacc gcgcggcctg cagtgtggat gctgcacgca 104700
tgtctgattt cctaattggt gttcatctta ctgttcgtcc cactcatgtg caccagtcac 104760
cagggcacag agttttccaa catcactgtt tttctggaaa agtcatttag ctcagacaga 104820
tgcccaattt gtaacaaccc acaagcaatt tattttgtaa aactgattct gccccatttt 104880
cttcacctat aagggatgtt tttgagtttg agcgattgtt catacaactt gggaagaatt 104940
ctatacacca aacatgaccc tttaagaaat ctgattacat ttttaaaaaa gtaatcctta 105000
ttcccctaca gtttgtagga gatctttatt ttaatgtctg agctgaaggc aggctgtgcg 105060
ttttcatggc tttccagagg ctcatggtcg cagccttccc agttagaaat gctgatgcca 105120
catttattat tttccccatt acaggtgaaa tcattagagt ctcacatccc caggcctata 105180
gtgccgctct cacaatgtct gtctgtcatt atgtatgctc actgaaggaa gcaggtgtct 105240
aaacctgtta tattatagac gtatggcttc tgtgctgggg catgtggaga tggtgctgaa 105300
agacaggcat gctcacccac tgtggtgcta gctatgggtt aataagtaca tagatggctg 105360
ccagcattat aaattcaagt caaacacact gctatgggct atacgatcta gcagtgcagt 105420
ggaggttttt gtccatgttg tagagcgagt agccaaggct aaagtttatg ttttgtgtcc 105480
ttgccagcaa taattttcaa ttcaggttta ctaattccct catcagttca gacagttcca 105540
tgacatggga aggaagcatc cttgaaggta gtacctagta ggaaggagaa ggccatgtgt 105600
caatgcccag ttgtgtccat ttgtccattt gcttttattc caagtcttgt tatgtagcat 105660
aaggtattat taaactctgg actatcttcc tgtctcaggt tcttaaatgc taggattatg 105720
gtgttatggg gatggaccac catgctcaac agaatggtgt ttgtatatat cctacatgta 105780
tgttagcctg gacaggttag taggatcaag ggtcatcttc tcactaaggt attttaatgt 105840
agtcctgata agtaggggtc tgctaaaggg ctgcagaatt gtgaagctct acaacacatt 105900
cagactgaat accctacaga gttgccagag gaggatgtag ttggaggata aggcaagagt 105960
agccttctga agtgtgccag gtggtagtgg ggactaagag gacaaggtgg gggcagggca 106020
ggatgtaagt gtgtgcatgg gttgatggga gtttaattgg ggtgctcaga ctgcatgtaa 106080
tcattccatg ttctatgaaa catctgattt tgtttacctt gactgttcag tttctatgtt 106140
ctagattatc ccactttcca cagctaatta gtaatttttc tatcttgaca aagataactt 106200
ggtgattttt catagtagca tcattcataa tagctccaaa gtgaggagaa ttcagatgtc 106260
cattggctga agaacagagg aataaaatga gctacaaaca tcaatggaat gttattcaag 106320
aatgaaaata atgacgtaat gaagcatgct gtaaggtgga taagtcccag aagcattaca 106380

-continued

```
tgtgcaggat gctatttggg aaagcatgtt tggtgatcat tccatttatt acagaatgcc 106440
taggaagggt aaatctgtgt tagagaaagt agagtaatgg ctgcccaggg ctgggacggg 106500
gcagggaggg atggagctga tgcctgattg gtgctgatgg catggggttt cttctggcgt 106560
gtgtgttata gttcagtaaa tttctttgta ctaacaataa gaacatggaa tcaaagtcac 106620
ctacaatttt ttttagaaaa caaacaaact tgtatggtag aatcccacat atggaatatg 106680
tcagagggtc aagtgaggaa ataaggaaaa gcaatgtcag caaaaaaaag gtaaattgta 106740
atacagtcat taaaagaaaa ttaacaaagc cacagaaaag attatcactt acagatacaa 106800
cctaaaaata gcctttgtgg acagtcttgg tataaatcca ctatcttatt cagttttcta 106860
gcctgaagca ctaaaagaac gccatttgag gccaagagac caaggatttt agaacaaata 106920
ttttattata tttttcaaca tttaagcaaa attcaagatt agtttcattt aactgaacaa 106980
tttagaaaat tgcctatctt taaagaaaaa acaatgaagt tttttaattg atttttgtta 107040
aggttagata caaaagagaa agagcttatt tgttaatgga aacaataaga gaaggaagct 107100
gtgctcacat aacaaggtgt cggaagcagc tcagccagga gtccttcagc ccttacagac 107160
tctttctgca ggcacgcatt gcaaagcatt tgcttgccct gcttctcatg tgttnnnnnn 107220
nnnnnnnnnn nnnnnnnnnn nnnnnnnnnn nnnnnnnnnn nnnnnnnnnn nnnnnnnnnn 107280
nnnnnnnnnn nnnnnnnnnn nnnnnnnnnn nnnntcacac acacacacac attctcacac 107340
acacacacac acgcacgcgc acagcagacg acaaaagaga ggaaaggctt gctttgctcc 107400
cagtttcaga agttccagcc tgtgggagtc atccagaact cagcagagca gaagtgtgtg 107460
gcagaggctt ccatgtcacc aagtccattg aagcaaggac caagttatgt ggccttcaga 107520
ggtccaaccc tcctgctcgg cttcctccag ccacaggctt acaaaataat tctaccagct 107580
gggaaataac ttttcaaaac tatatgagtc tgtgaggtgg gggagggtct ttcataatca 107640
agccaccatg ttctggccct ggttgccaag acctgaccat gtcataatga aaactgcatt 107700
tagtcctcct ttaagaaaca gcctgggcag tttccagctc tgttcagaag tacaaagttt 107760
aaagtctgct gacacttgac atttgttggc ctgttaaagt cgctattctt ctaatatata 107820
gtggtaacat taccattcta ttcaaatatg gaaaaacagg aagatagcaa agaaactttg 107880
ggccaaacca aaaccatcaa gatgcacatg acattctata attctgagct atcgtgtggg 107940
cttgggcccc taccttgtag ccgtctgcag cacacagtgc ccaagatggc tttccttgtt 108000
gcctgaagct ttccttggca aacacccatg ttctggcatc ttaagttcca ggtatctccc 108060
aggtttctct ggggatgtga tcttgatgtc cattgcgtag cctctttaaa atctttgtac 108120
aagtacactg ggtacccaac aacgccacct ggatgacacc aggttctgct gtctgctttg 108180
gaagtggcca ggccacagtg gaccatagca cctgcagcca ctgaatgcct gaatgacaac 108240
acttggaaaa agactttcct agatggccgt tttccaataa ggcaccccaa tcacagttcc 108300
ttttcacgta ggtcttataa agttttacat cttgcccatt tagaggccag ctcttgctac 108360
ttcctgaagt actcacacaa taccctttct gtggtcccat ggcagggatc ctggcttcgt 108420
atgtggtgct aatctgttta gtaattgcag atgcttgccc atacctcctt tgtcagaaat 108480
tttaaatgtg ctcacattct tttcctggcc atttgtatat ctatcacatc tttatgttct 108540
tttttccttt ctgttctgac tgtaaaccta agtgcagcca acgataacca taccagaccc 108600
agaatcctat gtattctttg aaatttcctc ccaagattaa tctattcctt tggaattagg 108660
ctgcacaagt tttcaggata cgggcagaac agggacagag ctccccctac ccaccccacc 108720
cccccaatcg tgaagtgagt agcctgctgt ttaatgtctc atcaacgatc ctaagatcac 108780
```

agcttgtgta ggcatcctgg tcctctgaat tcctagtgat cacccatcaa actctaccct 108840
ctgcatgcta tagttttcta gcctctacct ccagagcaca gcaaatcctt cttacaaatg 108900
tgctctcaaa gccttgtcag gcttaactgt agcagccacc tagctcctgg taccaacttt 108960
ctgtattagc cttcgcatga gtcaaacaag acagctcaag agagagaaag ttgtttgggc 109020
tcacagtttg aaagttttat gttcatttct ggtgggaaag aaagatatgg cagaggtcac 109080
agtgaaagaa atatggggtg aagagccttc acatcaagcc tgaccaggaa gcaaacaggg 109140
ctaggttcca gctttcagag gtttaaccct ctgagcaatt catccctgct aggctttacc 109200
ctctcaaggt tccgaacccc ttagaatgga ctagcacagc cagttgggaa gaggcactga 109260
acatgggaac ctgggagaga atgtttcaca ttcaagctga gacatctgct aagctctgct 109320
cacgaggagc ttaagatcat taacaggtat ttgcttagac agtgttttgg ctttagttta 109380
tattttattg tttgtctcaa ttttaggagg gtttcactta caaacaaaag caaagtgtga 109440
gttaataaaa attaacagaa attaaacaga aaactacatg tagtagatat aggtgatact 109500
tctgagttta aagaagttat ttttgtagta tatattgtgt gtgtgatgta tatgtggacg 109560
ggttgggcat gccaagtatg agtgtgcttg tcagaggaca gtttggtgaa gacatttata 109620
aacaccaggt gggacgtctc acttgcctga cctctgcttt attagagttc aagaggtact 109680
caatgcctag tgagtgcctg tatttaaatg tggaagacac aggtctttgt cccattggga 109740
ctttgtgtcc taaactttga gtttgctgtt ctttagtctg atcctccgta tcccagccag 109800
tccctcatct caaagcctgg acgacgtatc tgagtttcct ttcctgtctt tttaattgca 109860
gtgctgttat gggtcctgcc ctaattccta atttaggaat ttcctaattc ctcccttcgt 109920
attcatttaa tgtaggcata ccccttcac tgcagcagaa gacgcaggta ctcaatgtga 109980
aattcttcat caaagtaact gtgtctctga caattagaca attcttctca gtcaacattt 110040
tgccctatat tttacattga tggttcacaa agttatatgg gttttttgga cagactattt 110100
cagcagtatc agtagccata caacctttaa ttttcaaaag ttttgctgct taaacacaca 110160
aatcatggtt atctacaatc tggggttttc attgtagaat atgtacactg cagttagcat 110220
ggccccatgg tgtgatccag ttcagctctg tgttggagtt ctatttaatc aggaagggaa 110280
aattttctgt aagtctaaga aaacccttgc taatttagaa acaccttttc aaatgttctt 110340
ttctttcctc tgctgacctg gtcttgggct agcctgctgt tttccttcac cgtcatggct 110400
cctgagtagg cgctgaccat ttgtattact cagggacatg cagctatcaa aaggactgtg 110460
cgtggttctc ttacataatt aaggttctct tgtacagtta tctgtagcct gtgtttaggg 110520
gaaattttgg taaatacagc tctgactggt cttagtcctg tgtaagaact atttctcccc 110580
taatgtagtc ccattaggcc actgaattta tggtggcaat ttcgttttac tggttatttc 110640
ttctgaataa ttgtttgaca actgcaaatg aaagaagtga aatagaataa gagggttttt 110700
ttaattgtca tggttacgct taggcagtct gggtgaaaag gcccttcctg gccagtggcc 110760
ctctatgtaa tagtgaagag cctgggactc tgtgtagacc aggctgacct caagctcact 110820
taaatcttct agcctgttcc ccatgagtgc ttacactaag gcttgccctg ccttatccta 110880
gcttctaaat tttatttaat ttttgttaga gacagggttt ctctgtatag ccctggctgt 110940
cctggaccat agaccagact ggtatttaac tcagagattt acccaattct gccttttaag 111000
tgccaggatt aaaggggcat accaccatgc ctagaatctc agacattata atagacagaa 111060
gttctttttt tttggtaaga tttatttatt tattatatgt aagtacacta tagctgtctt 111120

-continued cagacacacc agaagagggc atcagatccc attacagatg gttgtgagcc accatgtggt 111180
tgctgggaat tgaactcagg acttttctct taaccgctga gccatctctc ctgcccctag 111240
acggaagttc ttattataac tgattccatc tgaggatctc agacccactc tgcagcccag 111300
atctgagtca gggcccctgg agccacagga ggaaagccca ggcagaacca ggctggaccc 111360
agagatcaca cactttcaac ctcatatagt ggattgctgg gttattaagc aaatcttaga 111420
acaattacta tattaaaata gccagtgtgg gagtgagaat tatttcgagg aatttctcaa 111480
acctttttgc taacagaaga aaaggtgtgt acacacacac acacacacac acacacacac 111540
acacacacac acacaccctg agcttctcag tgatgatgat cttacactct gcctactgga 111600
agctgttaca ctcttacact ctgcctactg gaagctctta cactctgcct actggaagct 111660
cttacactct tacactctgc ctactggaag ctgttacact cttacactct gcctactgga 111720
agctcttaca ctcttacact ctgcctactg gaagctctta cactcttaca ctctgcctac 111780
tggaagctct tacactctta cactctgcct actggaagct cttacactct tacactctgc 111840
ctactggaag ctcttacact cttacactct gcctgctgga agctcttaca ctcttacact 111900
ctgcctactg gaagctggtc tttcagtgag ggaaagttgg acctggattc ttttctaggt 111960
gatttaaaga aaagaaaaga aaagaaagaa attgttttgc aagattttat tgttgtgttt 112020
caaatgcttc ccctacatgt tgcttttggc acaaaattac aagttgcaac tcagacttct 112080
gaggtgtgtg ccaaccagtc ctcagccact cctaccttca tttaaaagct agaagtgcct 112140
ttttgtgtgt gtgtgtctat tgaaagagtc tctgatttat aaacagttta ggcaggtcac 112200
agattgactt taaaaattta agtcaccaag ataaagatgt tttaataaaa agcagaggta 112260
gtgatataca atgtggaatt tgctttgtaa tgatcagatt ttactgtttt cttaaagacg 112320
gggaagtcgt gacatttgtt tttttcagtg caattagtaa attagtaagt tattaattca 112380
tctctgaggc tttgaaaata aatagataga taaaaataaa cagctccaaa gaagatgtat 112440
ttgggaatta ctattctttt tgtaaacatt accatttatc ttcatgttct aacttagcac 112500
ccacctgtca ttttctggga ctttgatttg gacggttgta atataaccct tgtggcagat 112560
gtcaggaggt gggggaaagg gaagacctgc ctgaaggtcg gtcccagagg agactgctgt 112620
taaatctgtg gtcagggaaa aaaaatgctt tacgccttat aaaatttgcc ttatcaaagg 112680
ggggaagtga tgatgtaaac aggaaactga cagtgaagag cgaaggcacc agcagcagcg 112740
ttggcggcgg cggcagcggc agtagacttg aagatgaacc agacactgct ggggataggg 112800
tccagaggaa gggtagggtt atgtgttcaa agcatgtgct ttgctttgac agactctggc 112860
tgaattttat cctcctttca ggataaagtt tagccatgtc tgtgcctgta gaaaaatgct 112920
agctagtgtt gaaggtttag gacaatttaa agatgggagg gcagtttgag agcacaggct 112980
gcacagggaa tcacacttca aacccaggaa agtagtggct aggaagaggc ccacacggtg 113040
cagtcatgtg accacaaata ctgatttcct ggtgtctatg tgtttgtgta gtctctacaa 113100
cctcctttct tcttcagcct actaaactca tctttctctc atctcccccct cccccctccc 113160
ctctccccac ccccccaccc ccttnnnnnn nnnnnnnnnn nnnnnnnnnn nnnnnnnnnn 113220
nnnnnnnnnn nnnnnnnnnn nnnnnnnnnn nnnnnnnnnn nnnnnnnnnn nnnnnnnnnn 113280
nnnnnnnnnn nnnnnnnnnn nnnnnnnnnn nnnnnnnaag ccttgctgct ttgtgaaggc 113340
gtatctgttt gcagaggtag cagtaaggac ctggccaccc cactgtggct gggtgtccct 113400
gaagctggag cagaggagca ttgccgtgcc tctcttcctg cactgctata gaaagctcta 113460
acttacaggt tctgagaagc agttactcac agtagttctg gaacacacgg ccaagtcctc 113520
cagcagcacc atttaataac ttaccgttct gaaaagtatt tgttccctca aactctttat 113580
tcaggtttta ctttccttat ttttgctgtg ctgcagctta tacctaggcc ttcagacatg 113640
ctatgtaaat acccttctct actcagtcct agtccttacg tataacttga ttttaaatga 113700
ggaaagaacc gctccttctt ccagtatcag gaaggaaagc aaacataatg gcagcttact 113760
tactgcccag ccctcacata agccgcaccc ataggtgcag ggtacccttt ggggattctc 113820
agctgaacca gtgccctctg ccatgcttca tgctgggctt ttcttgctcc catttctttg 113880
attttattct tttctcttag gcagaacaca tggcagatct gcagtcaggt gagaagctgt 113940
gtgtatttgg aagagctcct ccatgctttc aaagttttaa aagtattttc atgtcttgtt 114000
ttttttaatt agacaaaata tattccaaca tatatttttc ttttattgaa gatgacaagc 114060
ataaatttac agaattaggc tcttagagta cattcattag agtttcagtt gataatttaa 114120
tgtgctttga aatctcacag caattctcta ttttcaataa atatgaggta ggtaattcag 114180
cattaagtaa ttgctcacag gtatatgttc aagataaacg agtgcaagca taatttcatg 114240
ggctttttta ttaactctgg gagcatgttt gtcagagcag ataccattag tgtttgttga 114300
ttgggcagat agtaaaatag gcttgaatat gtatcataaa atcagtatag gtctcctcac 114360
aagttttgat tttgttgctt taaaaaagat tcagagaatt aggttggcca aagaaggaag 114420
actttcttag ttttagtgtt gttttgtttt agaatattgt ccatttgttt agcacagaca 114480
gggacattct gaacataatc tcgagtcagt taggatatga catccaccaa ggggtcctgt 114540
gtcccacggc taccagtgaa gggagcgaca ggcctgtagt cctgttgtgt gcagtgcttc 114600
actcatcttt gttttagagc ggggaagcac taggcatttc tgtaccaaca ctgagcgccc 114660
gggcctggga gatgactctg ctgtcgggtg atcatggaca ctgctgggac cctagtctag 114720
gttctgactt tctgcagctc cttaaacaaa tctgctgttt ccctaattgc ttttctaaat 114780
aaaatgtttt tatgcattgc tgttcataaa aatgataggt attgaatctg tcagtcagtg 114840
attgagtttc agtgaatatc tgagcatttt tttatctgag aaactataat atccataagc 114900
tattacatgc caaattacag tttttatata gacacatgat ggaacctagc ttaatttgcc 114960
attaaattgg aatgtaagtg cattatttta tatatttgtt aatattaatt attttaattt 115020
taagatagag tcttgataaa tagtacagac cggccactcc cttcctcctt ctcccaactg 115080
ttaggttaat actgtgttct cccaagcctg gggtgtggtt acaagtgttt gctgccgtgc 115140
ctgatgggaa tctttgaata ttaacattta agctgacacc ataactttat tcaatatttt 115200
atcatgtttc tattttggtt tttcaagaca gggtttctct gtatagcccg ggctgcccta 115260
gaactcattc tgtagaccat gctggactcg aactcagaaa tccgcctgcc tctgcctccc 115320
aagtgctggg attaaaggcg tgcgccaccc ggcttttttt ggtcgtgttt cttagtgcag 115380
tgctccagca ttgttttggt gattgacatg gctgtgtgat tgctgtcgac catctatctg 115440
cattccatga ttgcagatct atcatttaaa ccaagcatgt gcacaccgtg aacaaaatgg 115500
caatggcgag gttgaagtta tgagaaagtt ctgccaggtt tactttaaac tataactgcc 115560
acttagaata ttatggcagt gttaaaagtt attttgccca gcagtcatga ggcagcggca 115620
ataatatgag ttctagtctt gattgggcca catagcagta cttcactact gtcagtttgt 115680
ctgcctgtcc tagctgcttt cctgtcagtc tgcctgactg tcttctgtct atctacttct 115740
ctccttcctc tgctcacacc tttgtctttc tctttgtttc tctctctcac acacacacat 115800
ttagacaaaa ggtcaaacac tgaaataagg aaatattttt attatagtgt tacagggaaa 115860

-continued tggtaggagt caattttata aattgatttt aaaattacct ttttgcctta aaattttcag 115920
aagtgaatat atcaacttaa atactatgtt cctacagtaa aaatatgcaa gctcggggct 115980
ggagagatgg ctcagcactt aagagcatta attgctcttc cgaaggtcct cagttcaaat 116040
tctattaacc acatagtggc tcacaaccat ccacaatgag atatgacgcc ctcttctggt 116100
gtgtctgaag acagctacag tgtacttgca tataataaat aaatcttttt taaaaatatg 116160
caagctcggg gcagtgggtg ggtaggggag tggggggtg ggtatggggg acttttggga 116220
tagcattgga aatgtaaatg aggaaaatac ctaataaaaa attattaaaa aaatatgcaa 116280
gctctttttc tttcttttct gtattttcct tgtacatttt tatatggaaa tgataaagct 116340
acccgggcgt ggtggccgtt cactgtggag gctgaggtag gaggatcata agtttcagac 116400
cagctcagac tcccaagtga gactctgtct cacatttaca aagaagacat tggacctgag 116460
gactgctgag gtggttcaac ccactaacat tcttgccatg caagcatact gtgtcacaga 116520
gaactatagt gagaggaagg acagatagtc ggtcatagtg tacctagtag aagctcttgt 116580
atctaactga acccacagat acacagtgca caaatctgtg ctgccagtga ccagattgga 116640
ggtcattaaa tgggtgtaaa aggccaaaga atagcaagaa aaatagagtg tgtacggcct 116700
gtgtggtagt tcagcaggta gtgctgcttg ctgatgtgtg cctatctgag gtccacatca 116760
gggcccacat agtgggagca gagaactata agttgtccct gacacatgta cacacacgca 116820
tgcacacaca ttatttaagt gtaaaagaga gtgtaaggca tattgggagg tcttaaacag 116880
acttacatgg tctattttat gttagctttt gtggggtaaa actcaaggag acaattgtgg 116940
gatccccagg tcattgcagt gcgtcaggga tgaggtgaag atctgtggcc ctggaggtcc 117000
actgcactgc tgttgttttt aaaagatttg tttattgtat ataagtacac tgtagctgtc 117060
ttcggacact ccagaagagg gcgtcagatc tcattgtgga tggttgtgag ccaccatgtg 117120
gttgctcagc tccggacctt cggaagagca gtcagtgctc ttacccactg agccatctct 117180
ccagtcctct gcactagttt tgttttgttt taaatactta ctctaattag caattttatt 117240
aacttttcaa atttttcctt taaaatttta aaacattgtg tatttatata tcagatatat 117300
ttgtatgtgt ttgctggtgg tgtgtgtacg tgtctgtctg tctgtcttac tgtctcagag 117360
gggatggctg actctaccac atgggtcctt cagatagtct ggcctgggaa caagtacatt 117420
tacctgctga gccaccccac cagcctctac tctgtgtgtt actcatagaa tagagacatt 117480
ttagaagtag gattattgaa tgacattcag agaagaggcg gcccaacagt taaatgcact 117540
tgctgtcttg cagaggacct actgttcaca atcatttgtg attccagttt tagtggcctc 117600
tgtgggtgtt gtggtcaaca tggtgcttat atatacttac atgtaggtag ataaaatact 117660
caaacacgga aaataaacag tctatttttt aaataaacag tcattttttt atttctgtag 117720
tcactctgtt ttcattaggc aaaagcagcg tccctgctgg ttgccaagga ggaaatgagt 117780
cttcgtaagc aggccttgta gtaaatgagg gtcttggcat cttttgagaa cagccttgta 117840
aatgtctgtt gggtaataaa caagttctac gcagtcttct tgtatagcaa caaacatctc 117900
ttcactcatt ccacataaca gccacaaaga tcctgtcaga agatggagtg tttttcatcc 117960
tattggaatg gatcatggtc agtgatggcc catgttggag ccccagctcc acacagacct 118020
tctgactcca agttcactgt tcttctgttc agttatatat aacacaagaa aatgtgttta 118080
ttcaaaaacg ccaaggataa actttaaact gtctattacc atatgcattt attatacatt 118140
taagcagagg acatttattg aaccccaacg acttgtaaaa tagtgttgaa gaaatttatg 118200
atatgcattt aaaatcaaca tacacagcaa ggagaaaaga aaaggagccc ttagcttcat 118260
ttgtgcacct gtgagttatg tcttgtgctg gcatccagca aatgctcaga gagagaatga 118320
gtaagctgga gtttgggtga ggtggttaag ggggccttta cataaaaaga aggagacccg 118380
gatttagcaa gacagtgaaa ctgcaatctc agaggaaggc actacgagag agagacgtaa 118440
catctgaagc aagaaagagt gtgaccaaag gagggggagc gagcagagcc tacacaggac 118500
tttgagtaaa gcagcaagac tagaaggagc catttttttac agagttgaca agctgtggct 118560
ttgagctaag ctttggggcc ttttaatttg ggataaagga gttttctaca gcttgtaaat 118620
accatcaaat atttaaatcc caagagttga caagtgtcat tacccaagtg gtattttatg 118680
aagattactt tgctcctggt ttattcagga tgcagttgag aaatggaaag ggaacaagca 118740
gagaaaggga gactggcgaa aggcaatgtg tgggcttaga gcagtagagg tggccttcta 118800
aaaggaccgc gtctctggca acagggagaa ggcttgctgg agcctctcac tgattagttt 118860
ggagaatgga aatttaatgt attgtattgt ataactatgt aagtataaaa acagtaggag 118920
tcatagtgta ttaatatata cttgcttata tgtacacatc tataaagaaa acacagacag 118980
gagccaccgt cgtccgttgt ttggatcatg tagtgctgag gtggataact ctccctgcct 119040
gcatttggtg gataactctc cctgcctgca tttggtggtt cctttttttca cctcctttga 119100
catcacctct ccaaatctgc cttcaaacac catcactgag tgtcaggact ttaacttgtg 119160
caggcaggtt ggtggtcctg aaacttacag taatgttttt cactctcccg ttcggtggat 119220
tactcgtaca attctctttt ctttttatca gagacaattg ccatagtgaa ttcattgttc 119280
agtgtaccaa gatcttaaag tgttccaccc actgtgtgcc cagttattga caccatttga 119340
tttactttaa ggtgtcactt gctgggctgt tttgtaactt gctttccccc taatacttct 119400
caaggtaatg gccacgtacg tgtagaggta ggctggtgct ctgcggcctc cattgtgtga 119460
atgcattctt catttggctt tgctccttgt cagggttggt cctctgcatc ttgacaaagg 119520
gcctcattct gcctgctcct tgaacaccta tgaggatttc cttggccatc acctagagaa 119580
gaacactccg gggataggct acagaaattt tccactgtaa ccggaagtgc aggtttgcat 119640
ttggtattta agacattttt atagggactt ggcatgggaa gaatgggaaa caatatcccc 119700
ttgatgcttt acagtggatt ttggatgctg ctgagactgt ataggggcta tttttatttc 119760
ttttttggaa ctgttaacac aatttgcgta ctttttagtg tgttggcttt tctggatgtt 119820
gatacatttt agatgtgtca ggttggagtt tttaagcttt ggttaaactc tgtacctatt 119880
cttctgattt ttctaactat tccaacatga atctatggag ctgcaggaaa aatgacccta 119940
atcaactgta tctttttttt tttttttttt tttttggtt ttttcgcaga cagggtttcc 120000
ctatagccct ggctgtcctg gaactcactt tgtagaccag gctggccttg aactcagaaa 120060
tccgcctgcc tctgcctccc gaatgctggg attaaaggta tgcgccacca cgcccggcta 120120
tcaactgtat cttgatagaa agttgaatgg aatgtaaata tctgagggga atcccagatt 120180
cagtctcctc aaaggaaata agggttttcc tcaccaggac cttgacgtgc tgccattact 120240
aaaaacttct tggaggccat agacaatcgt ggattagaag attctaactg ggcacttcct 120300
gctcctaccc acctagactt gcctgcctct gttgacatgg ctgcttgaat aggcatgagg 120360
tttagcaaaa tgcctgtctg gagtctgcca atgcatgtgt gatagctgtg agtctggttg 120420
tttagttata actaagagga taccttgcag ccatgttgcc agttaagatt gtcttagaaa 120480
tggctgtgag attgcttcga aggcctggga gatatatgag tcaccatagg cctgggagat 120540
acatgagtca ccaaaggcct ggggggatag gcaggttctt tgctatggtt tttctcgtcn 120600

-continued

```
nnnnnnnnnn nnnnnnnnnn nnnnnnnnnn nnnnnnnnnn nnnnnnnnnn nnnnnnnnnn 120660
nnnnnnnnnn nnnnnnnnnn nnnnnnnnnn nnnnnnnnng agccgggcgc ggggcgcagc 120720
ctttagtccc agcactcggg cactcgggac gcagaggcag gcgggtttct gagttccagg 120780
acagccaagg ctacacagag aaaccctgtc tcaaaacaaa aacaaaaaga gttagcttct 120840
gggctggagg tgtcaccaga gacagagccc ttcctcatga gtaaggccca agcttctgtc 120900
accagcaggg caaacatgta aacacacacc tacctcccag tatgttggat agttcaacaa 120960
aatgttcata actttcttag agtaaattta taatacagtt tctatatcct gataaacaat 121020
cgcagtcctc agttgaggag gaggaaagtc tcctggtttg taatgtatgc ctctggcatt 121080
ccccggccat cctatgagta ttttgcttgc ttttgatctc agaggttgag gacttgggcc 121140
agtgccgctt gtttgattgc tgttggaatc tatagttctc tctcacttgg atttccagcc 121200
cagctcatca ctggctttct cctttttcat gggatcatac ttttctctga tttgacatga 121260
atatggtatt tttatatgtg gatcaattta ggagcatata cttatttggt gatatataag 121320
ggtatactat ttactatatc atatactaac gtaaatataa gtatattttt tatcttgttg 121380
taaagttaac ccctccccat ttaaaatcca ttgtgacata cattcagtgt cattaaatat 121440
attaatgttg ctgtatagct tctatctccg gccatctcta gagtttatct ctcagagctc 121500
caactttcaa gtaggtaagg tctcttccct tttctggcca ctgtttgctc gtgcctaggt 121560
acttatcttt cacccctcct agaccagtgc aaagcatgtc cccatgtggc aggaactcaa 121620
gggctcattg aggctgtccc tgctgccctg tgtctgaagc tgtcaccacc cttgacgggt 121680
tctctctcca tatgacagtg ctgttcgttc tgtatgggat gtgcttgatg atgaaggaat 121740
agtccctttc tctcctgcca tgctcctccc ttgatgataa tggactggac ctctgaacct 121800
gtaagccagt cccaattaaa tactgtcttt tgtaagagtt gccttggcca tggtgtctgt 121860
tcaaaaacta agatgccatt tttagataga aatctcattt atacccgtcc ccctcccccc 121920
ctccccctcc cttcccttcc tctctcctgt gtgtagatgt gagtgtgggt atgcctgtgt 121980
gtcatcctgt gtgtagatgt gagtgtgggt atgcctgtgt gtcatcctgt gtgtagatgt 122040
gagtgtgggt atgcctgtgt gtcatcctgg gtgtagatgt gagtgtgggt atgcctgtgt 122100
atcatcctgg gtgtagatgt gagtgtgggt atgcctgtgt gtcagttctg ggactacaca 122160
cccagggctt tatggctgat aaaccagtgc catactgaat atcatcctct ggctgcagat 122220
ctgcttctta aagaatggat tctgtctcaa aagaaacgga agtattggtt atattcttaa 122280
acaaatagac aacctttagt atctacaaaa aggatataga ttctatcgtg ctgatttgca 122340
gattcttagt taactgtgtg attgtgcttg tcagatttat ttaacactgg cagttatgct 122400
attgatgtat ttactacaat gttgactgta tgggaagaga tggccctggg ttttcattca 122460
actctgccct gccgagtcgc agtcaccact gacttgagaa tcccacttgc agtgagagca 122520
gctatacgga gagcagacat actcagcccc agcactggtg agagctgggg gagggctgag 122580
gcagagggtt atgagattcc aacagtagct gcatagctgc acagtaaaat gtctcaaaga 122640
acccaaatca ccttgcctgt tgtggccttc tgagcagttt ccatgtctct gcggtttcta 122700
agctactgca tactggccgg catttggttt tcttatagat tgctttggtg agtgaggttc 122760
tagcccctca tggtaactga gacattgggt ttaaggggag gcgtccgagg aggagttttc 122820
tgtctacttg tcatcccccct gtctttgact cgtgtgtaac agcaggtcag gctcctctct 122880
tctcgttggt gtgtttttct gtgtgtgggg cctctcagct gtgaggcttt gaagcacgtt 122940
tgtactgcag tgagcagggc aagggcccag ctctgtaatg gcctcttact cagtcattgc 123000
```

ttcactgtgt ttctcataat ctgaagtttg ttgtcagtag ctaagactaa attctattcc 123060
tagttttgta tatttaaact atagcagaat ttatgtacaa aatctctata taattatttt 123120
tttcatttaa gaggttacag atagcccctt tctctcattt cttttacaat aggtaatcat 123180
tccttaagaa aacttgaaga ctctgtaata aaatgctgtg actgctgtca ggtttgagtc 123240
atatctcttg tgttgctgtc agaatacaaa gacgaataaa aacaagagac tctgacatca 123300
gactcaccct cactgtgctg gtcacggcca tgtctgcagt ctaccgaggg taagatacat 123360
ccgtagataa tagcaggctg atacagagaa agccacagtt tttctccttg gctgctgagg 123420
cctgaggaaa gggctgtgat ttagagagaa ctcctcagat ggtgggcatg gagatgataa 123480
gccttagaaa gactgcgggg taagctctta atcccaccag gcgagagtag gagtactacc 123540
acaatgtcga accaaatttg aagcaagctt taaacaaata ctgaccagga tgatggcccc 123600
tggcaaggtc tactcctggg ttcctagaaa atgttgatga gtcacatttt gcagaggctt 123660
aaaaacccat aaggccgtgt tttcccacca ggtccaactg gggggcaagca tgtatcctga 123720 catacttcct gcttgtgtat ctcctgcgtc catccaatca ggggcaagca tacatcttac 123780
gtacatgtga tcaagcacat tgacttcaat tggctcaaac agacttgttt agggaagtca 123840
aaacatgggg cttgttatcc tccctaaaca atagcctcta gcatttgagg aagtatctgc 123900
ccttgagcaa ggggcttaca agttagagaa atgttatttt atggaactct taggcacagt 123960
aattaagact ttggctctca cagaggtcat tatagtggaa gcagatagaa agcatgaaca 124020
gttagtgggc cagaccaggc tgatctcaga caacacagca cagggactgt ttgatggatc 124080
tggctggaaa acgaagagtg cacagcttcc tcagtgcagc ccctgtttgc tttgacagtg 124140
agaaaaagca cttgcgctcc tgcagtgtgt ggtgaactgc agggaaatta gcactgtatc 124200
ctctggccat ttctgtcctc ggttacactt gaaggatatg agacaactac aagttaaacc 124260
aaagtaacag cactggacgt gctggtccac acagaggccc aggaggggga agactgaaga 124320
tagcactgcg ttcagcgaga agaccctgct gctgtgggag gtggctttgt gagaagcatt 124380
gaagagaagg aaatctggga catccgagga gcaacagtct taaacagatc caaagttctg 124440
gaagtgggta ggcttcacag ttgaaggagg aaagggtttg taagaaattg tcagttgata 124500
gagtggggag cagcaggcac cagaaggttc catagacatg taaggagatc tattttggac 124560
acttccagtg agggagagaa atgtgggtga gaggctggaa gtgggcactg gaacttacgg 124620
tgatacccga agctacaaat gtaggggcct catttgccta gacactatca ctgaaacgtc 124680
agccatctgc gtgctgattt caaggagtgg ctttagagca ggaagaattg tgaggctcag 124740
ggtcacagag gcaaaggtga gggaggagag agcctgaaga caggctacag ttctgaccga 124800
gctggcttgg cgtgacttgg agccctgctc actctgtggt tctccaggag ccagtagaat 124860
aaattggctg ggtgagatgg gtgtgctgtg gctagaacca tgctgctggt ctggacggga 124920
gaaggcgtgc atgcacacac acacacacac acacattctc tctctctctc tctctcacac 124980
acacacacac acacacacac actctctctc acacacacac atactctctc tctcacacac 125040
acacacacac tctctctctc acacacacac actctctcac acacacacac actctcagac 125100
acacacacac actctcacac acacacactc tctctctcac acacagacac acacacacac 125160
tctctctcac acacacactc tctcacacac agacacacac acacactctc tctcacacac 125220
acacacactc agctgccttt tctgctggtg ttgaagcttg tgttcaagca tcttactatc 125280
tctagatggt catgtcagag ggccaagact tcactgtgtg caaatcctct gcagtgcaca 125340
catgcagcaa gtcttgattg atcaatacat ggaaatgatg gtatctgcac atctgtcctt 125400
tgtcactcag tgccctccaa acataatctg tagagtccag tcaaccttta taaggaagac 125460
ccgagtttgg ggttcgcttg gtgtgtgttt aacttctgtt cttgctagcc tgatcctaac 125520
tgaacttcca acatcttcaa agccccgttt tcccccgctg cagcatagaa gagagcagtc 125580
atgttgtctt ggctgttgag aggattgaag aaggacagtg gcagagcctg tgctcactcc 125640
agtctcactg gctgtgaagt gttgaatagg cctcactcac tgaggtttag ttttgtcatc 125700
tctagaattc taggggatgc ctgagctcac tttggtttca gaggaagtac cagccaccat 125760
atgcacaggg cctggctgct ttcctcttcc atgccaggca ggagtgcaag ccaccgagat 125820
ctctgtgcag cgtataagag cagttctgga tttgaaccta cgcagtgagg cttggtaatg 125880
acttcacttc tctgtaaact gggaggagtg ttgctatcca cttcacgtgg tcctatgaga 125940
acaatagagc aacacattgt gcactgttag caccctgtgt gccccactcc cacccctcac 126000
tcccgctagt tgtaacctaa tgtaaccatt atgagggaca agttaatctg taaagaagga 126060
ggcgcttttc taatgagatt ggccatgtcc aaagggggaa atgtaattca accacaataa 126120
tgctctttgg tggttcagca tgatgggtgt tgctgtggcc gggtcttcca ggtacaacag 126180
aggaaagact ccatctggcc tctgggctgg ccagtgtcct cctcagcaat ggcagtctgc 126240
agtctgactc cacacccagt ctccttgtcc tgccagctgc tctctaggaa gtgttgggaa 126300
tgtggagcat aaagattcca gagaggaata atgctgagtg gacaggtagc ctggaacagt 126360
ccaatctggt accttccctg actgggaaag gctggcttta ctagcaaacc acttttcaaa 126420
cagaactcat gccttaatcc taccaaggac aaggagcgct ggtggcttat gggaggagtg 126480
gctaaagcag taagaaaagg cagctactgc tgtctgcacg ttcaccctgc atccctgtgg 126540
caacctgcat ccctgcagca agctacccag actgtagtat cctggaggac cccccccccc 126600
actccagctc catttgatca cagagaccac ctggaatgct agcaacctag agggaagtga 126660
gaaaccacag acaggttctg ggaatgacct agcagctgag tcctctgtgg aagggagtgg 126720
tgagacttaa gcgtacagca gaaggattcc ctggggcagc acagccctga catgcaaagt 126780
cttgttttgt gtctttgaat gaatctattt tcccatgtta atctattcag ctggcttgta 126840
gaaaacctac atgcatttgt ttatttgtgg ctcacttaag aaaactctga cttttgagat 126900
aaatttgttc tctgggcttt tcatgatttt ctgttgctta gttggcatag tgttttgatc 126960
tctttctaga aagttcagca gaaaatacaa attttgagca atttcactta tgttttattt 127020
cttggggtgg gtgtatgtgt ggccttcaag tatgtgtatg tatgcatcat gtgtgtgctt 127080
gtgcccttga aggtcaccag agggcatcat gtatcctgag ttggagtact aatacctgct 127140
gctgagccgc tctggatgct ggggacctag gccctctgga agagcatcac cacctcttac 127200
ctcctcagcc atctctcctg cccattattt cagtagtgac cagtaggtta gcatcaatca 127260
ctagaaactt gggtgccggc tgtcatcgac ttttgtacag tgtgttgcct tttggcctct 127320
cagatagaac attgggggtt tctaatcact ctgaccacta agtcccaggg gatttcttct 127380
gttttgtttt ggtttggttt taggactccc tgtttttgta gctggagaga aacatttcta 127440
ctgaggcagt agtgttgaaa actaatgaag ctttaagaga acattgaaga gattattaaa 127500
tataaggccc ctgagcttca ggttctcacc atttttgagg tacagctttg aggcattctg 127560
tacacgtccc ctgccatgca gccgtgtcag gtgtctgggg tctgtgtcct ccccagctgt 127620
gagtgcatcg tgacatcccc agtcttctct ccttcgctgt gccagccagt gctctagttt 127680
ctgccattcc aggcccctca tgcccaagga atgacacggg tcttggggat tttccccatt 127740
ggcttatttc acttagcgca gtgtctttaa aggtaagtct ccattctgta ggtgactctt 127800
acatctgctc gcactctgcc ctactctctg ctgtgtttaa cctcccatcc cactcagtgc 127860
tggcctagtg tcatttgaca tagcagcagt gcagaaggga gccagcttct agatcctcat 127920
ggtcacattt tggcctctgg tcttttgata gtcattctca ggggcatgcg ctggtgtctc 127980
actttgcttc tggcttgcat ttctgtggtg attagtgatg gccaaggaga aatgtttgat 128040
caggaccctt tctcatcaat cactatagca gcacctttgt cctaatcatt tgatagatag 128100
cgtatgtgta taaacatgat tctgtgcccg attctcccct gcattactgc tgaggcctcc 128160
tgactcgcca taaccgaatt tcattttgca gataatctct ctgctatggc ctttgtggag 128220
ttttgtgggt cttgttttct gtttgtcctg gagaattggc tcttgcactg tgtgctgggc 128280
tccctgagct gggaggaagg gtttctctgc tccacagatg gcatttttct gctttgttgt 128340
gggtgttgct gggattgcag ctattcccac cttctgccta acaaagataa atagtaaata 128400
ttctagagct atttctagac aaaggagaaa gtgaggagtg tgaagggaag aagcccacgt 128460
tctcaaaaag tattatcaaa tggtgcttga agcagtcgga atcagctcag ctaataaacc 128520
acgctctgtc cactgagaga cttgcgggtc tagagacagc gcaaggcaca tccttcttag 128580
cacccctcgt tcggagtctt gctggttctt gcacaagtta ggaaaagatg aataattatc 128640
tgactctgaa taaatttagt tctcacataa agtaccttct ggtcttttat tctgtttgtg 128700
tggccaacta gtgaacaaag gaaaagtgat ctttgattaa acgggttgtc agtgaaagac 128760
ctaaggagga cgaggatgta tctctgtgga tgagagtgtt ggcctaacat gttcatagca 128820
tccctttca ttggatggga agatcaagtg tcatcccagt gttttgcact ttacgttctg 128880
tgtggatgaa gttaatacac agaacccaag tgtgaagagc agatcctgag ccctgcattt 128940
gtcatgtaca catatacaca tgtatgtata tgtatacatg attaattaga atggtttaca 129000
ggctgtggtc cagctaatcc agcaatgtct gactgtgaat ggaaagtcca agaacgcagt 129060
agctgctcag tccacaaggc tggatagctc agctgatctt cagtgtacac tggaatccca 129120
aagtagtcaa ctccagtgcc agagaaggaa tggacgtgct agcaaggtga gagcacacag 129180
gcaaagaaca aaagctcctt ccttctctcc ttagacagca gagacctcag cctcctaact 129240
aactctgtgg cccatgaata cagcagtgac ctcagccttc ctaactctgg gacccatgaa 129300
tacactcctg caggtctggg agccaaccat agaaatattt gattgctact tcatagctgt 129360
aattttgcta ttgttataaa tcattatgta aatacttgat atgcagggta tctgatacgc 129420
aaccttcgaa aggggtcaaa cccacgcgtt gagaatcacc tttgtatggg cttctagcag 129480
gtgtattcta tattagatct ggattcgtgg tatatcttcc tacctcaaac taagcagaaa 129540
tccctctcag ccatgtcctc tattttgggg ttttagttaa ttttagatat agccatgttg 129600
acaaccaaga acagccatca cattccctga atgaccaagg attcggggga acacaggtca 129660
aagggatgtg gcaaccttgt ctctaccacg tcgattcttt atagctcaaa gactaggtat 129720
agactagtct cacctttgct tactttgtga gttctaagta acatttttgg aatattggtt 129780
tttttagtt aatatataaa tagtttaaaa agtaaatact ggaaaagtct tggctggacc 129840
tggaactctc tgggcctggg gatttgaaat gagtgatggc ggctgtggtg ctcatctcca 129900
ctttagtcag acagtttaca gttctggtca gtcagagagc ctcgcaggca tctcagaaag 129960
tgatgagcgt tccctcatca gccctcggag ggctcagcta atccgtgaag cacactcctt 130020
tgacatagga tcatttctga acctcaggca ttcttgaaag cctatggtat aggtttaata 130080

-continued tttcctacac cactaacatt tgtattaatt ttggctacca ggtcacttaa tttcaatttt 130140
agtcctataa ttttgaagaa tagattcatc taaaaggaag tttagattgt ttgcagctgc 130200
accagtggcg agcctggggc tgtggtttga agcttctgaa atcttaggtg aggggcagaa 130260
gctggactgg aagtgcatcg tgcaccctgt gcctgacttc aaaagtggga cttggcagtg 130320
ttgtgtttag agaaagtcgc agttcgcagc ccttctcctc agtcctctcc tgcagtggga 130380
tggactgaga cattcatgca ctgctcttta taggagcgac tgctgaaaat aacccgacaa 130440
gctagcagtc tctactcaga atactgttgg gtcttctata aggctcattt tgctctggta 130500
gaaagaatgc agtccctagt gagtgttcat agggtgataa cccagcagca gaggctgtca 130560
gaggtgagcg tctcacttgc tctctgaagg aaggatgcta gaggctcaag tggctttgtg 130620
tacttccaca tctgctatgt acaggaattc aaatgacatt cttattgcat ttcttacaat 130680
tagttgtgaa actcgttatt gcattttaaa atagatttaa ccagtagtta taccatgata 130740
actactgtaa ctagtagtta taccatgatg atttaacgat aatgatggac gaatgatggt 130800
catgagatta tgagtacaca ctgtttgtcc atccacattc tacaaagtgt tgttcatgtc 130860
accttcagag cttacctcat tcctagtcac acaaacgtgt gctcacagtt gctatggagt 130920
atttctaggt tagaactttt taactttggg atagaataaa atcaggggtc tgttcttgtt 130980
ctgtgtttgt gttttgtctc tgtgacaagg tctctgttta tgttcctggg tgtcctggaa 131040
ttccctctat tccagactaa ccttgcactc acagtgccct gcctgccttg gtctctgcac 131100
tactcccggc accagggatg aaaggtgtgc acactatgcc cagtttgggt tttggggttt 131160
tttgacatat atatcacaga agtccattaa gaagtcattg actttgtttt gtgtgcatag 131220
agcttaggat ataaagacca tagattccca gctacaattg tccaattaac tttacatatg 131280
cacttttatt tttttcttat aattcttatt attttcaaat attatttctc tcttcctttt 131340
gttaaatcag aacattcctt ttgttgaatc tttttttttt aattagttag ggttctctcc 131400
tctctaatga ctgctgttta tttcaagttg acataaaacc agggagcaca cacgtcagcc 131460
taagaaacag cagtagctgc cattgaggtg tcttactaca tcaggccgga gctacacgtt 131520
gtacctgtaa cccacagatt tatagcagtc ccaattgtta ccctttcata taggacacat 131580
gagactcaga gaattgcatg ttgcttgggc atctctgtat tcagcatgtg aacgcagtgc 131640
tctttcctgc ctgtaagtgg gcttcgtcaa tggattttcc ctgtcaggcg tgatggcgca 131700
tgccttagca cctgtaaggc agaggcagga tgatctctga gttcaaagac agccgagttt 131760
agaaagggag accaagacag ccagggctac ccagagaaac cctgtcttga taaaatccaa 131820
aacaaaacaa ataaggaaac caaaaacaaa acaaaacaga aaacnnnnnn nnnnnnnnnn 131880
nnnnnnnnnn nnnnnnnnnn nnnnnnnnnn nnnnnnnnnn nnnnnnnnnn nnnnnnnnnn 131940
nnnnnnnnnn nnnnnnnnnn nnnnatttta cagaataaat actaggtcac aaatcacttt 132000
acagaatcgg tgttattcaa aactaagtaa aaaagttaca tactttagta cagaaaatcc 132060
agaaatttga cagaaactac ttaacaaaat gcctcctatc aaacacaact cctcccaggt 132120
ggggtgcagc tcaaggacgg gtcagaggtg tgattggcgc tccttgatgc ctgtgctccc 132180
agatgctctg ctcttaggag cctgattctc agataaacta gcaaagaagc ttagacccac 132240
ctgtaacccc caccttaaag ctgtggaacc acatgacata aactgatgaa tatagtaaag 132300
tcagccctaa ggtcagtgct gaggtatata tcattcagga tatgtaccca agagggagga 132360
gcgtgtctgt gaaccttttt agagttcttt gtatgacaag cttttccttg aaaatggttt 132420
gagtgcccct ctataggagt ttgggcaaac aggctgtaat atactcacat ttataggata 132480
ctcgccaatg aacaggagca caatatatgc aggaccttga atgagttgta gaaactcaag 132540
agtaattacc atgcatttgt gtttgaagtt ccacaaaaag cacaactggt ctgtagtaaa 132600
agaacatcag atgttagaac tgtctgcaga tgaggtaagg agccccttgc agcatgcgcc 132660
tgagacctgt acagggagaa agatttctag cttcatagag cctgagtcag ccacaccttt 132720
gttggtctcc actcctgatc tccgtgtaat gagctctgaa tcctatatat tgcaccgaat 132780
agaaattata tctcggttta caaactacag cagcattttg ctgagttgtt gttttattcc 132840
ttcctcatca agctcttgag ttaggacctg aacctaagct ctgtattgcc accagttata 132900
cattaccacc attatagatg ttgacaccag aaacaacttc acagattttc tcatttgatt 132960
cttttataaa cactgctgcc ttgatgaaga aaaaaagttt aaaattgcta atgataaaat 133020
ctgttgtagc cactgtctgc atccaagagt gaactcagat gattttaccg gtgtgtgcat 133080
gccagcagaa accatggcag agggatagac ttgctgacag cgatccatct tgcagtgtaa 133140
gcacagagtc tggtgaagac attctactga gatgtgtttg ataggaggca ttttgttaag 133200
tagtttctgt caaatctcag gattttctgt actaaagtat gtaacttttt tacttagttt 133260
tgaataacac cgattctgta aagtgatttg cgacctagta tttattctgt aaaatgtccg 133320
tacatgaagg gacagatatc gcacgggttc acttaccaga ggtgtctgag caagctggac 133380
tgctgggtgc tagggctggg aaacggggaa gcagggagct ttgggggacc tgaagtgtta 133440
gttttgtaaa atgcagtgtt ctacacatca gttgtgcaac agtctgaaaa cactgggcag 133500
cactgaactt aagatagtta acacactgag tctgatggca catggcttta atccatacta 133560
agtgctcaac aaactaaacc attattatac cccataaata catacaaatg tatgtcaaat 133620
aaataagagg cagagaaatg gctcagcaat taagaactgc atagtctttc tgaagacctg 133680
agttcagttc ctagagccct tgtgaaatca ctcacaacta cctactttag caccaagaga 133740
tctgatacat acacatggtc actctcatga acacacacac acttaaaaat acatttaaaa 133800
ctttttaaag agataaaagt gtaaaaacaa caacaacaaa aagaccttct ctgcagacct 133860
tgtagccaat tcctgtcacc caggtcagcc acttgtgctc attggcattg gcaagtctct 133920
ttgaagccat ttgcagacaa cgctttaaag ataacagacc gacctgctct gagcagcaga 133980
gagaaaggat tcttgttgcc cagactcatc ctaggagtca gtgctaggtg atgatgtcag 134040
gctctgtgat gaccctggca gcagctcctt ctcagagaaa atgaggatga agacttcatc 134100
ctgaagcaga tcctggtatc ttatccttgg caaatgctga actcaacatg ttctaggctt 134160
tccattggca cagccaaacc tgagtagctg atggcaagca agctgtggtt ttggggaagg 134220
ggaaagttag cgtgaacatg gtggaagcca tggggccttt tgagtttatg aacagcaagg 134280
tgagcaagat caccatgacg atcttagcca ccaggccagt ccttcagaga atcccaggca 134340
cctactgttc tcactgttcc tttagaaaac acaagtactt gatgccctca ggcacttcct 134400
gttttcctta accctccagg tctagctgga ctgtagttaa gtttatagct acacataaaa 134460
ctaaatgaag aaaaagaaag aaacaccgcc tttaatagag gaccagcagt tagcagaccc 134520
tgttgctgct gctgctgtta ttgttctcct ccctcttccc ccttcttccc tcctcctccc 134580
ccctcctcct tccttcttgg tcaaaaatag atcaaattaa ctaatgaagg gaactttctg 134640
tgttcttaat attgtgttag ccacggaagt acttttcttc ttggagtaac ttataaatta 134700
ctgaggataa ttactgtgct tatgagtatt ttgctaaaac aaggaatttg tttccagcat 134760
gtgagtagct attaaatctc caaagtgctc atcatgcgag attcgacagc tttatgtcac 134820

-continued

```
taggggcaaa gctctagaga ggagcaggaa ggggtgtgca tgatttcttc aaactgtccc 134880
gtcttctctg ccgaatattg tggttcctta agaagacttc agaatgctac atctagagaa 134940
gagaaaacct gaatcaaaat gcttgctctg agcagttatt tttagtaaca aatctagaaa 135000
ccatagaaga tatgtgagtg tctgccggta tatcatgcat gcacatagaa gatatatgag 135060
tgtctgccgg tatatcatgc atgcacatgt gtgttttcaa cagtgagatc ctgagttaca 135120
gactgtgtgt atggggttgg ggggaggtag ggctgtgggg gttgggggtg tgggcaagag 135180
atgacgtctg tctcttaata gcaagtgggg cagtggcttg ctcagtctgt tatcataaag 135240
ctctgttaat gtagcttttg caccatgtga ctgcaggaaa agctattatc tcaatgaaaa 135300
gaaagccagt tttagagcaa gcaatagact agaagcagga agaattttcg agtgttccac 135360
catgctggat tgtcaaaggg gtgggtatct gtgtggccag cagctgaaaa aggatccagt 135420
gatagtttgt cagctctccc cagaagggca ctcagcctgg gcttcagttc acatccagac 135480
aagctgtggg ctggggctga tggaggggat cgatctaaga tgacacttgc tcgttgctaa 135540
tctagagaga gcttgtttgg aagatggtgt gtgtgtgtat cactgaagat gcagatctga 135600
accacagagg ctgtggacaa tcaccaggtg tgtctcagaa gtgttctgac ttttatttgg 135660
taatgttcct ggaattccgt atgctctggg ctggagtgta cttgtggagc ggagggctga 135720
acatggcagc tagtgagagc acgccaagga caaatgtaca tagcatggca caaatgtatt 135780
ctagggtctt tatttatttc tgttatattt atttagtgtc taaaggttat ttgcagattt 135840
tcattctgct aattctcttg gttgtctgaa ggaagtattt tggtaagcat tttctgaaat 135900
tcagacaaat cttaaatcct taaggtacaa attaaattac taagagatga atgtctttat 135960
gcttctgtct cttttattca ttatcctttt gtaattgtaa gcacaaaaac gatctttgca 136020
gtgaatttga aatcattcca tgatttcagg agctttctaa ttttgactga ggttctcatt 136080
gcatgacttt gctatacagt acttaacttt ctctgctttg ttcttaagct gttacatgca 136140
gacaccaaat agcacccacc tagtcaagtt tcagatcgca cttgaccatt tgtaatgtta 136200
ttggttctct tgttagcatg tcccttcctc tcaacctagg aaggcatagt actcaaactc 136260
cccagatgct gtaagggaac gggcggccat ctgaggagtc agtcacctgt cacgtggcac 136320
tcagctcagg agtttcggtt tcaggggtgt gtgtgtgtgt gtgtgtgtgt gtgtccaaat 136380
cacatgtaat tctgaagcta agtggtgttt tataccattc cctttaaaaa tgatatcaaa 136440
ggaggtgagc aatcaaccaa gatatttgtg caatatgtgg cagtttaata aataattcct 136500
tgaccctttt ttaataaaag caactcccat aatttttaat tatacttagt caaggatcct 136560
tcttgcttat ccgatctata gaccagatat tgtacaacag ttggataaat cactcatctt 136620
agctttgctc ttgggaggag tggcagaggc accttggcct agtcttttct acatgaaata 136680
gtttggttca gatacttatg taaatgaagg tggatttaaa aaaaaaaaaa aactacagag 136740
ggctagagag atggctcaga ggttatgagc accaactgct tttccaaagg tcttgagttc 136800
aattcccagc aaccacatgg tggctcacaa ccttctgtaa tgggatctgc tgccttcttc 136860
tggtgtgtct gaagagagca atgatataac atataaaatt tgaagctaaa ttgtttgggc 136920
atttaatttt ttccattgtt ttgctgttta atttatagct tattgtgttt tctcatgtaa 136980
agacttcaga tgacctgagc agtttgtaaa agtaaaagat gttcccactg agtactgtta 137040
ctgtattaga ctgaaagcct gtgggacgcc aagagcaact gcagtagtta atccagtaag 137100
ataacttagt acctgtcatt gaatccatgc cttatgaaca tgaatatctt gaatctcatg 137160
tgacttttat gtgattgaag gaatttttat gcaaaatgtt tctgtctgat gacagtgcct 137220
```

tcctggtagc tttctgcatg actgcccact ggggtggctc tatatgagag tgtaaaatag 137280
tctgtgcctg ggcctatatt ttcttttatc acaacagaag tattcgtcat agggctgggg 137340
atagactagt gacctgggaa ctgagctgac ctggaagtca ctttgaacct aaaacggaag 137400
agtttgctgg atcgctggac ttttgcttgt tttctgtttt agttctgttt catttctgtg 137460
gcactgagtg attaaaccta agggttcaga ggcattttac gtccaatccg taagggtgct 137520
tttagataat acaatatagc aacatttttt taatgaaaat aatacaaact ggaggtagag 137580
taccccttcaa agttaggttc agtcactcgg tgccacagaa gtaaagcaag acgtcaggat 137640
aatgtccaaa caggctgaac aaccagcctg ccgatcctgc tggactccaa aacatagcca 137700
caataactaa ccacagatat tatgaccagg cctgatcgtg tcggccgagg gcttcattcc 137760
ttgcagttct gtttaatctg tgggtggagc tgacagcagc gctgtaagat gcggtggtgg 137820
ccatgggacc tctggcctct aaagtcagtt tggggctgat taagtcagaa ttcatgtacc 137880
acatatgttt taaacacagt tttactcata ggaagccaga gaaacgtaca gttcatgaag 137940
agtcatagcc agtgtgtttt ctgaaggcac aatttccagg attgggacac tgaaggcaag 138000
ggcataccta ttgctcgatg acatagcctg tccttgacac aggaggcagc ctgggcattt 138060
ctgatgtctt catttcattt gcagcagaga ctcttggcca agttcatgaa gtcccagctc 138120
atggctctta atcacaacac cataacagaa acagtgtgcc gtattttaac tgataaaaaa 138180
atagttttta tagtttgtgt ttttcagtga ttttatgtgg aacaaccaaa ttctgtactt 138240
gactttgcat gagttgtttc ttactggaac actgattcga ttgagtgggt ctctaaacct 138300
agaagctaga cgtttggttt tatcatctta gatgtctgct cagagtggta aatcagctgg 138360
ctagcgtaca gctggtcgaa gtagtccatg aggtttctat tccaataggt aaatgttaga 138420
atctagttaa aataagtgat aaatcttcca ccaagacttc agatcccaag agcttttgaa 138480
ataatgttta ttaactggcc tttaccagtt ttactttcat tttaagtatt gaaaatagat 138540
atcataccat tttttacaca tgatttttaa aaaatatgtt ttgtgggctt tctttgtccc 138600
atgtatgatg cacattgtat gagctataag tactttggcc aacactatca accatggagc 138660
tctcctggcc ttgaacttga atcacagtgt ccgtccatcc attccctcct cctgtcactg 138720
tcccatgcct ggcttacagt tgagcaaaca ctcagaggtc aggcaggcag tgcaaacata 138780
ggccatccgc ctcatgcttt gtctccagtg tctgtgctct gacgttgccg taggctggag 138840
ttcaggtagc attgatggtt tgttctacaa tgagagagca ggatggacat aggcacaggg 138900
agacgccctg tgaaggttga gtctttctgc ttctagtttt tgtgcattta atgaactttt 138960
acttctgcct taccttacat ataccaaaag taaaggattt cataaaggat gcttagtctg 139020
caatgaaaag aactgtttgc ttgtgggaaa ttcctgcaga gctcatgctg aagtattgca 139080
gaggaaagag gactgaagga ttcttgtggg gtaccagaga ttgctagaga gataagagta 139140
gcttgctatg ggactgataa gtagggaaaa gctctgaagt tgtggagtct aaaagccagt 139200
gtttgcgtgt gagctctctg ctgagtacac actgctcact tcctaggtcc cttgctcatc 139260
ccagaacagt tgctcagata gaaaaccgta gaggagccat gttaaagtgc taactttcag 139320
acaaggagaa cactctggaa tgcaaaccat ttactaagat ctgtggtaag tccttttaca 139380
tccatgcaga tcccctggag atgagttctg tccgggtagg ctttcaggtg agggtctttt 139440
gtactttgtc atacttttaa tggtctgtag ctttattatg accatgacag aatacctaag 139500
tcaagttagc tttataaaga aaagaccttt attttggctc ataatttaga agattcaagt 139560
caattgtttt aagagtcttg tggtgcggca gagcatgtgt tatgtctggt tctgtgtgtg 139620
cctgtctctc tcctttccat aaagccacaa gggttccatc aagcgttctg tcccaaagtc 139680
tttctctaag ccaggccaca ttccagagag tgtaactcac accattctca ggttctctgc 139740
ctcttattac cattggcatg tgacatgtgc agtggagact tcagacacca gcagctgtgc 139800
gttctcttgc tggtcatgtc actcttgctg gtagcccgct ttattgcctc taggttctgg 139860
ggatgatgag gagagcaaat tagatgtaac cttgccactt gtcctttctc gtggcctcca 139920
gtatgttgac ttgtttttgg caatcagaaa taaccactgc gggttcgttc tcagatcctc 139980
cagctgacct agctactgtt tgttgtaact gtggctgtgt gctccaggaa aacacaacag 140040
taacagtaac agtaactgcc tcttctggga gtgagaggag gattgatctg caagctggga 140100
cgggaaggtc tgaactgcag acagcactgc ctcgacatcc cagggattcg cagagtgtgc 140160
aggcttgcct gccccattgt ggtgataaga taagaataga tcaatttgca ttcttctaca 140220
tgatatctgc cagttctgcc agcaccattt gttgaaaatg tctttttttgc cactggatgg 140280
ttttagctcc cttgtcaaag atcaagtgac cataggtgtg tgatgcaaac cagtcactgc 140340
ttcaaagccc atggctttct ggagttgtga gttctctagc aaatggagtt ataggtagtt 140400
gtaagcctcc tgaagtaggt acaaggaact gctctgaggc cccctgccag agaagtaaat 140460
acccttaacc cctgagccat ctcttcagcc ccagatttta acagtgtcat cttttaaaaa 140520
tgtgtattgg tattttgcct acacatttgt ctgttacatg tgactgcctc gtgcctgcag 140580
aggccacatg acggtgtcag tccctgggac tggagttacc aatggctgtg agctgccatt 140640
tgggtgctgg caatcaaacc ctggtcctct agaagaatag ccagtgactt tttaactgct 140700
gagccatctc tccaccaccc ctctgcccta gattataact ttaacatgca tgacagaaaa 140760
atgtaaaagg aagtgtttac ttgagatgtc caataagaca gcagcgagca gttgtagtgt 140820
gctgactata ccttctgcct cctgccgcct agaggacttc aggtgtgtga tttcattttt 140880
ctgtgtttca gggattatgc taataattat ctcatacggt taattgtgag gtcaagttga 140940
aaaatacaga tatactacta aaagtagaca cattactatt tggaataaaa ctagaaatat 141000
tacctatttg gggttaaata gtcttgagct ctggtagttt gtgaagcgat catgagcatc 141060
aagctttttt gtatcaagca tgctgataga taagggacta agatagaaaa gaaagaacaa 141120
tatataattt tatgacttga aggcatttaa aatgcagtag tgacagggat gcaagaggaa 141180
gtaatgatgt ggtgttacag ctgttagtgg gcatatgcag gtggtctgtg gacagatggg 141240
ggtctgcagc agttctaaaa gagtggaatg agtttgaagt ggcttcatag aagataagca 141300
aatggactga gaccaggagg agcaaacaca aaagaacagg tgtgttggat agttcaggcc 141360
agcttgacac agctagtctt cagagtggag ggaggctcca ttaagaaaat acctccataa 141420
aatctggatg tagatgtgcc tgtggggtgt tttcttaatt agtgattgtt ggggaggacc 141480
cagccccttg tgggtagtgc cattcctggg ctggtagtcc tgggttttag aagaaagcag 141540
gttgagcaag ccgtggcgaa gaagccagta agcagcaccc ctctgcagcc tctgcatcag 141600
ctcctgcctc cagccttctg ttctcagtgc ttttgataat gaaccaggga ggacacagga 141660
cactcctcac attgcttttg gtcatggtgt ttcatcacag cagtagaaac cctaagaaac 141720
aaagacagag acaagggcag gccgttatgt cccctgcagt gcattccagt gacacaggga 141780
atcgatgaga accgtaaggc agatgctcag ctcaaacatc attccaggca gaggagaagg 141840
aaaggcgagt tcagagacgg aaaggtttga gaagaaagcc tgaaaggaag acttagagga 141900
aaccatagaa atagactgcc accaaagaag ctgccacacc atctgggaag cttagagaac 141960
agtagtgatg gctaaactat actgccaacc tctctgcttt gatggatcta gaagagccct 142020
tgttacaccc atttatttat ttaaatttct gttttgtctt gttttaatat ttttttgcag 142080
caagttacat gtaacataaa aatgattgtt tcacttcttc agtaacatta acacaccctc 142140
aaggttatat aatcattgct agtgtacatt tccagaacta cattatccca aacagaaact 142200
gcaaacttca aacagtcctc cctgtcctgt cccgagctct gatactttct cttctgtctt 142260
tgcgtcttta gctgtttagt gctattcttt ttagtgcctc cacacctgct ttcatttgct 142320
gtagttcact agtgtctaaa ggtgttgtca gtgttggttc ctctttaaag ttgcacaact 142380
gctctatgta tgtgtccatt ttctgtgtcc attcatttgt cctggatgtg catgttgcta 142440
ccactccttg gctactttgt cattcttagt cctgaatcac cctactttgg ttgcagtatg 142500
tatatattgt cttttaaagt cctgctttgg ttctttgggg tattgttgga tcaaggtttc 142560
cccagtgatt tacaaagaca tgtagccata gatgggaaaa ctgtgctgtg agacaagagt 142620
gcataaatct gcaaggctag aaacagtgca ctgagtttgg gacttttggg ggagattttg 142680
tcttattttg catgttttta tgcttttact ttatagcttt gattgagtag tttctcaaat 142740
ttgtttctaa acacaaacgc aacatggagt cactagggaa ttttttaaaa attaattaat 142800
gccaggcggt ggtggcgcaa gcctttaatc ccagcactgg agaggcagag gcaggtggat 142860
ttctgagttc gaggccagcc agggctacac agagtaaccc tgtctcgaaa aaaaaaaatt 142920
aattaatctt ttagtattgg tggtcaaagc caggacctca tgtgctatgt ctgtaatcat 142980
agaacactat ttttaacatg agcttatgag tccaaagtat acatcacaag agtctatgtc 143040
actagccaga tgatcagaaa gcatgctcat catccttaag tagctcggga agtttaatac 143100
accgaggtat acttccaacc caggcattga ctgtaataac taaaagcagg ggatgctggc 143160
cgtctgcaaa ggagttgaca tcagagtgcc cgccttgctg gctagaaacc caagtgcagt 143220
cgtgtggata tcagtttaat acagcatcag gaaatggaac ataggcttcc accatgacta 143280
tactaactcc tttctgaact ctacatccca gagaacttgg aaggaatagt ggaaaagtag 143340
aaacaagcca gtgttcatcc tgatagtgct actgaacctt gagaggatta taccaaagaa 143400
aataagtagt ttgcttattt taaaagattg gagacagaag gccagtcatt gaccaccagt 143460
agctggggca agtagaaagg acaagatgtc attgcatatc aagtatgagt tttctatctg 143520
aagatggaaa tactgtgaag ttaggtaaga agatatttgt atgactgaaa acacatatta 143580
aatatattaa gagtgagagg agagaaatcc aggaaggttg atgggcgcca agggggggt 143640
gtgtttataa gtgttacata gcagtgaaag agtttgacac tgtgtgccag atgcccatga 143700
gctcggtggt tttaagcttg tttagaggtt ccagctcagc tgctcatata ccctgggctg 143760
aggactagtc atcctctatt tgtggatagt cagcatcttt gacccagtgc acttaaggaa 143820
gagtgcaccc gtctagccag cctgaccaac tagcaggtga cagatgcttt ggtcagtcca 143880
gcctcacaac caggttttac atttgaatat tccagaaaac taaaaaggga gaattgacag 143940
aagaaaggtg agctttggaa cctgctagtg ttggaggcgg ggcaccagcc cgtagaccta 144000
catcccctgt ttggatctca gagtacaaca aactctgaaa ggtttcccaa ttcatttgta 144060
gtaaactctg acctaacaag tgtgagatga cataaactca tctgtcctgc ctggtgtgag 144120
tgaccgtgta tttcattgtg gagatagcat cgaatttgat tatagaacac ttctgtagat 144180
ccctcctaga ggcactacag aataagctgt cttccaagta ttgtatcgag aggcagacag 144240
ggagaggcgt gaattctaaa gcccacgtta tttggctcca tttctttgat gcaggggatg 144300
taaactccgt gatttggaca ggggtgaaag tgaagggaaa gcgagagcct gagttggtgg 144360
tacctaaaga gggattcaga ctaatggaac ttccccccaa gaatagggga gtagtttgaa 144420
tgtgccttgc atacagttta aagaggaaca ggtagaacat gatactaccc cttcccacct 144480
cagcaacaac ttttacagta atatcttgga gaacctaggg gtgggaagga gaaatggctg 144540
gcagtggtct gtgagaataa gtcgggtatc ctctgagatg gcagaaggaa agggatcagt 144600
atcttctgag attgactcca tgaaagctgg aaacacaggc tgacctgaga ataacgacgt 144660
ttctgacagg actaggagca gtgtcataaa ccatgaggag tctgtggggc tgtctctccc 144720
gagaacatgt ggtatgctcc atcagtcccc atctgtcccc ttctacgaga aacagaagca 144780
ctgtaggtca cgggagctag ggatgatgga aagtcagtga gaaaaaggat cccagttctt 144840
cataccagtg acggtcacat gaggagacta aaagtactgg tctcttcagg ggctggggga 144900
cgaggtgaca ttcaagtggg tacacctgaa aggaggataa gagctaacca tggctgaagt 144960
aaaatggaag tctgatcaga cctttggaga cagtaattac tagctcttca cagcctttga 145020
agtcactcag ggaaacaacc agattacggc tgggaaggaa gagctattca gaagccagat 145080
cttcactgat gtaaaagact gtgtggcgac tacgggatgc tggcgaagct ccacaaaagg 145140
agaggagatg gacaggaatg ttgttattta tagtccttgt ccttcatgaa aggaattaag 145200
gaccaggaat atggaagtag gaactggagg agagaccatg ggagaatgtt tcttactcag 145260
tctctcctca tggcttgcac agactgcttt cttatacaca cccggccacc tgcctaggtg 145320
ggcagctctg ctcccagtgg tctggaccct tccacatcag gcattagcca tgataatgtc 145380
ccacaggctt gcctgcaggc caatttgatg agggcttttt ctcagttgag gttccctctt 145440
ctcctctgat agctctaact taagttgaca aaaaaacaaa acaaaacaaa caaaaaaacc 145500
taattatggt tgtgggtgga gagcatgttc cacaggagct gggtttttaa gcagtgcacc 145560
tctagttgga tagtggcttc cagctcttct gcatactctc tgtatgtgag aatccagcaa 145620
cttctagagg actgcactac aaggaagagg tagcctgtca gagagccaaa aagaaccagt 145680
agttgattga cacagcatat tatcacactg gcttcgctcc tgtcgtcttc ttgcccagta 145740
gttgtagaca ttgttaggtc tttgtgatcc caggtcatca cccacagtct ggagtggagc 145800
cagaaaaggc agtgctgtct gcagactcct ctgctgattc ctttgctgtc caagtttgag 145860
gacctctagg aatccacctg tttttatttt ttatgtgttc actgtacatg tgtatagcat 145920
gcacatgcct ggtgttgagg gccagaagag gacttcaggt cctctgtagc tggattaaga 145980
ttctctcagt cactttgtgg gtgctgagaa cccagcctgg gtcctctaca ggagcaacaa 146040
gtgctgctta ttgggaccgg ctctccaact ccagactccc attttgctct catctctaca 146100
atagcacatg gatgtgaagc atacttctgc atctacagta ttcctacagt gcggccagaa 146160
atcttgtagg gaatgcagag acacctggtt tctgctgacc agtctaaact gtaaagctga 146220
actgtgcttt aattttcaaa tgagcaaagc ctttctagag ctcagtgttg ctctcagtgt 146280
tggctgtgag gcaggaggtc ctgcaagagt gcttgctgtc aggggatgca gctggcttgg 146340
aagacagtct ggcagggcca cacatatatg tatagcatgc acagtctgtg tgctctagtc 146400
ctcacaggtt taaaggagac aggcagaagt ggattgagtt acatagaagg aattcactat 146460
gctgttaact cgaaacaaag aaactggaaa ataggaactg gttaaatatt tatggtttac 146520
tcgtatgaga aattatagag ccattaaaag ttattcttta tttgcatggt ggtgccgtgg 146580
tggcacatgc ctttaattga agcattcaag aagcagagcc aggcagatct ctgtgtttga 146640
ggccagcctg gtctacagag tgagttccac aacagccagg gctacacaga gaaattctgt 146700

-continued ctcaaaacca aagaaaacaa atttaaacat ttttaaaatg ctcatacaga taaaacttag 146760
tggcctaata ttcttttttt tttaagattt atttatttaa tgagtacact gtagctgtct 146820
tcaggcacac cagaagggag ggtatcagat ctcattacag atggttgtga gccaccatgt 146880
ggttgctggg aactgatctc atgacctctg gaagagcagt cagtgctctt aacttctgtg 146940
caatctctcc agcctgtggc ttaatattct taattttact aattttctta atattaagaa 147000
aaaggaacaa atgtaaaatt agacgtgtgc atatgcattt taattgctta gcatgaaagt 147060
tttcaaggtt agtggtgagc atatgcagtt ttgtgtgtgt gtgtgtgtgt gtgtgtgtgt 147120
gtgtgtgtgt gtgtgctcta acccacagca ttgtgcaaga tttaacagtt tactggtgtg 147180
ctagaacggg tgcctgtggc atgttctcca ttaggacagg ctgaatcccc cccatctact 147240
cacaccccat ctctgctttc tgctccctcc tccctcctca ccttgatctc ttatcctttc 147300
tctcatacct agaatacagt catttcagtg atgttataga gcacccctgt gtaaactcta 147360
atgtattgac ctatgttgta ctaacagagc aggtacccct acctccatct gtagtccctg 147420
ctgtgaatcc cagccacctc tgagttggtg gctacttcag gacacctcac tcttctgaac 147480
ccagtgatgg tgtcttagac caaccaaaaa gccagattct tgtaaagcca gattcttgtt 147540
ttccaaccag tttattccag ttgtacttgt tactataatt gcatattgat cttgaaattt 147600
gaatttgaaa acatgtattt gttagaaata ataagatacg tcatgtggac aatttcctgt 147660
taaacgggga catgtaagac atctatagta gctgggggag tgatgttctt ttaggtaaac 147720
agtgaagaag cactcttaag ggcttagtag ggctgtgtaa agatgcatgc ctgcagtcag 147780
tgctatggag cctgaagtgc agggacctga ggtgaaggcc agtcagtatt cagtattcag 147840
gaggcagtac acccctgtcc cccaaaaaga aaaaacctta agtcttttta aataaataaa 147900
aatgggaaat catagcccct tcactgcagg tctggtttac accaggaagt gctgagagag 147960
cagtaaagat ggatattcat gcttatgtac ttatgatgaa atgcttaaag ttacaggcat 148020
cattttctat aattatcttt cacaacttta gtgttcttaa tcagccaatt actatttctg 148080
attttacaag gaaagttttc tgtttagagt gaaactgaga catcttggtg tgcctgagaa 148140
agtgcctagc aacttccttt ctttaaactc tgcggtctac aacagtaatg gagtcttatg 148200
tattgaccca ctggatagtt ctgaaggatg tgtgtttatt acacaatgaa aaaaagaaag 148260
attctatcaa atgatgaagt aagcctttaa taagttagat taagaaaata atttctataa 148320
cacattcaag tttataaatt ggtcttttca gtgatcatta tgtcctgaac agatcacttt 148380
agtgcccaca ttacagttaa aattaaaatt gagggacaat tgggtccctc ctacctctgc 148440
atttgagtgc tgggtttgaa ggtgagtgcc attgccattc ctggcaggat taacttttga 148500
gttctaaaat gtcttatgtg ccttgttcat gtttcagaac tgttctcttg gtgccttgtt 148560
ctcttcctgt gtgcagtggt ggtgagctca cacaggacgg gtgaagggca cgtatatcac 148620
tgtatgaggc actcagccag tgtcagttac tgagtcacac ctgagtttga gtccagcctg 148680
tcctttggta tctgtgagac tgaagttgct ttgcaagcag gttagagaag ttagataacc 148740
aacagggtgt atatgtgtcc atctcaagac atcaggcaga gtgaggtgtg caaagtgtct 148800
gtgtgcaacc tcctcctcct gagtgagtgc taaccaaaaa gccccaagga aagaagatgc 148860
tgtagggtga gagagagcgc catggaggtc aggaacaaag ctgattgcct caggctgaag 148920
gcctttgaca tcttagtcat tttctcacat caactgggaa ggctgttaag tctcagaaag 148980
aaattataag taacagtaaa gaaagatcat tgaatttacc tttgacaagt tatgaaagtc 149040

-continued taacataaat cttcttcctc tgctcttggt ttgctgattt ctttacattt atacttaagc 149100
aaattggatt ttaaaatgtt agctggaagc aggcacctca cttgcagtgc ggagaaaatg 149160
gcttatgggg tgcaaggagt ggtgctcttt ctgtgttttc tcatctgatg ccttattaaa 149220
aattgtcttg ctatttctgt ctagattcaa agagccccgt gagtgcctgc actgaggaat 149280
ttagcctgag aggacgcaga aaacagaaac tggctctagc cagtgatgtc acactgatat 149340
accccaaccc taccccaccc ccacaccact tacatattct gcaatgaatt ttgccagtga 149400
ggcatttggg gcttgggggg aatttctttc tcccacttta aggaagatgt agacatgaaa 149460
atgtcacaat gtaatatttg tgtcaccagt gactatgagt caagacattc atttgattat 149520
agcagtgcac attaaagagc caccacccgc ttctgtttaa tgtgtttatt actgtcttcc 149580
caatggcatc ttgaagtgtc tttcactaaa aaattcatga gtattattgg ctttcagaca 149640
gaaaatacaa tatgtctttt agtaactgtc taatagacca ctttaaggcc attatacaaa 149700
agtaaatcta agagcaaagc attttgggga ggaagaattt ttagcttaaa catttgttta 149760
tacagtcttc ttactcttgc gtagaagagg atctggaacg cagaaggtag ttgccgacgc 149820
catctccttg gagagtagtt gtagggtgtg ttgttttctt tagtcctggc aactgctgct 149880
gttgtagtat tgaagtcatt ttcttttttt tctttttttct tttttctttt tttccctgag 149940
acagggtttc tctgtgtagc cctggctgtc ctggaactca ctctgtagac caggctggcc 150000
tcaaactcat tttcttttct ttttttaaga tttttattta ttattataca taggcacact 150060
gtagctgact tcagatgcac cagaagaggg cgtcagatct cattatgggt ggttgtgggc 150120
caccatgtgg ttgctgggaa ttgaactcag gacttttgaa agagcagtca ctgctcataa 150180
ccgctgagcc atctcgccag ccccccttgaa ctcattttct aatgaggttg ttgtgtgcct 150240
gacctgctgt ttctttataa agtcaaatat acaatatggt actgtaaagg agtcagatta 150300
aactgagact ctgcttccaa ataagatgtc tttcatcatg ctttccttag aagtgactct 150360
tgtaaacgtt tgcaagctaa caactgtcag tgtggacagt gcatgtactg gtgtgcagtt 150420
tgtgagtctg aacatgtagg taactgtggg agccatagtg ttgtttaaga tgaagttaaa 150480
aggattcctg tgttctaata aaaatttaat actccttgca ggaaagtaat accccatttt 150540
actacctcag atactttaaa ctaatatatg atgtcctctc tccatttggt ttttctgtgt 150600
actttcaccc acattaagta cgtgtctcgt tctgcttcac tttgattggt atatatcgtg 150660
ctgctttgtt tgtgtgaatc ataagtattt tttatataat ctgtatattt actacattaa 150720
gtgaatgttt atttagctgt tggggcaaaa gttggaatct tatcagagta gcgcttgcct 150780
gggatagttt tgaccagtga gcacaattgg gaaccaggtt atttccaaaa tgtttgtccc 150840
ctctctctcc tcttcccagt actcacaagc agaagatcca ctttgtccgt tcaagtatta 150900
gctactgtgt tttcttacgt gtatcagaga aggcccaaga attgtgagtt tgtataatac 150960
agagctcctt ctccctggaa agtgtaggta gatctggaga gaattgagaa tggctgttct 151020
cacatgacct gataaactgg ggaagcgcag tgagtttcta agcaatgggc tctccctcaa 151080
agagcagaga tggagggtag tcttttatgt gtgttaacgt gcaaacattt ctcggcgttc 151140
tgaaaggtgg tccccagcac ttaggcagac ggattgggag ttcaggtctg ctgtgggcta 151200
cagaggataa ccctgttcag aaaaccaagg gctggaagag ttcttgtcta gcgctctcaa 151260
ggccctgggc ttgatcccca tcactgaaaa attgtgcaga tccagctacc attgtgcacc 151320
agtttcgtgg atcttaagtg agccgagaaa gattggaaag acctgggctg tggtggtgcg 151380
cacctttcct cccagcattg gagaggcagc attgggcagg cagatctctg agattgagcc 151440
caacctctac agattgaatt ccagaacagc caggacgacg aaaaaggctg gcccccatgg 151500
aaaagctatg atcaaaggac ttgttttacc tctctgtgtg gacatgtatc atttctgtcc 151560
atctcaaagt caggaactta ctagggccca actctcaaac tatgtctttt tggagctagg 151620
aagaggcctg gtgcttggtg gagttgttac atgtggagtt aagcaagggt gttatccttt 151680
aactgaattt gtttagcata tagtaaatct gacaggttta caggccttgt ttggaagatg 151740
gcctgtgctg ataagagata aagtgcgcat ttatcacttg caagaattct ggatgattaa 151800
ctagctctaa tgtcatgagg ctgttttgca aacaacagct ttgctgcctc ctatgttaga 151860
tggattcgct ctgcaaacaa agactgcttt ctttaattga attgaaattt gacattttat 151920
attgcttttt gtcacttgct gaggacttga ctatgggtat tgttcatccc tcccagatat 151980
tgctacttat aaaagctgaa gcttgctgaa ttgtgtgtct atatctcttc cttcttctac 152040
caagtacatt caagctgata tggagggatg ggaggacaag cctcctgtcc cagggaaagc 152100
actgccattg tgtgactatt gataacaaga atggcaaaaa gaaacatctc caggcttgtc 152160
cttcacagct cccatcaact ggtaaaaact ggtttgcccc cagtcactct aattatgtca 152220
gccacctcaa gttttatttg tgtcctagtc aatttctgtg atttacagtg aagtcttaag 152280
tttgatggtg acatgttcga gagctttaat ttcctggaag tgttgaaaac atgcagagat 152340
gtagagcata cctttactct ttcccatttc atactttaac tttggaaatt aatgtacaaa 152400
aatacattaa aactcatctc tatgtagttt tattttgctg tgaggtattc ttctgtaagt 152460
ctgaagtcga tcttatccat ctcacccacc tatgtcacct cggccctgcc tcatgtttta 152520
gtggtacatt gaagtgtttt ctaagtgatc tggagaaggt acagtaaggg ttttaaactg 152580
tcattgggct acagggcaca cagtctttgt ttttaagatt tattcattta ttttatatat 152640
gtgagaacac tatagctcta cagatggttg tgagccttcg tgtggttgtt gggaattaga 152700
tttttaggac ctctgcttgc cctggtcaac cccgcttgct cctgtcatcc cctccccagt 152760
caaccccact tgctcagtcc ctgcttgctc agactcaaag atttattttt tattattata 152820
tctaagtaca ctgtagctgt cttcagacgc accagaagag ggcgccagat ctcattacga 152880
gtggtcgtga gccaccatgc ggttgccggg atttgaactc aggaccttca gaagagcagt 152940
gagtgctctt acctgctgag ccatctcacc agctccagtg cacacattct tgattgactc 153000
aatccctcga gtccagttgt tgcaatgtgc ttgttggctg cttgtgtgca ttcagttgtt 153060
attgtgtgaa tttaaaggag aatttgaagc cagtgttcaa tcccaaatta actttctgtg 153120
actagcaagc acttatttta attgttgaga ggtttctggc ctttctggca gtatgatttt 153180
aatatgcatg gtgatagtta tatagctctt atcttcaata aagaatcatc cacaccttct 153240
gctcttgagt tttggtttgg tttgcttttg tttgcgctgt cctagtgaag gctgttcttt 153300
ataactttat atttttacaa cttgctgaca gctgattcaa gggaaaagtt acctggacca 153360
cttctcggga gattcctagg tgtgaagctt tctctttcac agtcgtgaat gaaaccttgg 153420
gaaatatggc tcagaaagaa ttaggaagaa tgagtgtttg tagcgtgttg tccctggctc 153480
cccagccctc tgtaactcac ccacttcatc ccagcctgca tggccctctt ggatctcagt 153540
gtgggaatgg atcgcagcac tgtccctgta ctcatctcca tttgccttgt ttctctcttg 153600
aacagcagta ttctgtctct gcccccctgc catgtccatc tacagtgaca ggaaggcagg 153660
tgttatatac tgaagtaaca atcattttgt gcacagaagc ccttgttggt tagatcttgt 153720
gactttttcc atggcgctct gcctgtagtg aatgaagacc aactcaccca tgacaggcaa 153780

-continued ggcaggaaga cgtatatgga tgactacctc aacagtgact tgctagtgaa gagcaagggt 153840
cctctccatc gaggtcccag accttcccct tccacctcct ctaggcagcc tgtgctacgg 153900
atgccagagg tgtgactcca gcttacagaa aatcagtagt gtgcagtagc aagttttaag 153960
gtcacatggc taaccacgca gtgaagcttg ggcctcaacg ttagcccttg gctacttagc 154020
aatacagatt tcaatgtgag gtgtgaatct gtaaattggc tttagtacat agcataaact 154080
aagtgaattc agcacttatt atcaggcaga aagtagagca ggaccttggg acttggttac 154140
attgcttcca cccacaggaa gcacaggcat cagttctcag attgtatgtg accatgtgac 154200
ctcctaaact gcatgtgcca ttgctgccac cgccctcttg ctgatgctcc ctaaaaacaa 154260
ttggttctgt aaaacacatg actcgcaaaa aaaaaagaga gagagagagg gacagagaga 154320
gaacaattgg ccctcctgct cgcttggatc agaacagtgg ccagaggagt gtgtgtggag 154380
cactgagact gagggctggg accacaccca agtcgaccgc agacagttgg actggtaggt 154440
gtccatgagg cccaggtctc tccacagctt tccttggcca attttactct tgctggtcct 154500
cctggtctgt gctgtgtttt gggggctcct gggctgctac tgacctcacc ttctcgctgg 154560
attctcctag tctatccaga gtaaaggacg gtagcagtct ttcaggatga agagtgagca 154620
taggacgcgt ttctaggaat gaagtaccac tgactctgga gcttgtgggc tgagctgttt 154680
tcctttgctg ggcatatcct aagcccttta aataactcat aagtgaattt ttctcagaac 154740
cggtgatagg gcttttgtct cttctagaac tgtcactttg tccttgcatg caagtcacat 154800
gatggcccca gtggcgtcca gcgtgaggac actgggtctc tttctgtgtg ccctttttcag 154860
tttctcatgg aaaacagttc agcaagcgga agctttatca gggccttcct ctcacaacca 154920
ttctaaagac ccttggtgat tatacctgca ctgccagaaa agggaacccc agcagaacgt 154980
gagaaaggaa ggaagccacc ttgctagctt aagagcaagg tgaactgccc gggggatggg 155040
gggggggggg ggtatgaggt tgaaggagga ggcttgaggc ttgaggggga gacaggaagg 155100
atctccattt tgacaaggga gtcagatcta ccaggccaaa tttggaaccc tttataaagg 155160
tgttcctgcc cacttcccta gactgtctgt caccgagcca ttccagcaca cacagcacat 155220
tggcaaaccc aacacaagag actgggaaga gcttgcaaca cctgtcattt ctctggtgca 155280
ggagcaccct caaaaccaga gactagccag gcccaggctg acagaaagca gctcatggta 155340
ttgttgagtc tctctgtcta aagagcctgg gctcagtgag gcgggagggg ttgttcttaa 155400
tattaacctt tgctcttgct tagcctttaa gtgtgcattt atgcacaccc tgtgttcaga 155460
actgcggtcg ggcttgggtt gaagtgggca gtccttacac cttggcaggc agagtgctgt 155520
gacagtttac taggactttc ttcacgccct tttcccatgt gttctgtttt agttgctgat 155580
atgtgttcaa gatgagtggg atgggagaaa acacctctga cccgtccagg gcagagacca 155640
gaaaacgcaa ggaatgtccc gaccagctcg gacccaggtg agccgatcgt caaccaaaga 155700
aaccgccttg tctgttagtt tcctgtgtgt gtcttcgttt attgcttttg catcgattta 155760
gtataactat tgtgttcagc ttttctcttt aatgatgaat ttttatgtaa tagcttaaat 155820
tttgaatatg tggattattt gcagaatcta ttccttttaa aaaacatttt tattgccctt 155880
gtgtatttta cttttataat cagttcattg ccataatgtt ttagttttcc atattttttta 155940
attaggaaca gaacattgta acaagtagat tttgtagtga aagatttgct atttgtttga 156000
tactgagttc ttatttgtct gtttgtttgt ttttgttttg tggcatgaag tattcaattc 156060
agttgttttt ttagttaaaa ataaattgtg gttcttcagt gactaaaaca aacacttcta 156120
aaacaagttg gcaatatcat aatggcagtt ctgatttcag gaatttcctc acggtagtgt 156180
ctgtatgtgc agagcactgt aagtgtgagg ttactcattt gcatccttgc ttagattcat 156240
aaaagagcag gaaacaattt ttgcagagaa cattttaaga tggtgtgtgg cctggaacac 156300
agtgcaaata tgataaacaa taaggctagt atttttaaag gcctcctaat actgaggcac 156360
agagccagta gtggtagtgt accctaaagt ctgaggcatg aggagtttaa gaccaagctg 156420
ggctacaaag gagttggggg ccagcctagg ctacatatat agttagatac tattccaaaa 156480
gatgctgtga gagagaaagg gcaaagttca aaagatgatt ttggagtata ccgcctgtta 156540
tattgaaaaa acaatttgga gaggaggagg catgtgcatt tgtgttgtag agtaatggct 156600
gctccctgct ttggtagatt agaaccggtg caaaagggaa acaaaggtgg aaaggtttgc 156660
ttccctgttg ctgtgatgaa acatcacaac caaagctctt tcagaaagtg agggttcatt 156720
catgatagca ggcagggagg cagagcagca agctgcagcc cggctgaagg agtaggaagc 156780
aggggagcag actagttgta gcacagttgt agcccgccca atcgtgtact tctccatcaa 156840
ggccacgcct cctaagcttg tctttacagg gccaccaact ggggaccagg cattcaagtg 156900
actgaacctg tggaggacat ttctcattta aaccaccaca aagagagatt tttttcccc 156960
cagactttta atattttcaa tcctgtaaat gttttttgtt gttgtatttg tgttgtcttt 157020
atcttcccag nnnnnnnnnn nnnnnnnnnn nnnnnnnnnn nnnnnnnnnn nnnnnnnnnn 157080
nnnnnnnnnn nnnnnnnnnn nnnnnnnnnn nnnnnnnnnn nnnnnnnnnn ggctgtcctg 157140
gaactctttt tagaccaggc tggtctcaaa ctcaaataga tccacctgtc tctgcatcct 157200
gattgctgag attaaaggtg tgtgcccacc acacccagca cctagaaatt agttttaaag 157260
ttaaataaaa acagtgctct agattgtgtg attaaaaaca acaggaatgt gggttagaaa 157320
aagttaccta ggcgggcatt ggtggcgcac acctttaatc ccagctcttg ggaagcagag 157380
gcaggcagat ttctgagttt gaggccagtc tggtctacag agtgagttcc aggacagccg 157440
gggggtaggg gggggagtta cctagagaag tggagagagg ttagaaaacc catggtttag 157500
gctattcctg cagcgctgat cacaggtctg tctaactccc tctccacacc cagccctgct 157560
accttttacc ctcaggttcc caacaacttc ttggtccgct ccacctgctg ctggctccca 157620
gatttccctt catgctttag taccctctg gggagagagg ttccagaggc cacatagtct 157680
ctggggctca gttgtggtag caaggagggc agcccttcct tgtgctgtct ccagggtctt 157740
gtgcctcagc tccttttctc actgacttgc catttatcct gtctttctca ttctaagaga 157800
gaggggtatg gggaggagcc aggtgaaccg ggctcctcta aggccctctt tcagccacct 157860
ccttcctgtg acttcagtaa agtagaacac cccagaaacg aggccaagga gacacagacc 157920
ctcttccccg cactgctgca gtgcactggc gatcttgggc aaatcgtgga gccactaaaa 157980
agggagaatc gtgttaaaaa tcttaggttt attaatttat gaaaataaaa ctaatagatt 158040
ccaatgtgag aatcctgaac ttgcaattaa tattttgtgt taattttaaa ttgatattat 158100
atatgaatac atataaaagt acagaaaatt aaatacagaa aactaaacaa ctcagcttct 158160
ttccttgttt tggggccatt taatggactt ctgcatgtac acagataact atattatttt 158220
caagaggaaa tttggagttt tgttattttg tcaaattcat atgagaagat ttttccagtt 158280
ttgatatttt tctccactca ctgaagttca gttgaactct gaccacttgg cttgcctgtc 158340
attggcacgg acagcgccca tgggtcacgt gggctttgct tagctgcttt agcacttttt 158400
accttacctg attggatcac agatattcta aggaagtctt tagaaattac agatctaaaa 158460
gaagaatcta aaggtgttat aaagatttgg tttttattac cctttatgat taccaaaata 158520

-continued aaacaaaagc gtgattgaaa cttacgtttc caattctaat tacattaatt ataacttgtt 158580
ccttctaaac taccttaagt agacgttgac tccttactaa ctctgtccag cagtaaggtc 158640
agtgctcacc ctgtcaagct ctgttgtagg ccagggccgt gctgccctcg ctgtggtgag 158700
actggagatg agcgatgagc atgctcagga agccatccac agagaacaaa agagaagcag 158760
agataccaga tcactccctc gctcttacct gctttcctga gcaggcagcc tgttgtctgt 158820
gttcacattt aaaagagttt agcagtttct ttcaaataaa tagtaatgtc ccgttccttc 158880
ttagccccaa aaggagcact gagaaacgga accgcgagca ggagaataag tacatagagg 158940
agctggccga gctgatcttc gcaaacttta atgatattga caacttcaac ttcaaacctg 159000
acaaatgtgc catcctaaaa gaaactgtga agcagatccg ccagatcaaa gagcaaggta 159060
agaggacggg aggggttctg cgcctccgcg tgggtgaagt cccctgaatc ttatttctta 159120
cacttaaatt attgatgaaa tgatgtcata ttaccagatg aatgcaagta tcacttgcag 159180
ggtttataaa caggctttac ataaaatcca gccgttccct caagaccaag gagatgtagg 159240
tgagccactg ataggacttt gcatctgcga acgcccccat atccctagag ttttggctgg 159300
tgtcattaca agtgagggcg actcttctat gtaatccctg aagaaggaag cagggaggac 159360
ctcctgctcc atccacttag ccaattggtc tggattagaa tttcacaccc tgaatgatgg 159420
agccttcaaa ggctctaatc gccagtaaag atccctttat gaagtcacag acatccttta 159480
acagctttct ttccttggtt ttctccccct acctcccacc ccaccacccc caaaattgtt 159540
ttatacttcc ctcttgaaat ttttgcctac ctaaaaaaaa ttataatagt ttttaaaaca 159600
tagttgactt tgtagtgcca aaaataaatc taaggcatgt acgagcaagg ctcttttgct 159660
cgaggctggc gcgtgctctg aagagtccac acactgagat ccttcaggtg tgaggatggt 159720
tacctctcag aatgcttttg atgaattatg taatttatat tcttttaaac tgccttttat 159780
atattagttg aaaaaaacaa tttcaggaaa attgtatctt tgtcttttta gatcttggag 159840
cctcaaactc tttttcctcc aaggaatgat aaaactttac ctctggggtg gggggggggg 159900 cccccccccct ggactgggga ggccttaaag atggataggt tcagggtccg aaagaatcta 159960
gaccccagtg gaggaggcta aaattagagg gtggagggca gcaaaatata aaagaacaaa 160020
gatataaccc ctgaccgatg gtcgnnnnnn nnnnnnnnnn nnnnnnnnnn nnnnnnnnnn 160080
nnnnnnnnnn nnnnnnnnnn nnnnnnnnnn nnnnnnnnnn nnnnnnnnnn nnnnnnnnnn 160140 nnnncccccca ccccgacact ttggggttta gcaggtaccg ctaatctcat cttgttaggt 160200
tctttctttg tgacattagc aaatggatca aatactatcc ctcgaacttg taggggaatt 160260
gctacctgta gtgtgcgtag tgcgtgaagt ctgtgctttt gataatagta aaaaatgtaa 160320
gcctgctgtt tcaggtctcc aaaaatcttg aatggttcca tttttgtgag catttcatgt 160380
tacaagtttg gtgtttcaga tagtcatact cgtattttca actacaatga gggtcttgca 160440
caaccttggt aaatccccct tccaaccaga aaccacatta agatgtgtcc cgctgggcct 160500
gcttctctgc agggttctct catcaagcac acaccacaac cacccagaag cagccatgta 160560
agcaccccat aggtcatagt ctcaaagcag gactgggcaa tttgaaaggc aatgggtttt 160620
gaaacaagaa gaaacgttaa atgtcaaata cacaaaagtt aaataccaag aagagaaata 160680
tacttctaag ttctcagtaa tctaatgctt taagaatatt cctgttttaa taatttttag 160740
taattgtatc agacagaagt taggtatgca ccagtgccaa agaagagtcc tttgcacccg 160800
tgcagtaggg tttttccctc tctctctctc tctctctctc tctctgcaag gcttctcaga 160860
tataattgag cagtgaccac agctggcaca cgtagctcct gaagagtgag cggtaccagc 160920
caggcagccc actcctgcca tggaaatgtg gtaggtgtgg tcttcttttc cacattaagc 160980
agacacttcc tccttccggt ggaaaacaaa gcaaaggagg ctgccagggg gtactctcct 161040
gcttccagag aggcctcgag aattaaaaag tgaagaatgt tttcctaggg tcagaactct 161100
ctgggatgga gcagttggac ccactttgat ttctgtctgc agctgacagc cagccaaggt 161160
tcaaagtacc acataagttt gggttgagct cttgcctctc ccggtgtctt ctctgttctg 161220
aactgagccc ccagcagtca gcataaataa aacccagcca ctacctctgc cccggtccta 161280
agcttacctc atatctcagt cggtcacact gtcagcctaa ataaaattat ttgagttatt 161340
gaggagaaaa tgtccatgat aatcactaaa cctgtgtgtt tggctcagag aaggtaagct 161400
gtgtctaggg tatggcacta aagaccactg aagaaggctc caggtgtgtg cgggcatcag 161460
ctgtgagtgt gcatcatggg ccttgttccc tcagctctcc atgtgccttg taaattgagg 161520
aaaatggaac gaaatgttaa aaatggcata tacttcaaga atttggaggg ggaattacca 161580
ggtgtttaaa ttaaccatcg tttcagacac aaaactttat gagatgcttt actctgacca 161640
aatgtggtaa cacttgggag gcagaggcag gaggattgcc acaagttcaa gatcaaacct 161700
gctttacatg tatcctaggc tggccagagc tacataataa aaccctgtct ggaagaaacc 161760
agcatctagg agcagacact ggaggcaggc atcctgagga gcagagcaag gctctgatag 161820
caagggttcg agactagcaa tacatcactg ttccgtttgg aattccattt gccttgatga 161880
ctttctgtgc ccacagtcat agaaccttag ctggtttgtt tggggttgtt ttgttttgtt 161940
ttgtttgttt gtttttgct tgtttgtttt ttttttaaac aaaggtagta actggttgat 162000
taagacctca tgttatgact aaattctctt tgacagtttt cagtaggagc cagttctttt 162060
tgtatgctgg atgccttgtt atatacttag gtttgcttgt ctacttaata ctccaaacat 162120
ggaaaatagc agttttactg ttttcccctc ttccaaatgg aaaatctgag atatgggaca 162180
gttaagtagc aaaatgtcat gctctagagg gaatgtcggg tggaatcctg ataacctggc 162240
ctcatagcta ccctcagatc cacacaactt gttagtacta aatatgacat ttctttgtat 162300
tctagtgtgg tgatgtttaa agtctctgcc ttcatccata acttagagtt atcttatgta 162360
acaaacacca actcgtctta actggagaac tgctgttgat atatcccaca gaatgctgag 162420
taaaggggaa atacagatct tagattttgg attactgtgt ccaatttcat tccatttagc 162480
agaaaacaaa aattctgtac aaaatatttg gggtacaaat atttaggact gtaaaaaggc 162540
taccaagtag agggaatttt aaaattaaga acatttctgc tgtcctgttt atgtctcctg 162600
ttactccaaa gtagccacac attgtatttc aaaaataatt aaagtgagtt tatcaattta 162660
aagtgagtat gaaaattata taagtctgtg ggcatggtag tataagtggg aaatcccagc 162720
acatggcaga agcgccaggt gttcagacac tgtctttaaa aaaaaaatca ttgaaacaca 162780
ttttatttca ttgcatttgg atttatcagt tagagcatca gtttcaaact tttgtttcac 162840
aaagttgaaa aaagaagagg ctgtatcaag tattcaagaa tatatttcaa aagaatatgt 162900
gttgatatac atgtcatcgc agtttttcat tacagttatt ctagagataa catacggtgt 162960
tgacatgaga atgtgggatt ctagattgct tcacacggga attttacctg ataggatagc 163020
atcactaagt gaagaaggac ctggaggagg agggcagggg cttggtggag ccggcaaagt 163080
taagccaggt agagtggtac ggcctttaat cccagcactc tggagccagc ctggtcttac 163140
atagtaattt taggacaggt aaggctctgt ctcaaaaaca tttttgttaa ttatgcaagt 163200
cagttgttaa gcatagccgt cgttactaac catgtggacg tggaagccgg tacactaagc 163260
aaaggtgaag aaaatggcag tgtttcttac ctctctgctg catgctctgg gatgcatgcg 163320
agctgtgcct ctgcctacga ggctggcgtc ctggctagtg gtgcctactg tacccctact 163380
gtgggaacac ctgaggtcag gaatgtggta tagttacatt gaagtccacc atgaggagaa 163440
tattcctgct acaggactgg gacactcaag tttgtgattt ttttttttt ttttttttt 163500
ttttggtggc tgttgctcta gactttaaca gtcagggaga ggattgatat tttgtttcca 163560
ccatcttagc tctggcagct ggcacatgaa tacacacaac ctgatagaca gcagaaagtc 163620
actcatggat ggacagttac atttatgggt atgatttaac cattagttct cttgtctact 163680
cattaattta aatggaaact agccatgagt cgctacagaa caagagttca atggaagcgt 163740
tctctgagag tcaagtgact gcatgtttac aatgacagtg tatgtgtcat tctcatttgt 163800
aagttacgaa tgcactactt accttttaca ctagagaaat atgccataaa cattgtgttg 163860
cactacacac actcaaagag ctggctttaa gcatttagca gtcgtctgtc attgagaggg 163920
caatggcggc aagacattca aacacatatc cgcctgtctg cctgcttgct ttctccccta 163980
tgattctgtg acctttactg taggtgcaga ccctgctgga caagcccagg cgatacacta 164040
gggcgagctt gcaaactggg acagaggatg gagagcacat ctccacaggg actggctgag 164100
gcagaccgtg aacctctggg tgtgttctat tctgcttctc tttgtgttcc tgaagcctgt 164160
agctgtacaa ggcacagaag ctgtttatat ctgagtgtga atacaggaga agctgccgtg 164220
tttaaggctc ttacctgctg agctgtctct ccatctctta cgatatggtt ttacttagca 164280
atattcagac tgctccagac acattcatgc agatctttat tcccttattc ttcctctagg 164340
aaacctgttg tgctctctac ctctaacctc catactcctt caggcttgct gttatcctgt 164400
gtgttgttaa tgaggcagat acccagaaac actaggctgg ctgagggcct caaactgatg 164460
agtgacaaag tagaattgac tgcagcacct gtctgatcgt ggccatgtgt gaaacttcct 164520
tgttttgttt gtttgtttgt ttgtttgttt gtttgtctga ggaaagaaaa atcatgttcc 164580
acagagtaat ttcacaaggt tcatgggcac tagttgcgca tggatggagg tagttttact 164640
tgtataattg cgagctagtt gtgcatggat ggaagtagtt ctactgtatt attgagagca 164700
gccctgatga ttgagccctc tgacttcacc catgtctgtg gctcggcccc agcacctcac 164760
agcaggacag accacctgga gctgcttcct gagagctcct cacagctgca gtttttttctt 164820
ttccatttct tttccttcct tttttgtttt tataagattg ggtttctcta tgtgctgaga 164880
ttaaaggtgt gtcgtcgtcc ccccatcccc gtctgcattt tgaacaggtg cctttaattt 164940
ctggtgagca tctagtaact aagacgaggt tatttcctgt ccctgaagat gctacaatgc 165000
tgattggtgg gaagggtctc ttatgtcacc tcaccttcgg agtactgttg ctttgccttc 165060
aaagcattct gacttcacta tggtttcacg aggagcctaa aaagggggta cagtggtgtt 165120
ctgtgtaatg gtgggtcctg cttgttgtat ctcaggtggt catagtaagt tgagtggatc 165180
tcggcaagtc tggggtggag aagagtgtaa tcaccgagct ctggggaaga gggcactgcc 165240
tgtggtgggg gaggtgggac atggagtgca cgcactcatc agtgttctgc agacacacag 165300
cgcttcatgg gaccatttat attttggggg acagaaatac ctggaaattt ggcacaacac 165360
agttgatcac aaaaataaga tataggacat aaaataagag tcttccaggc aaaagagact 165420
tgcatgacat taaaagaaag aacttactgc ctctgtgcca ggaatgaagc tcaggtgtca 165480
ggtccctgct cacactggcc ttgccacatg tcagtcagga gacacctcct aaacatttca 165540
gatctctctc tgcagagact gcagacggtg tgctccagct gtccaaactc tagcacttgt 165600
gctaatgatg gcccctccct ctgttagcca gctgtgtacc ctgtgaaatg tgggttcatc 165660
tctatactat atgggaattc tgtgactacc tgtcctttat tcatcttcat caaaaggcaa 165720
aagtcagctg ccaccatgga ggtgagaggc catcctggca gagtgcttcc tctgtcctaa 165780
gttttgctct gctgtcttca tatcctttga tctgtacaat gcccctgtag agtaagtctg 165840
cttattctct cagttttaca ggggaaggcc ttgggttagg gctggctgct ctaaagctac 165900
aaggcctcag atctaaatct ctacttcgtt cccacgcctg tgtgttcagg gagcctgtca 165960
tccagcctgc cctggtggtt ttgtctgcca tttggaggaa gttgttctga gcaaattggg 166020
ttaagtgtgg actcagctgt tattcaggat gcttcgtgta ccgagaggaa tatttcttac 166080
agagctctgt tttaaaggat agtatgcatg ttcaaggcag gtcatgtttt tcagtagcac 166140
acacgcacgc acacacactt taggagaaaa aaaaaatccc aagaaagaat gttatgtgtg 166200
ggagggaaaa gaaaagaaaa aacaacaact tggtatttag ccaaaagtag tgacattcca 166260
agcttgtttt cgagtatttg ttttgttcac tgttaattat aaaagaagag tccatctgtc 166320
agtcagtcag actggtgttc tgttgtctca tcatgttgtc ttttccatct taataagagg 166380
ccatgtgctc tgatttcagg agctgatatt cactgaccat cccagtactc attgcctcat 166440
tggccaaaag taaagagctg catgtgaggg ccccaggctg gaccactgtc tagcagagcc 166500
agggagtggc actgtgaggg cccaggctgg accactgtct agcagagcca aggagtggca 166560
ctgtgagggc ccaggctgga ccactgtcta gcagagtgta gtggctattc ctggttgtca 166620
acttgacaat atttggaatg aactacaatt tggaattgga aggctcacca gtgaccctta 166680
tctggaggct tggagatcct tatctggatc ttggtttgaa gatcttgagc cactagtggc 166740
tatggattcc agaagattga atctccgagt taaggaacac acctttaatc tgggctactg 166800
cctttcactc tgggattaaa ggtgtgagtg gaacacacct ttaatctggg ctacaccttt 166860
tgctggagac aatataagga cattggaaga agggagtcta gctctagttc ttgctcttgc 166920
tccttcgcct gcttgctgcg tgagactgag taactgctag atccttggac ttccattcac 166980
agctgcgact gaaccattgt tgggaattgg gctgccgact gtaagtcatc aataaattcc 167040
tttactatct agagactatc cataagttct gtgactctag agaaccctga ctaatacaca 167100
gagccaggga gtggcgctgt gaaggcccag gctggaccac tgtctagcag agccaggggg 167160
tggcactgtg aggctttggg tccctgcgct tacactgaga gaggagggag tgactcagaa 167220
agagtctttt cctcacgact gccctttgag cactgtgggc agacttagca ctaagttcca 167280
ctggacctgt ccatcgcaca agtggcacat ttcgtcctgt gtagaaaaag agtgaaataa 167340
ataatgccaa tattggcatc agcccctcca ggccttccca gtgatggcag tagtgaactt 167400
gcacaattcc tgggtgtgtt tgtctacttc cctgtactta aaagagtttc tcagtacagc 167460
aaggatttat tatttatgcc tatctacaca gacagatgtg tgcatgccac tacattttgt 167520
aagattccaa atgttataat tagcttgtta cataggagaa gggaagtggt ggtggtgagg 167580
tctagacatg ggcgtggtca atctggacag ggagggcact gtgggtacag gctggacagt 167640
agacctcgaa gctgagccag gggtgactct tcattatctg agtctgtacc tccccttctg 167700
ctctcttcta attattcttc agttctggga agtttcttat tctttggtct gccacaaccg 167760
ccaaactcag gttttgatgg gtccttctcc ccaaccagat gcgcaactct ttttgtaaat 167820
gtctaaggat tactgcccta caaaaaggaa gggcaaattc acaaataatc agaagagaag 167880
acagacttag aggaagtctt aggcctagtt gtgagctctc tgaaatgtaa gacggtcggt 167940
cggttctgat atttgcctgc ctgctgccca gtttcttagt tctcctccct ctcccctggg 168000
gtgggggtgg gggtgggggt tggggttgag atgggtttnn nnnnnnnnnn nnnnnnnnnn 168060
nnnnnnnnnn nnnnnnnnnn nnnnnnnnnn nnnnnnnnnn nnnnnnnnnn nnnnnnnnnn 168120
nnnnnnnnnn nnnnnnnnnn nnnnnnnnnn nnnnnnnnnn nnnnnnnnnn nnnnnnnnnn 168180
nnnnnnnnnn nnntaccttg gctgccctgg agctcactga gtagccgcct gctgtctgtg 168240
aaccctcagt cctgctgctt gagttcccag tggctgggat tacaggcttg caccacaggc 168300
ctagctttct ttcctttggc tctgctgaag gagaatccca gcaagtcttg gcttatataa 168360
agatctataa gaaggagcca tttccttttt ttcttttttg gtttttcga gacagggttt 168420 ttctgtgtag ctctggctgt cctggaactc actttgtaga ccaggctggc ctcgaactca 168480
gaaatccacc tgcctctgcc tcccgagtgc tgggattttc aaagtcactt caggctgatt 168540
tcctgagagt tccattgcca aaagatattc ccagtgaggg gctgggaagt atgaaggaag 168600
tctctgcagt ctatgtgtgg aggaatctcc agtcttgcca actggtgttt ggcttgtagt 168660
tctgaagtta ccttcagaac acattacctg acattgaagt ttggaatctc taggtgtgtt 168720
ttcaaagcct ggtaatttta tcaataatat agtcaatgat tcaatataat tcaataatgt 168780
gtttactgtc tcttcttggc ctataggaca tgacagcgct aattccatat attttaggta 168840
tacccattat gaacaattta ggttttttct tgatattatg ttttagatgg aggggtaggg 168900
attgtataag gattcagtgt acagctctgc agcacaagag ccatgtgcct gccatgacca 168960
cctctgttaa tttcctttct agtgagtcct tagctgcatt accaagttac tattccctaa 169020
tagatgttta gatgcccact caattttctt ccttgatcta gtcaagctga tgctaggcga 169080
ggctgcactc ttctgtaagt ccatcactta actgaattta actttaggaa tttaacaaag 169140
tattcttatc cctatagagt gtgttcttaa tctaaatttt tgagacatgt ctaatttcct 169200
cggcagttga tttatctaga gagggtaaca gaaaagatct ttattagcct acacattttc 169260
ttttccaaaa ctttttgag cggctccact tgaatggctg cttggaccca ttcacatcct 169320
gaggtgcctg cgttgctctg gcactgatgg aagcttattt tgagctcagc agtcagtctt 169380
gcgacgttcc ctcgcagatg aaagcatccc tggtcttaat cagcatctct tcattgaaca 169440
tcctagtaag tgctgtttcc tcaactcagc tggtccgaca actggctctc ccggctacat 169500
tcataaagta gtactacggc taacttaaat gttgaatttt ctatttttat acgtttatga 169560
catgttaaaa atagttcact cgttctattt ctgtgctcac cttagctgtg gcagtatgct 169620
cagactcagg agagcaaagc ccatgcagac tcctccaaaa aaatggaaaa tagtactttt 169680
tggaatgaaa attacaaaat cagattcctc agctgatttg tgtgcttggg tttaagacgg 169740
atcctctgtg aagaactctg tcctgttgtc tttcaaagtg gcagcgcctc tccctttcc 169800 tgagtgtgtt tacctgtgag cagtgtgggg catggagtca ggtgaagagc cagggtttgg 169860
ttccgagctc tggcagtcct ctggtaacac tgatactatc cagatacaac tcgatggctt 169920
ccagaagaca tagcaaattc cctcagccac gttaggaagt gcagagggaa accaacttgg 169980 attttttag atttcctaaa ggaaatggca gcaactgagt gaaaaatgct gagtcaccat 170040
tgagtgagga cagtggccct gtccctgcat gctgctttag tccagcctac tcagttggac 170100
atctccagtt gaacgttgac tggacttgtc cacagctcca caaaacatat tcctcttcct 170160
ttatcttttt ataaacacat caggtttccc atctcaaaag caacattatt ttaatatttt 170220
aaaaagaaat gaatggggtg gtgatacagt ttagcagata aaagctcctt ttgtacctgt 170280
gtacgcagga cgcacatggt gggagagaac ccactcccac agttatcttg tgaggtccac 170340
ctgtctcatg cgcacaatac tacaggttat tttctgttaa agtattcccg tattgccaca 170400

-continued

```
ggaactaaca tatgtgttct tgtctataaa gaaaagacaa gctagctatg gtgctgactt 170460
cggctttaaa tggatagaag aactgtatag cagggttata gtaagtagct tatcacaaat 170520
gtgtgtgata ctctttccct ctagaagaaa cctgtctgta gccttagagc ttagaattat 170580
aaatgtaccc attccatttt taagcctgag tagcttcaga ttttatcata aaatatcttg 170640
atgttttcaa agtctccttt tatttgtaat ttgtgagcag ctcctttaga gacttgtttt 170700
tctgaagctg tttgtagttg tgcacgcagg ataatcctgc ttggcacctg tcttccgtag 170760
aactcggtat ccacgtgcat tttttcctga agcctaatca tacccttgtg aagcagggcg 170820
ttttgcaagc gattaggggt tgctttgctg agtcagcata gccttacggc attatgataa 170880
gctcagaaaa gattgaggtc atgtactaac ttgctcctgg ggaaacccag ggtgcaacca 170940
atgtttttct tggcgactca aagctgacaa ctgccgatat tctctttcct ctgaagcaca 171000
ctgttcattg atgcgatttg aaaagacaac aaacagcaca tgtgtatctg agacaggcta 171060
tggcttgagt aacatgaact caggtgacat gaggctggtg ccatctcctg tagtcaaggc 171120
tggaaatcca tagagaaggg ctacctcctc ccctgcagag cttctgactg ggtcttccac 171180
cctgtcgtat cttcagccat attgtctgcc tcgcctgcaa gccatcacat ggtagcagca 171240
ttgcctcgcc tgcaagccgt cacatggtag cagcattgcc tcgcctgcaa gccgtcacat 171300
ggtagcagca ttgcctcgcc tgcaagccgt cacatggtag cagcattgcc tcgcatgcaa 171360
gccgtcacat ggtagcagca ttgcctcgca tgcaagccat cacatggtag cagcatttcc 171420
agagaggctt cttacttgca aactgtcaac ctttgctgag actacactgg attcaaaatg 171480
tcattaatgt actggggaca gcttcgttgc tgtgagcgtc ttcctgttca tggctactca 171540
ctgtgatgtg ttcccaaggc tcctcgcctt ctgagagatt ctcttcgtgt cttaaccact 171600
agagagccag gatactcgtg gcctataccc ctgccacagg tgtaaagatc cctggagagt 171660
ttactgaaga tgcagttgtc acactttaag tcagtccttc tgattttctg caggtggatc 171720
tgtctgcttg aacagtcttt ttaatttaga acatagaaca ttgtgagacc ctagggaatc 171780
actaaggcac ggtatctttc ctcaaacttc ccagatttgc tggagaatgg cagagatatg 171840
aaaggaaaag atttagtcat agaagagtag tcatgatcca aaattggaaa atttgtaaag 171900
ggaccttagt ttatttcatt ttgacctcag cgtgcaaatt ggccacttcc ttgcctatcg 171960
tttcacgggg ctctgaaata tgcggtgccg gcaaggtctt gtctgcctct gcacccggct 172020
gagcacggca agtccaagcc cagccgagca cgtgtctgct ctgatagttg ctgcccgagt 172080
gtcagtcgtg ggcatttgct tgatgatttg gtcactgccg ctcctgcttc agagttagaa 172140
agaaagcatc tgtgtcagaa ggaaccagtc agaaagactg ccttacacac tgctttcagt 172200
gcacactgtt gtctcgctga ggggcctcct gagtgaagac ttggtagaac ttcttcctat 172260
agcatctagg gttcaatcca gaggacacgt gtggttgtct ccatgacagt cgccatttct 172320
ctctccaccc agttgtccct gctcacccac atgtgtccca tgcccgtggt gttctcggtt 172380
gtccctgctc acccacccat gtcctgtgcc cttggtgttc ttggttgtcc ctgctcaccc 172440
acccatgtcc atggtgttct ctgccacatt ttgagtacac ttatcaaaaa tcaacagaga 172500
aaagtagggt ttcgttgagt aaaaaacaaa aaagcttgtg agatggctca ttggataaag 172560
gtgcaaggac caaggctgat tcggtcccga ctcaacagac ctgagtttga ccccagaagc 172620
ccacatgggg gaaggaaaga ggccggccac ctcttcacta ggcagctccc agcatttgca 172680
gcatttcgtt ttcatctctc catttagaaa aataaatgtg agattttttt ttctttttcc 172740
```

aagctgtgcc ttaatcccag cagcactcag gaggtagaga caagggaatc actgtgagtt 172800
atgactctag gccagccata gcttcatagt gagacctgtc taaaaaacca acagcagtcc 172860
ctccaccgct gccagacaac atgtaaaaac ctctctttga accaaagaaa aagtaagcat 172920
acagaggaaa gggtacccca tagaggatga ggacacccca tagactctgt gcaggagtca 172980
ctggccatga gctccacgta cagtaactgt ccacacatct ttggtgtcta gactcctgta 173040
gaaccaggtt gctagctgct agagactttc cacagagctg atgtgctggc ttgaacccgt 173100
aatgcctaca tccaggagac taaggcttct tttcctccac tgccacagga ttcctcacca 173160
gcctgagcta caatgtgtaa gatttttctg gaagaaagcc cctcctccac tatgtgacat 173220
ataaccctag gaataggttc tatgaacctt gattgaccct ctcaggagct tcaaacatgg 173280
gggcactgaa cttgcccccct tcctgtcact gcctttgttc tggtagatta gactgtttag 173340
ctcagcctac cccctgcgta gccaaaccat gatctctctt gtcagtgtgt tgctctctgc 173400
ttatgtgata tgacttggca taatttgagg tttggggtct ctaaattgga tgattggtgc 173460
ttaattatca gctgttttgc actgggggca ggggttaaat tgggaatacc tgcttttcac 173520
ccactgcatc atccggttct cttgtggatt cacagaggcc agagcaagag aaccagggat 173580
agacaggagt gatcagaaaa gattgctagg acccgaggag gtaaacagaa aatgcacaca 173640
gctgcttgtg gccatctcta gaatggaatc cactctactg tggaaagaaa ctaaaataga 173700
gatgcccaga cagagaagac tgaagggtcg gctgatctta gggaagttca accaaaactc 173760
tgactcagga tgagagcaaa gaggctctga aaggactgcc catgcagtga gggtcaggag 173820
gcaggatggg ttgcaggcct ctctggagcg ctgacagtgc ggtaacagag ccagccctct 173880
cctcctcctt tcctacaccc ctgtattatt ctctgctcct ttgctggctt tcttcataga 173940
acccaacttt actgttgtct ttgggtctac caagtgagtt gaataactct tgcagggatt 174000
gcgacccttg agcagaggtt ctcaaccttc atgatgctgc agctcctcct tcagtccctc 174060
tcatggtgac ctcccaaaca taaaattatt ttgttacttt atgactggat ttcgctacta 174120
ttatgaatgt aaatagaggt tcttcgaccc ccacaggttg aaagcagctc ttgtagatag 174180
attttgagca cgacttcatc ttcactagcc aaagcttctt gtagctttgg aaaggacaca 174240
gcttgtaaca ctgtctttca cacagattcc ctccctctcc cacacggatt ctgttctggg 174300
gattaaatct ggggtttcat gtgtctcaag actggcctta aactcagatc cacctacctc 174360
tgcctcccaa gagctgagat taaaggtgtg tgcaactact gtttagctag gatttatttt 174420
cttaagagca ctgaatgact agggaaggtt ctgatctagt aaaagctcat gatgcccaaa 174480
ttgctttgtt atatattgtg gctccctaga tgaaggttga ttaaatgggt ttttggggtc 174540
ttgccctctg aaacttaggt gtagggtgac ctctggagcc ttttcttcct cagggatgct 174600
tttcacagtg gctccatagc cttctgagct atcctgggat cctggctgtg accggtctgc 174660
ctttcactcc ctacttatga tggctccaaa gatctatctt cacatacatc tccacccagc 174720
catgtaagaa cagacaagta cacaggctct gtcttagggt tttacttctg tgaacagaca 174780
ccatgaccaa ggcaactctt ataaaggaca tctcattggg gttggcttat aggttcagag 174840
gtttagtcca gtatcatcaa ggtgggagca cagaagcatc caggcaggca tggtgcagtc 174900
ggagctgaga gttctacgtc ttcatctgaa ggctgctagc agaatactgg cttccaggca 174960
gctgagtgtc ttatagccca cacccacagt gacacaccta ctctaacagg gccacacctg 175020
gaaatagtgc tggtccatgg gctaggcata tacaaaccat cacagagccc gtggatcctg 175080
gctaaactga gctcaattcc tgcttctctg ggaagcactc agtatcaaca ctgcatgacg 175140
gagcacgagt gttagtggag tacggtgtga ggacagtggg acactcttgg gaagatgaca 175200
ttcctaggga tagtttttcg tggtgatgag gacaacagct ggagcaaaat gcttattcaa 175260
ctttgccctg gctctcaaga ttttagaaat agcctctgtc gaatgtattt ccaaactgag 175320
ctattatgac catattagtt tccatagttc atgagaaact ttgagtgttt ctataatttc 175380
gtggaacttg cttttttgag ccagcacgtg taatttttct ctgtatgtat gggtgttttg 175440
cctgtgtaca ttgttttgca gtgccccaca aggacaggag agggcgtcta ctctcctggg 175500
actggggata cagcgatagt gtgtgggaat ggaacccagg ccttctggaa aagcagccag 175560
caccatgtat gttttaaaga aatgaaacgt tcataatgag ggaggtatgc agtttggtcc 175620
tttgagaggc tgtttcctct gccccttcct tcagtttcat cctgccattc catccatctg 175680
tccaaaccct gagtcttctg ccccttgttc tgagagctcc taaagcccca ctagtcacag 175740
ttttacttat tggagtgcac ctgtggggtt agatgtgtgt gcaagcatgg gccaggcaca 175800
catgtgaaag ttcggggata actggtgtga gtctgttctt ccatcatgtg gatcccaggg 175860
ttcagaccca tgtggtgagg cttggttctt ggtgctgagc cacctcacta gtcctaaatg 175920
tacttgaaac aagtattttt tattggtatt ggcctttgcc tcgcaaactc ttgctgtaga 175980
agatgaaggt gcagatccac tcacattgaa cagttgggtg atagagagag agctggaggt 176040
gcacacacca caaatttagt ggttgatgcc ctgatgaact tgtttcctct ttgttacctc 176100
ttggtttctt cccttgtgga actgctgggg cagtgtccat gagctttcac tgccagtgtg 176160
gtttagccac cttatttggt tttgtttttc tcaccctttt ccttttgct tctgtaatgt 176220
atctttacac tccttcaggc cctgaccagt gcaatcacag ggatgtaaat tatcggaaag 176280
agatactttg gctaaattgt taaacactca cattgtctta gtcaaggttt ctattcctgc 176340
acaaacatca tgaccaagaa gcaagttggg gaggaaaggg tttattcagc ttactcttcc 176400
acattgctgt tcatcaccaa aggaagtcag gactgaaact caaacaggtc aggaagcagg 176460
agctgatgca gaggccatgg agggatgttc attactggct tgcttcccct ggcttgctca 176520
gcctgctctc ttatagaacc caagattacc agcccaggga tggcaccacc cacaatgggc 176580
cctccccact tgatcactaa ttgagaaaat gccttacagc tggatctcat ggaggcattt 176640
cctcaacgga agctcctttc tctgtgataa ctccagctgt gtcaagttga cacaaagcta 176700
gccagtacac acatgacttc cagtgtccat gttacctgcc agtgaatcca acaggtagtg 176760
tgttaaataa aagttgtttg tgggcataag agagtgagta gatctcttgg acaggcaggt 176820
tctagctagt tttacctagt gacctagtct tctctagtaa ccatctctct tggaaagtgt 176880
agtctttaaa ggagtttgtg ctggctagtt ttatgacaac ttgacacaag atttaatcat 176940
cagagaggat ggagccacac ttgagaaaat gcctccataa tattggtctg taggcaagac 177000
tatagggtat tttcttaatt agtgattgat ggtggagggt ccagcccctt gtgggtggtg 177060
ctatccctgg gcttgtgctc ctgggttcta aagctgagca agccatgggc gtaagccagt 177120
aagcagcact cctccatggc ctctgcttta gctcctgcct ccaggttcct tgccagttca 177180
gttgttgtcc tagctttctt cagtgatgga ctacagtgtg ggagtgtgag ctacagaaac 177240
ccttgcttcc ctcacttgat catggcgttc cattgaagaa tagaaaccct aactaagaca 177300
gaagtgagac caaggcttag ttctctaatg atgggtgtca gtcaggggat atgtgtaggg 177360
tgggaatggc cttgaagttg attgagtttg cttgatttgt gcagaaggaa agtcatgata 177420
tgctaagtag aagctcagtg tcaaaagtga gggaggcaac tcgggtctta ggctcctccc 177480

-continued actgctaaca aagtgcagct gcaggtttag tgtgcacgca cgcacgcagg gcaggtgatc 177540
ctgttgaaaa gatgaacccg ttggagagct caggaaggcc gtgtgttttc tgttagcaga 177600
atgcttccta atgagtagga atgtgctgcc ggtttcacgg agccatatgg caactttgct 177660
aattttagct gggtgcagtt gcctgattct ttccttttgc cttctagaac ctctgagatg 177720
ctgcacaact tttcttgtaa cttttaacct gtgctgcttg gccagacact atgtgtccct 177780
gtttccatga cttctttgtc cctcatgggt ctgtacaggt tgtactgcta ccaagtttca 177840
cagccaggta ctgcatgcaa cacagggcag gcagggcaga agcagtgcgt gtattcccgg 177900
taggatctta gagtctgcta tgcaggtgat tagacttgtg tttgacatca gcccattgaa 177960
aaatcgatag gtttctgagt gaatgctttt actcatttta aagcagtggg attaattata 178020
aaacctgtgt agtgtatctg gttcatttta gcaaaagatt ttaatgttct actctgaata 178080
acttggattc agtttttttt ttttaaaggc agtgctcttc atgcttggcc tgatgtgaaa 178140
gtcattaatt ggctttccag tcgagggtgg atctggtctc gagcacacag ggatttttat 178200
atgtataaat atctgtgcag tatcgtcatc agacaacatg tcacagagtg ggccctagtt 178260
gatgacgtct gtctttttaa agctaatgtt tgtaagcttc tacagccttt tttattgaga 178320
gagagagaga gagagtgagc gttcgcaatt gagcacacac gaaggtgtat atcatcttct 178380
cccgtgatga ttcctcacct catacctgta acgggtactc cagtggtact tgagtttctg 178440
tctgcctgac ggctgccact gctctgctgg agtagagcag tcatgtgact gcccatcaga 178500
gccaaggctg ccatccctct attctgaagg gagggaccct ctattctggc agtgttttat 178560
ggaaagacta cacttaaatg ttctcagtac acttggctaa taaacaaata cacaatacta 178620
atataaaaaa gcattagtta ccaccacaga ccaatgaata tacctcagag gaatctaaaa 178680
aaaaataaaa ctatttcata attcccaaat agctcatatg ttttctttta aaatgaattg 178740
ttttttacaa agctgtattt ttgatttatt gctgttctca ccagaatctg ggattttgct 178800
ttcagacttc tcctcgtgca tggcagtgac gaagagcaat ttaatccatc cacttcaaag 178860
aaatgttttt cctgcattaa gtcagtttta tttctagaga tcaaatgccc caccttttct 178920
tttgttctta gagaaagcac aaataataat tacttatgaa aaataggaat ttaatattaa 178980
tgatttcccc ccgtttgcag tatgactcat cttacacagt ccctgaagag acaggatttg 179040
ttctctgctt tgaaactgga aatctaatta attggtatta gatttttgga gtacaggcaa 179100
atggaagagg gagagggtgg gacatcggga acagccaccc aggaggacaa gggtgggcaa 179160
aggtagagaa agggttggtg ggagggctgt cctgccaggg cttggcgttt gtaaagcaga 179220
gctgtgacat agctgttcta tgcttttcag aaatcttctg gagagcattg tgccttcgct 179280
gtcactctct caagtcagag tctttatcta aagaacacgg ccggaatggc taagacacag 179340
cagggacatg tgaagtcaaa gcacagaggg actctggaat ttaaatgtta gcatctcttt 179400
ctctgatgtt gtgatgagat ttcataaggt tgtgatcatg gaaaatctgg taccagcctt 179460
ccactggttc ctctaccaaa gggtattttt ataacaatgt atttttatag ttaatggatg 179520
aagaaaacta aatatagttc ataaccactg agaaaattgc ctaatttaaa atattaaatg 179580
gtgtgtttta gtatagaaat gctgtactta cggaagtata aatatctaag aatcaaagct 179640
tatttttata tgctgcatac aaatggctta ctcattgctg cactgtctga gatacagcac 179700
atgtccagtt aacatacagt tagtcccaga ggagagctcc tcacccctcc cccagctccc 179760
tcctcctccc tcctctgctt tgcctcccta cctctgcagc tcttatttaa tgtcaaggcc 179820
gaactgaata ttgggcagaa gtggcaagta cttcatgaaa aagtacaaat actgaaaatt 179880
caggacaagt tttttgttta ttacaattgc tttagtaaag ctgggtttct gggtattttg 179940
tatcacttgt tattattgac tagtttttat tattttacta ctgagaagtg gcccaaacgt 180000
aaactcaatg cagaactgaa gaaccttaca acagattgtc tagaaaatgc attccaaaca 180060
gtgaggtgta caggactgcg aagctgggtt ttccctgcca gagactttct ggagacgctc 180120
tcaggctcca caccgcttgc cttgtcgtgg ttctgcacac ccgagtgatc tttaaagtta 180180
catgctccac taatacaact tcagcctaat actgaacatt gtttctttgg tcctcactac 180240
acctctagtt ttggtcattt ggggacacca gaatattggc ttttttcaca gtggggtagc 180300
agcagcgata gtgcacgcct ctgatcccac tacttggaag gcagaggcaa gtagccaagc 180360
ctggtctaca gagcaagttc caggacagtc agggtcacac agagaaactg tttctcaaaa 180420
aaacacaaaa aacaaaaaaa gagaaaagag gaatattgtt tgaaggcctg cctgagactt 180480
gtggtggtct tctgccactg gtccacaggt ctaaccccta gaatctaacc taaccaatct 180540
taacattcat gaaacacagc cacccatgcc cagccatccc tcccttctct gaactaaagt 180600
tggctcctta cggctcaagc cttcattttc ctcttctgct gaatgacacg tgttctgccc 180660
tcctggaagc attgtgaact actggccaat aaggactacc ttgacacacc acccactcac 180720
ccactccaag gccctcgggc tgtattccac tgcctatgtg ggctgtgatg ttagaatcac 180780
ctgctgcctt tttcctttta aagatttacc aggtgagtat taaaaggaga aaacagcata 180840
ttttgttatt ataaacagtt ttccagtatg gtacctattt ttatccaagt gttccaaagt 180900
ctctcctagc ccttgttccg tgttctatct gattgataag tttctaaaaa gaaacttgtg 180960
tgctgatttg ctcttggttc tttgtatctg tcttttccta aaggtgtaaa atggtctgtt 181020
tgagcatatt gctgcaacag ttagttacac acccaggcct ggagtttata agtggcaggg 181080
gtacttgcct gattgagttg tcataaggaa agttgtgtac tttacacaga actactaata 181140
gatgaattta ctgctatcag aaagctatca taccctttag atatatgtct cataaagtct 181200
aatgattgct caagggctat gacaaacatc actaagatgt gtttatttga ccctcaaaac 181260
aacaatagta ctccactgaa agaagcgatc agaatctcct ctgaccataa ccttaggttt 181320
tctagcaggt gattttaaaa actggagaag gagtctgagc accagccctc actctttgcc 181380
ccctaactct aggtcatggc cagctgcctt aggctctgcc ctcagactac agtggtcctc 181440
aacactgcct tcctgtgtgt catgagctag gtcaactttg attccttgtc aggttatttt 181500
tgttcaatga tgacaaaaat atctaataca catggtaaca tatttgagag gtattttctt 181560
tgatactagt ttttatactc ttaagttcaa gtagtagtat tttattccat tagggagaaa 181620
atgttgtttg ttttagatta aaacttttta agggctaggg agaaggatcg caggtgagag 181680
cccgggctgc tcttgtagct gtcagtaaca ggcacggagt tcccattcac agcaactgca 181740
gcttcatctc tcactggatc ccccaacatt accgtcagcc aagtgccccc ccacacacac 181800
actccttctc taacccggag cctcacattt accaccaagc tgcatgcctg acccaagtcc 181860
aaggaataag atagagattt aacagtggag gatgaactga gagaagagca gaggcgtggg 181920
aatttaccgt gtccacacaa atgtctctct gtagagcaat tctctggaaa ccctgcgccg 181980
tactcctcaa ccctgcccct cgccttgctt tctaggcttg agctgcaccc tgaagtggag 182040
ctcagagggg aataactttc cattccacca accttcgaat tcactaactc tcactgtgcc 182100
caggccaggg acagccctct ttgtcggcca aacagagtga cattcctggc ctacagtgct 182160
ggctgttgaa gatacagatg tcctgttctg gcttactaat ctgccttcag tgcagcggca 182220

-continued ttcgttctgt tttatggact gagaagacaa gagcactcag gcatcctcta gagcgttggt 182280
tctcaccctg tgagccatgg tccctttgca ggggaatgac ccttactctg gggtcaccta 182340
agaccagtgg aaaacaaaaa tgtacattat gattcctaac cgtagcaaaa gtagagctag 182400
gaagtagcaa tgaagataat ttagagtggg ggtcgccaca ccatgagcag ctgtatcaaa 182460
ggctgacagc attaggaagg tcgagaccca ctgctctgga tgcatatcgg actgatggaa 182520
ggcaagccct ctagtctgtg cccgtgtccc ctacagtctg aaaccttggg aggacacctc 182580
ttgtgtatcc ttctgccaga ggatatatct aggaggacac accccacaga cagtgagggg 182640
cacaggaaag gacaccgtgt gctccatctg agcaagggtt gtcagcacct cgctcctcca 182700
cactgaagag taaaactaag ggtgcacggg gagggcctca aacccacaca gaacatagtg 182760
catgcttcag aatcgatgac tcgtgggagc tcagtgccaa gcatgcaggt tcccttgtaa 182820
ggcggtgacc gctctgcagt gcccagagaa gtaggtaagg gatgtggtgg cacaggtctg 182880
ggtcctgtgc ttctaggtgg aagagtgagg gtctgactaa aaaccagcgt ccctgtcttt 182940
gggatttacc agagagaagg gagtcctata cagtaacaat agcagccagt cctatgtcct 183000
atgattggag aagagggtgt ttcctgcgct ctgaggacca ctaggatgag tcagagcctg 183060
tggagaggcg actttagggg agctcttagg gaagagagca aaccacgcca caggtaagac 183120
ggtagaggaa ccaagagaag tgggcacagt gtgtggccgg tcagctctct gaagaaaacg 183180
cagtgtgatg ctctttgaga agaccagagt gcacccagtg cttgtggtta gcagttgtcg 183240
catgaggaag gatggagagc cgaggacagc ctggggagga ggttctttcc tactttgtag 183300
tttctgaagt gtgttttaca tctgtcattg acatagccat gatgcacagg tggcagacac 183360
tgacacttgg tttgcctcgt tctgaactgt ggtgctaata atggactcaa gccggagcta 183420
caatcttctt tgtctactgg caaatagaca tcataaacac tttccattgg gagcagaaag 183480
atttggagga tctacataat tccctaatta tttttaggtt ccataaatta gactttaaca 183540
gattttttta aatactgcat aaaattgttt tttacaaaga aaatagttac tatggtcagg 183600
gaaaagcaag ttgattgtga atactaaatt gagttacagt ttcgtttgaa tctttaattt 183660
ttttacattt aattataatg aaaacatgca gcgtaaacaa ggatgtaatt tattcagttt 183720
acatgtaatt ggcacattgc ttttgtgttg ttttctaaca ggttgtggct gtgtatgtta 183780
tgctgtaaac ttacttgcca tccttgaagg agctcatttg cacatgtatt gatagctatg 183840
catcttttcc cctgtaagca actactctaa tgctgatggc acgggctgga gagatggctc 183900
aattgttaag agcactgact gctcttccag aggtcctgag ttcaattccc agcaaccaca 183960
tggtggctca caaccatctg taatgagatc tggtgccctc ttctggtgtg tctgaagata 184020
gctacaatgt attcatatat atatataaaa taaataaata aatagatttt aaaaaaaaat 184080
gctgatggca cgacttcagc gctgtctggg agtttgagtc ctggagtgct cgctgtccag 184140
ctcctctgta caaagtcaaa gctcagccat tgacatcctc tgagcgcctg atggggctgc 184200
tcaccccatc tgcgttgagt cattgagtgc tgtgagcagg ccaggtcaag gctctgaact 184260
cggagcaaga ggacctcacc ccaccccctt ataattgtgc cataggatgc tcagcttcat 184320
aatctatatt ttgaaaatgt ctgccaggaa cagcatgaac cctctaaact cattttctcc 184380
agagcctgaa aggaaatctg atacatgtat tctggaggtg agaggtgcca tctgggtcct 184440
cctcctagcc agtcccgccc tccagggcag ttggctgcac tctaattcat tcataggcac 184500
acctgacccc agcagagatt ttggtgttga tgtgcccttg gtgtgcacca ctatttaatt 184560
tgctcttgtg ttttgttgca gagaaagcag cagctgccaa catagatgaa gtgcagaagt 184620
cagatgtgtc gtccacgggg cagggtgtca tcgacaagga tgcactgggg cccatgatgc 184680
ttgaggtaac cacagcctta cctggttttg atgcttggag taccacgctc ccgtggcttt 184740
gtatcacaca tgtttcagta ttcatgtgct gcatttatgt atgttcaggt acatatgatt 184800
taaggagaat ccacattgct gtgcttactg atgcaagtgg gaatgtctat ctgtgagctc 184860
ttgccccagc aacattctct gtatgtggaa cagcatagac ttcaattaga tgaaaatacg 184920
aagtgcaggt gtgaattgtc agttgagcac ttattttctg aagctgaact tggacgtcct 184980
attgaagggt gggactcttg cctcaggctc agggttcctg tgtgccacat gcctcggcct 185040
gtgtagacgg tttaaaatgt gagagccaac aaaacgaggg ttatgctttt tagggctggt 185100
aattccaact agtatgtttt tctcatagaa gtcaaggtta aaataggaag aaggaacttt 185160
ttaaaagcat aaccgagtga ctggccttag ggccttaggg cagctactgt ctcaggctta 185220
taaaatcctc cttgtttttt taatgagtac taaacaccca gtgctttact gtccctcttt 185280
caaagttaaa attcaagatg tgggctatgg taaaatgaga gaagaaatag cagtgaatag 185340
acagagctgc ctgagacata aattatctca agtctcgtgg cgctctgctc tgctgaagac 185400
attctaagcg taaaggacca cgtggtcaga accgcggcgt tgtgcctgct ctgtgcctgc 185460
tgcagcaggc ttgtggattc aggactagga ttttttaaac aaagctagtt ggcactctct 185520
tgaccttact gtcccctttc tcatctagaa acgctaaatc tgcaggtatg tcctgtgtag 185580
ttgggagctc gcctttgcat taacaactaa cagctcatcc ctagggggca gaggggcact 185640
tcccacacac tgtaggagcg ggaaagaaag ctgtggccag gtgaccactt agaattacat 185700
aaaagagccg aggaggacag ctttctttag aaaaccttgt gaattgtaag cagagattta 185760
attggaattt ttccatataa ctgtttattc attatgcctc ggggagtggg aaatagcact 185820
gaaaccccaa ggaggacttt gaggccttta aaaagaaacg cttagagcaa ggcaggctgt 185880
ggcttagccc ttgcaacaag ttcattaatt gtagaaactg gattgcagga tggcagtggc 185940
ccttatttca taaaatcaaa ccaaaatttt tgctgtttga aaataatctt ctgagaatga 186000
gtggagtgca ttgaggaagc gcctgtgcaa gctgagtact aagtcagcgt gccagagagg 186060
aagctccggg atctagtggc ttacggctta actggagacc tttcaacagg gagagcatgt 186120
gtgtgctcgg agagctgttc ctaggcatag atgcacactc atgcttgcat catagcatag 186180
cggttgctag gcaacagaag caaatgtcag ctcttgccat cagagcatat catagtgagc 186240
tttaaaaaac acagttttat aaaacgagcc actttcattt ttcaatttta ttaggccaca 186300
aatgagcctt ctcaccatac tctaagaagc cacatgccct ttcaaagcca acactagtaa 186360
tgtagtattg aaagcctaag aactctgctg aacgaacacc cagcggtggc agtagtgaga 186420
agtaacaaga gatctgtaag tgccatgtgc tgttgctgtg cctctccagt gtacacagct 186480
tagtgcagcc tgtgttgttg gccacttagg tttctagagt cttgctttac cctgaatgtg 186540
catcatgcta tagagaaaac ctgacagact agttaaggaa agtctaaagc cagtgggttt 186600
ttttgtttgc tttggtttgg gtttcattgt tgttcgcttt tttgctgtta ttattacaag 186660
acaggtcctt gacctttagt ccagactggc cttgttcttc tactgtagcc caggtattaa 186720
gatagctgat gccatcacac ccagtttact ttttctttaa acaacttctt atttataccc 186780
cagaatcagt tttagattga tggaaatcta gtctgacaaa acagaagcct tttatataaa 186840
cagccttggg tggaccaagc attccggcca tccctcacca ccgtgtgggg actgggcatg 186900
ctttaaatgc agtagatatg tatctgaaga gcctaagtgg catcagctga ctgggaattt 186960
agctttgaag gtgtccaggt cttcttagac tgtgaaggga aactctgctc tgttctgaac 187020
aagcatcaga tgtaggagag acacggagct gccattgcca gggcagacca gaaggagtct 187080
taccaggaga agtatctgag ctcctggagt cgctagcgga ctatgtgcaa ttttccttcc 187140
ataacccctg atcccctctg tgccttggag aagagggcct tgggaggaca cagtatgccc 187200
acagcagagt gaacatgccc acagctgctg tttaccttct cttcctaaag tgtggagacc 187260
agtctctttc tggagtctag acatggtggg cacatggagt gacagtgagc ccgttatagc 187320
atgcaggcaa ccagcactga gctgttttag ccaccccCaa gacacttagc ccgtagcacc 187380
gtccccattc acctacctgg ccagagagcc tacccagatc cttccctaca caccagacag 187440
taaaggccgg atgttgcttt gaaggtctgc gaccatctgt gagttcactt aaatcctggc 187500
caccttaaaa gtaaaaatta ggggatttct cctgatattt ttaaactgag ggaaaaggt 187560 agcagcagcc cctttctctc ttggcatatg ccctgactcc tgcacttagc cctgtggtac 187620
tcccccatcc tgctttgttt atttggccat agttctcttc tggcaggtta acagacttca 187680
tgtttctttt ttggttttaa cagcagaccc taatctagcc tctcttccac tataatggaa 187740
tcacttctat ttccccagag aacatgtgtt cattgtttct gaagggcatc ggagatttct 187800
ttccttgaag aatcagttcc cccatgacag ctgcatgttt ttatgttgtt gcaccctgta 187860
ggccctcgat gggttcttct tcgttgtgaa cctggaaggc agtgtggtgt tcgtgtcaga 187920
gaatgtgaca cagtatctac ggtataacca agaagagctg atgaacaaga gtgtctacag 187980
catcctgcat gtcggggacc acactgaatt tgtcaagaac ctgctgccaa agtccatggg 188040
taaatgtcag tggatcccgc tgccccccac tactccaaca gattctcttg gtgagagtga 188100
gtcagtaaag cctgttgtgt ctgtcatagg catgtcagca accgtaagca ttcaggtagt 188160
catggaaggc tgccgatgct gctccttaat gcactgttga tcttatgagt tgtggaatga 188220
tgcaggcgga aggcccccag caactagcag gagggtttgt tatattttaa aacaaattgc 188280
aaccttccct ctctgcccac caacttgatc atccattttg cttctcgcct gccatcaaaa 188340
gagtgggcca tgacatgttt gagatttgac tcccttgagt tctatgtata agaagaatat 188400
gtgtgtatgg ggcattctga aaacagacac aggcacaatg taacagacag tgactccaga 188460
ggactggttc atgttagtct cctgagcagc tctgcaggtg gcattgcagg gcacagcccc 188520
tcagcccttc atgcccgtcc atctgtccct ccgttgttcc actttcccca agtttcttga 188580
cctctatcct tctttggagg attctgttca gaggttgcct gtggtgcagg ccgccgttgg 188640
cagtgagtgc ctggcagcgt ggagctgcct tagagggttg ctgttcactc ttagtggttc 188700
cttagtgttg tcactgttag ggatattttc acaggtaaaa cacagtacat atttcagtgc 188760
ttaggaaggt cattcctgga ttgcaagtat tctttttctt gaaactgttt gtatgtgcta 188820
gtcttatagt taaccagtaa atggggaaag atcctttttta tttaccatta tggctagttt 188880
tgcttcatga ggataaaaca tttgcaaacg cagccgtcct ccaagatgtg tgagcacttg 188940
tgtggaattc ttctgtttca gaagagtgga tttcatagtt gaagtaacca attttcttca 189000
gggattttct gttgctcaaa ggacttgtgc ttgttacctc ctgtctgaag acccctcccc 189060
ctggcctcac gcacctttttc tttagtttcc acttcttagt gtgggctgat aagcatgttt 189120
tcctttcttc ttggacagtt ctgtagcgtc tcattatgtt aatagatttc acaaatgctg 189180
atagactaaa ggtagaggtg taaaggtacc tggatgacca gagcagtggg caggcaagtg 189240
accttggctt cctgctctct gagtggtttt ccttccagcc tgtgagcaag ccttggcctg 189300
ggtccactgt ggcatctctg tccctgtcac ctgttaggcc aatgactgct tttcataagg 189360
ttgccatttc attgggggat ggtaaagaaa agcattaagg tggttttact tggggcactt 189420
ctgacaactc acatttctct ggaggagaaa ttaacacttg atcaattaac actctttagt 189480
aacccacatt agtcattctt ttctttcttt tgttttttc tctaatgtgt ttcagaaggt 189540
attgatgtat ttcccttcgt taagcagctc ttctttcttt tcattactca tttcctttac 189600
atcccagtat cggcctcccc tcgcctccca ttccccccaca attgtttta attttgacac 189660
taaaacaaga cagcatcact tgacacagta tcagcacttt gtctttaaga atgttcagtc 189720
ccactaagga agtctatatg aaccctaagg tagtctatag actgtaattg ggtggctcag 189780
gaacagctcg ttagagacaa cactctaaag tttatttgag aagtttgaca gcagcgtgtg 189840
tcagaggagg cccaagaagc tgggttgtgt ccagtagagc gagcaccctg ccatgctctg 189900
ctgtgctcag aagggagaag ctcagtggaa gcagcaggag cagacatcca tgtggggctg 189960
agggtggagt gtggacagcc tggccagctg ggcaggtggc tatcagcgag gtttgcatta 190020
tatgttgagg ttgctctcag gctaactcct accgtccgag tcctctggaa aacatcagtg 190080
cttgtcacag tcagtgccat tcccaaagtt ttaagcagta tttgcacctt gaaaaccaga 190140
atgcaagcag actgaactat atttccaaga aatcaaagat agaaacccaa aaatagagtg 190200
tgcagtattt tagtactatg tagtcagggt gtggccttga atagaagtgg tcatggtgga 190260
ggctctggag tatagaagat gtctgcaaag cccaagttcc taccaaggag gtaggaagtc 190320
cttgtgctct ccctgcaccc tcttagcaat gcagcagccc tggaacctat cgctccttgt 190380
gatcaggtgt ctctttcccc cctcgcagtg aatggaggat cctggtctgg agaacctccc 190440
aggcggagca gccatacctt caactgtcgc atgctggtga agcctttgcc agattcagaa 190500
gaggaaggcc atgatagcca ggaagcccat cagaaatacg aggcgatgca gtgcttcgct 190560
gtgtctcagc ccaagtccat caaagaggaa ggcgaaggta ggacgaccct gggagagaga 190620
ggtcacgtgt ctgcacctcc ctcctgtgca cgactctggc ttagtgatca caccctggca 190680
ggcgctcaca gagaagacca ggaagccact tcctgattcc ttcccatctt tattcgtttt 190740
gagcttctgt tgtttttttt tttcctctac aacattagac gttgaactct cacatgctaa 190800
gccgtgttgt cctctgagct gttctcagtt tgaaaatgct ctgtagtgat gtaagtggcc 190860
agtgcaggcc cagcacagca gccaggattc atatctgagg ccggcatttg aagctgcagc 190920
agggttgatt tcagttaagt gcttatgtac atagcatgtg ctcctggtga ctgtggcact 190980
tctgcacccc tgacagtagc agtttaggag atcctgggtt gctttgaata tctaatgtaa 191040
atcgtatgcc acagccccca aaaaacatgc ctgggtataa gcagcatttt tctatagact 191100
ttccagggag taacagaatg catgtaatta tctgtgcaca ccaggccttc aatgtgatat 191160
aacagcagag aggacaaaca gaagagcagg ggctggtgag ctctcagcaa ctgacagggt 191220
tgctccccat aatgagatgc tgatgtcata ccattccctg ccttccagtc actaagtgtc 191280
cctctgtagt gtaagatgtt ggtagaaaaa gcactctggg agttacagag ggaaacagct 191340
tttgactagc agtgcaatga aatattctag cagataatta ggcagaccaa cccccaattc 191400
agccatcagt tccgcctctg gacaaatgcc ttcacttctc tgtgtatcaa tgtattaagt 191460
caaattacca gtgtgagcat cagaatctgg tacagaatgg gcggcgtggg actccggggt 191520
ggaatactta cctgatatac gacaccctga gttctgttct cagcttgtgt gcacacacac 191580
acaaagggct tatgacaatg gctgaactat agtagccact gaatactaat gtagtactgc 191640
ttaattaaaa tgtgtaactg ttcttaaatt ttatcagaaa ggaattccag agagctatta 191700
tagagatacg gtatttcaaa atgaaccttt gctcaggtgt gactgtcaga cagtttgctt 191760
ctgttcaccc aacaagagag agcgacactg cagaatcatc cttggtagtc cacaggaaag 191820
tgaggcacag ccgtgctacc tgactgctct gcactggaga cgaaaatgga ttctggttga 191880
gatggagcct ggttggtgaa gtgcttgcct agaacgcaca aacgcctagg ttcagcccct 191940
aaagcacata gaatcagtca ttgtacccct ctaatcctag actcgggaga tagccaggtg 192000
agttagaata gtgagcgtca gcaagtgtga cgcccagcca agacgtagca gactctgtct 192060
ataaattcat tagttagttc atgaatgaga ttggattttc cggcagagtg tggtggtgca 192120
cacctctgat cctggcactc aggtgggatc gggtgcattt atgtggtaac tacaacttca 192180
gtgatcccag cacgggataa aggtgggagt cccggtaagc gacagagacc agcccgctct 192240
acaactgagt tgcaggggag gcagaggggc atagcaagac ccttgccttt aaaaaaaaaa 192300
aaaactgtat gtttataaaa aaacaagggc ttcttttctt tttcttcttc tttcttttat 192360
tgtagctaaa atactcatgg ccttacacat ggtagaaggt tcaaccactg acccacatat 192420
cccacttccc atggtgatta cattttaacc taaagacact agccattact tgagatctac 192480
ctgctcccaa aaaaaaagac aggaagcttc ccaagtttac aggggaccga gtgcagcccg 192540
tggcgggaga tgtgtgaaga gcctgcttgc ttttagccct ttggtcggcc ttcctctttt 192600
agcttgaaag agccatacga agtgctctac atgctacaca cttgttctcc agaagtaagc 192660
cccacgcaaa acacaatgaa agtgggggct ggagagatgt cggcagttag gagcactcgc 192720
tgtccttcca caggacctct gttcagttcc cagcacccac gtggtagttc acaaccatct 192780
gtaagtccag tcccagggga tctgtcagcc tcttccggac tccacaggca ccaggcctgt 192840
aagttataca cagacacata tacaggcaaa acatctatac aaataagtaa cattttaaag 192900
cgttcacgtg gggacaaggc taacccttac cactggctgt ggaggaactg gccatgtcgg 192960
atgctggcta caacagtgac tgctgcatgg acagtacact gtatccttga tcattgttgt 193020
gcaccctcgg tccatggcat cttgccatct tcatgaacct acatggtttg ttaagtataa 193080
ccgtgaagct gagaagcaga acccttccca actgtgtctg gtcttagttc tagcttttttg 193140 ttttgcttac tttattatga attaattttg cttttacacc cagtggctcc atacttttca 193200
tcattgggga ggtggtttcc agtcattaac cctggcttgg tgaatagact cttaccacga 193260
gtgctgtgta gtttcggcat ctgcccctgc tccagctcat cctaacagcc ggcttccact 193320
atactcaagc agagaatgaa gccagtgaga agctgagaac catggcaact cattgattca 193380
ccaggctgtg ctgtcataga tatttgagtt gatttgatca ctacaaatat gataaacaat 193440
tgtgtcctct taagatttgc agtcctgctt gatttgtgtg gcacgaagag tccccatgaa 193500
ggaaagacca actcttccct catcagaaag ctttaccacc cgccaggacc tccaaggtaa 193560
attcctgtca gagaagacaa aagtggtcgc ttgaaaatgc ataggtacct gaacacagtg 193620
cctgtctgga ggaccacagt gttcctcagc ggttgcagtg gtgaccttta gctgctgaga 193680
agcagcagcc ctctttcttc accatgctcc ctcctggagc tgtatttagg ctgccatctc 193740
caaacagcag ttctgtctct atgtggtcca ccaaccccag aacagaatga ctttaaaaga 193800
tcattgttct gtgtagaatg tgatattaat tagagatgac ttgcagtatt gggggtgaag 193860
ggagctaggc atgctagcac aggtctgaaa ccatgtcagg aagtaaggcc gagttccaga 193920
ccatcctgga ctctacaaga tctgtctaaa aatcagagat aattaagatg aataaaatag 193980
aaaggacaca ggacgataga gtcagctgta taaactgtgc cattttacat gaatccagtc 194040
cccacagata cagcccataa ctgtgagtaa atctatgtat tcctaagtgg taattgtttc 194100
tctggaaaat tggtgttata attgtaatgt ctgctgttat ctttcaggca agatcacttc 194160
actggacact agcaccatga gagccgccat gaagccgggc tgggaagatc tggtaagaag 194220
atgcattcag aagttccaca cacagcatga aggggagtct ctatcatatg ccaagaggca 194280
tcaccatgaa ggtaggcctc tctgcatact actctatgca gcctttacac atttgcttcc 194340
tgtggggacc gtctaccgaa gctcgcagtt cagggcttct atgtcctctg ctggtgctcc 194400
ccggcccagt acactacttg aggaaataaa gtaagaggtc ttgatatcac aaagatggag 194460
aaagaggtca ttttctgtgg tcctcatact tctggataca tgacaagata accaaggtct 194520
gtgtaattta agaaacagga ccaagttcat aagagcaatc tggaaggaag aatatataga 194580
tgggattttc aagagccagt caatcccaag ctctccttca taattcgaac agcagattcc 194640
agaagtttgc agaaggcctg gagaggcaac gggctctgct cttggtcaca gactaaaaga 194700
acagctggaa ggaaactcaa cactgccatt gcatggcctg gtcctccttt gtcttctcct 194760
caccccacac caagcctctg agagacgccc cacctacctg tgcacgttac aggtgttggg 194820
tggcacaggg tcctggccag catgtgctcc acagcccgtg agggactcag ggcagaccaa 194880
ggctctcggt ctcagcatgg accattgtct gctctgcaga agaaagtctt aagtcatctg 194940
tggcaaatgg agctgtagtt tgtcatccag ttagtgtgca tctatggcct tggctttcta 195000
accagtcagg tttgtacgtt gaagctttat gcttttgagg ccacttcatg agaaagcaca 195060
gacatagtaa atgtacaccg actaatctat ttgctcccca cacctgcatc tttttcaccc 195120
taatttcttg aaaattaaac aaataatcaa acattttgta ccttccaatg ttgtctagaa 195180
taagggcaaa tatatacagt acatttaaca gaaatcaata tttaacctgg tgtttcatta 195240
aataaaggct tggaatagaa gcagaaatta aagagatgcc cttagcaaac atgttcagtg 195300
ccgctgggtt ccaagtgccc tacatttaat tacctagacg gggctctgt tgtgtttaga 195360
gagatgggat ccactgaaag gaaactgcac atagatgtac aaaacaggga atgcagagcc 195420
cagggtgata gctcactcag taagaggact tcctggctag tcatgaggac ctgagttcag 195480
atccccaaga gcgtacttaa agataaaggt gtgcttgctt gctcacctct aaccccatac 195540
tgtggaaggt tggggtggga ttgctagggc acatacaggt gcacacacca tatgtacaca 195600
ctcatacaca cccccacaaa agtgactatg aatagccact tttaaaagaa acttgtaatg 195660
ctaggagctg ccccctgcat ctagtagaaa tgttctagaa ggttttcctt gagttggggg 195720
gcatctccgg ctcaggaaca ggcaggtgtg ctgactcatt attgctgcat agtatgcaga 195780
ccaaatggaa cgtcttcaga gatcacagcc aagggcagag gaaaatcgaa agtcataagc 195840
ccgagtcctt tacacagctg tatttctgtt acctttccac aaatgcttat tgtacaaagc 195900
acagcataca tagaacagga agtgatcccc agagcagcca cttcagcatc cctgcaggca 195960
gcagaggaca gcagccagcc atgtcccagt accctagctc cctgaggtta tagaggaagg 196020
cgctgtttga cagagtgaag ccttacggag aaatcagaga cctctcccct acctgtaatt 196080
ctctggcctg gccaccttgg ggcgagtagt tcaacccacc aaatctgtgt gacaactacg 196140
ttagaaacat gatacttttc ttaaaatcat ttaagaagca actgagtttt aacatttttt 196200
tcctgaatcg aagtcttctt tttgtgtgaa atgtttgtta tgaaatacag ttctataaat 196260
ctcaagatta ttttaagaga aaatacatta agccagttga tttactttgt atttcttgtc 196320
ttaacaatag aagtattggg agctggagag atggctcagc ggttaagagc actgactgct 196380
ctacctaaat tcaaatccca gcaaccacat ggtggttcac aaccatctgt agtgagatct 196440
gacaccctct tctggggtgt ctgaagacag ctatggtata cttagatata ataataaata 196500
aatctttatt ttttttatt tatttattta ttttatttta ttttattttt tggtttttcg 196560
agacagggtt tccctgtgta gccctggctg tcctggaact cgctctgtag accaggctgg 196620
cctcgaactc agaaatccac ctgcctctgc ctcccgagtg ctgggattaa aggcgtacac 196680
caccacgccc agcataaatc ttaaaaaaaa aaatagaagt atctgacctt tctgaaaaca 196740
ttaaagcaat tacactggct taggtctgtg cttgggtttc aggtatgttt agcgctttcg 196800
cctgacacac aatgcttttc agttttacta ctacaccgtg agaagaagca aagcctagca 196860
aagcagtgtg aggcggtggg ccggggaggt cgcctgagga cgagcgttcc atccgacact 196920
gcaaaggaaa gcagaggcag actgtcctta gacacaccat gcttgggggt tatgttgctt 196980
tcatggtgtt tttaatatta ttaagaaatt atggaaaggc ttattttgac ctgataaact 197040
gtttatactc tctttgcccc ataataataa tttgatttaa gaaagtttat ttagggtgcg 197100
agggagctag cccagagaga ggttaagaga gcactggctg ctcttcttga ccactcaggc 197160
tcacgttcat cagcgtccta catagattgg gtttacatac atgactcgta actcccagtt 197220
accacttaac atatagtttg tggcaaaata cacaaaatta aaaataaaaa caaattttta 197280
aaaataaagg atagtttgag tttccaagct gttattcttt gtcatacaaa aaaacaaaaa 197340
caaaaaccca cctaattcac tgtttggtat ttttaaaagt aactgctttt taaatggatg 197400
ttttctgacc tgtaactttt aacatactgg tagcaaaacc agtgaggtca atcactgttg 197460
tgccttgtca cactttcctt gacacttgac tccacttttc tgattttttt cccctttctt 197520 tagcttttttg ttctaatcat gctttgtttc cttttttgcc tgcagttctg agacaagggt 197580
tggcgttcag tcagatctat cgtttttctt tgtctgatgg cactctcgtt gctgcacaaa 197640
ccaagagcaa actcatccgt tctcagacta ctaatgagcc tcagcttgta atatctttac 197700
acatgcttca caggtaatca taaactcagc ctcggtttcc catcccttgt cgagagatgt 197760
gctacaaagc agtatgccac ccaaatgcct ctcgggttcc cggaatcctc ctttttttgac 197820 tatggcatta taaactgtca aatgagatgg ctgttaactg tcggctagaa accactgcac 197880
ggtgccagca aagcattttc ctttaacatt aggaactaca gcatcagatt gggtgtggtg 197940
gtgcactcct tagtcccaac acttggaggc agaggcaggt gaatctctga gagttctagg 198000
ccagcctgat ctactcagca aagtccacga cagccaggac tacatagaga gatcctgtct 198060
caaacaaaca aaagcagaag aagagtgccc agggcttggc tggaccttcc tgttacagtc 198120
cagaagggaa gttcccgagc agtacagtga ggacaggaac attaaagcca gtgctaagat 198180
ctctgatcct ggatgcttaa tccttcacat gagtattctt agactagttt tgatttttgt 198240
tcttgggttt aatttctttg cattagactt taaattgagt ggttttccta tagtaaaaga 198300
aagaaacatg aatgttgatt ttaaaataaa tgtcatagag catattgttt aagatactca 198360
tttgggaaaa tgattgaatt tcaaatttta taaatgttta tggatatgct gagggaaact 198420
ttacgaggtg ctgccaagag atatctacag ttgctctgct taaagagtgc cagtttatta 198480
gatttctcat ttattttgct ttctaggaga ggaataaaac tcaggtaggc ctggttgcca 198540
gctaatagta aagctgccct cacgctgcag ccctttgaaa gtggttatga ggcgcagact 198600
tcaccctgcc ccagctcagc tgccgtttga tgaccactga acatgtttgc taactcagaa 198660
gtagctgcca agactgaggc aaaagccctg gggcctggga gacctgctta taggtgtcag 198720
ggaagtggat tcaaattttc ctggaatgac ggccagttaa aatcacaaac tctgtcaccc 198780
cagaacccta ccacaccaca tttaatcctt tggcctgcag ggagttgagg agatgggcag 198840

```
gaacctatga ggcaacttga tattactaat acctgcatct ggaactggcc atctctctaa 198900
cagttagggc aaggtgttcc ccactaaggc ctctgtctac cgtgaacagg tgacacctat 198960
cagcacctct aggcctacag atgtgcccac agctacagat gtgcccacag ctacagatgt 199020
gcccacagct acagatgtgc ccacagctgg gagccgaagc tgtggcaaag ggttaaatca 199080
agcagtactt atgtggtcgt ttgtgtaagg ctgtggaagt tctcagtgat catcggggag 199140
atgcatattt gagatcttcc taatgtcctc tttacttact gaaatttcaa tatgggggta 199200
gtctaattta agctccatac acacacttca gtaaaaccac agacatcttg gtacgttgcc 199260
tgaaagcatc ccttagtcca gagctgtaca tgttcagtct agcccataag atgccataag 199320
gcatctttta aatgtagtcc acttttgtaa agaaaagagt ccctgccatt tttttaatta 199380
ataagtttac tttgtatttc tcttttatct tatatatgtt tctttcctca ttgtacagag 199440
agcagaatgt atgtgtaatg aatccggatc tgactggaca agcgatgggg aagccattga 199500
atccaattag ctctagcagc cctgcccacc aggccctgtg cagtgggaac ccaggtcagg 199560
acatgaccct cggtagcaat ataaattttc ccatgaatgg cccaaaggaa caaatgggca 199620
tgcctatggg caggtttggt ggttctgggg gcatgaacca tgtgtcaggc atgcaagcaa 199680
ccactcctca gggtagtaac tatgcactca aaatgaacag tccctcgcaa agcagccccg 199740
gcatgaaccc ggggcaagcc agctccgtgc tctccccaag gcagcgcatg agccccggcg 199800
tggctggcag tcctcgcatc ccacccagtc agttttcccc tgcaggaagc ttgcattccc 199860
ctgtgggagt ttgcagcagc acaggaaata gccatagtta taccaacagt tccctcaatg 199920
cactgcaagc cctcagcgag ggccatgggg tctcactcgg gtcctcgctg gcttcaccgg 199980
acctaaaaat gggcaatttg caaaactccc cagttaatat gaatcctccc ccactcagca 200040
agatgggaag cttggactcc aaagactgtt ttggacttta tggggagccc tcagaaggta 200100
caactggaca agcagaggcc agctgccatc ctgaagaaca aaaggggccc aatgattcca 200160
gcatgcccca ggcggccagc ggggacaggg ctgagggaca cagccggctg catgacagca 200220
aagggcagac caaactcctg cagctgctga ccaccaagtc cgaccagatg gagccttcac 200280
ccttgcccag ctccttgtcg gacacaaaca aggactcaac agggagcttg cctgggcctg 200340
ggtccacgca tggcacctcg ctcaaggaga agcataagat tttgcacaga ctcttacagg 200400
acagcagttc ccctgtggac ttggccaagc tgacagcaga agccacaggc aaagagctga 200460
gccaggagtc cagcagcaca gctcctgggt cggaagtgac tgtcaaacag gagccagcga 200520
gccccaagaa gaaagagaat gcactactgc gctatttgct cgacaaagat gatactaaag 200580
atattggttt accggaaata acccccaaac tcgagcgact ggacagtaag acagatcctg 200640
ccagtaacac aaagttaatt gctatgaaaa ctgtgaagga ggaggtgagc tttgagccca 200700
gtgaccaggt gagttttcta atgtcttctc ccaggtgtgc tcatctgtgt catagatgtt 200760
ctcaaagagg acatctgtga ctccctaaaa gtagtatttg tgttggtggg ccttaccgtg 200820
taacagttac tttgcatgaa gttgtgtgtt tacactgcaa agaattacag ggcacagaca 200880
cgagcttagg aggccatgta gcttgctctc agacactgta ggccagagca gctgtggaca 200940
ctgagcaaga aagtatggct gagctctgta cagttttaca gatacttaca gaccctgggg 201000
cagacaatgg gatggacaca aagtattttt ggggggggtgg ggggcagtca ttgttctttc 201060
tatgagcagg gtaaattcat ccttgggtta caggtcatgc gtaacaatgg cgagcaggag 201120
gaactgcagc gtgactgtag ctagctgaac ccagagtgct ggcaatccct tccttagacc 201180
```

agggcttgct cagaacagac ttgagcatct atttgttact ctctccatag gaccagagtt 201240
cagccagtaa agatcctctg cctcttccct ctctctgaac acttctgagt aatgtacagg 201300
aatctcagtg actgttggtt aaggcacacc aaaggaaatg gatagacaca tcaaagccat 201360
catgtatcga ttcaaaacca gaataccggg ttacattctc tctgcacttc tctccaaagt 201420
taatacctt ggaacaatcc aggggaccta agtaatgatt agaatcattc ttctatttaa 201480
ttaatttatt tatttttaac aaaaaacaat ccttatacaa tatgatcctc tgtagaatag 201540
cactatcaga ctagttaata tatcactgca tttgtgctgg tcatttttgt ggtacaaata 201600
cctttttaaa actcttttga gtgaccttca atatacatgt gttatggttt ccactacatt 201660
gtacaacaga cctctggaat gttttcatcc aaactgacat tttaatcctt ctccaacatt 201720
tcagccctag cccctctacc attcccagca agactgtggt ggggaaggcg ccacagtgga 201780
agcaaaccat tgatattttc actgacttac aaaaacaagt gatataagtt gttgcaactg 201840
cagtggtaga atcatgactg actgaaggtt aggacctagc ctcaccttcc ccaggctgaa 201900
caggtcctgt ctggaagact ctttcttctg tcatggttga ttaagcaggg aggaagtcac 201960
aggggcctct ctccttaaca tggctataat ttgcccttga aagctgtgtt gcaagtagga 202020
aggtagtgtc accagcttca agagagcagt gactgtgagc ccttgacccc acaaatccac 202080
ggaggctgca tttggggaca gtccctgcca gcctaactgg ttcctaagac ttaacctctt 202140
tcaatgtgat gtcaccggtt gtcgccattc ctgagaacag atacaaccat tcagacattg 202200
tgctgctcgc aggggaagca gactaagatt acatgaacat tattggtgat taatcctaaa 202260
gtccagcagc aggcttcatg cagcagctat tttataatgc tgtgaactca tgagttgggg 202320
caccgaggcc aacagaaagt taatagcaat gcctttgtga tgtgatgtga tgtgatgtga 202380
tgtgatgtga tgtgatgtga tgtgatgtga tgtgatgtga tgtgatgtga aaaccatatt 202440
gacgatgggc tttcatcttc cggggtgtac tgggttaaat gacacagagg tagtgctagt 202500
tcagaacaac aagcacagat agccagtgtc acataggtgt cttaccgtgc tagagggcag 202560
atcagtgact cgggagatga cccctgatgc tcagttacag catggctgcc ccaccctcca 202620
tagctagaat gagtttctct ctctgacctc agaccctagg gactgagagg gacagtgaaa 202680
ggtgtcactg acatgtctca ttactctgca tatatcacaa atgccaaaca agaaaaggct 202740
ttgtggggtt gggttggctt cacttttacg tctttgaatc acttggagtt ttcttatttg 202800
gaagaaataa ttttctaatc aaaattatgt gagaaacaaa gactagtatg aatcagtata 202860
aatctgttgt ttgaagatga aaaataaaac agggcacgca tgctcacata caggaagtat 202920
attgtcctta aagaaatctc accccttgct cacctcccct ccaccctctc ccagacccca 202980
tctaaaatac agtttcacag agccagttta gcatcaaaac catagcaagg ggaaaagtta 203040
ccacaggaag catgctttac ctaaatttag atccattatg aggagaagaa aactcaattg 203100
tttcacctct tgctcacctt ctgttcccta aggatggtct cctcaccttt catttcagag 203160
gaatgcagta attatttagt aaacatgcac acatagcaag cctggattgc aatggactgt 203220
cttgttattt tgactcaaaa aaaaaaaaaa aaaaaaaaaa gacctgagag cctgagtgtg 203280
tgtaatgcat tactgacttt gtaaggtcag ggagtacagt gcacttcagc agcacagtgt 203340
tactctacta aaaatgacat agttttacca ggcagagcat tcaaacaaga catttctaac 203400
gccatttcct agccaacagg aaacaaactg acagaaacat tgccagtgtg tttactgctc 203460
taagtcacgt gcttatttcc acaatggagc attgctggta ctcggccagc caatactttt 203520
ggctcctgct ttctttgagg acttggaacg gtctcccatt gcttaactcc attagaaaag 203580
ccatgttaag ctggtagtca ccagacactc cctccagata ctatagaatt ccttcacagg 203640
tctgtaccaa gcaaatggta tgatgctata gtttttattt aaaatgtttt caaaagctac 203700
tttttaattt attagattac tcatgtattt ctgtattcgg agaacaagtt gatttttgac 203760
tcatgaaaat aattataaca ctaaaaagaa aaattaaaga aatgaagtct atttttcatt 203820
ttgtagaact taaaaaaaaa caaaaaactt tctgactcat tttctgccag aaatagttga 203880
aactaactac tgaaattgat gtggctagtt tgagcattca aatagatgcc taagtgagac 203940
tctgaagtgt ctacaaggca ttttaaagaa aggcactgat ctctctgtct tgcaaagaca 204000
ctgcctaaca gagtgcaagg atcagaagaa catcagtgag atgtaagctc cagagctgta 204060
gaacacatct tccttcagaa acatctaatt atcacacttc agcccttcca gagcgtgcgc 204120
gaacactaag ggaagtatta aaatcaatct gcctgagggt tataagccat gctgaaatct 204180
atctcctata gaaatattta aacttaggcc agacatggtg gtgtgctcct gcaatcccaa 204240
cattctagag ctgagagaga attgtaaatt ccaggtcaac cttacctcag gataagaaaa 204300
gttaaactga taacaaatta atgataaatg catattccaa aaattgacaa ggaataaatt 204360
cagacaaagc aatgtctcta aaagttcctg gtgcatcttg aaatgtaacc tgagtgagtt 204420
cagatagtgc ctggagctct gagcctgtag aagcaggctg cccatagcaa agcgctgccg 204480
agctctcaga tttgctgctt ctcaagtcaa cgttgctgct gctaactttt cctccctccc 204540
tttcttcctt tcctgttctg gacattgaac ccaaggcctc ttaaaagcct catgactgaa 204600
ttacgctctc actcacatag gtagctggta aagctgtaaa tgggagtaat cagaatgtga 204660
aagtcagttt aagacatttc ttttaaagaa aaacaaaatt aagccgggcg tggtggcgca 204720
tgcctttaat cccagcactt gggaggcaga ggcaggcgga tttctgagtt cgaggccagc 204780
ctggtctaca aagtgagttc caggacagcc aaggctacac agagaaaccc tgtctcgaaa 204840
aaccaaaaaa aaaaaaaaga aaaacaaaat taggatgaga gggagaaggt aactcaggcc 204900
acatcacaca aagctggttt tgtccctagc actgcatgaa tacataaata aaaactttac 204960
attgagtaaa tatatatatg tgtatatata tatatatata tatatatata tatatatata 205020
tatatatatg cacacacaca tatatatact gattatgaaa ttttttactt agaaattatt 205080
tgagctggac attttccaca tccctgtagt cccaatgctt tgagggttag ggtaggaaga 205140
ccaagaggta aaagctggac tctgctccat agcaagtgga aaaccagcct gggtccctga 205200
ctcataattt tttctcatat aaattgattt tagttactca tatagcttaa cacatatgta 205260
ttaaacatta tatgtgcctg taatgttaaa atgtatgtca agtgtcaagt atttacatgt 205320
atatatatat acttaaatta atatgttaca cagaattaca caaacaacaa aagaagaact 205380
acggccagat gtgatttagt gccagcactc aggagtcaga agtaggcagt taggtctatg 205440
tagtgttcca gcacagccag caagagccac agagcctcta ggaagggagg gtaagaagga 205500
aaggaaagac caggcatgat acagtgtgcc tagaatccca gctcccggga ggcagacagt 205560
ataatacttc aagttcgagg ccattctggg cgacacagtg acctctgtct ccaaaatgtc 205620
tttttaaaaa accttgttag ttgtgattaa ggtggtttat aattttgata gtggactgta 205680
acggggaaag cattctgtca tggctcagat tggaggcaaa ctcaagtgca tctattaaga 205740
aaacacatag acacttctgg ctttgcttac atgagcctgt tttctataat tttcatcagg 205800
ggcaatctgc caggttttgt cagagacaga ctgtcattta cttcagctat cttcctcacc 205860
tgcacactga gctttaaatg tcctcaggct agggcatcat tgccatagga cactacttca 205920
aagaccagtg gtagctcgct gaagccctgt tcttaccaca gaagcatagg aaacactctt 205980
ctgaggactc gggaagctgt gggaatttct gttttagttt taatgatgac tgaccaccac 206040
ccacaccctt caggtctcac tgtcgatggg cctgtcagtc acagctgatc cacagtgtgc 206100
aaggcttccc ttgctcagga actttcaggg ccacgtctct tgcctgaacc tctcccatag 206160
aaagcttgtt gtcctgttgc aaataggtga cacaggaatg ttcttcttgt tttaagagta 206220
catgaagaat tttctggaaa ggagtggcta agttcactgc tgaagtagct acctctgaaa 206280
agactcaagt aaaatgtcac ttcaacaggg aacttcctaa cttgacaggc tcagttggca 206340
aaggcgtttg tcattgtcat gcctggtgat ccgagctctg tcccttagac tcgcgtgggg 206400
aagagagaat cggcacccac aggtcctcct cggatgttca cacacacgaa ggaatgagtg 206460
gacttttctt attagaaaga cacggtagac tacacagaag cacactccta taatttgcac 206520
atgagcgaat ccattagaag tcgttgccag tttcacgtgg actcagatac ttttgttcag 206580
ttttgaaacc atctccctct agcccagaat agcctacagc tcactgtagc tcaggctggc 206640
tttagcctca agtgctggga ttcaggcatg atcacacttg tttgaccact ttcctgtgta 206700
attgaaatct atgatcttaa atgctagcac cctgataggt tatacccaaa agaatgccag 206760
tgaagtcatt ctagctctta gacaaaaaaa aaaaaaaaaa gtaggcaata taatatagtg 206820
gtcatactta ggttattaat cagtattggt aattggaatt gaattcaaga aatgatttga 206880
agaaactggc gcatatgaaa tcaaatgaat acacgctatg cttggcatca gccggtggtg 206940
gcacacgcac gcctttaacc ccagcactcg ggaggcagag gcaggtgaaa ctctgagttc 207000
aaggccagcc tggtctgcag atcaagttcc aggacagaaa cctgtctcaa aaaacaaaga 207060
gggggtaggg ggagctagtt aggtcatcta agctggttaa taagaaagct actgacattc 207120
aaacctaaaa taaaagcaag caaaaagcac atttcaagtt gaaaaagcaa gacttagcta 207180
gtccatgaat atttgaagct tattttacag ccaactcaca cagacaaggg aaatagccat 207240
ggttatttgt accatattct acaccagctt tattgttatt atttcttaag aaaaaaaatg 207300
aaacctagat ccaaactgta agtcatggtc caattataag taattggata taatctttca 207360
taattaatgg ggtggttcaa ataaaataaa gggactacat aaactgctag tgagttgcaa 207420
ggtgggaaac agcttccttt ttttaagtcg gccatgccta gtttctaagg gagggagtca 207480
tggtcctcgg tggattcagt tacgagagat ggttggccca tcattaggcc ttacatttgc 207540
acatacctgc tttttttttc ctttttaaac ttggctggga tgccctgtgt gatggttggg 207600
tctgtactcg ccaatggcca gggttggggt cccctcttgc agcatggacc tggatgtaca 207660
cttctgtttg ttaactgcag cctggcagcg agctggacaa cttggaagag attttggatg 207720
atttgcagaa cagtcagtta ccacagcttt tcccagacac aaggccagga gctcctactg 207780
ggtcagttga caagcaagcc atcatcaatg acctcatgca actcacagct gacagcagtc 207840
ccgtcccacc tgccggagcc cagaaggcag cactgcgcat gtcacagagc agtaagtatg 207900
cactctaacc ccatcagaga ccaactcaag gctgccagag tcctggtctg tccggcagct 207960
taccgccata gtttcctttg gagaggaaaa ttcaaaccag gcatggttac tgcatgcctg 208020
taatcccaga catgaggctg aggcaggagg atggtgagag ttcaagggca acctgagcta 208080
catagtgaga ccctgtctca aaaagtttta attgttcaca aaaagggtgc tcacggtcaa 208140
atgccttatg ccattgactc tgatagaata ttttgcgatt tcagttttgt gtgaaaggac 208200
ggttttagtt tacagaaaga caagtcttca gtgctggtaa acaaaagcac cacttccacc 208260
tcaggagagc accaacgcca tgcctagcag cgctctcaag tctggaaaag cgaacctcag 208320
ccaagtcaca gataactacc tttagaaact acgtccttcc ttgcatggtt cctgaccatt 208380
ctggaaaggg gtaaaggaaa gtaagatgaa gttttatttg acctgggcaa atcacaaagc 208440
taaagaataa gagactagcc cggcatggtg gtgcacgcct ttaatcccag cactcgggag 208500
gcagaggcaa gcggatttct gagttcgagg tcagcctggt ctacaaagtg agttccagga 208560
cagccagggc tacacagaga aaccctgtct taaaaaaaaa aaaaaaaaaa aaatgagaga 208620
ctgaggtaag ctagtacttt ttaacccaga gaggagcaaa gaacacggtg ggggctcgca 208680
gctcgcagct acactcgctc aggagcccca gggaccctga aatggtgagc tgagccgtag 208740
gaaggcaggc ctgggagagg caagcaatgt ccattcccag cctggttttt ctgaatggtt 208800
tttctctacc ataggttttt gaaaagtctt ctttcttcta actgctagtg cagtctatgc 208860
ttataaaact aaaagaaagt aaagtcttga tatgactaat aaattagccc tgtaagttag 208920
tgtgtatagc attgagtgtt ttaataacat tgttataaaa ttacaggtca tctacttgac 208980
actagattac tgctcagtac acagtcaatt cttgtgaact aaccatcaaa accatttcaa 209040
atctaaatag tgcctggagt taaagccata ctgctagtca taggctacaa tggagttttg 209100
tttcaggtga cactcaacag ttttaacttc tagtggaagt atctacttct aacttattct 209160
aaaccttgag cccagttaag aaataatgta acatccaaac cacatgtgtg taggctgctg 209220
ctgcatgcaa gagatgttta taggctcctt actgtagaaa taagaactcc tgaagcagac 209280
aagtgcatac caaatttaag gggagatctt atcaaaagaa acaaaaaaaa aaatgggaaa 209340
cagaaaaaga ccacccacca acgtgtgaat agtataacat gaacactatc atattaatgt 209400
acgataatgg tttagttagc aaaaaacttt tcaatgctac aattcctgga gagaaaacat 209460
ggtacttttt tttacatccc ctttttgcaa ggccattgag agttatataa taccaaccag 209520
ggtgctgcat atgttttctg tagttgtctt tcatggagag agttaccaaa gatgtgcatc 209580
tttgtcatgc tacaggagac attttcccta aacactactt actgttaata ttctttttca 209640
ttgtccttta ttaaccttca atttttcatt tgttctttcc ttagctttta ataacccacg 209700
accagggcaa ctgggcaggt tattgccaaa ccagaactta ccacttgaca tcactttgca 209760
aagcccaact ggtgctggac ctttcccacc aatcagaaac agtagcccct actcagtgat 209820
acctcagcca ggaatgatgg gtaaccaagg gatgctagga agccaaggaa acttagggaa 209880
caatagcaca ggtaagggct cagcggtact gctgcttact ggcgggttgt gtaatttaac 209940
aatgtgttcg tccacatcaa aatggtagaa cttgaccatg ggcttgttag aaacctcacg 210000
gatcccctgt gagggtggcc ttgggaagcc actccatcaa gctgaccaag tcattcctca 210060
gctgctgctt tgaggaagtt cctgatctcg gtcttcttgt ctagccttgc tgcatttcca 210120
tcccaactgc tggtctgaac ttggaagaat atatgcaaaa taaaccaaaa ctggtgcttg 210180
ttagtccata gatatctgct gaaaactcca aaaacagatt gatggttttg gaatgggagt 210240
ttaaaattct accattcttc cacaattcta gatccttttt ccacttagga aaaaaaaaaa 210300
aaaaagaagt aaaagtgagg agctttttgc ctgtgttgcc acgtttccac tgtatgctca 210360
gccatgcagg acggctgctg gaggaccact tgagccacag actttgttgt gttttgtttt 210420
attggctttt gtgttctggt ttcttaacct taatgcattt taacagcttc aagtcagggc 210480
acagttaaat gagcacactg gtttgaagtc acaccaatca ggcggcttcc tggagattgg 210540
agaagctgcc tgtaatctag ctggagcttg acctgatagt tttccagtgt cctcccccat 210600
atttcctaag tggtacatct tcccgccaca gcggcataga attcagaatg agctcacagt 210660

-continued gcgggccgtg gagtggcatt tgttacgcgt ctgggagagt gctggcttcc taaggaagag 210720
ctggctgtag ctttctttcc ttgtctcagt gatgtgttag agacttgggc accctatcaa 210780
tacattacca ttttcgttca ctgaagatca gagcactgct caaggggaag tgatggatgc 210840
tgcatttctg attgctaaga gcgaattcat gggaagtgtg agctatagtg tgtcggttta 210900
ttcattcaac agatactcac ccctgcctaa ttacacacct gtactgactc cctcattaaa 210960
ttacagatcc ctgaaaacag tgccatattc actccattac tcttaaataa aagcacgact 211020
catagatata ttggtgatga gaaactcttt aaagaaaagt agcagatgag tgactaggag 211080
tcgctcccta tcggtgaata caatgcttac actgttgaag tcttgtatag gaccttggga 211140
ccatggggac ggcctctgca tgtcccagaa cctagtagtg cccaggctgt caggatcaca 211200
tggtataaag accagcacca tagggaacag tgtccattct tgctgcactg atactgttga 211260
gtttcaggtg acttcaccct cctcctctcg tcttattatg ctatttaaat aggttgtttt 211320
gaaactaaaa tgcctttcca cttatccact tatagataaa atataaatgg ttttaaatat 211380
gtcttaatat tgcagttttt aaccctaact aatcaccctt ctccttttaa catctcagca 211440
catccctcat ttcacacatg aggaaacacc catgttccat ctacatgttc attataccaa 211500
atttgcttaa ccgaaataaa gtaatctaaa gcaagccata aatttgaaag caaatcttta 211560
tatcccctgt atcacgtttc agaacaaaga gatgtttctg aggcttcttc ttcagtatgt 211620
cttaggcagt gtttggccac tgccgtcacc tagagcctgg acactaatag aacagaccct 211680
gagtcctgcc tggtcatgtt gagttctcat tgttccgtgt gatcagatgc caagtgtaga 211740
tttccctcac gcctctgcta gcccattctg catcggtgtg gcctggaatg cagtgcttca 211800
ggagggtggg accctttgct caggcactgt gtcaggaaag tctttaactt cctgagtgct 211860
tagaggctac ccttggtaaa ttttgaaatt tactaaattt tttttttga tggaagttgt 211920
tgctgaagta tcctgtccat gcagacgtat gcctgtggtg gggcagcttc acttgatggt 211980
cacccagcga acatgtctgc atgctccaga agtgtagcag gcgccgaccc cctgaaagga 212040
tgaggatgct cagctctctc tcgcaaaagc tttgcaggat agtctctgac tggggtcgat 212100
aattttggga ttgattatca gttcttacct tgttcctcct caccttacct catctcacct 212160
ccccttttgga aagtagagct ctgacgtata cgtcagctaa tgtgattcac ttcctgagga 212220
aggaagttgg ggttatccac ttgccgcagt gcctgttcta ataagtacat atgggaacag 212280
ttttaacagc tcttctgagc agatgcatgc tgtgaaaact gtagtaatca ccaactctta 212340
gttcttagcc cagggcccac atctgccctg ggggagtgtt tgctgttgag ccaactgcag 212400
gttacagtca tggtctgagt cttgtaggta ggtctggcat gcgtgcatat gctgttttca 212460
atgtctgcgt ctctcagttt cctctgtctt ggatgcagga atgattggca gcagcacttc 212520
ccggcccagc atgccttctg gggaatgggc accacagagt ccagctgtga gagtcacttg 212580
tgctgctacc actggtgcca tgaaccgacc agtccaagga ggcatgattc ggaacccaac 212640
agccagcatc cccatgcgag ccaacagcca gcctggccaa agacagatgc ttcagtctca 212700
ggtcatgaac ataggtaagg ctccttccct gctgccctta ccccgtggtc cttcaggatg 212760
tgcagtcctc aatggcattt gctaaaaccc tgttaaatca tggactgatt acctaatttt 212820
aatttggaag caaaatacat taaaatgtca cattataaat gccacatata taaaatgtca 212880
catatatatg catgtatatg gtagtttaaa ggcaacgaaa tagtttggtt gtacagcctc 212940
tatgtggtca tcctaaacca ctaatgccct caggcaggct gtgaagtcag cgtctccctc 213000
agcctcattg atagtgcgac cactcaagaa catgacacag cacccaagca tctctagcat 213060

```
tctagctgga ggcagttcac atgtcacgga aatgaatttt ttgtgtacac tccacaaaac 213120
cttcatcata gctgcctata gctgaaggcc tggaaggagg caggaagtga gtcctgagac 213180
aagggcttcc tcttcaggta agtgaaagtg cctgagttga tgtggtagtg gtacactcga 213240
acacattgac acctacagga tgctgcacct gaagtcatga gttgtatgta tgatgaatga 213300
atcatcagga aacttgttac tacatattga tgtacacact tagaatcctg agccttggga 213360
ggtccaggca agagttcagc atcctcagct ccttagcaag tctgaggcct gactgagctg 213420
aacaaggccc tgtctcaagg gaaaaagatc agttgcctat acagctccta cttgatatta 213480
tttgtaaccg tagacatagg acttaaatct taaacattag ctcaattcta aaaagtctgt 213540
gtgtgtaaac ttttgtgtta gatattgccc aggaagtgct aattcattcc caggaaaatg 213600
caagattgtt ttgacagaag agcaggcctc ttgccagaac tttgaatcag gtttcttcca 213660
taggtgttga agtgctgtgt gtgtgttgac tcagtatttc tgagagtgac atttataatt 213720
aattacattt ctacatatat gctcatggta gtaggtggaa aattaagctg agacatgagt 213780
aagatgttta taaaagtgac agtaagaggt cttgcataaa tatttaattt attccccatc 213840
ttgctgatag tttggaactc ccagtacagc tctgtaagat ttagtatgta gctgaatttc 213900
tctagtggta agtacagtca ataaatcgga atttgcccaa tacaacattg cctgttatgg 213960
atgtccagtc aatggataat aaaataaaac aattagaaag ctcatgtgca ttagagccac 214020
aaaaagagaa cgctgtgtat ctgagtgtgt gtcctgtggg agagctaaga cttgtgaaag 214080
tactggtgca ggtgatctgc tccctggtgc cttgcagctt gtctctgcag ccttacatgt 214140
ttgcaccata ttgcagggaa gaagggagtt ggaggttctg ctaactcaca tgtgcatgtt 214200
tatgattttt tttaaaaaat gagttagcat tttcaatatt ttccatacaa acaaaagctt 214260
taagtaagag accagatatc ctgctgtcac tactgaccta gacgtgccct aagttgggcg 214320
gtattagcct tgtgttcatc acttgtattt gtacctcaca ccagagctgc atccaactct 214380
gcattttcta tcaaccaaca attttatttg ctattacaca gtaaacctgt gctttctaaa 214440
ttataagatt caaaaattta ggtctttctt ctcttttttt ttcctccctc tttcaggccc 214500
ttctgagtta gagatgaaca tgggaggacc tcagtataat caacagcagg cccctccgaa 214560
ccaaactgcc ccgtggcctg agagcatcct gcctatagac caggcatcgt ttgccagcca 214620
gaacaggtaa gtccaggccc ccggagagct agaagagcat tagctcatgg ctcctggctc 214680
ccagagttgt ttcacatgta cgctgggtga atcccttcgg aatggatgat acctgcccag 214740
tcatcctttc ttcagaccga gtcatctgct aggctcagcg tgaaagaaag gtgcagaact 214800
cggcatgacc tgagcacacc tttaaacacc ggcagcttag ttgggaaaat gatatgtttg 214860
aactgctaat cgctattagg cagcagtgta gatgctgtat acagtataga tgctgtaagg 214920
ggaggaatca gtagctcatc cggcaaggct gacagagaag gtttcagagt cttgggggaa 214980
gtgcacaggc atagcagcct agtgcatatg gccggccaca cagcaccatg ttccatcggg 215040
ggttacatgg tacgtgtagg gtaacaggga atgatcttat tttgaattgt gtttatttta 215100
ccacagttta caaaaaatag aaagggaggg ggggtccatg gtctagctag gtaagtcctc 215160
ctccctcgtc aaaaaagctt ctttgcaaca gagaccattg taaaaaagaa tcccagccag 215220
gcgtggtggc acacgccttt agtcccagca cttgggaggc agaggcaggc ggatttctga 215280
gttcaaggtc agcctggtct acagagtgag tcccaggaca gccagggcta cacagagaaa 215340
ccctgtcttg gaaaaaaaaa aaaaagaaaa gaaagaaaaa aatcacaaac aatcaaaatg 215400
```

-continued atggttgtag agccctattt caatgataca tctgtaaaac acacccatac ctaaggctca 215460
gggaacattg tgaaggaagg gatgggcagg atataatatc cagacagcca tggagagact 215520
agtgacatct gaaggctgca cccatgaagt ctcaccgcat gacaaggata acaataaaca 215580
ctccatagtg gatggaggaa tccccacgag gcctcagtcc tacataagag ctgcgggcca 215640
ctaaggaatg ctgggaggga ggaacagtcc tcctcagaga agagcacacc aattggttat 215700
caataccaag tggtcagccc tgaacacatg cacatgcaag tgtagcatta tataggctaa 215760
gcaggtcata cttacacaca cacacacaca tacacacata tgtgcctgta acaacaacaa 215820
atgaaaaagg aagctctgaa tttgagctga gctgggagag gtatatggaa ggcttgaagg 215880
aagaaataat gtattgcagt tggagctagg aagataacac agttgatcaa gtgcttgctt 215940
cactaacatg aaaacctgag ttcaggtcca gaacatattg aaaagccagt gatggtggcc 216000
cacattgtag acctaagcac tgcagaggca gaggcaagag gatctacagg gcccaggggc 216060
cagctgctct agagtaagca gtaggcacag aggggatggg agaaagagag aggggggggag 216120 gagagaggag agagagagga gagaagagga gagggagaga aagagagaga gagagagaat 216180
gagaatgaga ggagagagat ctcccaacac ttaggacagc cggggctaca cagagaaacc 216240
ctgtttcaaa aaaaaaaacc aaaactgaaa accaaaaccg ccggggccta gcaaacacag 216300
aagtggatgc tcacagtcag ctaatgaatg gatcacaagg tccccaatgg aggagctaga 216360
gaaagtaccc aaggagctaa agggaactgc agccctatag gtggaacaac attatgaact 216420
aaccagtacc ccggagctct tgactctagc tgcatatgta tcaaaagatg gcctagtcgg 216480
ccatcactgg aaagagaggc ccatataaag gcaaacttta tatgccccag tacaggggaa 216540
tgccagggcc aaaaaggggg agtaggtggg gaggggagtg ggggtgggtg ggtatggggg 216600
acttttggta tagcattgga aatgtaaatg agctaaatac ctaataaaaa atgaaaaaga 216660
aaaaagaaaa ccaaaaccaa acttgcagtc cttctgcatg ggcctccgag agctgggatc 216720
acaggtgtgt gctgcacact gggctgtagt aaatcattgt gaatgggtgt gtctagaaga 216780
ctcctgccac tgtttacaca ctgcattatg tgttttcagt tctttgttga aatatgacag 216840
tatgtcagac cttctctcta tttcatccac acattgtcgt cctgtgtgtg tgtgtgcgtg 216900
cgtgcgagcg tgcgtgcgtg cgtgcgtgcg tgcatgttgg gaagcagagt cagatggatc 216960
tctaacttca aagctacata gtgagtcctg tgcactaggc tgtagtgccc agggacttcc 217020
tccaagactc tgctggagga gcttctgaaa catgcaactg ggctgcatag tgagaccctg 217080
tctcagaaaa agcacaaaca acacaacaca aaacagtatt ttattattca gtgtacgtgt 217140
ctaacttggg catctgtttt ctgttgtaag tactgggttg ctgcagggtt aagaatttat 217200
tctcagaaaa gatgattcct tctactgtca ctgtttgaaa ttaattgttg gtttaggtgc 217260
tcagcaggac accatgttca gttctaagtc agagtaacac attagactgc ctaagaaaac 217320
acagtagact gaactgggtc agggccagac aactctgtcc cttgatacat tgattgccac 217380
ttgtttaaga atgagctttc tggggtgtga gcatgcctca cctggcacat aggatgccct 217440
gggttcaatt cccagtacca cacacaataa aacgtaagct agcttctctg taaaactgtg 217500
tgttctccac aggattccat agtaggtcta cagcacaaag ctgactttgg tgaagtgctg 217560
gcattatgtc ccctctcagg gttgcagtga ctagaagatc ctctaatctg gtaacttaat 217620
tataatgtta gataccatag aaatggcagc ttagtgtcaa gatcacatat tgccttatag 217680
caattacatt agaaggtttg agattccctt ctaattcctg agggctaaca ggtaaacttc 217740
ttcggagttt tggtaaatgc ttgcaaattc tggttctgca taaacacaca gtttcataga 217800
ccagccaagt tcacaagccc agattgtatt caagtgtgtg agtgtgctgc tctctccttt 217860
gctcatcgta gtcgcattga aaaggactgt gtatgagtca ctgcgttctg cattcacctg 217920
tcactgcaca gcagatacac acacacagac cagtgcaggt ctgtgaactt aggtaggtga 217980
gccccgaaca cacacacatc aaagtagctt ttacggcggt gcctttccga ctttgcacag 218040
atgtgagtac ctggctaagc taaccctgta ctttatggga agatggagaa acataactgg 218100
ttaactggcc tttattaaca ctaaataaaa tagatttttc agatgcatat tttcagaagt 218160
cttcattctg tccagtgctt ggctggagga agagtttggt gaagtcaact ggtatttcta 218220
ccagcccatg gtgaagtttg tctctttaca ggcagccctt cggcagctcc cctgatgacc 218280
tgctgtgtcc acatcctgca gcagagtcgc caagcgatga gggcgctctt cttgaccagc 218340
tgtatctggc cttgcggaac ttcgatggcc ttgaggagat tgatagagct ctggggatac 218400
cagaactggt cagccaggta ggccagagca tcagagcggc caagcactgc gtaggccaaa 218460
ggtctctgtt cctgcaggct tctctgggat gctttttccc tccccaccag caggcctccc 218520
tactcctcct ctttactctc atactctcac ataaactgtt gcccaagaag caaacacctg 218580
ggaaggacca ttgcacaaga caagttaagc agaaaggcag aagcaagccg agagcctctt 218640
gtccacgctt gctgaaaggg cagattagga aaacaagtta gagaagccac agggtcactg 218700
cttcctgggg gccttggtcc tcgatgctgg gatgggagac catgtgagca ggcctcagtc 218760
cggccatgcc tattcactga gacaggcagc cgctacttag aaaggactgt ttcacacaca 218820
ggtagcagaa gcatcttaag tgtgactgca gctcaccaaa cactacaacc cttatgtggg 218880
tgtcgcccgt aacaatttta ggatgccaac caccctagtg agcctagttc tctctctgct 218940
ccctcgttag tttatttgaa gaagtaacag actttgtctt tctttgattt gagaaagccc 219000
tgaggctgtg ataataaccc catggcccct cagcatctga aacaacctcc tcctggtcct 219060
ccttcctgtc cagtgccagt ctccctgtca caagcatctt ccaaggccag gctgcctggc 219120
cctgcagcat gtcactgtga ggatagtgat agtcatcgaa gactctggaa ccttaaaaac 219180
agtcataatt cccagagttt agcagacaca ggtgggagtt cagacttgtt gattcatatt 219240
gaaaacagca gaatggaaag aaatgactgg aggttgcaca gtacaccctg acttaaaacc 219300
agaaaggaaa tggggtacct atttcctgca tgactggtcg gcttcgcctt tagcttcagc 219360
tagagttcag cttttctgcg attatccttg agtttatgca ggtgacattc ttaaatgtcc 219420
ttggagttcc tcagtgactg gaatactttg agggactttg gaagcggggg ttatgtttta 219480
agagattaga tttttaagaa atttaagaga tcccagccca acctaggctc aaatttatgg 219540
cagttgacct gtcttggcat ctaaaatatt gaaatacttt ttaaaaatta aaaccagtat 219600
tacatcattt tgaatgctct cctcaggtca gtcaccgtgt cgtttaagct gaactacaga 219660
cggcattctt aggggcagcg gtggaaatgt ggtgtgnnnn nnnnnnnnnn nnnnnnnnnn 219720
nnnnnnnnnn nnnnnnnnnn nnnnnnnnnn nnnnnnnnnn nnnnnnnnnn nnnnnnnnnn 219780
nnnnnnnnnn nnnnnnttta gccagagttg catacacagt atagaaataa agttcttgtc 219840
tcacaaacat ccccagagcc caggaaaacc accaggctca gtggtacaca cgttacccca 219900
gcaatggtga gtttgtgacg gtggaaacag gaggattccc acagcaccag ccagtctagc 219960
gtaatcagtg agttctaaac agaagtgaga cctgtctcaa acagagcaaa aactaaatag 220020
atcaatatgg aaataaccta agtagatttt ctattaaata tgggcagatg taaagttctg 220080
aaatatttca acaaggagtg gtctccctgc tggtggtact ccatacacac tttttttttt 220140

-continued aattatcaag aggagagggc agtatactga cgctgtcctg ctgaccacag accacaggca 220200
gcgttatcat cctagggcgt ctggaaggaa ggactaaggc tgccagagca gtaacctgat 220260
ggcggcttga gatgtgactt ctgctgcggc ttgccctcta aagaccttca gatgtctagt 220320
cgtggcttct agaaggacaa gggtatatta gatcttcata ttgacactag agcatcgccc 220380
tgagagagcg ctagattccc tatgcatgga aacaggacag tcagccagaa gtttccatgt 220440
tcagctcagt agcagaaatg acaagacccc ttgtctcaga aactgagtga aagggccgca 220500
tccccagaaa ccctccaggc ttcacacact cgtgtgcgct tgcttgggct ggctccctct 220560
ctccttcctt tctttctctc tctctctctc tctctgtgta tgtgtgtatc actcacatgt 220620
gcacacactt ttttaaaaac taaatagcta atgcaagatg caactggaat ttatgcagct 220680
ctctctgtaa aacacatatc agctgggcat ggtatcacat gccttcaatc cagtactcat 220740
tgagacaggc agatctttgt gagtttgaag ctaactcagt ctacatagtg ggttccagga 220800
cagcgggact acataatgag accatgtctt ggggtttaaa aaaatgcatc tttcagacaa 220860
ttaaattaac caaatatata caaactagtc ttgcagatac tctgtcagat gctggtcagg 220920
gcacagggag gacctgctac atgcccttac accaccttcc attcctttcc ctctgtaggt 220980
ctttggtagg agaaaagctg ttgaaaaatc aaatgacaaa cacattgaat atgtctagca 221040
tgtagtagtg aattatagca aagtgtacgc atgtaagaag ttccactaac catagagaac 221100
agcgtagtaa acagtacaca gtgtaaggca ggcattgtga cactgacctc gaatcccagc 221160
acttgggagg tggaggccag agactcatgg ttgaaaccca tcctgggctg catagcaagt 221220
cagaaaccaa cttgggctat gtaagaccgt atatcaaact cttttcacca aaacataata 221280
ggcagtaagt ttatcacccc actggtgagc ttaagtccca catcacagta cgcaccacag 221340
cctacccgcc cggtctttgc tagaaagtct ccctcgagtg ggcctcatgt ccccaagtct 221400
gtgggtgtct agagtggaga ctgtaggctg cttccccagc attgcttatg gtgactaagg 221460
tgaccatagg ttaaaataac tgacatgggg ctgtgtctct gtcaaaagag gaaacatttg 221520
cagctgcctg ctcactaaag gccctgccag gttctcactg gaaggaagga ggaagctctg 221580
cagggaggca gcccaaccct tgcttcttcc ctcgaggagt tgcaaagagg cattgggtag 221640
aaggaaaagt agaggcaaac taaaaaaaaa tacattggta aacttggtac agtatttcta 221700
aatcatcact tacaggaggg ggggagcgca gcctcgtgtt cagtacagta gtagtagtag 221760
tagctttact gtgtgcttat ttggggcttc ttttcagagc caagctgtgg atgcagagca 221820
gttctcaagt caggagtcca gcataatgct ggagcagaag ccccccgttt tcccacagca 221880
gtacgcatct caggcacaaa tggcccaggg tggctataat cccatgcaag atccaaactt 221940
tcacaccatg ggacagcggc caaattacac cacactccgt atgcagccac ggccaggcct 222000
caggcccaca ggcattgtgc agaaccagcc aaaccaactg agacttcagc ttcagcaccg 222060
cctccaagca cagcaggtta gtttctcatg ggactcaggc gggggccctg gctggctgag 222120
gaatgaagaa gagttaagtt tttggagagg gctgttaatt ggaaaagatg atttgaaata 222180
cacatgtcct gttgtttaaa tgtattgagc taggaatagc taccttactc tttagtctca 222240
gtactcagga ggcagagtcc tggtctacag agtgaaacac aggacagaca gggctatata 222300
gagaaaccgt gtctcaaaaa aatatggatg gattctaggt cagcctgggt tacatagtaa 222360
gaccccgtct taaagtcccc ctcccgacga gtgctaatgc ccgtgtttgt gtgtagaatc 222420
gccagccgct tatgaatcag atcagcagtg tttccaatgt gaacctgact ctgaggcctg 222480
gagtgcccac tcaggtgaga agcctctcat tttcctccc agataggctg agtgacctgg 222540

-continued gttttcctag ttcctctgac tccctgtgtt agttctgaat gccatccctg ttgccagggt 222600
cagctgattc ctataataca caagagttgt attacaaaaa tgtatcaacc aattctggat 222660
tcaagtactg cccactgttc ccatgagaac acgggtttag ccttcaagac tggccacaac 222720
attgctctcg gcaatagcct tgtttctatg gagtttctgt gtgaagacac tttacgtgta 222780
tgtaatttac ttattaaact caatggacag gctatctcag actcaaacaa gccttgccta 222840
acactcgtac ttttcttcgt aagcacacct atgtcttcca cttgagaaca ctggacagtc 222900
ctgcaccagc acagagcctg ttaggttctg tcggccacat cagaaggcca cacatccatc 222960
tagccctccc cttggcagga agcaggcgag tgctaagcat aggaaatccg tgctgctgtc 223020
cttacagtca taaatggctt gacagtgctg cgcacactca tgtttgcatt gcagataaac 223080
tttagagtag gcagccttgt gagtggcgag gggatgccat tccagcacca gcgtacagca 223140
cacgcccagg gcccctcctc acatcatgtc actcatcctg gcctctcagc agacatctaa 223200
agaccattct gagatcaggt gcatctgaca tgatgtagcc atagaccagg gggacacagg 223260
ggacacaggg gacacaggga cacaggggac acctgtgcag ccagccagag cagcctggag 223320
atcagtaaag taacagaaat tactgtcaga tcaccccccac ctccatctct ccgaagtcac 223380
caagtcacct ttggcagtgg cttggtttct tgttaagttg gaatgttcct tcaaagagac 223440
tctaaatgct gtcctcaact tacataaagt cttctgccag gccagggtag ctgcgctgta 223500
accccagtgc tgtagtagct cccagcactt gggatactaa agcagaaaag aggtgacagt 223560
caagctagag gacccagaaa gcagcacgtg ggcacctgta actccatttc ctggtgatta 223620
gccgccctct tctggcctcc atgagcactg cacacataaa aataaatttt aaaaataaac 223680
ataaagtctt cctgtagaaa ggcctgtgct cttttgacat cttttgattg actgtaccct 223740
cgagaaatga gttggtcact atcagagggt tacagaatcg tcatcacaca ggctgaactt 223800
agagcactcg catgcgtgct cactaggtgc tctgctccga ggaccccccct tcatggaact 223860
ttgtttttca aatgatttta catacagtat gccattggta tcctgtctaa cctatctatc 223920
cttgatttcc cttcatgatt gcccacaatt tcaggctcct attaatgcac agatgctggc 223980
ccagaggcag agggaaatcc tcaaccaaca tcttcggcag agacagatgc agcagcaggt 224040
gcagcagcgg actttgatga tgagaggaca gggcttgaat gtgaccccaa gcatggtggc 224100
tcccgctggc ctaccagcag ccatgagcaa tccccggatc cccaggcca atgcccagca 224160
gttcccattt cctccgaact acggtactga cttagatccc tcccaccgtt gctgtcccgt 224220
cttggcctat ctgttctttc tcctttctcc cgaggcacct cagtcctggt cacggcttcc 224280
ttctcacggc tatgtgcctg gttagccagg aaacgatagg aggcctggag cagattaggg 224340
cctggcaagt ctcccagtcc cgcacagtgc ctacctgtta gctcgggtcc tccttttctt 224400
tgggtgcagg tctttaagaa tgaccaaagt taagtgtcat gtgtctctgg tgagcatgca 224460
tggatgttat ctgctcaggt cagggtctat gaatgtaata cacattgcta cttatccttg 224520
attgtttctg agtctgacac aaagaaatca gtagctaaat atgaaatgtc agaagacata 224580
agccaattta aatattacaa atagtctaca gcttttaaaa aataaaggct ttgtttgtta 224640
ctgacaacac ttatcaaaac aaaaaaataaa aactttcaag attgtaccaa gtcttcactg 224700
gattggtcgt tcctgaagtg ttactcggag ccacgtggga ggcctctggc tttacttaat 224760
cctgatttgt tctcggatgt cattctaaca gacgagacac caagggtgat gtcatggaga 224820
ttgacatccg gttgttatct tccgctaaca gtgggagtct cggtgcttcc atagtgcgtc 224880

-continued catgcttgca tgttccagat ggctctgctt tgccctgtct gagggatctg taaggaacca 224940
tgaacatgga agcctttgtg ttgcctaaat acaaacgtcg tgtctcctta aagagcagag 225000
atagtgcatt gtgttcttct cctcttcaga ctcttctctt gtagctactt ttaaatatta 225060
agtgttgcgc aggattaagc gaatgggtcc ttactctgtc cctgaaatgc cccctcgctg 225120
tcttcctttt ggtgcctttg ctcgctttcc gttgctagct cagggaagtc tgctgagatt 225180
ccttttcttt tgctgtgaat tcttttaccc taaactatac aagaaatgga taatcctgac 225240
agcactcaag tgccacaagc ccttttccaa aaacaaaata agccaatgtg ggcgtgcagt 225300
tgtgtatttt ctgaaataca tctcctgaac atgagatgat gtaagttaat ttagtgtaag 225360
ttattcatat gttgactgtt ggtatataga tgaatttaat gagctcagac taaatttaaa 225420
aggaacgata ctattacact gactgaccgg ctcagataaa atcaagtctc tacatagtag 225480
actcgtcctt ggtttagaga gggcttcagg aacaaatgtc atttctctga ctctagccct 225540
gatgctagtg tgcatcctcg gagccctgtg actcttggag agctttcaag tatagagagg 225600
gttttctcca tgtacttctg tctcagcttc tttcaaatat ctaataattt gcacataatc 225660
agataattga aagtaatttt tctgtgtata cttaatttgg aacattctct ctatgatata 225720
gataacaatc tcctttgggc ttctgttttg tttttgtttt taaggaataa gtcaacaacc 225780
tgatcctggc tttactgggg ctacaactcc ccagagtcct ctaatgtctc cccggatggc 225840
acatactcag agtcccatga tgcagcagtc tcaagccaac ccagcctacc agcccacctc 225900
agacatgaat ggatgggcac aggggagcat gggtggaaac aggtaacatc acattactgc 225960
gtctgatata aatgatcacc cctagccagg cggtggtggc gtttagcaag caatagcaaa 226020
tgaactgcta aaaagctagc ttattcttag caaaagtcaa caatttcaca gaagcctagc 226080
acagcacctc ttgttttaga gcaaaaacat tacctctaag cagttgccac tcctaactgt 226140
agaattcctg tggatggcgg tggcacagag ccaggcttca tcagtgcaca tgctaagaag 226200
caaacagcaa gcccccagca gctgggaaag caggagtgtg tgtgcttccc agcaatgtgt 226260
gcaagggaag aagcaagcct gatgcctggg ccagcaccca tttagataga gactgcctca 226320
gcttaccatc agactaactc tgtctcccac gctacagcat gttctcacag cagtccccac 226380
cacactttgg gcaacaagca aacaccagca tgtatagtaa caacatgaac atcagtgtgt 226440
cgatggcaac caacacgggt ggcttgagca gcatgaacca gatgacaggc cagatgagca 226500
tgacctcagt gacctccgtg cctacgtcag gactgccctc catgggtccc gagcaggtaa 226560
gagcctcaga gaagcagctc agaacgttct ccttggcttt gtgtctgttt atgccacaaa 226620
tcccatatct attttgaaaa gtgtttttttc accttatttt cacctgtgcc agtgagattt 226680
aacaaaaaat acttgttaat gacgaaggaa ctattgggaa ggactcctgg ctgctaacat 226740
gttgggggtt ttttgctttg ttttggtttt tatttcctaa ttttcacatc attaaccttt 226800
tttatcattt gtgggattta gaaatggagt ggtaggtgtt aggaagtttc tgctgggcat 226860
ggtgacccac acctttagtc ccagcactgg ggaggcagag gcaggtggat ctccgagttc 226920
aagtccagcc tgctctgcag agcatattcc ggaatgggca gggctacaca cagaaatcct 226980
ctctcaaaaa acaaaacaaa actagctttt taaaacctct ggtaagcatg gccacacagc 227040
ctaccagccg gtcactctcg gggccgcttt gcttacgtga caaggctggc acactgttgc 227100
ccccttgatg ctccagtgct ggtgacttta gttccagacc agcctggact ctaagcgcat 227160
gttagaaagg gtagggagaa gatgtgtagc ccacacgggc caggagcacc ttctgctctg 227220
tcgggccagt gttgagagtg aggtacacag agacacagaa ccgagcgtaa tcatgggcca 227280
gcccactcag gaacattcat caacccagac catttgaaat gtgtgcatgg atttaaatat 227340
ttttgagttt cggagtttat atagaagccc aggtccaaac ccacaacccc agtgtgtctg 227400
ctgaaaaatc attgtcttat tagccctggt gggctagctc catgagtaaa agtgcctgcc 227460
accaagcctc accacctgag tgtagtcccc agactccccc gagagagctg gcctctacac 227520
tccggcctcg gacatacatg cagccatcac acacaagtaa atgtaatgag aagagttttt 227580
tttaaaaaca cataaatgct gatgagtagg ttttttggcc agtccattcc caaaagccag 227640
tttgggtgtt ctcacgtcat tcttgctaat taatgacttg cctgagagca gaagtggcag 227700
atggtctcag gtgcttcacg ctctcagggc tgagtcacca gcctataaat gaaaatgtgc 227760
aaataagctg tgcttttgaa ggtaagtagt gtttgcagcc tcctctgccc catgtgtgca 227820
catggaaagc tgttagctgt gggatacagc ctcttttccc tagggccaca aaacttaaaa 227880
tcggaaatgt gtcatgttgt caccacaggt caatgaccct gctctgaggg gaggcaacct 227940
tttcccaaac caactgcctg gaatggacat gatcaagcag gagggagatg catctcgggt 228000
aagcagcagg agcccagagt gcaccttagg gtggctgtgg gccttctgaa ggccaaacgc 228060
ttctctctgc cttgtcggcc tggaaagtgc tgggatcaaa agagcacact acaaaaacag 228120
caggcatgat ggtgcatgcc tgtaactctg gctctgagga ggcagagaca agagagtcag 228180
gagttcaagg tcaactacac tgtgagttta agaccagcct gggctacaca ttaccctatc 228240
ttagagcaaa caaaaaaaca acactcccac cttgaaaaaa aacaagaaaa taactattta 228300
cacgcagaaa gcagcctaca gcaaatgcaa ctgtgacgtg ctttccagct cttcctaaca 228360
cactgatgta cactgccacg tccaaccctc aggaaaggtt catcctgtca gagagacgca 228420
ggagggtggg gactcggcat cattagcaag tcttaagcca gccccggtta tgagagatcc 228480
agtctcaaaa aatgaagagg gccagggaga actgaattaa atccccgaag tcagagtgga 228540
aagagccaac tctccacatt gtcctcgtgc ctgcacacgg gtgcctgcac acgggtgcct 228600
gcacacgcca cagaaacagt aaaatgttta aagaaataac ctcttaggcc acctccgcat 228660
actcaaaacc aagcaatagc ttgatcccat tggagagagt ggagtgtaaa tgagcactga 228720
acttcctcac tccagagcct ttgtgttgtt agcagcaggg ctacagtaga cctcacccgc 228780
ccattgctca gcaatgtcct ggattggctt tcccactgtg gcttttctgg gttttgtaac 228840
cctgattgtg ggcttcagag atactactga cagcgggtag gagtcctgta gctgtttctc 228900
acacgtgtcc ttaaaacgtg ataattaggt gcacgaagct taccatatct tccttcctta 228960
ctgtatgtgt atctggtatg tatacatagc aggtaagaat gtcagacagc ggggtagatt 229020
gtacactaac catgtgttcc tttgtttggg tttatcactt cccaagggct gatacctctc 229080
ctatagccat ggttttcaca ggcagggagt gctaagagct cagaggtaac tccatgcaaa 229140
agcagaggtc caaaacctga ggcacagtga cagcaggtga cactcacaca ctcagagagg 229200
acattgtaac tgcaaagtgc caggggagcc tagccagagt gctgtaagta tgagtgagag 229260
tgagccagct agcatttgaa cagctatcta ggaaaagccc cttgccagcc aagccctctg 229320
aagcagaccc aggcttctgc tttctcctag gagcaccagg aatctccctg ctttgtttct 229380
cctgccttct tgcctcctgt aaagcacagc atggttgtca atgcatgtta tgtccttgaa 229440
tattgcaaga gcagccaagc ataaccgcgc atgcaggaaa gtcactacaa gagcagcctg 229500
gttgacatag aattctagcc agccagcact gcatagagag gcatggtctc aaaaagatgg 229560
agggagagaa ggaaaaaaag gaaagaaaat catggaagca gcattgacat agaattctag 229620

-continued ccagccagca ctgcatagag aggcatggtc tcaaaaagat ggagggagag aaggaaaaaa 229680
aggaaagaaa atcatggaag cagccgatag gaatcaatca gttgctcact tagtaggcac 229740
catactgtct ggtctaacta cagccttacg aatgtaacga tttgtcctag gcctggggag 229800
atcagaaagc aagcaagctg acctctgaat gccttcctat tctttctttt tttttttttt 229860
aatttatttt atttatatga gtacactgta gttgtcatcc gacacaccag aagagggcat 229920
cagatcccat tacagatggt tgtgagccac catgtggttg ctgggatttg aactcaggac 229980
cactggaaga gcagtcagtg ctctcaaccg agatctctcc agaccatgcc tgcctatttt 230040
taacctgagc accactgtcc tctcccaaga gagacaagca ggctctcaca aggattttct 230100
caggggctat gtagcctcat ttaagaaggc ccagaggggc aagttgtttc tttggtgccc 230160
tcctccacct tgctactcaa gtcctgaagg aaggcagggt cagaaagaca ccacagaagt 230220
ttcaactacg tgtttaaatg tcatcggtct tcttttgttt tgttttgttt tgttttgttt 230280
tgttttgttc tgtttttttt cgagacaggg tttctctgta tagccctagc tgtcctggaa 230340
ctcactttgt agaccaggct ggcctcgaac tcaaaaatct acctgcctct gcctcccgag 230400
tgctgggatt aaaggcgtgc accaccatgc ccggctgtca tcagtctttt taagcatcca 230460
ggtgcttcat cccaggaggg gagaacctcc aatgctgaga cacagtgtcc cttttggact 230520
ctgtcaggcc tacatggatg ttaaaggctt cctggccatc ctgtggaaga atgtaggtga 230580
ggatcaaggg agctggtgac caacaccaac ccaactgagg aagaaagcct ggagcactgg 230640
gtgtcgccca gtccagagcc acctccccgc aaggactcat ctgaggaggc taatggagtc 230700
ctgttgctga tcaccagacc gcttacaggg acacagcagg cacatatacg atttcaggct 230760
ggcttcctct cttcaaatag atattcttag tggccctcta gtacctgctg ctcaatacag 230820
ccttggcata tatagtcatc tagattatga gttgagagtg gggtgggttt atcttaatga 230880
agtcagagtg agcacaccct cctaggacct gacagtgact cagagacgat ctagggaggg 230940
gagcgcttac gcgggcctct actcccagga ctcaggaagt agagacaggt gactcgatga 231000
ttagaggcca cactgtctag gtaaagaatt ctaaggccct gacttaaaaa atgaggagga 231060
gggctggaga gatgcctcag tggttaagag cactgactgc tcttccaaag gtcctgagtt 231120
caaattccag caaccacatg gtggctcaaa gccatctgta atgggatcca gtgccctatt 231180
ctggtgtctg aggccagcca tagtattctc acatacgtga aataaataaa atctttaaaa 231240
aaaaaaaagt ggggaggaaa actggagaga tggctcagtg gatagaagca cctactactc 231300
tctcagaagt tctgtgctca acagcaggcc agtggctcac agctacctgg aactctactt 231360
ccaggggctc tgacaccctt ttctgtgtgt ggaatataca catacaaatt aaaaatatat 231420
atatcaaatc atgatttttt taaatcagta gtagccaggc atgtgggtgc cacacacctt 231480
agtcccagca cttggaagaa aaagtaggag gatcttggtg aagccaaggc cagtctggtc 231540
tacataacga gttccaggat aaccaggatt acatagacac tgtctcaaaa acaagcacat 231600
tctttaaaaa gtcaaaggga tcaccctggg ctggggaggc actcggtggg taaagtgcca 231660
tgcaaacatg agagaggctc tcggatcaaa cccccagctc cccggttgtt ctgtacagac 231720
gggtggtcgt ccacagactg actacagcct gcgggagctt cacactgatg gatggagcgt 231780
gcacctgcgc cattcagtta gggacagcgc cacctgcctt cccgtgtcag aaacccacca 231840
ctcaccaaat gcggagcctt cgtactctag aataagctag tatgttgtgt tttatgatga 231900
tcactccatt gttttcattt caaacaaaaa caaacaaaca aaaaaactct tgatattgcc 231960
agtgtggtgg cgcacgcatt tgaaagacta gtgtatgggg gcacagaatc tgccaatagg 232020
ccagggtggc agcagaaaaa actatgcaaa cataaagagc cccttgtctt cacacaacct 232080
ttctgtctgt ttcccctcag aaatactgct gaccctggag aaactgtctg catctttctt 232140
caacccactg ggcttacaaa catttaccag tctggagagc tgcgtctctt tgtgttgcca 232200
cctgacatgc cgccagttct cccaggacat agcagcagac agtcgggccc tgggcccgca 232260
gcatagagcg tgctggcttg gctgccaccg gaagagttgc ctctcccgac agcctgcagc 232320
tcgcctccag accaacccgc agtctgttca ctgcattcac cgtagtgcaa cttagatctc 232380
ctgcagagta actgtcccca ggccgacttc atccccatca gattgaatgt atttaaatgt 232440
gtgtgtttga ggagagccat gcccttggcc tgttcctgct cggctccaga cactggtttc 232500
ttgctttgtt ctctgtggct cttctgtgta aaagatgaga atcttatcta caggaaagaa 232560
aggaactttt aacacagtac aacccaaggt gttctaagct taaagcctgc atttgactgg 232620
gatggagaca gggcagacac tgtgcacagc gctgtgtatg ccggcacacc tagtcagcaa 232680
cacgtaaccg aggcagagtt ctgtctccag gaaggagtgt cccgtcactg aacagatgga 232740
aggctcttga gagaggctgt tagcattaac aagtatctgt tcccacttct ctctgttaaa 232800
accaaactag tttcccctaa atcatgaatc aaaaagaaat acttgtttct aaattgtttt 232860
tagatcagat agtttgattg gcatctcttc ccttcctctc cccaccttct ctcgtccctc 232920
cctctttcat tcctttaaag taaaaacatc aacagcagca tacaccatag agaccaggga 232980
agcccttagg atctctcagt gctgtgccag ccacttacag cagcttccca gtgaccatgc 233040
atttcctatc agagaggaac aaagtcaggc tgtgacatct gcttaggtag cctgggctgc 233100
cccatcagct caggcctcca aaatgagaga acttactaat gaaatcaaca gcagacgtca 233160
cgacagatct aacctctgcc atatggggtt gttttttatt tttggttttt agcagtgctg 233220
acgaagccga agttttgtaa ggtacataaa gatccaattt atatgtaaac aagcaataat 233280
ttaagttctg aacttaagtg ttttaactgt ataattttgt gaggtataca tattgtggga 233340
ttgactcaaa atgaggtact tcagtattaa attagatatc ttcatagcaa tgtctcctaa 233400
aggtgttttg taacggctgc caatgccttg gttagacctg acttgtagac gtaagacctt 233460
ttgttttcta acccttgaga ctctcctcat gaatcctgta tctaatctat atgatatgca 233520
gccgctgtca gaaccaagtc ttgattttat atgtttatat tctttcttaa taaaccttag 233580
aaagacaaca ttactaagca gcccactttg atggttgttt tcttgcccac tgtcggggat 233640
aacctctatt aactggtgtc agtttcagac agctgcagta cccagaaccg agaccttttc 233700
aattctcccc aaccttgata cacacacttt cgtacctaaa tttcagaatg atgtcttttt 233760
gatgtctaaa aacaaagcat tttataatat ctcattatcc aagctttcta ggaacagaga 233820
agattttcct tgaagtttgt ttattcctgg cagggttaaa aacatataaa ctaccctatt 233880
tatatttatg tctccctata tatctacaga ttgtagaaat atagaaagag atgtgaccca 233940
aagacaaatg gtcagtcatc tgaaagtgtt gctgcgtgct aaggaactct ggaaatttgc 234000
atttccatac ctttttccac ttagagaaga atctcagtga gggaggtggc ccaggaacag 234060
cgcttccccg ttggccacca gttcctgtgt ctgctcgaga ctccaccaaa ccattggctt 234120
gcacatctgt cctgcaaagg gagcagatag aacccagaac tccaggccct gccccaggag 234180
tgaggctcag gtgcactact gagctcgacc tgttctcaga taagtcagaa atgtgaggta 234240
ggtaaaaatg acttcacaca gcacaagaga aaaaggaatt taaaacatac ttgttttgta 234300
ttaaatccca tctcactgta acatcaagcc acaatatctt acctttcagc cttcatccaa 234360

-continued

```
tctcccactg ctttctaatg ttgacccggc tgttagcgta gcccatggtc atggcaaatc 234420
ctctcacagg tcagagcagc catgaactgt gtgccatctc atcaggagga tcaatcgcat 234480
cagcaaaggc atcctgatca tgttctcaga gccagggcca gcccagcctc ccctgccatc 234540
agtattgctc acgctctgca caacacattt gtacttggtt ttgtctgaca gaacatagaa 234600
tcagtgttct cttagatgac tcaatgtgaa aagcgtaatg tgaaaagtac acacctgatc 234660
gtggttgtaa aatccattta agtgttcatg caacatggtg agttttaaaa gtgaagtgtg 234720
ctgtgatact acaaccaatt gactcaaaga ttaaagcacg cacgcacaca cacacacaca 234780
tacacacgtg tatctcttac gacctgtaat gattgaaagc aatggttttt ttgcagttta 234840
agatgcaatt tttaatctgt gtttaaaaac ggagttcata tgggtgtgac acgtgaactg 234900
ggaggcacag atccacttgc agaacccaaa gatacacaat caattttgaa atgcaactta 234960
agccattaat tgttggtgtg aatttaaaat tttctagttg tttatatggt agtatgctgc 235020
cgaagagcaa agcattctct gcacaaaaga aaacactgta gtggcttcga ttttaattag 235080
aactttctcc ctggtgtttc tttatagact aaaacaaaat cttttaagtt tctttactac 235140
aggtaaaagc tatgtgcaag aacctcaaaa tgctaaaacc tagcataatg ccttagatct 235200
gtttttaagt cttgtatatt cctacatagc tgtccaatgt attatatttg tatagtgaat 235260
tgtgtaaaat ttttgaataa gtaagtcatc gcttacccgt atgttactga acagtgatga 235320
caactcgttt cttcaaacat ttaactgtct tctcttttttc ctttgtcatt tgtgggtttt 235380
atttgtacag ttcctcatga agttgcattt gagatatgtg tatatgaaaa aattatacaa 235440
gggtaaaatt aagcaatata ttaactatgg ttcttcagga gaaagcttac agtgtttcag 235500
gttgtgattt attttcaaaa cagagttgac tctgaacatc actttgttca tctgcattga 235560
tgtttgtatt tctagtgtga gcagtttatg caaaggtaga tatatacaga gaaattttaa 235620
atacatttat gcaagttact attgctttgc tgatgctatt tgcttatttg atgttaaata 235680
atgctattgt aaataaagaa tctgttgtta ctgcatcatt taataaattt taatgccttc 235740
gggttttaca tggctttaga gattttaatg tggcgatacg gtatcttctt ttgtagttta 235800
aacttaaaaa tacctgagaa ctactactgg ctgctctttc agaagaccca gattcaattt 235860
ctagcaccca cacatcatct cagaatcatc tgtaactcca gttccaggag gtccagcccc 235920
ttcttcctgc tcttacaggc attaggacca ctcctgatac agttttcaaa caaacaaagc 235980
atctatagac atacaacctt ttaaaaaaat atattaacga cattatcttt taagaatttc 236040
ttgggctggg tgggtaggga agtggggggg agggtatgga ggacttttgg gatagcattg 236100
gaaatgtaat tgaggaaaat atgtaataaa aaaaaagaat ttcttgggct aggcatgatg 236160
gtgcacacct ttgaccccag cactccagag gcagaggctg gtggatctgc cccgtctaca 236220
gagcaagctc cagggtagcc tgggctgttg ggggggaaaa aaaaaaaaaa aaaacagaag 236280
gaaaaaggga atttcttgtt tctggagcga tgactcaata tgcttattgc ttttatgcag 236340
gagcccactt ctcttcccag cactcaggtc aggaggctca caactgcctg taagtccttt 236400
tcctgggggga tacactgccc tcttatggcc tctatagaca ctgcactcgg gtgcacatat 236460
ccacaaggag aaacacccat gcacataatt aaaaatacat tttaaaaatg gtagtcagtg 236520
gtcacagcac tcttaacacc ttgccctccc agagaagcca agtatatcct agttgacatc 236580
actagctctt tatggcagat gtggcctgtc tagttcctgc tacaaatatt gctgcagtat 236640
ctgtggatgt gaggagtcac ggcgtacctg tgctggtcag aggtcaactc tcaggagttg 236700
gctctctccc gccactctat gggtcctgga gatggaaccc caggtcacca gacttggcaa 236760
```

gtgagcacct ttaccagctg agccctcccc cagcccacac tgtttataaa gatggaaagt 236820
actgtgtcct cttcaaaagt gctggtgccc ctctcacaag cttgcgtctt acaggattcg 236880
tgaagggcat atcttctggg ccttcccagt gtggacgatt aggttttcca caatgtatcc 236940
actctaccat tgcaatttcc ctgagcctta aaatcccttc atcaacacta agccgaggga 237000
catcaggcat cttcaactcc ttttcagtag gccatctttt tttttttttt tttttttttt 237060
ttttgagaca ggggtttctc tgtatagccc tgacggtcct ggaactcact ttgtagacca 237120
ggctggcctc gaactcagaa atctgcttgc ctctgcctcc aaatgctggg attaaaggtg 237180
tgtgccaccc acgcccggct tgtaggccat cttttgataa acacttcagc caaccattca 237240
aacaaacaaa cttctgacag cttttttaac tgtgcaagct tccatattaa acctagaatc 237300
tccactcaga gggaccacat cagtaaactc agcctgctct agttttatgt tccttccacc 237360
attttcccac acccttaaaa tccattccca cacatatccc ccaggtttct gcttgaatca 237420
attagcaaac tcatgaagct cctttgtagt gaagcgcatt tcctcccctc tatggctctc 237480
ttctgccttg agtctggtta taggtctaga agaagctatt ggtgggcctt gagaaacatc 237540
agtattgtct ggcattttct tcagcgaaag tcactgctgg tttaacagac tctgagggat 237600
taattttctc atgtgaaaat ggcattattt caaggggtgg ggcactactt cctcaggtgg 237660
ggcaaaccct tgagaatctg aagattcaaa attctcagct tcaacatggt cttcccacac 237720
atccccatcc caagttttaa gatcccattc tttgccttta actgctgaca ccctctgaga 237780
cttgaatttt cgctgtaatt caaccaacct tataatgagg gcttcagttt gattttctgc 237840
aacttgagct ctatggctgc tgaagagaag attctcttca aggacacaca tagcaacttt 237900
tagatcactt ccttgcatct ggagccattt gatattatca cacaataact tcttttcctt 237960
catccttttt ccccaagatg ctaagagcaa ccagccagca aaatcatttt ccaatttttc 238020
cccatcttgt agaaagcttt gtacactgaa tcatctaata cattaagata atcaaaggca 238080
ttagcttctt taaacttgaa atacagtttc aaccacgggt cttcaatatt ctccaagctc 238140
ccaggaggga gagaatctgg agaggtttca gtcgttgaag gtgctggtga attatcaaac 238200
caactccaga atttcatcct tatacttctg ctcctctaga actcctcctg gtaccagctt 238260
ctgtaatagt cagggctctc tagagtctag aacttacggg tagtctgtat atagtaaggg 238320
aatctgttga cgtaagtctg tagtccaact cccagccatg gtcagcagca gctgtgaatg 238380
gatgtccaag gatctagcag tttctcagcc ccacaggcaa gcaggggaag gaaagagggg 238440
taaacagtgc aattacgctg ccttcaaccc aggtcctaaa tcgcatgcag tgctagaggc 238500
ccagtttggg tttttccctt ctctagcatg aagggaaaca ttggccattg caggtggtgg 238560
cccagagagg actgtgttaa gctgctgctg ctgctgctgg caagggtacc ccgtcccagg 238620
aaggtaccag aagcgagcag tcagtttcat agatctctgc agagctgttg gcctatagca 238680
ccgagccagc tgtccacttt ccctttccct ttttcttttt ggatactggc caagccaaag 238740
caatattatc tctaatattt tacagaagct accacactcc gttgtgtggt tgcttacaag 238800
aggtgtggat ttttatctct cctgtcttcc tcctccagtg acatctgaaa ctcactgtgc 238860
agcaaaacct ggccttgaac ccctcctgca tctatctcct aggtgctgaa attgcaggtg 238920
tgccccatca tcccaggcat caaccctgga ttgctctcta agaaacgctg ctagctcatt 238980
cctgcaacca caaataccag tcatgcacaa gttgtaccca ggggctggtg acaggaagaa 239040
gagaactggt ggccagtcaa agcactgcct gcctagttag ggtgtccagc agcatcacaa 239100
aatagaaatg atacatcatg attggtcctc atccggcaac acagttcagc aagtaaaggc 239160
acttgccacc aagcctgaac gtcatggtag ggattaagt gactcctgca ggttgtcgtc 239220
tgtcctagtt agggttacta gcactgctgt gatgaaacac catgaccaaa gcaacctgca 239280
gaggaaagga ttcattcagc ttctacatca cagttcatca tcaaaggaaa ttaggacaac 239340
ttaagcaggg aggaacctgg aggcaggagc tgatgcagag gccatagagg ggtgctgctt 239400
actgcttccc atggcttgtt caagcctgct ttcttagaga gcccaggacc accagcccag 239460
agtgaacccc tcctacaata ggctaggcct cctccatcaa tcacaaagaa aatgccctac 239520
agactctctc tgataactcc agcttgtgtc aaatcaacat aaaacaaacc agtacctcct 239580
ctgacctcca aacgtgtgca agtgtggcac tttcatgcca ctagcaaaca tctgacccaa 239640
gatcagcacc acatagccag ggagactcgg aaactggcta gctgacactg aaagatcctg 239700
agagagaaga gtgaaaaatt atgtaagccc ctagacttgt gtccaaaata gacctgacta 239760
atggcaggga gtaaaagttt aactcacccc attgttttag gttgtactaa ccacaaagta 239820
gaagtttaac ttccattgtt ttaggaaatg ttcatacaga atattccaac tatttcttga 239880
acccgttgtg cttgccaaat gctatagccc atgccaggtg tttacggttt ctgcctttat 239940
aagcccctta tcctttgagc tgggggcgac tcctctaccc cttcgtggga tacgagtcgt 240000
c 240001

<210> SEQ ID NO 33
<211> LENGTH: 4039
<212> TYPE: DNA
<213> ORGANISM: M. musculus

<400> SEQUENCE: 33
actccccaga gtcctctaat gtctccccgg atggcacata ctcagagtcc catgatgcag 60
cagtctcaag ccaacccagc ctaccagccc acctcagaca tgaatggatg ggcacagggg 120
agcatgggtg gaaacagcat gttctcacag cagtccccac cacactttgg gcaacaagca 180
aacaccagca tgtatagtaa caacatgaac atcagtgtgt cgatggcaac caacacgggt 240
ggcttgagca gcatgaacca gatgacaggc cagatgagca tgacctcagt gacctccgtg 300
cctacgtcag gactgccctc catgggtccc gagcaggtca atgaccctgc tctgaggggga 360 ggcaaccttt tcccaaacca actgcctgga atggacatga tcaagcagga gggagatgca 420
tctcggaaat actgctgacc ctggagaaac tgtctgcatc tttcttcaac ccactgggct 480
tacaaacatt taccagtctg gagagctgcg tctctttgtg ttgccacctg acatgcccca 540
gttctcccag gacatagcag cagacagtcg ggccctgggc ccgcagcata gagcgtgctg 600
gcttggctgc caccggaaga gttgcctctc ccgacagcct gcagctcgcc tccagaccaa 660
cccgcagtct gttcactgca ttcaccgtag tgcaacttag atctcctgca gagtaactgt 720
ccccaggccg acttcatccc catcagattg aatgtattta aatgtgtgtg tttgaggaga 780
gccatgccct tggcctgttc ctgctcggct ccagacactg gtttcttgct ttgttctctg 840
tggctcttct gtgtaaaaga tgagaatctt atctacagga aagaaaggaa cttttaacac 900
agtacaaccc aaggtgttct aagcttaaag cctgcatttg actgggatgg agacagggca 960
gacactgtgc acagcgctgt gtatgccggc acacctagtc agcaacacgt aaccgaggca 1020
gagttctgtc tccaggaagg agtgtcccgt cactgaacag atggaaggct cttgagagag 1080
gctgttagca ttaacaagta tctgttccca cttctctctg ttaaaaccaa actagtttcc 1140
cctaaatcat gaatcaaaaa gaaatacttg tttctaaatt gtttttagat cagatagttt 1200

```
gattggcatc tcttcccttc ctctccccac cttctctcgt ccctccctct ttcattcctt   1260
taaagtaaaa acatcaacag cagcatacac catagagacc agggaagccc ttaggatctc   1320
tcagtgctgt gccagccact tacagcagct tcccagtgac catgcatttc ctatcagaga   1380
ggaacaaagt caggctgtga catctgctta ggtagcctgg gctgccccat cagctcaggc   1440
ctccaaaatg agagaactta ctaatgaaat caacagcaga cgtcacgaca gatctaacct   1500
ctgccatatg ggttgtttt ttatttttgg tttttagcag tgctgacgaa gccgaagttt   1560
tgtaaggtac ataaagatcc aatttatatg taaacaagca ataatttaag ttctgaactt   1620
aagtgtttta actgtataat tttgtgaggt atacatattg tgggattgac tcaaaatgag   1680
gtacttcagt attaaattag atatcttcat agcaatgtct cctaaaggtg ttttgtaacg   1740
gctgccaatg ccttggttag acctgacttg tagacgtaag accttttgtt ttctaaccct   1800
tgagactctc ctcatgaatc ctgtatctaa tctatatgat atgcagccgc tgtcagaacc   1860
aagtcttgat tttatatgtt tatattcttt cttaataaac cttagaaaga caacattact   1920
aagcagccca ctttgatggt tgttttcttg cccactgtcg gggataacct ctattaactg   1980
gtgtcagttt cagacagctg cagtacccag aaccgagacc ttttcaattc tccccaacct   2040
tgatacacac actttcgtac ctaaatttca gaatgatgtc tttttgatgt ctaaaaacaa   2100
agcattttat aatatctcat tatccaagct ttctaggaac agagaagatt ttccttgaag   2160
tttgtttatt cctggcaggg ttaaaaacat ataaactacc ctatttatat ttatgtctcc   2220
ctatatatct acagattgta gaaatataga aagagatgtg acccaaagac aaatggtcag   2280
tcatctgaaa gtgatgctgc gtgctaagga actctggaaa tttgcatttc catacctttt   2340
tccacttaga gaagaatctc agtgagggag gtggcccagg aacagcgctt ccccgttggc   2400
caccagttcc tgtgtctgct cgagactcca ccaaaccatt ggcttgcaca tctgtcctgc   2460
aaagggagca gatagaaccc agaactccag gccctgcccc aggagtgagg ctcaggtgca   2520
ctactgagct cgacctgttc tcagataagt cagaaatgtg aggtaggtaa aaatgacttc   2580
acacagcaca agagaaaaag gaatttaaaa catacttgtt ttgtattaaa tcccatctca   2640
ctgtaacatc aagccacaat atcttacctt tcagccttca tccaatctcc cactgctttc   2700
taatgttgac ccggctgtta gcgtagccca tggtcatggc aaatcctctc acaggtcaga   2760
gcagccatga actgtgtgcc atctcatcag gaggatcaat cgcatcagca aaggcatcct   2820
gatcatgttc tcagagccag ggccagccca gcctcccctg ccatcagtat tgctcacgct   2880
ctgcacaaca catttgtact tggttttgtc tgacagaaca tagaatcagt gttctcttag   2940
atgactcaat gtgaaaagcg taatgtgaaa agtacacacc tgatcgtggt tgtaaaatcc   3000
atttaagtgt tcatgcaaca tggtgagttt taaaagtgaa gtgtgctgtg atactacaac   3060
caattgactc aaagattaaa gcacgcacgc acacacacac acacatacac acgtgtatct   3120
cttacgacct gtaatgattg aaagcaatgg tttttttgca gtttaagatg caatttttaa   3180
tctgtgttta aaaacggagt tcatatgggt gtgacacgtg aactgggagg cacagatcca   3240
cttgcagaac ccaaagatac acaatcaatt ttgaaatgca acttaagcca ttaattgttg   3300
gtgtgaattt aaaattttct agttgtttat atggtagtat gctgccgaag agcaaagcat   3360
tctctgcaca aaagaaaaca ctgtagtggc ttcgatttta attagaactt tctccctggt   3420
gtttctttat agactaaaac aaaatctttt aagtttcttt actacaggta aaagctatgt   3480
gcaagaacct caaaatgcta aaacctagca taatgcctta gatctgtttt taagtcttgt   3540
```

-continued atattcctac atagctgtcc aatgtattat atttgtatag tgaattgtgt aaaatttttg 3600
aataagtaag tcatcgctta cccgtatgtt actgaacagt gatgacaact cgtttcttca 3660
aacatttaac tgtcttctct ttttcctttg tcatttgtgg gttttatttg tacagttcct 3720
catgaagttg catttgagat atgtgtatat gaaaaaatta tacaagggta aaattaagca 3780
atatattaac tatggttctt caggagaaag cttacagtgt ttcaggttgt gatttatttt 3840
caaaacagag ttgactctga acatcacttt gttcatctgc attgatgttt gtatttctag 3900
tgtgagcagt ttatgcaaag gtagatatat acagagaaat tttaaataca tttatgcaag 3960
ttactattgc tttgctgatg ctatttgctt atttgatgtt aaataatgct attgtaaata 4020
aagaatctgt tgttactgc 4039

<210> SEQ ID NO 34
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 34
aaccacactt acccatgggc 20

<210> SEQ ID NO 35
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 35
atgcactcaa gaactcggta 20

<210> SEQ ID NO 36
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 36
atgtccagtt ttccgccctt 20

<210> SEQ ID NO 37
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 37
atttgcatcc atgagctcca 20

<210> SEQ ID NO 38
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 38
caggagatgt tggccgtggt 20

<210> SEQ ID NO 39
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 39
ccagggctgc ctcagacaca 20

<210> SEQ ID NO 40
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 40
cgctcgtact cgtaggccag 20

<210> SEQ ID NO 41
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 41
ctcgtgaacc agagcaccac 20

<210> SEQ ID NO 42
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 42
ctgctagcct ctggatttga 20

<210> SEQ ID NO 43
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 43
gagctttgcc ttcttgccat 20

<210> SEQ ID NO 44
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 44
gcactttgtg gtgccaaggc 20

<210> SEQ ID NO 45
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 45
gctccttcca ctgatcctgc 20

<210> SEQ ID NO 46
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 46
ggacctgtag ccatagccaa 20

<210> SEQ ID NO 47
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 47
gtgtttctga gaacttgtgg 20

<210> SEQ ID NO 48
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 48
gttcctgtca aagctcgtgc 20

<210> SEQ ID NO 49
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 49
gttggtctcc tttgcctgga 20

<210> SEQ ID NO 50
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 50
tcaaggactg ctgatcttcg 20

<210> SEQ ID NO 51
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 51
tcaagtttct ctgtgcccaa 20

<210> SEQ ID NO 52
<211> LENGTH: 20

<212> TYPE: DNA
<213> ORGANISM: Artificial Sequence
<220> FEATURE:
<223> OTHER INFORMATION: Oligomeric Compound

<400> SEQUENCE: 52
tccatttatt agtctaggaa 20

<210> SEQ ID NO 53
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 53
tctacagtca tgctgagtaa 20

<210> SEQ ID NO 54
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 54
tgtcatcggg ttcccagcct 20

<210> SEQ ID NO 55
<211> LENGTH: 18
<212> TYPE: DNA
<213> ORGANISM: Artificial Sequence
<220> FEATURE:
<223> OTHER INFORMATION: Oligomeric Compound

<400> SEQUENCE: 55
tgtgctattc tgtgaatt 18

<210> SEQ ID NO 56
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 56
tgttgcaaga atttctcatg 20

<210> SEQ ID NO 57
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 57
ttcatgaact gcacagaggt 20

<210> SEQ ID NO 58
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 58

-continued ttctcatgat gaggtgtacc 20

<210> SEQ ID NO 59
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 59
ttgttgacat tgtactcggc 20

<210> SEQ ID NO 60
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 60
ttgttgacgt tgtactcagc 20

<210> SEQ ID NO 61
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 61
cctgatccct ctaatgatgc 20

<210> SEQ ID NO 62
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 62
cctgctcact ctaatgctgc 20

<210> SEQ ID NO 63
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 63
cctgctccct ctaatgctgc 20

<210> SEQ ID NO 64
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 64
ccttccctga aggttcctcc 20

<210> SEQ ID NO 65
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 65
cgttattaac ctccgttgaa 20

<210> SEQ ID NO 66
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 66
cttctagcct ctggattgga 20

<210> SEQ ID NO 67
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 67
gcgatttccc gttttcacct 20

<210> SEQ ID NO 68
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 68
gttcgtgttc tctggctcga 20

<210> SEQ ID NO 69
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 69
tacttgacct acagagtgga 20

<210> SEQ ID NO 70
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 70
tcaagtcctt ccacacccaa 20

<210> SEQ ID NO 71
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 71
ttgttaacgg tgttctcagc 20

-continued

<210> SEQ ID NO 72
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 72
tttgtaacgg tgttcactga 20

<210> SEQ ID NO 73

<400> SEQUENCE: 73

000

<210> SEQ ID NO 74

<400> SEQUENCE: 74

000

<210> SEQ ID NO 75
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 1-20
<223> OTHER INFORMATION: n = A,T,C or G

<400> SEQUENCE: 75
nnnnnnnnnn nnnnnnnnnn 20

<210> SEQ ID NO 76
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 76
attcttaaac ctgagggagc 20

<210> SEQ ID NO 77
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 77
tgatcgtctt ccaagctccc 20

<210> SEQ ID NO 78
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 78
gagagatgca gctggagcca 20

<210> SEQ ID NO 79
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 79
tgccatcatc tgatgcccgg 20

<210> SEQ ID NO 80
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 80
ttagaaggat ctgtgagttt 20

<210> SEQ ID NO 81
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 81
gcacattgac cactgttctt 20

<210> SEQ ID NO 82
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 82
agtgctttca taaggcagtc 20

<210> SEQ ID NO 83
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 83
ctctggttgc aggcccctca 20

<210> SEQ ID NO 84
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 84
aagtctgaac actgcacagc 20

<210> SEQ ID NO 85
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 85
ttacctttgt gttcgtggag 20

<210> SEQ ID NO 86
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 86
gcagcatcag tattccaatc 20

<210> SEQ ID NO 87
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 87
tcttccgagc aaagttgtgt 20

<210> SEQ ID NO 88
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 88
tgagcaggaa tttctgacag 20

<210> SEQ ID NO 89
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 89
tggaaacaat aagagttgtc 20

<210> SEQ ID NO 90
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 90
ggaaacagac tctcgcatac 20

<210> SEQ ID NO 91
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 91
gtgctgagaa ctaacaggca 20

<210> SEQ ID NO 92
<211> LENGTH: 20

<212> TYPE: DNA
<213> ORGANISM: Artificial Sequence
<220> FEATURE:
<223> OTHER INFORMATION: Oligomeric Compound

<400> SEQUENCE: 92
tgaccatgtg gacattaggt 20

<210> SEQ ID NO 93
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 93
ctgtccacag gcagcgtggt 20

<210> SEQ ID NO 94
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 94
gaaggtgagg ctgattcgct 20

<210> SEQ ID NO 95
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 95
cacgaggcct aattttgttt 20

<210> SEQ ID NO 96
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 96
atttcccaat aatagcttga 20

<210> SEQ ID NO 97
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 97
gcaacatctc cgtgccattt 20

<210> SEQ ID NO 98
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 98
tcctgaaggc ctggaattgc 20

<210> SEQ ID NO 99
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 99
ccgtgttttg cgcagaacag 20

<210> SEQ ID NO 100
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 100
caggttgtcc tttgtcatgt 20

<210> SEQ ID NO 101
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 101
ggacatgcag gtgtttgtag 20

<210> SEQ ID NO 102
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 102
attagctgga acatctgaaa 20

<210> SEQ ID NO 103
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 103
atgcaaatag tccattccct 20

<210> SEQ ID NO 104
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 104
gaaatatatt gttggatttc 20

<210> SEQ ID NO 105
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 105
cgtgacttta ctgttgccaa 20

<210> SEQ ID NO 106
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 106
gggccatcca gaggacagag 20

<210> SEQ ID NO 107
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 107
tgaagatgat ctgatctcgg 20

<210> SEQ ID NO 108
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 108
atatagctta ctaagatctg 20

<210> SEQ ID NO 109
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 109
aatggaagac aggatctggg 20

<210> SEQ ID NO 110
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 110
cttcggtaga gagtgttgga 20

<210> SEQ ID NO 111
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 111
tatcctcagt gtgggctgcc 20

-continued

<210> SEQ ID NO 112
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 112
tgcaaagtca actagaagac 20

<210> SEQ ID NO 113
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 113
ttctgcctct ggagaaaggg 20

<210> SEQ ID NO 114
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 114
aggtccttag cagagcttct 20

<210> SEQ ID NO 115
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 115
aaatggcttc cttctcccag 20

<210> SEQ ID NO 116
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 116
tacagaaggc tgggccttga 20

<210> SEQ ID NO 117
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 117
tttttgtact accatcaaca 20

<210> SEQ ID NO 118
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 118
acttcctcta aatactcatg 20

<210> SEQ ID NO 119
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 119
tccacatcag ggctggactg 20

<210> SEQ ID NO 120
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 120
gaagctgatt tccaaaatcc 20

<210> SEQ ID NO 121
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 121
tcccgcctgt gacatgcatt 20

<210> SEQ ID NO 122
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 122
accactctct gaagaaagtc 20

<210> SEQ ID NO 123
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 123
gtgccttatg tgcaaaatgt 20

<210> SEQ ID NO 124
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 124
ggcggccaga gtctcggcag 20

<210> SEQ ID NO 125

<211> LENGTH: 20
<212> TYPE: DNA
<213> ORGANISM: Artificial Sequence
<220> FEATURE:
<223> OTHER INFORMATION: Oligomeric Compound

<400> SEQUENCE: 125
ctaagaaaag ttccatagta 20

<210> SEQ ID NO 126
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 126
gaagctgtga aaggaggacg 20

<210> SEQ ID NO 127
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 127
gggcagctcc tggaagacaa 20

<210> SEQ ID NO 128
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 128
tgtatacaca tgatgtgact 20

<210> SEQ ID NO 129
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 129
aacatagcta tttgaagcta 20

<210> SEQ ID NO 130
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 130
aagcaataat ttcaatttct 20

<210> SEQ ID NO 131
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 131
gcccagctta acgtgtattt 20

<210> SEQ ID NO 132
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 132
tcatcaggcc cagcttaacg 20

<210> SEQ ID NO 133
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 133
ccatccatgg aaacattatc 20

<210> SEQ ID NO 134
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 134
acagcatcta acatcactgt 20

<210> SEQ ID NO 135
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 135
agtcaatctc ccgaggatag 20

<210> SEQ ID NO 136
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 136
agtgacgctt tccaagaaga 20

<210> SEQ ID NO 137
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 137
atgtaagcta acgatgaata 20

<210> SEQ ID NO 138
<211> LENGTH: 20
<212> TYPE: DNA

<213> ORGANISM: Artificial Sequence
<220> FEATURE:
<223> OTHER INFORMATION: Oligomeric Compound

<400> SEQUENCE: 138
ttccctgggc tattctccca 20

<210> SEQ ID NO 139
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 139
aattgagaat tacactcacc 20

<210> SEQ ID NO 140
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 140
aacgcctcct aaattgagaa 20

<210> SEQ ID NO 141
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 141
tggattggct tagggaccca 20

<210> SEQ ID NO 142
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 142
actattttgc ccttatgaag 20

<210> SEQ ID NO 143
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 143
tcttaaaatc tactctgaaa 20

<210> SEQ ID NO 144
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 144
cttaactgtc ttaaaatcta 20

<210> SEQ ID NO 145
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 145
tgaaaaatgt acttttctat 20

<210> SEQ ID NO 146
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 146
aaagttttct ttaaacaatg 20

<210> SEQ ID NO 147
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 147
gcccatgttc tcagaataaa 20

<210> SEQ ID NO 148
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 148
aatctaggtc tgttgaactc 20

<210> SEQ ID NO 149
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 149
aaggtaattt gctcaaggcc 20

<210> SEQ ID NO 150
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 150
agaaaactgg gactctaaga 20

<210> SEQ ID NO 151
<211> LENGTH: 20
<212> TYPE: DNA
<213> ORGANISM: Artificial Sequence
<220> FEATURE:

<223> OTHER INFORMATION: Oligomeric Compound

<400> SEQUENCE: 151
tatttctatc tgaaaaataa 20

<210> SEQ ID NO 152
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 152
aacaaaccta tgaagtaggt 20

<210> SEQ ID NO 153
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 153
tgccacctac ctgagggagc 20

<210> SEQ ID NO 154
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 154
attcttaaac ctggtaagaa 20

<210> SEQ ID NO 155
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 155
gttcacatac cactgttctt 20

<210> SEQ ID NO 156
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 156
gcacattgac ctacaaacaa 20

<210> SEQ ID NO 157
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 157
gagctcttac cctttgtgtt 20

<210> SEQ ID NO 158
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 158
tgcaacttac aaagttgtgt 20

<210> SEQ ID NO 159
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 159
tcttccgagc ctacaacaag 20

<210> SEQ ID NO 160
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 160
aatgccttac aagagttgtc 20

<210> SEQ ID NO 161
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 161
gtgctgagaa ctaggaggag 20

<210> SEQ ID NO 162
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 162
gccctattac ctcaatcatc 20

<210> SEQ ID NO 163
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 163
gaattgcatc ctgaaacaga 20

<210> SEQ ID NO 164
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 164
ggaaaagtac ctgattcgct 20

<210> SEQ ID NO 165
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 165
gaaggtgagg cttaatagac 20

<210> SEQ ID NO 166
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 166
cacgaggcct ctgaaacaag 20

<210> SEQ ID NO 167
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 167
ccaagcttac cgtgccattt 20

<210> SEQ ID NO 168
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 168
gcaacatctc ctgcaaaatt 20

<210> SEQ ID NO 169
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 169
ttctactcac cgcagaacag 20

<210> SEQ ID NO 170
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 170
tctactcact ccattccctg 20

<210> SEQ ID NO 171
<211> LENGTH: 20

<212> TYPE: DNA
<213> ORGANISM: Artificial Sequence
<220> FEATURE:
<223> OTHER INFORMATION: Oligomeric Compound

<400> SEQUENCE: 171
atgcaaatag ctgtgaaggg 20

<210> SEQ ID NO 172
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 172
caaaggatac tgttggattt 20

<210> SEQ ID NO 173
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 173
agaaatatat ctcaatgctt 20

<210> SEQ ID NO 174
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 174
agattctcac catccagagg 20

<210> SEQ ID NO 175
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 175
acagacttac ctgatctcgg 20

<210> SEQ ID NO 176
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 176
tgaagatgat ctaagggaaa 20

<210> SEQ ID NO 177
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 177
ggaagacagg atctgaaaca 20

<210> SEQ ID NO 178
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 178
gtgcgcgcga gcccgaaatc 20

<210> SEQ ID NO 179
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 179
tatcagcaac tgtgcctgta 20

<210> SEQ ID NO 180
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 180
cccactcatc ttgaacacat 20

<210> SEQ ID NO 181
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 181
tctgcacttc atctatgttg 20

<210> SEQ ID NO 182
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 182
cagctcttct tggttatacc 20

<210> SEQ ID NO 183
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 183
tgtctcagaa cttcatggtg 20

<210> SEQ ID NO 184
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 184
gaacggatga gtttgctctt 20

<210> SEQ ID NO 185
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 185
tcattagtag tctgagaacg 20

<210> SEQ ID NO 186
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 186
acctgggttc ccactgcaca 20

<210> SEQ ID NO 187
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 187
gggaaaattt atattgctac 20

<210> SEQ ID NO 188
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 188
atgcccattt gttcctttgg 20

<210> SEQ ID NO 189
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 189
tgcttctcct tgagcgaggt 20

<210> SEQ ID NO 190
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 190
aggatctgtc ttactgtcca 20

<210> SEQ ID NO 191
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 191
tgttactggc aggatctgtc 20

<210> SEQ ID NO 192
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 192
tgcaaatcat ccaaaatctc 20

<210> SEQ ID NO 193
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 193
atggcttgct tgtcaactga 20

<210> SEQ ID NO 194
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 194
tgatgatggc ttgcttgtca 20

<210> SEQ ID NO 195
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 195
gttgcatgag gtcattgatg 20

<210> SEQ ID NO 196
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 196
gtgggttatt aaaagtgctc 20

<210> SEQ ID NO 197
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 197
tggtcgtggg ttattaaaag 20

<210> SEQ ID NO 198
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 198
ccagttgccc tggtcgtggg 20

<210> SEQ ID NO 199
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 199
cctgcccagt tgccctggtc 20

<210> SEQ ID NO 200
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 200
ctggtttggc aataacctgc 20

<210> SEQ ID NO 201
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 201
gtccagcacc agttgggctt 20

<210> SEQ ID NO 202
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 202
gaaaggtcca gcaccagttg 20

<210> SEQ ID NO 203
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 203
tgattggtgg gaaaggtcca 20

<210> SEQ ID NO 204

<211> LENGTH: 20
<212> TYPE: DNA
<213> ORGANISM: Artificial Sequence
<220> FEATURE:
<223> OTHER INFORMATION: Oligomeric Compound

<400> SEQUENCE: 204
ctactgtttc tgattggtgg 20

<210> SEQ ID NO 205
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 205
ggctgaggta tcactgagta 20

<210> SEQ ID NO 206
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 206
ttcctggctg aggtatcact 20

<210> SEQ ID NO 207
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 207
ttacccatca ttcctggctg 20

<210> SEQ ID NO 208
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 208
gtctttggcc aggctggctg 20

<210> SEQ ID NO 209
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 209
tggctctggc tgaccagttc 20

<210> SEQ ID NO 210
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 210
agtttggatc ttgcatggga 20

<210> SEQ ID NO 211
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 211
ttctgctgtg cttggaggcg 20

<210> SEQ ID NO 212
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 212
gtcgtagccc cagtaaagcc 20

<210> SEQ ID NO 213
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 213
agttgcacta cggtgaatgc 20

<210> SEQ ID NO 214
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 214
gcatctttac cacttcagga 20

<210> SEQ ID NO 215
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 215
gaaaactcac ctggtcactg 20

<210> SEQ ID NO 216
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 216
aacaggtcga gctcagtagt 20

<210> SEQ ID NO 217
<211> LENGTH: 40
<212> TYPE: DNA

-continued

```
<213> ORGANISM: Artificial Sequence
<220> FEATURE:
<223> OTHER INFORMATION: Oligomeric Compound

<400> SEQUENCE: 217

gttggaggca atggcaagaa ggcaaagctc ttcaggagga                        40


<210> SEQ ID NO 218
<211> LENGTH: 21
<212> TYPE: RNA
<213> ORGANISM: Artificial Sequence
<220> FEATURE:
<223> OTHER INFORMATION: Oligomeric Compound

<400> SEQUENCE: 218

cucauccucu guggcaaacu u                                             21


<210> SEQ ID NO 219
<211> LENGTH: 21
<212> TYPE: RNA
<213> ORGANISM: Artificial Sequence
<220> FEATURE:
<223> OTHER INFORMATION: Oligomeric Compound

<400> SEQUENCE: 219

aaguuugcca cagaggauga g                                             21


<210> SEQ ID NO 220
<211> LENGTH: 21
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 1-19
<223> OTHER INFORMATION: bases at these positions are RNA

<400> SEQUENCE: 220

ggagccuugc guccugggct t                                             21


<210> SEQ ID NO 221
<211> LENGTH: 21
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 1-19
<223> OTHER INFORMATION: bases at these positions are RNA

<400> SEQUENCE: 221

gcccaggacg caaggcucct t                                             21
```